US011732261B2

(12) United States Patent
Seth et al.

(10) Patent No.: US 11,732,261 B2
(45) Date of Patent: Aug. 22, 2023

(54) SELECTIVE ANTISENSE COMPOUNDS AND USES THEREOF

(71) Applicant: Ionis Pharmaceuticals, Inc., Carlsbad, CA (US)

(72) Inventors: Punit P. Seth, Carlsbad, CA (US); Michael Oestergaard, Carlsbad, CA (US); Eric E. Swayze, Encinitas, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 102 days.

(21) Appl. No.: 17/011,395

(22) Filed: Sep. 3, 2020

(65) Prior Publication Data

US 2021/0238591 A1  Aug. 5, 2021

Related U.S. Application Data

(63) Continuation of application No. 14/238,439, filed as application No. PCT/US2012/050015 on Aug. 8, 2012, now abandoned.

(60) Provisional application No. 61/603,196, filed on Feb. 24, 2012, provisional application No. 61/596,723, filed on Feb. 8, 2012, provisional application No. 61/522,659, filed on Aug. 11, 2011.

(51) Int. Cl.
*C12N 15/11* (2006.01)
*C12N 15/113* (2010.01)

(52) U.S. Cl.
CPC .......... *C12N 15/113* (2013.01); *C12N 15/111* (2013.01); *C12N 2310/11* (2013.01); *C12N 2310/312* (2013.01); *C12N 2310/315* (2013.01); *C12N 2310/316* (2013.01); *C12N 2310/3125* (2013.01); *C12N 2310/321* (2013.01); *C12N 2310/3231* (2013.01); *C12N 2310/3341* (2013.01); *C12N 2310/341* (2013.01); *C12N 2310/351* (2013.01); *C12N 2320/34* (2013.01)

(58) Field of Classification Search
CPC .................................... C12N 15/113
See application file for complete search history.

(56) References Cited

U.S. PATENT DOCUMENTS

| | | |
|---|---|---|
| 3,687,808 A | 8/1972 | Merigan et al. |
| 4,845,205 A | 7/1989 | Dinh et al. |
| 4,981,957 A | 1/1991 | Lebleu et al. |
| 5,118,800 A | 6/1992 | Smith et al. |
| 5,130,302 A | 7/1992 | Spielvogel et al. |
| 5,134,066 A | 7/1992 | Rogers et al. |
| 5,175,273 A | 12/1992 | Bischofberger et al. |
| 5,319,080 A | 6/1994 | Leumann |
| 5,359,044 A | 10/1994 | Cook et al. |
| 5,367,066 A | 11/1994 | Urdea et al. |
| 5,393,878 A | 2/1995 | Leumann |
| 5,432,272 A | 7/1995 | Benner |
| 5,446,137 A | 8/1995 | Maag et al. |
| 5,446,786 A | 8/1995 | Shtulman |
| 5,457,187 A | 10/1995 | Gmeiner et al. |
| 5,459,255 A | 10/1995 | Cook et al. |
| 5,484,908 A | 1/1996 | Froehler et al. |
| 5,502,177 A | 3/1996 | Matteucci et al. |
| 5,514,785 A | 5/1996 | Van Ness et al. |
| 5,519,134 A | 5/1996 | Acevedo et al. |
| 5,525,711 A | 6/1996 | Hawkins et al. |
| 5,552,540 A | 9/1996 | Haralambidis |
| 5,567,811 A | 10/1996 | Misiura et al. |
| 5,576,427 A | 11/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,595,756 A | 1/1997 | Bally et al. |
| 5,596,091 A | 1/1997 | Switzer |
| 5,597,909 A | 1/1997 | Urdea et al. |
| 5,610,300 A | 3/1997 | Altmann et al. |
| 5,614,617 A | 3/1997 | Cook et al. |
| 5,627,053 A | 5/1997 | Usman et al. |
| 5,639,873 A | 6/1997 | Barascut et al. |
| 5,645,985 A | 7/1997 | Froehler et al. |
| 5,646,265 A | 7/1997 | McGee |
| 5,658,873 A | 8/1997 | Bertsch-Frank et al. |
| 5,670,633 A | 9/1997 | Cook et al. |
| 5,681,941 A | 10/1997 | Cook et al. |
| 5,700,920 A | 12/1997 | Altmann et al. |
| 5,700,922 A | 12/1997 | Cook |
| 5,750,692 A | 5/1998 | Cook et al. |
| 5,763,588 A | 6/1998 | Matteucci et al. |
| 5,792,747 A | 8/1998 | Schally et al. |

(Continued)

FOREIGN PATENT DOCUMENTS

| | | |
|---|---|---|
| JP | 2008-513507 | 5/2008 |
| WO | WO 93/24510 | 12/1993 |

(Continued)

OTHER PUBLICATIONS

Abifadel et al., "Mutations and polymorphisms in the proprotein convertase subtilisin kexin 9 (PCSK9) gene in cholesterol metabolism and disease" Hum Mutat. (2009) 30(4): 520-529.

(Continued)

*Primary Examiner* — Ekaterina Poliakova-Georgantas

(74) *Attorney, Agent, or Firm* — McNeill Baur PLLC

(57) ABSTRACT

The present invention provides oligomeric compounds. Certain such oligomeric compounds are useful for hybridizing to a complementary nucleic acid, including but not limited, to nucleic acids in a cell. In certain embodiments, hybridization results in modulation of the amount activity or expression of the target nucleic acid in a cell.

20 Claims, No Drawings

Specification includes a Sequence Listing.

(56) References Cited

U.S. PATENT DOCUMENTS

| | | |
|---|---|---|
| 5,801,154 A | 9/1998 | Baracchini et al. |
| 5,830,653 A | 11/1998 | Froehler et al. |
| 5,998,148 A | 12/1999 | Bennett et al. |
| 6,005,096 A | 12/1999 | Matteucci et al. |
| 6,043,060 A | 3/2000 | Imanishi |
| 6,147,200 A | 11/2000 | Manoharan et al. |
| 6,268,490 B1 | 7/2001 | Imanishi et al. |
| 6,525,191 B1 | 2/2003 | Ramasamy |
| 6,582,908 B2 | 6/2003 | Fodor et al. |
| 6,600,032 B1 | 7/2003 | Manoharan et al. |
| 6,670,461 B1 | 12/2003 | Wengel et al. |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel |
| 7,098,192 B2 | 8/2006 | Karras |
| 7,320,965 B2 | 1/2008 | Sah et al. |
| 7,399,845 B2 | 7/2008 | Seth et al. |
| 7,427,672 B2 | 9/2008 | Imanishi et al. |
| 7,741,457 B2 | 6/2010 | Swayze et al. |
| 7,951,934 B2 | 5/2011 | Freier et al. |
| 8,084,437 B2 | 12/2011 | Freier et al. |
| 8,093,222 B2 | 1/2012 | Freier et al. |
| 8,501,805 B2 | 8/2013 | Seth et al. |
| 8,530,640 B2 | 9/2013 | Seth et al. |
| 8,546,556 B2 | 10/2013 | Seth et al. |
| 8,679,750 B2 | 3/2014 | Hayden et al. |
| 9,695,418 B2 | 7/2017 | Seth et al. |
| 10,202,599 B2 | 2/2019 | Seth et al. |
| 10,260,069 B2 | 4/2019 | Oestergaard et al. |
| 11,236,335 B2 | 2/2022 | Oestergaard et al. |
| 2001/0053519 A1 | 12/2001 | Fodor et al. |
| 2002/0081611 A1 | 6/2002 | O'Brien et al. |
| 2002/0165189 A1 | 11/2002 | Crooke |
| 2002/0187931 A1 | 12/2002 | Hayden et al. |
| 2003/0073123 A1 | 4/2003 | Shen et al. |
| 2003/0082807 A1 | 5/2003 | Wengel |
| 2003/0087853 A1 | 5/2003 | Crooke et al. |
| 2003/0109476 A1 | 6/2003 | Kmiec et al. |
| 2003/0125241 A1 | 7/2003 | Wissenbach et al. |
| 2003/0144242 A1 | 7/2003 | Ward et al. |
| 2003/0207841 A1 | 11/2003 | Kaneko et al. |
| 2003/0228597 A1 | 12/2003 | Cowsert et al. |
| 2004/0014959 A1 | 1/2004 | Sorensen et al. |
| 2004/0092465 A1 | 5/2004 | Dobie |
| 2004/0096880 A1 | 5/2004 | Kmiec |
| 2004/0137471 A1 | 7/2004 | Vickers et al. |
| 2004/0143114 A1 | 7/2004 | Imanishi et al. |
| 2004/0171570 A1 | 9/2004 | Allerson et al. |
| 2004/0219565 A1 | 11/2004 | Kauppinen et al. |
| 2005/0042646 A1 | 2/2005 | Davidson |
| 2005/0059066 A1 | 3/2005 | Swayze et al. |
| 2005/0096284 A1 | 5/2005 | McSwiggen |
| 2005/0130923 A1 | 6/2005 | Bhat et al. |
| 2005/0153921 A1 | 7/2005 | Monia et al. |
| 2005/0176045 A1 | 8/2005 | Fedorov et al. |
| 2005/0191638 A1 | 9/2005 | McSwiggen |
| 2005/0255086 A1 | 11/2005 | Davidson |
| 2005/0255487 A1 | 11/2005 | Khvorova et al. |
| 2006/0051769 A1 | 3/2006 | Barts |
| 2006/0063730 A1 | 3/2006 | Monia et al. |
| 2007/0031844 A1 | 2/2007 | Khvorova et al. |
| 2007/0099860 A1 | 5/2007 | Sah |
| 2007/0123484 A1 | 5/2007 | Bhat et al. |
| 2007/0161590 A1 | 7/2007 | Van Bilsen et al. |
| 2007/0287831 A1 | 12/2007 | Seth et al. |
| 2008/0015158 A1 | 1/2008 | Ichiro |
| 2008/0015162 A1 | 1/2008 | Bhanot et al. |
| 2008/0039418 A1 | 2/2008 | Freier |
| 2008/0039618 A1 | 2/2008 | Allerson et al. |
| 2008/0274989 A1 | 11/2008 | Davidson et al. |
| 2009/0012281 A1 | 1/2009 | Swayze et al. |
| 2009/0092981 A1 | 4/2009 | Swayze et al. |
| 2009/0318536 A1 | 12/2009 | Freier et al. |
| 2010/0069472 A1 | 3/2010 | Hung et al. |
| 2010/0299768 A1 | 11/2010 | Perrin et al. |
| 2011/0213010 A1 | 9/2011 | Hayden et al. |
| 2013/0035366 A1 | 2/2013 | Swayze et al. |
| 2014/0303235 A1 | 10/2014 | Oestergaard et al. |
| 2015/0051389 A1 | 2/2015 | Seth et al. |
| 2015/0184153 A1 | 7/2015 | Freier et al. |
| 2020/0056187 A1 | 2/2020 | Oestergaard et al. |
| 2020/0377946 A1 | 12/2020 | Bennett et al. |
| 2021/0147838 A1 | 5/2021 | Seth et al. |
| 2022/0403386 A1 | 12/2022 | Bennett et al. |
| 2023/0002763 A1 | 1/2023 | Oestergaard et al. |

FOREIGN PATENT DOCUMENTS

| | | |
|---|---|---|
| WO | WO 94/26764 | 11/1994 |
| WO | WO 98/39352 | 9/1998 |
| WO | WO 99/14226 | 3/1999 |
| WO | WO 2001/079283 | 10/2001 |
| WO | WO 2003/004602 | 1/2003 |
| WO | WO 2003/013437 | 2/2003 |
| WO | WO 2003/064625 | 8/2003 |
| WO | WO 2004/044181 | 5/2004 |
| WO | WO 2004/048601 | 6/2004 |
| WO | WO 2004/069991 | 8/2004 |
| WO | WO 2004/101787 | 11/2004 |
| WO | WO 2004/013280 | 12/2004 |
| WO | WO 2004/106356 | 12/2004 |
| WO | WO 2005/021570 | 3/2005 |
| WO | WO 2005/023825 | 3/2005 |
| WO | WO 2005/027980 | 3/2005 |
| WO | WO 2005/028628 | 3/2005 |
| WO | WO 2005/045032 | 5/2005 |
| WO | WO 2005/061710 | 7/2005 |
| WO | WO 2005/095607 | 10/2005 |
| WO | WO 2005/105995 | 11/2005 |
| WO | WO 2005/116204 | 12/2005 |
| WO | WO 2005/121371 | 12/2005 |
| WO | WO 2007/002904 | 1/2007 |
| WO | WO 2007/027775 | 3/2007 |
| WO | WO 2007/027894 | 3/2007 |
| WO | WO 2007/089584 | 8/2007 |
| WO | WO 2007/090071 | 8/2007 |
| WO | WO 2007/131237 | 11/2007 |
| WO | WO 2007/134181 | 11/2007 |
| WO | WO 2007/146511 | 12/2007 |
| WO | WO 2008/005562 | 1/2008 |
| WO | WO 2008/018795 | 2/2008 |
| WO | WO 2008/049085 | 4/2008 |
| WO | WO 2008/066776 | 6/2008 |
| WO | WO 2008/101157 | 8/2008 |
| WO | WO 2008/147887 | 12/2008 |
| WO | WO 2008/147930 | 12/2008 |
| WO | WO 2008/150729 | 12/2008 |
| WO | WO 2008/154401 | 12/2008 |
| WO | WO 2009/006478 | 1/2009 |
| WO | WO 2009/061851 | 5/2009 |
| WO | WO 2009/124295 | 10/2009 |
| WO | WO 2009/135322 | 11/2009 |
| WO | WO 2010/048585 | 4/2010 |
| WO | WO 2011/097388 | 8/2011 |
| WO | WO 2011/097643 | 8/2011 |
| WO | WO 2011/097644 | 8/2011 |
| WO | WO 2011/139702 | 11/2011 |
| WO | WO 2012/109395 | 8/2012 |
| WO | WO 2013/022967 | 2/2013 |

OTHER PUBLICATIONS

Albaek et al., "Analogues of a Locked Nucleic Acid with Three-Carbon 2′,4′-Linkages: Synthesis by Ring-Closing Metathesis and Influence on Nucleic Acid Duplex Stability and Structure" J. Org. Chem. (2006) 71:7731-7740.

Altmann et al., "Second Generation Antisense Oligonucleotides—Inhibition of PKC-a and c-RAF Kinase Expression by Chimeric Oligonucleotides Incorporating 6′-Substituted Carbocyclic Nucleosides and 2′-O-Ethylene Glycol Substituted Ribonucleosides" Nucleosides Nucleotides (1997) 16:917-926.

(56) References Cited

OTHER PUBLICATIONS

Altmann et al., "Second Generation of Antisense Oligonucleotides: From Nuclease Resistance to Biological Efficacy in Animals" Chimia (1996) 50:168-176.

Altmann et al., "Second-generation antisense oligonucleotides: structure-activity relationships and the design of improved signal-transduction inhibitors" Biochem. Soc. Trans. (1996) 24:630-637.

Alves et al., "Allele-Specific RNA Silencing of Mutan Ataxin-3 Mediates Neuroprotection in a Rat Model of Machado-Joseph Disease" PLOS One (2008) 3(10): e3341.

Anderson et al., "An Overview of Psychiatric Symptoms in Huntington's Disease" Current Psychiatry Reports (2001) 3:379-388.

Arzumanov et al., "A structure-activity study of the inhibition of HIV-1 Tat-dependent trans-activation by mixmer 2'-O-methyl oligoribonucleotides containing locked nucleic acid (LNA), alpha-L-LNA, or 2'-thio-LNA residues" Antisense & Nucleic Acid Drug Development (2003) 13(6):435-453.

Arzumanov et al., "Inhibition of HIV-1 Tat-dependent trans activation by steric block chimeric 2'-O-methyl/LNA oligoribonucleotides" Biochemistry (2001) 40(48):14645-14654.

Belikova et al., "Synthesis of Ribonucleosides and Diribonucleoside Phosphate Containing 2'-Chloro-Ethylamine and Nitrogen Mustard Residues" Tet. Lett. (1967) 37:3557-3562.

Bennett et al., "Antisense oligonucleotides as a tool for gene functionalization and target validation" Biochimica Biophysica Acta (1999) 1489:19-30.

Berger et al., "Universal bases for hybridization, replication and chain termination" Nuc. Acid Res. (2000) 28:2911-2914.

Boado et al., "Antisense-mediated down-regulation of the human huntington gene" *Journal of Pharmacology and Experimental Therapeutics* (2000) 295:239-243.

Boffa et al., "Isolation of active genes containing CAG repeats by DNA strands invasion by a peptide nucleic acid" PNAS (1995) 92:1901-5.

Bonini et al., "Silencing Poly glutamine Degeneration with RNAi" Neuron (2005) 48:715-718.

Borovecki et al., "Genome-wide expression profiling of human blood reveals biomarkers for Huntington's disease" *Proc. Natl. Acad. Sci. USA* (2005) 102:11023-11028.

Braasch et al., "Locked nucleic acid (LNA): fine-tuning the recognition of DNA and RNA" Chem. Biol. (2001) 8:1-7.

Branch et al., "A good antisense molecule is hard to find," TIBS (1998) 23:45-50.

Brookes, "The essence of SNPs" Gene (1999) 234(2):177-186.

Bruge et al., "A novel Real Time PCR strategy to detect SOD3 SNP using LNA probes" Mutation Res (2009) 669(1): 80-84.

Bruijn et al., "Aggregation and Motor Neuron Toxicity of an ALS-Linked SOD1 Mutant Independent from Wild-Type SOD1" Science (1998) 281: 1851-1854.

Caplen et al., "Rescue of polyglutamine-mediated cytotoxicity by double-stranded RNA-mediated RNA interference" Human Molecular Genetics (2002) 11(2):175-184.

Carrell et al., "Alphal-Antitrypsin Deficiency—A Model for Conformational Diseases" New Engl J Med (2002) 346: 45-53.

Carroll et al., "Potent and Selective Antisense Oligonucleotides Targeting Single-Nucleotide Polymorphisms in the Huntington Disease Gene / Allele-Specific Silencing of Mutant Huntingtin" Molecular Therapy (2011) 19(12):2178-2185.

Chan et al., "Antisense Oligonucleotides: From Design to Therapeutic Application" Clin. Exp. Pharmacol. Physiol. (2006) 33:533-540.

Chang et al., "Structural Analysis of Complementary DNA and Amino Acid Sequences of Human and Rat Androgen Receptors" PNAS (1988) 85:7211-7215.

Chen et al., "Allelic origin of the abnormal prion protein isoform in familial prion diseases." Nat. Med. (1997) 3(9): 1009-1015.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1: 1-50.

Crooke et al., "Pharmacokinetic Properties of Several Novel Oligonucleotide Analogs in mice" J. Pharmacol. Exp. Ther. (1996) 277(2):923-937.

Daiger et al., "Mutations in known genes account for 58% of autosomal dominant retinitis pigmentosa (adRP)." Adv Exp Med Biol (2008) 613: 203-219.

Davidson et al., "Molecular medicine for the brain: silencing of disease genes with RNA interference" Lancet Neurol. (2004) 3:145-149.

Dawson et al., "Rare genetic mutations shed light on the pathogenesis of Parkinson disease." J. Clin. Invest. (2003) 111(2): 145-151.

De Gobbi et al., "A regulatory SNP causes a human genetic disease by creating a new transcriptional promoter." Science (2006) 312(5777): 1215-1217.

Denovan-Wright et al., "RNAi: a potential therapy for dominantly inherited nucleotide repeat diseases" Gene Therapy (2006) 13(6):525-531.

Diaz-Hernandez et al., "Full Motor Recovery Despite Striatal Neuron Loss and Formation of Irreversible Amyloid-Like Inclusions in a Conditional Mouse Model of Huntington's Disease" *J. Neurosci* (2005) 25:9773-9781.

Dragatsis et al., "Inactivation of Hdh in the brain and testis results in progressive neurodegeneration and sterility in mice" Nat. Genet. (2000) 26:300-306.

Eder et al., "Inhibition of LNCaP Prostate Cancer Cells by Means of Androgen Receptor Antisense Oligonucleotides" Cancer Gene Therapy (2000) 7(7):997-1007.

Elayadi et al., "Application of PNA and LNA oligomers to chemotherapy" Curr. Opinions Invens. Drugs (2001) 2:558-561.

Ellis, "Spot-On SNP Genotyping" Genome Res. (2000) 10:895-897.

Englisch et al., "Chemically Modified Oligonucleotides as Probes and Inhibitors" Angewandte Chemie, International Edition (1991) 30(6): 613-629.

Ewart-Toland et al., "A gain of function TGFB1 polymorphism may be associated with late stage prostate cancer," Cancer Epidemiol Biomarkers Prey (2004) 13(5): 759-764.

Feng et al., "Allele-specific silencing of Alzheimer's disease genes: The amyloid precursor protein genes with Swedish or London mutations" Gene (2006) 371: 68-74.

Fluiter et al., "Killing cancer by targeting genes that cancer cells have lost: allele-specific inhibition, a novel approach to the treatment of genetic disorders." Cell Mol Life Sci (2003) 60: 834-43.

Fluiter et al., "On the in vitro and in vivo properties of four locked nucleic acid nucleotides incorporated into an anti-h-ras antisense oligonucleotide" Chembiochem—A European Journal of Chemical Biology (2005) 6(6): 1104-1109.

Fluiter et al., "Tumor Genotype-specific Growth Inhibition in Vivo by Antisense Oligonucleotides against a Polymorphic Site of the Large Subunit of Human RNA Polymerase II" Cancer Res. (2002) 62:2024-2028.

Fontana et al., "P2Y12 H2 Haplotype Is Associated With Peripheral Arterial Disease: a case-control study" Circulation (2003) 108: 2971-2973.

Freier et al., "The ups and downs of nucleic acid duplex stability: structure-stability studies on chemically-modified DNA:RNA duplexes" Nucleic Acids Res. (1997) 25:4429-4443.

Freden et al., "Expanding the design horizon of antisense oligonucleotides with alpha-L-LNA" Nucleic Acids Research (2003) 21:6365-6372.

Gagnon et al. "Allele-selective inhibition of mutatn huntington expression with antisense oligonucleotides targeting the expanded CAG repeat" Biochemistry (2010) 49:10166-78.

Gait et al., "Applications of Chemically synthesized RNA" in RNA: Protein Interactions, Ed. Smith, 1998, p. 1-36.

Gallo et al., "2'-C-Methyluridine phosphoramidite: a new building block for the preparation of RNA analogues carrying the 2'-hydroxyl group" Tetrahedron (2001) 57:5707-5717.

Gautschi et al., "Activity of a Novel bcl-2/bcl-xL-Bispecific Antisense Oligonucleotide Against Tumors of Diverse Histologic Origins" J. Natl. Cancer Inst. (2001) 93:463-471.

(56) References Cited

OTHER PUBLICATIONS

Gonzalez-Alegre et al., "Technology Insight: therapeutic RNA interference—how far from the neurology clinic?" Nature Clinical Practice 3:394-404.
Gossen et al., "Tight control of gene expression in mammalian cells by tetracycline-responsive promoters." PNAS (1992) 89:5547-5551.
Gow et al., "The unfolded protein response in protein aggregating diseases" NeuroMol. Med. (2003) 4(1 -2):73-94.
Gray et al., "Full-Length Human Mutant Huntingtin with a Stable Polyglutamine Repeat Can Elicit Progressive and Selective Neuropathogenesis in BACHD Mice" J. Neurosc. (2008) 28(24):6182-6195.
Griffin et al., "Single-nucleotide polymorphism analysis by MALDI-TOF mass spectrometry" Trends Biotechnol. (2000) 18(2):77-84.
Gryaznov et al., "Oligodeoxyribonucleotide N3'->P5' Phosphoramidates Synthesis and Hybridization Properties" J. Am. Chem. Soc. (1994) 116:3143-3144.
Gryk et al., "Local knowledge helps determine protein structures" PNAS (2008) 105: 4533-4534.
Guillerm et al., "Synthesis of 4'-fluoroadenosine as an inhibitor of S-adenosyl-L-homocysteine hydrolase" Bioorganic and Medicinal Chemistry Letters (1995) 5(14): 1455-1460.
Gutekunst et al., "Identification and localization of huntingtin in brain and human lymphoblastoid cell lines with anti-fusion protein antibodies" PNAS (1995) 92(19):8710-8714.
Hagemann et al., "Alexander Disease-Associated Glial Fibrillary Acidic Protein Mutations in Mice Induce Rosenthal Fiber Formation and a White Matter Stress Response" J. Neurosci. (2006) 26(43): 11162-11173.
Handley et al., "Pharmaceutical, cellular and genetic therapies for Huntington's disease" Clin Sci. (2006) 110:73-88.
Haque et al., "Antisense gene therapy for neurodegenerative disease" *Experimental Neurology* (1997) 144:139-146.
Harlan et al., "Variants in Apaf-1 segregating with major depression promote apoptosome function" Mol Psychiatry (2006) 11: 76-85.
Harper et al., "RNA interference improves motor and neuropathological abnormalities in a Huntington's disease mouse model" *PNAS* (2005) 102:5820-5825.
Harper et al., "Ten years of presymptomatic testing for Huntington's disease: the experience of the UK Huntington's Disease Prediction Consortium" J. Med. Genet. (2000) 37:567-571.
Harry-O'Kura et al., "A Short, Flexible Route toward 2'-C-Branched Ribonucleosides" J Org Chem (1997) 62(6) 1754-1759.
Hasholt et al., "Antisense downregulation of mutant huntingtin in a cell model" *Journal of Gene Medicine* (2003) 5:528-538.
Henry et al., Antisense Drug Technology—Second Edition CRC Press. Chapter 12, pp. 327-363.
Hersch et al., "Neuroprotection for Huntington's disease: Ready, set, slow" Neurotherapeutics (2008) 5(2):226-236.
Hersch et al., "Translating Therapies for Huntington's Disease from Genetic Animal Models to Clinical Trials" *NeuroRX* (2004) 1:298-306.
Hizawa et al., "Functional single nucleotide polymorphisms of the CCL5 gene and nonemphysematous phenotype in COPD patients" Eur. Respir. J. (2008) 32(2):372-378.
Horie et al. "Hepatocyte-specific Pten deficiency results in steatohepatitis and hepatocellular carcinomas" J. Clincal Investigation (2004) 113(12): 1774-1783.
Hu et al., "Allele-specific silencing of mutant huntingtin and ataxin-3 genes by targeing expanded CAG repeats in mRNAs" Nature Biotechnology (2009) 27(5):478-484.
Hu et al., "Serotonin transporter promoter gain-of-function genotypes are linked to obsessive-compulsive disorder." Am J Hum Genet (2006) 78(5): 815-826.
Jacobson et al., "Methanocarba Analogues of Purine Nucleosides as Potent and Selective Adenosine Receptor Agonists" J. Med. Chem. Lett. (2000) 43(11): 2196-2203.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327.
Kabashi et al., "Gain and loss of function of ALS-related mutations of TARDBP (TDP-43) cause motor deficits in vivo," Hum Mol Genet (2010) 19(4): 671-683.
Kawasaki et al., "Uniformly Modified 2'-Deoxy-2'-fluoro Phosphorothioate Oligonucleotides as Nuclease-Resistant Antisense Compounds with High Affinity and Specificity for RNA Targets" J. Med. Chem. (1993) 36: 831-841.
Kierzek et al., "The influence of locked nucleic acid residues on thermodyanmic properties of 2'-O-methyl RNA/RNA heteroduplexes" Nucleic Acids Research (2005) 33(16):5082-5093.
Kordasiewicz et al., "Sustained Therapeutic Reversal of Huntington's Disease by Transient Repression of Huntingtin Synthesis" Neuron (2012) 74:1031-1044.
Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) 54:3607-3630.
Kroshwitz, The Concise Encyclopedia Of Polymer Science And Engineering, Kroschwitz, J.I., Ed., John Wiley & Sons, 1990, 858-859.
Kumar et al., "The First Analogues of LNA (Locked Nucleic Acids): Phosphorothioate-LNA and 2'-Thio-LNA" Bioorg. Med. Chem. Lett. (1998) 8:2219-2222.
Kurreck et al., "Antisense Technologies Improvement Through Novel Chemical Modifications" European Journal of Biochemistry (2003) 270: 1628-1644.
Landgraf, "The involvement of the vasopressin system in stress-related disorders." CNS Neurol. Disord. Drug Targets (2006) 5(2): 167-179.
Lee et al., "Ring-Constrained (N)-Methanocarba nucleosides as adenosine receptor agonists: independent 5'-Uronamide and 2'-deoxy modifications" Bioorganic and Medicinal Chemistry Letters (2001) 11: 1333-1337.
Letsinger et al., "Cholesteryl-conjugated oligonucleotides: Synthesis, properties, and activity as inhibitors of replication of human immunodeficiency virus in cell culture" PNAS (1989) 86:6553-6556.
Leumann, "DNA Analogues: From Supramolecular Principles to Biological Properties" Bioorganic & Medicinal Chemistry (2002) 10:841-854.
Li et al., "Gain-of-function polymorphism in mouse and human Ltk: implications for the pathogenesis of systemic lupus erythematosus" Hum Mol Gen (2004) 13(2): 171-179.
Liu et al., "Linking SNP identity to CAG repeat length in Huntington's Disease patients," Nature Methods (2008) 5(11): 951-953.
Liu et al., "Specific inhibition of Huntington's disease gene expression by siRNAs in cultures cells" *Proceedings of the Japan Academy. Series B, Physical and Biological Sciences* (2003) 79B:293-298.
Lombardi et al., "A majority of Huntington's disease patients may be treatable by individualized allele-specific RNA interference" Experimental Neurology (2009) 217(2): 312-319.
MacDonald et al., "A novel gene containing a trinucleotide repeat that is expanded and unstable on Huntington's disease chromosomes" Huntington's Disease Collaborative Research Group, Cell (1993) 72(6):971-983.
Machida et al., "rAAV-mediated shRNA ameliorated neuropathology in Huntington disease model mouse" *Biochem. Biophys. Res. Commun.* (2006) 343:190-197.
MacMillan et al., "Molecular analysis and clinical correlations of the Huntington's disease mutation" Lancet (1993) 342:954-958.
Maher et al., "Comparative hybrid arrest by tandem antisense oligodeoxyribonucleotides or oligodeoxyribonucleoside methylphosphonates in a cell-free system" Nuc. Acid. Res. (1988) 16:3341-3358.
Manoharan et al., "Chemical Modifications to Improve Uptake and Bioavailability of Antisense Oligonucleotides" Ann. N.Y. Acad. Sci. (1992) 660:306.

(56) References Cited

OTHER PUBLICATIONS

Manoharan et al., "Cholic Acid-Oligonucleotide Conjugates for Antisense Applications" Bioorg. Med. Chem. Lett. (1994) 4:1053-1060.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Lipidic Nucleic Acids" Tetrahedron Lett. (1995) 36(21):3651-3654.
Manoharan et al., "Oligonucleotide Conjugates: Alteration of the Pharmacokinetic Properties of Antisense Agents" Nucleosides & Nucleotides (1995) 14(3-5):969-973.
Mantaring et al., "Genotypic variation in ATP-binding cassette transporter-1 (ABCA1) as contributors to the high and low high-density lipoprotein-cholesterol (HDL-C) phenotype" Transl Res (2007) 149(4): 205-210.
Margolis et al., "Expansion explosion: new clues to the pathogenesis of repeat expansion neurodegenerative diseases." Trends Mol. Med. (2001) 7: 479-482.
Martin et al., "38. Ein neuer Zugang zu 2'-O-Alkylribonucleosidenund Eigenschaften deren Oligonucleotide" *Helv. Chim. Acta* (1995) 78:486-504.
Marzolini et al., "A common polymorphism in the bile acid receptor farnesoid X receptor is associated with decreased hepatic target gene expression." Mol Endocrinol (2007) 21(8): 1769-1780.
McWhinney et al., "Intronic single nucleotide polymorphisms in the RET protooncogene are associated with a subset of apparently sporadic pheochromocytoma and may modulate age of onset" J. Clin. Endocrinol. Metab. (2003) 88(10):4911-4916.
Mishra et al., "Improved leishmanicidal effect of phosphorotioate antisense oligonucleotides by LDL-mediated delivery" Biochim. Biophys. Acta (1995) 1264:229-237.
Morita et al., "2'-O,4'-C-ethylene-bridged nucleic acids (ENA): highly nuclease-resistant and thermodynamically stable oligonucleotides for antisense drug" Bioorganic & Medicinal Chemistry Letters (2002) 12(1): 73-76.
Morita et al., "Synthesis and Properties of 2'-O,4'-C-Ethylene-Bridged Nucleic Acids (ENA) as Effective Antisense Oligonucleotides" Bioorganic Medicinal Chemistry (2003) 11:2211-2226.
Murray et al., "TricycloDNA-modified oligo-20-deoxyribonucleotides reduce scavenger receptorB1 mRNA in hepatic and extra-hepatic tissues—a comparative study of oligonucleotide length, design and chemistry" Nucleic Acids Res (2012) 40(13): 6135-6143.
Nasir et al., "Targeted disruption of the Huntington's disease gene results in embryonic lethality and behavioral and morphological changes in heterozygotes" Cell (1995) 81(5):811-823.
Nellemann et al., "Inhibition of Huntington synthesis by antisense oligonucleotides" *Molecular and Cellular Neurosciences* (2000) 16:313-323.
New England Biolabs 1998/99 Catalog (cover page and pp. 121 and 284).
Nguyen et al., "Clioquinol down-regulates mutant huntingtin expression in vitro and mitigates pathology in a Huntington's disease mouse model" *PNAS* (2005) 102:11840-11845.
Nikiforov et al., "The Use of Phosphorothioate Primers and Exonuclease Hydrolysis for the Preparation of Single-stranded PCR Products and their Detection by Solid-phase Hybridization" PCR Methods and Applications (1994) 3:285-291.
Oberhauser et al., "Effective incorporation of 2'-O-methyl-oligoribonucleotides into liposomes and enhanced cell association through modifications with thiocholesterol" Nucl. Acids Res. (1992) 20(3):533-538.
O'Connor et al., "Nonalcoholic fatty liver (NASH syndrome)" Gastroenterologist 5(4): 316-29 abstract. Dec. 1997.
Ostergaard et al. "Rational design of antisense oligonucleotides targeting single nucleotide polymorphisms for potent and allele selective suppression of mutant Huntingtin in the CNS." Nucleic Acids Res. (2013) 41:9634-50.

Orum et al., "Locked nucleic acids: A promising molecular family for gene-function analysis and antisense drug development" Curr. Opinion Mol. Ther. (2001) 3:239-243.
Owen et al., "4'-Substituted nucleosides. 3. Synthesis of some 4'-fluorouridine derivatives" J. Org. Chem. (1976) 41(18): 3010-3017.
Palazzolo et al., "The role of the poly glutamine tract in androgen receptor" J Steroid Biochem Mol Biol (2008) 108(3-5): 245-252.
Persichetti et al., "Differential expression of normal and mutant Huntington's disease gene alleles." Neurobiol Dis (1996) 3(3): 183-190.
Pfister et al., "Five siRNAs targeting three SNPs may provide therapy for three-quarters of Huntington's Disease patients," Current Biology (2009) 19:774-778.
Prakash et al., "Antisense Oligonucleotides Containing Conformationally Constrainted 2, 4-(N-Methoxy)aminomethylene and 2,4-Aminooxymethylene and 2 -O,4 C-Aminomethylene Bridged Nucleoside Analogues Show Improved Potency in Animal Models" Journal of Medicinal Chemistry (2010) 53(4):163-1650.
Rajasekaran et al., "Human alpha B-crystallin mutation causes oxido-reductive stress and protein aggregation cardiomyopathy in mice" Cell (2007) 130(3): 427-439.
Reynolds et al., "Rational siRNA design for RNA interference" Nature Biotechnology (2004) 22(3):326-330.
Robertson et al., "Localized mutations in the gene encoding the cytoskeletal protein filamin A cause diverse malformations in humans." Nat Genet (2003) 33(4): 487-491.
Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.
Sambrook et al., "Molecular Cloning, A Laboratory Manual" 2nd Edition, Cold Spring Harbor Laboratory Press, 1989.
Sanghvi et al., "Heterocyclic Base Modifications in Nucleic Acids and Their Applications in Antisense Oligonucleotides" Antisense Research and Applications (1993) pp. 273-288.
Scaringe, "RNA Oligonucleotide Synthesis via 5'-Silyl-2'-Orthoester Chemistry" Methods (2001) 23:206-217.
Scholefield et al., "Design of RNAi hairpins for mutation-specific silencing of ataxin-7 and correction of a SCA7 phenotype." PLoS One (2009) 4(9): e7232.
Schwarz et al., "Designing siRNA that distinguish between genes that differ by a single nucleotide" PLOS Genetics (2006) 2(9): p. e140.
Sen et al., "Role of histidine interruption in mitigating the pathological effects of long polyglutamine stretches in SCA1: A molecular approach," Protein Sci. (2003) 12(5): 953-962.
Seth et al., "Short Antisense Oligonucleotides with Novel 2'-4' Conformationaly Restricted Nucleoside Analogues Show Improved Potency without Increased Toxicity in Animals" Journal of Medicinal Chemistry (2009) 52(1):10-13.
Sewell et al., "Phase I Trial of ISIS 104838, a 2'-Methoxyexthyl Modified Antisense Oligonucleotide Targeting Tumor Necrosis Factor-Alpha" The Journal of Pharmacology and Experimental Therapeutics (2002) 303(3):1334-1343.
Shashidharan etal., "TorsinA accumulation in Lewy bodies in sporadic Parkinson's disease" Brain Res. (2000) 877: 379-381.
Shea et al., "Synthesis, hybridization properties and antiviral activity of lipid-oligodeoxynucleotide conjugates" Nucl. Acids Res. (1990) 18(13):3777-3783.
Sheehan et al., "Biochemical properties of phosphonoacetate and thiophosphonoacetate oligodeoxyribonucleotides" *Nucleic Acids Research* (2003) 31:4109-4118.
Shiels et al., "CHMP4B, a Novel Gene for Autosomal Dominant Cataracts Linked to Chromosome 20q" Am J Hum Genet (2007) 81(3): 596-606.
Singh et al., "LNA (locked nucleic acids): synthesis and high-affinity nucleic acid recognition" Chem. Commun. (1998) 4:455-456.
Singh et al., "Synthesis of 2'-Amino-LNA: A Novel Conformationally Restricted High-Affinity Oligonucleotide Analogue with a Handle" J. Org. Chem. (1998) 63:10035-10039.

(56) References Cited

OTHER PUBLICATIONS

Southwell et al. "Antisense oligonuceltide therapeutics for inherited neurodegenerative diseases" Trends Mol Med (2012) 18:634-43.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Straarup et al., "Short locked nucleic acid antisense oligonucleotides potently reduce apolipoprotein B mRNA and semm cholesterol in mice and non-human primates" Nucleic Acids Research (2010) 38: 7100-7111.
Suzuki et al. "Portrait of PTEN: Messages from mutant mice" Cancer Sci. (2008) vol. 99(2):209-213.
Svinarchuk et al., "Inhibition of HIV proliferation in MT-4 cells by antisense oligonucleotide conjugated to lipophilic groups" Biochimie (1993) 75:49-54.
Swayze et al., "Antisense oligonucleotides containing locked nucleic acid improve potency but cause significant hepatotoxicity in animals" Nucleic Acids Research (2006) 35(2):687-700.
Takagi-Sato et al., "Fine-tuning of ENA gapmers as antisense oligonucleotides for sequence-specific inhibition" Oligonucleotides (2007) 17(3): 291-301.
Tang et al., "2'-C-Branched Ribonucleosides: Synthesis of the Phosphoramidite Derivatives of 2'-C-beta-Methylcytidine and Their Incorporation into Oligonucleotides." J Org Chem (1999) 64(3) 747-754.
Uhlmann et al., "Antisense oligonucleotides: a new therapeutic principle" *Chemical Reviews* (1990) 90:543-584.
Van Bilsen et al., "Identification and allele-specific silencing of the mutant huntingtin allele in Huntington's disease patient-derived fibroblasts" Human Gene Therapy (2008) 19:710-718.
Vezzoli et al., "R990G polymorphism of calcium-sensing receptor does produce a gain-of-function and predispose to primaiy hyperealciuria" Kidney Int. (2007) 71: 1155-1162.
Vickers et al., "Efficient Reduction of Target RNAs by Small Interfering RNA and Rnase H-dependent Antisense Agents. A comparative analysis." J Biol. Chem. (2003) 278:7108-7118.
Wahlesiedt et al., "Potent and nontoxic antisense oligonucleotides containing locked nucleic acids" PNAS (2000) 97:5633-5638.
Wang et al., "Clinico-pathological rescue of a model mouse of Huntington's disease by siRNA" *Neurosci. Res.* (2005) 53:241-249.
Warby et al., "CAG expansion in the Huntington disease gene is associated with a specific and targetable predisposing haplogroup" The American Journal of Human Genetics (2009) 84(3):351-366.
Webster et al., "Mutation in the AChR ion channel gate underlies a fast channel congenital myasthenic syndrome." Neurology (2004) 62(7): 1090-1096.
Weinstein et al., "Genetic diseases associated with heterotrimeric G proteins" Trends Pharmacol Sci (2006) 27(5): 260-266.
Woolf et al., "Specificity of antisense oligonucleotide in vivo" PNAS (1992) 89:7305-7309.
Yagi et al., "Chimeric RNA and 2'-O, 4'-C-ethylene-bridged nucleic acids have stronger activity than phosphorothioate oligodeoxynucleotides in induction of exon 19 skipping in dystrophin mRNA" Oligonucleotides (2004) 14(1):33-40.
Yen et al., "Sequence-specific cleavage of Huntingtin mRNA by catalytic DNA" Annals of Neurology (1999) 46(3):366-373.
Yu et al., "Structure, inhibitor, and regulatory mechanism of Lyp, a lymphoid-specific tyrosine phosphatase implicated in autoimmune diseases" PNAS (2007) 104(50): 19767-19772.
Zamecnik et al., "Inhibition of Rous sarcoma virus replication and cell transformation by a specific oligodeoxynucleotide" PNAS (1978) 75(1):280-284.

Zhou et al., "Fine Tuning of Electrostatics around the Intemucleotidic Phosphate through Incorporation of Modified 2',4'-Carbocyclic-LNAs and -ENAs Leads to Significant Modulation of Antisense Properties" J. Org. Chem. (2009) 74:118-134.
U.S. Appl. No. 60/746,631 dated May 5, 2006.
Response and Amendment to European application EP 07844422.1 dated Sep. 8, 2010.
Opposition against European Patent No. 2092065B1 granted to Isis Pharmaceuticals, Inc. dated Oct. 3, 2012.
European Search Report for application 11186203.3 dated Nov. 18, 2011.
European Search report for application EP 09741640.8 dated Dec. 11, 2012.
European Search Report for application EP 11186113.4 dated Nov. 30, 2011.
European Search report for application EP 11740542.3 dated Aug. 14, 2014.
European Search report for application EP 11740543 dated Sep. 18, 2013.
Extended European Search report for application EP 17206749.8 dated Feb. 13, 2018.
Extended European Search report for EP 19161655.6 dated Aug. 29, 2019.
Extended European Search report for EP 19164928.4 dated Sep. 17, 2019.
Extended European Search report for EP 19191293.0 dated Feb. 24, 2020.
International Search Report for Application No. PCT/US2007/081850 dated Mar. 12, 2008.
International Search Report for Application No. PCT/US2012/024385 dated May 10, 2012.
International Search Report for application PCT/CA2009/000645 dated Aug. 25, 2009.
International Search Report for application PCT/US11/24103 dated Jul. 15, 2011.
International Search Report for application PCT/US11/24104 dated Jul. 20, 2011.
International Search Report for application PCT/US12/50015 dated Nov. 2, 2012.
International Search Report for application PCT/US12/50023 dated Oct. 16, 2012.
International Search Report for application PCT/US13/064666 dated Apr. 23, 2014.
International Search Report for application PCT/US14/14722 dated Aug. 25, 2014.
De Mesmaeker et al., "Amide Backbones with Conformationally Restricted Furanose Rings: Highly Improved Affinity of the Modified Oligonucleotides for Their RNA Complements" Angew Chem Int Ed Engl (1996) 35: 2790-2794.
Extended European Search report for EP 21161967.1 dated Nov. 12, 2021, 10 pages.
Extended European Search report for EP 22166711.6 dated Dec. 13, 2022, 9 pages.
Gousset et al., "Conformational Study of DNA-RNA Duplexes Containing MMI Substituted Phosphodiester Linkages by FTIR Spectroscopy" Journal of Biolmolecular Structure and Dynamics (1998) 15: 931-936.
Hu et al., "Allele-selective Inhibition of Mutant Huntingtin by Peptide Nucleic Acid-Peptide Conjugates, Locked Nucleic Acid, and Small Interfering RNA" Oligonucleotide Therapeutics Ann NY Acad Sci (2009) 1175: 24-31.
Nagahama et al., "Nuclease resistant methylphosphonate-DNA/LNA chinagmeric oligonucleotides" Bioorganic & Medicinal Chemistry Letters (2009) 19: 2707-2709.

SELECTIVE ANTISENSE COMPOUNDS AND USES THEREOF

FIELD OF THE INVENTION

The present invention pertains generally to chemically-modified oligonucleotides for use in research, diagnostics, and/or therapeutics.

SEQUENCE LISTING

The present application is being filed along with a Sequence Listing in electronic format. The Sequence Listing is provided as a file entitled CORE0099USC1_SEQ_ST25.txt, created Apr. 12, 2021 which is 326 Kb in size. The information in the electronic format of the sequence listing is incorporated herein by reference in its entirety.

BACKGROUND OF THE INVENTION

Antisense compounds have been used to modulate target nucleic acids. Antisense compounds comprising a variety of chemical modifications and motifs have been reported. In certain instances, such compounds are useful as research tools, diagnostic reagents, and as therapeutic agents. In certain instances antisense compounds have been shown to modulate protein expression by binding to a target messenger RNA (mRNA) encoding the protein. In certain instances, such binding of an antisense compound to its target mRNA results in cleavage of the mRNA. Antisense compounds that modulate processing of a pre-mRNA have also been reported. Such antisense compounds alter splicing, interfere with polyadenlyation or prevent formation of the 5'-cap of a pre-mRNA.

SUMMARY OF THE INVENTION

In certain embodiments, the present invention provides oligomeric compounds comprising oligonucleotides. In certain embodiments, such oligonucleotides comprise a region having a gapmer motif. In certain embodiments, such oligonucleotides consist of a region having a gapmer motif.

The present disclosure provides the following non-limiting numbered embodiments:

Embodiment 1: A oligomeric compound comprising a modified oligonucleotide consisting of 10 to 30 linked nucleosides, wherein the modified oligonucleotide has a modification motif comprising:
  a 5'-region consisting of 2-8 linked 5'-region nucleosides, each independently selected from among a modified nucleoside and an unmodified deoxynucleoside, provided that at least one 5'-region nucleoside is a modified nucleoside and wherein the 3'-most 5'-region nucleoside is a modified nucleoside;
  a 3'-region consisting of 2-8 linked 3'-region nucleosides, each independently selected from among a modified nucleoside and an unmodified deoxynucleoside, provided that at least one 3'-region nucleoside is a modified nucleoside and wherein the 5'-most 3'-region nucleoside is a modified nucleoside; and
  a central region between the 5'-region and the 3'-region consisting of 6-12 linked central region nucleosides, each independently selected from among: a modified nucleoside and an unmodified deoxynucleoside, wherein the 5'-most central region nucleoside is an unmodified deoxynucleoside and the 3'-most central region nucleoside is an unmodified deoxynucleoside; wherein the modified oligonucleotide has a nucleobase sequence complementary to the nucleobase sequence of a target region of a target nucleic acid.

Embodiment 2: The oligomeric compound of embodiment 1, wherein the nucleobase sequence of the target region of the target nucleic acid differs from the nucleobase sequence of at least one non-target nucleic acid by 1-3 differentiating nucleobases.

Embodiment 3: The oligomeric compound of embodiment 1, the nucleobase sequence of the target region of the target nucleic acid differs from the nucleobase sequence of at least one non-target nucleic acid by a single differentiating nucleobase.

Embodiment 4: The oligomeric compound of embodiment 2 or 3, wherein the target nucleic acid and the non-target nucleic acid are alleles of the same gene.

Embodiment 5: The oligomeric compound of embodiment 4, wherein the single differentiating nucleobase is a single-nucleotide polymorphism.

Embodiment 6: The oligomeric compound of embodiment 5, wherein the single-nucleotide polymorphism is associated with a disease.

Embodiment 7: The oligomeric compound of embodiment 6, wherein the disease is selected from among: Alzheimer's disease, Creutzfeldt-Jakob disease, fatal familial insomnia, Alexander disease, Parkinson's disease, amyotrophic lateral sclerosis, dentato-rubral and pallido-luysian atrophy DRPA, spino-cerebellar ataxia, Torsion dystonia, cardiomyopathy, chronic obstructive pulmonary disease (COPD), liver disease, hepatocellular carcinoma, systemic lupus erythematosus, hypercholesterolemia, breast cancer, asthma, Type 1 diabetes, Rheumatoid arthritis, Graves disease, SLE, spinal and bulbar muscular atrophy, Kennedy's disease, progressive childhood posterior subcapsular cataracts, cholesterol gallstone disease, arthrosclerosis, cardiovascular disease, primary hypercalciuria, alpha-thallasemia, obsessive compulsive disorder, Anxiety, comorbid depression, congenital visual defects, hypertension, metabolic syndrome, prostate cancer, congenital myasthenic syndrome, peripheral arterial disease, atrial fibrillation, sporadic pheochromocytoma, congenital malformations, Machado-Joseph disease, Huntington's disease, and Autosomal Dominant Retinitis Pigmentosa disease.

Embodiment 8: The oligomeric compound of embodiment 6, wherein the single-nucleotide polymorphism is selected from among: rs6446723, rs3856973, rs2285086, rs363092, rs916171, rs6844859, rs7691627, rs4690073, rs2024115, rs11731237, rs362296, rs10015979, rs7659144, rs363096, rs362273, rs16843804, rs362271, rs362275, rs3121419, rs362272, rs3775061, rs34315806, rs363099, rs2298967, rs363088, rs363064, rs363102, rs2798235, rs363080, rs363072, rs363125, rs362303, rs362310, rs10488840, rs362325, rs35892913, rs363102, rs363096, rs11731237, rs10015979, rs363080, rs2798235, rs1936032, rs2276881, rs363070, rs35892913, rs12502045, rs6446723, rs7685686, rs3733217, rs6844859, and rs362331.

Embodiment 9: The oligomeric compound of embodiment 8, wherein the single-nucleotide polymorphism is selected from among: rs7685686, rs362303 rs4690072 and rs363088

Embodiment 10: The oligomeric compound of embodiment 2 or 3, wherein the target nucleic acid and the non-target nucleic acid are transcripts from different genes.

Embodiment 11: The oligomeric compound of any of embodiments 1-10, wherein the 3'-most 5'-region nucleoside comprises a bicyclic sugar moiety.

Embodiment 12: The oligomeric compound of embodiment 11, wherein the 3'-most 5'-region nucleoside comprises a cEt sugar moiety.

Embodiment 13: The oligomeric compound of embodiment 11, wherein the 3'-most 5'-region nucleoside comprises an LNA sugar moiety.

Embodiment 14: The oligomeric compound of any of embodiments 1-13, wherein the central region consists of 6-10 linked nucleosides.

Embodiment 15: The oligomeric compound of any of embodiments 1-14, wherein the central region consists of 6-9 linked nucleosides.

Embodiment 16: The oligomeric compound of embodiment 15, wherein the central region consists of 6 linked nucleosides.

Embodiment 17: The oligomeric compound of embodiment 15, wherein the central region consists of 7 linked nucleosides.

Embodiment 18: The oligomeric compound of embodiment 15, wherein the central region consists of 8 linked nucleosides.

Embodiment 19: The oligomeric compound of embodiment 15, wherein the central region consists of 9 linked nucleosides.

Embodiment 20: The oligomeric compound of any of embodiments 1-19, wherein each central region nucleoside is an unmodified deoxynucleoside.

Embodiment 21: The oligomeric compound of any of embodiments 1-19, wherein at least one central region nucleoside is a modified nucleoside.

Embodiment 22: The oligomeric compound of embodiment 21, wherein one central region nucleoside is a modified nucleoside and each of the other central region nucleosides is an unmodified deoxynucleoside.

Embodiment 23: The oligomeric compound of embodiment 21, wherein two central region nucleosides are modified nucleosides and each of the other central region nucleosides is an unmodified deoxynucleoside.

Embodiment 24: The oligomeric compound of any of embodiments 21-23 wherein at least one modified central region nucleoside is an RNA-like nucleoside.

Embodiment 25: The oligomeric compound of any of embodiments 21-23 comprising at least one modified central region nucleoside comprising a modified sugar moiety.

Embodiment 26: The oligomeric compound of any of embodiments 21-25 comprising at least one modified central region nucleoside comprising a 5'-methyl-2'-deoxy sugar moiety.

Embodiment 27: The oligomeric compound of any of embodiments 21-26 comprising at least one modified central region nucleoside comprising a bicyclic sugar moiety.

Embodiment 28: The oligomeric compound of any of embodiments 21-27 comprising at least one modified central region nucleoside comprising a cEt sugar moiety.

Embodiment 29: The oligomeric compound of any of embodiments 21-28 comprising at least one modified central region nucleoside comprising an LNA sugar moiety.

Embodiment 30: The oligomeric compound of any of embodiments 21-29 comprising at least one modified central region nucleoside comprising an α-LNA sugar moiety.

Embodiment 31: The oligomeric compound of any of embodiments 21-29 comprising at least one modified central region nucleoside comprising a 2'-substituted sugar moiety.

Embodiment 32: The oligomeric compound of embodiment 31 wherein at least one modified central region nucleoside comprises a 2'-substituted sugar moiety comprising a 2' substituent selected from among: halogen, optionally substituted allyl, optionally substituted amino, azido, optionally substituted SH, CN, OCN, $CF_3$, $OCF_3$, O, S, or N(Rm)-alkyl; O, S, or N(Rm)-alkenyl; O, S or N(Rm)-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, $O(CH_2)_2SCH_3$, $O—(CH_2)_2$—O—N(Rm)(Rn) or O—$CH_2$-C(=O)—N(Rm)(Rn), where each Rm and Rn is, independently, H, an amino protecting group or substituted or unsubstituted $C_1$-$C_{10}$ alkyl;

wherein each optionally substituted group is optionally substituted with a substituent group independently selected from among: hydroxyl, amino, alkoxy, carboxy, benzyl, phenyl, nitro ($NO_2$), thiol, thioalkoxy (S-alkyl), halogen, alkyl, aryl, alkenyl and alkynyl.

Embodiment 33: The oligomeric compound of embodiment 32 wherein at least one modified central region nucleoside comprises a 2'-substituted sugar moiety comprising a 2' substituent selected from among: a halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH=$CH_2$, $O(CH_2)_2$—$OCH_3$, $O(CH_2)_2$—$SCH_3$, $O(CH_2)_2$—$OCF_3$, $O(CH_2)_3$—N($R_1$)($R_2$), $O(CH_2)_2$—N($R_1$)($R_2$), $O(CH_2)_2$—O($CH_2)_2$—N($R_1$)($R_2$), $OCH_2$C(=O)—N($R_1$)($R_2$), $OCH_2$C(=O)—N($R_3$)—($CH_2)_2$—N($R_1$)($R_2$), and $O(CH_2)_2$—N($R_3$)—C(=N$R_4$)[N($R_1$)($R_2$)]; wherein $R_1$, $R_2$, $R_3$ and $R_4$ are each, independently, H or $C_1$-$C_6$ alkyl.

Embodiment 34: The oligomeric compound of embodiment 33 wherein the 2' substituent is selected from among: a halogen, $OCH_3$, $OCF_3$, $OCH_2CH_3$, $OCH_2CF_3$, $OCH_2$—CH=$CH_2$, $O(CH_2)_2$—$OCH_3$ (MOE), $O(CH_2)_2$—$O(CH_2)_2$—N($CH_3)_2$, $OCH_2$C(=O)—N(H)$CH_3$, $OCH_2$C(=O)—N(H)—($CH_2)_2$—N($CH_3)_2$, and $OCH_2$—N(H)—C(=NH)$NH_2$.

Embodiment 35: The oligomeric compound of any of embodiments 21-34 comprising at least one modified central region nucleoside comprising a 2'-MOE sugar moiety.

Embodiment 36: The oligomeric compound of any of embodiments 21-35 comprising at least one modified central region nucleoside comprising a 2'-OMe sugar moiety.

Embodiment 37: The oligomeric compound of any of embodiments 21-36 comprising at least one modified central region nucleoside comprising a 2'-F sugar moiety.

Embodiment 38: The oligomeric compound of any of embodiments 21-37 comprising at least one modified central region nucleoside comprising a 2'-(ara)-F sugar moiety.

Embodiment 39: The oligomeric compound of any of embodiments 21-38 comprising at least one modified central region nucleoside comprising a sugar surrogate.

Embodiment 40: The oligomeric compound of embodiment 39 comprising at least one modified central region nucleoside comprising an F-HNA sugar moiety.

Embodiment 41: The oligomeric compound of embodiment 39 or 40 comprising at least one modified central region nucleoside comprising an HNA sugar moiety.

Embodiment 42: The oligomeric compound of any of embodiments 21-41 comprising at least one modified central region nucleoside comprising a modified nucleobase.

Embodiment 43: The oligomeric compound of embodiment 42 comprising at least one modified central region nucleoside comprising a modified nucleobase selected from a 2-thio pyrimidine and a 5-propyne pyrimidine.

Embodiment 44: The oligomeric compound of any of embodiments 21-43, wherein the $2^{nd}$ nucleoside from the 5'-end of the central region is a modified nucleoside.

Embodiment 45: The oligomeric compound of any of embodiments 21-44, wherein the $3^{rd}$ nucleoside from the 5'-end of the central region is a modified nucleoside.

Embodiment 46: The oligomeric compound of any of embodiments 21-45, wherein the $4^{th}$ nucleoside from the 5'-end of the central region is a modified nucleoside.

Embodiment 47: The oligomeric compound of any of embodiments 21-46, wherein the $5^{th}$ nucleoside from the 5'-end of the central region is a modified nucleoside.

Embodiment 48: The oligomeric compound of any of embodiments 21-47, wherein the $6^{th}$ nucleoside from the 5'-end of the central region is a modified nucleoside.

Embodiment 49: The oligomeric compound of any of embodiments 21-48, wherein the $8^{th}$ nucleoside from the 3'-end of the central region is a modified nucleoside.

Embodiment 50: The oligomeric compound of any of embodiments 21-49, wherein the $7^{th}$ nucleoside from the 3'-end of the central region is a modified nucleoside.

Embodiment 51: The oligomeric compound of any of embodiments 21-50, wherein the $6^{th}$ nucleoside from the 3'-end of the central region is a modified nucleoside.

Embodiment 52: The oligomeric compound of any of embodiments 21-51, wherein the $5^{th}$ nucleoside from the 3'-end of the central region is a modified nucleoside.

Embodiment 53: The oligomeric compound of any of embodiments 21-52, wherein the $4^{th}$ nucleoside from the 3'-end of the central region is a modified nucleoside.

Embodiment 54: The oligomeric compound of any of embodiments 21-53, wherein the $3^{rd}$ nucleoside from the 3'-end of the central region is a modified nucleoside.

Embodiment 55: The oligomeric compound of any of embodiments 21-54, wherein the $2^{nd}$ nucleoside from the 3'-end of the central region is a modified nucleoside.

Embodiment 56: The oligomeric compound of any of embodiments 21-55, wherein the modified nucleoside is a 5'-methyl-2'-deoxy sugar moiety.

Embodiment 57: The oligomeric compound of any of embodiments 21-55, wherein the modified nucleoside is a 2-thio pyrimidine.

Embodiment 58: The oligomeric compound of any of embodiments 21-55, wherein the central region comprises no region having more than 4 contiguous unmodified deoxynucleosides.

Embodiment 59: The oligomeric compound of any of embodiments 21-55, wherein the central region comprises no region having more than 5 contiguous unmodified deoxynucleosides.

Embodiment 60: The oligomeric compound of any of embodiments 21-55, wherein the central region comprises no region having more than 6 contiguous unmodified deoxynucleosides.

Embodiment 61: The oligomeric compound of any of embodiments 21-55, wherein the central region comprises no region having more than 7 contiguous unmodified deoxynucleosides.

Embodiment 62: The oligomeric compound of any of embodiments 1-14 or 21-59, wherein the central region has a nucleoside motif selected from among: DDDDDDDDD, DDDDXDDDDD; DDDDDXDDDDD; DDDXDDDDD; DDDDXDDDDDD; DDDDXDDDD; DDXDDDDDD; DDDXDDDDDD; DXDDDDDD; DDXDDDDDDD; DDXDDDDD; DDXDDDDXDDD; DDDXDDDXDDD; DXDDDDXDDD; DDXDDDXDD; DDXDDDDXDDD; DDXDDDDDXDD; DXDDDDXDDD; DDDDDXDDD; DDDXDDD; DXDDDDDDD; DDDDXXDDD; and DXXDXXDXX; wherein
each D is an unmodified deoxynucleoside; and each X is a modified nucleoside.

Embodiment 63: The oligomeric compound of any of embodiments 1-14 or 21-59, wherein the central region has a nucleoside motif selected from among: DDDDDDDDD; DXDDDDDDD; DDXDDDDDD; DDDXDDDDD; DDDDXDDDD; DDDDDXDDD; DDDDDDXDD; DDDDDDDXD; DXXDDDDDD; DDDDDDXXD; DDXXDDDDD; DDDXXDDDD; DDDDXXDDD; DDDDDXXDD; DXDDDDDXD; DXDDDDXDD; DXDDDXDDD; DXDDXDDDD; DXDXDDDDD; DDXDDDDXD; DDXDDDXDD; DDXDDXDDD; DDXDXDDDD; DDDXDDDXD; DDDXDDXDD; DDDXDXDDD; DDDDXDDXD; DDDDXDXDD; and DDDDDXDXD wherein each D is an unmodified deoxynucleoside; and each X is a modified nucleoside.

Embodiment 64: The oligomeric compound of any of embodiments 1-14 or 21-59, wherein the central region has a nucleoside motif selected from among: DDDDXDDDD, DXDDDDDDD, DXXDDDDDD, DDXDDDDDD, DDDXDDDDD, DDDDXDDDD, DDDDDXDDD, DDDDDDXDD, and DDDDDDDXD.

Embodiment 65: The oligomeric compound of any of embodiments 1-14 or 21-59, wherein the central region has a nucleoside motif selected from among: DDDDDDDD, DXDDDDDD, DDXDDDDD, DDDXDDDD, DDDDXDDD, DDDDDXDD, DDDDDDXD, DXDDDDXD, DXDDDXDD, DXDDXDDD, DXDXDDDD, DXXDDDDD, DDXXDDDD, DDXDXDDD, DDXDDXDD, DXDDDDXD, DDDXXDDD, DDDXDXDD, DDDXDDXD, DDDDXXDD, DDDDXDXD, and DDDDDXXD.

Embodiment 66: The oligomeric compound of any of embodiments 1-14 or 21-59, wherein the central region has a nucleoside motif selected from among: DDDDDDD, DXDDDDD, DDXDDDD, DDDXDDD, DDDDXDD, DDDDDXD, DXDDDXD, DXDDXDD, DXDXDDD, DXXDDDD, DDXXDDD, DDXDXDD, DDXDDXD, DDDXXDD, DDDXDXD, and DDDDXXD.

Embodiment 67: The oligomeric compound of any of embodiments 1-14 or 21-59, wherein the central region has a nucleoside motif selected from among: DDDDDD, DXDDDD, DDXDDD, DDDXDD, DDDDXD, DXXDDD, DXDXDD, DXDDXD, DDXXDD, DDXDXD, and DDDXXD.

Embodiment 68: The oligomeric compound of any of embodiments 1-14 or 21-59, wherein the central region has a nucleoside motif selected from among: DDDDDD, DDDDDDD, DDDDDDDD, DDDDDDDDD, DXDDDD, DDXDDD, DDDXDD, DDDDXD, DXDDDDD, DDXDDDD, DDDXDDD, DDDDXDD, DDDDDXD, DXDDDDDD, DDXDDDDD, DDDXDDDD, DDDDXDDD, DDDDDXDD, DDDDDDXD, DXDDDDDDD, DDXDDDDDD, DDDXDDDDD, DDDDXDDDD, DDDDDXDDD, DDDDDDXDD, DDDDDDDXD, DXDDDDDDDD, DDXDDDDDDD, DDDXDDDDDD, DDDDXDDDDD, DDDDDXDDDD, DDDDDDXDDD, DDDDDDDXDD, and DDDDDDDDXD.

Embodiment 69: The oligomeric compound of embodiments 62-68, wherein each X comprises a modified nucleobase.

Embodiment 70: The oligomeric compound of embodiments 62-68, wherein each X comprises a modified sugar moiety.

Embodiment 71: The oligomeric compound of embodiments 62-68, wherein each X comprises 2-thio-thymidine.

Embodiment 72: The oligomeric compound of embodiments 62-68, wherein each X nucleoside comprises an F-HNA sugar moiety.

Embodiment 73: The oligomeric compound of embodiments 62-68, wherein the nucleobase sequence of the target region of the target nucleic acid differs from the nucleobase sequence of at least one non-target nucleic acid by a single differentiating nucleobase, and wherein the location of the single differentiating nucleobase is represented by X.

Embodiment 74: The oligomeric compound of embodiment 73, wherein the target nucleic acid and the non-target nucleic acid are alleles of the same gene.

Embodiment 75: The oligomeric compound of embodiment 73, wherein the single differentiating nucleobase is a single-nucleotide polymorphism.

Embodiment 76: The oligomeric compound of any of embodiments 1-75, wherein the 5' region consists of 2 linked 5'-region nucleosides.

Embodiment 77: The oligomeric compound of any of embodiments 1-75, wherein the 5' region consists of 3 linked 5'-region nucleosides.

Embodiment 78: The oligomeric compound of any of embodiments 1-75, wherein the 5' region consists of 4 linked 5'-region nucleosides.

Embodiment 79: The oligomeric compound of any of embodiments 1-75, wherein the 5' region consists of 5 linked 5'-region nucleosides.

Embodiment 80: The oligomeric compound of any of embodiments 1-75, wherein the 5' region consists of 6 linked 5'-region nucleosides.

Embodiment 81: The oligomeric compound of any of embodiments 1-80, wherein at least one 5'-region nucleoside is an unmodified deoxynucleoside.

Embodiment 82: The oligomeric compound of any of embodiments 1-80, wherein each 5'-region nucleoside is a modified nucleoside.

Embodiment 83: The oligomeric compound of any of embodiments 1-80 wherein at least one 5'-region nucleoside is an RNA-like nucleoside.

Embodiment 84: The oligomeric compound of any of embodiments 1-80 wherein each 5'-region nucleoside is an RNA-like nucleoside.

Embodiment 85: The oligomeric compound of any of embodiments 1-80 comprising at least one modified 5'-region nucleoside comprising a modified sugar.

Embodiment 86: The oligomeric compound of embodiment 80 comprising at least one modified 5'-region nucleoside comprising a bicyclic sugar moiety.

Embodiment 87: The oligomeric compound of embodiment 86 comprising at least one modified 5'-region nucleoside comprising a cEt sugar moiety.

Embodiment 88: The oligomeric compound of embodiment 85 or 86 comprising at least one modified 5'-region nucleoside comprising an LNA sugar moiety.

Embodiment 89: The oligomeric compound of any of embodiments 76-80 comprising of at least one modified 5'-region nucleoside comprising a 2'-substituted sugar moiety.

Embodiment 90: The oligomeric compound of embodiment 89 wherein at least one modified central region nucleoside comprises a 2'-substituted sugar moiety comprising a 2' substituent selected from among: halogen, optionally substituted allyl, optionally substituted amino, azido, optionally substituted SH, CN, OCN, $CF_3$, $OCF_3$, O, S, or $N(R_m)$-alkyl; O, S, or $N(R_m)$-alkenyl; O, S or $N(R_m)$-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, $O(CH_2)_2SCH_3$, $O-(CH_2)_2-O-N(R_m)(R_n)$ or $O-CH_2-C(=O)-N(R_m)(R_n)$, where each $R_m$ and is, independently, H, an amino protecting group or substituted or unsubstituted $C_1-C_{10}$ alkyl;
wherein each optionally substituted group is optionally substituted with a substituent group independently selected from among: hydroxyl, amino, alkoxy, carboxy, benzyl, phenyl, nitro ($NO_2$), thiol, thioalkoxy (S-alkyl), halogen, alkyl, aryl, alkenyl and alkynyl.

Embodiment 91: The oligomeric compound of embodiment 90 wherein at least one modified 5'-region nucleoside comprises a 2'-substituted sugar moiety comprising a 2'-substituent selected from among: a halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2-CH=CH_2$, $O(CH_2)_2-OCH_3$ (MOE), $O(CH_2)_2-SCH_3$, $O(CH_2)_2-OCF_3$, $O(CH_2)_3-N(R_1)(R_2)$, $O(CH_2)_2-ON(R_1)(R_2)$, $O(CH_2)_2-O(CH_2)_2-N(R_1)(R_2)$, $OCH_2C(=O)-N(R_1)(R_2)$, $OCH_2C(=O)-N(R_3)-(CH_2)_2-N(R_1)(R_2)$, and $O(CH_2)_2-N(R_3)-C(=NR_4)[N(R_1)(R_2)]$; wherein $R_1$, $R_2$, $R_3$ and $R_4$ are each, independently, H or $C_1-C_6$ alkyl.

Embodiment 92: The oligomeric compound of embodiment 91, wherein the 2'-substituent is selected from among: a halogen, $OCH_3$, $OCF_3$, $OCH_2CH_3$, $OCH_2CF_3$, $OCH_2-CH=CH_2$, $O(CH_2)_2-OCH_3$, $O(CH_2)_2-O(CH_2)_2-N(CH_3)_2$, $OCH_2C(=O)-N(H)CH_3$, $OCH_2C(=O)-N(H)-(CH_2)_2-N(CH_3)_2$, and $OCH_2-N(H)-C(=NH)NH_2$.

Embodiment 93: The oligomeric compound of any of embodiments 89-92 comprising at least one modified 5'-region nucleoside comprising a 2'-MOE sugar moiety.

Embodiment 94: The oligomeric compound of any of embodiments 89-92 comprising at least one modified 5'-region nucleoside comprising a 2'-OMe sugar moiety.

Embodiment 95: The oligomeric compound of any of embodiments 89-92 comprising at least one modified 5'-region nucleoside comprising a 2'-F sugar moiety.

Embodiment 96: The oligomeric compound of any of embodiments 89-92 comprising at least one modified 5'-region nucleoside comprising a 2'-(ara)-F sugar moiety.

Embodiment 97: The oligomeric compound of any of embodiments 82-96 comprising of at least one modified 5'-region nucleoside comprising a sugar surrogate.

Embodiment 98: The oligomeric compound of embodiment 97 comprising at least one modified 5'-region nucleoside comprising an F-HNA sugar moiety.

Embodiment 99: The oligomeric compound of embodiment 97 or 98 comprising at least one modified 5'-region nucleoside comprising an HNA sugar moiety.

Embodiment 100: The oligomeric compound of any of embodiments 1-99 comprising at least one modified 5'-region nucleoside comprising a modified nucleobase.

Embodiment 101: The oligomeric compound of embodiment 100, wherein the modified nucleoside comprises 2-thio-thymidine.

Embodiment 102: The oligomeric compound of any of embodiments 1-101, wherein the 5'-region has a motif selected from among:
ADDA; ABDAA; ABBA; ABB; ABAA; AABAA; AAABAA; AAAABAA; AAAAABAA; AAABAA; AABAA; ABAB; ABADB; ABADDB; AAABB; AAAAA; ABBDC; ABDDC; ABBDCC; ABBDDC; ABBDCC; ABBC; AA; AAA; AAAA; AAAAB; AAAAAAA; AAAAAAAA; ABBB; AB; ABAB; AAAAB; AABBB; AAAAB; and AABBBB,
wherein each A is a modified nucleoside of a first type, each B is a modified nucleoside of a second type, each C is a modified nucleoside of a third type, and each D is an unmodified deoxynucleoside.

Embodiment 103: The oligomeric compound of any of embodiments 1-101, wherein the 5'-region has a motif selected from among:
AB, ABB, AAA, BBB, BBBAA, AAB, BAA, BBAA, AABB, AAAB, ABBW, ABBWW, ABBB, ABBBB, ABAB, ABABAB, ABABBB, ABABAA, AAABB, AAAABB, AABB, AAAAB, AABBB, ABBBB, BBBBB, AAABW, AAAAA, BBBBAA, and AAABW wherein each A is a modified nucleoside of a first type, each B is a modified nucleoside of a second type, and each W is a modified nucleoside of a third type.

Embodiment 104: The oligomeric compound of any of embodiments 1-101, wherein the 5'-region has a motif selected from among: ABB; ABAA; AABAA; AAABAA; ABAB; ABADB; AAABB; AAAAA; AA; AAA; AAAA; AAAAB; ABBB; AB; and ABAB, wherein each A is a modified nucleoside of a first type, each B is a modified nucleoside of a second type, and each W is a modified nucleoside of a third type.

Embodiment 105: The oligomeric compound of embodiments 102-104, wherein each A nucleoside comprises a 2'-substituted sugar moiety.

Embodiment 106: The oligomeric compound of embodiment 105 wherein at least one central region nucleoside comprises a 2'-substituted sugar moiety comprising a 2' substituent selected from among: halogen, optionally substituted allyl, optionally substituted amino, azido, optionally substituted SH, CN, OCN, $CF_3$, $OCF_3$, O, S, or $N(R_m)$-alkyl; O, S, or $N(R_m)$-alkenyl; O, S or $N(R_m)$-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, $O(CH_2)_2SCH_3$, $O—(CH_2)_2—O—N(R_m)(R_n)$ or $O—CH_2—C(=O)—N(R_m)(R_n)$, where each $R_m$ and $R_n$ is, independently, H, an amino protecting group or substituted or unsubstituted $C_1$-$C_{10}$ alkyl; wherein each optionally substituted group is optionally substituted with a substituent group independently selected from among: hydroxyl, amino, alkoxy, carboxy, benzyl, phenyl, nitro ($NO_2$), thiol, thioalkoxy (S-alkyl), halogen, alkyl, aryl, alkenyl and alkynyl.

Embodiment 107: The oligomeric compound of embodiment 102-106, wherein each A nucleoside comprises a 2'-substituted sugar moiety comprising a 2'-substituent selected from among: a halogen, $OCH_3$, $OCF_3$, $OCH_2CH_3$, $OCH_2CF_3$, $OCH_2—CH—CH_2$, $O(CH_2)_2—OCH_3$, $O(CH_2)_2—O(CH_2)_2—N(CH_3)_2$, $OCH_2C(=O)—N(H)CH_3$, $OCH_2C(=O)—N(H)—(CH_2)_2—N(CH_3)_2$, and $OCH_2—N(H)—C(=NH)NH_2$.

Embodiment 108: The oligomeric compound of embodiment 107, wherein each A nucleoside comprises a 2'-substituted sugar moiety comprising a 2'-substituent selected from among: F, $OCH_3$, $O(CH_2)_2—OCH_3$.

Embodiment 109: The oligomeric compound of embodiments 102-106, wherein each A nucleoside comprises a bicyclic sugar moiety.

Embodiment 110: The oligomeric compound of embodiment 109, wherein each A nucleoside comprises a bicyclic sugar moiety selected from among: cEt, cMOE, LNA, α-LNA, ENA and 2'-thio LNA.

Embodiment 111: The oligomeric compound of any of embodiments 102-110, wherein each A comprises a modified nucleobase.

Embodiment 112: The oligomeric compound of embodiment 111, wherein each A comprises a modified nucleobase selected from among a 2-thio pyrimidine and a 5-propyne pyrimidine.

Embodiment 113: The oligomeric compound of embodiment 112, wherein each A comprises 2-thio-thymidine.

Embodiment 114: The oligomeric compound of embodiment 102-106, wherein each A nucleoside comprises an unmodified 2'-deoxyfuranose sugar moiety.

Embodiment 115: The oligomeric compound of embodiment 102-106, wherein each A nucleoside comprises an F-HNA sugar moiety.

Embodiment 116: The oligomeric compound of any of embodiments 102-115, wherein each B nucleoside comprises a 2'-substituted sugar moiety.

Embodiment 117: The oligomeric compound of embodiment 116, wherein at least one central region nucleoside comprises a 2'-substituted sugar moiety comprising a 2' substituent selected from among: halogen, optionally substituted allyl, optionally substituted amino, azido, optionally substituted SH, CN, OCN, $CF_3$, $OCF_3$, O, S, or $N(R_m)$-alkyl; O, S, or $N(R_m)$- alkenyl; O, S or N($R_m$)-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, O($CH_2$)$_2$S$CH_3$, O—($CH_2$)$_2$—O—N($R_m$)($R_n$) or O—$CH_2$—C(=O)—N($R_m$)($R_n$), where each $R_m$ and $R_n$ is, independently, H, an amino protecting group or substituted or unsubstituted $C_1$-$C_{10}$ alkyl; wherein each optionally substituted group is optionally substituted with a substituent group independently selected from among: hydroxyl, amino, alkoxy, carboxy, benzyl, phenyl, nitro (N$O_2$), thiol, thioalkoxy (S-alkyl), halogen, alkyl, aryl, alkenyl and alkynyl.

Embodiment 118: The oligomeric compound of embodiment 117, wherein each B nucleoside comprises a 2'-substituted sugar moiety comprising a 2'-substituent selected from among: a halogen, O$CH_3$, OC$F_3$, O$CH_2$C$H_3$, O$CH_2$C$F_3$, O$CH_2$—CH—$CH_2$, O($CH_2$)$_2$—O$CH_3$, O($CH_2$)$_2$—O($CH_2$)$_2$—N($CH_3$)$_2$, O$CH_2$C(=O)—N(H)$CH_3$, O$CH_2$C(=O)—N(H)—($CH_2$)$_2$—N($CH_3$)$_2$, and O$CH_2$—N(H)—C(=NH)N$H_2$.

Embodiment 119: The oligomeric compound of embodiment 118, wherein each B nucleoside comprises a 2'-substituted sugar moiety comprising a 2'-substituent selected from among: F, O$CH_3$, O($CH_2$)$_2$—O$CH_3$.

Embodiment 120: The oligomeric compound of any of embodiments 102-115, wherein each B nucleoside comprises a bicyclic sugar moiety.

Embodiment 121: The oligomeric compound of embodiment 120, wherein each B nucleoside comprises a bicyclic sugar moiety selected from among: cEt, cMOE, LNA, α-LNA, ENA and 2'-thio LNA.

Embodiment 122: The oligomeric compound of any of embodiments 102-115, wherein each B comprises a modified nucleobase.

Embodiment 123: The oligomeric compound of embodiment 122, wherein each B comprises a modified nucleobase selected from among a 2-thio pyrimidine and a 5-propyne pyrimidine.

Embodiment 124: The oligomeric compound of embodiment 123, wherein each B comprises 2-thio-thymidine.

Embodiment 125: The oligomeric compound of embodiment 102-106, wherein each B nucleoside comprises an unmodified 2'-deoxyfuranose sugar moiety.

Embodiment 126: The oligomeric compound of embodiment 102-115, wherein each B nucleoside comprises an F-HNA sugar moiety.

Embodiment 127: The oligomeric compound of any of embodiments 102-126, wherein each C nucleoside comprises a 2'-substituted sugar moiety.

Embodiment 128: The oligomeric compound of embodiment 127, wherein at least one central region nucleoside comprises a 2'-substituted sugar moiety comprising a 2' substituent selected from among: halogen, optionally substituted allyl, optionally substituted amino, azido, optionally substituted SH, CN, OCN, C$F_3$, OC$F_3$, O, S, or N($R_m$)-alkyl; O, S, or N($R_m$)-alkenyl; O, S or N($R_m$)-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, O($CH_2$)$_2$S$CH_3$, O—($CH_2$)$_2$—O—N($R_m$)($R_n$) or O—$CH_2$—C(=O)—N($R_m$)($R_n$), where each $R_m$ and $R_n$ is, independently, H, an amino protecting group or substituted or unsubstituted $C_1$-$C_{10}$ alkyl; wherein each optionally substituted group is optionally substituted with a substituent group independently selected from among: hydroxyl, amino, alkoxy, carboxy, benzyl, phenyl, nitro (N$O_2$), thiol, thioalkoxy (S-alkyl), halogen, alkyl, aryl, alkenyl and alkynyl.

Embodiment 129: The oligomeric compound of embodiment 128, wherein each C nucleoside comprises a 2'-substituted sugar moiety comprising a 2'-substituent selected from among: a halogen, O$CH_3$, OC$F_3$, O$CH_2$C$H_3$, O$CH_2$C$F_3$, O$CH_2$—CH—$CH_2$, O($CH_2$)$_2$—O$CH_3$, O($CH_2$)$_2$—O($CH_2$)$_2$—N($CH_3$)$_2$, O$CH_2$C(=O)—N(H)$CH_3$, O$CH_2$C(=O)—N(H)—($CH_2$)$_2$—N($CH_3$)$_2$, and O$CH_2$—N(H)—C(=NH)N$H_2$.

Embodiment 130: The oligomeric compound of embodiment 129, wherein each C nucleoside comprises a 2'-substituted sugar moiety comprising a 2'-substituent selected from among: F, O$CH_3$, O($CH_2$)$_2$—O$CH_3$.

Embodiment 131: The oligomeric compound of any of embodiments 102-126, wherein each C nucleoside comprises a bicyclic sugar moiety.

Embodiment 132: The oligomeric compound of embodiment 131, wherein each C nucleoside comprises a bicyclic sugar moiety selected from among: cEt, cMOE, LNA, α-LNA, ENA and 2'-thio LNA.

Embodiment 133: The oligomeric compound of any of embodiments 102-126, wherein each C comprises a modified nucleobase.

Embodiment 134: The oligomeric compound of embodiment 133, wherein each C comprises a modified nucleobase selected from among a 2-thio pyrimidine and a 5-propyne pyrimidine.

Embodiment 135: The oligomeric compound of embodiment 134, wherein each C comprises 2-thio-thymidine.

Embodiment 136: The oligomeric compound of embodiment 102-126, wherein each C comprises an F-HNA sugar moiety.

Embodiment 137: The oligomeric compound of embodiment 102-126, wherein each C nucleoside comprises an unmodified 2'-deoxyfuranose sugar moiety.

Embodiment 138: The oligomeric compound of any of embodiments 102-138, wherein each W nucleoside comprises a 2'-substituted sugar moiety.

Embodiment 139: The oligomeric compound of embodiment 138, wherein at least one central region nucleoside comprises a 2'-substituted sugar moiety comprising a 2' substituent selected from among: halogen, optionally substituted allyl, optionally substituted amino, azido, optionally substituted SH, CN, OCN, C$F_3$, OC$F_3$, O, S, or N($R_m$)-alkyl; O, S, or N($R_m$)-alkenyl; O, S or N($R_m$)-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, O($CH_2$)$_2$S$CH_3$, O—($CH_2$)$_2$—O—N($R_m$)($R_n$) or O—$CH_2$—C(=O)—N($R_m$)($R_n$), where each $R_m$ and $R_n$ is, independently, H, an amino protecting group or substituted or unsubstituted $C_1$-$C_{10}$ alkyl; wherein each optionally substituted group is optionally substituted with a substituent group independently selected from among: hydroxyl, amino, alkoxy, carboxy, benzyl, phenyl, nitro (N$O_2$), thiol, thioalkoxy (S-alkyl), halogen, alkyl, aryl, alkenyl and alkynyl.

Embodiment 140: The oligomeric compound of embodiment 139, wherein each W nucleoside comprises a 2'-substituted sugar moiety comprising a 2'-substituent selected from among: a halogen, O$CH_3$, OC$F_3$, OCH$_2$CH$_3$, OCH$_2$CF$_3$, OCH$_2$—CH=CH$_2$, O(CH$_2$)$_2$—OCH$_3$, O(CH$_2$)$_2$—O(CH$_2$)$_2$—N(CH$_3$)$_2$, OCH$_2$C(=O)—N(H)CH$_3$, OCH$_2$C(=O)—N(H)—(CH$_2$)$_2$—N(CH$_3$)$_2$, and OCH$_2$—N(H)—C(=NH)NH$_2$.

Embodiment 141: The oligomeric compound of embodiment 139, wherein each W nucleoside comprises a 2'-substituted sugar moiety comprising a 2'-substituent selected from among: F, OCH$_3$, O(CH$_2$)$_2$—OCH$_3$.

Embodiment 142: The oligomeric compound of any of embodiments 102-137, wherein each W nucleoside comprises a bicyclic sugar moiety.

Embodiment 143: The oligomeric compound of embodiment 142, wherein each W nucleoside comprises a bicyclic sugar moiety selected from among: cEt, cMOE, LNA, α-LNA, ENA and 2'-thio LNA.

Embodiment 144: The oligomeric compound of any of embodiments 102-137, wherein each W comprises a modified nucleobase.

Embodiment 145: The oligomeric compound of embodiment 144, wherein each W comprises a modified nucleobase selected from among a 2-thio pyrimidine and a 5-propyne pyrimidine.

Embodiment 146: The oligomeric compound of embodiment 145, wherein each W comprises 2-thio-thymidine.

Embodiment 147: The oligomeric compound of embodiment 102-137, wherein each W comprises an F-HNA sugar moiety.

Embodiment 148: The oligomeric compound of embodiment 102-137, wherein each W nucleoside comprises an unmodified 2'-deoxyfuranose sugar moiety.

Embodiment 149: The oligomeric compound of any of embodiments 1-148, wherein the 3' region consists of 2 linked 3'-region nucleosides.

Embodiment 150: The oligomeric compound of any of embodiments 1-148, wherein the 3' region consists of 3 linked 3'-region nucleosides.

Embodiment 151: The oligomeric compound of any of embodiments 1-148, wherein the 3' region consists of 4 linked 3'-region nucleosides.

Embodiment 152: The oligomeric compound of any of embodiments 1-148, wherein the 3' region consists of 5 linked 3'-region nucleosides.

Embodiment 153: The oligomeric compound of any of embodiments 1-148, wherein the 3' region consists of 6 linked 3'-region nucleosides.

Embodiment 154: The oligomeric compound of any of embodiments 1-153, wherein at least one 3'-region nucleoside is an unmodified deoxynucleoside.

Embodiment 155: The oligomeric compound of any of embodiments 1-154, wherein each 3'-region nucleoside is a modified nucleoside.

Embodiment 156: The oligomeric compound of any of embodiments 1-153, wherein at least one 3'-region nucleoside is an RNA-like nucleoside.

Embodiment 157: The oligomeric compound of any of embodiments 1-154, wherein each 3'-region nucleoside is an RNA-like nucleoside.

Embodiment 158: The oligomeric compound of any of embodiments 1-153, comprising at least one modified 3'-region nucleoside comprising a modified sugar.

Embodiment 159: The oligomeric compound of embodiment 158, comprising at least one modified 3'-region nucleoside comprising a bicyclic sugar moiety.

Embodiment 160: The oligomeric compound of embodiment 159, comprising at least one modified 3'-region nucleoside comprising a cEt sugar moiety.

Embodiment 161: The oligomeric compound of embodiment 159, comprising at least one modified 3'-region nucleoside comprising an LNA sugar moiety.

Embodiment 162: The oligomeric compound of any of embodiments 1-162 comprising of at least one modified 3'-region nucleoside comprising a 2'-substituted sugar moiety.

Embodiment 163: The oligomeric compound of embodiment 162, wherein at least one central region nucleoside comprises a 2'-substituted sugar moiety comprising a 2' substituent selected from among: halogen, optionally substituted allyl, optionally substituted amino, azido, optionally substituted SH, CN, OCN, CF$_3$, OCF$_3$, O, S, or N(R$_m$)-alkyl; O, S, or N(R$_m$)-alkenyl; O, S or N(R$_m$)-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl; wherein each optionally substituted group is optionally substituted with a substituent group independently selected from among: hydroxyl, amino, alkoxy, carboxy, benzyl, phenyl, nitro (NO$_2$), thiol, thioalkoxy (S-alkyl), halogen, alkyl, aryl, alkenyl and alkynyl.

Embodiment 164: The oligomeric compound of embodiment 163 wherein at least one modified 3'-region nucleoside comprises a 2'-substituted sugar moiety comprising a 2'-substituent selected from among: a halogen, OCH$_3$, OCH$_2$F, OCHF$_2$, OCF$_3$, OCH$_2$CH$_3$, O(CH$_2$)$_2$F, OCH$_2$CHF$_2$, OCH$_2$CF$_3$, OCH$_2$—CH=CH$_2$, O(CH$_2$)$_2$—OCH$_3$ (MOE), O(CH$_2$)$_2$—SCH$_3$, O(CH$_2$)$_2$—OCF$_3$, O(CH$_2$)$_3$—N(R$_1$)(R$_2$), O(CH$_2$)$_2$—ON(R$_1$)(R$_2$), O(CH$_2$)$_2$—O(CH$_2$)$_2$—N(R$_1$)(R$_2$), OCH$_2$C(=O)—N(R$_1$)(R$_2$), OCH$_2$C(=O)—N(R$_3$)—(CH$_2$)$_2$—N(R$_1$)(R$_2$), and O(CH$_2$)$_2$—N(R$_3$)—C(=NR$_4$[N(R$_1$)(R$_2$)]; wherein R$_1$, R$_2$, R$_3$ and R$_4$ are each, independently, H or C$_1$-C$_6$ alkyl.

Embodiment 165: The oligomeric compound of embodiment 164, wherein the 2'-substituent is selected from among: a halogen, OCH$_3$, OCF$_3$, OCH$_2$CH$_3$, OCH$_2$CF$_3$, OCH$_2$—CH=CH$_2$, O(CH$_2$)$_2$—OCH$_3$, O(CH$_2$)$_2$—O(CH$_2$)$_2$—N(CH$_3$)$_2$, OCH$_2$C(=O)—N(H)CH$_3$, OCH$_2$C(=O)—N(H)—(CH$_2$)$_2$—N(CH$_3$)$_2$, and OCH$_2$—N(H)—C(=NH)NH$_2$.

Embodiment 166: The oligomeric compound of any of embodiments 162-165 comprising at least one modified 3'-region nucleoside comprising a 2'-MOE sugar moiety.

Embodiment 167: The oligomeric compound of any of embodiments 162-166 comprising at least one modified 3'-region nucleoside comprising a 2'-OMe sugar moiety.

Embodiment 168: The oligomeric compound of any of embodiments 162-167 comprising at least one modified 3'-region nucleoside comprising a 2'-F sugar moiety.

Embodiment 169: The oligomeric compound of any of embodiments 162-168 comprising at least one modified 3'-region nucleoside comprising a 2'-(ara)-F sugar moiety.

Embodiment 170: The oligomeric compound of any of embodiments 162-169 comprising of at least one modified 3'-region nucleoside comprising a sugar surrogate.

Embodiment 171: The oligomeric compound of embodiment 170 comprising at least one modified 3'-region nucleoside comprising an F-HNA sugar moiety.

Embodiment 172: The oligomeric compound of embodiment 170 comprising at least one modified 3'-region nucleoside comprising an HNA sugar moiety.

Embodiment 173: The oligomeric compound of any of embodiments 1-172 comprising at least one modified 3'-region nucleoside comprising a modified nucleobase.

Embodiment 174: The oligomeric compound of any of embodiments 1-173, wherein each A comprises a 2'-substituted sugar moiety comprising a 2'-substituent selected from among: F, $OCH_3$, $O(CH_2)_2$—$OCH_3$, and each B comprises a bicylic sugar moiety selected from among: LNA and cEt.

Embodiment 175: The oligomeric compound of embodiment 174, wherein each A comprises $O(CH_2)_2$—$OCH_3$ and each B comprises cEt.

Embodiment 176: The oligomeric compound of any of embodiments 1-175, wherein the 3'-region has a motif selected from among: ABB, ABAA, AAABAA, AAAAABAA, AABAA, AAAABAA, AAABAA, ABAB, AAAAA, AAABB, AAAAAAAA, AAAAAAA, AAAAAA, AAAAB, AAAA, AAA, AA, AB, ABBB, ABAB, AABBB, wherein each A is a modified nucleoside of a first type, each B is a modified nucleoside of a second type.

Embodiment 177: The oligomeric compound of embodiments 1-175, wherein the 3'-region has a motif selected from among: ABB; AAABAA; AABAA; AAAABAA; AAAAA; AAABB; AAAAAAAA; AAAAAAA; AAAAAA; AAAAB; AB; ABBB; and ABAB, wherein each A is a modified nucleoside of a first type, each B is a modified nucleoside of a second type.

Embodiment 178: The oligomeric compound of embodiments 1-175, wherein the 3'-region has a motif selected from among: BBA, AAB, AAA, BBB, BBAA, AABB, WBBA, WAAB, BBBA, BBBBA, BBBB, BBBBBA, ABBBBB, BBAAA, AABBB, BBBAA, BBBBA, BBBBB, BABA, AAAAA, BBAAAA, AABBBB, BAAAA, and ABBBBB, wherein each A is a modified nucleoside of a first type, each B is a modified nucleoside of a second type, and each W is a modified nucleoside of a first type, a second type, or a third type.

Embodiment 179: The oligomeric compound of embodiments 176-178, wherein each A nucleoside comprises a 2'-substituted sugar moiety.

Embodiment 180: The oligomeric compound of embodiments 176-178, wherein at least one central region nucleoside comprises a 2'-substituted sugar moiety comprising a 2' substituent selected from among: halogen, optionally substituted allyl, optionally substituted amino, azido, optionally substituted SH, CN, OCN, $CF_3$, $OCF_3$, O, S, or $N(R_m)$-alkyl; O, S, or $N(R_m)$-alkenyl; O, S or $N(R_m)$-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, $O(CH_2)_2SCH_3$, O—$(CH_2)_2$—O—$N(R_m)(R_n)$ or O—$CH_2$—C(=O)—$N(R_m)(R_n)$, where each $R_m$ and R is, independently, H, an amino protecting group or substituted or unsubstituted $C_1$-$C_{10}$ alkyl;

wherein each optionally substituted group is optionally substituted with a substituent group independently selected from among: hydroxyl, amino, alkoxy, carboxy, benzyl, phenyl, nitro ($NO_2$), thiol, thioalkoxy (S-alkyl), halogen, alkyl, aryl, alkenyl and alkynyl.

Embodiment 181: The oligomeric compound of embodiment 180, wherein each A nucleoside comprises a 2'-substituted sugar moiety comprising a 2'-substituent selected from among: a halogen, $OCH_3$, $OCF_3$, $OCH_2CH_3$, $OCH_2CF_3$, $OCH_2$—CH—$CH_2$, $O(CH_2)_2$—$OCH_3$, $O(CH_2)_2$—$O(CH_2)_2$—$N(CH_3)_2$, $OCH_2C$(=O)—$N(H)CH_3$, $OCH_2C$(=O)—N(H)—$(CH_2)_2$—N$(CH_3)_2$, and $OCH_2$—N(H)—C(=NH)$NH_2$.

Embodiment 182: The oligomeric compound of embodiment 181, wherein each A nucleoside comprises a 2'-substituted sugar moiety comprising a 2'-substituent selected from among: F, $OCH_3$, $O(CH_2)_2$—$OCH_3$.

Embodiment 183: The oligomeric compound of embodiments 176-178, wherein each A nucleoside comprises a bicyclic sugar moiety.

Embodiment 184: The oligomeric compound of embodiment 183, wherein each A nucleoside comprises a bicyclic sugar moiety selected from among: cEt, cMOE, LNA, α-LNA, ENA and 2'-thio LNA.

Embodiment 185: The oligomeric compound of any of embodiments 176-178, wherein each B nucleoside comprises a 2'-substituted sugar moiety.

Embodiment 186: The oligomeric compound of embodiment 185, wherein at least one modified central region nucleoside comprises a 2'-substituted sugar moiety comprising a 2' substituent selected from among: halogen, optionally substituted allyl, optionally substituted amino, azido, optionally substituted SH, CN, OCN, $CF_3$, $OCF_3$, O, S, or $N(R_m)$-alkyl; O, S, or $N(R_m)$-alkenyl; O, S or $N(R_m)$-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, $O(CH_2)_2SCH_3$, O—$(CH_2)_2$—O—$N(R_m)(R_n)$ or O—$CH_2$—C(=O)—$N(R_m)(R_n)$, where each $R_m$ and is, independently, H, an amino protecting group or substituted or unsubstituted $C_1$-$C_{10}$ alkyl;

wherein each optionally substituted group is optionally substituted with a substituent group independently selected from among: hydroxyl, amino, alkoxy, carboxy, benzyl, phenyl, nitro ($NO_2$), thiol, thioalkoxy (S-alkyl), halogen, alkyl, aryl, alkenyl and alkynyl.

Embodiment 187: The oligomeric compound of embodiment 185, wherein each B nucleoside comprises a 2'-substituted sugar moiety comprising a 2'-substituent selected from among: a halogen, $OCH_3$, $OCF_3$, $OCH_2CH_3$, $OCH_2CF_3$, $OCH_2$—CH—$CH_2$, $O(CH_2)_2$—$OCH_3$, $O(CH_2)_2$—$O(CH_2)_2$—$N(CH_3)_2$, $OCH_2C$(=O)—$N(H)CH_3$, $OCH_2C$(=O)—N(H)—$(CH_2)_2$—N$(CH_3)_2$, and $OCH_2$—N(H)—C(=NH)$NH_2$.

Embodiment 188: The oligomeric compound of embodiment 187, wherein each B nucleoside comprises a 2'-substituted sugar moiety comprising a 2'-substituent selected from among: F, $OCH_3$, $O(CH_2)_2$—$OCH_3$.

Embodiment 189: The oligomeric compound of any of embodiments 176-178, wherein each B nucleoside comprises a bicyclic sugar moiety.

Embodiment 190: The oligomeric compound of embodiment 189, wherein each B nucleoside comprises a bicyclic sugar moiety selected from among: cEt, cMOE, LNA, α-LNA, ENA and 2'-thio LNA.

Embodiment 191: The oligomeric compound of any of embodiments 176-190, wherein each A comprises a 2'-substituted sugar moiety comprising a 2'-substituent selected from among: F, OCH₃, O(CH₂)₂—OCH₃, and each B comprises a bicylic sugar moiety selected from among: LNA and cEt.

Embodiment 192: The oligomeric compound of embodiment 191, wherein each A comprises O(CH₂)₂—OCH₃ and each B comprises cEt.

Embodiment 193: The oligomeric compound of any of embodiments 176-192, wherein each W nucleoside comprises a 2'-substituted sugar moiety.

Embodiment 194: The oligomeric compound of embodiment 193, wherein at least one central region nucleoside comprises a 2'-substituted sugar moiety comprising a 2' substituent selected from among: halogen, optionally substituted allyl, optionally substituted amino, azido, optionally substituted SH, CN, OCN, CF₃, OCF₃, O, S, or N($R_m$)-alkyl; O, S, or N($R_m$)-alkenyl; O, S or N($R_m$)-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, O(CH₂)₂SCH₃, O—(CH₂)₂—O—N($R_m$)($R_n$) or O—CH₂—C(=O)—N($R_m$)($R_n$), where each $R_m$ and $R_n$ is, independently, H, an amino protecting group or substituted or unsubstituted $C_1$-$C_{10}$ alkyl; wherein each optionally substituted group is optionally substituted with a substituent group independently selected from among: hydroxyl, amino, alkoxy, carboxy, benzyl, phenyl, nitro (NO₂), thiol, thioalkoxy (S-alkyl), halogen, alkyl, aryl, alkenyl and alkynyl.

Embodiment 195: The oligomeric compound of embodiment 193, wherein each W nucleoside comprises a 2'-substituted sugar moiety comprising a 2'-substituent selected from among: a halogen, OCH₃, OCF₃, OCH₂CH₃, OCH₂CF₃, OCH₂—CH—CH₂, O(CH₂)₂—OCH₃, O(CH₂)₂—O(CH₂)₂—N(CH₃)₂, OCH₂C(=O)—N(H)CH₃, OCH₂C(=O)—N(H)—(CH₂)₂—N(CH₃)₂, and OCH₂—N(H)—C(=NH)NH₂.

Embodiment 196: The oligomeric compound of embodiment 195, wherein each W nucleoside comprises a 2'-substituted sugar moiety comprising a 2'-substituent selected from among: F, OCH₃, O(CH₂)₂—OCH₃.

Embodiment 197: The oligomeric compound of any of embodiments 176-192, wherein each W nucleoside comprises a bicyclic sugar moiety.

Embodiment 198: The oligomeric compound of embodiment 197, wherein each W nucleoside comprises a bicyclic sugar moiety selected from among: cEt, cMOE, LNA, α-LNA, ENA and 2'-thio LNA.

Embodiment 199: The oligomeric compound of any of embodiments 176-192, wherein each W comprises a modified nucleobase.

Embodiment 200: The oligomeric compound of embodiment 199, wherein each W comprises a modified nucleobase selected from among a 2-thio pyrimidine and a 5-propyne pyrimidine.

Embodiment 201: The oligomeric compound of embodiment 200, wherein each W comprises 2-thio-thymidine.

Embodiment 202: The oligomeric compound of embodiment 176-192, wherein each W comprises an F-HNA sugar moiety.

Embodiment 203: The oligomeric compound of embodiment 202, wherein each W nucleoside comprises an unmodified 2'-deoxyfuranose sugar moiety.

Embodiment 204: The oligomeric compound of embodiments 1-203, wherein the 5'-region has a motif selected from among: AB, ABB, AAA, BBB, BBBAA, AAB, BAA, BBAA, AABB, AAAB, ABBW, ABBWW, ABBB, ABBBB, ABAB, ABABAB, ABABBB, ABABAA, AAABB, AAAABB, AABB, AAAAB, AABBB, ABBBB, BBBBB, AAABW, AAAAA, and BBBBAA;

wherein the 3'-region has a motif selected from among: BBA, AAB, AAA, BBB, BBAA, AABB, WBBA, WAAB, BBBA, BBBBA, BBBB, BBBBBA, ABBBBB, BBAAA, AABBB, BBBAA, BBBBA, BBBBB, BABA, AAAAA, BBAAAA, AABBBB, BAAAA, and ABBBB;

wherein the central region has a nucleoside motif selected from among: DDDDDD, DDDDDDD, DDDDDDDD, DDDDDDDDD, DDDDDDDDDD, DXDDDDDDD, DDXDDDDDD, DDDXDDDDD, DDDDXDDDD, DDDDDXDDD, DDDDDDXDD, DDDDDDDXD, DXXDDDDDD, DDDDDDXXD, DDXXDDDDD, DDDXXDDDD, DDDDXXDDD, DDDDDXXDD, DXDDDDDXD, DXDDDDXDD, DXDDDXDDD, DXDDXDDDD, DXDXDDDDD, DDXDDDDXD, DDXDDDXDD, DDXDDXDDD, DDXDXDDDD, DDDXDDDXD, DDDXDDXDD, DDDXDXDDD, DDDDXDDXD, DDDDXDXDD, DDDDXDXDD, and DDDDDXDXD, DDDDDDDD, DXDDDDDD, DDXDDDDD, DDDXDDDD, DDDDXDDD, DDDDDXDD, DDDDDDXD, DXDDDXD, DXDDDXDD, DXDDXDDD, DXDXDDDD, DXXDDDDD, DDXXDDDD, DDXDXDDD, DDXDDXDD, DXDDDDXD, DDDXXDDD, DDDXDXDD, DDDXDDXD, DDDDXXDD, DDDDXDXD, and DDDDDXXD, DXDDDDD, DDXDDDD, DDDXDDD, DDDDXDD, DDDDDXD, DXDDDXD, DXDDDXD, DXDXDDD, DXXDDDD, DDXXDDD, DDXDXDD, DDXDDXD, DDDXXDD, DDDXDXD, and DDDDXXD, DXDDDD, DDXDDD, DDDXDD, DDDDXD, DXXDDD, DXDXDD, DXDDXD, DDXXDD, DDXDXD, and DDDXXD; and wherein each A is a modified nucleoside of a first type, each B is a modified nucleoside of a second type, each W is a modified nucleoside of a first type, a second type, or a third type, each D is an unmodified deoxynucleoside, and each X is a modified nucleoside or a modified nucleobase.

Embodiment 205: The oligomeric compound of embodiment 204, wherein the 5'-region has a motif selected from among:
AB, ABB, AAA, BBB, BBBAA, AAB, BAA, BBAA, AABB, ABBW, ABBWW, ABBB, ABBBB, ABAB, ABABAB, ABABBB, ABABAA, AAABB, AAAABB, AABB, AAAAB, AABBB, ABBBB, BBBBB, AAABW, and BBBBAA; and wherein the 3'-region has a BBA motif.

Embodiment 206: The oligomeric compound of embodiment 204 or 205, wherein one of A or B comprises a bicyclic sugar moiety, another of A or B comprises a 2'-MOE sugar moiety, and W comprises a 2-thio-thymidine nucleobase.

Embodiment 207: The oligomeric compound of embodiment 204 or 205, wherein one of A or B comprises a bicyclic sugar moiety, another of A or B comprises a 2'-MOE sugar moiety, and W comprises FHNA.

Embodiment 208: The oligomeric compound of embodiment 204 or 205, wherein one of A or B comprises cEt, another of A or B comprises a 2'-modified sugar moiety, and W comprises a 2-thio-thymidine nucleobase.

Embodiment 209: The oligomeric compound of embodiment 204 or 205, wherein one of A or B comprises cEt, another of A or B comprises a 2'-modified sugar moiety, and W comprises FHNA.

Embodiment 210: The oligomeric compound of embodiment 204 or 205, wherein each A comprises MOE, each B comprises cEt, and each W is selected from among cEt or FHNA.

Embodiment 211: The oligomeric compound of embodiment 204 or 205, wherein each W comprises cEt.

Embodiment 212: The oligomeric compound of embodiment 204 or 205, wherein each W comprises 2-thiothymidine.

Embodiment 213: The oligomeric compound of embodiment 204 or 205, wherein each W comprises FHNA.

Embodiment 214: The oligomeric compound of any of embodiments 1-213 comprising at least one modified internucleoside linkage.

Embodiment 215: The oligomeric compound of embodiment 214, wherein each internucleoside linkage is a modified internucleoside linkage.

Embodiment 216: The oligomeric compound of embodiment 214 or 215 comprising at least one phosphorothioate internucleoside linkage.

Embodiment 217: The oligomeric compound of any of embodiments 214 or 215 comprising at least one methylphosphonate internucleoside linkage.

Embodiment 218: The oligomeric compound of any of embodiments 214 or 215 comprising one methylphosphonate internucleoside linkage.

Embodiment 219: The oligomeric compound of any of embodiments 214 or 215 comprising two methylphosphonate internucleoside linkages.

Embodiment 220: The oligomeric compound of embodiment 217, wherein at least one of the $3^{rd}$, $4^{th}$, $5^{th}$, $6^{th}$ and/or $7^{th}$ internucleoside from the 5'-end is a methylphosphonate internucleoside linkage.

Embodiment 221: The oligomeric compound of embodiment 217, wherein at least one of the $3^{rd}$, $4^{th}$, $5^{th}$, $6^{th}$ and/or $7^{th}$ internucleoside from the 3'-end is a methylphosphonate internucleoside linkage.

Embodiment 222: The oligomeric compound of embodiment 217, wherein at least one of the $3^{rd}$, $4^{th}$, $5^{th}$, $6^{th}$, $7^{th}$, $8^{th}$, $9^{th}$, $10^{th}$, $11^{th}$, and/or $12^{th}$ internucleoside from the 5'-end is a methylphosphonate internucleoside linkage, and wherein at least one of the $3^{rd}$, $4^{th}$, $5^{th}$, $6^{th}$, $7^{th}$, $8^{th}$, $9^{th}$, $10^{th}$, $11^{th}$, and/or $12^{th}$ internucleoside from the 5'-end is a modified nucleoside.

Embodiment 223: The oligomeric compound of embodiment 217, wherein at least one of the $3^{rd}$, $4^{th}$, $5^{th}$, $6^{th}$, $7^{th}$, $8^{th}$, $9^{th}$, $10^{th}$, $11^{th}$, and/or $12^{th}$ internucleoside from the 3'-end is a methylphosphonate internucleoside linkage, and wherein at least one of the $3^{rd}$, $4^{th}$, $5^{th}$, $6^{th}$, $7^{th}$, $8^{th}$, $9^{th}$, $10^{th}$, $11^{th}$, and/or $12^{th}$ internucleoside from the 3'-end is a modified nucleoside.

Embodiment 224: The oligomeric compound of any of embodiments 1-223 comprising at least one conjugate group.

Embodiment 225: The oligomeric compound of embodiment 1-223, wherein the conjugate group consists of a conjugate.

Embodiment 226: The oligomeric compound of embodiment 225, wherein the conjugate group consists of a conjugate and a conjugate linker.

Embodiment 227: The oligomeric compound of any of embodiments 1-226, wherein the nucleobase sequence of the modified oligonucleotide is 100% complementary to the nucleobase sequence of the target region of the target nucleic acid.

Embodiment 228: The oligomeric compound of any of embodiments 1-226, wherein the nucleobase sequence of the modified oligonucleotide contains one mismatch relative to the nucleobase sequence of the target region of the target nucleic acid.

Embodiment 229: The oligomeric compound of any of embodiments 1-226, wherein the nucleobase sequence of the modified oligonucleotide contains two mismatches relative to the nucleobase sequence of the target region of the target nucleic acid.

Embodiment 230: The oligomeric compound of any of embodiments 1-226, wherein the nucleobase sequence of the modified oligonucleotide comprises a hybridizing region and at least one non-targeting region, wherein the nucleobase sequence of the hybridizing region is complementary to the nucleobase sequence of the target region of the target nucleic acid.

Embodiment 231: The oligomeric compound of embodiment 230, wherein the nucleobase sequence of the hybridizing region is 100% complementary to the nucleobase sequence of the target region of the target nucleic acid.

Embodiment 232: The oligomeric compound of embodiment 230, wherein the nucleobase sequence of the hybridizing region contains one mismatched relative to the nucleobase sequence of the target region of the target nucleic acid.

Embodiment 233: The oligomeric compound of any of embodiments 230-232, wherein the nucleobase sequence of at least one non-targeting region is complementary to a portion of the hybridizing region of the modified oligonucleotide.

Embodiment 234: The oligomeric compound of embodiment 233, wherein the nucleobase sequence of at least one non-targeting region is 100% complementary to a portion of the hybridizing region of the modified oligonucleotide.

Embodiment 235: The oligomeric compound of embodiment 1-234 wherein the nucleobase sequence of the modified oligonucleotide comprises two non-targeting regions flanking a central hybridizing region.

Embodiment 236: The oligomeric compound of embodiment 235, wherein the two non-targeting regions are complementary to one another.

Embodiment 237: The oligomeric compound of embodiment 236, wherein the two non-targeting regions are 100% complementary to one another.

Embodiment 238: The oligomeric compound of any of embodiments 2-237, wherein the nucleobase sequence of the modified oligonucleotide aligns with the nucleobase of the target region of the target nucleic acid such that a distinguishing nucleobase of the target region of the target nucleic acid aligns with a target-selective nucleoside within the central region of the modified oligonucleotide.

Embodiment 239: The oligomeric compound of any of embodiments 3-237, wherein the nucleobase sequence of the modified oligonucleotide aligns with the nucleobase of the target region of the target nucleic acid such that the single distinguishing nucleobase of the target region of the target nucleic acid aligns with a target-selective nucleoside within the central region of the modified oligonucleotide.

Embodiment 240: The oligomeric compound of embodiment 238 or 239, wherein the target-selective nucleoside is the 5'-most nucleoside of the central region.

Embodiment 241: The oligomeric compound of embodiment 238 or 239, wherein the target-selective nucleoside is the $2^{nd}$ nucleoside from the 5'-end of the central region.

Embodiment 242: The oligomeric compound of embodiment 238 or 239, wherein the target-selective nucleoside is at the $3^{rd}$ nucleoside from the 5'-end of the central region.

Embodiment 243: The oligomeric compound of embodiment 238 or 239, wherein the target-selective nucleoside is at the $5^{th}$ nucleoside from the 5'-end of the central region.

Embodiment 244: The oligomeric compound of embodiment 238 or 239, wherein the target-selective nucleoside is at the $7^{th}$ nucleoside from the 5'-end of the central region.

Embodiment 245: The oligomeric compound of embodiment 238 or 239, wherein the target-selective nucleoside is at the $9^{th}$ nucleoside from the 5'-end of the central region.

Embodiment 246: The oligomeric compound of any of embodiments 238 or 239, or 241-245, wherein the target-selective nucleoside is at the $2^{nd}$ nucleoside from the 3'-end of the central region.

Embodiment 247: The oligomeric compound of any of embodiments 238 or 239, or 241-245, wherein the target-selective nucleoside is at the $5^{th}$ nucleoside from the 3'-end of the central region.

Embodiment 248: The oligomeric compound of any of embodiments 1-247, wherein target-selective nucleoside is an unmodified deoxynucleoside.

Embodiment 249: The oligomeric compound of any of embodiments 1-247, wherein target-selective nucleoside is a modified nucleoside.

Embodiment 250: The oligomeric compound of embodiment 249, wherein the target-selective nucleoside is a sugar modified nucleoside.

Embodiment 251: The oligomeric compound of embodiment 250, wherein the target-selective nucleoside comprises a sugar modification selected from among: 2'-MOE, 2'-F, 2'-(ara)-F, HNA, FHNA, cEt, and α-L-LNA.

Embodiment 252: The oligomeric compound of any of embodiments 1-251, wherein the target-selective nucleoside comprises a nucleobase modification.

Embodiment 253: The oligomeric compound of embodiment 252, wherein the modified nucleobase is selected from among: a 2-thio pyrimidine and a 5-propyne pyrimidine.

Embodiment 254: The oligomeric compound of any of embodiments 1-253, wherein the oligomeric compound is an antisense compound.

Embodiment 255: The oligomeric compound of embodiment 254, wherein the oligomeric compound selectively reduces expression of the target relative to the non-target.

Embodiment 256: The oligomeric compound of embodiment 255, wherein the oligomeric compound reduces expression of target at least two-fold more than it reduces expression of the non-target.

Embodiment 257: The oligomeric compound of embodiment 256, having an $EC_{50}$ for reduction of expression of target that is at least two-fold lower than its $EC_{50}$ for reduction of expression of the non-target, when measured in cells.

Embodiment 258: The oligomeric compound of embodiment 256, having an $ED_{50}$ for reduction of expression of target that is at least two-fold lower than its $ED_{50}$ for reduction of expression of the non-target, when measured in an animal.

Embodiment 259: The oligomeric compound of embodiments 1-10, having an E-E-E-K-K-(D)$_7$-E-E-K motif, wherein each E is a 2'-MOE nucleoside and each K is a cEt nucleoside.

Embodiment 260: A method comprising contacting a cell with an oligomeric compound of any of embodiments 1-259.

Embodiment 261: The method of embodiment 260, wherein the cell is in vitro.

Embodiment 262: The method of embodiment 260, wherein the cell is in an animal.

Embodiment 263: The method of embodiment 262, wherein the animal is a human.

Embodiment 264: The method of embodiment 263, wherein the animal is a mouse.

Embodiment 265: A pharmaceutical composition comprising an oligomeric compound of any of embodiments 1-259 and a pharmaceutically acceptable carrier or diluent.

Embodiment 266: A method of administering a pharmaceutical composition of embodiment 265 to an animal.

Embodiment 267: The method of embodiment 266, wherein the animal is a human.

Embodiment 268: The method of embodiment 266, wherein the animal is a mouse.

Embodiment 269: Use of an oligomeric compound of any of embodiments 1-259 for the preparation of a medicament for the treatment or amelioration of Alzheimer's disease, Creutzfeldt-Jakob disease, fatal familial insomnia, Alexander disease, Parkinson's disease, amyotrophic lateral sclerosis, dentato-rubral and pallido-luysian atrophy DRPA, spino-cerebellar ataxia, Torsion dystonia, cardiomyopathy, chronic obstructive pulmonary disease (COPD), liver disease, hepatocellular carcinoma, systemic lupus erythematosus, hypercholesterolemia, breast cancer, asthma, Type 1 diabetes, Rheumatoid arthritis, Graves disease, SLE, spinal and bulbar muscular atrophy, Kennedy's disease, progressive childhood posterior subcapsular cataracts, cholesterol gallstone disease, arthrosclerosis, cardiovascular disease, primary hypercalciuria, alpha-thallasemia, obsessive compulsive disorder, Anxiety, comorbid depression, congenital visual defects, hypertension, metabolic syndrome, prostate cancer, congential myasthenic syndrome, peripheral arterial disease, atrial fibrillation, sporadic pheochromocytoma, congenital malformations, Machado-Joseph disease, Huntington's disease, and Autosomal Dominant Retinitis Pigmentosa disease.

Embodiment 270: A method of ameliorating a symptom of Alzheimer's disease, Creutzfeldt-Jakob disease, fatal familial insomnia, Alexander disease, Parkinson's disease, amyotrophic lateral sclerosis, dentato-rubral and pallido-luysian atrophy DRPA, spino-cerebellar ataxia, Torsion dystonia, cardiomyopathy, chronic obstructive pulmonary disease (COPD), liver disease, hepatocellular carcinoma, systemic lupus erythematosus, hypercholesterolemia, breast cancer, asthma, Type 1 diabetes, Rheumatoid arthritis, Graves disease, SLE, spinal and bulbar muscular atrophy, Kennedy's disease, progressive childhood posterior subcapsular cataracts, cholesterol gallstone disease, arthrosclerosis, cardiovascular disease, primary hypercalciuria, alpha-thallasemia, obsessive compulsive disorder, Anxiety, comorbid depression, congenital visual defects, hypertension, metabolic syndrome, prostate cancer, congential myasthenic syndrome, peripheral arterial disease, atrial fibrillation, sporadic pheochromocytoma, congenital malformations, Machado-Joseph disease, Huntington's disease, and Autosomal Dominant Retinitis Pigmentosa disease, comprising administering an oligomeric compound of any of embodiments 1-259 to an animal in need thereof.

Embodiment 271: The method of embodiment 270, wherein the animal is a human.

Embodiment 272: The method of embodiment 270, wherein the animal is a mouse.

In certain embodiments, including but not limited to any of the above numbered embodiments, oligomeric compounds including oligonucleotides described herein are capable of modulating expression of a target RNA. In certain embodiments, the target RNA is associated with a disease or disorder, or encodes a protein that is associated with a disease or disorder. In certain embodiments, the oligomeric compounds or oligonucleotides provided herein modulate the expression of function of such RNA to alleviate one or more symptom of the disease or disorder.

In certain embodiments, oligomeric compounds including oligonucleotides describe herein are useful in vitro. In certain embodiments such oligomeric compounds are used in diagnostics and/or for target validation experiments.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

A. Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21$^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2$^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "2'-F nucleoside" refers to a nucleoside comprising a sugar comprising fluoroine at the 2' position. Unless otherwise indicated, the fluorine in a 2'-F nucleoside is in the ribo position (replacing the OH of a natural ribose).

As used herein, "2'-(ara)-F" refers to a 2'-F substituted nucleoside, wherein the fluoro group is in the arabino position.

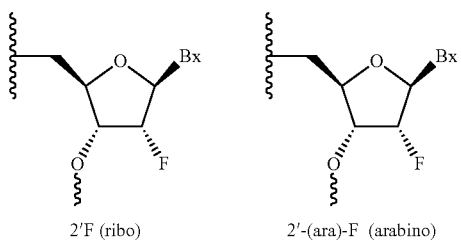

2'F (ribo)      2'-(ara)-F (arabino)

As used herein the term "sugar surrogate" means a structure that does not comprise a furanosyl and that is capable of replacing the naturally occurring sugar moiety of a nucleoside, such that the resulting nucleoside sub-units are capable of linking together and/or linking to other nucleosides to form an oligomeric compound which is capable of hybridizing to a complementary oligomeric compound. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)—O-2'-bridge.

As used herein, "locked nucleic acid nucleoside" or "LNA" means a nucleoside comprising a bicyclic sugar moiety comprising a 4'-CH$_2$—O-2'-bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "RNA-like nucleoside" means a modified nucleoside that adopts a northern configuration and functions like RNA when incorporated into an oligonucleotide. RNA-like nucleosides include, but are not limited to 3'-endo furanosyl nucleosides and RNA surrogates.

As used herein, "3'-endo-furanosyl nucleoside" means an RNA-like nucleoside that comprises a substituted sugar moiety that has a 3'-endo conformation. 3'-endo-furanosyl nucleosides include, but are not limited to: 2'-MOE, 2'-F, 2'-OMe, LNA, ENA, and cEt nucleosides.

As used herein, "RNA-surrogate nucleoside" means an RNA-like nucleoside that does not comprise a furanosyl. RNA-surrogate nucleosides include, but are not limited to hexitols and cyclopentanes.

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measureable activity" means a measurable activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound is intended to hybridize.

As used herein, "non-target nucleic acid" means a nucleic acid molecule to which hybridization of an antisense compound is not intended or desired. In certain embodiments, antisense compounds do hybridize to a non-target, due to homology between the target (intended) and non-target (un-intended).

As used herein, "mRNA" means an RNA molecule that encodes a protein.

As used herein, "pre-mRNA" means an RNA transcript that has not been fully processed into mRNA. Pre-RNA includes one or more intron.

As used herein, "object RNA" means an RNA molecule other than a target RNA, the amount, activity, splicing, and/or function of which is modulated, either directly or indirectly, by a target nucleic acid.

In certain embodiments, a target nucleic acid modulates splicing of an object RNA. In certain such embodiments, an antisense compound modulates the amount or activity of the target nucleic acid, resulting in a change in the splicing of an object RNA and ultimately resulting in a change in the activity or function of the object RNA.

As used herein, "microRNA" means a naturally occurring, small, non-coding RNA that represses gene expression of at least one mRNA. In certain embodiments, a microRNA represses gene expression by binding to a target site within a 3' untranslated region of an mRNA. In certain embodiments, a microRNA has a nucleobase sequence as set forth in miRBase, a database of published microRNA sequences found at http://microrna.sanger.ac.uk/sequences/. In certain embodiments, a microRNA has a nucleobase sequence as set forth in miRBase version 12.0 released September 2008, which is herein incorporated by reference in its entirety.

As used herein, "microRNA mimic" means an oligomeric compound having a sequence that is at least partially identical to that of a microRNA. In certain embodiments, a microRNA mimic comprises the microRNA seed region of a microRNA. In certain embodiments, a microRNA mimic modulates translation of more than one target nucleic acids. In certain embodiments, a microRNA mimic is double-stranded.

As used herein, "differentiating nucleobase" means a nucleobase that differs between two nucleic acids. In certain instances, a target region of a target nucleic acid differs by 1-4 nucleobases from a non-target nucleic acid. Each of those differences is referred to as a differentiating nucleobase. In certain instances, a differentiating nucleobase is a single-nucleotide polymorphism.

As used herein, "target-selective nucleoside" means a nucleoside of an antisense compound that corresponds to a differentiating nucleobase of a target nucleic acid.

As used herein, "allele" means one of a pair of copies of a gene existing at a particular locus or marker on a specific chromosome, or one member of a pair of nucleobases existing at a particular locus or marker on a specific chromosome, or one member of a pair of nucleobase sequences existing at a particular locus or marker on a specific chromosome. For a diploid organism or cell or for autosomal chromosomes, each allelic pair will normally occupy corresponding positions (loci) on a pair of homologous chromosomes, one inherited from the mother and one inherited from the father. If these alleles are identical, the organism or cell is said to be "homozygous" for that allele; if they differ, the organism or cell is said to be "heterozygous" for that allele. "Wild-type allele" refers to the genotype typically not associated with disease or dysfunction of the gene product. "Mutant allele" refers to the genotype associated with disease or dysfunction of the gene product.

As used herein, "allelic variant" means a particular identity of an allele, where more than one identity occurs. For example, an allelic variant may refer to either the mutant allele or the wild-type allele.

As used herein, "single nucleotide polymorphism" or "SNP" means a single nucleotide variation between the genomes of individuals of the same species. In some cases, a SNP may be a single nucleotide deletion or insertion. In general, SNPs occur relatively frequently in genomes and thus contribute to genetic diversity. The location of a SNP is generally flanked by highly conserved sequences. An individual may be homozygous or heterozygous for an allele at each SNP site.

As used herein, "single nucleotide polymorphism site" or "SNP site" refers to the nucleotides surrounding a SNP contained in a target nucleic acid to which an antisense compound is targeted.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "modification motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)R$_{aa}$), carboxyl (—C(O)O—R$_{aa}$), aliphatic groups, alicyclic groups, alkoxy, substituted oxy (—O—R$_{aa}$), aryl, aralkyl, heterocyclic radical, heteroaryl, heteroarylalkyl, amino (—N(R$_{bb}$)(R$_{cc}$)), imino (=NR$_{bb}$), amido (—C(O)N(R$_{bb}$)(R$_{cc}$) or —N(R$_{bb}$)C(O)R$_{aa}$), azido (—N$_3$), nitro (—NO$_2$), cyano (—CN), carbamido (—OC(O)N(R$_{bb}$)(R$_{cc}$) or —N(R$_{bb}$)C(O)OR$_{aa}$), ureido (—N(R$_{bb}$)C(O)N(R$_{bb}$)(R$_{cc}$)), thioureido (—N(R$_{bb}$)C(S)N(R$_{bb}$)—(R$_{cc}$)), guanidinyl (—N(R$_{bb}$)C(=NR$_{bb}$)N(R$_{bb}$)(R$_{cc}$)), amidinyl (—C(=NR$_{bb}$)N(R$_{bb}$)(R$_{cc}$) or —N(R$_{bb}$)C(=NR$_{bb}$)(R$_{aa}$)), thiol (—SR$_{bb}$), sulfinyl (—S(O)R$_{bb}$), sulfonyl (—S(O)$_2$R$_{bb}$) and sulfonamidyl (—S(O)$_2$N(R$_{bb}$)(R$_{cc}$) or —N(R$_{bb}$)S—(O)$_2$R$_{bb}$). Wherein each R$_{aa}$, R$_{bb}$ and R$_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or polycyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

B. Oligomeric Compounds

In certain embodiments, the present invention provides oligomeric compounds. In certain embodiments, such oligomeric compounds comprise oligonucleotides optionally comprising one or more conjugate and/or terminal groups. In certain embodiments, an oligomeric compound consists of an oligonucleotide. In certain embodiments, oligonucleotides comprise one or more chemical modifications. Such chemical modifications include modifications of one or more nucleoside (including modifications to the sugar moiety and/or the nucleobase) and/or modifications to one or more internucleoside linkage.

a. Certain Modified Nucleosides

In certain embodiments, provided herein are oligomeric compounds comprising or consisting of oligonucleotides comprising at least one modified nucleoside. Such modified nucleosides comprise a modified sugar moiety, a modified nucleobase, or both a modified sugar moiety and a modified nucleobase.

i. Certain Modified Sugar Moieties

In certain embodiments, compounds of the invention comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In certain embodiments, modified sugar moieties are substituted sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, SH, CN, OCN, CF$_3$, OCF$_3$, O, S, or N(R$_m$)-alkyl; O, S, or N(R$_m$)-alkenyl; O, S or N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$—C(=O)—N (R$_m$)(R$_n$), where each R$_m$ and is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$) (R$_n$) where each R$_m$ and R$_n$ is, independently, H, an amino protecting group or substituted or unsubstituted C$_1$-C$_{10}$ alkyl.

In certain embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$SCH$_3$, O—(CH$_2$)$_2$—O—N(CH$_3$)$_2$, —O(CH$_2$)$_2$O (CH$_2$)$_2$N(CH$_3$)$_2$, and O—CH$_2$—C(=O)—N(H)CH$_3$.

In certain embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to:

—[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2', 4'-(CH$_2$)$_2$-2', 4'-(CH$_2$)—O-2' (LNA); 4'-(CH$_2$)—S-2; 4'-(CH$_2$)$_2$—O-2' (ENA); 4'-CH(CH$_3$)—O-2' (cEt) and 4'-CH(CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, e.g., Chattopadhyaya, et al., *J. Org. Chem.*, 2009, 74, 118-134); and 4'-CH$_2$—C(=CH$_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH$_2$—O-2') BNA, (B) β-D-Methyleneoxy (4'-CH$_2$—O-2') BNA (also referred to as locked nucleic acid or LNA), (C) Ethyleneoxy (4'-(CH$_2$)$_2$—O-2') BNA, (D) Aminooxy (4'-CH$_2$—O—N(R)-2) BNA, (E) Oxyamino (4'-CH$_2$—N(R)—O-2') BNA, (F) Methyl(methyleneoxy) (4'-CH(CH$_3$)—O-2') BNA (also referred to as constrained ethyl or cEt), (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, (J) propylene carbocyclic (4'-(CH$_2$)$_3$-2') BNA, and (K) Ethylene(methoxy) (4'-(CH(CH$_2$OMe)-O-2') BNA (also referred to as constrained MOE or cMOE) as depicted below.

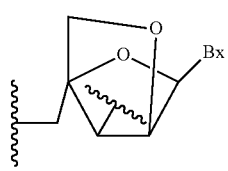
(A)

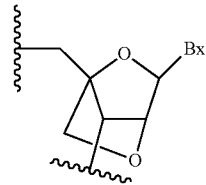
(B)

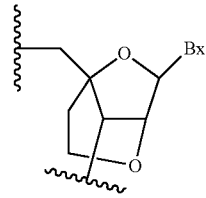
(C)

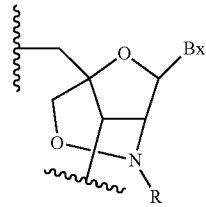
(D)

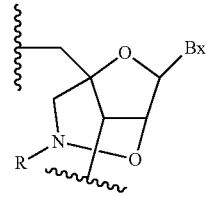
(E)

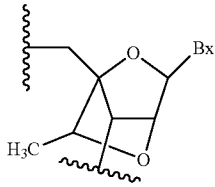
(F)

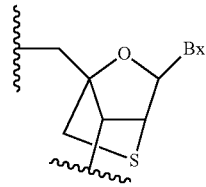
(G)

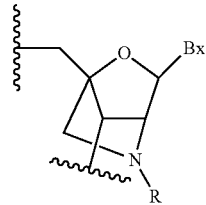
(H)

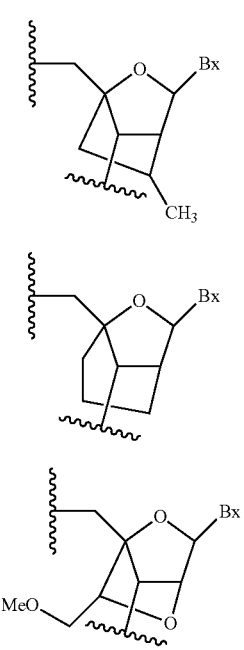

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') bicyclic nucleosides have been incorporated into antisense oligonucleotides that showed antisense activity (Frieden et al., *Nucleic Acids Research*, 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfur, carbon or nitrogen atom. In certain such embodiments, such modified sugar moiety also comprises bridging and/or non-bridging substituents as described above. For example, certain sugar surrogates comprise a 4'-sulfur atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research*, 1997, 25(22), 4429-4443 and Albaek et al., *J. Org. Chem.*, 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VII:

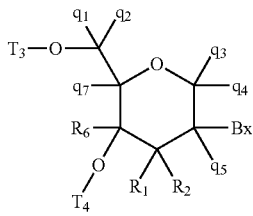

VII wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry*, 2002, 10, 841-854).

Combinations of modifications are also provided without limitation, such as 2'-F-5'-methyl substituted nucleosides (see PCT International Application WO 2008/101157 Published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, the present invention provides oligonucleotides comprising modified nucleosides. Those modified nucleotides may include modified sugars, modified nucleobases, and/or modified linkages. The specific modifications are selected such that the resulting oligonucleotides possess desirable characteristics. In certain embodiments, oligonucleotides comprise one or more RNA-like nucleosides. In certain embodiments, oligonucleotides comprise one or more DNA-like nucleotides.

ii. Certain Modified Nucleobases

In certain embodiments, nucleosides of the present invention comprise one or more unmodified nucleobases. In certain embodiments, nucleosides of the present invention comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C)—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

b. Certain Internucleoside Linkages

In certain embodiments, nucleosides may be linked together using any internucleoside linkage to form oligonucleotides. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(=O)—N (H)—S), amide-4 (3'-CH$_2$—N(H)—C(=O)-5'), formacetal (3'-O—CH$_2$—O-5), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

i. 3'-Endo Modifications

In one aspect of the present disclosure, oligomeric compounds include nucleosides synthetically modified to induce a 3'-endo sugar conformation. A nucleoside can incorporate synthetic modifications of the heterocyclic base moiety, the sugar moiety or both to induce a desired 3'-endo sugar conformation. These modified nucleosides are used to mimic RNA like nucleosides so that particular properties of an oligomeric compound can be enhanced while maintaining the desirable 3'-endo conformational geometry. There is an apparent preference for an RNA type duplex (A form helix, predominantly 3'-endo) as a requirement of RNA interference which is supported in part by the fact that duplexes composed of 2'-deoxy-2'-F-nucleosides appear efficient in triggering RNAi response in the *C. elegans* system. Properties that are enhanced by using more stable 3'-endo nucleosides include but aren't limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric compounds having one or more nucleosides modified in such a way as to favor a C3'-endo type conformation.

Scheme 1

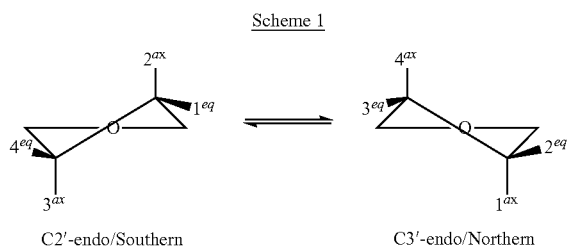

C2'-endo/Southern      C3'-endo/Northern

Nucleoside conformation is influenced by various factors including substitution at the 2',3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element, as exemplified in Example 35, below (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2'deoxy-2'F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Some modifications actually lock the conformational geometry by formation of a bicyclic sugar moiety e.g. locked nucleic acid (LNA, Singh et al, Chem. Commun. (1998), 4, 455-456), and ethylene bridged nucleic acids (ENA, Morita et al, Bioorganic & Medicinal Chemistry Letters (2002), 12, 73-76.)

c. Certain Motifs

In certain embodiments, oligomeric compounds comprise or consist of oligonucleotides. In certain embodiments, such oligonucleotides comprise one or more chemical modification. In certain embodiments, chemically modified oligonucleotides comprise one or more modified sugars. In certain embodiments, chemically modified oligonucleotides comprise one or more modified nucleobases. In certain embodiments, chemically modified oligonucleotides comprise one or more modified internucleoside linkages. In certain embodiments, the chemical modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

i. Certain Sugar Motifs

In certain embodiments, oligonucleotides comprise one or more type of modified sugar moieties and/or naturally occurring sugar moieties arranged along an oligonucleotide or region thereof in a defined pattern or sugar motif. Such sugar motifs include but are not limited to any of the sugar modifications discussed herein.

In certain embodiments, the oligonucleotides comprise or consist of a region having a gapmer sugar motif, which comprises two external regions or "wings" and a central or internal region or "gap." The three regions of a gapmer sugar motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric sugar gapmer). In certain embodiments, the sugar motifs of the 5'-wing differs from the sugar motif of the 3'-wing (asymmetric sugar gapmer).

ii. Certain Nucleobase Modification Motifs

In certain embodiments, oligonucleotides comprise chemical modifications to nucleobases arranged along the oligonucleotide or region thereof in a defined pattern or nucleobases modification motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, oligonucleotides comprise one or more nucleosides comprising a modified nucleobase. In certain embodiments, oligonucleotides having a gapmer sugar motif comprise a nucleoside comprising a modified nucleobase. In certain such embodiments, one nucleoside comprising a modified nucleobases is in the central gap of an oligonucleotide having a gapmer sugar motif. In certain embodiments, the sugar is an unmodified 2'deoxynucleoside. In certain embodiments, the modified nucleobase is selected from: a 2-thio pyrimidine and a 5-propyne pyrimidine In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

iii. Certain Nucleoside Motifs

In certain embodiments, oligonucleotides comprise nucleosides comprising modified sugar moieties and/or nucleosides comprising modified nucleobases. Such motifs can be described by their sugar motif and their nucleobase motif separately or by their nucleoside motif, which provides positions or patterns of modified nucleosides (whether modified sugar, nucleobase, or both sugar and nucleobase) in an oligonucleotide.

In certain embodiments, the oligonucleotides comprise or consist of a region having a gapmer nucleoside motif, which comprises two external regions or "wings" and a central or internal region or "gap." The three regions of a gapmer nucleoside motif (the 5'-wing, the gap, and the 3'-wing) form a contiguous sequence of nucleosides wherein at least some of the sugar moieties and/or nucleobases of the nucleosides of each of the wings differ from at least some of the sugar moieties and/or nucleobase of the nucleosides of the gap. Specifically, at least the nucleosides of each wing that are closest to the gap (the 3'-most nucleoside of the 5'-wing and the 5'-most nucleoside of the 3'-wing) differ from the neighboring gap nucleosides, thus defining the boundary between the wings and the gap. In certain embodiments, the nucleosides within the gap are the same as one another. In certain embodiments, the gap includes one or more nucleoside that differs from one or more other nucleosides of the gap. In certain embodiments, the nucleoside motifs of the two wings are the same as one another (symmetric gapmer). In certain embodiments, the nucleoside motifs of the 5'-wing differs from the nucleoside motif of the 3'-wing (asymmetric gapmer).

iv. Certain 5'-Wings

In certain embodiments, the 5'-wing of a gapmer consists of 1 to 6 linked nucleosides. In certain embodiments, the 5'-wing of a gapmer consists of 1 to 5 linked nucleosides. In certain embodiments, the 5'-wing of a gapmer consists of 2 to 5 linked nucleosides. In certain embodiments, the 5'-wing of a gapmer consists of 3 to 5 linked nucleosides. In certain embodiments, the 5'-wing of a gapmer consists of 4 or 5 linked nucleosides. In certain embodiments, the 5'-wing of a gapmer consists of 1 to 4 linked nucleosides. In certain embodiments, the 5'-wing of a gapmer consists of 1 to 3 linked nucleosides. In certain embodiments, the 5'-wing of a gapmer consists of 1 or 2 linked nucleosides. In certain embodiments, the 5'-wing of a gapmer consists of 2 to 4 linked nucleosides. In certain embodiments, the 5'-wing of a gapmer consists of 2 or 3 linked nucleosides. In certain embodiments, the 5'-wing of a gapmer consists of 3 or 4 linked nucleosides. In certain embodiments, the 5'-wing of a gapmer consists of 1 nucleoside. In certain embodiments, the 5'-wing of a gapmer consists of 2 linked nucleosides. In certain embodiments, the 5'-wing of a gapmer consists of 3 linked nucleosides. In certain embodiments, the 5'-wing of a gapmer consists of 4 linked nucleosides. In certain embodiments, the 5'-wing of a gapmer consists of 5 linked nucleosides. In certain embodiments, the 5'-wing of a gapmer consists of 6 linked nucleosides.

In certain embodiments, the 5'-wing of a gapmer comprises at least one bicyclic nucleoside. In certain embodiments, the 5'-wing of a gapmer comprises at least two bicyclic nucleosides. In certain embodiments, the 5'-wing of a gapmer comprises at least three bicyclic nucleosides. In certain embodiments, the 5'-wing of a gapmer comprises at least four bicyclic nucleosides. In certain embodiments, the 5'-wing of a gapmer comprises at least one constrained ethyl nucleoside. In certain embodiments, the 5'-wing of a gapmer comprises at least one LNA nucleoside. In certain embodiments, each nucleoside of the 5'-wing of a gapmer is a bicyclic nucleoside. In certain embodiments, each nucleoside of the 5'-wing of a gapmer is a constrained ethyl nucleoside. In certain embodiments, each nucleoside of the 5'-wing of a gapmer is a LNA nucleoside.

In certain embodiments, the 5'-wing of a gapmer comprises at least one non-bicyclic modified nucleoside. In certain embodiments, the 5'-wing of a gapmer comprises at least one 2'-substituted nucleoside. In certain embodiments, the 5'-wing of a gapmer comprises at least one 2'-MOE nucleoside. In certain embodiments, the 5'-wing of a gapmer comprises at least one 2'-OMe nucleoside. In certain embodiments, each nucleoside of the 5'-wing of a gapmer is a non-bicyclic modified nucleoside. In certain embodiments, each nucleoside of the 5'-wing of a gapmer is a 2'-substituted nucleoside. In certain embodiments, each nucleoside of the 5'-wing of a gapmer is a 2'-MOE nucleoside. In certain embodiments, each nucleoside of the 5'-wing of a gapmer is a 2'-OMe nucleoside.

In certain embodiments, the 5'-wing of a gapmer comprises at least one 2'-deoxynucleoside. In certain embodiments, each nucleoside of the 5'-wing of a gapmer is a 2'-deoxynucleoside. In a certain embodiments, the 5'-wing of a gapmer comprises at least one ribonucleoside. In certain embodiments, each nucleoside of the 5'-wing of a gapmer is a ribonucleoside. In certain embodiments, one, more than one, or each of the nucleosides of the 5'-wing is an RNA-like nucleoside.

In certain embodiments, the 5'-wing of a gapmer comprises at least one bicyclic nucleoside and at least one non-bicyclic modified nucleoside. In certain embodiments, the 5'-wing of a gapmer comprises at least one bicyclic nucleoside and at least one 2'-substituted nucleoside. In certain embodiments, the 5'-wing of a gapmer comprises at least one bicyclic nucleoside and at least one 2'-MOE nucleoside. In certain embodiments, the 5'-wing of a gapmer comprises at least one bicyclic nucleoside and at least one 2'-OMe nucleoside. In certain embodiments, the 5'-wing of a gapmer comprises at least one bicyclic nucleoside and at least one 2'-deoxynucleoside.

In certain embodiments, the 5'-wing of a gapmer comprises at least one constrained ethyl nucleoside and at least one non-bicyclic modified nucleoside. In certain embodiments, the 5'-wing of a gapmer comprises at least one constrained ethyl nucleoside and at least one 2'-substituted nucleoside. In certain embodiments, the 5'-wing of a gapmer comprises at least one constrained ethyl nucleoside and at least one 2'-MOE nucleoside. In certain embodiments, the 5'-wing of a gapmer comprises at least one constrained ethyl nucleoside and at least one 2'-OMe nucleoside. In certain embodiments, the 5'-wing of a gapmer comprises at least one constrained ethyl nucleoside and at least one 2'-deoxynucleoside.

In certain embodiments, the 5'-wing of a gapmer has a nucleoside motif selected from among the following: ADDA; ABDAA; ABBA; ABB; ABAA; AABAA; AAA-BAA; AAAABAA; AAAAABAA; AAABAA; AABAA; ABAB; ABADB; ABADDB; AAABB; AAAAA; ABBDC; ABDDC; ABBDCC; ABBDDC; ABBDCC; ABBC; AA; AAA; AAAA; AAAAB; AAAAAAA; AAAAAAAA; ABBB; AB; ABAB; AAAAB; AABBB; AAAAB; and AABBB, wherein each A is a modified nucleoside of a first type, each B is a modified nucleoside of a second type, each C is a modified nucleoside of a third type, and each D is an unmodified deoxynucleoside.

In certain embodiments, the 5'-wing of a gapmer has a nucleoside motif selected from among the following: AB, ABB, AAA, BBB, BBBAA, AAB, BAA, BBAA, AABB, AAAB, ABBW, ABBWW, ABBB, ABBBB, ABAB, ABA-BAB, ABABBB, ABABAA, AAABB, AAAABB, AABB, AAAAB, AABBB, ABBBB, BBBBB, AAABW, AAAAA, BBBBAA, and AAABW; wherein each A is a modified nucleoside of a first type, each B is a modified nucleoside of a second type, and each W is a modified nucleoside of either the first type, the second type or a third type.

In certain embodiments, the 5'-wing of a gapmer has a nucleoside motif selected from among the following: ABB; ABAA; AABAA; AAABAA; ABAB; ABADB; AAABB; AAAAA; AA; AAA; AAAA; AAAAB; ABBB; AB; and ABAB; wherein each A is a modified nucleoside of a first type, each B is a modified nucleoside of a second type, and each W is a modified nucleoside of either the first type, the second type or a third type.

In certain embodiments, an oligonucleotide comprises any 5'-wing motif provided herein. In certain such embodiments, the oligonucleotide is a 5'-hemimer (does not comprise a 3'-wing). In certain embodiments, such an oligonucleotide is a gapmer. In certain such embodiments, the 3'-wing of the gapmer may comprise any nucleoside motif.

In certain embodiments, the 5'-wing of a gapmer has a sugar motif selected from among those listed in the following non-limiting tables:

TABLE 1

| Certain 5'-Wing Sugar Motifs | | | | |
|---|---|---|---|---|
| AAAAA | ABCBB | BABCC | BCBBA | CBACC |
| AAAAB | ABCBC | BACAA | BCBBB | CBBAA |
| AAAAC | ABCCA | BACAB | BCBBC | CBBAB |
| AAABA | ABCCB | BACAC | BCBCA | CBBAC |
| AAABB | ABCCC | BACBA | BCBCB | CBBBA |
| AAABC | ACAAA | BACBB | BCBCC | CBBBB |

TABLE 1-continued

| Certain 5'-Wing Sugar Motifs | | | | |
|---|---|---|---|---|
| AAACA | ACAAB | BACBC | BCCAA | CBBBC |
| AAACB | ACAAC | BACCA | BCCAB | CBBCA |
| AAACC | ACABA | BACCB | BCCAC | CBBCB |
| AABAA | ACABB | BACCC | BCCBA | CBBCC |
| AABAB | ACABC | BBAAA | BCCBB | CBCAA |
| AABAC | ACACA | BBAAB | BCCBC | CBCAB |
| AABBA | ACACB | BBAAC | BCCCA | CBCAC |
| AABBB | ACACC | BBABA | BCCCB | CBCBA |
| AABBC | ACBAA | BBABB | BCCCC | CBCBC |
| AABCA | ACBAB | BBABC | CAAAA | CBCBC |
| AABCB | ACBAC | BBACA | CAAAB | CBCCA |
| AABCC | ACBBA | BBACB | CAAAC | CBCCB |
| AACAA | ACBBB | BBACC | CAABA | CBCCC |
| AACAB | ACBBC | BBAAA | CAABB | CCAAA |
| AACAC | ACBCA | BBBAB | CAABC | CCAAB |
| AACBA | ACBCB | BBBAC | CAACA | CCAAC |
| AACBB | ACBCC | BBBBA | CAACB | CCABA |
| AACBC | ACCAA | BBBBB | CAACC | CCABB |
| AACCA | ACCAB | BBBBC | CABAA | CCABC |
| AACCB | ACCAC | BBBCA | CABAB | CCACA |
| AACCC | ACCBA | BBBCB | CABAC | CCACB |
| ABAAA | ACCBB | BBBCC | CABBA | CCACC |
| ABAAB | ACCBC | BBCAA | CABBB | CCBAA |
| ABAAC | ACCCA | BBCAB | CABBC | CCBAB |
| ABABA | ACCCB | BBCAC | CABCA | CCBAC |
| ABABB | ACCCC | BBCBA | CABCB | CCBBA |
| ABABC | BAAAA | BBCBB | CABCC | CCBBB |
| ABACA | BAAAB | BBCBC | CACAA | CCBBC |
| ABACB | BAAAC | BBCCA | CACAB | CCBCA |
| ABACC | BAABA | BBCCB | CACAC | CCBCB |
| ABBAA | BAABB | BBCCC | CACBA | CCBCC |
| ABBAB | BAABC | BCAAA | CACBB | CCCAA |
| ABBAC | BAACA | BCAAB | CACBC | CCCAB |
| ABBBA | BAACB | BCAAC | CACCA | CCCAC |
| ABBBB | BAACC | BCABA | CACCB | CCCBA |
| ABBBC | BABAA | BCABB | CACCC | CCCBB |
| ABBCA | BABAB | BCABC | CBAAA | CCCBC |
| ABBCB | BABAC | BCACA | CBAAB | CCCCA |
| ABBCC | BABBA | BCACB | CBAAC | CCCCB |
| ABCAA | BABBB | BCACC | CBABA | CCCCC |
| ABCAB | BABBC | BCBAA | CBABB | |
| ABCAC | BABCA | BCBAB | CBABC | |
| ABCBA | BABCB | BCBAC | CBACA | |

TABLE 2

| Certain 5'-Wing Sugar Motifs | | | | |
|---|---|---|---|---|
| AAAAA | BABC | CBAB | ABBB | BAA |
| AAAAB | BACA | CBAC | BAAA | BAB |
| AAABA | BACB | CBBA | BAAB | BBA |
| AAABB | BACC | CBBB | BABA | BBB |
| AABAA | BBAA | CBBC | BABB | AA |
| AABAB | BBAB | CBCA | BBAA | AB |
| AABBA | BBAC | CBCB | BBAB | AC |
| AABBB | BBBA | CBCC | BBBA | BA |
| ABAAA | BBBB | CCAA | BBBB | BB |
| ABAAB | BBBC | CCAB | AAA | BC |
| ABABA | BBCA | CCAC | AAB | CA |
| ABABB | BBCB | CCBA | AAC | CB |
| ABBAA | BBCC | CCBB | ABA | CC |
| ABBAB | BCAA | CCBC | ABB | AA |
| ABBBA | BCAB | CCCA | ABC | AB |
| ABBBB | BCAC | CCCB | ACA | BA |
| BAAAA | ABCB | BCBA | ACB | |
| BAAAB | ABCC | BCBB | ACC | |
| BAABA | ACAA | BCBC | BAA | |
| BAABB | ACAB | BCCA | BAB | |
| BABAA | ACAC | BCCB | BAC | |
| BABAB | ACBA | BCCC | BBA | |
| BABBA | ACBB | CAAA | BBB | |
| BABBB | ACBC | CAAB | BBC | |
| BBAAA | ACCA | CAAC | BCA | |

TABLE 2-continued

Certain 5'-Wing Sugar Motifs
Certain 5'-Wing Sugar Motifs

| | | | |
|---|---|---|---|
| BBAAB | ACCB | CABA | BCB |
| BBABA | ACCC | CABB | BCC |
| BBABB | BAAA | CABC | CAA |
| BBBAA | BAAB | CACA | CAB |
| BBBAB | BAAC | CACB | CAC |
| BBBBA | BABA | CACC | CBA |
| BBBBB | BABB | CBAA | CBB |
| AAAA | AACC | CCCC | CBC |
| AAAB | ABAA | AAAA | CCA |
| AAAC | ABAB | AAAB | CCB |
| AABA | ABAC | AABA | CCC |
| AABB | ABBA | AABB | AAA |
| AABC | ABBB | ABAA | AAB |
| AACA | ABBC | ABAB | ABA |
| AACB | ABCA | ABBA | ABB |

In certain embodiments, each A, each B, and each C located at the 3'-most 5'-wing nucleoside is a modified nucleoside. For example, in certain embodiments the 5'-wing motif is selected from among AB<u>B</u>, BB<u>B</u>, and CB$\vec{B}$, wherein the underlined nucleoside represents the 3'-most 5'-wing nucleoside and wherein the underlined nucleoside is a modified nucleoside. In certain embodiments, the 3'-most 5'-wing nucleoside comprises a bicyclic sugar moiety selected from among cEt, cMOE, LNA, α-L-LNA, ENA and 2'-thio LNA. In certain embodiments, the 3'-most 5'-wing nucleoside comprises a bicyclic sugar moiety selected from among cEt and LNA. In certain embodiments, the 3'-most 5'-wing nucleoside comprises cEt. In certain embodiments, the 3'-most 5'-wing nucleoside comprises LNA.

In certain embodiments, each A comprises an unmodified 2'-deoxyfuranose sugar moiety. In certain embodiments, each A comprises a modified sugar moiety. In certain embodiments, each A comprises a 2'-substituted sugar moiety. In certain embodiments, each A comprises a 2'-substituted sugar moiety selected from among F, ara-F, $OCH_3$ and $O(CH_2)_2$—$OCH_3$. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A comprises a modified nucleobase. In certain embodiments, each A comprises a modified nucleobase selected from among 2-thio-thymidine nucleoside and 5-propyne uridine nucleoside. In certain embodiments, each A comprises an HNA. In certain embodiments, each A comprises a F-HNA. In certain embodiments, each A comprises a 5'-substituted sugar moiety selected from among 5'-Me DNA, and 5'-(R)-Me DNA.

In certain embodiments, each B comprises an unmodified 2'-deoxyfuranose sugar moiety. In certain embodiments, each B comprises a modified sugar moiety. In certain embodiments, each B comprises a 2'-substituted sugar moiety. In certain embodiments, each B comprises a 2'-substituted sugar moiety selected from among F, (ara)-F, $OCH_3$ and $O(CH_2)_2$—$OCH_3$. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA. In certain embodiments, each B comprises a modified nucleobase. In certain embodiments, each B comprises a modified nucleobase selected from among 2-thio-thymidine nucleoside and 5-propyne uridine nucleoside. In certain embodiments, each B comprises an HNA. In certain embodiments, each B comprises a F-HNA. In certain embodiments, each B comprises a 5'-substituted sugar moiety selected from among 5'-Me DNA, and 5'-(R)-Me DNA.

In certain embodiments, each A comprises a 2'-substituted sugar moiety selected from among F, ara-F, $OCH_3$ and $O(CH_2)_2$—$OCH_3$ and each B comprises a bicyclic sugar moiety selected from among cEt, cMOE, LNA, α-L-LNA, ENA and 2'-thio LNA. In certain embodiments, each A comprises $O(CH_2)_2$—$OCH_3$ and each B comprises cEt.

In certain embodiments, each C comprises an unmodified 2'-deoxyfuranose sugar moiety. In certain embodiments, each C comprises a modified sugar moiety. In certain embodiments, each C comprises a 2'-substituted sugar moiety. In certain embodiments, each C comprises a 2'-substituted sugar moiety selected from among F, (ara)-F, $OCH_3$ and $O(CH_2)_2$—$OCH_3$. In certain embodiments, each C comprises a 5'-substituted sugar moiety. In certain embodiments, each C comprises a 5'-substituted sugar moiety selected from among 5'-Me DNA, and 5'-(R)-Me DNA. In certain embodiments, each C comprises a bicyclic sugar moiety. In certain embodiments, each C comprises a bicyclic sugar moiety selected from among cEt, cMOE, LNA, α-L-LNA, ENA and 2'-thio LNA. In certain embodiments, each C comprises a modified nucleobase. In certain embodiments, each C comprises a modified nucleobase selected from among 2-thio-thymidine and 5-propyne uridine. In certain embodiments, each C comprises a 2-thio-thymidine nucleoside. In certain embodiments, each C comprises an HNA. In certain embodiments, each C comprises an F-HNA.

v. Certain 3'-Wings

In certain embodiments, the 3'-wing of a gapmer consists of 1 to 6 linked nucleosides. In certain embodiments, the 3'-wing of a gapmer consists of 1 to 5 linked nucleosides. In certain embodiments, the 3'-wing of a gapmer consists of 2 to 5 linked nucleosides. In certain embodiments, the 3'-wing of a gapmer consists of 3 to 5 linked nucleosides. In certain embodiments, the 3'-wing of a gapmer consists of 4 or 5 linked nucleosides. In certain embodiments, the 3'-wing of a gapmer consists of 1 to 4 linked nucleosides. In certain embodiments, the 3'-wing of a gapmer consists of 1 to 3 linked nucleosides. In certain embodiments, the 3'-wing of a gapmer consists of 1 or 2 linked nucleosides. In certain embodiments, the 3'-wing of a gapmer consists of 2 to 4 linked nucleosides. In certain embodiments, the 3'-wing of a gapmer consists of 2 or 3 linked nucleosides. In certain embodiments, the 3'-wing of a gapmer consists of 3 or 4 linked nucleosides. In certain embodiments, the 3'-wing of a gapmer consists of 1 nucleoside. In certain embodiments, the 3'-wing of a gapmer consists of 2 linked nucleosides. In certain embodiments, the 3'-wing of a gapmer consists of 3 linked nucleosides. In certain embodiments, the 3'-wing of a gapmer consists of 4 linked nucleosides. In certain embodiments, the 3'-wing of a gapmer consists of 5 linked nucleosides. In certain embodiments, the 3'-wing of a gapmer consists of 6 linked nucleosides.

In certain embodiments, the 3'-wing of a gapmer comprises at least one bicyclic nucleoside. In certain embodiments, the 3'-wing of a gapmer comprises at least one constrained ethyl nucleoside. In certain embodiments, the 3'-wing of a gapmer comprises at least one LNA nucleoside. In certain embodiments, each nucleoside of the 3'-wing of a gapmer is a bicyclic nucleoside. In certain embodiments, each nucleoside of the 3'-wing of a gapmer is a constrained ethyl nucleoside. In certain embodiments, each nucleoside of the 3'-wing of a gapmer is a LNA nucleoside.

In certain embodiments, the 3'-wing of a gapmer comprises at least one non-bicyclic modified nucleoside. In certain embodiments, the 3'-wing of a gapmer comprises at least two non-bicyclic modified nucleosides. In certain embodiments, the 3'-wing of a gapmer comprises at least three non-bicyclic modified nucleosides. In certain embodiments, the 3'-wing of a gapmer comprises at least four non-bicyclic modified nucleosides. In certain embodiments, the 3'-wing of a gapmer comprises at least one 2'-substituted nucleoside. In certain embodiments, the 3'-wing of a gapmer comprises at least one 2'-MOE nucleoside. In certain embodiments, the 3'-wing of a gapmer comprises at least one 2'-OMe nucleoside. In certain embodiments, each nucleoside of the 3'-wing of a gapmer is a non-bicyclic modified nucleoside. In certain embodiments, each nucleoside of the 3'-wing of a gapmer is a 2'-substituted nucleoside. In certain embodiments, each nucleoside of the 3'-wing of a gapmer is a 2'-MOE nucleoside. In certain embodiments, each nucleoside of the 3'-wing of a gapmer is a 2'-OMe nucleoside.

In certain embodiments, the 3'-wing of a gapmer comprises at least one 2'-deoxynucleoside. In certain embodiments, each nucleoside of the 3'-wing of a gapmer is a 2'-deoxynucleoside. In a certain embodiments, the 3'-wing of a gapmer comprises at least one ribonucleoside. In certain embodiments, each nucleoside of the 3'-wing of a gapmer is a ribonucleoside. In certain embodiments, one, more than one, or each of the nucleosides of the 5'-wing is an RNA-like nucleoside.

In certain embodiments, the 3'-wing of a gapmer comprises at least one bicyclic nucleoside and at least one non-bicyclic modified nucleoside. In certain embodiments, the 3'-wing of a gapmer comprises at least one bicyclic nucleoside and at least one 2'-substituted nucleoside. In certain embodiments, the 3'-wing of a gapmer comprises at least one bicyclic nucleoside and at least one 2'-MOE nucleoside. In certain embodiments, the 3'-wing of a gapmer comprises at least one bicyclic nucleoside and at least one 2'-OMe nucleoside. In certain embodiments, the 3'-wing of a gapmer comprises at least one bicyclic nucleoside and at least one 2'-deoxynucleoside.

In certain embodiments, the 3'-wing of a gapmer comprises at least one constrained ethyl nucleoside and at least one non-bicyclic modified nucleoside. In certain embodiments, the 3'-wing of a gapmer comprises at least one constrained ethyl nucleoside and at least one 2'-substituted nucleoside. In certain embodiments, the 3'-wing of a gapmer comprises at least one constrained ethyl nucleoside and at least one 2'-MOE nucleoside. In certain embodiments, the 3'-wing of a gapmer comprises at least one constrained ethyl nucleoside and at least one 2'-OMe nucleoside. In certain embodiments, the 3'-wing of a gapmer comprises at least one constrained ethyl nucleoside and at least one 2'-deoxynucleoside.

In certain embodiments, the 3'-wing of a gapmer comprises at least one LNA nucleoside and at least one non-bicyclic modified nucleoside. In certain embodiments, the 3'-wing of a gapmer comprises at least one LNA nucleoside and at least one 2'-substituted nucleoside. In certain embodiments, the 3'-wing of a gapmer comprises at least one LNA nucleoside and at least one 2'-MOE nucleoside. In certain embodiments, the 3'-wing of a gapmer comprises at least one LNA nucleoside and at least one 2'-OMe nucleoside. In certain embodiments, the 3'-wing of a gapmer comprises at least one LNA nucleoside and at least one 2'-deoxynucleoside.

In certain embodiments, the 3'-wing of a gapmer comprises at least one bicyclic nucleoside, at least one non-bicyclic modified nucleoside, and at least one 2'-deoxynucleoside. In certain embodiments, the 3'-wing of a gapmer comprises at least one constrained ethyl nucleoside, at least one non-bicyclic modified nucleoside, and at least one 2'-deoxynucleoside. In certain embodiments, the 3'-wing of a gapmer comprises at least one LNA nucleoside, at least one non-bicyclic modified nucleoside, and at least one 2'-deoxynucleoside.

In certain embodiments, the 3'-wing of a gapmer comprises at least one bicyclic nucleoside, at least one 2'-substituted nucleoside, and at least one 2'-deoxynucleoside. In certain embodiments, the 3'-wing of a gapmer comprises at least one constrained ethyl nucleoside, at least one 2'-substituted nucleoside, and at least one 2'-deoxynucleoside. In certain embodiments, the 3'-wing of a gapmer comprises at least one LNA nucleoside, at least one 2'-substituted nucleoside, and at least one 2'-deoxynucleoside.

In certain embodiments, the 3'-wing of a gapmer comprises at least one bicyclic nucleoside, at least one 2'-MOE nucleoside, and at least one 2'-deoxynucleoside. In certain embodiments, the 3'-wing of a gapmer comprises at least one constrained ethyl nucleoside, at least one 2'-MOE nucleoside, and at least one 2'-deoxynucleoside. In certain embodiments, the 3'-wing of a gapmer comprises at least one LNA nucleoside, at least one 2'-MOE nucleoside, and at least one 2'-deoxynucleoside.

In certain embodiments, the 3'-wing of a gapmer comprises at least one bicyclic nucleoside, at least one 2'-OMe nucleoside, and at least one 2'-deoxynucleoside. In certain embodiments, the 3'-wing of a gapmer comprises at least one constrained ethyl nucleoside, at least one 2'-OMe nucleoside, and at least one 2'-deoxynucleoside. In certain embodiments, the 3'-wing of a gapmer comprises at least one LNA nucleoside, at least one 2'-OMe nucleoside, and at least one 2'-deoxynucleoside.

In certain embodiments, the 3'-wing of a gapmer has a nucleoside motif selected from among the following: ABB, ABAA, AAABAA, AAAAABAA, AABAA, AAAABAA, AAABAA, ABAB, AAAAA, AAABB, AAAAAAAA, AAAAAAA, AAAAAA, AAAAB, AAAA, AAA, AA, AB, ABBB, ABAB, AABBB; wherein each A is a modified nucleoside of a first type, each B is a modified nucleoside of a second type. In certain embodiments, an oligonucleotide comprises any 3'-wing motif provided herein. In certain such embodiments, the oligonucleotide is a 3'-hemimer (does not comprise a 5'-wing). In certain embodiments, such an oligonucleotide is a gapmer. In certain such embodiments, the 5'-wing of the gapmer may comprise any nucleoside motif.

In certain embodiments, the 3'-wing of a gapmer has a nucleoside motif selected from among the following: BBA, AAB, AAA, BBB, BBAA, AABB, WBBA, WAAB, BBBA, BBBBA, BBBB, BBBBBA, ABBBBB, BBAAA, AABBB, BBBAA, BBBBA, BBBBB, BABA, AAAAA, BBAAAA, AABBBB, BAAAA, and ABBBB, wherein each A is a modified nucleoside of a first type, each B is a modified nucleoside of a second type, and each W is a modified nucleoside of either the first type, the second type or a third type.

In certain embodiments, the 3'-wing of a gapmer has a nucleoside motif selected from among the following: ABB; AAABAA; AABAA; AAAABAA; AAAAA; AAABB; AAAAAAAA; AAAAAAA; AAAAAA; AAAAB; AB; ABBB; and ABAB, wherein each A is a modified nucleoside of a first type, each B is a modified nucleoside of a second type, and each W is a modified nucleoside of either the first type, the second type or a third type.

In certain embodiments, the 3'-wing of a gapmer has a sugar motif selected from among those listed in the following non-limiting tables:

TABLE 3

Certain 3'-Wing Sugar Motifs
Certain 3'-Wing Sugar Motifs

| | | | | |
|---|---|---|---|---|
| AAAAA | ABCBB | BABCC | BCBBA | CBACC |
| AAAAB | ABCBC | BACAA | BCBBB | CBBAA |
| AAAAC | ABCCA | BACAB | BCBBC | CBBAB |
| AAABA | ABCCB | BACAC | BCBCA | CBBAC |
| AAABB | ABCCC | BACBA | BCBCB | CBBBA |
| AAABC | ACAAA | BACBB | BCBCC | CBBBB |
| AAACA | ACAAB | BACBC | BCCAA | CBBBC |
| AAACB | ACAAC | BACCA | BCCAB | CBBCA |
| AAACC | ACABA | BACCB | BCCAC | CBBCB |
| AABAA | ACABB | BACCC | BCCBA | CBBCC |
| AABAB | ACABC | BBAAA | BCCBB | CBCAA |
| AABAC | ACACA | BBAAB | BCCBC | CBCAB |
| AABBA | ACACB | BBAAC | BCCCA | CBCAC |
| AABBB | ACACC | BBABA | BCCCB | CBCBA |
| AABBC | ACBAA | BBABB | BCCCC | CBCBB |
| AABCA | ACBAB | BBABC | CAAAA | CBCBC |
| AABCB | ACBAC | BBACA | CAAAB | CBCCA |
| AABCC | ACBBA | BBACB | CAAAC | CBCCB |
| AACAA | ACBBB | BBACC | CAABA | CBCCC |
| AACAB | ACBBC | BBBAA | CAABB | CCAAA |
| AACAC | ACBCA | BBBAB | CAABC | CCAAB |
| AACBA | ACBCB | BBBAC | CAACA | CCAAC |
| AACBB | ACBCC | BBBBA | CAACB | CCABA |
| AACBC | ACCAA | BBBBB | CAACC | CCABB |
| AACCA | ACCAB | BBBBC | CABAA | CCABC |
| AACCB | ACCAC | BBBCA | CABAB | CCACA |
| AACCC | ACCBA | BBBCB | CABAC | CCACB |
| ABAAA | ACCBB | BBBCC | CABBA | CCACC |
| ABAAB | ACCBC | BBCAA | CABBB | CCBAA |
| ABAAC | ACCCA | BBCAB | CABBC | CCBAB |
| ABABA | ACCCB | BBCAC | CABCA | CCBAC |
| ABABB | ACCCC | BBCBA | CABCB | CCBBA |
| ABABC | BAAAA | BBCBB | CABCC | CCBBB |
| ABACA | BAAAB | BBCBC | CACAA | CCBBC |
| ABACB | BAAAC | BBCCA | CACAB | CCBCA |
| ABACC | BAABA | BBCCB | CACAC | CCBCB |
| ABBAA | BAABB | BBCCC | CACBA | CCBCC |
| ABBAB | BAABC | BCAAA | CACBB | CCCAA |
| ABBAC | BAACA | BCAAB | CACBC | CCCAB |
| ABBBA | BAACB | BCAAC | CACCA | CCCAC |
| ABBBB | BAACC | BCABA | CACCB | CCCBA |
| ABBBC | BABAA | BCABB | CACCC | CCCBB |
| ABBCA | BABAB | BCABC | CBAAA | CCCBC |
| ABBCB | BABAC | BCACA | CBAAB | CCCCA |
| ABBCC | BABBA | BCACB | CBAAC | CCCCB |
| ABCAA | BABBB | BCACC | CBABA | CCCCC |
| ABCAB | BABBC | BCBAA | CBABB | |
| ABCAC | BABCA | BCBAB | CBABC | |
| ABCBA | BABCB | BCBAC | CBACA | |

TABLE 4

Certain 3'-Wing Sugar Motifs
Certain 3'-Wing Sugar Motifs

| | | | | |
|---|---|---|---|---|
| AAAAA | BABC | CBAB | ABBB | BAA |
| AAAAB | BACA | CBAC | BAAA | BAB |
| AAABA | BACB | CBBA | BAAB | BBA |
| AAABB | BACC | CBBB | BABA | BBB |
| AABAA | BBAA | CBBC | BABB | AA |
| AABAB | BBAB | CBCA | BBAA | AB |
| AABBA | BBAC | CBCB | BBAB | AC |
| AABBB | BBBA | CBCC | BBBA | BA |
| ABAAA | BBBB | CCAA | BBBB | BB |
| ABAAB | BBBC | CCAB | AAA | BC |
| ABABA | BBCA | CCAC | AAB | CA |
| ABABB | BBCB | CCBA | AAC | CB |
| ABBAA | BBCC | CCBB | ABA | CC |
| ABBAB | BCAA | CCBC | ABB | AA |
| ABBBA | BCAB | CCCA | ABC | AB |
| ABBBB | BCAC | CCCB | ACA | BA |
| BAAAA | ABCB | BCBA | ACB | |
| BAAAB | ABCC | BCBB | ACC | |
| BAABA | ACAA | BCBC | BAA | |

TABLE 4-continued

Certain 3'-Wing Sugar Motifs
Certain 3'-Wing Sugar Motifs

| | | | |
|---|---|---|---|
| BAABB | ACAB | BCCA | BAB |
| BABAA | ACAC | BCCB | BAC |
| BABAB | ACBA | BCCC | BBA |
| BABBA | ACBB | CAAA | BBB |
| BABBB | ACBC | CAAB | BBC |
| BBAAA | ACCA | CAAC | BCA |
| BBAAB | ACCB | CABA | BCB |
| BBABA | ACCC | CABB | BCC |
| BBABB | BAAA | CABC | CAA |
| BBBAA | BAAB | CACA | CAB |
| BBBAB | BAAC | CACB | CAC |
| BBBBA | BABA | CACC | CBA |
| BBBBB | BABB | CBAA | CBB |
| AAAA | AACC | CCCC | CBC |
| AAAB | ABAA | AAAA | CCA |
| AAAC | ABAB | AAAB | CCB |
| AABA | ABAC | AABA | CCC |
| AABB | ABBA | AABB | AAA |
| AABC | ABBB | ABAA | AAB |
| AACA | ABBC | ABAB | ABA |
| AACB | ABCA | ABBA | ABB |

In certain embodiments, each A, each B, and each C located at the 5'-most 3'-wing region nucleoside is a modified nucleoside. For example, in certain embodiments the 3'-wing motif is selected from among ABB, BBB, and CBB, wherein the underlined nucleoside represents the 5'-most 3'-wing region nucleoside and wherein the underlined nucleoside is a modified nucleoside.

In certain embodiments, each A comprises an unmodified 2'-deoxyfuranose sugar moiety. In certain embodiments, each A comprises a modified sugar moiety. In certain embodiments, each A comprises a 2'-substituted sugar moiety. In certain embodiments, each A comprises a 2'-substituted sugar moiety selected from among F, ara-F, OCH$_3$ and O(CH$_2$)$_2$—OCH$_3$. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A comprises a modified nucleobase. In certain embodiments, each A comprises a modified nucleobase selected from among 2-thio-thymidine nucleoside and 5-propyne uridine nucleoside. In certain embodiments, each A comprises a 5'-substituted sugar moiety selected from among 5'-Me DNA, and 5'-(R)-Me DNA.

In certain embodiments, each B comprises an unmodified 2'-deoxyfuranose sugar moiety. In certain embodiments, each B comprises a modified sugar moiety. In certain embodiments, each B comprises a 2'-substituted sugar moiety. In certain embodiments, each B comprises a 2'-substituted sugar moiety selected from among F, (ara)-F, OCH$_3$ and O(CH$_2$)$_2$—OCH$_3$. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA. In certain embodiments, each B comprises a modified nucleobase. In certain embodiments, each B comprises a modified nucleobase selected from among 2-thio-thymidine nucleoside and 5-propyne uridine nucleoside. In certain embodiments, each B comprises an HNA. In certain embodiments, each B comprises an F-HNA. In certain embodiments, each B comprises a 5'-substituted sugar moiety selected from among 5'-Me DNA, and 5'-(R)-Me DNA.

In certain embodiments, each A comprises a 2'-substituted sugar moiety selected from among F, ara-F, OCH$_3$ and O(CH$_2$)$_2$—OCH$_3$ and each B comprises a bicyclic sugar moiety selected from among cEt, cMOE, LNA, α-L-LNA, ENA and 2'-thio LNA. In certain embodiments, each A comprises O(CH$_2$)$_2$—OCH$_3$ and each B comprises cEt.

In certain embodiments, each C comprises an unmodified 2'-deoxyfuranose sugar moiety. In certain embodiments, each C comprises a modified sugar moiety. In certain embodiments, each C comprises a 2'-substituted sugar moiety. In certain embodiments, each C comprises a 2'-substituted sugar moiety selected from among F, (ara)-F, OCH$_3$ and O(CH$_2$)$_2$—OCH$_3$. In certain embodiments, each C comprises a 5'-substituted sugar moiety. In certain embodiments, each C comprises a 5'-substituted sugar moiety selected from among 5'-Me, and 5'-(R)-Me. In certain embodiments, each C comprises a bicyclic sugar moiety. In certain embodiments, each C comprises a bicyclic sugar moiety selected from among cEt, cMOE, LNA, α-L-LNA, ENA and 2'-thio LNA. In certain embodiments, each C comprises a modified nucleobase. In certain embodiments, each C comprises a modified nucleobase selected from among 2-thio-thymidine and 5-propyne uridine. In certain embodiments, each C comprises a 2-thio-thymidine nucleoside. In certain embodiments, each C comprises an HNA. In certain embodiments, each C comprises an F-HNA.

vi. Certain Central Regions (Gaps)

In certain embodiments, the gap of a gapmer consists of 6 to 20 linked nucleosides. In certain embodiments, the gap of a gapmer consists of 6 to 15 linked nucleosides. In certain embodiments, the gap of a gapmer consists of 6 to 12 linked nucleosides. In certain embodiments, the gap of a gapmer consists of 6 to 10 linked nucleosides. In certain embodiments, the gap of a gapmer consists of 6 to 9 linked nucleosides. In certain embodiments, the gap of a gapmer consists of 6 to 8 linked nucleosides. In certain embodiments, the gap of a gapmer consists of 6 or 7 linked nucleosides. In certain embodiments, the gap of a gapmer consists of 7 to 10 linked nucleosides. In certain embodiments, the gap of a gapmer consists of 7 to 9 linked nucleosides. In certain embodiments, the gap of a gapmer consists of 7 or 8 linked nucleosides. In certain embodiments, the gap of a gapmer consists of 8 to 10 linked nucleosides. In certain embodiments, the gap of a gapmer consists of 8 or 9 linked nucleosides. In certain embodiments, the gap of a gapmer consists of 6 linked nucleosides. In certain embodiments, the gap of a gapmer consists of 7 linked nucleosides. In certain embodiments, the gap of a gapmer consists of 8 linked nucleosides. In certain embodiments, the gap of a gapmer consists of 9 linked nucleosides. In certain embodiments, the gap of a gapmer consists of 10 linked nucleosides. In certain embodiments, the gap of a gapmer consists of 11 linked nucleosides. In certain embodiments, the gap of a gapmer consists of 12 linked nucleosides.

In certain embodiments, each nucleoside of the gap of a gapmer is a 2'-deoxynucleoside. In certain embodiments, the gap comprises one or more modified nucleosides. In certain embodiments, each nucleoside of the gap of a gapmer is a 2'-deoxynucleoside or is a modified nucleoside that is "DNA-like." In such embodiments, "DNA-like" means that the nucleoside has similar characteristics to DNA, such that a duplex comprising the gapmer and an RNA molecule is capable of activating RNase H. For example, under certain conditions, 2'-(ara)-F have been shown to support RNase H activation, and thus is DNA-like. In certain embodiments, one or more nucleosides of the gap of a gapmer is not a 2'-deoxynucleoside and is not DNA-like. In certain such embodiments, the gapmer nonetheless supports RNase H activation (e.g., by virtue of the number or placement of the non-DNA nucleosides).

In certain embodiments, gaps comprise a stretch of unmodified 2'-deoxynucleoside interrupted by one or more modified nucleosides, thus resulting in three sub-regions (two stretches of one or more 2'-deoxynucleosides and a stretch of one or more interrupting modified nucleosides). In certain embodiments, no stretch of unmodified 2'-deoxynucleosides is longer than 5, 6, or 7 nucleosides. In certain embodiments, such short stretches is achieved by using short gap regions. In certain embodiments, short stretches are achieved by interrupting a longer gap region.

In certain embodiments, the gap comprises one or more modified nucleosides. In certain embodiments, the gap comprises one or more modified nucleosides selected from among cEt, FHNA, LNA, and 2-thio-thymidine. In certain embodiments, the gap comprises one modified nucleoside. In certain embodiments, the gap comprises a 5'-substituted sugar moiety selected from among 5'-Me, and 5'-(R)-Me. In certain embodiments, the gap comprises two modified nucleosides. In certain embodiments, the gap comprises three modified nucleosides. In certain embodiments, the gap comprises four modified nucleosides. In certain embodiments, the gap comprises two or more modified nucleosides and each modified nucleoside is the same. In certain embodiments, the gap comprises two or more modified nucleosides and each modified nucleoside is different.

In certain embodiments, the gap comprises one or more modified linkages. In certain embodiments, the gap comprises one or more methyl phosphonate linkages. In certain embodiments the gap comprises two or more modified linkages. In certain embodiments, the gap comprises one or more modified linkages and one or more modified nucleosides. In certain embodiments, the gap comprises one modified linkage and one modified nucleoside. In certain embodiments, the gap comprises two modified linkages and two or more modified nucleosides.

In certain embodiments, the gap comprises a nucleoside motif selected from among the following: DDDDXDDDD; DDDDDXDDDDD; DDDXDDDDD; DDDDXDDDDDD; DDDDXDDDD; DDXDDDDDD; DDDXDDDDDD; DXDDDDDD; DDXDDDDDDD; DDXDDDDDD; DDXDDDXDDD; DDDXDDDXDDD; DXDDDXDDD; DDDDDXDD; DDXDDDDXDDD; DDXDDDDXDD; DXDDDDDXDD; DDDDDXDDD; DDDXDDD; DXDDDDDDD; DDDDXXDDD; and DXXDXXDXX; wherein each D is an unmodified deoxynucleoside; and each X is a modified nucleoside or a substituted sugar moiety.

In certain embodiments, the gap comprises a nucleoside motif selected from among the following: DDDDDDDDD; DXDDDDDDD; DDXDDDDDD; DDDXDDDDD; DDDDXDDDD; DDDDDXDDD; DDDDDDXDD; DDDDDDDXD; DXXDDDDDD; DDDDDDXXD; DDXXDDDDD; DDDXXDDDD; DDDDXXDDD; DDDDDXXDD; DXDDDDDXD; DXDDDDXDD; DXDDDXDDD; DXDDXDDDD; DXDXDDDDD; DDXDDDDXD; DDXDDDXDD; DDXDDXDDD; DDXDXDDDD; DDDXDDDXD; DDDXDDXDD; DDDXDXDDD; DDDDXDXDD; and DDDDXDXD, wherein each D is an unmodified deoxynucleoside; and each X is a modified nucleoside or a substituted sugar moiety.

In certain embodiments, the gap comprises a nucleoside motif selected from among the following: DDDDXDDDD, DXDDDDDDD, DXXDDDDDD, DDXDDDDDD, DDDXDDDDD, DDDDXDDDD, DDDDDXDDD, DDDDDDXDD, and DDDDDDDXD, wherein each D is an unmodified deoxynucleoside; and each X is a modified nucleoside or a substituted sugar moiety.

In certain embodiments, the gap comprises a nucleoside motif selected from among the following: DDDDDDDD, DXDDDDDD, DDXDDDDD, DDDXDDDD, DDDDXDDD, DDDDDXDD, DDDDDDXD, DXDDDDXD, DXDDDXDD, DXDDXDDD, DXDXDDDD, DXXDDDDD, DDXXDDDD, DDXDXDDD, DDXDDXDD, DXDDDDXD, DDDXXDDD, DDDXDXDD, DDDXDDXD, DDDDXXDD, DDDDXDXD, and DDDDDXXD, wherein each D is an unmodified deoxynucleoside; and each X is a modified nucleoside or a substituted sugar moiety.

In certain embodiments, the gap comprises a nucleoside motif selected from among the following: DXDDDDD, DDXDDDD, DDDXDDD, DDDDXDD, DDDDDXD, DXDDDXD, DXDDXDD, DXDXDDD, DXXDDDD, DDXXDDD, DDXDXDD, DDXDDXD, DDDXXDD, DDDXDXD, and DDDDXXD, wherein each D is an unmodified deoxynucleoside; and each X is a modified nucleoside or a substituted sugar moiety.

In certain embodiments, the gap comprises a nucleoside motif selected from among the following: DXDDDD, DDXDDD, DDDXDD, DDDDXD, DXXDDD, DXDXDD, DXDDXD, DDXXDD, DDXDXD, and DDDXXD, wherein each D is an unmodified deoxynucleoside; and each X is a modified nucleoside or a substituted sugar moiety.

In certain embodiments, the gap comprises a nucleoside motif selected from among the following: DXDDDD, DDXDDD, DDDXDD, DDDDXD, DXDDDDD, DDXDDDD, DDDXDDD, DDDDXDD, DDDDDXD, DXDDDDDD, DDXDDDDD, DDDXDDDD, DDDDXDDD, DDDDDXDD, DDDDDDXD, DXDDDDDDD, DDXDDDDDD, DDDXDDDDD, DDDDXDDDD, DDDDDXDDD, DDDDDDXDD, and DDDDDDDXD, wherein each D is an unmodified deoxynucleoside; and each X is a modified nucleoside or a substituted sugar moiety.

In certain embodiments, each X comprises an unmodified 2'-deoxyfuranose sugar moiety. In certain embodiments, each X comprises a modified sugar moiety. In certain embodiments, each X comprises a 2'-substituted sugar moiety. In certain embodiments, each X comprises a 2'-substituted sugar moiety selected from among F, (ara)-F, OCH$_3$ and O(CH$_2$)$_2$—OCH$_3$. In certain embodiments, each X comprises a 5'-substituted sugar moiety. In certain embodiments, each X comprises a 5'-substituted sugar moiety selected from among 5'-Me, and 5'-(R)-Me. In certain embodiments, each X comprises a bicyclic sugar moiety. In certain embodiments, each X comprises a bicyclic sugar moiety selected from among cEt, cMOE, LNA, α-L-LNA, ENA and 2'-thio LNA. In certain embodiments, each X comprises a modified nucleobase. In certain embodiments, each X comprises a modified nucleobase selected from among 2-thio-thymidine and 5-propyne uridine. In certain embodiments, each X comprises a 2-thio-thymidine nucleoside. In certain embodiments, each X comprises an HNA. In certain embodiments, each C comprises an F-HNA. In certain embodiments, X represents the location of a single differentiating nucleobase.

vii. Certain Gapmer Motifs

In certain embodiments, a gapmer comprises a 5'-wing, a gap, and a 3' wing, wherein the 5'-wing, gap, and 3' wing are independently selected from among those discussed above. For example, in certain embodiments, a gapmer has a 5'-wing, a gap, and a 3'-wing having features selected from among any of those listed in the tables above and any 5'-wing may be paired with any gap and any 3'-wing. For example, in certain embodiments, a 5'-wing may comprise AAABB, a 3'-wing may comprise BBA, and the gap may comprise DDDDDD. For example, in certain embodiments, a gapmer has a 5'-wing, a gap, and a 3'-wing having features selected from among those listed in the following non-limiting table, wherein each motif is represented as (5'-wing)-(gap)-(3'-wing), wherein each number represents the number of linked nucleosides in each portion of the motif, for example, a 5-10-5 motif would have a 5'-wing comprising 5 nucleosides, a gap comprising 10 nucleosides, and a 3'-wing comprising 5 nucleosides:

TABLE 5

Certain Gapmer Sugar Motifs
Certain Gapmer Sugar Motifs

| | | | |
|---|---|---|---|
| 2-10-2 | 3-10-2 | 4-10-2 | 5-10-2 |
| 2-10-3 | 3-10-3 | 4-10-3 | 5-10-3 |
| 2-10-4 | 3-10-4 | 4-10-4 | 5-10-4 |
| 2-10-5 | 3-10-5 | 4-10-5 | 5-10-5 |
| 2-9-2 | 3-9-2 | 4-9-2 | 5-9-2 |
| 2-9-3 | 3-9-3 | 4-9-3 | 5-9-3 |
| 2-9-4 | 3-9-4 | 4-9-4 | 5-9-4 |
| 2-9-5 | 3-9-5 | 4-9-5 | 5-9-5 |
| 2-11-2 | 3-11-2 | 4-11-2 | 5-11-2 |
| 2-11-3 | 3-11-3 | 4-11-3 | 5-11-3 |
| 2-11-4 | 3-11-4 | 4-11-4 | 5-11-4 |
| 2-11-5 | 3-11-5 | 4-11-5 | 5-11-5 |
| 2-8-2 | 3-8-2 | 4-8-2 | 5-8-2 |
| 2-8-3 | 3-8-3 | 4-8-3 | 5-8-3 |
| 2-8-4 | 3-8-4 | 4-8-4 | 5-8-4 |
| 2-8-5 | 3-8-5 | 4-8-5 | 5-8-5 |

In certain embodiments, a gapmer comprises a 5'-wing, a gap, and a 3' wing, wherein the 5'-wing, gap, and 3' wing are independently selected from among those discussed above. For example, in certain embodiments, a gapmer has a 5'-wing, a gap, and a 3'-wing having features selected from among those listed in the following non-limiting tables:

TABLE 6

Certain Gapmer Nucleoside Motifs

| 5'-wing region | Central gap region | 3'-wing region |
|---|---|---|
| ADDA | DDDDDD | ABB |
| ABBA | DDDADDDD | ABAA |
| AAAAAAA | DDDDDDDDDD | AAA |
| AAAAABB | DDDDDDDD | BBAAAAA |
| ABB | DDDDADDDD | ABB |
| ABB | DDDDBDDDD | BBA |
| ABB | DDDDDDDDD | BBA |
| AABAA | DDDDDDDD | AABAA |
| ABB | DDDDDD | AABAA |
| AAABAA | DDDDDDDD | AAABAA |
| AAABAA | DDDDDDDD | AAB |
| ABAB | DDDDDDDD | ABAB |
| AAABB | DDDDDD | BBA |
| ABADB | DDDDDD | BBA |
| ABA | DBDDDDDD | BBA |
| ABA | DADDDDDD | BBA |
| ABAB | DDDDDDDD | BBA |
| AA | DDDDDDDD | BBBBBBBB |
| ABB | DDDDDD | ABADB |
| AAAAB | DDDDDD | BAAAA |
| ABBB | DDDDDDDD | AB |
| AB | DDDDDDDD | BBBA |
| ABBB | DDDDDDDD | BBBA |

TABLE 6-continued

Certain Gapmer Nucleoside Motifs

| 5'-wing region | Central gap region | 3'-wing region |
|---|---|---|
| AB | DDDDDDD | ABA |
| ABB | DDDDWDDD | BBA |
| AAABB | DDDWDDD | BBAAA |
| ABB | DDDDWWDDD | BBA |
| ABADB | DDDDDDD | BBA |
| ABBDC | DDDDDDD | BBA |
| ABBDDC | DDDDDD | BBA |
| ABBDCC | DDDDDD | BBA |
| ABB | DWWDWWDWW | BBA |
| ABB | DWDDDDDD | BBA |
| ABB | DDWDDDDD | BBA |
| ABB | DWWDDDDDD | BBA |
| AAABB | DDWDDDDDD | AA |
| BB | DDWDWDDDD | BBABBBB |
| ABB | DDDD($^N$D)DDDD | BBA |
| AAABB | DDD($^N$D)DDD | BBAAA |
| ABB | DDDD($^N$D)($^N$D)DDD | BBA |
| ABB | D($^N$D)($^N$D)D($^N$D)($^N$D)D($^N$D)($^N$D) | BBA |
| ABB | D($^N$D)DDDDDDD | BBA |
| ABB | DD($^N$D)DDDDDD | BBA |
| ABB | D($^N$D)($^N$D)DDDDDD | BBA |
| AAABB | DD($^N$D)DDDDDD | AA |
| BB | DD($^N$D)D($^N$D)DDDD | BBABBBB |
| ABAB | DDDDDDDD | BABA |

TABLE 7

Certain Gapmer Nucleoside Motifs

| 5'-wing region | Central gap region | 3'-wing region |
|---|---|---|
| ABBW | DDDDDDDD | BBA |
| ABB | DWDDDDDDD | BBA |
| ABB | DDWDDDDDD | BBA |
| ABB | DDDWDDDDD | BBA |
| ABB | DDDDWDDDD | BBA |
| ABB | DDDDDWDDD | BBA |
| ABB | DDDDDDWDD | BBA |
| ABB | DDDDDDDWD | BBA |
| ABB | DDDDDDDD | WBBA |
| ABBWW | DDDDDDD | BBA |
| ABB | DWWDDDDDD | BBA |
| ABB | DDWWDDDDD | BBA |
| ABB | DDDWWDDDD | BBA |
| ABB | DDDDWWDDD | BBA |
| ABB | DDDDDWWDD | BBA |
| ABB | DDDDDDWWD | BBA |
| ABB | DDDDDDD | WWBBA |
| ABBW | DDDDDDD | WBBA |
| ABBW | DDDDDWD | BBA |
| ABBW | DDDDDWDD | BBA |
| ABBW | DDDDWDDD | BBA |
| ABBW | DDDWDDDD | BBA |
| ABBW | DDWDDDDD | BBA |
| ABBW | DWDDDDDD | BBA |
| ABB | DWDDDDDD | WBBA |
| ABB | DWDDDDDWD | BBA |
| ABB | DWDDDDWDD | BBA |
| ABB | DWDDDWDDD | BBA |
| ABB | DWDDWDDDD | BBA |
| ABB | DWDWDDDDD | BBA |
| ABB | DDWDDDDD | WBBA |
| ABB | DDWDDDDWD | BBA |
| ABB | DDWDDDWDD | BBA |
| ABB | DDWDDWDDD | BBA |
| ABB | DDWDWDDDD | BBA |
| ABB | DDWWDDDDD | BBA |
| ABB | DDDWDDDD | WBBA |
| ABB | DDDWDDDWD | BBA |
| ABB | DDDWDDWDD | BBA |
| ABB | DDDWDWDDD | BBA |
| ABB | DDDWWDDDD | BBA |

TABLE 7-continued

Certain Gapmer Nucleoside Motifs

| 5'-wing region | Central gap region | 3'-wing region |
|---|---|---|
| ABB | DDDDWDDD | WBBA |
| ABB | DDDDWDDWD | BBA |
| ABB | DDDDWDWDD | BBA |
| ABB | DDDDWWDDD | BBA |
| ABB | DDDDDWDD | WBBA |
| ABB | DDDDDWDWD | BBA |
| ABB | DDDDDWWDD | BBA |
| ABB | DDDDDDWD | WBBA |

TABLE 8

Certain Gapmer Nucleoside Motifs

| 5'-wing region | Central gap region | 3'-wing region |
|---|---|---|
| ABBB | DDDDDDDD | BBA |
| ABB | DBDDDDDDD | BBA |
| ABB | DDBDDDDDD | BBA |
| ABB | DDDBDDDDD | BBA |
| ABB | DDDDBDDDD | BBA |
| ABB | DDDDDBDDD | BBA |
| ABB | DDDDDDBDD | BBA |
| ABB | DDDDDDDBD | BBA |
| ABB | DDDDDDDD | BBBA |
| ABBBB | DDDDDDD | BBA |
| ABB | DBBDDDDDD | BBA |
| ABB | DDBBDDDDD | BBA |
| ABB | DDDBBDDDD | BBA |
| ABB | DDDDBBDDD | BBA |
| ABB | DDDDDBBDD | BBA |
| ABB | DDDDDDBBD | BBA |
| ABB | DDDDDDD | BBBBA |
| ABBB | DDDDDDD | BBBA |
| ABB | DDDDDDBD | BBA |
| ABBB | DDDDDBDD | BBA |
| ABBB | DDDDBDDD | BBA |
| ABBB | DDDBDDDD | BBA |
| ABBB | DDBDDDDD | BBA |
| ABBB | DBDDDDDD | BBA |
| ABB | DBDDDDDD | BBBA |
| ABB | DBDDDDBD | BBA |
| ABB | DBDDDBDD | BBA |
| ABB | DBDDBDDD | BBA |
| ABB | DBDBDDDD | BBA |
| ABB | DBDBDDDDD | BBA |
| ABB | DDBDDDDD | BBBA |
| ABB | DDBDDDBD | BBA |
| ABB | DDBDDBDD | BBA |
| ABB | DDBDBDDD | BBA |
| ABB | DDBDBDDDD | BBA |
| ABB | DDBBDDDDD | BBA |
| ABB | DDDBDDDD | BBBA |
| ABB | DDDBDDBD | BBA |
| ABB | DDDBDBDD | BBA |
| ABB | DDDBBDDD | BBA |
| ABB | DDDBBDDDD | BBA |
| ABB | DDDDBDDD | BBBA |
| ABB | DDDDBDBD | BBA |
| ABB | DDDDBBDD | BBA |
| ABB | DDDDBBDDD | BBA |
| ABB | DDDDDBDD | BBBA |
| ABB | DDDDDBDBD | BBA |
| ABB | DDDDDBBDD | BBA |
| ABB | DDDDDDBD | BBBA |

TABLE 9

Certain Gapmer Nucleoside Motifs

| 5'-wing region | Central gap region | 3'-wing region |
|---|---|---|
| ABB | DDDDDDDD | BBA |
| AB | DBDDDDDDD | BBA |
| AB | DDBDDDDDD | BBA |
| AB | DDDBDDDDD | BBA |
| AB | DDDDBDDDD | BBA |
| AB | DDDDDBDDD | BBA |
| AB | DDDDDDBDD | BBA |
| AB | DDDDDDDBD | BBA |
| AB | DDDDDDDD | BBBA |
| ABBB | DDDDDDD | BBA |
| AB | DBBDDDDDD | BBA |
| AB | DDBBDDDDD | BBA |
| AB | DDDBBDDDD | BBA |
| AB | DDDDBBDDD | BBA |
| AB | DDDDDBBDD | BBA |
| AB | DDDDDDBBD | BBA |
| AB | DDDDDDDD | BBBBA |
| ABBBB | DDDDDDD | BBA |
| AB | DBBBDDDDD | BBA |
| AB | DDBBBDDDD | BBA |
| AB | DDDBBBDDD | BBA |
| AB | DDDDBBBDD | BBA |
| AB | DDDDDBBBD | BBA |
| AB | DDDDDDD | BBBBBA |
| AB | DDDDDDDD | BBBA |
| AB | DDDDDDBD | BBBA |
| AB | DDDDDBDD | BBBA |
| AB | DDDDBDDD | BBBA |
| AB | DDDBDDDD | BBBA |
| AB | DDBDDDDD | BBBA |
| AB | DBDDDDDD | BBBA |
| AB | DDDDDBD | BBBBA |
| AB | DDDDBDD | BBBBA |
| AB | DDDBDDD | BBBBA |
| AB | DDBDDDD | BBBBA |
| AB | DBDDDDD | BBBBA |
| AB | DDDDBD | BBBBBA |
| AB | DDDBDD | BBBBBA |
| AB | DDBDDD | BBBBBA |
| AB | DBDDDD | BBBBBA |
| AB | DBDDDD | BBBBBA |

TABLE 10

Certain Gapmer Nucleoside Motifs

| 5'-wing region | Central gap region | 3'-wing region |
|---|---|---|
| AAAAAA | DDDDDDD | BABA |
| AAAAAB | DDDDDDD | BABA |
| AAAABA | DDDDDDD | BABA |
| AAABAA | DDDDDDD | BABA |
| AABAAA | DDDDDDD | BABA |
| ABAAAA | DDDDDDD | BABA |
| BAAAAA | DDDDDDD | BABA |
| ABAAAB | DDDDDDD | BABA |
| ABAABA | DDDDDDD | BABA |
| ABABAA | DDDDDDD | BABA |
| ABBAAA | DDDDDDD | BABA |
| AABAAB | DDDDDDD | BABA |
| AABABA | DDDDDDD | BABA |
| AABBAA | DDDDDDD | BABA |
| AAABAB | DDDDDDD | BABA |
| AAABBA | DDDDDDD | BABA |
| AAAABB | DDDDDDD | BABA |
| BAAAAB | DDDDDDD | BABA |
| BAAABA | DDDDDDD | BABA |
| BAABAA | DDDDDDD | BABA |
| BABAAA | DDDDDDD | BABA |
| BBAAAA | DDDDDDD | BABA |
| BBAAAA | DDDDDDD | BABA |
| BBABAA | DDDDDDD | BABA |
| BBAABA | DDDDDDD | BABA |
| BBAAAB | DDDDDDD | BABA |
| ABABAB | DDDDDDD | BABA |
| BBBBAA | DDDDDDD | BABA |
| BBBABA | DDDDDDD | BABA |
| BBBAAB | DDDDDDD | BABA |
| BBBBBA | DDDDDDD | BABA |
| BBBBAB | DDDDDDD | BABA |
| AAABBB | DDDDDDD | BABA |
| AABABB | DDDDDDD | BABA |
| ABAABB | DDDDDDD | BABA |
| BAAABB | DDDDDDD | BABA |
| AABBBB | DDDDDDD | BABA |
| ABABBB | DDDDDDD | BABA |
| BAABBB | DDDDDDD | BABA |
| ABBBBB | DDDDDDD | BABA |
| BABBBB | DDDDDDD | BABA |
| BBBBBB | DDDDDDD | BABA |

TABLE 11

Certain Gapmer Nucleoside Motifs

| 5'-wing region | Central gap region | 3'-wing region |
|---|---|---|
| AAAAA | DDDDDDD | AAAAA |
| AAAAB | DDDDDDD | AAAAA |
| AAABA | DDDDDDD | AAAAA |
| AAABB | DDDDDDD | AAAAA |
| AABAA | DDDDDDD | AAAAA |
| AABAB | DDDDDDD | AAAAA |
| AABBA | DDDDDDD | AAAAA |
| AABBB | DDDDDDD | AAAAA |
| ABAAA | DDDDDDD | AAAAA |
| ABAAB | DDDDDDD | AAAAA |
| ABABA | DDDDDDD | AAAAA |
| ABABB | DDDDDDD | AAAAA |
| ABBAA | DDDDDDD | AAAAA |
| ABBAB | DDDDDDD | AAAAA |
| ABBBA | DDDDDDD | AAAAA |
| ABBBB | DDDDDDD | AAAAA |
| BAAAA | DDDDDDD | AAAAA |
| BAAAB | DDDDDDD | AAAAA |
| BAABA | DDDDDDD | AAAAA |
| BAABB | DDDDDDD | AAAAA |
| BABAA | DDDDDDD | AAAAA |
| BABAB | DDDDDDD | AAAAA |
| BABBA | DDDDDDD | AAAAA |
| BABBB | DDDDDDD | AAAAA |
| BBAAA | DDDDDDD | AAAAA |
| BBAAB | DDDDDDD | AAAAA |
| BBABA | DDDDDDD | AAAAA |
| BBABB | DDDDDDD | AAAAA |
| BBBAA | DDDDDDD | AAAAA |
| BBBAB | DDDDDDD | AAAAA |
| BBBBA | DDDDDDD | AAAAA |
| BBBBB | DDDDDDD | AAAAA |
| AAAAA | DDDDDDD | BAAAA |
| AAAAB | DDDDDDD | BAAAA |
| AAABA | DDDDDDD | BAAAA |
| AAABB | DDDDDDD | BAAAA |
| AABAA | DDDDDDD | BAAAA |
| AABAB | DDDDDDD | BAAAA |
| AABBA | DDDDDDD | BAAAA |
| AABBB | DDDDDDD | BAAAA |
| ABAAA | DDDDDDD | BAAAA |
| ABAAB | DDDDDDD | BAAAA |
| ABABA | DDDDDDD | BAAAA |
| ABABB | DDDDDDD | BAAAA |
| ABBAA | DDDDDDD | BAAAA |
| ABBAB | DDDDDDD | BAAAA |
| ABBBA | DDDDDDD | BAAAA |

TABLE 11-continued

Certain Gapmer Nucleoside Motifs

| 5'-wing region | Central gap region | 3'-wing region |
|---|---|---|
| ABBBB | DDDDDDD | BAAAA |
| BAAAA | DDDDDDD | BAAAA |
| BAAAB | DDDDDDD | BAAAA |
| BAABA | DDDDDDD | BAAAA |
| BAABB | DDDDDDD | BAAAA |
| BABAA | DDDDDDD | BAAAA |
| BABAB | DDDDDDD | BAAAA |
| BABBA | DDDDDDD | BAAAA |
| BABBB | DDDDDDD | BAAAA |
| BBAAA | DDDDDDD | BAAAA |
| BBAAB | DDDDDDD | BAAAA |
| BBABA | DDDDDDD | BAAAA |
| BBABB | DDDDDDD | BAAAA |
| BBBAA | DDDDDDD | BAAAA |
| BBBAB | DDDDDDD | BAAAA |
| BBBBA | DDDDDDD | BAAAA |
| BBBBB | DDDDDDD | BAAAA |
| AAAAA | DDDDDDD | BBAAA |
| AAAAB | DDDDDDD | BBAAA |
| AAABA | DDDDDDD | BBAAA |
| AAABB | DDDDDDD | BBAAA |
| AABAA | DDDDDDD | BBAAA |
| AABAB | DDDDDDD | BBAAA |
| AABBA | DDDDDDD | BBAAA |
| AABBB | DDDDDDD | BBAAA |
| ABAAA | DDDDDDD | BBAAA |
| ABAAB | DDDDDDD | BBAAA |
| ABABA | DDDDDDD | BBAAA |
| ABABB | DDDDDDD | BBAAA |
| ABBAA | DDDDDDD | BBAAA |
| ABBAB | DDDDDDD | BBAAA |
| ABBBA | DDDDDDD | BBAAA |
| ABBBB | DDDDDDD | BBAAA |
| BAAAA | DDDDDDD | BBAAA |
| BAAAB | DDDDDDD | BBAAA |
| BAABA | DDDDDDD | BBAAA |
| BAABB | DDDDDDD | BBAAA |
| BABAA | DDDDDDD | BBAAA |
| BABAB | DDDDDDD | BBAAA |
| BABBA | DDDDDDD | BBAAA |
| BABBB | DDDDDDD | BBAAA |
| BBAAA | DDDDDDD | BBAAA |
| BBAAB | DDDDDDD | BBAAA |
| BBABA | DDDDDDD | BBAAA |
| BBABB | DDDDDDD | BBAAA |
| BBBAA | DDDDDDD | BBAAA |
| BBBAB | DDDDDDD | BBAAA |
| BBBBA | DDDDDDD | BBAAA |
| BBBBB | DDDDDDD | BBAAA |
| AAAAA | DDDDDDD | BBBAA |
| AAAAB | DDDDDDD | BBBAA |
| AAABA | DDDDDDD | BBBAA |
| AAABB | DDDDDDD | BBBAA |
| AABAA | DDDDDDD | BBBAA |
| AABAB | DDDDDDD | BBBAA |
| AABBA | DDDDDDD | BBBAA |
| AABBB | DDDDDDD | BBBAA |
| ABAAA | DDDDDDD | BBBAA |
| ABAAB | DDDDDDD | BBBAA |
| ABABA | DDDDDDD | BBBAA |
| ABABB | DDDDDDD | BBBAA |
| ABBAA | DDDDDDD | BBBAA |
| ABBAB | DDDDDDD | BBBAA |
| ABBBA | DDDDDDD | BBBAA |
| ABBBB | DDDDDDD | BBBAA |
| BAAAA | DDDDDDD | BBBAA |
| BAAAB | DDDDDDD | BBBAA |
| BAABA | DDDDDDD | BBBAA |
| BAABB | DDDDDDD | BBBAA |
| BABAA | DDDDDDD | BBBAA |
| BABAB | DDDDDDD | BBBAA |
| BABBA | DDDDDDD | BBBAA |
| BABBB | DDDDDDD | BBBAA |
| BBAAA | DDDDDDD | BBBAA |
| BBAAB | DDDDDDD | BBBAA |
| BBABA | DDDDDDD | BBBAA |
| BBABB | DDDDDDD | BBBAA |
| BBBAA | DDDDDDD | BBBAA |
| BBBAB | DDDDDDD | BBBAA |
| BBBBA | DDDDDDD | BBBAA |
| BBBBB | DDDDDDD | BBBAA |
| AAAAA | DDDDDDD | BBBBA |
| AAAAB | DDDDDDD | BBBBA |
| AAABA | DDDDDDD | BBBBA |
| AAABB | DDDDDDD | BBBBA |
| AABAA | DDDDDDD | BBBBA |
| AABAB | DDDDDDD | BBBBA |
| AABBA | DDDDDDD | BBBBA |
| AABBB | DDDDDDD | BBBBA |
| ABAAA | DDDDDDD | BBBBA |
| ABAAB | DDDDDDD | BBBBA |
| ABABA | DDDDDDD | BBBBA |
| ABABB | DDDDDDD | BBBBA |
| ABBAA | DDDDDDD | BBBBA |
| ABBAB | DDDDDDD | BBBBA |
| ABBBA | DDDDDDD | BBBBA |
| ABBBB | DDDDDDD | BBBBA |
| BAAAA | DDDDDDD | BBBBA |
| BAAAB | DDDDDDD | BBBBA |
| BAABA | DDDDDDD | BBBBA |
| BAABB | DDDDDDD | BBBBA |
| BABAA | DDDDDDD | BBBBA |
| BABAB | DDDDDDD | BBBBA |
| BABBA | DDDDDDD | BBBBA |
| BABBB | DDDDDDD | BBBBA |
| BBAAA | DDDDDDD | BBBBA |
| BBAAB | DDDDDDD | BBBBA |
| BBABA | DDDDDDD | BBBBA |
| BBABB | DDDDDDD | BBBBA |
| BBBAA | DDDDDDD | BBBBA |
| BBBAB | DDDDDDD | BBBBA |
| BBBBA | DDDDDDD | BBBBA |
| BBBBB | DDDDDDD | BBBBA |
| AAAAA | DDDDDDD | BBBBB |
| AAAAB | DDDDDDD | BBBBB |
| AAABA | DDDDDDD | BBBBB |
| AAABB | DDDDDDD | BBBBB |
| AABAA | DDDDDDD | BBBBB |
| AABAB | DDDDDDD | BBBBB |
| AABBA | DDDDDDD | BBBBB |
| AABBB | DDDDDDD | BBBBB |
| ABAAA | DDDDDDD | BBBBB |
| ABAAB | DDDDDDD | BBBBB |
| ABABA | DDDDDDD | BBBBB |
| ABABB | DDDDDDD | BBBBB |
| ABBAA | DDDDDDD | BBBBB |
| ABBAB | DDDDDDD | BBBBB |
| ABBBA | DDDDDDD | BBBBB |
| ABBBB | DDDDDDD | BBBBB |
| BAAAA | DDDDDDD | BBBBB |
| BAAAB | DDDDDDD | BBBBB |
| BAABA | DDDDDDD | BBBBB |
| BAABB | DDDDDDD | BBBBB |
| BABAA | DDDDDDD | BBBBB |
| BABAB | DDDDDDD | BBBBB |
| BABBA | DDDDDDD | BBBBB |
| BABBB | DDDDDDD | BBBBB |
| BBAAA | DDDDDDD | BBBBB |
| BBAAB | DDDDDDD | BBBBB |
| BBABA | DDDDDDD | BBBBB |
| BBABB | DDDDDDD | BBBBB |
| BBBAA | DDDDDDD | BBBBB |
| BBBAB | DDDDDDD | BBBBB |
| BBBBA | DDDDDDD | BBBBB |
| BBBBB | DDDDDDD | BBBBB |

TABLE 12

Certain Gapmer Nucleoside Motifs

| 5'-wing region | Central gap region | 3'-wing region |
|---|---|---|
| AAAW | DDDDDDD | BBA |
| AABW | DDDDDDD | BBA |
| ABAW | DDDDDDD | BBA |
| ABBW | DDDDDDD | BBA |
| BAAW | DDDDDDD | BBA |
| BABW | DDDDDDD | BBA |
| BBAW | DDDDDDD | BBA |
| BBBW | DDDDDDD | BBA |
| ABB | DDDDDDD | WAAA |
| ABB | DDDDDDD | WAAB |
| ABB | DDDDDDD | WABA |
| ABB | DDDDDDD | WABB |
| ABB | DDDDDDD | WBAA |
| ABB | DDDDDDD | WBAB |
| ABB | DDDDDDD | WBBA |
| ABB | DDDDDDD | WBBB |
| AAAWW | DDDDDDD | BBA |
| AABWW | DDDDDDD | BBA |
| ABAWW | DDDDDDD | BBA |
| ABBWW | DDDDDDD | BBA |
| BAAWW | DDDDDDD | BBA |
| BABWW | DDDDDDD | BBA |
| BBAWW | DDDDDDD | BBA |
| BBBWW | DDDDDDD | BBA |
| ABB | DDDDDDD | WWAAA |
| ABB | DDDDDDD | WWAAB |
| ABB | DDDDDDD | WWABA |
| ABB | DDDDDDD | WWABB |
| ABB | DDDDDDD | WWBAA |
| ABB | DDDDDDD | WWBAB |
| ABB | DDDDDDD | WWBBA |
| ABB | DDDDDDD | WWBBB |
| AAAAW | DDDDDDD | BBA |
| AAABW | DDDDDDD | BBA |
| AABAW | DDDDDDD | BBA |
| AABBW | DDDDDDD | BBA |
| ABAAW | DDDDDDD | BBA |
| ABABW | DDDDDDD | BBA |
| ABBAW | DDDDDDD | BBA |
| ABBBW | DDDDDDD | BBA |
| BAAAW | DDDDDDD | BBA |
| BAABW | DDDDDDD | BBA |
| BABAW | DDDDDDD | BBA |
| BABBW | DDDDDDD | BBA |
| BBAAW | DDDDDDD | BBA |
| BBABW | DDDDDDD | BBA |
| BBBAW | DDDDDDD | BBA |
| BBBBW | DDDDDDD | WAAAA |
| ABB | DDDDDDD | WAAAB |
| ABB | DDDDDDD | WAABA |
| ABB | DDDDDDD | WAABB |
| ABB | DDDDDDD | WABAA |
| ABB | DDDDDDD | WABAB |
| ABB | DDDDDDD | WABBA |
| ABB | DDDDDDD | WABBB |
| ABB | DDDDDDD | WBAAA |
| ABB | DDDDDDD | WBAAB |
| ABB | DDDDDDD | WBABA |
| ABB | DDDDDDD | WBABB |
| ABB | DDDDDDD | WBBAA |
| ABB | DDDDDDD | WBBAB |
| ABB | DDDDDDD | WBBBA |
| ABB | DDDDDDD | WBBBB | wherein each A is a modified nucleoside of a first type, each B is a modified nucleoside of a second type and each W is a modified nucleoside or nucleobase of either the first type, the second type or a third type, each D is a nucleoside comprising an unmodified 2'deoxy sugar moiety and unmodified nucleobase, and $^N$D is modified nucleoside comprising a modified nucleobase and an unmodified 2'deoxy sugar moiety.

In certain embodiments, each A comprises a modified sugar moiety. In certain embodiments, each A comprises a 2'-substituted sugar moiety. In certain embodiments, each A comprises a 2'-substituted sugar moiety selected from among F, ara-F, $OCH_3$ and $O(CH_2)_2$—$OCH_3$. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A comprises a modified nucleobase. In certain embodiments, each A comprises a modified nucleobase selected from among 2-thio-thymidine nucleoside and 5-propyne uridine nucleoside. In certain embodiments, each A comprises an HNA. In certain embodiments, each A comprises an F-HNA. In certain embodiments, each A comprises a 5'-substituted sugar moiety selected from among 5'-Me, and 5'-(R)-Me.

In certain embodiments, each B comprises a modified sugar moiety. In certain embodiments, each B comprises a 2'-substituted sugar moiety. In certain embodiments, each B comprises a 2'-substituted sugar moiety selected from among F, (ara)-F, $OCH_3$ and $O(CH_2)_2$—$OCH_3$. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA. In certain embodiments, each B comprises a modified nucleobase. In certain embodiments, each B comprises a modified nucleobase selected from among 2-thio-thymidine nucleoside and 5-propyne uridine nucleoside. In certain embodiments, each B comprises an HNA. In certain embodiments, each B comprises an F-HNA. In certain embodiments, each B comprises a 5'-substituted sugar moiety selected from among 5'-Me, and 5'-(R)-Me.

In certain embodiments, each C comprises a modified sugar moiety. In certain embodiments, each C comprises a 2'-substituted sugar moiety. In certain embodiments, each C comprises a 2'-substituted sugar moiety selected from among F, (ara)-F, $OCH_3$ and $O(CH_2)_2$—$OCH_3$. In certain embodiments, each C comprises a 5'-substituted sugar moiety. In certain embodiments, each C comprises a 5'-substituted sugar moiety selected from among 5'-Me, and 5'-(R)-Me. In certain embodiments, each C comprises a bicyclic sugar moiety. In certain embodiments, each C comprises a bicyclic sugar moiety selected from among cEt, cMOE, LNA, α-L-LNA, ENA and 2'-thio LNA. In certain embodiments, each C comprises a modified nucleobase. In certain embodiments, each C comprises a modified nucleobase selected from among 2-thio-thymidine and 5-propyne uridine. In certain embodiments, each C comprises a 2-thio-thymidine nucleoside. In certain embodiments, each C comprises an HNA. In certain embodiments, each C comprises an F-HNA.

In certain embodiments, each W comprises a modified sugar moiety. In certain embodiments, each W comprises a 2'-substituted sugar moiety. In certain embodiments, each W comprises a 2'-substituted sugar moiety selected from among F, (ara)-F, $OCH_3$ and $O(CH_2)_2$—$OCH_3$. In certain embodiments, each W comprises a 5'-substituted sugar moiety. In certain embodiments, each W comprises a 5'-substituted sugar moiety selected from among 5'-Me, and 5'-(R)-Me. In certain embodiments, each W comprises a bicyclic sugar moiety. In certain embodiments, each W comprises a bicyclic sugar moiety selected from among cEt, cMOE, LNA, α-L-LNA, ENA and 2'-thio LNA. In certain embodiments, each W comprises a sugar surrogate. In certain embodiments, each W comprises a sugar surrogate selected from among HNA and F-HNA. In certain embodiments, each W comprises a 2-thio-thymidine nucleoside.

In certain embodiments, at least one of A or B comprises a bicyclic sugar moiety, and the other comprises a 2'-substituted sugar moiety. In certain embodiments, one of A or B is an LNA nucleoside and the other of A or B comprises a 2'-substituted sugar moiety. In certain embodiments, one of A or B is a cEt nucleoside and the other of A or B comprises a 2'-substituted sugar moiety. In certain embodiments, one of A or B is an α-L-LNA nucleoside and the other of A or B comprises a 2'-substituted sugar moiety. In certain embodiments, one of A or B is an LNA nucleoside and the other of A or B comprises a 2'-MOE sugar moiety. In certain embodiments, one of A or B is a cEt nucleoside and the other of A or B comprises a 2'-MOE sugar moiety. In certain embodiments, one of A or B is an α-L-LNA nucleoside and the other of A or B comprises a 2'-MOE sugar moiety. In certain embodiments, one of A or B is an LNA nucleoside and the other of A or B comprises a 2'-F sugar moiety. In certain embodiments, one of A or B is a cEt nucleoside and the other of A or B comprises a 2'-F sugar moiety. In certain embodiments, one of A or B is an α-L-LNA nucleoside and the other of A or B comprises a 2'-F sugar moiety. In certain embodiments, one of A or B is an LNA nucleoside and the other of A or B comprises a 2'-(ara)-F sugar moiety. In certain embodiments, one of A or B is a cEt nucleoside and the other of A or B comprises a 2'-(ara)-F sugar moiety. In certain embodiments, one of A or B is an α-L-LNA nucleoside and the other of A or B comprises a 2'-(ara)-F sugar moiety.

In certain embodiments, A comprises a bicyclic sugar moiety, and B comprises a 2'-substituted sugar moiety. In certain embodiments, A is an LNA nucleoside and B comprises a 2'-substituted sugar moiety. In certain embodiments, A is a cEt nucleoside and B comprises a 2'-substituted sugar moiety. In certain embodiments, A is an α-L-LNA nucleoside and B comprises a 2'-substituted sugar moiety.

In certain embodiments, A comprises a bicyclic sugar moiety, and B comprises a 2'-MOE sugar moiety. In certain embodiments, A is an LNA nucleoside and B comprises a 2'-MOE sugar moiety. In certain embodiments, A is a cEt nucleoside and B comprises a 2'-MOE sugar moiety. In certain embodiments, A is an α-L-LNA nucleoside and B comprises a 2'-MOE sugar moiety.

In certain embodiments, A comprises a bicyclic sugar moiety, and B comprises a 2'-F sugar moiety. In certain embodiments, A is an LNA nucleoside and B comprises a 2'-F sugar moiety. In certain embodiments, A is a cEt nucleoside and B comprises a 2'-F sugar moiety. In certain embodiments, A is an α-L-LNA nucleoside and B comprises a 2'-F sugar moiety.

In certain embodiments, A comprises a bicyclic sugar moiety, and B comprises a 2'-(ara)-F sugar moiety. In certain embodiments, A is an LNA nucleoside and B comprises a 2'-(ara)-F sugar moiety. In certain embodiments, A is a cEt nucleoside and B comprises a 2'-(ara)-F sugar moiety. In certain embodiments, A is an α-L-LNA nucleoside and B comprises a 2'-(ara)-F sugar moiety.

In certain embodiments, B comprises a bicyclic sugar moiety, and A comprises a 2'-MOE sugar moiety. In certain embodiments, B is an LNA nucleoside and A comprises a 2'-MOE sugar moiety. In certain embodiments, B is a cEt nucleoside and A comprises a 2'-MOE sugar moiety. In certain embodiments, B is an α-L-LNA nucleoside and A comprises a 2'-MOE sugar moiety.

In certain embodiments, B comprises a bicyclic sugar moiety, and A comprises a 2'-F sugar moiety. In certain embodiments, B is an LNA nucleoside and A comprises a 2'-F sugar moiety. In certain embodiments, B is a cEt nucleoside and A comprises a 2'-F sugar moiety. In certain embodiments, B is an α-L-LNA nucleoside and A comprises a 2'-F sugar moiety.

In certain embodiments, B comprises a bicyclic sugar moiety, and A comprises a 2'-(ara)-F sugar moiety. In certain embodiments, B is an LNA nucleoside and A comprises a 2'-(ara)-F sugar moiety. In certain embodiments, B is a cEt nucleoside and A comprises a 2'-(ara)-F sugar moiety. In certain embodiments, B is an α-L-LNA nucleoside and A comprises a 2'-(ara)-F sugar moiety.

In certain embodiments, at least one of A or B comprises a bicyclic sugar moiety, another of A or B comprises a 2'-substituted sugar moiety and W comprises a modified nucleobase. In certain embodiments, one of A or B is an LNA nucleoside, another of A or B comprises a 2'-substituted sugar moiety, and W comprises a modified nucleobase. In certain embodiments, one of A or B is a cEt nucleoside, another of A or B comprises a 2'-substituted sugar moiety, and C comprises a modified nucleobase. In certain embodiments, one of A or B is an α-L-LNA nucleoside, another of A or B comprises a 2'-substituted sugar moiety, and W comprises a modified nucleobase.

In certain embodiments, one of A or B comprises a bicyclic sugar moiety, another of A or B comprises a 2'-MOE sugar moiety, and W comprises a modified nucleobase. In certain embodiments, one of A or B is an LNA nucleoside, another of A or B comprises a 2'-MOE sugar moiety, and W comprises a modified nucleobase. In certain embodiments, one of A or B is a cEt nucleoside, another of A or B comprises a 2'-MOE sugar moiety, and W comprises a modified nucleobase. In certain embodiments, one of A or B is an α-L-LNA nucleoside, another of A or B comprises a 2'-MOE sugar moiety, and W comprises a modified nucleobase.

In certain embodiments, one of A or B comprises a bicyclic sugar moiety, another of A or B comprises a 2'-F sugar moiety, and W comprises a modified nucleobase. In certain embodiments, one of A or B is an LNA nucleoside, another of A or B comprises a 2'-F sugar moiety, and W comprises a modified nucleobase. In certain embodiments, one of A or B is a cEt nucleoside, another of A or B comprises a 2'-F sugar moiety, and W comprises a modified nucleobase. In certain embodiments, one of A or B is an α-L-LNA nucleoside, another of A or B comprises a 2'-F sugar moiety, and W comprises a modified nucleobase.

In certain embodiments, one of A or B comprises a bicyclic sugar moiety, another of A or B comprises a 2'-(ara)-F sugar moiety, and W comprises a modified nucleobase. In certain embodiments, one of A or B is an LNA nucleoside, another of A or B comprises a 2'-(ara)-F sugar moiety, and W comprises a modified nucleobase. In certain embodiments, one of A or B is a cEt nucleoside, another of A or B comprises a 2'-(ara)-F sugar moiety, and W comprises a modified nucleobase. In certain embodiments, one of A or B is an α-L-LNA nucleoside, another of A or B comprises a 2'-(ara)-F sugar moiety, and W comprises a modified nucleobase.

In certain embodiments, one of A or B comprises a bicyclic sugar moiety, another of A or B comprises a 2'-substituted sugar moiety, and W comprises a 2-thio-thymidine nucleobase. In certain embodiments, one of A or B is an LNA nucleoside, another of A or B comprises a 2'-substituted sugar moiety, and W comprises a 2-thio-thymidine nucleobase. In certain embodiments, one of A or B is a cEt nucleoside, another of A or B comprises a 2'-substituted sugar moiety, and W comprises a 2-thio-thymidine nucleobase. In certain embodiments, one of A or B is an α-L-LNA nucleoside, another of A or B comprises a 2'-substituted sugar moiety, and W comprises a 2-thio-thymidine nucleobase.

In certain embodiments, one of A or B comprises a bicyclic sugar moiety, another of A or B comprises a 2'-MOE sugar moiety, and W comprises a 2-thio-thymidine nucleobase. In certain embodiments, one of A or B is an LNA nucleoside, another of A or B comprises a 2'-MOE sugar moiety, and W comprises a 2-thio-thymidine nucleobase. In certain embodiments, one of A or B is a cEt nucleoside, another of A or B comprises a 2'-MOE sugar moiety, and W comprises a 2-thio-thymidine nucleobase. In certain embodiments, one of A or B is an α-L-LNA nucleoside, another of A or B comprises a 2'-MOE sugar moiety, and W comprises a 2-thio-thymidine nucleobase.

In certain embodiments, one of A or B comprises a bicyclic sugar moiety, another of A or B comprises a 2'-F sugar moiety, and W comprises a 2-thio-thymidine nucleobase. In certain embodiments, one of A or B is an LNA nucleoside, another of A or B comprises a 2'-F sugar moiety, and W comprises a 2-thio-thymidine nucleobase. In certain embodiments, one of A or B is a cEt nucleoside, another of A or B comprises a 2'-F sugar moiety, and W comprises a 2-thio-thymidine nucleobase. In certain embodiments, one of A or B is an α-L-LNA nucleoside, another of A or B comprises a 2'-F sugar moiety, and W comprises a 2-thio-thymidine nucleobase.

In certain embodiments, one of A or B comprises a bicyclic sugar moiety, another of A or B comprises a 2'-(ara)-F sugar moiety, and W comprises a 2-thio-thymidine nucleobase. In certain embodiments, one of A or B is an LNA nucleoside, another of A or B comprises a 2'-(ara)-F sugar moiety, and W comprises a 2-thio-thymidine nucleobase. In certain embodiments, one of A or B is a cEt nucleoside, another of A or B comprises a 2'-(ara)-F sugar moiety, and W comprises a 2-thio-thymidine nucleobase. In certain embodiments, one of A or B is an α-L-LNA nucleoside, another of A or B comprises a 2'-(ara)-F sugar moiety, and W comprises 2-thio-thymidine nucleobase.

In certain embodiments, one of A or B comprises a bicyclic sugar moiety, another of A or B comprises a 2'-MOE sugar moiety, and W comprises a 5-propyne uridine nucleobase. In certain embodiments, one of A or B is an LNA nucleoside, another of A or B comprises a 2'-MOE sugar moiety, and C comprises a 5-propyne uridine nucleobase. In certain embodiments, one of A or B is a cEt nucleoside, another of A or B comprises a 2'-MOE sugar moiety, and W comprises a 5-propyne uridine nucleobase. In certain embodiments, one of A or B is an α-L-LNA nucleoside, another of A or B comprises a 2'-MOE sugar moiety, and C comprises a 5-propyne uridine nucleobase.

In certain embodiments, one of A or B comprises a bicyclic sugar moiety, another of A or B comprises a 2'-F sugar moiety, and W comprises a 5-propyne uridine nucleobase. In certain embodiments, one of A or B is an LNA nucleoside, another of A or B comprises a 2'-F sugar moiety, and C comprises a 5-propyne uridine nucleobase. In certain embodiments, one of A or B is a cEt nucleoside, another of A or B comprises a 2'-F sugar moiety, and W comprises a 5-propyne uridine nucleobase. In certain embodiments, one of A or B is an α-L-LNA nucleoside, another of A or B comprises a 2'-F sugar moiety, and W comprises a 5-propyne uridine nucleobase.

In certain embodiments, one of A or B comprises a bicyclic sugar moiety, another of A or B comprises a 2'-(ara)-F sugar moiety, and W comprises a 5-propyne uridine nucleobase. In certain embodiments, one of A or B is an LNA nucleoside, another of A or B comprises a 2'-(ara)-F sugar moiety, and W comprises a 5-propyne uridine nucleobase. In certain embodiments, one of A or B is a cEt nucleoside, another of A or B comprises a 2'-(ara)-F sugar moiety, and W comprises a 5-propyne uridine nucleobase. In certain embodiments, one of A or B is an α-L-LNA nucleoside, another of A or B comprises a 2'-(ara)-F sugar moiety, and W comprises a 5-propyne uridine nucleobase.

In certain embodiments, one of A or B comprises a bicyclic sugar moiety, another of A or B comprises a 2'-MOE sugar moiety, and W comprises a sugar surrogate. In certain embodiments, one of A or B is an LNA nucleoside, another of A or B comprises a 2'-MOE sugar moiety, and W comprises a sugar surrogate. In certain embodiments, one of A or B is a cEt nucleoside, another of A or B comprises a 2'-MOE sugar moiety, and W comprises a sugar surrogate. In certain embodiments, one of A or B is an α-L-LNA nucleoside, another of A or B comprises a 2'-MOE sugar moiety, and W comprises a sugar surrogate.

In certain embodiments, one of A or B comprises a bicyclic sugar moiety, another of A or B comprises a 2'-F sugar moiety, and W comprises a sugar surrogate. In certain embodiments, one of A or B is an LNA nucleoside, another of A or B comprises a 2'-F sugar moiety, and W comprises a sugar surrogate. In certain embodiments, one of A or B is a cEt nucleoside, another of A or B comprises a 2'-F sugar moiety, and W comprises a sugar surrogate. In certain embodiments, one of A or B is an α-L-LNA nucleoside, another of A or B comprises a 2'-F sugar moiety, and W comprises a sugar surrogate.

In certain embodiments, one of A or B comprises a bicyclic sugar moiety, another of A or B comprises a 2'-(ara)-F sugar moiety, and W comprises a sugar surrogate. In certain embodiments, one of A or B is an LNA nucleoside, another of A or B comprises a 2'-(ara)-F sugar moiety, and W comprises a sugar surrogate. In certain embodiments, one of A or B is a cEt nucleoside, another of A or B comprises a 2'-(ara)-F sugar moiety, and W comprises a sugar surrogate. In certain embodiments, one of A or B is an α-L-LNA nucleoside, another of A or B comprises a 2'-(ara)-F sugar moiety, and W comprises sugar surrogate.

In certain embodiments, one of A or B comprises a bicyclic sugar moiety, another of A or B comprises a 2'-MOE sugar moiety, and W comprises a HNA sugar surrogate. In certain embodiments, one of A or B is an LNA nucleoside, another of A or B comprises a 2'-MOE sugar moiety, and W comprises a HNA sugar surrogate. In certain embodiments, one of A or B is a cEt nucleoside, another of A or B comprises a 2'-MOE sugar moiety, and W comprises a HNA sugar surrogate. In certain embodiments, one of A or B is an α-L-LNA nucleoside, another of A or B comprises a 2'-MOE sugar moiety, and W comprises a HNA sugar surrogate.

In certain embodiments, one of A or B comprises a bicyclic sugar moiety, another of A or B comprises a 2'-F sugar moiety, and W comprises a HNA sugar surrogate. In certain embodiments, one of A or B is an LNA nucleoside, another of A or B comprises a 2'-F sugar moiety, and W comprises a HNA sugar surrogate. In certain embodiments, one of A or B is a cEt nucleoside, another of A or B comprises a 2'-F sugar moiety, and W comprises a HNA sugar surrogate. In certain embodiments, one of A or B is an α-L-LNA nucleoside, another of A or B comprises a 2'-F sugar moiety, and W comprises a sugar HNA surrogate.

In certain embodiments, one of A or B comprises a bicyclic sugar moiety, another of A or B comprises a 2'-(ara)-F sugar moiety, and W comprises a HNA sugar surrogate. In certain embodiments, one of A or B is an LNA nucleoside, another of A or B comprises a 2'-(ara)-F sugar moiety, and W comprises a HNA sugar surrogate. In certain embodiments, one of A or B is a cEt nucleoside, another of A or B comprises a 2'-(ara)-F sugar moiety, and W comprises a HNA sugar surrogate. In certain embodiments, one of A or B is an α-L-LNA nucleoside, another of A or B comprises a 2'-(ara)-F sugar moiety, and W comprises a HNA sugar surrogate.

In certain embodiments, one of A or B comprises a bicyclic sugar moiety, another of A or B comprises a 2'-MOE sugar moiety, and W comprises a F-HNA sugar surrogate. In certain embodiments, one of A or B is an LNA nucleoside, another of A or B comprises a 2'-MOE sugar moiety, and W comprises a F-HNA sugar surrogate. In certain embodiments, one of A or B is a cEt nucleoside, another of A or B comprises a 2'-MOE sugar moiety, and W comprises a F-HNA sugar surrogate. In certain embodiments, one of A or B is an α-L-LNA nucleoside, another of A or B comprises a 2'-MOE sugar moiety, and W comprises a F-HNA sugar surrogate.

In certain embodiments, one of A or B comprises a bicyclic sugar moiety, another of A or B comprises a 2'-F sugar moiety, and W comprises a F-HNA sugar surrogate. In certain embodiments, one of A or B is an LNA nucleoside, another of A or B comprises a 2'-F sugar moiety, and W comprises a F-HNA sugar surrogate. In certain embodiments, one of A or B is a cEt nucleoside, another of A or B comprises a 2'-F sugar moiety, and W comprises a F-HNA sugar surrogate. In certain embodiments, one of A or B is an α-L-LNA nucleoside, another of A or B comprises a 2'-F sugar moiety, and W comprises a F-HNA sugar surrogate.

In certain embodiments, one of A or B comprises a bicyclic sugar moiety, another of A or B comprises a 2'-(ara)-F sugar moiety, and W comprises a F-HNA sugar surrogate. In certain embodiments, one of A or B is an LNA nucleoside, another of A or B comprises a 2'-(ara)-F sugar moiety, and W comprises a F-HNA sugar surrogate. In certain embodiments, one of A or B is a cEt nucleoside, another of A or B comprises a 2'-(ara)-F sugar moiety, and W comprises a F-HNA sugar surrogate. In certain embodiments, one of A or B is an α-L-LNA nucleoside, another of A or B comprises a 2'-(ara)-F sugar moiety, and W comprises a F-HNA sugar surrogate.

In certain embodiments, one of A or B comprises a bicyclic sugar moiety, another of A or B comprises a 2'-MOE sugar moiety, and W comprises a 5'-Me DNA sugar moiety. In certain embodiments, one of A or B is an LNA nucleoside, another of A or B comprises a 2'-MOE sugar moiety, and W comprises a 5'-Me DNA sugar moiety. In certain embodiments, one of A or B is a cEt nucleoside, another of A or B comprises a 2'-MOE sugar moiety, and W comprises a 5'-Me DNA sugar moiety. In certain embodiments, one of A or B is an α-L-LNA nucleoside, another of A or B comprises a 2'-MOE sugar moiety, and W comprises a 5'-Me DNA sugar moiety.

In certain embodiments, one of A or B comprises a bicyclic sugar moiety, another of A or B comprises a 2'-F sugar moiety, and W comprises a 5'-Me DNA sugar moiety. In certain embodiments, one of A or B is an LNA nucleoside, another of A or B comprises a 2'-F sugar moiety, and W comprises a 5'-Me DNA sugar moiety. In certain embodiments, one of A or B is a cEt nucleoside, another of A or B comprises a 2'-F sugar moiety, and W comprises a 5'-Me DNA sugar moiety. In certain embodiments, one of A or B is an α-L-LNA nucleoside, another of A or B comprises a 2'-F sugar moiety, and W comprises a 5'-Me DNA sugar moiety.

In certain embodiments, one of A or B comprises a bicyclic sugar moiety, another of A or B comprises a 2'-(ara)-F sugar moiety, and W comprises a 5'-Me DNA sugar moiety. In certain embodiments, one of A or B is an LNA nucleoside, another of A or B comprises a 2'-(ara)-F sugar moiety, and W comprises a 5'-Me DNA sugar moiety. In certain embodiments, one of A or B is a cEt nucleoside, another of A or B comprises a 2'-(ara)-F sugar moiety, and W comprises a 5'-Me DNA sugar moiety. In certain embodiments, one of A or B is an α-L-LNA nucleoside, another of A or B comprises a 2'-(ara)-F sugar moiety, and W comprises a 5'-Me DNA sugar moiety.

In certain embodiments, one of A or B comprises a bicyclic sugar moiety, another of A or B comprises a 2'-MOE sugar moiety, and W comprises a 5'-(R)-Me DNA sugar moiety. In certain embodiments, one of A or B is an LNA nucleoside, another of A or B comprises a 2'-MOE sugar moiety, and W comprises a 5'-(R)-Me DNA sugar moiety. In certain embodiments, one of A or B is a cEt nucleoside, another of A or B comprises a 2'-MOE sugar moiety, and W comprises a 5'-(R)-Me DNA sugar moiety. In certain embodiments, one of A or B is an α-L-LNA nucleoside, another of A or B comprises a 2'-MOE sugar moiety, and W comprises a 5'-(R)-Me DNA sugar moiety.

In certain embodiments, one of A or B comprises a bicyclic sugar moiety, another of A or B comprises a 2'-F sugar moiety, and W comprises a 5'-(R)-Me DNA sugar moiety. In certain embodiments, one of A or B is an LNA nucleoside, another of A or B comprises a 2'-F sugar moiety, and W comprises a 5'-(R)-Me DNA sugar moiety. In certain embodiments, one of A or B is a cEt nucleoside, another of A or B comprises a 2'-F sugar moiety, and W comprises a 5'-(R)-Me DNA sugar moiety. In certain embodiments, one of A or B is an α-L-LNA nucleoside, another of A or B comprises a 2'-F sugar moiety, and W comprises a 5'-(R)-Me DNA sugar moiety.

In certain embodiments, one of A or B comprises a bicyclic sugar moiety, another of A or B comprises a 2'-(ara)-F sugar moiety, and W comprises a 5'-(R)-Me DNA sugar moiety. In certain embodiments, one of A or B is an LNA nucleoside, another of A or B comprises a 2'-(ara)-F sugar moiety, and W comprises a 5'-(R)-Me DNA sugar moiety. In certain embodiments, one of A or B is a cEt nucleoside, another of A or B comprises a 2'-(ara)-F sugar moiety, and W comprises a 5'-(R)-Me DNA sugar moiety. In certain embodiments, one of A or B is an α-L-LNA nucleoside, another of A or B comprises a 2'-(ara)-F sugar moiety, and W comprises a 5'-(R)-Me DNA sugar moiety.

In certain embodiments, at least two of A, B or W comprises a 2'-substituted sugar moiety, and the other comprises a bicyclic sugar moiety. In certain embodiments, at least two of A, B or W comprises a bicyclic sugar moiety, and the other comprises a 2'-substituted sugar moiety. In certain embodiments, a gapmer has a sugar motif other than: E-K-K-(D)$_9$-K-K-E; E-E-E-E-K-(D)$_9$-E-E-E-E-E; E-K-K-K-(D)$_9$-K-K-K-E; K-E-E-K-(D)$_9$-K-E-E-K; K-D-D-K-(D)$_9$-K-D-D-K; K-E-K-E-K-(D)$_9$-K-E-K-E-K; K-D-K-D-K-(D)$_9$-K-D-K-D-K; E-K-E-K-(D)$_9$-K-E-K-E; E-E-E-E-K-(D)$_8$-E-E-E-E; or E-K-E-K-E-(D)$_9$-E-K-E-K-E, E-E-E-K-K-(D)$_7$-E-E-K, E-K-E-K-K-(D)$_7$-K-E-K-E, E-K-E-K-E-K-(D)$_7$-K-E-K-E, wherein K is a nucleoside comprising a cEt sugar moiety and E is a nucleoside comprising a 2'-MOE sugar moiety.

In certain embodiments a gapmer comprises a A-(D)$_4$-A-(D)$_4$-A-(D)$_4$-AA motif. In certain embodiments a gapmer comprises a B-(D)$_4$-A-(D)$_4$-A-(D)$_4$-AA motif. In certain embodiments a gapmer comprises a A-(D)$_4$-B-(D)$_4$-

A-(D)₄-AA motif. In certain embodiments a gapmer comprises a A-(D)₄-A-(D)₄-B-(D)₄-AA motif. In certain embodiments a gapmer comprises a A-(D)₄-A-(D)₄-A-(D)₄-BA motif. In certain embodiments a gapmer comprises a A-(D)₄-A-(D)₄-A-(D)₄-BB motif. In certain embodiments a gapmer comprises a K-(D)₄-K-(D)₄-K-(D)₄-K-E motif.

viii. Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif, as described above for nucleoside motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The nucleoside motif is independently selected, so such oligonucleotides having a gapped internucleoside linkage motif may or may not have a gapped nucleoside motif and if it does have a gapped nucleoside motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosponate linkages. In certain embodiments, oligonucleotides having a gapmer nucleoside motif comprise a linkage motif comprising all phosphorothioate linkages except for one or two methylphosponate linkages. In certain embodiments, one methylphosponate linkage is in the central gap of an oligonucleotide having a gapmer nucleoside motif.

ix. Certain Modification Motifs

Modification motifs define oligonucleotides by nucleoside motif (sugar motif and nucleobase motif) and linkage motif. For example, certain oligonucleotides have the following modification motif:

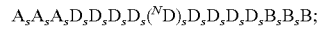

wherein each A is a modified nucleoside comprising a 2'-substituted sugar moiety; each D is an unmodified 2'-deoxynucleoside; each B is a modified nucleoside comprising a bicyclic sugar moiety; $^N$D is a modified nucleoside comprising a modified nucleobase; and s is a phosphorothioate internucleoside linkage. Thus, the sugar motif is a gapmer motif. The nucleobase modification motif is a single modified nucleobase at $8^{th}$ nucleoside from the 5'-end. Combining the sugar motif and the nucleobase modification motif, the nucleoside motif is an interrupted gapmer where the gap of the sugar modified gapmer is interrupted by a nucleoside comprising a modified nucleobase. The linkage motif is uniform phosphorothioate. The following non-limiting Table further illustrates certain modification motifs:

TABLE 13

Certain Modification Motifs

| 5'-wing region | Central gap region | 3'-wing region |
|---|---|---|
| B$_s$B$_s$ | $_s$D$_s$D$_s$D$_s$D$_s$D$_s$D$_s$D$_s$D$_s$ | A$_s$A$_s$A$_s$A$_s$A$_s$A$_s$A$_s$A$_s$ |
| AsBsBs | DsDsDsDsDsDsDsDs | BsBsA |
| AsBsBs | DsDsDsDs($^N$D)sDsDsDs | BsBsA |
| AsBsBs | DsDsDsDsAsDsDsDs | BsBsA |
| AsBsBs | DsDsDsDsBsDsDsDs | BsBsA |
| AsBsBs | DsDsDsDsWsDsDsDs | BsBsA |
| AsBsBsBs | DsDsDsDsDsDsDsDs | BsBsAsBsB |
| AsBsBs | DsDsDsDsDsDsDsDs | BsBsAsBsB |
| BsBsAsBsBs | DsDsDsDsDsDsDsDs | BsBsA |
| AsBsBs | DsDsDsDsDsDsDsDs | BsBsAsBsBsBsB |
| AsAsBsAsAs | DsDsDsDsDsDsDsDs | BsBsA |
| AsAsAsBsAsAs | DsDsDsDsDsDsDsDs | BsBsA |
| AsAsBsAsAs | DsDsDsDsDsDsDsDs | AsAsBsAsA |
| AsAsAsBsAsAs | DsDsDsDsDsDsDsDs | AsAsBsAsAsA |
| AsAsAsAsBsAsAs | DsDsDsDsDsDsDsDs | BsBsA |
| AsBsAsBs | DsDsDsDsDsDsDsDs | BsAsBsA |
| AsBsAsBs | DsDsDsDsDsDsDsDs | AsAsBsAsAs |
| AsBsBs | DsDsDsDsDsDsDsDs | BsBsA |
| BsBsAsBsBsBsB | DsDsDsDsDsDsDsDs | BsAsBsA |
| AsAsAsAsAs | DsDsDsDsDsDsDsDs | AsAsAsAsA |
| AsAsAsAsAs | DsDsDsDsDsDs | AsAsAsAsA |

TABLE 13-continued

Certain Modification Motifs

| 5'-wing region | Central gap region | 3'-wing region |
|---|---|---|
| AsAsAsAsAs | DsDsDsDsDsDsDsDs | BsBsAsBsBsBsB |
| AsAsAsBsBs | DsDsDsDsDsDs | BsBsA |
| AsBsAsBs | DsDsDsDsDsDsDs | BsBsA |
| AsBsAsBs | DsDsDsDsDsDs | AsAsAsBsBs |
| AsAsAsAsBs | DsDsDsDsDsDs | BsAsAsAsA |
| BsBs | DsDsDsDsDsDs | AsA |
| AsAs | DsDsDsDsDsDs | AsAsAsAsAsAsA |
| AsAsAs | DsDsDsDsDsDs | AsAsAsAsAsA |
| AsAsAs | DsDsDsDsDsDs | AsAsAsAsA |
| AsBs | DsDsDsDsDsDs | BsBsBsA |
| AsBsBsBs | DsDsDsDsDsDsDs | BsA |
| AsBs | DsDsDsDsDsDsDs | BsBsBsA |
| AsAsAsBsBs | DsDsDs($^N$D)sDsDsDs | BsBsAsAsA |
| AsAsAsBsBs | DsDsDsAsDsDsDs | BsBsAsAsA |
| AsAsAsBsBs | DsDsDsBsDsDsDs | BsBsAsAsA |
| AsAsAsAsBs | DsDsDsDsDsDs | BsAsAsAsA |
| AsAsBsBsBs | DsDsDsDsDsDs | BsBsBsAsA |
| AsAsAsAsBs | DsDsDsDsDsDs | AsAsAsAsAs |
| AsAsAsBsBs | DsDsDsDsDsDs | AsAsAsAsAs |
| AsBsBsBs | DsDsDsDsDsDs | AsAsAsAsAs |
| AsAsAsAs | DsDsDsDsDsDs | BsAsAsAsAs |
| AsAsAsAs | DsDsDsDsDsDs | BsBsAsAsAs |
| AsAsAsAs | DsDsDsDsDsDs | BsBsBsAsAs |
| AsBsBs | DsDsDsDs($^N$D)s($^N$D)sDsDs | BsBsA |
| AsBsBs | Ds($^N$D)s($^N$D)s($^N$D)s($^N$D)sDs($^N$D)s($^N$D)s | BsBsA |
| AsBsBs | Ds($^N$D)sDsDsDsDsDsDs | BsBsA |
| AsBsBs | DsDs($^N$D)sDsDsDsDsDs | BsBsA |
| AsBsBs | Ds($^N$D)s($^N$D)sDsDsDsDsDs | BsBsA |
| AsBsBs | DsDs(D)zDsDsDsDsDs | BsBsA |
| AsBsBs | Ds(D)zDsDsDsDsDsDs | BsBsA |
| AsBsBs | (D)zDsDsDsDsDsDsDs | BsBsA |
| AsBsBs | DsDsAsDsDsDsDsDs | BsBsA |
| AsBsBs | DsDsDsDsDsDsDsDs | BsBsA |
| AsBsBs | AsDsDsDsDsDsDsDs | BsBsA |
| AsBsBs | DsDsDsDsDsDsDsDs | BsBsA |
| AsBsAsBs | DsDs(D)zDsDsDsDsDs | BsBsBsAsAs |
| AsAsAsBsBs | DsDs($^N$D)sDsDsDsDsDs | AsA |
| AsBsBsBs | Ds(D)zDsDsDsDsDsDs | AsAsAsBsBs |
| AsBsBs | DsDsDsDsDsDsDs(D)z | BsBsA |
| AsAsAsBsBs | DsDsDsAsDsDsDs | BsBsBsAsA |
| AsAsBsBsBs | DsDsDsBsDsDsDs | BsBsBsAsA |
| AsBsAsBs | DsDsDsAsDsDsDs | BsBsAsBsBsBsB |
| AsBsBsBs | DsDsDs(D)zDsDsDs | BsA |
| AsAsBsBsBs | DsDsAsDsDsDs | BsBsA |
| AsBsBs | DsDsDs(D)zDsDsDs | BsBsBsA |
| BsBs | DsDs($^N$D)sDs($^N$D)sDsDsDs | BsBsAsBsBsBsB | wherein each A and B are nucleosides comprising differently modified sugar moieties, each D is a nucleoside comprising an unmodified 2'deoxy sugar moiety, each W is a modified nucleoside of either the first type, the second type or a third type, each $^N$D is a modified nucleoside comprising a modified nucleobase, s is a phosphorothioate internucleoside linkage, and z is a non-phosphorothioate internucleoside linkage.

In certain embodiments, each A comprises a modified sugar moiety. In certain embodiments, each A comprises a 2'-substituted sugar moiety. In certain embodiments, each A comprises a 2'-substituted sugar moiety selected from among F, (ara)-F, OCH$_3$ and O(CH$_2$)$_2$—OCH$_3$. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A comprises a modified nucleobase. In certain embodiments, each A comprises a modified nucleobase selected from among 2-thio-thymidine nucleoside and 5-propyne uridine nucleoside. In certain embodiments, each B comprises a modified sugar moiety. In certain embodiments, each B comprises a 2'-substituted sugar moiety. In certain embodiments, each B comprises a 2'-substituted sugar moiety selected from among F, (ara)-F, OCH$_3$ and O(CH$_2$)$_2$—OCH$_3$. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA. In certain embodiments, each B comprises a modified nucleobase. In certain embodiments, each B comprises a modified nucleobase selected from among 2-thio-thymidine nucleoside and 5-propyne uridine nucleoside. In certain embodiments, each A comprises an HNA. In certain embodiments, each A comprises an F-HNA.

In certain embodiments, each W comprises a modified sugar moiety. In certain embodiments, each W comprises a 2'-substituted sugar moiety. In certain embodiments, each W comprises a 2'-substituted sugar moiety selected from among F, (ara)-F, OCH$_3$ and O(CH$_2$)$_2$—OCH$_3$. In certain embodiments, each W comprises a 5'-substituted sugar moiety. In certain embodiments, each W comprises a 5'-substituted sugar moiety selected from among 5'-Me, and 5'-(R)-Me. In certain embodiments, each W comprises a bicyclic sugar moiety. In certain embodiments, each W comprises a bicyclic sugar moiety selected from among cEt, cMOE, LNA, α-L-LNA, ENA and 2'-thio LNA. In certain embodiments, each W comprises a sugar surrogate. In certain embodiments, each W comprises a sugar surrogate selected from among HNA and F-HNA.

In certain embodiments, at least one of A or B comprises a bicyclic sugar moiety, and the other comprises a 2'-substituted sugar moiety. In certain embodiments, one of A or B is an LNA nucleoside and the other of A or B comprises a 2'-substituted sugar moiety. In certain embodiments, one of A or B is a cEt nucleoside and the other of A or B comprises a 2'-substituted sugar moiety. In certain embodiments, one of A or B is an α-L-LNA nucleoside and the other of A or B comprises a 2'-substituted sugar moiety. In certain embodiments, one of A or B is an LNA nucleoside and the other of A or B comprises a 2'-MOE sugar moiety. In certain embodiments, one of A or B is a cEt nucleoside and the other of A or B comprises a 2'-MOE sugar moiety. In certain embodiments, one of A or B is an α-L-LNA nucleoside and the other of A or B comprises a 2'-MOE sugar moiety. In certain embodiments, one of A or B is an LNA nucleoside and the other of A or B comprises a 2'-F sugar moiety. In certain embodiments, one of A or B is a cEt nucleoside and the other of A or B comprises a 2'-F sugar moiety. In certain embodiments, one of A or B is an α-L-LNA nucleoside and the other of A or B comprises a 2'-F sugar moiety. In certain embodiments, one of A or B is an LNA nucleoside and the other of A or B comprises a 2'-(ara)-F sugar moiety. In certain embodiments, one of A or B is a cEt nucleoside and the other of A or B comprises a 2'-(ara)-F sugar moiety. In certain embodiments, one of A or B is an α-L-LNA nucleoside and the other of A or B comprises a 2'-(ara)-F sugar moiety.

In certain embodiments, A comprises a bicyclic sugar moiety, and B comprises a 2'-substituted sugar moiety. In certain embodiments, A is an LNA nucleoside and B comprises a 2'-substituted sugar moiety. In certain embodiments, A is a cEt nucleoside and B comprises a 2'-substituted sugar moiety. In certain embodiments, A is an α-L-LNA nucleoside and B comprises a 2'-substituted sugar moiety.

In certain embodiments, A comprises a bicyclic sugar moiety, and B comprises a 2'-MOE sugar moiety. In certain embodiments, A is an LNA nucleoside and B comprises a 2'-MOE sugar moiety. In certain embodiments, A is a cEt nucleoside and B comprises a 2'-MOE sugar moiety. In certain embodiments, A is an α-L-LNA nucleoside and B comprises a 2'-MOE sugar moiety.

In certain embodiments, A comprises a bicyclic sugar moiety, and B comprises a 2'-F sugar moiety. In certain embodiments, A is an LNA nucleoside and B comprises a 2'-F sugar moiety. In certain embodiments, A is a cEt nucleoside and B comprises a 2'-F sugar moiety. In certain embodiments, A is an α-L-LNA nucleoside and B comprises a 2'-F sugar moiety.

In certain embodiments, A comprises a bicyclic sugar moiety, and B comprises a 2'-(ara)-F sugar moiety. In certain embodiments, A is an LNA nucleoside and B comprises a 2'-(ara)-F sugar moiety. In certain embodiments, A is a cEt nucleoside and B comprises a 2'-(ara)-F sugar moiety. In certain embodiments, A is an α-L-LNA nucleoside and B comprises a 2'-(ara)-F sugar moiety.

In certain embodiments, B comprises a bicyclic sugar moiety, and A comprises a 2'-MOE sugar moiety. In certain embodiments, B is an LNA nucleoside and A comprises a 2'-MOE sugar moiety. In certain embodiments, B is a cEt nucleoside and A comprises a 2'-MOE sugar moiety. In certain embodiments, B is an α-L-LNA nucleoside and A comprises a 2'-MOE sugar moiety.

In certain embodiments, B comprises a bicyclic sugar moiety, and A comprises a 2'-F sugar moiety. In certain embodiments, B is an LNA nucleoside and A comprises a 2'-F sugar moiety. In certain embodiments, B is a cEt nucleoside and A comprises a 2'-F sugar moiety. In certain embodiments, B is an α-L-LNA nucleoside and A comprises a 2'-F sugar moiety.

In certain embodiments, B comprises a bicyclic sugar moiety, and A comprises a 2'-(ara)-F sugar moiety. In certain embodiments, B is an LNA nucleoside and A comprises a 2'-(ara)-F sugar moiety. In certain embodiments, B is a cEt nucleoside and A comprises a 2'-(ara)-F sugar moiety. In certain embodiments, B is an α-L-LNA nucleoside and A comprises a 2'-(ara)-F sugar moiety.

In certain embodiments, at least one of A or B comprises a bicyclic sugar moiety, another of A or B comprises a 2'-substituted sugar moiety and W comprises a modified nucleobase. In certain embodiments, one of A or B is an LNA nucleoside, another of A or B comprises a 2'-substituted sugar moiety, and W comprises a modified nucleobase. In certain embodiments, one of A or B is a cEt nucleoside, another of A or B comprises a 2'-substituted sugar moiety, and C comprises a modified nucleobase. In certain embodiments, one of A or B is an α-L-LNA nucleoside, another of A or B comprises a 2'-substituted sugar moiety, and W comprises a modified nucleobase.

In certain embodiments, one of A or B comprises a bicyclic sugar moiety, another of A or B comprises a 2'-MOE sugar moiety, and W comprises a modified nucleobase. In certain embodiments, one of A or B is an LNA nucleoside, another of A or B comprises a 2'-MOE sugar moiety, and W comprises a modified nucleobase. In certain embodiments, one of A or B is a cEt nucleoside, another of A or B comprises a 2'-MOE sugar moiety, and W comprises a modified nucleobase. In certain embodiments, one of A or B is an α-L-LNA nucleoside, another of A or B comprises a 2'-MOE sugar moiety, and W comprises a modified nucleobase.

In certain embodiments, one of A or B comprises a bicyclic sugar moiety, another of A or B comprises a 2'-F sugar moiety, and W comprises a modified nucleobase. In certain embodiments, one of A or B is an LNA nucleoside, another of A or B comprises a 2'-F sugar moiety, and W comprises a modified nucleobase. In certain embodiments, one of A or B is a cEt nucleoside, another of A or B comprises a 2'-F sugar moiety, and W comprises a modified nucleobase. In certain embodiments, one of A or B is an α-L-LNA nucleoside, another of A or B comprises a 2'-F sugar moiety, and W comprises a modified nucleobase.

In certain embodiments, one of A or B comprises a bicyclic sugar moiety, another of A or B comprises a 2'-(ara)-F sugar moiety, and W comprises a modified nucleobase. In certain embodiments, one of A or B is an LNA nucleoside, another of A or B comprises a 2'-(ara)-F sugar moiety, and W comprises a modified nucleobase. In certain embodiments, one of A or B is a cEt nucleoside, another of A or B comprises a 2'-(ara)-F sugar moiety, and W comprises a modified nucleobase. In certain embodiments, one of A or B is an α-L-LNA nucleoside, another of A or B comprises a 2'-(ara)-F sugar moiety, and W comprises a modified nucleobase.

In certain embodiments, one of A or B comprises a bicyclic sugar moiety, another of A or B comprises a 2'-substituted sugar moiety, and W comprises a 2-thio-thymidine nucleobase. In certain embodiments, one of A or B is an LNA nucleoside, another of A or B comprises a 2'-substituted sugar moiety, and W comprises a 2-thio-thymidine nucleobase. In certain embodiments, one of A or B is a cEt nucleoside, another of A or B comprises a 2'-substituted sugar moiety, and W comprises a 2-thio-thymidine nucleobase. In certain embodiments, one of A or B is an α-L-LNA nucleoside, another of A or B comprises a 2'-substituted sugar moiety, and W comprises a 2-thio-thymidine nucleobase.

In certain embodiments, one of A or B comprises a bicyclic sugar moiety, another of A or B comprises a 2'-MOE sugar moiety, and W comprises a 2-thio-thymidine nucleobase. In certain embodiments, one of A or B is an LNA nucleoside, another of A or B comprises a 2'-MOE sugar moiety, and W comprises a 2-thio-thymidine nucleobase. In certain embodiments, one of A or B is a cEt nucleoside, another of A or B comprises a 2'-MOE sugar moiety, and W comprises a 2-thio-thymidine nucleobase. In certain embodiments, one of A or B is an α-L-LNA nucleoside, another of A or B comprises a 2'-MOE sugar moiety, and W comprises a 2-thio-thymidine nucleobase.

In certain embodiments, one of A or B comprises a bicyclic sugar moiety, another of A or B comprises a 2'-F sugar moiety, and W comprises a 2-thio-thymidine nucleobase. In certain embodiments, one of A or B is an LNA nucleoside, another of A or B comprises a 2'-F sugar moiety, and W comprises a 2-thio-thymidine nucleobase. In certain embodiments, one of A or B is a cEt nucleoside, another of A or B comprises a 2'-F sugar moiety, and W comprises a 2-thio-thymidine nucleobase. In certain embodiments, one of A or B is an α-L-LNA nucleoside, another of A or B comprises a 2'-F sugar moiety, and W comprises a 2-thio-thymidine nucleobase.

In certain embodiments, one of A or B comprises a bicyclic sugar moiety, another of A or B comprises a 2'-(ara)-F sugar moiety, and W comprises a 2-thio-thymidine nucleobase. In certain embodiments, one of A or B is an LNA nucleoside, another of A or B comprises a 2'-(ara)-F sugar moiety, and W comprises a 2-thio-thymidine nucleobase. In certain embodiments, one of A or B is a cEt nucleoside, another of A or B comprises a 2'-(ara)-F sugar moiety, and W comprises a 2-thio-thymidine nucleobase. In certain embodiments, one of A or B is an α-L-LNA nucleoside, another of A or B comprises a 2'-(ara)-F sugar moiety, and W comprises 2-thio-thymidine nucleobase.

In certain embodiments, one of A or B comprises a bicyclic sugar moiety, another of A or B comprises a 2'-MOE sugar moiety, and W comprises a 5-propyne uridine nucleobase. In certain embodiments, one of A or B is an LNA nucleoside, another of A or B comprises a 2'-MOE sugar moiety, and C comprises a 5-propyne uridine nucleobase. In certain embodiments, one of A or B is a cEt nucleoside, another of A or B comprises a 2'-MOE sugar moiety, and W comprises a 5-propyne uridine nucleobase. In certain embodiments, one of A or B is an α-L-LNA nucleoside, another of A or B comprises a 2'-MOE sugar moiety, and C comprises a 5-propyne uridine nucleobase.

In certain embodiments, one of A or B comprises a bicyclic sugar moiety, another of A or B comprises a 2'-F sugar moiety, and W comprises a 5-propyne uridine nucleobase. In certain embodiments, one of A or B is an LNA nucleoside, another of A or B comprises a 2'-F sugar moiety, and C comprises a 5-propyne uridine nucleobase. In certain embodiments, one of A or B is a cEt nucleoside, another of A or B comprises a 2'-F sugar moiety, and W comprises a 5-propyne uridine nucleobase. In certain embodiments, one of A or B is an α-L-LNA nucleoside, another of A or B comprises a 2'-F sugar moiety, and W comprises a 5-propyne uridine nucleobase.

In certain embodiments, one of A or B comprises a bicyclic sugar moiety, another of A or B comprises a 2'-(ara)-F sugar moiety, and W comprises a 5-propyne uridine nucleobase. In certain embodiments, one of A or B is an LNA nucleoside, another of A or B comprises a 2'-(ara)-F sugar moiety, and W comprises a 5-propyne uridine nucleobase. In certain embodiments, one of A or B is a cEt nucleoside, another of A or B comprises a 2'-(ara)-F sugar moiety, and W comprises a 5-propyne uridine nucleobase. In certain embodiments, one of A or B is an α-L-LNA nucleoside, another of A or B comprises a 2'-(ara)-F sugar moiety, and W comprises a 5-propyne uridine nucleobase.

In certain embodiments, one of A or B comprises a bicyclic sugar moiety, another of A or B comprises a 2'-MOE sugar moiety, and W comprises a sugar surrogate. In certain embodiments, one of A or B is an LNA nucleoside, another of A or B comprises a 2'-MOE sugar moiety, and W comprises a sugar surrogate. In certain embodiments, one of A or B is a cEt nucleoside, another of A or B comprises a 2'-MOE sugar moiety, and W comprises a sugar surrogate. In certain embodiments, one of A or B is an α-L-LNA nucleoside, another of A or B comprises a 2'-MOE sugar moiety, and W comprises a sugar surrogate.

In certain embodiments, one of A or B comprises a bicyclic sugar moiety, another of A or B comprises a 2'-F sugar moiety, and W comprises a sugar surrogate. In certain embodiments, one of A or B is an LNA nucleoside, another of A or B comprises a 2'-F sugar moiety, and W comprises a sugar surrogate. In certain embodiments, one of A or B is a cEt nucleoside, another of A or B comprises a 2'-F sugar moiety, and W comprises a sugar surrogate. In certain embodiments, one of A or B is an α-L-LNA nucleoside, another of A or B comprises a 2'-F sugar moiety, and W comprises a sugar surrogate.

In certain embodiments, one of A or B comprises a bicyclic sugar moiety, another of A or B comprises a 2'-(ara)-F sugar moiety, and W comprises a sugar surrogate. In certain embodiments, one of A or B is an LNA nucleoside, another of A or B comprises a 2'-(ara)-F sugar moiety, and W comprises a sugar surrogate. In certain embodiments, one of A or B is a cEt nucleoside, another of A or B comprises a 2'-(ara)-F sugar moiety, and W comprises a sugar surrogate. In certain embodiments, one of A or B is an α-L-LNA nucleoside, another of A or B comprises a 2'-(ara)-F sugar moiety, and W comprises sugar surrogate.

In certain embodiments, one of A or B comprises a bicyclic sugar moiety, another of A or B comprises a 2'-MOE sugar moiety, and W comprises a HNA sugar surrogate. In certain embodiments, one of A or B is an LNA nucleoside, another of A or B comprises a 2'-MOE sugar moiety, and W comprises a HNA sugar surrogate. In certain embodiments, one of A or B is a cEt nucleoside, another of A or B comprises a 2'-MOE sugar moiety, and W comprises a HNA sugar surrogate. In certain embodiments, one of A or B is an α-L-LNA nucleoside, another of A or B comprises a 2'-MOE sugar moiety, and W comprises a HNA sugar surrogate.

In certain embodiments, one of A or B comprises a bicyclic sugar moiety, another of A or B comprises a 2'-F sugar moiety, and W comprises a HNA sugar surrogate. In certain embodiments, one of A or B is an LNA nucleoside, another of A or B comprises a 2'-F sugar moiety, and W comprises a HNA sugar surrogate. In certain embodiments, one of A or B is a cEt nucleoside, another of A or B comprises a 2'-F sugar moiety, and W comprises a HNA sugar surrogate. In certain embodiments, one of A or B is an α-L-LNA nucleoside, another of A or B comprises a 2'-F sugar moiety, and W comprises a sugar HNA surrogate.

In certain embodiments, one of A or B comprises a bicyclic sugar moiety, another of A or B comprises a 2'-(ara)-F sugar moiety, and W comprises a HNA sugar surrogate. In certain embodiments, one of A or B is an LNA nucleoside, another of A or B comprises a 2'-(ara)-F sugar moiety, and W comprises a HNA sugar surrogate. In certain embodiments, one of A or B is a cEt nucleoside, another of A or B comprises a 2'-(ara)-F sugar moiety, and W comprises a HNA sugar surrogate. In certain embodiments, one of A or B is an α-L-LNA nucleoside, another of A or B comprises a 2'-(ara)-F sugar moiety, and W comprises a HNA sugar surrogate.

In certain embodiments, one of A or B comprises a bicyclic sugar moiety, another of A or B comprises a 2'-MOE sugar moiety, and W comprises a F-HNA sugar surrogate. In certain embodiments, one of A or B is an LNA nucleoside, another of A or B comprises a 2'-MOE sugar moiety, and W comprises a F-HNA sugar surrogate. In certain embodiments, one of A or B is a cEt nucleoside, another of A or B comprises a 2'-MOE sugar moiety, and W comprises a F-HNA sugar surrogate. In certain embodiments, one of A or B is an α-L-LNA nucleoside, another of A or B comprises a 2'-MOE sugar moiety, and W comprises a F-HNA sugar surrogate.

In certain embodiments, one of A or B comprises a bicyclic sugar moiety, another of A or B comprises a 2'-F sugar moiety, and W comprises a F-HNA sugar surrogate. In certain embodiments, one of A or B is an LNA nucleoside, another of A or B comprises a 2'-F sugar moiety, and W comprises a F-HNA sugar surrogate. In certain embodiments, one of A or B is a cEt nucleoside, another of A or B comprises a 2'-F sugar moiety, and W comprises a F-HNA sugar surrogate. In certain embodiments, one of A or B is an α-L-LNA nucleoside, another of A or B comprises a 2'-F sugar moiety, and W comprises a F-HNA sugar surrogate.

In certain embodiments, one of A or B comprises a bicyclic sugar moiety, another of A or B comprises a 2'-(ara)-F sugar moiety, and W comprises a F-HNA sugar surrogate. In certain embodiments, one of A or B is an LNA nucleoside, another of A or B comprises a 2'-(ara)-F sugar moiety, and W comprises a F-HNA sugar surrogate. In certain embodiments, one of A or B is a cEt nucleoside, another of A or B comprises a 2'-(ara)-F sugar moiety, and W comprises a F-HNA sugar surrogate. In certain embodiments, one of A or B is an α-L-LNA nucleoside, another of A or B comprises a 2'-(ara)-F sugar moiety, and W comprises a F-HNA sugar surrogate.

In certain embodiments, one of A or B comprises a bicyclic sugar moiety, another of A or B comprises a 2'-MOE sugar moiety, and W comprises a 5'-Me DNA sugar moiety. In certain embodiments, one of A or B is an LNA nucleoside, another of A or B comprises a 2'-MOE sugar moiety, and W comprises a 5'-Me DNA sugar moiety. In certain embodiments, one of A or B is a cEt nucleoside, another of A or B comprises a 2'-MOE sugar moiety, and W comprises a 5'-Me DNA sugar moiety. In certain embodiments, one of A or B is an α-L-LNA nucleoside, another of A or B comprises a 2'-MOE sugar moiety, and W comprises a 5'-Me DNA sugar moiety.

In certain embodiments, one of A or B comprises a bicyclic sugar moiety, another of A or B comprises a 2'-F sugar moiety, and W comprises a 5'-Me DNA sugar moiety. In certain embodiments, one of A or B is an LNA nucleoside, another of A or B comprises a 2'-F sugar moiety, and W comprises a 5'-Me DNA sugar moiety. In certain embodiments, one of A or B is a cEt nucleoside, another of A or B comprises a 2'-F sugar moiety, and W comprises a 5'-Me DNA sugar moiety. In certain embodiments, one of A or B is an α-L-LNA nucleoside, another of A or B comprises a 2'-F sugar moiety, and W comprises a 5'-Me DNA sugar moiety.

In certain embodiments, one of A or B comprises a bicyclic sugar moiety, another of A or B comprises a 2'-(ara)-F sugar moiety, and W comprises a 5'-Me DNA sugar moiety. In certain embodiments, one of A or B is an LNA nucleoside, another of A or B comprises a 2'-(ara)-F sugar moiety, and W comprises a 5'-Me DNA sugar moiety. In certain embodiments, one of A or B is a cEt nucleoside, another of A or B comprises a 2'-(ara)-F sugar moiety, and W comprises a 5'-Me DNA sugar moiety. In certain embodiments, one of A or B is an α-L-LNA nucleoside, another of A or B comprises a 2'-(ara)-F sugar moiety, and W comprises a 5'-Me DNA sugar moiety.

In certain embodiments, one of A or B comprises a bicyclic sugar moiety, another of A or B comprises a 2'-MOE sugar moiety, and W comprises a 5'-(R)-Me DNA sugar moiety. In certain embodiments, one of A or B is an LNA nucleoside, another of A or B comprises a 2'-MOE sugar moiety, and W comprises a 5'-(R)-Me DNA sugar moiety. In certain embodiments, one of A or B is a cEt nucleoside, another of A or B comprises a 2'-MOE sugar moiety, and W comprises a 5'-(R)-Me DNA sugar moiety. In certain embodiments, one of A or B is an α-L-LNA nucleoside, another of A or B comprises a 2'-MOE sugar moiety, and W comprises a 5'-(R)-Me DNA sugar moiety.

In certain embodiments, one of A or B comprises a bicyclic sugar moiety, another of A or B comprises a 2'-F sugar moiety, and W comprises a 5'-(R)-Me DNA sugar moiety. In certain embodiments, one of A or B is an LNA nucleoside, another of A or B comprises a 2'-F sugar moiety, and W comprises a 5'-(R)-Me DNA sugar moiety. In certain embodiments, one of A or B is a cEt nucleoside, another of A or B comprises a 2'-F sugar moiety, and W comprises a 5'-(R)-Me DNA sugar moiety. In certain embodiments, one of A or B is an α-L-LNA nucleoside, another of A or B comprises a 2'-F sugar moiety, and W comprises a 5'-(R)-Me DNA sugar moiety.

In certain embodiments, one of A or B comprises a bicyclic sugar moiety, another of A or B comprises a 2'-(ara)-F sugar moiety, and W comprises a 5'-(R)-Me DNA sugar moiety. In certain embodiments, one of A or B is an LNA nucleoside, another of A or B comprises a 2'-(ara)-F sugar moiety, and W comprises a 5'-(R)-Me DNA sugar moiety. In certain embodiments, one of A or B is a cEt nucleoside, another of A or B comprises a 2'-(ara)-F sugar moiety, and W comprises a 5'-(R)-Me DNA sugar moiety. In certain embodiments, one of A or B is an α-L-LNA nucleoside, another of A or B comprises a 2'-(ara)-F sugar moiety, and W comprises a 5'-(R)-Me DNA sugar moiety.

In certain embodiments, at least two of A, B or W comprises a 2'-substituted sugar moiety, and the other comprises a bicyclic sugar moiety. In certain embodiments, at least two of A, B or W comprises a bicyclic sugar moiety, and the other comprises a 2'-substituted sugar moiety.

d. Certain Overall Lengths In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range.

e. Certain Oligonucleotides

In certain embodiments, oligonucleotides of the present invention are characterized by their modification motif and overall length. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. One of skill in the art will appreciate that such motifs may be combined to create a variety of oligonucleotides. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

f. Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxy-cholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3'-end of an oligomeric compound, but before one or more terminal group nucleosides. In certain embodiments, conjugate groups are placed within a terminal group.

In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the motifs discussed above. Thus, for example, an oligomeric compound comprising an oligonucleotide having region of alternating nucleosides may comprise a terminal group.

C. Antisense Compounds

In certain embodiments, oligomeric compounds provided herein are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

a. Certain Antisense Activities and Mechanisms

In certain antisense activities, hybridization of an antisense compound results in recruitment of a protein that cleaves of the target nucleic acid. For example, certain antisense compounds result in RNase H mediated cleavage of target nucleic acid. RNase H is a cellular endonuclease that cleaves the RNA strand of an RNA:DNA duplex. The "DNA" in such an RNA:DNA duplex, need not be unmodified DNA. In certain embodiments, the invention provides antisense compounds that are sufficiently "DNA-like" to elicit RNase H activity. Such DNA-like antisense compounds include, but are not limited to gapmers having unmodified deoxyfuronose sugar moieties in the nucleosides of the gap and modified sugar moieties in the nucleosides of the wings.

Antisense activities may be observed directly or indirectly. In certain embodiments, observation or detection of an antisense activity involves observation or detection of a change in an amount of a target nucleic acid or protein encoded by such target nucleic acid; a change in the ratio of splice variants of a nucleic acid or protein; and/or a phenotypic change in a cell or animal.

In certain embodiments, compounds comprising oligonucleotides having a gapmer nucleoside motif described herein have desirable properties compared to non-gapmer oligonucleotides or to gapmers having other motifs. In certain circumstances, it is desirable to identify motifs resulting in a favorable combination of potent antisense activity and relatively low toxicity. In certain embodiments, compounds of the present invention have a favorable therapeutic index (measure of activity divided by measure of toxicity).

b. Certain Selective Antisense Compounds

In certain embodiments, antisense compounds provided are selective for a target relative to a non-target nucleic acid.

In certain embodiments, the nucleobase sequences of the target and non-target nucleic acids differ by no more than 4 differentiating nucleobases in the targeted region. In certain embodiments, the nucleobase sequences of the target and non-target nucleic acids differ by no more than 3 differentiating nucleobases in the targeted region. In certain embodiments, the nucleobase sequences of the target and non-target nucleic acids differ by no more than 2 differentiating nucleobases in the targeted region. In certain embodiments, the nucleobase sequences of the target and non-target nucleic acids differ by a single differentiating nucleobase in the targeted region. In certain embodiments, the target and non-target nucleic acids are transcripts from different genes. In certain embodiments, the target and non-target nucleic acids are different alleles for the same gene. In certain embodiments, the introduction of a mismatch between an antisense compound and a non-target nucleic acid may alter the RNase H cleavage site of a target nucleic acid compared to a non-target nucleic acid. In certain embodiments, the target and non-target nucleic acids are not functionally related to one another (e.g., are transcripts from different genes). In certain embodiments, the target and not-target nucleic acids are allelic variants of one another. In certain embodiments, the allelic variant contains a single nucleotide polymorphism (SNP). In certain embodiments, a SNP is associated with a mutant allele. In certain embodiments, a mutant SNP is associated with a disease. In certain embodiments a mutant SNP is associated with a disease, but is not causative of the disease. In certain embodiments, mRNA and protein expression of a mutant allele is associated with disease.

Selectivity of antisense compounds is achieved, principally, by nucleobase complementarity. For example, if an antisense compound has no mismatches for a target nucleic acid and one or more mismatches for a non-target nucleic acid, some amount of selectivity for the target nucleic acid will result. In certain embodiments, provided herein are antisense compounds with enhanced selectivity (i.e. the ratio of activity for the target to the activity for non-target is greater). For example, in certain embodiments, a selective nucleoside comprises a particular feature or combination of features (e.g., chemical modification, motif, placement of selective nucleoside, and/or self-complementary region) that increases selectivity of an antisense compound compared to an antisense compound not having that feature or combination of features. In certain embodiments, such feature or combination of features increases antisense activity for the target. In certain embodiments, such feature or combination of features decreases activity for the target, but decreases activity for the non-target by a greater amount, thus resulting in an increase in selectivity.

Without being limited by mechanism, enhanced selectivity may result from a larger difference in the affinity of an antisense compound for its target compared to its affinity for the non-target and/or a larger difference in RNase H activity for the resulting duplexes. For example, in certain embodiments, a selective antisense compound comprises a modified nucleoside at that same position as a differentiating nucleobase (i.e., the selective nucleoside is modified). That modification may increase the difference in binding affinity of the antisense compound for the target relative to the non-target. In addition or in the alternative, the chemical modification may increase the difference in RNAse H activity for the duplex formed by the antisense compound and its target compared to the RNase activity for the duplex formed by the antisense compound and the non-target. For example, the modification may exaggerate a structure that is less compatible for RNase H to bind, cleave and/or release the non-target.

In certain embodiments, an antisense compound binds its intended target to form a target duplex. In certain embodiments, RNase H cleaves the target nucleic acid of the target duplex. In certain such embodiments, there is a primary cleavage site between two particular nucleosides of the target nucleic acid (the primary target cleavage site), which accounts for the largest amount of cleavage of the target nucleic acid. In certain embodiments, there are one or more secondary target cleavage sites. In certain embodiments, the same antisense compound hybridizes to a non-target to form a non-target duplex. In certain such embodiments, the non-target differs from the target by a single nucleobase within the target region, and so the antisense compound hybridizes with a single mismatch. Because of the mismatch, in certain embodiments, RNase H cleavage of the non-target may be reduced compared to cleavage of the target, but still occurs. In certain embodiments, though, the primary site of that cleavage of the non-target nucleic acid (primary non-target cleavage site) is different from that of the target. That is; the primary site is shifted due to the mismatch. In such a circumstance, one may use a modification placed in the antisense compound to disrupt RNase H cleavage at the primary non-target cleavage site. Such modification will result in reduced cleavage of the non-target, but will result little or no decrease in cleavage of the target. In certain embodiments, the modification is a modified sugar, nucleobase and/or linkage.

In certain embodiments, the primary non-target cleavage site is towards the 5'-end of the antisense compound, and the 5'-end of an antisense compound may be modified to prevent RNaseH cleavage. In this manner, it is thought that one having skill in the art may modify the 5'-end of an antisense compound, or modify the nucleosides in the gap region of the 5'-end of the antisense compound, or modify the 3'-most 5'-region nucleosides of the antisense compound to selectively inhibit RNaseH cleavage of the non-target nucleic acid duplex while retaining RNase H cleavage of the target nucleic acid duplex. In certain embodiments, 1-3 of the 3'-most 5'-region nucleosides of the antisense compound comprises a bicyclic sugar moiety.

For example, in certain embodiments the target nucleic acid may have an allelic variant, e.g. a non-target nucleic acid, containing a single nucleotide polymorphism. An antisense compound may be designed having a single nucleobase mismatch from the non-target nucleic acid, but which has full complementarity to the target nucleic acid. The mismatch between the antisense compound and the non-target nucleic acid may destabilize the antisense compound non-target nucleic acid duplex, and consequently the cleavage site of RNaseH may shift upstream towards the 5'-end of the antisense compound. Modification of the 5'-end of the antisense compound or the gap region near the 5'-end of the antisense compound, or one or more of the 3'-most nucleosides of the 5'-wing region, will then prevent RNaseH cleavage of the non-target nucleic acid. Since the target nucleic acid is fully complementary to the antisense compound, the antisense compound and the target nucleic acid will form a more stabilized antisense compound-target nucleic acid duplex and the cleavage site of RnaseH will be more downstream, towards the 3' end of the antisense compound. Accordingly, modifications at the 5'-end of the antisense compound will prevent RNaseH cleavage of the non-target nucleic acid, but will not substantially effect RNaseH cleavage of the target nucleic acid, and selectivity between a target nucleic acid and its allelic variant may be achieved. In certain embodiments, one or more of the 3'-most nucleosides of the 5'-wing region comprises a bicyclic sugar moiety. In certain embodiments, one or more of the 3'-most nucleosides of the 5'-wing region comprises a bicyclic sugar moiety selected from cEt and LNA. In certain embodiments, one or more of the 3'-most nucleosides of the 5'-wing region comprises cEt. In certain embodiments, one or more of the 3'-most nucleosides of the 5'-wing region comprises LNA.

In certain embodiments, the introduction of a mismatch between an antisense compound and a target nucleic acid may alter the RNase H cleavage site of a target nucleic acid compared to a non-target nucleic acid by shifting the RNaseH cleavage site downstream from the mismatch site and towards the 3'-end of the antisense compound. In certain embodiments where the cleavage site of a target nucleic acid compared to a non-target nucleic acid has shifted downstream towards the 3'-end of the antisense compound, the 3'-end of an antisense compound may be modified to prevent RNaseH cleavage. In this manner, it is thought that one having skill in the art may modify the 3'-end of an antisense compound, or modify the nucleosides in the gap region near the 3'-end of antisense compound, to selectively inhibit RNaseH cleavage of the non-target nucleic acid while retaining RNase H cleavage of the target nucleic acid.

For example, in certain embodiments the target nucleic acid may have an allelic variant, e.g. a non-target nucleic acid, containing a single nucleotide polymorphism. An antisense compound may be designed having a single nucleobase mismatch from the non-target nucleic acid, but which has full complementarity to target nucleic acid. The mismatch between the antisense compound and the non-target nucleic acid may destabilize the antisense compound-non-target nucleic acid duplex, and consequently the cleavage site of RNaseH may shift downstream towards the 3'-end of the antisense compound. Modification of the 3'-end of the antisense compound, or one or more of the 5'-most nucleosides of the 3'-wing region, or the gap region of the antisense compound near the 3'-end will then prevent RNaseH cleavage of the non-target nucleic acid. Since the target nucleic acid is fully complementary to the antisense compound, the antisense compound and the target nucleic acid will form a more stabilized antisense compound-target nucleic acid duplex and the cleavage site of RnaseH will be more upstream, towards the 5' end of the antisense compound. Accordingly, modifications at the 3'-end of the antisense compound will prevent RNaseH cleavage of the non-target nucleic acid, but will not substantially effect RNaseH cleavage of the target nucleic acid, and selectivity between a target nucleic acid and its allelic variant may be achieved. In certain embodiments, one or more of the 5'-most nucleosides of the 3'-wing region comprises a bicyclic sugar moiety. In certain embodiments, one or more of the 5'-most nucleosides of the 3'-wing region comprises a bicyclic sugar moiety selected from cEt and LNA. In certain embodiments, one or more of the 5'-most nucleosides of the 3'-wing region comprises cEt. In certain embodiments, one or more of the 5'-most nucleosides of the 3'-wing region comprises LNA.

In certain embodiments, the selectivity of antisense compounds having certain gaps, e.g. gaps of 7 nucleosides or longer, may be improved by the addition of one or more bicyclic nucleosides at the 3'-most 5'-wing nucleoside. In certain embodiments, the selectivity of antisense compounds having certain gaps, e.g. gaps of 7 nucleosides or longer, may be improved by the addition of two or more bicyclic nucleosides at the 3'-most 5'-wing nucleoside. In certain embodiments, the selectivity of antisense compounds having certain gaps, e.g. gaps of 7 nucleosides or longer, may be improved by the addition of one bicyclic nucleoside at the 3'-most 5'-wing nucleoside. In certain embodiments, the selectivity of antisense compounds having certain gaps, e.g. gaps of 7 nucleosides or longer, may be improved by the addition of two bicyclic nucleosides at the 3'-most 5'-wing nucleoside. In certain embodiments, the selectivity of antisense compounds having certain gaps, e.g. gaps of 7 nucleosides or longer, may be improved by the addition of three bicyclic nucleosides at the 3'-most 5'-wing nucleoside. In certain embodiments, the selectivity of antisense compounds having certain gaps, e.g. gaps of 7 nucleosides or longer, may be improved by the addition of four bicyclic nucleosides at the 3'-most 5'-wing nucleoside. In certain embodiments, the selectivity of antisense compounds having certain gaps, e.g. gaps of 7 nucleosides or longer, may be improved by the addition of five bicyclic nucleosides at the 3'-most 5'-wing nucleoside. In certain embodiments discussed above, the bicyclic nucleosides at the 3'-most 5'-wing nucleoside are selected from among cEt, cMOE, LNA, α-LNA, ENA and 2'-thio LNA. In certain embodiments discussed above, the bicyclic nucleosides at the 3'-most 5'-wing nucleoside comprise cEt. In certain embodiments discussed above, the bicyclic nucleosides at the 3'-most 5'-wing nucleoside comprise LNA.

In certain embodiments, the selectivity of antisense compounds having certain gaps, e.g. gaps of 7 nucleosides or longer, may be improved by the addition of one or more bicyclic nucleosides at the 3'-most 5'-wing nucleoside and the addition of one or more bicylic nucleosides at the 5'-most 3'-wing nucleoside. In certain embodiments, the selectivity of antisense compounds having certain gaps, e.g. gaps of 7 nucleosides or longer, may be improved by the addition of two or more bicyclic nucleosides at the 3'-most 5'-wing nucleoside and the addition of one or more bicylic nucleosides at the 5'-most 3'-wing nucleoside. In certain embodiments, the selectivity of antisense compounds having certain gaps, e.g. gaps of 7 nucleosides or longer, may be improved by the addition of one bicyclic nucleoside at the 3'-most 5'-wing nucleoside and the addition of one or more bicylic nucleosides at the 5'-most 3'-wing nucleoside. In certain embodiments, the selectivity of antisense compounds having certain gaps, e.g. gaps of 7 nucleosides or longer, may be improved by the addition of two bicyclic nucleosides at the 3'-most 5'-wing nucleoside and the addition of one or more bicylic nucleosides at the 5'-most 3'-wing nucleoside. In certain embodiments, the selectivity of antisense compounds having certain gaps, e.g. gaps of 7 nucleosides or longer, may be improved by the addition of three bicyclic nucleosides at the 3'-most 5'-wing nucleoside and the addition of one or more bicylic nucleosides at the 5'-most 3'-wing nucleoside. In certain embodiments, the selectivity of antisense compounds having certain gaps, e.g. gaps of 7 nucleosides or longer, may be improved by the addition of four bicyclic nucleosides at the 3'-most 5'-wing nucleoside and the addition of one or more bicylic nucleosides at the 5'-most 3'-wing nucleoside. In certain embodiments, the selectivity of antisense compounds having certain gaps, e.g. gaps of 7 nucleosides or longer, may be improved by the addition of four bicyclic nucleosides at the 3'-most 5'-wing nucleoside and the addition of one or more bicyclic nucleosides at the 5'-most 3'-wing nucleoside.

In certain embodiments, the selectivity of antisense compounds having certain gaps, e.g. gaps of 7 nucleosides or shorter, may be improved by the addition of one or more bicyclic nucleosides at the 3'-most 5'-wing nucleoside. In certain embodiments, the selectivity of antisense compounds having certain gaps, e.g. gaps of 7 nucleosides or shorter, may be improved by the addition of two or more bicyclic nucleosides at the 3'-most 5'-wing nucleoside. In certain embodiments, the selectivity of antisense compounds having certain gaps, e.g. gaps of 7 nucleosides or shorter, may be improved by the addition of one bicyclic nucleoside at the 3'-most 5'-wing nucleoside. In certain embodiments, the selectivity of antisense compounds having certain gaps, e.g. gaps of 7 nucleosides or shorter, may be improved by the addition of two bicyclic nucleosides at the 3'-most 5'-wing nucleoside. In certain embodiments, the selectivity of antisense compounds having certain gaps, e.g. gaps of 7 nucleosides or shorter, may be improved by the addition of three bicyclic nucleosides at the 3'-most 5'-wing nucleoside. In certain embodiments, the selectivity of antisense compounds having certain gaps, e.g. gaps of 7 nucleosides or shorter, may be improved by the addition of four bicyclic nucleosides at the 3'-most 5'-wing nucleoside. In certain embodiments, the selectivity of antisense compounds having certain gaps, e.g. gaps of 7 nucleosides or shorter, may be improved by the addition of five bicyclic nucleosides at the 3'-most 5'-wing nucleoside. In certain embodiments discussed above, the bicyclic nucleosides at the 3'-most 5'-wing nucleoside are selected from among cEt, cMOE, LNA, α-LNA, ENA and 2'-thio LNA. In certain embodiments discussed above, the bicyclic nucleosides at the 3'-most 5'-wing nucleoside comprise cEt. In certain embodiments discussed above, the bicyclic nucleosides at the 3'-most 5'-wing nucleoside comprise LNA.

Antisense compounds having certain specified motifs have enhanced selectivity, including, but not limited to motifs described above. In certain embodiments, enhanced selectivity is achieved by oligonucleotides comprising any one or more of:

a modification motif comprising a long 5'-wing (longer than 5, 6, or 7 nucleosides);

a modification motif comprising a long 3'-wing (longer than 5, 6, or 7 nucleosides);

a modification motif comprising a short gap region (shorter than 8, 7, or 6 nucleosides); and a modification motif comprising an interrupted gap region (having no uninterrupted stretch of unmodified 2'-deoxynucleosides longer than 7, 6 or 5).

i. Certain Selective Nucleobase Sequence Elements

In certain embodiments, selective antisense compounds comprise nucleobase sequence elements. Such nucleobase sequence elements are independent of modification motifs. Accordingly, oligonucleotides having any of the motifs (modification motifs, nucleoside motifs, sugar motifs, nucleobase modification motifs, and/or linkage motifs) may also comprise one or more of the following nucleobase sequence elements.

ii. Alignment of Differentiating Nucleobase/Target-Selective Nucleoside

In certain embodiments, a target region and a region of a non-target nucleic acid differ by 1-4 differentiating nucleobase. In such embodiments, selective antisense compounds have a nucleobase sequence that aligns with the non-target nucleic acid with 1-4 mismatches. A nucleoside of the antisense compound that corresponds to a differentiating nucleobase of the target nucleic acid is referred to herein as a target-selective nucleoside. In certain embodiments, selective antisense compounds having a gapmer motif align with a non-target nucleic acid, such that a target-selective nucleoside is positioned in the gap. In certain embodiments, a target-selective nucleoside is the $1^{st}$ nucleoside of the gap from the 5' end. In certain embodiments, a target-selective nucleoside is the $2^{nd}$ nucleoside of the gap from the 5' end. In certain embodiments, a target-selective nucleoside is the $3^{rd}$ nucleoside of the gap from the 5'-end. In certain embodiments, a target-selective nucleoside is the $4^{th}$ nucleoside of the gap from the 5'-end. In certain embodiments, a target-selective nucleoside is the $5^{th}$ nucleoside of the gap from the 5'-end. In certain embodiments, a target-selective nucleoside is the $6^{rd}$ nucleoside of the gap from the 5'-end. In certain embodiments, a target-selective nucleoside is the $8^{th}$ nucleoside of the gap from the 3'-end. In certain embodiments, a target-selective nucleoside is the $7^{th}$ nucleoside of the gap from the 3'-end. In certain embodiments, a target-selective nucleoside is the $6^{th}$ nucleoside of the gap from the 3'-end. In certain embodiments, a target-selective nucleoside is the $5^{th}$ nucleoside of the gap from the 3'-end. In certain embodiments, a target-selective nucleoside is the $4^{th}$ nucleoside of the gap from the 3'-end. In certain embodiments, a target-selective nucleoside is the $3^{rd}$ nucleoside of the gap from the 3'-end. In certain embodiments, a target-selective nucleoside is the $2^{nd}$ nucleoside of the gap from the 3'-end.

In certain embodiments, a target-selective nucleoside comprises a modified nucleoside. In certain embodiments, a target-selective nucleoside comprises a modified sugar. In certain embodiments, a target-selective nucleoside comprises a sugar surrogate. In certain embodiments, a target-selective nucleoside comprises a sugar surrogate selected from among HNA and F-HNA. In certain embodiments, a target-selective nucleoside comprises a 2'-substituted sugar moiety. In certain embodiments, a target-selective nucleoside comprises a 2'-substituted sugar moiety selected from among MOE, F and (ara)-F. In certain embodiments, a target-selective nucleoside comprises a 5'-substituted sugar moiety. In certain embodiments, a target-selective nucleoside comprises a 5'-substituted sugar moiety selected from 5'-(R)-Me DNA. In certain embodiments, a target-selective nucleoside comprises a bicyclic sugar moiety. In certain embodiments, a target-selective nucleoside comprises a bicyclic sugar moiety selected from among cEt, and α-L-LNA. In certain embodiments, a target-selective nucleoside comprises a modified nucleobase. In certain embodiments, a target-selective nucleoside comprises a modified nucleobase selected from among 2-thio-thymidine and 5-propyne uridine.

iii. Mismatches to the Target Nucleic Acid

In certain embodiments, selective antisense compounds comprise one or more mismatched nucleobases relative to the target nucleic acid. In certain such embodiments, antisense activity against the target is reduced by such mismatch, but activity against the non-target is reduced by a greater amount. Thus, in certain embodiments selectivity is improved. Any nucleobase other than the differentiating nucleobase is suitable for a mismatch. In certain embodiments, however, the mismatch is specifically positioned within the gap of an oligonucleotide having a gapmer motif. In certain embodiments, a mismatch relative to the target nucleic acid is at positions 1, 2, 3, 4, 5, 6, 7, or 8 from the 5'-end of the gap region. In certain embodiments, a mismatch relative to the target nucleic acid is at positions 9, 8, 7, 6, 5, 4, 3, 2, 1 of the antisense compounds from the 3'-end of the gap region. In certain embodiments, a mismatch relative to the target nucleid acid is at positions 1, 2, 3, or 4 of the antisense compounds from the 5'-end of the wing region. In certain embodiments, a mismatch relative to the target nucleid acid is at positions 4, 3, 2, or 1 of the antisense compounds from the 3'-end of the wing region.

iv. Self Complementary Regions

In certain embodiments, selective antisense compounds comprise a region that is not complementary to the target. In certain embodiments, such region is complementary to another region of the antisense compound. Such regions are referred to herein as self-complementary regions. For example, in certain embodiments, an antisense compound has a first region at one end that is complementary to a second region at the other end. In certain embodiments, one of the first and second regions is complementary to the target nucleic acid. Unless the target nucleic acid also includes a self-complementary region, the other of the first and second region of the antisense compound will not be complementary to the target nucleic acid. For illustrative purposes, certain antisense compounds have the following nucleobase motif:

```
ABCXXXXXXXXXC'B'A';

ABCXXXXXXXX(X/C')(X/B')(X/A');

(X/A)(X/B)(X/C)XXXXXXXXXC'B'A'
``` where each of A, B, and C are any nucleobase; A', B', and C' are the complementary bases to A, B, and C, respectively; each X is a nucleobase complementary to the target nucleic acid; and two letters in parentheses (e.g., (X/C')) indicates that the nucleobase is complementary to the target nucleic acid and to the designated nucleoside within the antisense oligonucleotide.

Without being bound to any mechanism, in certain embodiments, such antisense compounds are expected to form self-structure, which is disrupted upon contact with a target nucleic acid. Contact with a non-target nucleic acid is expected to disrupt the self-structure to a lesser degree, thus increasing selectivity compared to the same antisense compound lacking the self-complementary regions.

v. Combinations of Features

Though it is clear to one of skill in the art, the above motifs and other elements for increasing selectivity may be used alone or in combination. For example, a single antisense compound may include any one, two, three, or more of: self-complementary regions, a mismatch relative to the target nucleic acid, a short nucleoside gap, an interrupted gap, and specific placement of the selective nucleoside.

D. Certain Short Gap Antisense Compounds

In certain embodiments, an antisense compound of interest may modulate the expression of a target nucleic acid but possess undesirable properties. In certain embodiments, for example, an antisense compound of interest may have an undesirably high affinity for one or more non-target nucleic acids. In certain embodiments, whether as a result of such affinity for one or more non-target nucleic acid or by some other mechanism, an antisense compound of interest may produce undesirable increases in ALT and/or AST levels when administered to an animal. In certain embodiments, such an antisense compound of interest may produce undesirable increases in organ weight.

In certain such embodiments wherein an antisense compound of interest effectively modulates the expression of a target nucleic acid, but possess one or more undesirable properties, a person having skill in the art may selectively incorporate one or more modifications into the antisense compound of interest that retain some or all of the desired property of effective modulation of expression of a target nucleic acid while reducing one or more of the antisense compound's undesirable properties. In certain embodiments, the present invention provides methods of altering such an antisense compound of interest to form an improved antisense compound. In certain embodiments, altering the number of nucleosides in the 5'-region, the 3'-region, and/or the central region of such an antisense compound of interest results in improved properties. For example, in certain embodiments, one may alter the modification state of one or more nucleosides at or near the 5'-end of the central region. Having been altered, those nucleosides may then be characterized as being part of the 5'-region. Thus, in such embodiments, the overall number of nucleosides of the 5'-region is increased and the number of nucleosides in the central region is decreased. For example, an antisense compound having a modification motif of 3-10-3 could be altered to result in an improved antisense compound having a modification motif of 4-9-3 or 5-8-3. In certain embodiments, the modification state of one or more of nucleosides at or near the 3'-end of the central region may likewise be altered. In certain embodiments, the modification of one or more of the nucleosides at or near the 5'-end and the 3'-end of the central region may be altered. In such embodiments in which one or more nucleosides at or near the 5'-end and the 3'-end of the central region is altered the central region becomes shorter relative to the central region of the original antisense compound of interest. In such embodiments, the modifications to the one or more nucleosides that had been part of the central region are the same as one or more modification that had been present in the 5'-region and/or the 3'-region of the original antisense compound of interest. In certain embodiments, the improved antisense compound having a shortened central region may retain its ability to effectively modulate the expression of a target nucleic acid, but not possess some or all of the undesirable properties possessed by antisense compound of interest having a longer central region. In certain embodiments, reducing the length of the central region reduces affinity for off-target nucleic acids. In certain embodiments, reducing the length of the central region results in reduced cleavage of non-target nucleic acids by RNase H. In certain embodiments, reducing the length of the central region does not produce undesirable increases in ALT levels. In certain embodiments, reducing the length of the central region does not produce undesirable increases in AST levels. In certain embodiments, reducing the length of the central region does not produce undesirable increases organ weights.

In certain embodiments it is possible to retain the same nucleobase sequence and overall length of an antisense compound while decreasing the length of the central region. In certain embodiments retaining the same nucleobase sequence and overall length of an antisense compound while decreasing the length of the central region ameliorates one or more undesirable properties of an antisense compound. In certain embodiments retaining the same nucleobase sequence and overall length of an antisense compound while decreasing the length of the central region ameliorates one or more undesirable properties of an antisense compound but does not substantially affect the ability of the antisense compound to modulate expression of a target nucleic acid. In certain such embodiments, two or more antisense compounds would have the same overall length and nucleobase sequence, but would have a different central region length, and different properties. In certain embodiments, the length of the central region is 9 nucleobases. In certain embodiments, the length of the central region is 8 nucleobases. In certain embodiments, the length of the central region is 7 nucleobases. In certain embodiments, the central region consists of unmodified deoxynucleosides. In certain embodiments, the length of the central region can be decreased by increasing the length of the 5'-region, the 3'-region, or both the 5'-region and the 3'-region.

In certain embodiments, the length of the central region can be decreased by increasing the length of the 5'-region with modified nucleosides. In certain embodiments, the length of the central region can be decreased by increasing the length of the 5'-region with modified nucleosides. In certain embodiments, the length of the central region can be decreased by increasing the length of the 5'-region with modified nucleosides comprising a bicyclic sugar moiety selected from among: cEt, cMOE, LNA, α-LNA, ENA and 2'-thio LNA. In certain embodiments, the length of the central region can be decreased by increasing the length of the 5'-region with a cEt substituted sugar moiety.

In certain embodiments, the length of the central region can be decreased by increasing the length of the 5'-region with modified nucleosides. In certain embodiments, the length of the central region can be decreased by increasing the length of the 5'-region with modified nucleosides. In certain embodiments, the length of the central region can be decreased by increasing the length of the 5'-region with modified nucleosides comprising a bicyclic sugar moiety comprising a 2' substituent selected from among: a halogen, $OCH_3$, $OCF_3$, $OCH_2CH_3$, $OCH_2CF_3$, $OCH_2\text{—}CH\text{=}CH_2$, $O(CH_2)_2\text{—}OCH_3$ (MOE), $O(CH_2)_2\text{—}O(CH_2)_2\text{—}N(CH_3)_2$, $OCH_2C(\text{=}O)\text{—}N(H)CH_3$, $OCH_2C(\text{=}O)\text{—}N(H)\text{—}(CH_2)_2\text{—}N(CH_3)_2$, and $OCH_2\text{—}N(H)\text{—}C(\text{=}NH)NH_2$. In certain embodiments, the length of the central region can be decreased by increasing the length of the 5'-region with 2'-$O(CH_2)_2\text{—}OCH_3$ (MOE) substituted sugar moiety.

In certain embodiments, the length of the central region can be decreased by increasing the length of the 3'-region with modified nucleosides. In certain embodiments, the length of the central region can be decreased by increasing the length of the 3'-region with modified nucleosides. In certain embodiments, the length of the central region can be decreased by increasing the length of the 3'-region with modified nucleosides comprising a bicyclic sugar moiety selected from among: cEt, cMOE, LNA, α-LNA, ENA and 2'-thio LNA. In certain embodiments, the length of the central region can be decreased by increasing the length of the 3'-region with a cEt substituted sugar moiety.

In certain embodiments, the length of the central region can be decreased by increasing the length of the 3'-region with modified nucleosides. In certain embodiments, the length of the central region can be decreased by increasing the length of the 3'-region with modified nucleosides. In certain embodiments, the length of the central region can be decreased by increasing the length of the 3'-region with modified nucleosides comprising a bicyclic sugar moiety comprising a 2' substituent selected from among: a halogen, $OCH_3$, $OCF_3$, $OCH_2CH_3$, $OCH_2CF_3$, $OCH_2\text{—}CH\text{=}CH_2$, $O(CH_2)_2\text{—}OCH_3$ (MOE), $O(CH_2)_2\text{—}O(CH_2)_2\text{—}N(CH_3)_2$, $OCH_2C(\text{=}O)\text{—}N(H)CH_3$, $OCH_2C(\text{=}O)\text{—}N(H)\text{—}(CH_2)_2\text{—}N(CH_3)_2$, and $OCH_2\text{—}N(H)\text{—}C(\text{=}NH)NH_2$. In certain embodiments, the length of the central region can be decreased by increasing the length of the 3'-region with 2'-$O(CH_2)_2\text{—}OCH_3$ (MOE) substituted sugar moiety.

In certain embodiments, the length of the central region can be decreased by increasing the length of the 5'-region with modified nucleosides and increasing the length of the 3'-region with modified nucleosides.

E. Certain Target Nucleic Acids

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid is a non-coding RNA. In certain such embodiments, the target non-coding RNA is selected from: a long-non-coding RNA, a short non-coding RNA, an intronic RNA molecule, a snoRNA, a scaRNA, a microRNA (including pre-microRNA and mature microRNA), a ribosomal RNA, and promoter directed RNA. In certain embodiments, the target nucleic acid encodes a protein. In certain such embodiments, the target nucleic acid is selected from: an mRNA and a pre-mRNA, including intronic, exonic and untranslated regions. In certain embodiments, oligomeric compounds are at least partially complementary to more than one target nucleic acid. For example, antisense compounds of the present invention may mimic microRNAs, which typically bind to multiple targets.

In certain embodiments, the target nucleic acid is a nucleic acid other than a mature mRNA. In certain embodiments, the target nucleic acid is a nucleic acid other than a mature mRNA or a microRNA. In certain embodiments, the target nucleic acid is a non-coding RNA other than a microRNA. In certain embodiments, the target nucleic acid is a non-coding RNA other than a microRNA or an intronic region of a pre-mRNA. In certain embodiments, the target nucleic acid is a long non-coding RNA. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron. In certain embodiments, the target nucleic acid is selected from among non-coding RNA, including exonic regions of pre-mRNA. In certain embodiments, the target nucleic acid is a ribosomal RNA (rRNA). In certain embodiments, the target nucleic acid is a non-coding RNA associated with splicing of other pre-mRNAs. In certain embodiments, the target nucleic acid is a nuclear-retained non-coding RNA.

In certain embodiments, antisense compounds described herein are complementary to a target nucleic acid comprising a single-nucleotide polymorphism. In certain such embodiments, the antisense compound is capable of modulating expression of one allele of the single-nucleotide polymorphism-containing-target nucleic acid to a greater or lesser extent than it modulates another allele. In certain embodiments an antisense compound hybridizes to a single-nucleotide polymorphism-containing-target nucleic acid at the single-nucleotide polymorphism site. In certain embodiments, the target nucleic acid is a Huntingtin gene transcript. In certain embodiments, the target nucleic acid is a single-nucleotide polymorphism-containing-target nucleic acid of a Huntingtin gene transcript. In certain embodiments, the target nucleic acid is not a Huntingtin gene transcript. In certain embodiments, the target nucleic acid is a single-nucleotide polymorphism-containing-target nucleic acid of a gene transcript other than Huntingtin. In certain embodiments, the target nucleic acid is any nucleic acid other than a Huntingtin gene transcript.

a. Single-Nucleotide Polymorphism

In certain embodiments, the invention provides selective antisense compounds that have greater activity for a target nucleic acid than for a homologous or partially homologous non-target nucleic acid. In certain such embodiments, the target and non-target nucleic acids are not functionally related to one another (e.g., are transcripts from different genes). In certain embodiments, the target and not-target nucleic acids are allelic variants of one another. Certain embodiments of the present invention provide methods, compounds, and compositions for selectively inhibiting mRNA and protein expression of an allelic variant of a particular gene or DNA sequence. In certain embodiments, the allelic variant contains a single nucleotide polymorphism (SNP). In certain embodiments, a SNP is associated with a mutant allele. In certain embodiments, a mutant SNP is associated with a disease. In certain embodiments a mutant SNP is associated with a disease, but is not causative of the disease. In certain embodiments, mRNA and protein expression of a mutant allele is associated with disease.

In certain embodiments, the expressed gene product of a mutant allele results in aggregation of the mutant proteins causing disease. In certain embodiments, the expressed gene product of a mutant allele results in gain of function causing disease. In certain embodiments, genes with an autosomal dominant mutation resulting in a toxic gain of function of the protein are the APP gene encoding amyloid precursor protein involved in Alzheimer's disease (Gene, 371: 68, 2006); the PrP gene encoding prion protein involved in Creutzfeldt-Jakob disease and in fatal familial insomnia (Nat. Med. 1997, 3: 1009); GFAP gene encoding glial fibrillary acidic protein involved in Alexander disease (J. Neurosci. 2006, 26:111623); alpha-synuclein gene encoding alpha-synuclein protein involved in Parkinson's disease (J. Clin. Invest. 2003, 111: 145); SOD-1 gene encoding the SOD-1 protein involved in amyotrophic lateral sclerosis (Science 1998, 281: 1851); atrophin-1 gene encoding atrophin-1 protein involved in dentato-rubral and pallido-luysian atrophy (DRPA) (Trends Mol. Med. 2001, 7: 479); SCA1 gene encoding ataxin-1 protein involved in spino-cerebellar ataxia-1 (SCA1) (Protein Sci. 2003, 12: 953); PLP gene encoding proteolipid protein involved in Pelizaeus-Merzbacher disease (NeuroMol Med. 2007, 4: 73); DYT1 gene encoding torsinA protein involved in Torsion dystonia (Brain Res. 2000, 877: 379); and alpha-B crystalline gene encoding alpha-B crystalline protein involved in protein aggregation diseases, including cardiomyopathy (Cell 2007, 130: 427); alpha1-antitrypsin gene encoding alpha1-antitrypsin protein involved in chronic obstructive pulmonary disease (COPD), liver disease and hepatocellular carcinoma (New Engl J Med. 2002, 346: 45); Ltk gene encoding leukocyte tyrosine kinase protein involved in systemic lupus erythematosus (Hum. Mol. Gen. 2004, 13: 171); PCSK9 gene encoding PCSK9 protein involved in hypercholesterolemia (Hum Mutat. 2009, 30: 520); prolactin receptor gene encoding prolactin receptor protein involved in breast tumors (Proc. Natl. Assoc. Sci. 2008, 105: 4533); CCLS gene encoding the chemokine CCLS involved in COPD and asthma (Eur. Respir. J. 2008, 32: 327); PTPN22 gene encoding PTPN22 protein involved in Type 1 diabetes, Rheumatoid arthritis, Graves disease, and SLE (Proc. Natl. Assoc. Sci. 2007, 104: 19767); androgen receptor gene encoding the androgen receptor protein involved in spinal and bulbar muscular atrophy or Kennedy's disease (J Steroid Biochem. Mol. Biol. 2008, 108: 245); CHMP4B gene encoding chromatin modifying protein-4B involved in progressive childhood posterior subcapsular cataracts (Am. J. Hum. Genet 2007, 81: 596); FXR/NR1H4 gene encoding Farnesoid X receptor protein involved in cholesterol gallstone disease, arthrosclerosis and diabetes (Mol. Endocrinol. 2007, 21: 1769); ABCA1 gene encoding ABCA1 protein involved in cardiovascular disease (Transl. Res. 2007, 149: 205); CaSR gene encoding the calcium sensing receptor protein involved in primary hypercalciuria (Kidney Int. 2007, 71: 1155); alpha-globin gene encoding alpha-globin protein involved in alpha-thallasemia (Science 2006, 312: 1215); httlpr gene encoding HTTLPR protein involved in obsessive compulsive disorder (Am. J. Hum. Genet. 2006, 78: 815); AVP gene encoding arginine vasopressin protein in stress-related disorders such as anxiety disorders and comorbid depression (CNS Neurol. Disord. Drug Targets 2006, 5: 167); GNAS gene encoding G proteins involved in congenital visual defects, hypertension, metabolic syndrome (Trends Pharmacol. Sci. 2006, 27: 260); APAF1 gene encoding APAF1 protein involved in a predisposition to major depression (Mol. Psychiatry 2006, 11: 76); TGF-beta1 gene encoding TGF-beta1 protein involved in breast cancer and prostate cancer (Cancer Epidemiol. Biomarkers Prev. 2004, 13: 759); AChR gene encoding acetylcholine receptor involved in congenital myasthenic syndrome (Neurology 2004, 62: 1090); P2Y12 gene encoding adenosine diphosphate (ADP) receptor protein involved in risk of peripheral arterial disease (Circulation 2003, 108: 2971); LQT1 gene encoding LQT1 protein involved in atrial fibrillation (Cardiology 2003, 100: 109); RET protooncogene encoding RET protein involved in sporadic pheochromocytoma (J. Clin. Endocrinol. Metab. 2003, 88: 4911); filamin A gene encoding filamin A protein involved in various congenital malformations (Nat. Genet. 2003, 33: 487); TARDBP gene encoding TDP-43 protein involved in amyotrophic lateral sclerosis (Hum. Mol. Gene.t 2010, 19: 671); SCA3 gene encoding ataxin-3 protein involved in Machado-Joseph disease (PLoS One 2008, 3: e3341); SCAT gene encoding ataxin-7 protein involved in spino-cerebellar ataxia-7 (PLoS One 2009, 4: e7232); and HTT gene encoding huntingtin protein involved in Huntington's disease (Neurobiol Dis. 1996, 3:183); and the CA4 gene encoding carbonic anhydrase 4 protein, CRX gene encoding cone-rod homeobox transcription factor protein, FSCN2 gene encoding retinal fascin homolog 2 protein, IMPDH1 gene encoding inosine monophosphate dehydrogenase 1 protein, NR2E3 gene encoding nuclear receptor subfamily 2 group E3 protein, NRL gene encoding neural retina leucine zipper protein, PRPF3 (RP18) gene encoding pre-mRNA splicing factor 3 protein, PRPF8 (RP13) gene encoding pre-mRNA splicing factor 8 protein, PRPF31 (RP11) gene encoding pre-mRNA splicing factor 31 protein, RDS gene encoding peripherin 2 protein, ROM1 gene encoding rod outer membrane protein 1 protein, RHO gene encoding rhodopsin protein, RP1 gene encoding RP1 protein, RPGR gene encoding retinitis pigmentosa GTPase regulator protein, all of which are involved in Autosomal Dominant Retinitis Pigmentosa disease (Adv Exp Med Biol. 2008, 613:203)

In certain embodiments, the mutant allele is associated with any disease from the group consisting of Alzheimer's disease, Creutzfeldt-Jakob disease, fatal familial insomnia, Alexander disease, Parkinson's disease, amyotrophic lateral sclerosis, dentato-rubral and pallido-luysian atrophy DRPA, spino-cerebellar ataxia, Torsion dystonia, cardiomyopathy, chronic obstructive pulmonary disease (COPD), liver disease, hepatocellular carcinoma, systemic lupus erythematosus, hypercholesterolemia, breast cancer, asthma, Type 1 diabetes, Rheumatoid arthritis, Graves disease, SLE, spinal and bulbar muscular atrophy, Kennedy's disease, progressive childhood posterior subcapsular cataracts, cholesterol gallstone disease, arthrosclerosis, cardiovascular disease, primary hypercalciuria, alpha-thallasemia, obsessive compulsive disorder, Anxiety, comorbid depression, congenital visual defects, hypertension, metabolic syndrome, prostate cancer, congenital myasthenic syndrome, peripheral arterial disease, atrial fibrillation, sporadic pheochromocytoma, congenital malformations, Machado-Joseph disease, Huntington's disease, and Autosomal Dominant Retinitis Pigmentosa disease.

i. Certain Huntingtin Targets

In certain embodiments, an allelic variant of huntingtin is selectively reduced. Nucleotide sequences that encode huntingtin include, without limitation, the following: GENBANK Accession No. NT_006081.18, truncated from nucleotides 1566000 to 1768000 (replaced by GENBANK Accession No. NT_006051), incorporated herein as SEQ ID NO: 1, and NM_002111.6, incorporated herein as SEQ ID NO: 2.

Table 14 provides SNPs found in the GM04022, GM04281, GM02171, and GM02173B cell lines. Also provided are the allelic variants found at each SNP position, the genotype for each of the cell lines, and the percentage of HD patients having a particular allelic variant. For example, the two allelic variants for SNP rs6446723 are T and C. The GM04022 cell line is heterozygous TC, the GM02171 cell line is homozygous CC, the GM02173 cell line is heterozygous TC, and the GM04281 cell line is homozygous TT. Fifty percent of HD patients have a T at SNP position rs6446723.

TABLE 14

Allelic Variations for SNPs Associated with HD

| SNP | Variation | GM04022 | GM02171 | GM02173 | GM04281 | TargetPOP | allele |
|---|---|---|---|---|---|---|---|
| rs6446723 | T/C | TC | CC | TC | TT | 0.50 | T |
| rs3856973 | A/G | AG | AA | AG | GG | 0.50 | G |
| rs2285086 | A/G | AG | GG | AG | AA | 0.50 | A |
| rs363092 | A/C | AC | AA | AC | CC | 0.49 | C |
| rs916171 | C/G | GC | GG | GC | CC | 0.49 | C |
| rs6844859 | T/C | TC | CC | TC | TT | 0.49 | T |
| rs7691627 | A/G | AG | AA | AG | GG | 0.49 | G |
| rs4690073 | A/G | AG | AA | AG | GG | 0.49 | G |
| rs2024115 | A/G | AG | GG | AG | AA | 0.48 | A |
| rs11731237 | T/C | CC | CC | TC | TT | 0.43 | T |
| rs362296 | A/C | CC | AC | AC | AC | 0.42 | C |
| rs10015979 | A/G | AA | AA | AG | GG | 0.42 | G |
| rs7659144 | C/G | CG | CG | CG | CC | 0.41 | C |
| rs363096 | T/C | CC | CC | TC | TT | 0.40 | T |
| rs362273 | A/G | AA | AG | AG | AA | 0.39 | A |
| rs16843804 | T/C | CC | TC | TC | CC | 0.38 | C |
| rs362271 | A/G | GG | AG | AG | GG | 0.38 | G |
| rs362275 | T/C | CC | TC | TC | CC | 0.38 | C |
| rs3121419 | T/C | CC | TC | TC | CC | 0.38 | C |
| rs362272 | A/G | GG | — | AG | GG | 0.38 | G |
| rs3775061 | A/G | AA | AG | AG | AA | 0.38 | A |
| rs34315806 | T/C | CC | TC | TC | CC | 0.38 | C |
| rs363099 | T/C | CC | TC | TC | CC | 0.38 | C |
| rs2298967 | T/C | TT | TC | TC | TT | 0.38 | T |
| rs363088 | A/T | AA | TA | TA | AA | 0.38 | A |
| rs363064 | T/C | CC | TC | TC | CC | 0.35 | C |
| rs363102 | A/G | AG | AA | AA | AA | 0.23 | G |
| rs2798235 | A/G | AG | GG | GG | GG | 0.21 | A |
| rs363080 | T/C | TC | CC | CC | CC | 0.21 | T |
| rs363072 | A/T | TA | TA | AA | AA | 0.13 | A |
| rs363125 | A/C | AC | AC | CC | CC | 0.12 | C |
| rs362303 | T/C | TC | TC | CC | CC | 0.12 | C |
| rs362310 | T/C | TC | TC | CC | CC | 0.12 | C |
| rs10488840 | A/G | AG | AG | GG | GG | 0.12 | G |
| rs362325 | T/C | TC | TC | TT | TT | 0.11 | T |
| rs35892913 | A/G | GG | GG | GG | GG | 0.10 | A |
| rs363102 | A/G | AG | AA | AA | AA | 0.09 | A |
| rs363096 | T/C | CC | CC | TC | TT | 0.09 | C |
| rs11731237 | T/C | CC | CC | TC | TT | 0.09 | C |
| rs10015979 | A/G | AA | AA | AG | GG | 0.08 | A |
| rs363080 | T/C | TC | CC | CC | CC | 0.07 | C |
| rs2798235 | A/G | AG | GG | GG | GG | 0.07 | G |
| rs1936032 | C/G | GC | CC | CC | CC | 0.06 | G |
| rs2276881 | A/G | GG | GG | GG | GG | 0.06 | G |
| rs363070 | A/G | AA | AA | AA | AA | 0.06 | A |
| rs35892913 | A/G | GG | GG | GG | GG | 0.04 | G |
| rs12502045 | T/C | CC | CC | CC | CC | 0.04 | C |
| rs6446723 | T/C | TC | CC | TC | TT | 0.04 | C |
| rs7685686 | A/G | AG | GG | AG | AA | 0.04 | G |
| rs3733217 | T/C | CC | CC | CC | CC | 0.03 | C |
| rs6844859 | T/C | TC | CC | TC | TT | 0.03 | C |
| rs362331 | T/C | TC | CC | TC | TT | 0.03 | C |

F. Certain Indications

In certain embodiments, provided herein are methods of treating an animal or individual comprising administering one or more pharmaceutical compositions as described herein. In certain embodiments, the individual or animal has Huntington's disease.

In certain embodiments, compounds targeted to huntingtin as described herein may be administered to reduce the severity of physiological symptoms of Huntington's disease. In certain embodiments, compounds targeted to huntingtin as described herein may be administered to reduce the rate of degeneration in an individual or an animal having Huntington's disease. In certain embodiments, compounds targeted to huntingtin as described herein may be administered regeneration function in an individual or an animal having Huntington's disease. In certain embodiments, symptoms of Huntingtin's disease may be reversed by treatment with a compound as described herein.

In certain embodiments, compounds targeted to huntingtin as described herein may be administered to ameliorate one or more symptoms of Huntington's disease. In certain embodiments administration of compounds targeted to huntingtin as described herein may improve the symptoms of Huntington's disease as measured by any metric known to those having skill in the art. In certain embodiments, administration of compounds targeted to huntingtin as described herein may improve a rodent's rotaraod assay performance. In certain embodiments, administration of compounds targeted to huntingtin as described herein may improve a rodent's plus maze assay. In certain embodiments, administration of compounds targeted to huntingtin as described herein may improve a rodent's open field assay performance.

Accordingly, provided herein are methods for ameliorating a symptom associated with Huntington's disease in a subject in need thereof. In certain embodiments, provided is a method for reducing the rate of onset of a symptom associated with Huntington's disease. In certain embodiments, provided is a method for reducing the severity of a symptom associated with Huntington's disease. In certain embodiments, provided is a method for regenerating neurological function as shown by an improvement of a symptom associated with Huntington's disease. In such embodiments, the methods comprise administering to an individual or animal in need thereof a therapeutically effective amount of a compound targeted to a huntingtin nucleic acid.

Huntington's disease is characterized by numerous physical, neurological, psychiatric, and/or peripheral symptoms. Any symptom known to one of skill in the art to be associated with Huntington's disease can be ameliorated or otherwise modulated as set forth above in the methods described above. In certain embodiments, the symptom is a physical symptom selected from the group consisting of restlessness, lack of coordination, unintentionally initiated motions, unintentionally uncompleted motions, unsteady gait, chorea, rigidity, writhing motions, abnormal posturing, instability, abnormal facial expressions, difficulty chewing, difficulty swallowing, difficulty speaking, seizure, and sleep disturbances. In certain embodiments, the symptom is a cognitive symptom selected from the group consisting of impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination and dementia. In certain embodiments, the symptom is a psychiatric symptom selected from the group consisting of anxiety, depression, blunted affect, egocentrisms, aggression, compulsive behavior, irritability and suicidal ideation. In certain embodiments, the symptom is a peripheral symptom selected from the group consisting of reduced brain mass, muscle atrophy, cardiac failure, impaired glucose tolerance, weight loss, osteoporosis, and testicular atrophy.

In certain embodiments, the symptom is restlessness. In certain embodiments, the symptom is lack of coordination. In certain embodiments, the symptom is unintentionally initiated motions. In certain embodiments, the symptom is unintentionally uncompleted motions. In certain embodiments, the symptom is unsteady gait. In certain embodiments, the symptom is chorea. In certain embodiments, the symptom is rigidity. In certain embodiments, the symptom is writhing motions. In certain embodiments, the symptom is abnormal posturing. In certain embodiments, the symptom is instability. In certain embodiments, the symptom is abnormal facial expressions. In certain embodiments, the symptom is difficulty chewing. In certain embodiments, the symptom is difficulty swallowing. In certain embodiments, the symptom is difficulty speaking. In certain embodiments, the symptom is seizures. In certain embodiments, the symptom is sleep disturbances.

In certain embodiments, the symptom is impaired planning. In certain embodiments, the symptom is impaired flexibility. In certain embodiments, the symptom is impaired abstract thinking. In certain embodiments, the symptom is impaired rule acquisition. In certain embodiments, the symptom is impaired initiation of appropriate actions. In certain embodiments, the symptom is impaired inhibition of inappropriate actions. In certain embodiments, the symptom is impaired short-term memory. In certain embodiments, the symptom is impaired long-term memory. In certain embodiments, the symptom is paranoia. In certain embodiments, the symptom is disorientation. In certain embodiments, the symptom is confusion. In certain embodiments, the symptom is hallucination. In certain embodiments, the symptom is dementia.

In certain embodiments, the symptom is anxiety. In certain embodiments, the symptom is depression. In certain embodiments, the symptom is blunted affect. In certain embodiments, the symptom is egocentrism. In certain embodiments, the symptom is aggression. In certain embodiments, the symptom is compulsive behavior. In certain embodiments, the symptom is irritability. In certain embodiments, the symptom is suicidal ideation.

In certain embodiments, the symptom is reduced brain mass. In certain embodiments, the symptom is muscle atrophy. In certain embodiments, the symptom is cardiac failure. In certain embodiments, the symptom is impaired glucose tolerance. In certain embodiments, the symptom is weight loss. In certain embodiments, the symptom is osteoporosis. In certain embodiments, the symptom is testicular atrophy.

In certain embodiments, symptoms of Huntington's disease may be quantifiable. For example, osteoporosis may be measured and quantified by, for example, bone density scans. For such symptoms, in certain embodiments, the symptom may be reduced by about 15, 20, 25, 30, 35, 40, 45, 50, 55, 60, 65, 70, 75, 80, 85, 90, 95 or 99%, or a range defined by any two of these values.

In certain embodiments, provided are methods of treating an individual comprising administering one or more pharmaceutical compositions as described herein. In certain embodiments, the individual has Huntington's disease.

In certain embodiments, administration of an antisense compound targeted to a huntingtin nucleic acid results in reduction of huntingtin expression by at least about 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to huntingtin are used for the preparation of a medicament for treating a patient suffering or susceptible to Huntington's disease.

G. Certain Pharmaceutical Compositions

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or polycationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain.

H. Administration

In certain embodiments, the compounds and compositions as described herein are administered parenterally.

In certain embodiments, parenteral administration is by infusion. Infusion can be chronic or continuous or short or intermittent. In certain embodiments, infused pharmaceutical agents are delivered with a pump. In certain embodiments, parenteral administration is by injection.

In certain embodiments, compounds and compositions are delivered to the CNS. In certain embodiments, compounds and compositions are delivered to the cerebrospinal fluid. In certain embodiments, compounds and compositions are administered to the brain parenchyma. In certain embodiments, compounds and compositions are delivered to an animal by intrathecal administration, or intracerebroventricular administration. Broad distribution of compounds and compositions, described herein, within the central nervous system may be achieved with intraparenchymal administration, intrathecal administration, or intracerebroventricular administration.

In certain embodiments, parenteral administration is by injection. The injection may be delivered with a syringe or a pump. In certain embodiments, the injection is a bolus injection. In certain embodiments, the injection is administered directly to a tissue, such as striatum, caudate, cortex, hippocampus and cerebellum.

Therefore, in certain embodiments, delivery of a compound or composition described herein can affect the pharmacokinetic profile of the compound or composition. In certain embodiments, injection of a compound or composition described herein, to a targeted tissue improves the pharmacokinetic profile of the compound or composition as compared to infusion of the compound or composition. In a certain embodiment, the injection of a compound or composition improves potency compared to broad diffusion, requiring less of the compound or composition to achieve similar pharmacology. In certain embodiments, similar pharmacology refers to the amount of time that a target mRNA and/or target protein is down-regulated (e.g. duration of action). In certain embodiments, methods of specifically localizing a pharmaceutical agent, such as by bolus injection, decreases median effective concentration (EC50) by a factor of about 50 (e.g. 50 fold less concentration in tissue is required to achieve the same or similar pharmacodynamic effect). In certain embodiments, methods of specifically localizing a pharmaceutical agent, such as by bolus injection, decreases median effective concentration (EC50) by a factor of 20, 25, 30, 35, 40, 45 or 50. In certain embodiments the pharmaceutical agent in an antisense compound as further described herein. In certain embodiments, the targeted tissue is brain tissue. In certain embodiments the targeted tissue is striatal tissue. In certain embodiments, decreasing EC50 is desirable because it reduces the dose required to achieve a pharmacological result in a patient in need thereof.

In certain embodiments, an antisense oligonucleotide is delivered by injection or infusion once every month, every two months, every 90 days, every 3 months, every 6 months, twice a year or once a year.

I. Certain Combination Therapies

In certain embodiments, one or more pharmaceutical compositions are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions as described herein. In certain embodiments, one or more pharmaceutical compositions are co-administered with another pharmaceutical agent to treat an undesired effect of that other pharmaceutical agent. In certain embodiments, one or more pharmaceutical compositions are co-administered with another pharmaceutical agent to produce a combinational effect. In certain embodiments, one or more pharmaceutical compositions are co-administered with another pharmaceutical agent to produce a synergistic effect.

In certain embodiments, one or more pharmaceutical compositions and one or more other pharmaceutical agents are administered at the same time. In certain embodiments, one or more pharmaceutical compositions and one or more other pharmaceutical agents are administered at different times. In certain embodiments, one or more pharmaceutical compositions and one or more other pharmaceutical agents are prepared together in a single formulation. In certain embodiments, one or more pharmaceutical compositions and one or more other pharmaceutical agents are prepared separately.

In certain embodiments, pharmaceutical agents that may be co-administered with a pharmaceutical composition of include antipsychotic agents, such as, e.g., haloperidol, chlorpromazine, clozapine, quetapine, and olanzapine; antidepressant agents, such as, e.g., fluoxetine, sertraline hydrochloride, venlafaxine and nortriptyline; tranquilizing agents such as, e.g., benzodiazepines, clonazepam, paroxetine, venlafaxin, and beta-blockers; mood-stabilizing agents such as, e.g., lithium, valproate, lamotrigine, and carbamazepine; paralytic agents such as, e.g., Botulinum toxin; and/or other experimental agents including, but not limited to, tetrabenazine (Xenazine), creatine, conezyme Q10, trehalose, docosahexanoic acids, ACR16, ethyl-EPA, atomoxetine, citalopram, dimebon, memantine, sodium phenylbutyrate, ramelteon, ursodiol, zyprexa, xenasine, tiapride, riluzole, amantadine, [123I]MNI-420, atomoxetine, tetrabenazine, digoxin, detromethorphan, warfarin, alprozam, ketoconazole, omeprazole, and minocycline.

NONLIMITING DISCLOSURE AND INCORPORATION BY REFERENCE

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^{me}$CGAUCG," wherein $^{me}$C indicates a cytosine base comprising a methyl group at the 5-position.

EXAMPLES

The following examples illustrate certain embodiments of the present invention and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

To allow assessment of the relative effects of nucleobase sequence and chemical modification, throughout the examples, oligomeric compounds are assigned a "Sequence Code." Oligomeric compounds having the same Sequence Code have the same nucleobase sequence. Oligomeric compounds having different Sequence Codes have different nucleobase sequences.

Example 1

Modified Antisense Oligonucleotides Targeting Human Target-X

Antisense oligonucleotides were designed targeting a Target-X nucleic acid and were tested for their effects on Target-X mRNA in vitro. ISIS 407939, which was described in an earlier publication (WO 2009/061851) was also tested.

The newly designed chimeric antisense oligonucleotides and their motifs are described in Table 15. The internucleoside linkages throughout each gapmer are phosphorothioate linkages (P=S). Nucleosides followed by "d" indicate 2'-deoxyribonucleosides. Nucleosides followed by "k" indicate 6'-(S)—CH$_3$ bicyclic nucleoside (e.g cEt) nucleosides. Nucleosides followed by "e" indicate 2'-O-methoxyethyl (2'-MOE) nucleosides. "N" indicates modified or naturally occurring nucleobases (A, T, C, G, U, or 5-methyl C).

Each gapmer listed in Table 15 is targeted to the human Target-X genomic sequence.

Activity of the newly designed gapmers was compared to a 5-10-5 2'-MOE gapmer, ISIS 407939 targeting human Target-X Cultured Hep3B cells at a density of 20,000 cells per well were transfected using electroporation with 2,000 nM antisense oligonucleotide. After a treatment period of approximately 24 hours, RNA was isolated from the cells and Target-X mRNA levels were measured by quantitative real-time PCR. Human primer probe set RTS2927 was used to measure mRNA levels. Target-X mRNA levels were adjusted according to total RNA content, as measured by RIBOGREEN®. Results are presented as percent inhibition of Target-X, relative to untreated control cells, and indicate that several of the newly designed antisense oligonucleotides are more potent than ISIS 407939. A total of 771 oligonucleotides were tested. Only those oligonucleotides which were selected for further studies are shown in Table 15. Each of the newly designed antisense oligonucleotides provided in Table 1 achieved greater than 80% inhibition and, therefore, are more active than ISIS 407939.

TABLE 15

Inhibition of human Target-X mRNA levels by chimeric antisense oligonucleotides targeted to Target-X

| Sequence (5' to 3') | ISIS NO | % inhibition | Motif | Gap Chemistry | Wing Chemistry 5' | Wing Chemistry 3' | SEQ CODE | SEQ ID NO |
|---|---|---|---|---|---|---|---|---|
| NkNkNkNdNdNdNdNkNd NdNdNdNdNeNeNe | 473359 | 92 | 3-10-3 | Deoxy/cEt | kkk | eee | 21 | 6 |
| NkNkNkNdNdNdNdNkNd NdNdNdNdNeNeNe | 473360 | 96 | 3-10-3 | Deoxy/cEt | kkk | eee | 22 | 6 |
| NkNkNkNdNdNdNdNdNd NdNdNdNdNkNkNk | 473168 | 94 | 3-10-3 | Full deoxy | kkk | kkk | 23 | 6 |
| NkNkNkNdNdNdNdNdNd NdNdNdNdNeNeNe | 473317 | 95 | 3-10-3 | Full deoxy | kkk | eee | 23 | 6 |
| NkNkNkNdNdNdNdNkNd NdNdNdNdNeNeNe | 473471 | 90 | 3-10-3 | Deoxy/cEt | kkk | eee | 23 | 6 |
| NkNdNkNdNkNdNdNdNd NdNdNdNdNdNeNeNe | 473620 | 94 | 5-9-2 | Full deoxy | kdkdk | ee | 23 | 6 |

TABLE 15-continued

Inhibition of human Target-X mRNA levels by chimeric antisense oligonucleotides targeted to Target-X

| Sequence (5' to 3') | ISIS NO | % inhibition | Gap Motif | Chemistry | Wing Chemistry 5' | Wing Chemistry 3' | SEQ CODE | SEQ ID NO |
|---|---|---|---|---|---|---|---|---|
| NkNkNdNdNdNdNdNdNdNdNdNdNdNkNk | 473019 | 88 | 2-10-2 | Full deoxy | kk | kk | 24 | 7 |
| NkNkNdNdNdNdNdNdNdNdNdNdNkNk | 473020 | 93 | 2-10-2 | Full deoxy | kk | kk | 25 | 7 |
| NkNkNkNdNdNdNdNdNdNdNdNdNeNeNe | 473321 | 93 | 3-10-3 | Full deoxy | kkk | eee | 26 | 6 |
| NkNkNkNdNdNdNdNdNdNdNdNdNeNeNe | 473322 | 94 | 3-10-3 | Full deoxy | kkk | eee | 27 | 6 |
| NkNkNkNdNdNdNdNdNdNdNdNdNeNeNe | 473323 | 96 | 3-10-3 | Full deoxy | kkk | eee | 28 | 6 |
| NkNkNkNdNdNdNdNdNdNdNdNdNeNeNe | 473326 | 94 | 3-10-3 | Full deoxy | kkk | eee | 29 | 6 |
| NkNkNkNdNdNdNdNdNkNdNdNdNdNeNeNe | 473480 | 92 | 3-10-3 | Deoxy/cEt | kkk | eee | 29 | 6 |
| NkNkNkNdNdNdNdNdNdNdNdNdNkNkNk | 473178 | 96 | 3-10-3 | Full deoxy | kkk | kkk | 30 | 6 |
| NkNkNkNdNdNdNdNdNdNdNdNdNeNeNe | 473327 | 96 | 3-10-3 | Full deoxy | kkk | eee | 30 | 6 |
| NkNkNkNdNdNdNdNdNkNdNdNdNdNeNeNe | 473481 | 93 | 3-10-3 | Deoxy/cEt | kkk | eee | 30 | 6 |
| NkNdNkNdNkNdNdNdNdNdNdNdNdNeNe | 473630 | 89 | 5-9-2 | Full deoxy | kdkdk | ee | 30 | 6 |
| NkNkNdNdNdNdNdNdNdNdNdNdNkNk | 473029 | 96 | 2-10-2 | Full deoxy | kk | kk | 31 | 7 |
| NkNkNdNdNdNdNdNdNdNdNdNdNkNk | 472925 | 93 | 2-10-2 | Full deoxy | kk | kk | 32 | 7 |
| NkNkNdNdNdNdNdNdNdNdNdNdNkNk | 472926 | 85 | 2-10-2 | Full deoxy | kk | kk | 33 | 7 |
| NkNkNkNdNdNdNdNdNdNdNdNdNkNkNk | 473195 | 97 | 3-10-3 | Full deoxy | kkk | kkk | 34 | 6 |
| NkNkNdNdNdNdNdNdNdNdNdNdNkNk | 473046 | 90 | 2-10-2 | Full deoxy | kk | kk | 35 | 7 |
| NkNkNdNdNdNdNdNdNdNdNdNdNkNk | 472935 | 92 | 2-10-2 | Full deoxy | kk | kk | 36 | 7 |
| NkNkNkNdNdNdNdNdNdNdNdNdNkNkNk | 473089 | 95 | 3-10-3 | Full deoxy | kkk | kkk | 37 | 6 |
| NkNkNkNdNdNdNdNdNdNdNdNdNeNeNe | 473350 | 93 | 3-10-3 | Full deoxy | kkk | eee | 38 | 6 |
| NkNkNkNdNdNdNdNdNdNdNdNdNeNeNe | 473353 | 93 | 3-10-3 | Full deoxy | kkk | eee | 39 | 6 |
| NkNkNdNdNdNdNdNdNdNdNdNdNkNk | 473055 | 91 | 2-10-2 | Full deoxy | kk | kk | 40 | 7 |
| NkNkNkNdNdNdNdNdNkNdNdNdNdNeNeNe | 473392 | 95 | 3-10-3 | Deoxy/cEt | kkk | eee | 41 | 6 |
| NkNkNkNdNdNdNdNdNdNdNdNdNkNkNk | 473095 | 100 | 3-10-3 | Full deoxy | kkk | kkk | 42 | 6 |
| NkNkNkNdNdNdNdNdNdNdNdNdNeNeNe | 473244 | 99 | 3-10-3 | Full deoxy | kkk | eee | 42 | 6 |

TABLE 15-continued

Inhibition of human Target-X mRNA levels by chimeric antisense oligonucleotides targeted to Target-X

| Sequence (5' to 3') | ISIS NO | % inhibition | Gap Motif | Chemistry | Wing Chemistry 5' | Wing Chemistry 3' | SEQ CODE | SEQ ID NO |
|---|---|---|---|---|---|---|---|---|
| NkNkNkNdNdNdNdNkNd NdNdNdNdNeNeNe | 473393 | 99 | 3-10-3 | Deoxy/cEt | kkk | eee | 42 | 6 |
| NkNdNkNdNkNdNdNdNd NdNdNdNdNdNeNe | 473547 | 98 | 5-9-2 | Full deoxy | kdkdk | ee | 42 | 6 |
| NkNkNkNdNdNdNdNdNd NdNdNdNdNkNk | 472942 | 87 | 2-10-2 | Full deoxy | kk | kk | 43 | 7 |
| NkNkNkNdNdNdNdNdNd NdNdNdNdNkNkNk | 473098 | 97 | 3-10-3 | Full deoxy | kkk | kkk | 44 | 6 |
| NkNkNkNdNdNdNdNkNd NdNdNdNdNeNeNe | 473408 | 92 | 3-10-3 | Deoxy/cEt | kkk | eee | 45 | 6 |
| NkNkNdNdNdNdNdNdNd NdNdNdNkNk | 472958 | 89 | 2-10-2 | Full deoxy | kk | kk | 46 | 7 |
| NkNkNdNdNdNdNdNdNd NdNdNdNkNk | 472959 | 90 | 2-10-2 | Full deoxy | kk | kk | 47 | 7 |
| NkNdNkNdNkNdNdNdNd NdNdNdNdNdNeNe | 473566 | 94 | 5-9-2 | Full deoxy | kdkdk | ee | 48 | 6 |
| NkNdNkNdNkNdNdNdNd NdNdNdNdNeNe | 473567 | 95 | 5-9-2 | Full deoxy | kdkdk | ee | 49 | 6 |
| NkNdNkNdNkNdNdNdNd NdNdNdNdNeNe | 473569 | 92 | 5-9-2 | Full deoxy | kdkdk | ee | 50 | 6 |
| NkNkNdNdNdNdNdNdNd NdNdNdNkNk | 457851 | 90 | 2-10-2 | Full deoxy | kk | kk | 51 | 7 |
| NkNkNdNdNdNdNdNdNd NdNdNdNkNk | 472970 | 91 | 2-10-2 | Full deoxy | kk | kk | 32 | 7 |
| NkNkNkNdNdNdNdNdNd NdNdNdNkNkNk | 473125 | 90 | 3-10-3 | Full deoxy | kkk | kkk | 53 | 6 |
| NkNkNkNdNdNdNdNdNd NdNdNdNeNeNe | 473274 | 98 | 3-10-3 | Full deoxy | kkk | eee | 53 | 6 |
| NkNkNkNdNdNdNkNd NdNdNdNdNeNeNe | 473428 | 90 | 3-10-3 | Deoxy/cEt | kkk | eee | 53 | 6 |
| NkNdNkNdNkNdNdNdNd NdNdNdNdNeNe | 473577 | 93 | 5-9-2 | Full deoxy | kdkdk | ee | 53 | 6 |
| NkNkNdNdNdNdNdNdNd NdNdNdNkNk | 472976 | 97 | 2-10-2 | Full deoxy | kk | kk | 54 | 7 |
| NkNkNdNdNdNdNdNd NdNdNdNdNkNk | 472983 | 94 | 2-10-2 | Full deoxy | kk | kk | 55 | 7 |
| NkNkNdNdNdNdNdNd NdNdNdNdNkNk | 472984 | 90 | 2-10-2 | Full deoxy | kk | kk | 56 | 7 |
| NkNkNkNdNdNdNdNd NdNdNdNdNkNkNk | 473135 | 97 | 3-10-3 | Full deoxy | kkk | kkk | 57 | 6 |
| NkNkNdNdNdNdNdNd NdNdNdNkNk | 472986 | 95 | 2-10-2 | Full deoxy | kk | kk | 58 | 7 |
| NkNkNkNdNdNdNdNd NdNdNdNdNkNkNk | 473137 | 95 | 3-10-3 | Full deoxy | kkk | kkk | 59 | 6 |
| NkNkNkNdNdNdNdNd NdNdNdNdNeNeNe | 473286 | 95 | 3-10-3 | Full deoxy | kkk | eee | 59 | 6 |
| NkNkNkNdNdNdNkNd NdNdNdNdNeNeNe | 473440 | 88 | 3-10-3 | Deoxy/cEt | kkk | eee | 59 | 6 |

TABLE 15-continued

Inhibition of human Target-X mRNA levels by chimeric antisense oligonucleotides targeted to Target-X

| Sequence (5' to 3') | ISIS NO | % inhibition | Gap Motif | Chemistry | Wing Chemistry 5' | Wing Chemistry 3' | SEQ CODE | SEQ ID NO |
|---|---|---|---|---|---|---|---|---|
| NkNdNkNdNkNdNdNd NdNdNdNdNdNeNe | 473589 | 97 | 5-9-2 | Full deoxy | kdkdk | ee | 59 | 6 |
| NkNkNdNdNdNdNdNd NdNdNdNdNkNk | 472988 | 85 | 2-10-2 | Full deoxy | kk | kk | 60 | 7 |
| NkNkNkNdNdNdNdNd NdNdNdNdNkNkNk | 473140 | 96 | 3-10-3 | Full deoxy | kkk | kkk | 61 | 6 |
| NkNkNdNdNdNdNdNd NdNdNdNdNkNk | 472991 | 90 | 2-10-2 | Full deoxy | kk | kk | 62 | 7 |
| NkNkNkNdNdNdNkNd NdNdNdNdNeNeNe | 473444 | 94 | 3-10-3 | Deoxy/cEt | kkk | eee | 63 | 6 |
| NkNkNkNdNdNdNdNd NdNdNdNdNkNkNk | 473142 | 96 | 3-10-3 | Full deoxy | kkk | kkk | 64 | 6 |
| NkNkNkNdNdNdNdNd NdNdNdNdNeNeNe | 473291 | 95 | 3-10-3 | Full deoxy | kkk | eee | 64 | 6 |
| NkNdNkNdNkNdNdNd NdNdNdNdNdNeNe | 473594 | 95 | 5-9-2 | Full deoxy | kdkdk | ee | 64 | 6 |
| NkNkNkNdNdNdNdNdNd NdNdNdNdNkNkNk | 473143 | 97 | 3-10-3 | Full deoxy | kkk | kkk | 65 | 6 |
| NkNkNkNdNdNdNdNd NdNdNdNdNeNeNe | 473292 | 96 | 3-10-3 | Full deoxy | kkk | eee | 65 | 6 |
| NkNkNkNdNdNdNdNkNd NdNdNdNdNeNeNe | 473446 | 96 | 3-10-3 | Deoxy/cEt | kkk | eee | 65 | 6 |
| NkNdNkNdNkNdNdNd NdNdNdNdNdNeNe | 473595 | 84 | 5-9-2 | Full deoxy | kdkdk | ee | 65 | 6 |
| NkNkNkNdNdNdNdNdNd NdNdNdNkNk | 472994 | 96 | 2-10-2 | Full deoxy | kk | kk | 66 | 7 |
| NkNkNkNdNdNdNdNd NdNdNdNdNkNkNk | 473144 | 98 | 3-10-3 | Full deoxy | kkk | kkk | 67 | 6 |
| NkNkNkNdNdNdNdNdNd NdNdNdNdNeNeNe | 473293 | 96 | 3-10-3 | Full deoxy | kkk | eee | 67 | 6 |
| NkNkNkNdNdNdNdNdNd NdNdNdNkNk | 472995 | 96 | 2-10-2 | Full deoxy | kk | kk | 68 | 7 |
| NkNkNkNdNdNdNd NdNdNdNdNeNeNe | 473294 | 91 | 3-10-3 | Full deoxy | kkk | eee | 69 | 6 |
| NkNdNkNdNkNdNdNd NdNdNdNdNdNeNe | 473597 | 94 | 5-9-2 | Full deoxy | kdkdk | ee | 69 | 6 |
| NkNkNkNdNdNdNdNd NdNdNdNkNk | 472996 | 94 | 2-10-2 | Full deoxy | kk | kk | 70 | 7 |
| NkNkNkNdNdNdNd NdNdNdNdNeNeNe | 473295 | 92 | 3-10-3 | Full deoxy | kkk | eee | 71 | 6 |
| NeNeNeNeNeNdNdNdNd NdNdNdNdNeNeNeNeNe | 407939 | 80 | 5-10-5 | Full deoxy | eeeee | eeeee | 72 | 8 |
| NkNkNkNdNdNdNdNd NdNdNdNdNeNeNe | 473296 | 98 | 3-10-3 | Full deoxy | kkk | eee | 73 | 6 |

TABLE 15-continued

Inhibition of human Target-X mRNA levels by chimeric antisense oligonucleotides targeted to Target-X

| Sequence (5' to 3') | ISIS NO | % inhibition | Motif | Gap Chemistry | Wing Chemistry 5' | 3' | SEQ CODE | SEQ ID NO |
|---|---|---|---|---|---|---|---|---|
| NkNkNkNdNdNdNdNkNd NdNdNdNdNeNeNe | 473450 | 95 | 3-10-3 | Deoxy/cEt | kkk | eee | 73 | 6 |
| NkNkNdNdNdNdNdNdNd NdNdNdNkNk | 472998 | 97 | 2-10-2 | Full deoxy | kk | kk | 74 | 7 | e = 2'-MOE, k = cEt, c = 2'-deoxyribonucleoside

Example 2

Modified Antisense Oligonucleotides Comprising 6'-(S)—CH$_3$ Bicyclic Nucleoside (cEt) and F-HNA Modifications Targeting Human Target-X Additional antisense oligonucleotides were designed targeting a Target-X nucleic acid and were tested for their effects on Target-X mRNA in vitro. ISIS 407939 was also tested.

The chimeric antisense oligonucleotides and their motifs are described in Table 16. The internucleoside linkages throughout each gapmer are phosphorothioate linkages (P=S). Nucleosides followed by "d" indicate 2'-deoxyribonucleosides. Nucleosides followed by "k" indicate 6'-(S)—CH$_3$ bicyclic nucleosides (e.g. cEt). Nucleosides followed by "e" indicate 2'-O-methoxyethyl (2'-MOE) modified nucleosides. Nucleosides followed by 'g' indicate F-HNA modified nucleosides. "N" indicates modified or naturally occurring nucleobases (A, T, C, G, U, or 5-methyl C).

Each gapmer listed in Table 16 is targeted to the human Target-X genomic sequence.

Activity of the newly designed gapmers was compared to a 5-10-5 2'-MOE gapmer, ISIS 407939 targeting human Target-X. Cultured Hep3B cells at a density of 20,000 cells per well were transfected using electroporation with 2,000 nM antisense oligonucleotide. After a treatment period of approximately 24 hours, RNA was isolated from the cells and Target-X mRNA levels were measured by quantitative real-time PCR. Human primer probe set RTS2927 was used to measure mRNA levels. Target-X mRNA levels were adjusted according to total RNA content, as measured by RIBOGREEN®. Results are presented as percent inhibition of Target-X, relative to untreated control cells, and demonstrate that several of the newly designed gapmers are more potent than ISIS 407939. A total of 765 oligonucleotides were tested. Only those oligonucleotides which were selected for further studies are shown in Table 16. All but one of the newly designed antisense oligonucleotides provided in Table 16 achieved greater than 30% inhibition and, therefore, are more active than ISIS 407939.

TABLE 16

Inhibition of human Target-X mRNA levels by chimeric antisense oligonucleotides targeted to Target-X

| Sequence (5' to 3') | ISIS No | % inhibition | Motif | Gap Chemistry | Wing Chemistry 5' | 3' | SEQ CODE | SEQ ID NO |
|---|---|---|---|---|---|---|---|---|
| NgNgNdNdNdNdNdNd NdNdNdNgNg | 482838 | 81 | 2-10-2 | Full deoxy | gg | gg | 25 | 7 |
| NgNgNgNdNdNdNdNd NdNdNdNgNgNg | 482992 | 93 | 3-10-3 | Full deoxy | ggg | ggg | 28 | 6 |
| NgNgNgNdNdNdNdNd NdNdNdNgNgNg | 482996 | 97 | 3-10-3 | Full deoxy | ggg | ggg | 30 | 6 |
| NgNdNgNdNgNdNdNd NdNdNdNdNeNe | 483284 | 82 | 5-9-2 | Full deoxy | gdgdg | ee | 23 | 6 |
| NgNdNgNdNgNdNdNd NdNdNdNdNeNe | 483289 | 70 | 5-9-2 | Full deoxy | gdgdg | ee | 27 | 6 |
| NgNdNgNdNgNdNdNd NdNdNdNdNeNe | 483290 | 80 | 5-9-2 | Full deoxy | gdgdg | ee | 28 | 6 |
| NgNdNgNdNgNdNdNd NdNdNdNdNeNe | 483294 | 69 | 5-9-2 | Full deoxy | gdgdg | ee | 30 | 6 |
| NgNgNdNdNdNdNdNd NdNdNdNeNeNeNe | 483438 | 81 | 2-10-4 | Full deoxy | gg | eeee | 23 | 6 |
| NgNgNdNdNdNdNdNd NdNdNdNeNeNeNe | 483444 | 84 | 2-10-4 | Full deoxy | gg | eeee | 28 | 6 |

TABLE 16-continued

Inhibition of human Target-X mRNA levels by chimeric antisense oligonucleotides targeted to Target-X

| Sequence (5' to 3') | ISIS No | % inhibition | Motif | Gap Chemistry | Wing Chemistry 5' | Wing Chemistry 3' | SEQ CODE | SEQ ID NO |
|---|---|---|---|---|---|---|---|---|
| NgNgNdNdNdNdNdNdNdNdNdNdNeNeNeNe | 483448 | 77 | 2-10-4 | Full deoxy | gg | eeee | 30 | 6 |
| NgNgNdNdNdNdNdNdNdNdNdNdNgNg | 482847 | 79 | 2-10-2 | Full deoxy | gg | gg | 31 | 7 |
| NgNgNdNdNdNdNdNdNdNdNdNgNg | 482747 | 85 | 2-10-2 | Full deoxy | gg | gg | 32 | 7 |
| NgNgNdNdNdNdNdNdNdNdNdNgNg | 482873 | 81 | 2-10-2 | Full deoxy | gg | gg | 40 | 7 |
| NgNgNdNdNdNdNdNdNdNdNdNdNgNg | 482874 | 82 | 2-10-2 | Full deoxy | gg | gg | 75 | 7 |
| NgNgNdNdNdNdNdNdNdNdNdNdNgNg | 482875 | 82 | 2-10-2 | Full deoxy | gg | gg | 76 | 7 |
| NgNgNgNdNdNdNdNdNdNdNdNdNgNgNg | 482896 | 95 | 3-10-3 | Full deoxy | ggg | ggg | 77 | 6 |
| NgNgNgNdNdNdNdNdNdNdNdNdNgNgNg | 483019 | 89 | 3-10-3 | Full deoxy | ggg | ggg | 38 | 6 |
| NgNdNgNdNdNdNdNdNdNdNdNdNdNdNg | 483045 | 92 | 3-10-3 | Full deoxy | gdg | gdg | 77 | 6 |
| NgNdNgNdNgNdNdNdNdNdNdNdNdNeNe | 483194 | 64 | 3-10-3 | Full deoxy | gdg | gdg | 77 | 6 |
| NgNdNgNdNgNdNdNdNdNdNdNdNeNe | 483317 | 79 | 5-9-2 | Full deoxy | gdgdg | ee | 38 | 6 |
| NgNgNdNdNdNdNdNdNdNdNdNeNeNeNe | 483343 | 75 | 2-10-4 | Full deoxy | gg | eeee | 57 | 6 |
| NgNgNdNdNdNdNdNdNdNdNdNdNeNeNeNe | 483471 | 76 | 2-10-4 | Full deoxy | gg | eeee | 38 | 6 |
| NgNgNdNdNdNdNdNdNdNdNdNeNeNe | 483478 | 20 | 2-10-4 | Full deoxy | gg | eeee | 78 | 6 |
| NeNeNeNeNeNdNdNdNdNdNdNdNdNdNeNeNeNeNe | 407939 | 30 | 5-10-5 | Full deoxy | eeeee | eeeee | 72 | 8 |
| NgNgNdNdNdNdNdNdNdNdNdNdNgNg | 482784 | 83 | 2-10-2 | Full deoxy | gg | gg | 79 | 7 |
| NgNgNdNdNdNdNdNdNdNdNdNdNgNg | 482794 | 91 | 2-10-2 | Full deoxy | gg | gg | 54 | 7 |
| NgNgNdNdNdNdNdNdNdNdNdNdNgNg | 482804 | 80 | 2-10-2 | Full deoxy | gg | gg | 58 | 7 |
| NgNgNdNdNdNdNdNdNdNdNdNdNgNg | 482812 | 81 | 2-10-2 | Full deoxy | gg | gg | 66 | 7 |
| NgNgNdNdNdNdNdNdNdNdNdNdNgNg | 482813 | 92 | 2-10-2 | Full deoxy | gg | gg | 68 | 7 |
| NgNgNdNdNdNdNdNdNdNdNdNdNgNg | 482814 | 94 | 2-10-2 | Full deoxy | gg | gg | 70 | 7 |
| NgNgNdNdNdNdNdNdNdNdNdNdNgNg | 482815 | 81 | 2-10-2 | Full deoxy | gg | gg | 80 | 7 |
| NgNgNdNdNdNdNdNdNdNdNdNdNgNg | 482816 | 71 | 2-10-2 | Full deoxy | gg | gg | 74 | 7 |
| NgNgNgNdNdNdNdNdNdNdNdNdNdNgNgNg | 482916 | 90 | 3-10-3 | Full deoxy | ggg | ggg | 44 | 6 |
| NgNgNgNdNdNdNdNdNdNdNdNdNgNgNg | 482932 | 89 | 3-10-3 | Full deoxy | ggg | ggg | 48 | 6 |

TABLE 16-continued

Inhibition of human Target-X mRNA levels by chimeric antisense oligonucleotides targeted to Target-X

| Sequence (5' to 3') | ISIS No | % inhibition | Motif | Gap Chemistry | Wing Chemistry 5' | 3' | SEQ CODE | SEQ ID NO |
|---|---|---|---|---|---|---|---|---|
| NgNgNgNdNdNdNdNd NdNdNdNdNdNgNgNg | 482953 | 93 | 3-10-3 | Full deoxy | ggg | ggg | 57 | 6 |
| NgNgNgNdNdNdNdNd NdNdNdNdNdNgNgNg | 482962 | 97 | 3-10-3 | Full deoxy | ggg | ggg | 67 | 6 |
| NgNgNgNdNdNdNdNd NdNdNdNdNdNgNgNg | 482963 | 96 | 3-10-3 | Full deoxy | ggg | ggg | 69 | 6 |
| NgNgNgNdNdNdNdNd NdNdNdNdNdNgNgNg | 482965 | 89 | 3-10-3 | Full deoxy | ggg | ggg | 73 | 6 |
| NgNdNgNdNdNdNdNd NdNdNdNdNdNgNdNg | 483065 | 69 | 3-10-3 | Full deoxy | ggg | ggg | 44 | 6 |
| NgNgNgNdNdNdNdNd NdNdNdNdNdNgNdNg | 483092 | 89 | 3-10-3 | Full deoxy | gdg | gdg | 53 | 6 |
| NgNdNgNdNgNdNdNd NdNdNdNdNdNeNe | 483241 | 79 | 5-9-2 | Full deoxy | gdgdg | ee | 53 | 6 |
| NgNdNgNdNgNdNdNd NdNdNdNdNdNeNe | 483253 | 76 | 5-9-2 | Full deoxy | gdgdg | ee | 59 | 6 |
| NgNdNgNdNgNdNdNd NdNdNdNdNdNeNe | 483258 | 70 | 5-9-2 | Full deoxy | gdgdg | ee | 64 | 6 |
| NgNgNgNdNdNgNdNd NdNdNdNdNdNeNe | 483260 | 62 | 5-9-2 | Full deoxy | gdgdg | ee | 67 | 6 |
| NgNgNgNdNgNdNdNd NdNdNdNdNdNeNe | 483261 | 76 | 5-9-2 | Full deoxy | gdgdg | ee | 69 | 6 |
| NgNgNgNdNgNdNdNd NdNdNdNdNdNeNe | 483262 | 75 | 5-9-2 | Full deoxy | gdgdg | ee | 71 | 6 |
| NgNgNgNdNgNdNdNd NdNdNdNdNdNeNe | 483263 | 73 | 5-9-2 | Full deoxy | gdgdg | ee | 73 | 6 |
| NgNgNdNdNdNdNdNd NdNdNdNdNeNeNeNe | 483364 | 78 | 2-10-4 | Full deoxy | gg | eeee | 81 | 6 |
| NgNgNdNdNdNdNdNd NdNdNdNdNeNeNeNe | 483395 | 86 | 2-10-4 | Full deoxy | gg | eeee | 53 | 6 |
| NgNgNdNdNdNdNdNd NdNdNdNdNeNeNeNe | 483413 | 83 | 2-10-4 | Full deoxy | gg | eeee | 65 | 6 |
| NgNgNdNdNdNdNdNd NdNdNdNdNeNeNeNe | 483414 | 76 | 2-10-4 | Full deoxy | gg | eeee | 67 | 6 |
| NgNgNdNdNdNdNdNd NdNdNdNdNeNeNeNe | 483415 | 85 | 2-10-4 | Full deoxy | gg | eeee | 69 | 6 |
| NgNgNdNdNdNdNdNd NdNdNdNdNeNeNeNe | 483416 | 77 | 2-10-4 | Full deoxy | gg | eeee | 71 | 6 |
| NgNgNdNdNdNdNdNd NdNdNdNdNeNeNeNe | 483417 | 83 | 2-10-4 | Full deoxy | gg | eeee | 73 | 6 | e = 2'-MOE, d = 2'-deoxyribonucleoside, g = F-HNA

Example 3

Modified Antisense Oligonucleotides Comprising 2'-MOE and 6'-(S)—CH₃ Bicyclic Nucleoside (e.g cEt) Modifications Targeting Human Target-X Additional antisense oligonucleotides were designed targeting a Target-X nucleic acid and were tested for their effects on Target-X mRNA in vitro. ISIS 403052, ISIS 407594, ISIS 407606, ISIS 407939, and ISIS 416438, which were described in an earlier publication (WO 2009/061851) were also tested.

The newly designed chimeric antisense oligonucleotides are 16 nucleotides in length and their motifs are described in Table 17. The chemistry column of Table 17 presents the sugar motif of each oligonucleotide, wherein "e" indicates a 2'-O-methoxyethyl (2'-MOE) nucleoside, "k" indicates a 6'-(S)-CH₃ bicyclic nucleoside (e.g cEt) and "d" indicates a 2'-deoxyribonucleoside. The internucleoside linkages throughout each gapmer are hosphorothioate (P=S) linkages. All cytosine residues throughout each oligonucleotide are 5-methylcytosines.

Each gapmer listed in Table 17 is targeted to the human Target-X genomic sequence.

Activity of the newly designed gapmers was compared to ISIS 403052, ISIS 407594, ISIS 407606, ISIS 407939, and ISIS 416438. Cultured Hep3B cells at a density of 20,000 cells per well were transfected using electroporation with 2,000 nM antisense oligonucleotide. After a treatment period of approximately 24 hours, RNA was isolated from the cells and Target-X mRNA levels were measured by quantitative real-time PCR. Human primer probe set RTS2927 (described hereinabove in Example 1) was used to measure mRNA levels. Target-X mRNA levels were adjusted according to total RNA content, as measured by RIBOGREEN. Results are presented as percent inhibition of Target-X, relative to untreated control cells. A total of 380 oligonucleotides were tested. Only those oligonucleotides which were selected for further studies are shown in Table 17. Each of the newly designed antisense oligonucleotides provided in Table 17 achieved greater than 64% inhibition and, therefore, are more potent than each of ISIS 403052, ISIS 407594, ISIS 407606, ISIS 407939, and ISIS 416438.

TABLE 17

Inhibition of human Target-X mRNA levels by chimeric antisense oligonucleotides targeted to Target-X

| ISIS No | Chemistry | Motif | % inhibition | SEQ CODE |
|---|---|---|---|---|
| 403052 | eeeee-(d10)-eeeee | 5-10-5 | 64 | 82 |
| 407594 | eeeee-(d10)-eeeee | 5-10-5 | 40 | 83 |
| 407606 | eeeee-(d10)-eeeee | 5-10-5 | 39 | 84 |
| 407939 | eeeee-(d10)-eeeee | 5-10-5 | 57 | 72 |
| 416438 | eeeee-(d10)-eeeee | 5-10-5 | 62 | 85 |
| 484487 | kdk-(d10)-dkdk | 3-10-3 | 91 | 77 |
| 484539 | kdk-d(10)-kdk | 3-10-3 | 92 | 53 |
| 484546 | kdk-d(10)-kdk | 3-10-3 | 92 | 86 |
| 484547 | kdk-d(10)-kdk | 3-10-3 | 89 | 87 |
| 484549 | kdk-d(10)-kdk | 3-10-3 | 91 | 57 |
| 484557 | kdk-d(10)-kdk | 3-10-3 | 92 | 65 |
| 484558 | kdk-d(10)-kdk | 3-10-3 | 94 | 67 |
| 484559 | kdk-d(10)-kdk | 3-10-3 | 90 | 69 |
| 484582 | kdk-d(10)-kdk | 3-10-3 | 88 | 23 |
| 484632 | kk-d(10)-eeee | 2-10-4 | 90 | 88 |
| 484641 | kk-d(10)-eeee | 2-10-4 | 91 | 77 |
| 484679 | kk-d(10)-eeee | 2-10-4 | 90 | 49 |
| 484693 | kk-d(10)-eeee | 2-10-4 | 93 | 53 |
| 484711 | kk-d(10)-eeee | 2-10-4 | 92 | 65 |
| 484712 | kk-d(10)-eeee | 2-10-4 | 92 | 67 |
| 484713 | kk-d(10)-eeee | 2-10-4 | 85 | 69 |
| 484714 | kk-d(10)-eeee | 2-10-4 | 83 | 71 |
| 484715 | kk-d(10)-eeee | 2-10-4 | 93 | 73 |
| 484736 | kk-d(10)-eeee | 2-10-4 | 89 | 23 |
| 484742 | kk-d(10)-eeee | 2-10-4 | 93 | 28 |
| 484746 | kk-d(10)-eeee | 2-10-4 | 88 | 30 |
| 484771 | kk-d(10)-eeee | 2-10-4 | 89 | 89 | e = 2'-MOE, k = cEt, d = 2'-deoxyribonucleoside

Example 4

Antisense Inhibition of Human Target-X with 5-10-5 2'-MOE Gapmers

Additional antisense oligonucleotides were designed targeting a Target-X nucleic acid and were tested for their effects on Target-X mRNA in vitro. Also tested were ISIS 403094, ISIS 407641, ISIS 407643, ISIS 407662, ISIS 407900, ISIS 407910, ISIS 407935, ISIS 407936, ISIS 407939, ISIS 416446, ISIS 416449, ISIS 416455, ISIS 416472, ISIS 416477, ISIS 416507, ISIS 416508, ISIS 422086, ISIS 422087, ISIS 422140, and ISIS 422142, 5-10-5 2'-MOE gapmers targeting human Target-X, which were described in an earlier publication (WO 2009/061851), incorporated herein by reference.

The newly designed modified antisense oligonucleotides are 20 nucleotides in length and their motifs are described in Tables 18 and 19. The chemistry column of Tables 18 and 19 present the sugar motif of each oligonucleotide, wherein "e" indicates a 2'-O-methoxyethyl (2'-MOE) nucleoside and "d" indicates a 2'-deoxyribonucleoside. The internucleoside linkages throughout each gapmer are hosphorothioate (P=S) linkages. All cytosine residues throughout each oligonucleotide are 5-methylcytosines.

Each gapmer listed in Table 18 is targeted to the human Target-X genomic sequence.

Activity of the newly designed gapmers was compared to ISIS 403094, ISIS 407641, ISIS 407643, ISIS 407662, ISIS 407900, ISIS 407910, ISIS 407935, ISIS 407936, ISIS 407939, ISIS 416446, ISIS 416449, ISIS 416455, ISIS 416472, ISIS 416477, ISIS 416507, ISIS 416508, ISIS 422086, ISIS 422087, ISIS 422140, and ISIS 422142. Cultured Hep3B cells at a density of 20,000 cells per well were transfected using electroporation with 2,000 nM antisense oligonucleotide. After a treatment period of approximately 24 hours, RNA was isolated from the cells and Target-X mRNA levels were measured by quantitative real-time PCR. Human primer probe set RTS2927 (described hereinabove in Example 1) was used to measure mRNA levels. Target-X mRNA levels were adjusted according to total RNA content, as measured by RIBOGREEN. Results are presented as percent inhibition of Target-X, relative to untreated control cells. A total of 916 oligonucleotides were tested. Only those oligonucleotides which were selected for further studies are shown in Tables 18 and 19.

TABLE 18

Inhibition of human Target-X mRNA levels by chimeric antisense oligonucleotides targeted to Target-X

| ISIS No | Chemistry | % inhibition | SEQ CODE |
|---|---|---|---|
| 490275 | e5-d(10)-e5 | 35 | 90 |
| 490277 | e5-d(10)-e5 | 73 | 91 |
| 490278 | e5-d(10)-e5 | 78 | 92 |
| 490279 | e5-d(10)-e5 | 66 | 93 |
| 490323 | e5-d(10)-e5 | 65 | 94 |
| 490368 | e5-d(10)-e5 | 78 | 95 |
| 490396 | e5-d(10)-e5 | 76 | 96 |
| 416507 | e5-d(10)-e5 | 73 | 97 |
| 422140 | e5-d(10)-e5 | 59 | 98 |
| 422142 | e5-d(10)-e5 | 73 | 99 |
| 416508 | e5-d(10)-e5 | 75 | 100 |
| 490424 | e5-d(10)-e5 | 57 | 101 |
| 490803 | e5-d(10)-e5 | 70 | 102 |
| 416446 | e5-d(10)-e5 | 73 | 103 |
| 416449 | e5-d(10)-e5 | 33 | 104 |
| 407900 | e5-d(10)-e5 | 66 | 105 |
| 490103 | e5-d(10)-e5 | 87 | 106 |
| 416455 | e5-d(10)-e5 | 42 | 107 |
| 407910 | e5-d(10)-e5 | 25 | 108 |
| 490149 | e5-d(10)-e5 | 82 | 109 |
| 403094 | e5-d(10)-e5 | 60 | 110 |
| 416472 | e5-d(10)-e5 | 78 | 111 |
| 407641 | e5-d(10)-e5 | 64 | 112 |
| 416477 | e5-d(10)-e5 | 25 | 113 |
| 407643 | e5-d(10)-e5 | 78 | 114 |
| 490196 | e5-d(10)-e5 | 81 | 115 |
| 490197 | e5-d(10)-e5 | 85 | 116 |

TABLE 18-continued

Inhibition of human Target-X mRNA levels by chimeric antisense oligonucleotides targeted to Target-X

| ISIS No | Chemistry | % inhibition | SEQ CODE |
|---|---|---|---|
| 490208 | e5-d(10)-e5 | 89 | 117 |
| 490209 | e5-d(10)-e5 | 81 | 118 |
| 422086 | e5-d(10)-e5 | 90 | 119 |
| 407935 | e5-d(10)-e5 | 91 | 120 |
| 422087 | e5-d(10)-e5 | 89 | 121 |
| 407936 | e5-d(10)-e5 | 80 | 122 |
| 407939 | e5-d(10)-e5 | 67 | 72 | e = 2'-MOE, d = 2'-deoxynucleoside

TABLE 19

Inhibition of human Target-X mRNA levels by chimeric antisense oligonucleotides

| ISIS No | Motif | % inhibition | SEQ CODE |
|---|---|---|---|
| 407662 | e5-d(10)-e5 | 76 | 123 |
| 416446 | e5-d(10)-e5 | 73 | 103 | e = 2-MOE, d = 2'-deoxynucleoside

Example 5

Modified Chimeric Antisense Oligonucleotides Comprising 6'-(S)—CH₃ Bicyclic Nucleoside (e.g cEt) Modifications at 5' and 3' Wing Regions Targeting Human Target-X Additional antisense oligonucleotides were designed targeting a Target-X nucleic acid and were tested for their effects on Target-X mRNA in vitro. ISIS 407939, which was described in an earlier publication (WO 2009/061851) were also tested. ISIS 457851, ISIS 472925, ISIS 472926, ISIS 472935, ISIS 472942, ISIS 472958, ISIS 472959, ISIS 472970, ISIS 472976, ISIS 472983, ISIS 472984, ISIS 472988, ISIS 472991, ISIS 472994, ISIS 472995, ISIS 472996, ISIS 472998, and ISIS 473020, described in the Examples above were also included in the screen.

The newly designed chimeric antisense oligonucleotides in Table 20 were designed as 2-10-2 cEt gapmers. The newly designed gapmers are 14 nucleosides in length, wherein the central gap segment comprises of ten 2'-deoxyribonucleosides and is flanked by wing segments on the 5' direction and the 3' direction comprising five nucleosides each. Each nucleoside in the 5' wing segment and each nucleoside in the 3' wing segment comprises 6'-(S)—CH₃ bicyclic nucleoside (e.g cEt) modification. The internucleoside linkages throughout each gapmer are phosphorothioate (P=S) linkages. All cytosine residues throughout each gapmer are 5-methylcytosines.

Each gapmer listed in Table 20 is targeted to the human Target-X genomic sequence.

Activity of the newly designed oligonucleotides was compared to ISIS 407939. Cultured Hep3B cells at a density of 20,000 cells per well were transfected using electroporation with 2,000 nM antisense oligonucleotide. After a treatment period of approximately 24 hours, RNA was isolated from the cells and Target-X mRNA levels were measured by quantitative real-time PCR. Human primer probe set RTS2927 (described hereinabove in Example 1) was used to measure mRNA levels. Target-X mRNA levels were adjusted according to total RNA content, as measured by RIBOGREEN. Results are presented as percent inhibition of Target-X, relative to untreated control cells. A total of 614 oligonucleotides were tested. Only those oligonucleotides which were selected for further studies are shown in Table 20. Many of the newly designed antisense oligonucleotides provided in Table 20 achieved greater than 72% inhibition and, therefore, are more potent than ISIS 407939.

TABLE 20

Inhibition of human Target-X mRNA levels by chimeric antisense oligonucleotides targeted to Target-X

| ISIS No | % inhibition | Motif | Wing Chemistry | SEQ CODE |
|---|---|---|---|---|
| 407939 | 72 | 5-10-5 | cEt | 72 |
| 473020 | 90 | 2-10-2 | cEt | 25 |
| 492465 | 83 | 2-10-2 | cEt | 124 |
| 492467 | 74 | 2-10-2 | cEt | 125 |
| 492492 | 84 | 2-10-2 | cEt | 126 |
| 492494 | 91 | 2-10-2 | cEt | 127 |
| 492503 | 89 | 2-10-2 | cEt | 128 |
| 492530 | 91 | 2-10-2 | cEt | 129 |
| 492534 | 91 | 2-10-2 | cEt | 130 |
| 492536 | 90 | 2-10-2 | cEt | 131 |
| 492541 | 84 | 2-10-2 | cEt | 132 |
| 492545 | 89 | 2-10-2 | cEt | 133 |
| 492566 | 90 | 2-10-2 | cEt | 134 |
| 492571 | 82 | 2-10-2 | cEt | 135 |
| 492572 | 89 | 2-10-2 | cEt | 136 |
| 492573 | 90 | 2-10-2 | cEt | 137 |
| 492574 | 92 | 2-10-2 | cEt | 138 |
| 492575 | 88 | 2-10-2 | cEt | 139 |
| 492593 | 83 | 2-10-2 | cEt | 140 |
| 492617 | 91 | 2-10-2 | cEt | 141 |
| 492618 | 92 | 2-10-2 | cEt | 142 |
| 492619 | 90 | 2-10-2 | cEt | 143 |
| 492621 | 75 | 2-10-2 | cEt | 144 |
| 492104 | 89 | 2-10-2 | cEt | 145 |
| 492105 | 86 | 2-10-2 | cEt | 146 |
| 492189 | 88 | 2-10-2 | cEt | 147 |
| 492194 | 92 | 2-10-2 | cEt | 148 |
| 492195 | 90 | 2-10-2 | cEt | 149 |
| 472925 | 87 | 2-10-2 | cEt | 32 |
| 492196 | 91 | 2-10-2 | cEt | 150 |
| 472926 | 88 | 2-10-2 | cEt | 33 |
| 492205 | 92 | 2-10-2 | cEt | 151 |
| 492215 | 77 | 2-10-2 | cEt | 152 |
| 492221 | 79 | 2-10-2 | cEt | 153 |
| 472935 | 82 | 2-10-2 | cEt | 36 |
| 492234 | 86 | 2-10-2 | cEt | 154 |
| 472942 | 85 | 2-10-2 | cEt | 43 |
| 492276 | 75 | 2-10-2 | cEt | 155 |
| 492277 | 75 | 2-10-2 | cEt | 156 |
| 492306 | 85 | 2-10-2 | cEt | 157 |
| 492317 | 93 | 2-10-2 | cEt | 158 |
| 472958 | 92 | 2-10-2 | cEt | 46 |
| 472959 | 88 | 2-10-2 | cEt | 47 |
| 492329 | 88 | 2-10-2 | cEt | 159 |
| 492331 | 95 | 2-10-2 | cEt | 160 |
| 492333 | 85 | 2-10-2 | cEt | 161 |
| 492334 | 88 | 2-10-2 | cEt | 162 |
| 457851 | 89 | 2-10-2 | cEt | 51 |
| 472970 | 92 | 2-10-2 | cEt | 52 |
| 492365 | 69 | 2-10-2 | cEt | 163 |
| 472976 | 94 | 2-10-2 | cEt | 54 |
| 472983 | 76 | 2-10-2 | cEt | 55 |
| 472984 | 72 | 2-10-2 | cEt | 56 |
| 492377 | 70 | 2-10-2 | cEt | 164 |
| 492380 | 80 | 2-10-2 | cEt | 165 |
| 492384 | 61 | 2-10-2 | cEt | 166 |
| 472988 | 59 | 2-10-2 | cEt | 60 |
| 492388 | 70 | 2-10-2 | cEt | 167 |
| 492389 | 70 | 2-10-2 | cEt | 168 |
| 492390 | 89 | 2-10-2 | cEt | 169 |
| 492391 | 80 | 2-10-2 | cEt | 170 |
| 472991 | 84 | 2-10-2 | cEt | 62 |
| 492398 | 88 | 2-10-2 | cEt | 171 |
| 492399 | 94 | 2-10-2 | cEt | 172 |
| 492401 | 91 | 2-10-2 | cEt | 173 |

TABLE 20-continued

Inhibition of human Target-X mRNA levels by chimeric antisense oligonucleotides targeted to Target-X

| ISIS No | % inhibition | Motif | Wing Chemistry | SEQ CODE |
|---------|--------------|-------|----------------|----------|
| 492403  | 78           | 2-10-2| cEt            | 174      |
| 472994  | 95           | 2-10-2| cEt            | 66       |
| 472995  | 91           | 2-10-2| cEt            | 68       |
| 492404  | 84           | 2-10-2| cEt            | 175      |
| 492405  | 87           | 2-10-2| cEt            | 176      |
| 472996  | 85           | 2-10-2| cEt            | 70       |
| 492406  | 43           | 2-10-2| cEt            | 177      |
| 472998  | 92           | 2-10-2| cEt            | 74       |
| 492440  | 89           | 2-10-2| cEt            | 178      |

Example 6

Modified Chimeric Antisense Oligonucleotides Comprising 6'-(S)—CH₃ Bicyclic Nucleoside (e.g cEt) Modifications at 5' and 3' Wing Regions Targeting Human Target-X Additional antisense oligonucleotides were designed targeting a Target-X nucleic acid and were tested for their effects on Target-X mRNA in vitro. Also tested was ISIS 407939, a 5-10-5 MOE gapmer targeting human Target-X, which was described in an earlier publication (WO 2009/061851). ISIS 472998 and ISIS 473046, described in the Examples above were also included in the screen.

The newly designed chimeric antisense oligonucleotides in Table 21 were designed as 2-10-2 cEt gapmers. The newly designed gapmers are 14 nucleosides in length, wherein the central gap segment comprises of ten 2'-deoxyribonucleosides and is flanked by wing segments on the 5' direction and the 3' direction comprising five nucleosides each. Each nucleoside in the 5' wing segment and each nucleoside in the 3' wing segment comprise 6'-(S)—CH₃ bicyclic nucleoside (e.g cEt) modification. The internucleoside linkages throughout each gapmer are phosphorothioate (P=S) linkages. All cytosine residues throughout each gapmer are 5-methylcytosines.

Each gapmer listed in Table 21 is targeted to the human Target-X genomic sequence.

Activity of the newly designed gapmers was compared to ISIS 407939. Cultured Hep3B cells at a density of 20,000 cells per well were transfected using electroporation with 2,000 nM antisense oligonucleotide. After a treatment period of approximately 24 hours, RNA was isolated from the cells and Target-X mRNA levels were measured by quantitative real-time PCR. Human primer probe set RTS2927 (described hereinabove in Example 1) was used to measure mRNA levels. Target-X mRNA levels were adjusted according to total RNA content, as measured by RIBOGREEN. Results are presented as percent inhibition of Target-X, relative to untreated control cells. A total of 757 oligonucleotides were tested. Only those oligonucleotides which were selected for further studies are shown in Table 21. Each of the newly designed antisense oligonucleotides provided in Table 21 achieved greater than 67% inhibition and, therefore, are more potent than 407939.

TABLE 21

Inhibition of human Target-X mRNA levels by chimeric antisense oligonucleotides targeted to Target-X

| ISIS No | % inhibition | Motif  | Wing chemistry | SEQ CODE |
|---------|--------------|--------|----------------|----------|
| 407939  | 67           | 5-10-5 | cEt            | 72       |
| 492651  | 77           | 2-10-2 | cEt            | 179      |
| 492652  | 84           | 2-10-2 | cEt            | 180      |
| 492658  | 87           | 2-10-2 | cEt            | 181      |
| 492725  | 74           | 2-10-2 | cEt            | 182      |
| 492730  | 78           | 2-10-2 | cEt            | 183      |
| 492731  | 72           | 2-10-2 | cEt            | 184      |
| 492784  | 72           | 2-10-2 | cEt            | 185      |
| 492816  | 70           | 2-10-2 | cEt            | 186      |
| 492818  | 73           | 2-10-2 | cEt            | 187      |
| 492877  | 83           | 2-10-2 | cEt            | 188      |
| 492878  | 79           | 2-10-2 | cEt            | 189      |
| 492913  | 73           | 2-10-2 | cEt            | 190      |
| 492914  | 82           | 2-10-2 | cEt            | 191      |
| 492928  | 76           | 5-10-5 | cEt            | 192      |
| 492938  | 80           | 2-10-2 | cEt            | 193      |
| 492991  | 91           | 2-10-2 | cEt            | 194      |
| 492992  | 73           | 2-10-2 | cEt            | 195      |
| 493087  | 81           | 2-10-2 | cEt            | 196      |
| 493114  | 80           | 2-10-2 | cEt            | 197      |
| 493178  | 86           | 2-10-2 | cEt            | 198      |
| 493179  | 69           | 2-10-2 | cEt            | 199      |
| 493182  | 79           | 2-10-2 | cEt            | 200      |
| 493195  | 71           | 2-10-2 | cEt            | 201      |
| 473046  | 79           | 2-10-2 | cEt            | 35       |
| 493201  | 86           | 2-10-2 | cEt            | 202      |
| 493202  | 76           | 2-10-2 | cEt            | 203      |
| 493255  | 80           | 2-10-2 | cEt            | 204      |
| 493291  | 84           | 2-10-2 | cEt            | 205      |
| 493292  | 90           | 2-10-2 | cEt            | 206      |
| 493296  | 82           | 2-10-2 | cEt            | 207      |
| 493298  | 77           | 2-10-2 | cEt            | 208      |
| 493299  | 76           | 5-10-5 | cEt            | 209      |
| 493304  | 77           | 2-10-2 | cEt            | 210      |
| 493312  | 75           | 2-10-2 | cEt            | 211      |
| 493333  | 76           | 2-10-2 | cEt            | 212      |
| 472998  | 85           | 2-10-2 | cEt            | 74       |

Example 7

Dose-Dependent Antisense Inhibition of Human Target-X in Hep3B Cells

Antisense oligonucleotides from the studies above, exhibiting in vitro inhibition of Target-X mRNA, were selected and tested at various doses in Hep3B cells. Cells were plated at a density of 20,000 cells per well and transfected using electroporation with 0.67 μM, 2.00 μM, 1.11 μM, and 6.00 μM concentrations of antisense oligonucleotide, as specified in Table 22. After a treatment period of approximately 16 hours, RNA was isolated from the cells and Target-X mRNA levels were measured by quantitative real-time PCR. Human Target-X primer probe set RTS2927 was used to measure mRNA levels. Target-X mRNA levels were adjusted according to total RNA content, as measured by RIBOGREEN®. Results are presented as percent inhibition of Target-X, relative to untreated control cells.

The half maximal inhibitory concentration ($IC_{50}$) of each oligonucleotide is also presented in Table 22. As illustrated in Table 22, Target-X mRNA levels were reduced in a dose-dependent manner in antisense oligonucleotide treated cells. The data also confirms that several of the newly designed gapmers are more potent than ISIS 407939 of the previous publication.

TABLE 22

Dose-dependent antisense inhibition of human Target-X in Hep3B cells using electroporation

| ISIS No | 666.6667 nM | 2000.0 nM | 6000.0 nM | IC$_{50}$ (μM) |
|---|---|---|---|---|
| 407939 | 47 | 68 | 85 | 0.7 |
| 457851 | 60 | 80 | 93 | <0.6 |
| 472916 | 53 | 80 | 87 | <0.6 |
| 472925 | 62 | 86 | 95 | <0.6 |
| 472926 | 66 | 77 | 85 | <0.6 |
| 472935 | 54 | 84 | 94 | <0.6 |
| 472958 | 66 | 82 | 88 | <0.6 |
| 472959 | 64 | 81 | 93 | <0.6 |
| 472970 | 72 | 87 | 86 | <0.6 |
| 472976 | 78 | 92 | 97 | <0.6 |
| 472994 | 79 | 92 | 96 | <0.6 |
| 472995 | 61 | 82 | 93 | <0.6 |
| 472996 | 73 | 91 | 95 | <0.6 |
| 472998 | 63 | 90 | 95 | <0.6 |
| 473019 | 55 | 80 | 86 | <0.6 |
| 473020 | 61 | 76 | 85 | <0.6 |
| 473046 | 61 | 80 | 94 | <0.6 |
| 473055 | 55 | 84 | 94 | <0.6 |
| 492104 | 53 | 76 | 88 | <0.6 |
| 492105 | 62 | 80 | 90 | <0.6 |
| 492189 | 57 | 80 | 92 | <0.6 |
| 492194 | 57 | 83 | 91 | <0.6 |
| 492195 | 58 | 81 | 95 | <0.6 |
| 492196 | 62 | 86 | 95 | <0.6 |
| 492205 | 62 | 87 | 95 | <0.6 |
| 492215 | 60 | 78 | 89 | <0.6 |
| 492221 | 63 | 76 | 92 | <0.6 |
| 492234 | 51 | 74 | 91 | 0.5 |
| 492276 | 50 | 56 | 95 | 0.8 |
| 492277 | 58 | 73 | 81 | <0.6 |
| 492306 | 61 | 75 | 84 | <0.6 |
| 492317 | 59 | 80 | 93 | <0.6 |
| 492329 | 59 | 70 | 89 | <0.6 |
| 492331 | 69 | 87 | 95 | <0.6 |
| 492333 | 47 | 70 | 85 | 0.7 |
| 492334 | 57 | 77 | 90 | <0.6 |
| 492390 | 72 | 88 | 95 | <0.6 |
| 492399 | 68 | 91 | 96 | <0.6 |
| 492401 | 68 | 89 | 95 | <0.6 |
| 492404 | 65 | 87 | 94 | <0.6 |
| 492405 | 44 | 81 | 90 | 0.7 |
| 492406 | 65 | 82 | 92 | <0.6 |
| 492440 | 50 | 70 | 89 | 0.6 |
| 492465 | 16 | 80 | 79 | 1.4 |
| 492467 | 58 | 77 | 92 | <0.6 |
| 492492 | 45 | 80 | 94 | 0.7 |
| 492494 | 63 | 82 | 93 | <0.6 |
| 492503 | 55 | 81 | 93 | <0.6 |
| 492530 | 70 | 86 | 90 | <0.6 |
| 492534 | 67 | 85 | 91 | <0.6 |
| 492536 | 54 | 81 | 89 | <0.6 |
| 492541 | 54 | 71 | 85 | <0.6 |
| 492545 | 59 | 78 | 89 | <0.6 |
| 492566 | 59 | 84 | 85 | <0.6 |
| 492571 | 52 | 81 | 89 | <0.6 |
| 492572 | 67 | 83 | 90 | <0.6 |
| 492573 | 69 | 83 | 92 | <0.6 |
| 492574 | 65 | 82 | 91 | <0.6 |
| 492575 | 72 | 83 | 91 | <0.6 |
| 492593 | 61 | 78 | 90 | <0.6 |
| 492617 | 62 | 80 | 93 | <0.6 |
| 492618 | 47 | 79 | 94 | 0.6 |
| 492619 | 54 | 82 | 95 | <0.6 |
| 492621 | 44 | 85 | 92 | 0.6 |
| 492651 | 53 | 66 | 91 | 0.6 |
| 492652 | 61 | 78 | 88 | <0.6 |
| 492658 | 59 | 79 | 88 | <0.6 |
| 492725 | 43 | 84 | 89 | 0.6 |
| 492730 | 51 | 87 | 93 | 0.4 |
| 492731 | 46 | 82 | 90 | 0.6 |
| 492784 | 56 | 88 | 96 | <0.6 |
| 492816 | 68 | 89 | 97 | <0.6 |
| 492818 | 64 | 84 | 96 | <0.6 |
| 492877 | 67 | 91 | 93 | <0.6 |
| 492878 | 80 | 89 | 93 | <0.6 |
| 492913 | 53 | 87 | 92 | <0.6 |
| 492914 | 75 | 89 | 96 | <0.6 |
| 492928 | 60 | 83 | 94 | <0.6 |
| 492938 | 70 | 90 | 92 | <0.6 |
| 492991 | 67 | 93 | 99 | <0.6 |
| 492992 | 0 | 82 | 95 | 2.1 |
| 493087 | 54 | 81 | 90 | <0.6 |
| 493114 | 50 | 73 | 90 | 0.6 |
| 493178 | 71 | 88 | 96 | <0.6 |
| 493179 | 47 | 82 | 95 | 0.6 |
| 493182 | 79 | 87 | 91 | <0.6 |
| 493195 | 55 | 78 | 90 | <0.6 |
| 493201 | 87 | 93 | 96 | <0.6 |
| 493202 | 68 | 89 | 94 | <0.6 |
| 493255 | 57 | 79 | 93 | <0.6 |
| 493291 | 57 | 87 | 93 | <0.6 |
| 493292 | 70 | 89 | 93 | <0.6 |
| 493296 | 35 | 84 | 91 | 0.9 |
| 493298 | 57 | 84 | 92 | <0.6 |
| 493299 | 65 | 84 | 93 | <0.6 |
| 493304 | 68 | 86 | 94 | <0.6 |
| 493312 | 53 | 82 | 91 | <0.6 |
| 493333 | 66 | 84 | 87 | <0.6 |

Example 8

Dose-Dependent Antisense Inhibition of Human Target-X in Hep3B Cells

Additional antisense oligonucleotides from the studies described above, exhibiting in vitro inhibition of Target-X mRNA, were selected and tested at various doses in Hep3B cells. Cells were plated at a density of 20,000 cells per well and transfected using electroporation with 0.67 μM, 2.00 μM, 1.11 μM, and 6.00 μM concentrations of antisense oligonucleotide, as specified in Table 23. After a treatment period of approximately 16 hours, RNA was isolated from the cells and Target-X mRNA levels were measured by quantitative real-time PCR. Human Target-X primer probe set RTS2927 was used to measure mRNA levels. Target-X mRNA levels were adjusted according to total RNA content, as measured by RIBOGREEN®. Results are presented as percent inhibition of Target-X, relative to untreated control cells. As illustrated in Table 23, Target-X mRNA levels were reduced in a dose-dependent manner in antisense oligonucleotide treated cells. The data also confirms that several of the newly designed gapmers are more potent than ISIS 407939.

TABLE 23

Dose-dependent antisense inhibition of human Target-X in Hep3B cells using electroporation

| ISIS No | 0.67 μM | 2.00 μM | 6.00 μM | IC$_{50}$ (μM) |
|---|---|---|---|---|
| 407939 | 52 | 71 | 86 | 0.6 |
| 472983 | 49 | 83 | 97 | 0.5 |
| 472984 | 51 | 82 | 95 | 0.5 |
| 472991 | 49 | 82 | 95 | 0.5 |
| 472998 | 59 | 88 | 96 | <0.6 |
| 492365 | 74 | 91 | 96 | <0.6 |
| 492377 | 56 | 76 | 91 | <0.6 |

TABLE 23-continued

Dose-dependent antisense inhibition of human Target-X in Hep3B cells using electroporation

| ISIS No | 0.67 μM | 2.00 μM | 6.00 μM | IC$_{50}$ (μM) |
|---------|---------|---------|---------|----------------|
| 492380 | 63 | 79 | 95 | <0.6 |
| 492384 | 67 | 84 | 94 | <0.6 |
| 492388 | 69 | 87 | 97 | <0.6 |
| 492389 | 62 | 90 | 96 | <0.6 |
| 492391 | 56 | 84 | 94 | <0.6 |
| 492398 | 63 | 80 | 95 | <0.6 |
| 492403 | 58 | 81 | 91 | <0.6 |

Example 9

Modified Chimeric Antisense Oligonucleotides Comprising 2'-Methoxyethyl (2'-MOE) Modifications at 5' and 3' Wing Regions Targeting Human Target-X Additional antisense oligonucleotides were designed targeting a Target-X nucleic acid and were tested for their effects on Target-X mRNA in vitro. Also tested were ISIS 403052, ISIS 407939, ISIS 416446, ISIS 416472, ISIS 416507, ISIS 416508, ISIS 422087, ISIS 422096, ISIS 422130, and ISIS 422142 which were described in an earlier publication (WO 2009/061851), incorporated herein by reference. ISIS 490149, ISIS 490197, ISIS 490209, ISIS 490275, ISIS 490277, and ISIS 490424, described in the Examples above, were also included in the screen.

The newly designed chimeric antisense oligonucleotides in Table 24 were designed as 3-10-4 2'-MOE gapmers. These gapmers are 17 nucleosides in length, wherein the central gap segment comprises of ten 2'-deoxyribonucleosides and is flanked by wing segments on the 5' direction with three nucleosides and the 3' direction with four nucleosides. Each nucleoside in the 5' wing segment and each nucleoside in the 3' wing segment has 2'-MOE modifications. The internucleoside linkages throughout each gapmer are phosphorothioate (P=S) linkages. All cytosine residues throughout each gapmer are 5-methylcytosines.

Each gapmer listed in Table 24 is targeted to the human Target-X genomic sequence.

Activity of the newly designed oligonucleotides was compared to ISIS 403052, ISIS 407939, ISIS 416446, ISIS 416472, ISIS 416507, ISIS 416508, ISIS 422087, ISIS 422096, ISIS 422130, and ISIS 422142. Cultured Hep3B cells at a density of 20,000 cells per well were transfected using electroporation with 2,000 nM antisense oligonucleotide. After a treatment period of approximately 24 hours, RNA was isolated from the cells and Target-X mRNA levels were measured by quantitative real-time PCR. Human primer probe set RTS2927 (described hereinabove in Example 1) was used to measure mRNA levels. Target-X mRNA levels were adjusted according to total RNA content, as measured by RIBOGREEN®. Results are presented as percent inhibition of Target-X, relative to untreated control cells. A total of 272 oligonucleotides were tested. Only those oligonucleotides which were selected for further studies are shown in Table 24. Several of the newly designed antisense oligonucleotides provided in Table 24 are more potent than antisense oligonucleotides from the previous publication.

TABLE 24

Inhibition of human Target-X mRNA levels by chimeric antisense oligonucleotides targeted to Target-X

| ISIS No | % inhibition | Motif | Wing Chemistry | SEQ CODE |
|---------|--------------|-------|----------------|----------|
| 403052 | 51 | 5-10-5 | 2'-MOE | 82 |
| 407939 | 78 | 5-10-5 | 2'-MOE | 72 |
| 416446 | 70 | 5-10-5 | 2'-MOE | 103 |
| 416472 | 79 | 5-10-5 | 2'-MOE | 111 |
| 416507 | 84 | 5-10-5 | 2'-MOE | 97 |
| 416508 | 80 | 5-10-5 | 2'-MOE | 100 |
| 422087 | 89 | 5-10-5 | 2'-MOE | 121 |
| 422096 | 78 | 5-10-5 | 2'-MOE | 219 |
| 422130 | 81 | 5-10-5 | 2'-MOE | 225 |
| 422142 | 84 | 5-10-5 | 2'-MOE | 99 |
| 490275 | 77 | 5-10-5 | 2'-MOE | 90 |
| 513462 | 79 | 3-10-4 | 2'-MOE | 213 |
| 513463 | 81 | 3-10-4 | 2'-MOE | 214 |
| 490277 | 74 | 5-10-5 | 2'-MOE | 91 |
| 513487 | 83 | 3-10-4 | 2'-MOE | 215 |
| 513504 | 81 | 3-10-4 | 2'-MOE | 216 |
| 513507 | 86 | 3-10-4 | 2'-MOE | 217 |
| 513508 | 85 | 3-10-4 | 2'-MOE | 218 |
| 490424 | 69 | 5-10-5 | 2'-MOE | 101 |
| 491122 | 87 | 5-10-5 | 2'-MOE | 220 |
| 513642 | 79 | 3-10-4 | 2'-MOE | 221 |
| 490149 | 71 | 5-10-5 | 2'-MOE | 109 |
| 513419 | 90 | 3-10-4 | 2'-MOE | 222 |
| 513420 | 89 | 3-10-4 | 2'-MOE | 223 |
| 513421 | 88 | 3-10-4 | 2'-MOE | 224 |
| 490197 | 77 | 5-10-5 | 2'-MOE | 116 |
| 513446 | 89 | 3-10-4 | 2'-MOE | 226 |
| 513447 | 83 | 3-10-4 | 2'-MOE | 227 |
| 490209 | 79 | 5-10-5 | 2'-MOE | 118 |
| 513454 | 84 | 3-10-4 | 2'-MOE | 228 |
| 513455 | 92 | 3-10-4 | 2'-MOE | 229 |
| 513456 | 89 | 3-10-4 | 2'-MOE | 230 |
| 513457 | 83 | 3-10-4 | 2'-MOE | 231 |

Example 10

Dose-Dependent Antisense Inhibition of Human Target-X in Hep3B Cells

Antisense oligonucleotides from the studies above, exhibiting in vitro inhibition of Target-X mRNA, were selected and tested at various doses in Hep3B cells. ISIS 403052, ISIS 407643, ISIS 407935, ISIS 407936, ISIS 407939, ISIS 416446, ISIS 416459, ISIS 416472, ISIS 416507, ISIS 416508, ISIS 416549, ISIS 422086, ISIS 422087, ISIS 422130, ISIS and 422142, 5-10-5 MOE gapmers targeting human Target-X, which were described in an earlier publication (WO 2009/061851).

Cells were plated at a density of 20,000 cells per well and transfected using electroporation with 0.625 μM, 1.25 μM, 2.50 μM, 5.00 μM and 10.00 μM concentrations of antisense oligonucleotide, as specified in Table 25. After a treatment period of approximately 16 hours, RNA was isolated from the cells and Target-X mRNA levels were measured by quantitative real-time PCR. Human Target-X primer probe set RTS2927 was used to measure mRNA levels. Target-X mRNA levels were adjusted according to total RNA content, as measured by RIBOGREEN®. Results are presented as percent inhibition of Target-X, relative to untreated control cells.

The half maximal inhibitory concentration (IC$_{50}$) of each oligonucleotide is also presented in Table 25. As illustrated in Table 25, Target-X mRNA levels were reduced in a dose-dependent manner in antisense oligonucleotide treated cells. The data also confirms that the newly designed gapmers are potent than gapmers from the previous publication.

TABLE 25

Dose-dependent antisense inhibition of human Target-X in Hep3B cells using electroporation

| ISIS No | 0.625 µM | 1.25 µM | 2.50 µM | 5.00 µM | 10.00 µM | IC$_{50}$ (µM) |
|---|---|---|---|---|---|---|
| 403052 | 21 | 35 | 63 | 82 | 89 | 1.9 |
| 407643 | 29 | 46 | 67 | 83 | 90 | 1.4 |
| 407935 | 52 | 68 | 80 | 89 | 91 | <0.6 |
| 407936 | 31 | 51 | 62 | 78 | 84 | 1.4 |
| 407939 | 30 | 61 | 74 | 83 | 88 | 1.0 |
| 416446 | 37 | 53 | 64 | 76 | 83 | 1.2 |
| 416459 | 51 | 76 | 83 | 90 | 92 | <0.6 |
| 416472 | 37 | 52 | 66 | 78 | 85 | 1.2 |
| 416507 | 45 | 68 | 82 | 87 | 90 | 0.7 |
| 416508 | 33 | 56 | 74 | 84 | 89 | 1.1 |
| 416549 | 57 | 71 | 78 | 82 | 85 | <0.6 |
| 422086 | 46 | 67 | 77 | 89 | 92 | 0.7 |
| 422087 | 50 | 69 | 74 | 86 | 91 | 0.6 |
| 422130 | 32 | 65 | 78 | 92 | 93 | 0.9 |
| 422142 | 59 | 73 | 84 | 86 | 88 | <0.6 |
| 490103 | 52 | 57 | 66 | 83 | 88 | 0.9 |
| 490149 | 34 | 58 | 71 | 85 | 91 | 1.0 |
| 490196 | 26 | 59 | 66 | 79 | 84 | 1.3 |
| 490197 | 39 | 63 | 74 | 81 | 90 | 0.8 |
| 490208 | 44 | 70 | 76 | 83 | 88 | 0.6 |
| 490275 | 36 | 58 | 76 | 85 | 89 | 1.0 |
| 490277 | 37 | 63 | 73 | 87 | 87 | 0.8 |
| 490279 | 40 | 54 | 72 | 83 | 89 | 1.0 |
| 490323 | 49 | 68 | 79 | 86 | 90 | <0.6 |
| 490368 | 39 | 62 | 76 | 86 | 91 | 0.8 |
| 490396 | 36 | 53 | 69 | 80 | 87 | 1.1 |
| 490424 | 45 | 65 | 69 | 76 | 82 | 0.6 |
| 490803 | 57 | 74 | 85 | 89 | 92 | <0.6 |
| 513419 | 60 | 71 | 85 | 95 | 96 | <0.6 |
| 513420 | 37 | 69 | 79 | 94 | 96 | 0.7 |
| 513421 | 46 | 64 | 84 | 95 | 97 | 0.6 |
| 513446 | 47 | 81 | 88 | 95 | 96 | <0.6 |
| 513447 | 56 | 74 | 81 | 92 | 96 | <0.6 |
| 513454 | 50 | 77 | 82 | 93 | 95 | <0.6 |
| 513455 | 74 | 82 | 91 | 96 | 96 | <0.6 |
| 513456 | 66 | 80 | 88 | 94 | 95 | <0.6 |
| 513457 | 54 | 67 | 80 | 87 | 89 | <0.6 |
| 513462 | 49 | 72 | 84 | 87 | 89 | <0.6 |
| 513463 | 36 | 62 | 76 | 85 | 89 | 0.9 |
| 513487 | 42 | 56 | 73 | 87 | 93 | 0.9 |
| 513504 | 47 | 65 | 81 | 90 | 91 | 0.6 |
| 513505 | 39 | 50 | 78 | 85 | 92 | 1.0 |
| 513507 | 52 | 73 | 83 | 89 | 93 | <0.6 |
| 513508 | 56 | 78 | 85 | 91 | 94 | <0.6 |

Example 11

Dose-Dependent Antisense Inhibition of Human Target-X in Hep3B Cells

Additional antisense oligonucleotides from the studies above, exhibiting in vitro inhibition of Target-X mRNA, were tested at various doses in Hep3B cells. ISIS 407935, ISIS 407939, ISIS 416446, ISIS 416472, ISIS 416507, ISIS 416549, ISIS 422086, ISIS 422087, ISIS 422096, and ISIS 422142 5-10-5 MOE gapmers targeting human Target-X, which were described in an earlier publication (WO 2009/061851).

Cells were plated at a density of 20,000 cells per well and transfected using electroporation with 0.3125 µM, 0.625 µM, 1.25 µM, 2.50 µM, 5.00 µM and 10.00 µM concentrations of antisense oligonucleotide, as specified in Table 26. After a treatment period of approximately 16 hours, RNA was isolated from the cells and Target-X mRNA levels were measured by quantitative real-time PCR. Human Target-X primer probe set RTS2927 was used to measure mRNA levels. Target-X mRNA levels were adjusted according to total RNA content, as measured by RIBOGREEN®. Results are presented as percent inhibition of Target-X, relative to untreated control cells. As illustrated in Table 26, Target-X mRNA levels were reduced in a dose-dependent manner in antisense oligonucleotide treated cells. The data also confirms that the newly designed gapmers are more potent than gapmers from the previous publication.

TABLE 26

Dose-dependent antisense inhibition of human Target-X in Hep3B cells using electroporation

| ISIS No | 0.3125 µM | 0.625 µM | 1.250 µM | 2.500 µM | 5.000 µM | 10.000 µM | IC$_{50}$ (µM) |
|---|---|---|---|---|---|---|---|
| 407935 | 30 | 49 | 75 | 86 | 91 | 94 | 0.6 |
| 407939 | 30 | 48 | 61 | 78 | 85 | 90 | 0.8 |
| 416446 | 27 | 52 | 63 | 75 | 85 | 90 | 0.7 |
| 416472 | 38 | 51 | 72 | 83 | 88 | 94 | 0.5 |
| 416507 | 58 | 81 | 76 | 84 | 89 | 92 | <0.3 |
| 416549 | 52 | 67 | 75 | 81 | 88 | 89 | 0.3 |
| 422086 | 48 | 49 | 68 | 78 | 86 | 91 | 0.5 |
| 422087 | 30 | 56 | 66 | 83 | 72 | 92 | 0.6 |
| 422096 | 47 | 63 | 70 | 77 | 83 | 85 | <0.3 |
| 422142 | 69 | 85 | 87 | 85 | 89 | 91 | <0.3 |
| 490103 | 52 | 57 | 68 | 78 | 87 | 93 | 0.4 |
| 490149 | 33 | 64 | 62 | 77 | 86 | 93 | 0.5 |
| 490197 | 38 | 46 | 60 | 75 | 87 | 93 | 0.7 |

TABLE 26-continued

Dose-dependent antisense inhibition of human Target-X in Hep3B cells using electroporation

| ISIS No | 0.3125 µM | 0.625 µM | 1.250 µM | 2.500 µM | 5.000 µM | 10.000 µM | IC$_{50}$ (µM) |
|---|---|---|---|---|---|---|---|
| 490208 | 46 | 62 | 73 | 83 | 88 | 91 | 0.4 |
| 490209 | 40 | 54 | 72 | 79 | 85 | 94 | 0.5 |
| 490275 | 52 | 61 | 67 | 78 | 85 | 91 | 0.3 |
| 490277 | 33 | 59 | 77 | 79 | 91 | 94 | 0.5 |
| 490323 | 43 | 61 | 72 | 69 | 84 | 87 | 0.4 |
| 490368 | 50 | 64 | 78 | 83 | 90 | 92 | <0.3 |
| 490396 | 46 | 64 | 68 | 84 | 84 | 90 | 0.3 |
| 490424 | 24 | 47 | 58 | 72 | 76 | 82 | 1.0 |
| 490803 | 45 | 60 | 70 | 84 | 88 | 89 | 0.3 |
| 513419 | 32 | 53 | 76 | 88 | 93 | 95 | 0.5 |
| 513420 | 35 | 59 | 72 | 82 | 94 | 97 | 0.5 |
| 513421 | 46 | 67 | 78 | 86 | 94 | 96 | <0.3 |
| 513446 | 26 | 61 | 77 | 89 | 91 | 97 | 0.5 |
| 513447 | 22 | 48 | 60 | 82 | 91 | 95 | 0.8 |
| 513454 | 25 | 59 | 76 | 86 | 94 | 96 | 0.5 |
| 513455 | 60 | 73 | 85 | 89 | 95 | 96 | <0.3 |
| 513456 | 49 | 60 | 81 | 88 | 94 | 95 | <0.3 |
| 513457 | 43 | 50 | 72 | 77 | 87 | 92 | 0.5 |
| 513462 | 25 | 48 | 58 | 76 | 83 | 88 | 0.8 |
| 513463 | 22 | 45 | 66 | 73 | 85 | 88 | 0.9 |
| 513487 | 41 | 56 | 65 | 79 | 86 | 90 | 0.4 |
| 513504 | 19 | 48 | 63 | 76 | 87 | 92 | 0.9 |
| 513505 | 11 | 21 | 54 | 73 | 85 | 90 | 1.4 |
| 513507 | 47 | 55 | 72 | 82 | 90 | 91 | 0.3 |
| 513508 | 31 | 59 | 74 | 85 | 92 | 93 | 0.5 |
| 513642 | 43 | 55 | 67 | 80 | 88 | 92 | 0.4 |

Example 12

Tolerability of 2'-MOE Gapmers Targeting Human Target-X in BALB/c Mice

BALB/c mice are a multipurpose mice model, frequently utilized for safety and efficacy testing. The mice were treated with ISIS antisense oligonucleotides selected from studies described above and evaluated for changes in the levels of various plasma chemistry markers.

Treatment

Groups of male BALB/c mice were injected subcutaneously twice a week for 3 weeks with 50 mg/kg of ISIS 407935, ISIS 416472, ISIS 416549, ISIS 422086, ISIS 422087, ISIS 422096, ISIS 422142, ISIS 490103, ISIS 490149, ISIS 490196, ISIS 490208, ISIS 490209, ISIS 513419, ISIS 513420, ISIS 513421, ISIS 513454, ISIS 513455, ISIS 513456, ISIS 513457, ISIS 513462, ISIS 513463, ISIS 513487, ISIS 513504, ISIS 513508, and ISIS 513642. One group of male BALB/c mice was injected subcutaneously twice a week for 3 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, bilirubin, albumin, and BUN were measured using an automated clinical chemistry analyzer (Hitachi Olympus AU400e, Melville, N.Y.).

ISIS oligonucleotides that did not cause any increase in the levels of transaminases, or which caused an increase within three times the upper limit of normal (ULN) were deemed very tolerable. ISIS oligonucleotides that caused an increase in the levels of transaminases between three times and seven times the ULN were deemed tolerable. Based on these criteria, ISIS 407935, ISIS 416472, ISIS 416549, ISIS 422087, ISIS 422096, ISIS 490103, ISIS 490196, ISIS 490208, ISIS 513454, ISIS 513455, ISIS 513456, ISIS 513457, ISIS 513487, ISIS 513504, and ISIS 513508 were considered very tolerable in terms of liver function. Based on these criteria, ISIS 422086, ISIS 490209, ISIS 513419, ISIS 513420, and ISIS 513463 were considered tolerable in terms of liver function.

Example 13

Dose-Dependent Antisense Inhibition of Human Target-X in Hep3B Cells

Additional antisense oligonucleotides from the studies above, exhibiting in vitro inhibition of Target-X mRNA were selected and tested at various doses in Hep3B cells. Also tested was ISIS 407939, a 5-10-5 MOE gapmer, which was described in an earlier publication (WO 2009/061851).

Cells were plated at a density of 20,000 cells per well and transfected using electroporation with 0.074 µM, 0.222 µM, 0.667 µM, 2.000 µM, and 6.000 µM concentrations of antisense oligonucleotide, as specified in Table 27. After a treatment period of approximately 16 hours, RNA was isolated from the cells and Target-X mRNA levels were measured by quantitative real-time PCR. Human Target-X primer probe set RTS2927 (described hereinabove in Example 1) was used to measure mRNA levels. Target-X mRNA levels were adjusted according to total RNA content, as measured by RIBOGREEN®. Results are presented as percent inhibition of Target-X, relative to untreated control cells.

The half maximal inhibitory concentration (IC$_{50}$) of each oligonucleotide is also presented in Table 27. As illustrated in Table 27, Target-X mRNA levels were reduced in a dose-dependent manner in antisense oligonucleotide treated cells. Many of the newly designed antisense oligonucleotides provided in Table 27 achieved an IC$_{50}$ of less than 0.9 µM and, therefore, are more potent than ISIS 407939.

TABLE 27

Dose-dependent antisense inhibition of human Target-X in Hep3B cells using electroporation

| ISIS No | 0.074 µM | 0.222 µM | 0.667 µM | 2.000 µM | 6.000 µM | IC$_{50}$ (µM) |
|---|---|---|---|---|---|---|
| 407939 | 2 | 17 | 53 | 70 | 87 | 0.9 |
| 472970 | 17 | 47 | 75 | 92 | 95 | 0.3 |
| 472988 | 0 | 8 | 21 | 54 | 92 | 1.4 |
| 472996 | 18 | 59 | 74 | 93 | 95 | 0.2 |
| 473244 | 91 | 95 | 97 | 99 | 99 | <0.07 |
| 473286 | 6 | 53 | 85 | 92 | 98 | 0.3 |
| 473359 | 2 | 3 | 20 | 47 | 67 | 2.6 |
| 473392 | 71 | 85 | 88 | 92 | 96 | <0.07 |
| 473393 | 91 | 96 | 97 | 98 | 99 | <0.07 |
| 473547 | 85 | 88 | 93 | 97 | 98 | <0.07 |
| 473567 | 0 | 25 | 66 | 88 | 95 | 0.7 |
| 473589 | 8 | 47 | 79 | 94 | 99 | 0.3 |
| 482814 | 23 | 68 | 86 | 93 | 96 | 0.1 |
| 482815 | 6 | 48 | 65 | 90 | 96 | 0.4 |
| 482963 | 3 | 68 | 85 | 94 | 96 | 0.2 |
| 483241 | 14 | 33 | 44 | 76 | 93 | 0.6 |
| 483261 | 14 | 21 | 41 | 72 | 88 | 0.7 |
| 483290 | 0 | 1 | 41 | 69 | 92 | 1.0 |
| 483414 | 8 | 1 | 36 | 76 | 91 | 0.9 |
| 483415 | 0 | 40 | 52 | 84 | 94 | 0.6 |
| 484559 | 26 | 51 | 78 | 87 | 97 | 0.2 |
| 484713 | 6 | 5 | 53 | 64 | 88 | 0.9 |

Example 14

Modified Antisense Oligonucleotides Comprising 2'-O-Methoxyethyl (2'-MOE) and 6'-(S)—$CH_3$ Bicyclic Nucleoside (e.g cEt) Modifications Targeting Human Target-X Additional antisense oligonucleotides were designed targeting a Target-X nucleic acid and were tested for their effects on Target-X mRNA in vitro. Also tested was ISIS 407939, a 5-10-5 MOE gapmer targeting human Target-X, which was described in an earlier publication (WO 2009/061851). ISIS 472998, ISIS 492878, and ISIS 493201 and 493182, 2-10-2 cEt gapmers, described in the Examples above were also included in the screen.

The newly designed modified antisense oligonucleotides are 16 nucleotides in length and their motifs are described in Table 28. The chemistry column of Table 28 presents the sugar motif of each oligonucleotide, wherein "e" indicates a 2'-O-methoxyethyl (2'-MOE) nucleoside, "k" indicates a 6'-(S)—$CH_3$ bicyclic nucleoside (e.g cEt) and "d" indicates a 2'-deoxyribonucleoside. The internucleoside linkages throughout each gapmer are phosphorothioate (P=S) linkages. All cytosine residues throughout each oligonucleotide are 5-methylcytosines.

Each gapmer listed in Table 28 is targeted to the human Target-X genomic sequence.

Activity of newly designed gapmers was compared to ISIS 407939. Cultured Hep3B cells at a density of 20,000 cells per well were transfected using electroporation with 2,000 nM antisense oligonucleotide. After a treatment period of approximately 24 hours, RNA was isolated from the cells and Target-X mRNA levels were measured by quantitative real-time PCR. Human primer probe set RTS2927 was used to measure mRNA levels. Target-X mRNA levels were adjusted according to total RNA content, as measured by RIBOGREEN®. Results are presented as percent inhibition of Target-X, relative to untreated control cells and demonstrate that several of the newly designed gapmers are more potent than ISIS 407939. A total of 685 oligonucleotides were tested. Only those oligonucleotides which were selected for further studies are shown in Table 28.

TABLE 28

Inhibition of human Target-X mRNA levels by chimeric antisense oligonucleotides targeted to Target-X

| ISIS No | % inhibition | Chemistry | SEQ CODE |
|---|---|---|---|
| 407939 | 68 | eeeee-d(10)-eeeee | 72 |
| 492878 | 73 | kk-d(10)-kk | |
| 493182 | 80 | kk-d(10)-kk | |
| 493201 | 84 | kk-d(10)-kk | |
| 472998 | 91 | kk-d(10)-kk | |
| 515640 | 75 | eee-d(10)-kkk | 23 |
| 515637 | 77 | eee-d(10)-kkk | 232 |
| 515554 | 72 | eee-d(10)-kkk | 233 |
| 515406 | 80 | kkk-d(10)-eee | 234 |
| 515558 | 81 | eee-d(10)-kkk | 234 |
| 515407 | 88 | kkk-d(10)-eee | 235 |
| 515408 | 85 | kkk-d(10)-eee | 236 |
| 515422 | 86 | kkk-d(10)-eee | 237 |
| 515423 | 90 | kkk-d(10)-eee | 238 |
| 515575 | 84 | eee-d(10)-kkk | 238 |
| 515424 | 87 | kkk-d(10)-eee | 239 |
| 515432 | 78 | kkk-d(10)-eee | 240 |
| 515433 | 71 | kkk-d(10)-eee | 241 |
| 515434 | 76 | kkk-d(10)-eee | 242 |
| 515334 | 85 | kkk-d(10)-eee | 243 |
| 515649 | 61 | eee-d(10)-kkk | 88 |
| 515338 | 86 | kkk-d(10)-eee | 244 |
| 515438 | 76 | kkk-d(10)-eee | 245 |
| 515439 | 75 | kkk-d(10)-eee | 246 |
| 516003 | 87 | eee-d(10)-kkk | 247 |
| 515647 | 60 | eee-d(10)-kkk | 77 |
| 515639 | 78 | eee-d(10)-kkk | 34 |
| 493201 | 84 | eee-d(10)-kkk | 202 |
| 515648 | 36 | kkk-d(10)-eee | 248 |
| 515641 | 69 | kk-d(10)-eeee | 39 |
| 515650 | 76 | kkk-d(10)-eee | 44 |
| 515354 | 87 | eee-d(10)-kkk | 249 |
| 515926 | 87 | eee-d(10)-kkk | 250 |
| 515366 | 87 | kk-d(10)-eeee | 251 |
| 515642 | 58 | kkk-d(10)-eee | 252 |
| 515643 | 81 | eee-d(10)-kkk | 53 |
| 515944 | 84 | kk-d(10)-eeee | 253 |
| 515380 | 90 | kkk-d(10)-eee | 254 |
| 515532 | 83 | kkk-d(10)-eee | 254 |
| 515945 | 85 | kk-d(10)-eeee | 254 |
| 515381 | 82 | kk-d(10)-eeee | 255 |
| 515382 | 95 | kkk-d(10)-eee | 256 |
| 515948 | 94 | eee-d(10)-kkk | 256 |
| 515949 | 87 | eee-d(10)-kkk | 257 |
| 515384 | 89 | kkk-d(10)-eee | 258 |
| 515635 | 82 | kk-d(10)-eeee | 65 |
| 515638 | 90 | kkk-d(10)-eee | 67 |
| 515386 | 92 | kk-d(10)-eeee | 259 |
| 515951 | 84 | eee-d(10)-kkk | 259 |
| 515387 | 78 | kkk-d(10)-eee | 260 |
| 515952 | 89 | kkk-d(10)-eee | 260 |
| 515636 | 90 | kkk-d(10)-eee | 69 |
| 515388 | 84 | eee-d(10)-kkk | 261 | e = 2'-MOE, k = cEt, d = 2'-deoxyribonucleoside

Example 15

Tolerability of Modified Oligonucleotides Comprising 2'-O-Methoxyethyl (2'-MOE) and 6'-(S)—$CH_3$ Bicyclic Nucleoside (e.g cEt) Modifications Targeting Human Target-X in BALB/c Mice BALB/c mice were treated with ISIS antisense oligonucleotides selected from studies described above and evaluated for changes in the levels of various plasma chemistry markers.

Additionally, the newly designed modified antisense oligonucleotides were also added to this screen. The newly designed chimeric antisense oligonucleotides are 16 nucleotides in length and their motifs are described in Table 29. The chemistry column of Table 29 presents the sugar motif of each oligonucleotide, wherein "e" indicates a 2'-O-methoxyethyl (2'-MOE) nucleoside, "k" indicates a 6'-(S)—$CH_3$ bicyclic nucleoside (e.g cEt) and "d" indicates a 2'-deoxyribonucleoside. The internucleoside linkages throughout each gapmer are hosphorothioate (P=S) linkages. All cytosine residues throughout each oligonucleotide are 5-methylcytosines.

Each gapmer listed in Table 29 is targeted to the human Target-X genomic sequence.

TABLE 29

Modified chimeric antisense oligonucleotides targeted to Target-X

| ISIS No | Chemistry | SEQ CODE |
|---|---|---|
| 516044 | eee-d(10)-kkk | 21 |
| 516045 | eee-d(10)-kkk | 22 |
| 516058 | eee-d(10)-kkk | 26 |

TABLE 29-continued

Modified chimeric antisense oligonucleotides targeted to Target-X

| ISIS No | Chemistry | SEQ CODE |
|---|---|---|
| 516059 | eee-d(10)-kkk | 27 |
| 516060 | eee-d(10)-kkk | 28 |
| 516061 | eee-d(10)-kkk | 29 |
| 516062 | eee-d(10)-kkk | 30 |
| 516046 | eee-d(10)-kkk | 37 |
| 516063 | eee-d(10)-kkk | 38 |
| 516064 | eee-d(10)-kkk | 89 |
| 516065 | eee-d(10)-kkk | 262 |
| 516066 | eee-d(10)-kkk | 263 |
| 516047 | eee-d(10)-kkk | 41 |
| 516048 | eee-d(10)-kkk | 42 |
| 516049 | eee-d(10)-kkk | 81 |
| 516050 | eee-d(10)-kkk | 45 |
| 516051 | eee-d(10)-kkk | 48 |
| 516052 | eee-d(10)-kkk | 49 |
| 515652 | eee-d(10)-kkk | 50 |
| 508039 | eee-d(10)-kkk | 264 |
| 516053 | eee-d(10)-kkk | 265 |
| 515654 | eee-d(10)-kkk | 76 |
| 515656 | eee-d(10)-kkk | 77 |
| 516054 | eee-d(10)-kkk | 57 |
| 516055 | eee-d(10)-kkk | 59 |
| 515655 | eee-d(10)-kkk | 61 |
| 516056 | eee-d(10)-kkk | 63 |
| 516057 | eee-d(10)-kkk | 64 |
| 515653 | eee-d(10)-kkk | 71 |
| 515657 | eee-d(10)-kkk | 73 | e = 2'-MOE, k = cEt, d = 2'-deoxyribonucleoside

Treatment

Groups of 4-6-week old male BALB/c mice were injected subcutaneously twice a week for 3 weeks with 50 mg/kg/week of ISIS 457851, ISIS 515635, ISIS 515636, ISIS 515637, ISIS 515638, ISIS 515639, ISIS 515640, ISIS 515641, ISIS 515642, ISIS 515643, ISIS 515647, ISIS 515648, ISIS 515649, ISSI 515650, ISIS 515652, ISIS 515653, ISIS 515654, ISIS 515655, ISIS 515656, ISIS 515657, ISIS 516044, ISIS 516045, ISIS 516046, ISIS 516047, ISIS 516048, ISIS 516049, ISIS 516050, ISIS 516051, ISIS 516052, ISIS 516053, ISIS 516054, ISIS 516055, ISIS 516056, ISIS 516057, ISIS 516058, ISIS 516059, ISIS 516060, ISIS 516061, ISIS 516062, ISIS 516063, ISIS 516064, ISIS 516065, and ISIS 516066. One group of 4-6-week old male BALB/c mice was injected subcutaneously twice a week for 3 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, bilirubin, albumin, and BUN were measured using an automated clinical chemistry analyzer (Hitachi Olympus AU400e, Melville, N.Y.).

ISIS oligonucleotides that did not cause any increase in the levels of transaminases, or which caused an increase within three times the upper limit of normal (ULN) were deemed very tolerable. ISIS oligonucleotides that caused an increase in the levels of transaminases between three times and seven times the ULN were deemed tolerable. Based on these criteria, ISIS 515636, ISIS 515639, ISIS 515641, ISIS 515642, ISIS 515648, ISIS 515650, ISIS 515652, ISIS 515653, ISIS 515655, ISIS 515657, ISIS 516044, ISIS 516045, ISIS 516047, ISIS 516048, ISIS 516051, ISIS 516052, ISIS 516053, ISIS 516055, ISIS 516056, ISIS 516058, ISIS 516059, ISIS 516060, ISIS 516061, ISIS 516062, ISIS 516063, ISIS 516064, ISIS 516065, and ISIS 516066 were considered very tolerable in terms of liver function. Based on these criteria, ISIS 457851, ISIS 515635, ISIS 515637, ISIS 515638, ISIS 515643, ISIS 515647, ISIS 515649, ISIS 515650, ISIS 515652, ISIS 515654, ISIS 515656, ISIS 516056, and ISIS 516057 were considered tolerable in terms of liver function.

Example 16

Efficacy of Modified Oligonucleotides Comprising 2'-O-Methoxyethyl (2'-MOE) and 6'-(S)—$CH_3$ Bicyclic Nucleoside (e.g cEt) Modifications Targeting Human Target-X in Transgenic Mice Transgenic mice were developed at Taconic farms harboring a Target-X genomic DNA fragment. The mice were treated with ISIS antisense oligonucleotides selected from studies described above and evaluated for efficacy.

Treatment

Groups of 3-4 male and female transgenic mice were injected subcutaneously twice a week for 3 weeks with 20 mg/kg/week of ISIS 457851, ISIS 515636, ISIS 515639, ISIS 515653, ISIS 516053, ISIS 516065, and ISIS 516066. One group of mice was injected subcutaneously twice a week for 3 weeks with control oligonucleotide, ISIS 141923 (CCTTCCCTGAAGGTTCCTCC, 5-10-5 MOE gapmer with no known murine target, SEQ ID NO: 9). One group of mice was injected subcutaneously twice a week for 3 weeks with PBS. Mice were euthanized 48 hours after the last dose, and organs and plasma were harvested for further analysis.

RNA Analysis

RNA was extracted from plasma for real-time PCR analysis of Target-X, using primer probe set RTS2927. The mRNA levels were normalized using RIBOGREEN®. Results are presented as percent inhibition of Target-X, relative to control. As shown in Table 30, each of the antisense oligonucleotides achieved reduction of human Target-X mRNA expression over the PBS control. Treatment with the control oligonucleotide did not achieve reduction in Target-X levels, as expected.

TABLE 30

Percent inhibition of Target-X mRNA in transgenic mice

| ISIS No | % inhibition |
|---|---|
| 141923 | 0 |
| 457851 | 76 |
| 515636 | 66 |
| 515639 | 49 |
| 515653 | 78 |
| 516053 | 72 |
| 516065 | 59 |
| 516066 | 39 |

Protein Analysis

Plasma protein levels of Target-X were estimated using a Target-X ELISA kit (purchased from Hyphen Bio-Med). Results are presented as percent inhibition of Target-X, relative to control. As shown in Table 31, several antisense oligonucleotides achieved reduction of human Target-X protein expression over the PBS control.

TABLE 31

Percent inhibition of Target-X protein levels in transgenic mice

| ISIS No | % inhibition |
|---|---|
| 141923 | 0 |
| 457851 | 64 |
| 515636 | 68 |
| 515639 | 46 |
| 515653 | 0 |
| 516053 | 19 |
| 516065 | 0 |
| 516066 | 7 |

Example 17

Efficacy of Modified Oligonucleotides Comprising 2'-O-Methoxyethyl (2'-MOE) and 6'-(S)—CH$_3$ Bicyclic Nucleoside (e.g cEt) Modifications Targeting Human Target-X in Transgenic Mice Transgenic mice were treated with ISIS antisense oligonucleotides selected from studies described above and evaluated for efficacy.

Treatment

Groups of 2-4 male and female transgenic mice were injected subcutaneously twice a week for 3 weeks with 10 mg/kg/week of ISIS 407935, ISIS 416472, ISIS 416549, ISIS 422087, ISIS 422096, ISIS 473137, ISIS 473244, ISIS 473326, ISIS 473327, ISIS 473359, ISIS 473392, ISIS 473393, ISIS 473547, ISIS 473567, ISIS 473589, ISIS 473630, ISIS 484559, ISIS 484713, ISIS 490103, ISIS 490196, ISIS 490208, ISIS 513419, ISIS 513454, ISIS 513455, ISIS 513456, ISIS 513457, ISIS 513487, ISIS 513508, ISIS 515640, ISIS 515641, ISIS 515642, ISIS 515648, ISIS 515655, ISIS 515657, ISIS 516045, ISIS 516046, ISIS 516047, ISIS 516048, ISIS 516051, ISIS 516052, ISIS 516055, ISIS 516056, ISIS 516059, ISIS 516061, ISIS 516062, and ISIS 516063. One group of mice was injected subcutaneously twice a week for 3 weeks with PBS. Mice were euthanized 48 hours after the last dose, and organs and plasma were harvested for further analysis.

Protein Analysis

Plasma protein levels of Target-X were estimated using a Target-X ELISA kit (purchased from Hyphen Bio-Med). Results are presented as percent inhibition of Target-X, relative to control. As shown in Table 32, several antisense oligonucleotides achieved reduction of human Target-X over the PBS control.

TABLE 32

Percent inhibition of Target-X plasma protein levels in transgenic mice

| ISIS No | % inhibition |
|---|---|
| 407935 | 80 |
| 416472 | 49 |
| 416549 | 29 |
| 422087 | 12 |
| 422096 | 21 |
| 473137 | 57 |
| 473244 | 67 |
| 473326 | 42 |
| 473327 | 100 |
| 473359 | 0 |
| 473392 | 22 |
| 473393 | 32 |
| 473547 | 73 |
| 473567 | 77 |
| 473589 | 96 |
| 473630 | 75 |
| 484559 | 75 |
| 484713 | 56 |
| 490103 | 0 |
| 490196 | 74 |
| 490208 | 90 |
| 513419 | 90 |
| 513454 | 83 |
| 513455 | 91 |
| 513456 | 81 |
| 513457 | 12 |
| 513487 | 74 |
| 513508 | 77 |
| 515640 | 83 |
| 515641 | 87 |
| 515642 | 23 |
| 515648 | 32 |
| 515655 | 79 |
| 515657 | 81 |
| 516045 | 52 |
| 516046 | 79 |
| 516047 | 65 |
| 516048 | 79 |
| 516051 | 84 |
| 516052 | 72 |
| 516055 | 70 |
| 516056 | 0 |
| 516059 | 39 |
| 516061 | 64 |
| 516062 | 96 |
| 516063 | 24 |

Example 18

Dose-Dependent Antisense Inhibition of Human Target-X in Hep3B Cells

Antisense oligonucleotides exhibiting in vitro inhibition of Target-X mRNA were selected and tested at various doses in Hep3B cells. Also tested was ISIS 407939, a 5-10-5 MOE gapmer targeting human Target-X, which was described in an earlier publication (WO 2009/061851).

Cells were plated at a density of 20,000 cells per well and transfected using electroporation with 0.074 µM, 0.222 µM, 0.667 µM, 2.000 µM, and 6.000 µM concentrations of antisense oligonucleotide, as specified in Table 33. After a treatment period of approximately 16 hours, RNA was isolated from the cells and Target-X mRNA levels were measured by quantitative real-time PCR. Human Target-X primer probe set RTS2927 (described hereinabove in Example 1) was used to measure mRNA levels. Target-X mRNA levels were adjusted according to total RNA content, as measured by RIBOGREEN®. Results are presented as percent inhibition of Target-X, relative to untreated control cells.

The half maximal inhibitory concentration (IC$_{50}$) of each oligonucleotide is also presented in Table 33. As illustrated in Table 33, Target-X mRNA levels were reduced in a dose-dependent manner in antisense oligonucleotide treated cells. Many of the newly designed antisense oligonucleotides provided in Table 33 achieved an IC$_{50}$ of less than 2.0 µM and, therefore, are more potent than ISIS 407939.

TABLE 33

Dose-dependent antisense inhibition of human Target-X in Hep3B cells using electroporation

| ISIS No | 0.074 μM | 0.222 μM | 0.667 μM | 2.000 μM | 6.000 μM | IC$_{50}$ (μM) |
|---|---|---|---|---|---|---|
| 407939 | 0 | 9 | 21 | 58 | 76 | 2.0 |
| 515636 | 14 | 32 | 50 | 62 | 81 | 0.7 |
| 515639 | 10 | 24 | 41 | 61 | 67 | 1.3 |
| 515640 | 4 | 16 | 35 | 52 | 63 | 2.0 |
| 515641 | 0 | 21 | 27 | 55 | 66 | 1.9 |
| 515642 | 3 | 13 | 36 | 44 | 66 | 2.2 |
| 515648 | 8 | 10 | 10 | 5 | 16 | >6.0 |
| 515653 | 9 | 35 | 26 | 55 | 71 | 1.5 |
| 515655 | 0 | 0 | 6 | 13 | 42 | >6.0 |
| 515657 | 0 | 13 | 17 | 38 | 51 | 6.0 |
| 516045 | 0 | 6 | 15 | 19 | 40 | >6.0 |
| 516046 | 0 | 7 | 32 | 48 | 69 | 2.1 |
| 516047 | 12 | 27 | 41 | 50 | 63 | 1.8 |
| 516051 | 9 | 8 | 34 | 52 | 66 | 2.0 |
| 516052 | 17 | 42 | 27 | 53 | 75 | 1.2 |
| 516053 | 9 | 7 | 28 | 63 | 77 | 1.3 |
| 516055 | 0 | 3 | 27 | 54 | 75 | 2.0 |
| 516056 | 0 | 4 | 14 | 52 | 66 | 2.6 |
| 516057 | 0 | 34 | 33 | 51 | 70 | 1.6 |
| 516058 | 13 | 12 | 25 | 47 | 74 | 2.0 |
| 516059 | 4 | 15 | 36 | 47 | 68 | 1.9 |
| 516060 | 0 | 1 | 39 | 29 | 63 | 3.2 |
| 516061 | 0 | 0 | 24 | 0 | 3 | <6.0 |
| 516062 | 0 | 20 | 43 | 65 | 78 | 1.0 |
| 516063 | 0 | 8 | 10 | 37 | 61 | 3.8 |
| 516064 | 0 | 3 | 13 | 45 | 69 | 2.7 |
| 516065 | 0 | 14 | 38 | 63 | 76 | 1.3 |
| 516066 | 0 | 3 | 30 | 55 | 75 | 1.7 |

Example 19

Modified Oligonucleotides Comprising 2'-O-Methoxyethyl (2'-MOE) and 6'-(S)—CH$_3$ Bicyclic Nucleoside (e.g cEt) Modifications Targeting Human Target-X Additional antisense oligonucleotides were designed targeting a Target-X nucleic acid and were tested for their effects on Target-X mRNA in vitro. ISIS 472998, ISIS 515652, ISIS 515653, ISIS 515654, ISIS 515655, ISIS 515656, and ISIS 515657, described in the Examples above were also included in the screen.

The newly designed chimeric antisense oligonucleotides are 16 or 17 nucleotides in length and their motifs are described in Table 34. The chemistry column of Table 34 presents the sugar motif of each oligonucleotide, wherein "e" indicates a 2'-O-methoxyethyl (2'-MOE) nucleoside, "k" indicates a 6'-(S)—CH$_3$ bicyclic nucleoside (e.g cEt) and "d" indicates a 2'-deoxyribonucleoside. The internucleoside linkages throughout each gapmer are hosphorothioate (P=S) linkages. All cytosine residues throughout each oligonucleotide are 5-methylcytosines.

Each gapmer listed in Table 34 is targeted to the human Target-X genomic sequence.

Activity of newly designed gapmers was compared to ISIS 407939. Cultured Hep3B cells at a density of 20,000 cells per well were transfected using electroporation with 2,000 nM antisense oligonucleotide. After a treatment period of approximately 24 hours, RNA was isolated from the cells and Target-X mRNA levels were measured by quantitative real-time PCR. Human primer probe set RTS2927 (described hereinabove in Example 1) was used to measure mRNA levels. Target-X mRNA levels were adjusted according to total RNA content, as measured by RIBOGREEN®.

Results are presented as percent inhibition of Target-X, relative to untreated control cells.

TABLE 34

Inhibition of human Target-X mRNA levels by chimeric antisense oligonucleotides targeted to Target-X

| ISIS No | % inhibition | Chemistry | SEQ CODE |
|---|---|---|---|
| 472998 | 85 | kk-d(10)-kk | 74 |
| 515652 | 63 | eee-d(10)-kkk | 50 |
| 515653 | 67 | eee-d(10)-kkk | 71 |
| 515654 | 78 | eee-d(10)-kkk | 86 |
| 515655 | 41 | eee-d(10)-kkk | 61 |
| 515656 | 74 | eee-d(10)-kkk | 87 |
| 515657 | 49 | eee-d(10)-kkk | 73 |
| 529265 | 52 | eek-d(10)-keke | 267 |
| 529332 | 82 | eek-d(10)-keke | 268 |
| 529334 | 78 | eek-d(10)-keke | 269 |
| 529186 | 85 | eek-d(10)-keke | 213 |
| 529223 | 81 | eek-d(10)-kkke | 213 |
| 529129 | 75 | eee-d(10)-kkk | 270 |
| 529149 | 82 | kkk-d(10)-eee | 270 |
| 529177 | 77 | eek-d(10)-keke | 214 |
| 529214 | 78 | eek-d(10)-kkke | 214 |
| 529178 | 79 | eek-d(10)-keke | 271 |
| 529215 | 82 | eek-d(10)-kkke | 271 |
| 529179 | 71 | eek-d(10)-keke | 272 |
| 529216 | 77 | eek-d(10)-kkke | 272 |
| 529193 | 69 | eek-d(10)-keke | 273 |
| 529230 | 70 | eek-d(10)-kkke | 273 |
| 529136 | 48 | eee-d(10)-kkk | 274 |
| 529156 | 68 | kkk-d(10)-eee | 274 |
| 529194 | 44 | eek-d(10)-keke | 275 |
| 529231 | 56 | eek-d(10)-kkke | 275 |
| 529137 | 34 | eee-d(10)-kkk | 276 |
| 529157 | 79 | kkk-d(10)-eee | 276 |
| 529336 | 57 | eek-d(10)-keke | 277 |
| 529338 | 73 | eek-d(10)-keke | 278 |
| 529195 | 55 | eek-d(10)-keke | 279 |
| 529232 | 68 | eek-d(10)-kkke | 279 |
| 529340 | 65 | eek-d(10)-keke | 280 |
| 529342 | 69 | eek-d(10)-keke | 281 |
| 529812 | 69 | k-d(10)-kekee | 282 |
| 529831 | 62 | k-d(10)-kdkee | 282 |
| 529733 | 64 | ke-d(10)-keke | 283 |
| 529753 | 52 | ek-d(10)-keke | 283 |
| 529773 | 57 | ke-d(10)-kdke | 283 |
| 529793 | 36 | ek-d(10)-kdke | 283 |
| 529862 | 48 | kde-d(10)-kdke | 284 |
| 529882 | 35 | edk-d(10)-kdke | 284 |
| 529902 | 44 | k-(d4)-k-(d4)-k-(d4)-ke | 284 |
| 529559 | 71 | eek-d(10)-kke | 26 |
| 529584 | 57 | kee-d(10)-kke | 26 |
| 529609 | 58 | edk-d(10)-kke | 26 |
| 529634 | 49 | kde-d(10)-kke | 26 |
| 529659 | 52 | kddk-d(9)-kke | 26 |
| 529684 | 48 | kdde-d(9)-kke | 26 |
| 529709 | 61 | eddk-d(9)-kke | 26 |
| 529922 | 52 | eeee-d(9)-kke | 26 |
| 529344 | 50 | eek-d(10)-keke | 285 |
| 529138 | 32 | eee-d(10)-kkk | 286 |
| 529158 | 75 | kkk-d(10)-eee | 286 |
| 529184 | 75 | eek-d(10)-keke | 215 |
| 529221 | 78 | eek-d(10)-kkke | 215 |
| 529127 | 67 | eee-d(10)-kkk | 287 |
| 529147 | 79 | kkk-d(10)-eee | 287 |
| 529346 | 58 | eek-d(10)-keke | 288 |
| 529348 | 65 | eek-d(10)-keke | 289 |
| 529350 | 77 | eek-d(10)-keke | 290 |
| 529813 | 20 | k-d(10)-kekee | 291 |
| 529832 | 47 | k-d(10)-kdkee | 291 |
| 529734 | 63 | ke-d(10)-keke | 292 |
| 529754 | 58 | ek-d(10)-keke | 292 |
| 529774 | 49 | ke-d(10)-kdke | 292 |
| 529794 | 51 | ek-d(10)-kdke | 292 |
| 529863 | 64 | kde-d(10)-kdke | 293 |
| 529883 | 78 | edk-d(10)-kdke | 293 |
| 529903 | 36 | k-d(4)-k-d(4)-k-d(4)-ke | 293 |

TABLE 34-continued

Inhibition of human Target-X mRNA levels by chimeric antisense oligonucleotides targeted to Target-X

| ISIS No | % inhibition | Chemistry | SEQ CODE |
|---|---|---|---|
| 529560 | 71 | eek-d(10)-kke | 27 |
| 529585 | 70 | kee-d(10)-kke | 27 |
| 529610 | 66 | edk-d(10)-kke | 27 |
| 529635 | 45 | kde-d(10)-kke | 27 |
| 529660 | 53 | kddk-d(9)-kke | 27 |
| 529685 | 42 | kdde-d(9)-kke | 27 |
| 529710 | 60 | eddk-d(9)-kke | 27 |
| 529923 | 63 | eeee-d(9)-kke | 27 |
| 529196 | 74 | eek-d(10)-keke | 294 |
| 529233 | 80 | eek-d(10)-kkke | 294 |
| 529139 | 75 | eee-d(10)-kkk | 295 |
| 529159 | 62 | kkk-d(10)-eee | 295 |
| 529352 | 74 | eek-d(10)-eee | 296 |
| 529354 | 67 | eek-d(10)-keke | 297 |
| 529197 | 43 | eek-d(10)-keke | 298 |
| 529234 | 58 | eek-d(10)-kkke | 298 |
| 529140 | 29 | eee-d(10)-kkk | 299 |
| 529160 | 59 | kkk-d(10)-eee | 299 |
| 529180 | 80 | eek-d(10)-keke | 216 |
| 529217 | 79 | eek-d(10)-kkke | 216 |
| 529814 | 51 | k-d(10)-kekee | 300 |
| 529833 | 52 | k-d(10)-kdkee | 300 |
| 529735 | 43 | ke-d(10)-keke | 301 |
| 529755 | 60 | ek-d(10)-keke | 301 |
| 529775 | 38 | ke-d(10)-kdke | 301 |
| 529795 | 58 | ek-d(10)-kdke | 301 |
| 529864 | 41 | kde-d(10)-kdke | 302 |
| 529884 | 48 | edk-d(10)-kdke | 302 |
| 529904 | 44 | k-d(4)-k-(d4)-k-d(4)-ke | 302 |
| 529934 | 61 | eek-d(10)-keke | 302 |
| 529356 | 71 | eek-d(10)-keke | 303 |
| 529561 | 75 | eek-d(10)-kke | 28 |
| 529586 | 65 | kee-d(10)-kke | 28 |
| 529611 | 54 | edk-d(10)-kke | 28 |
| 529636 | 39 | kde-d(10)-kke | 28 |
| 529661 | 67 | kddk-d(9)-kke | 28 |
| 529686 | 66 | kdde-d(9)-kke | 28 |
| 529711 | 60 | eddk-d(9)-kke | 28 |
| 529924 | 62 | eeee-d(9)-kke | 28 |
| 529358 | 82 | eek-d(10)-keke | 304 |
| 529181 | 79 | eek-d(10)-keke | 217 |
| 529218 | 73 | eek-d(10)-kkke | 217 |
| 529182 | 85 | eek-d(10)-keke | 218 |
| 529219 | 84 | eek-d(10)-kkke | 218 |
| 529360 | 84 | eek-d(10)-keke | 305 |
| 529362 | 87 | eek-d(10)-keke | 306 |
| 529364 | 81 | eek-d(10)-keke | 307 |
| 529366 | 77 | eek-d(10)-keke | 308 |
| 529198 | 28 | eek-d(10)-keke | 309 |
| 529235 | 8 | eek-d(10)-kkke | 309 |
| 529141 | 34 | eee-d(10)-kkk | 310 |
| 529161 | 66 | kkk-d(10)-eee | 310 |
| 529368 | 27 | eek-d(10)-keke | 311 |
| 529370 | 44 | eek-d(10)-keke | 312 |
| 529372 | 61 | eek-d(10)-keke | 313 |
| 529374 | 71 | eek-d(10)-keke | 314 |
| 529376 | 63 | eek-d(10)-keke | 315 |
| 529378 | 68 | eek-d(10)-keke | 316 |
| 529380 | 79 | eek-d(10)-keke | 317 |
| 529382 | 77 | eek-d(10)-keke | 318 |
| 529384 | 75 | eek-d(10)-keke | 319 |
| 529386 | 40 | eek-d(10)-keke | 320 |
| 529240 | 73 | eek-d(10)-keke | 321 |
| 529241 | 67 | eek-d(10)-keke | 322 |
| 529242 | 42 | eek-d(10)-keke | 323 |
| 529243 | 60 | eek-d(10)-keke | 324 |
| 529388 | 65 | eek-d(10)-keke | 325 |
| 529815 | 37 | k-d(10)-kekee | 326 |
| 529834 | 44 | k-d(10)-kdkee | 326 |
| 529736 | 47 | ke-d(10)-keke | 327 |
| 529756 | 78 | ek-d(10)-keke | 327 |
| 529776 | 37 | ke-d(10)-kdke | 327 |
| 529796 | 71 | ek-d(10)-kdke | 327 |
| 529865 | 70 | kde-d(10)-kdke | 328 |
| 529885 | 59 | edk-d(10)-kdke | 328 |
| 529905 | 54 | k-(d4)-k-(d4)-k-(d4)-ke | 328 |
| 529935 | 70 | eek-d(10)-keke | 328 |
| 529562 | 87 | eek-d(10)-kke | 29 |
| 529587 | 68 | kee-d(10)-kke | 29 |
| 529612 | 67 | edk-d(10)-kke | 29 |
| 529637 | 64 | kde-d(10)-kke | 29 |
| 529662 | 62 | kddk-d(9)-kke | 29 |
| 529687 | 63 | kdde-d(9)-kke | 29 |
| 529712 | 61 | eddk-d(9)-kke | 29 |
| 529925 | 61 | eeee-d(9)-kke | 29 |
| 529816 | 77 | k-d(10)-kekee | 329 |
| 529835 | 80 | k-d(10)-kdkee | 329 |
| 529737 | 82 | ke-d(10)-keke | 330 |
| 529757 | 83 | ek-d(10)-keke | 330 |
| 529777 | 68 | ke-d(10)-kdke | 330 |
| 529797 | 77 | ek-d(10)-kdke | 330 |
| 529866 | 15 | kde-d(10)-kdke | 331 |
| 529886 | 71 | edk-d(10)-kdke | 331 |
| 529906 | 63 | k-(d4)-k-(d4)-k-(d4)-ke | 331 |
| 529936 | 78 | eek-d(10)-keke | 331 |
| 529563 | 89 | eek-d(10)-kke | 30 |
| 529588 | 84 | kee-d(10)-kke | 30 |
| 529613 | 80 | edk-d(10)-kke | 30 |
| 529638 | 48 | kde-d(10)-kke | 30 |
| 529663 | 85 | kddk-d(9)-kke | 30 |
| 529688 | 42 | kdde-d(9)-kke | 30 |
| 529713 | 81 | eddk-d(9)-kke | 30 |
| 529926 | 67 | eeee-d(9)-kke | 30 |
| 529390 | 53 | eek-d(10)-keke | 332 |
| 529392 | 63 | eek-d(10)-keke | 333 |
| 529394 | 58 | eek-d(10)-keke | 334 |
| 529396 | 56 | eek-d(10)-keke | 335 |
| 529398 | 62 | eek-d(10)-keke | 336 |
| 529400 | 44 | eek-d(10)-keke | 337 |
| 529402 | 39 | eek-d(10)-keke | 338 |
| 529404 | 46 | eek-d(10)-keke | 339 |
| 529406 | 63 | eek-d(10)-keke | 340 |
| 529244 | 58 | eek-d(10)-keke | 341 |
| 529245 | 68 | eek-d(10)-keke | 342 |
| 529246 | 60 | eek-d(10)-keke | 343 |
| 529247 | 36 | eek-d(10)-keke | 344 |
| 529248 | 43 | eek-d(10)-keke | 345 |
| 529249 | 23 | eek-d(10)-keke | 346 |
| 529250 | 69 | eek-d(10)-keke | 347 |
| 529251 | 15 | eek-d(10)-keke | 348 |
| 529252 | 44 | eek-d(10)-keke | 349 |
| 529253 | 42 | eek-d(10)-keke | 350 |
| 529408 | 67 | eek-d(10)-keke | 351 |
| 529410 | 19 | eek-d(10)-keke | 352 |
| 529412 | 57 | eek-d(10)-keke | 353 |
| 529414 | 80 | eek-d(10)-keke | 354 |
| 529416 | 85 | eek-d(10)-keke | 355 |
| 529418 | 70 | eek-d(10)-keke | 356 |
| 529420 | 78 | eek-d(10)-keke | 357 |
| 529422 | 19 | eek-d(10)-keke | 358 |
| 529424 | 48 | eek-d(10)-keke | 359 |
| 529426 | 66 | eek-d(10)-keke | 360 |
| 529428 | 59 | eek-d(10)-keke | 361 |
| 529430 | 83 | eek-d(10)-keke | 362 |
| 529432 | 84 | eek-d(10)-keke | 363 |
| 529199 | 71 | eek-d(10)-keke | 364 |
| 529236 | 76 | eek-d(10)-kkke | 364 |
| 529142 | 64 | eee-d(10)-kkk | 365 |
| 529162 | 60 | kkk-d(10)-eee | 365 |
| 529254 | 46 | eek-d(10)-keke | 366 |
| 529255 | 52 | eek-d(10)-keke | 367 |
| 529256 | 57 | eek-d(10)-keke | 368 |
| 529257 | 55 | eek-d(10)-keke | 369 |
| 529258 | 3 | eek-d(10)-keke | 370 |
| 529259 | 71 | eek-d(10)-keke | 371 |
| 529260 | 72 | eek-d(10)-keke | 372 |
| 529261 | 56 | eek-d(10)-keke | 373 |
| 529262 | 56 | eek-d(10)-keke | 374 |

TABLE 34-continued

Inhibition of human Target-X mRNA levels by chimeric antisense oligonucleotides targeted to Target-X

| ISIS No | % inhibition | Chemistry | SEQ CODE |
|---|---|---|---|
| 529263 | 59 | eek-d(10)-keke | 375 |
| 529264 | 49 | eek-d(10)-keke | 376 |
| 529434 | 83 | eek-d(10)-keke | 377 |
| 529436 | 80 | eek-d(10)-keke | 378 |
| 529438 | 79 | eek-d(10)-keke | 379 |
| 529440 | 87 | eek-d(10)-keke | 380 |
| 529442 | 68 | eek-d(10)-keke | 381 |
| 529443 | 72 | eek-d(10)-keke | 382 |
| 529444 | 68 | eek-d(10)-keke | 383 |
| 529445 | 85 | eek-d(10)-keke | 384 |
| 529446 | 72 | eek-d(10)-keke | 385 |
| 529447 | 60 | eek-d(10)-keke | 386 |
| 529448 | 77 | eek-d(10)-keke | 387 |
| 529807 | 78 | k-d(10)-kekee | 388 |
| 529826 | 61 | k-d(10)-kdkee | 388 |
| 529449 | 81 | eek-d(10)-keke | 389 |
| 529728 | 75 | ke-d(10)-keke | 390 |
| 529748 | 80 | ek-d(10)-keke | 390 |
| 529768 | 68 | ke-d(10)-kdke | 390 |
| 529788 | 74 | ek-d(10)-kdke | 390 |
| 529857 | 67 | kde-d(10)-kdke | 389 |
| 529877 | 77 | edk-d(10)-kdke | 389 |
| 529897 | 26 | k-(d4)-k-(d4)-k-(d4)-ke | 389 |
| 529200 | 78 | eek-d(10)-keke | 391 |
| 529237 | 84 | eek-d(10)-kkke | 391 |
| 529564 | 90 | eek-d(10)-kke | 34 |
| 529589 | 86 | kee-d(10)-kke | 34 |
| 529614 | 82 | edk-d(10)-kke | 34 |
| 529639 | 80 | kde-d(10)-kke | 34 |
| 529664 | 69 | kddk-d(9)-kke | 34 |
| 529689 | 71 | kdde-d(9)-kke | 34 |
| 529714 | 73 | eddk-d(9)-kke | 34 |
| 529917 | 73 | eeee-d(9)-kke | 34 |
| 529143 | 68 | eee-d(10)-kkk | 392 |
| 529163 | 50 | kkk-d(10)-eee | 392 |
| 529201 | 76 | eek-d(10)-keke | 393 |
| 529238 | 72 | eek-d(10)-kkke | 393 |
| 529144 | 57 | eee-d(10)-kkk | 394 |
| 529164 | 71 | kkk-d(10)-eee | 394 |
| 529450 | 91 | eek-d(10)-keke | 395 |
| 529451 | 85 | eek-d(10)-keke | 396 |
| 529266 | 63 | eek-d(10)-keke | 397 |
| 529806 | 52 | k-d(10)-kekee | 398 |
| 529825 | 44 | k-d(10)-kdkee | 398 |
| 529267 | 56 | eek-d(10)-keke | 399 |
| 529727 | 67 | ke-d(10)-keke | 400 |
| 529747 | 63 | ek-d(10)-keke | 400 |
| 529767 | 67 | ke-d(10)-kdke | 400 |
| 529787 | 68 | ek-d(10)-kdke | 400 |
| 529856 | 42 | kde-d(10)-kdke | 399 |
| 529876 | 36 | edk-d(10)-kdke | 399 |
| 529896 | 56 | k-(d4)-k-(d4)-k-(d4)-ke | 399 |
| 529546 | 65 | eek-d(10)-kke | 248 |
| 529571 | 80 | kee-d(10)-kke | 248 |
| 529596 | 43 | edk-d(10)-kke | 248 |
| 529621 | 38 | kde-d(10)-kke | 248 |
| 529646 | 68 | kddk-d(9)-kke | 248 |
| 529671 | 50 | kdde-d(9)-kke | 248 |
| 529696 | 53 | eddk-d(9)-kke | 248 |
| 529916 | 22 | eeee-d(9)-kke | 248 |
| 529547 | 86 | eek-d(10)-kke | 37 |
| 529572 | 75 | kee-d(10)-kke | 37 |
| 529597 | 58 | edk-d(10)-kke | 37 |
| 529622 | 58 | kde-d(10)-kke | 37 |
| 529647 | 18 | kddk-d(9)-kke | 37 |
| 529672 | 23 | kdde-d(9)-kke | 37 |
| 529697 | 28 | eddk-d(9)-kke | 37 |
| 529928 | 36 | eeee-d(9)-kke | 37 |
| 529452 | 63 | eek-d(10)-keke | 401 |
| 529453 | 73 | eek-d(10)-keke | 402 |
| 529454 | 82 | eek-d(10)-keke | 403 |
| 529455 | 84 | eek-d(10)-keke | 404 |
| 529202 | 61 | eek-d(10)-keke | 405 |
| 529239 | 59 | eek-d(10)-kkke | 405 |
| 529145 | 54 | eee-d(10)-kkk | 406 |
| 529165 | 77 | kkk-d(10)-eee | 406 |
| 529456 | 69 | eek-d(10)-keke | 407 |
| 529457 | 81 | eek-d(10)-keke | 408 |
| 529458 | 72 | eek-d(10)-keke | 409 |
| 529459 | 86 | eek-d(10)-keke | 410 |
| 529460 | 88 | eek-d(10)-keke | 411 |
| 529817 | 46 | k-d(10)-kekee | 412 |
| 529836 | 49 | k-d(10)-kdkee | 412 |
| 529738 | 51 | ke-d(10)-keke | 413 |
| 529758 | 53 | ek-d(10)-keke | 413 |
| 529778 | 39 | ke-d(10)-kdke | 413 |
| 529798 | 52 | ek-d(10)-kdke | 413 |
| 529867 | 56 | kde-d(10)-kdke | 414 |
| 529887 | 68 | edk-d(10)-kdke | 414 |
| 529907 | 28 | k-(d4)-k-(d4)-k-(d4)-ke | 414 |
| 529938 | 64 | eek-d(10)-keke | 414 |
| 529565 | 81 | eek-d(10)-kke | 38 |
| 529590 | 49 | kee-d(10)-kke | 38 |
| 529615 | 65 | edk-d(10)-kke | 38 |
| 529640 | 54 | kde-d(10)-kke | 38 |
| 529665 | 77 | kddk-d(9)-kke | 38 |
| 529690 | 77 | kdde-d(9)-kke | 38 |
| 529715 | 63 | eddk-d(9)-kke | 38 |
| 529927 | 62 | eeee-d(9)-kke | 38 |
| 529185 | 66 | eek-d(10)-keke | 221 |
| 529222 | 62 | eek-d(10)-kkke | 221 |
| 529808 | 75 | k-d(10)-kekee | 89 |
| 529827 | 67 | k-d(10)-kdkee | 89 |
| 529128 | 64 | eee-d(10)-kkk | 415 |
| 529148 | 78 | kkk-d(10)-eee | 415 |
| 529461 | 87 | eek-d(10)-keke | 416 |
| 529729 | 71 | ke-d(10)-keke | 415 |
| 529749 | 83 | ek-d(10)-keke | 415 |
| 529769 | 63 | ke-d(10)-kdke | 415 |
| 529789 | 10 | ek-d(10)-kdke | 415 |
| 529800 | 69 | k-d(10)-kekee | 415 |
| 529819 | 78 | k-d(10)-kdkee | 415 |
| 529858 | 60 | kde-d(10)-kdke | 416 |
| 529878 | 75 | edk-d(10)-kdke | 416 |
| 529898 | 34 | k-(d4)-k-(d4)-k-(d4)-ke | 416 |
| 529566 | 61 | eek-d(10)-kke | 39 |
| 529591 | 71 | kee-d(10)-kke | 39 |
| 529616 | 71 | edk-d(10)-kke | 39 |
| 529641 | 65 | kde-d(10)-kke | 39 |
| 529666 | 70 | kddk-d(9)-kke | 39 |
| 529691 | 67 | kdde-d(9)-kke | 39 |
| 529716 | 75 | eddk-d(9)-kke | 39 |
| 529721 | 71 | ke-d(10)-keke | 39 |
| 529741 | 81 | ek-d(10)-keke | 39 |
| 529761 | 66 | ke-d(10)-kdke | 39 |
| 529781 | 65 | ek-d(10)-kdke | 39 |
| 529801 | 71 | k-d(10)-kekee | 39 |
| 529820 | 74 | k-d(10)-kdkee | 39 |
| 529850 | 63 | kde-d(10)-kdke | 417 |
| 529870 | 72 | edk-d(10)-kdke | 417 |
| 529890 | 23 | k-(d4)-k-(d4)-k-(d4)-ke | 417 |
| 529918 | 54 | eeee-d(9)-kke | 39 |
| 529567 | 75 | eek-d(10)-kke | 262 |
| 529592 | 80 | kee-d(10)-kke | 262 |
| 529617 | 65 | edk-d(10)-kke | 262 |
| 529642 | 62 | kde-d(10)-kke | 262 |
| 529667 | 75 | kddk-d(9)-kke | 262 |
| 529692 | 53 | kdde-d(9)-kke | 262 |
| 529717 | 69 | eddk-d(9)-kke | 262 |
| 529722 | 74 | ke-d(10)-keke | 262 |
| 529742 | 81 | ek-d(10)-keke | 262 |
| 529762 | 66 | ke-d(10)-kdke | 262 |
| 529782 | 68 | ek-d(10)-kdke | 262 |
| 529851 | 68 | kde-d(10)-kdke | 418 |
| 529871 | 77 | edk-d(10)-kdke | 418 |
| 529891 | 36 | k-(d4)-k-(d4)-k-(d4)-ke | 418 |
| 529910 | 60 | eeee-d(9)-kke | 262 |
| 529568 | 79 | eek-d(10)-kke | 263 |

TABLE 34-continued

Inhibition of human Target-X mRNA levels by chimeric antisense oligonucleotides targeted to Target-X

| ISIS No | % inhibition | Chemistry | SEQ CODE |
|---|---|---|---|
| 529593 | 70 | kee-d(10)-kke | 263 |
| 529618 | 77 | edk-d(10)-kke | 263 |
| 529643 | 72 | kde-d(10)-kke | 263 |
| 529668 | 73 | kddk-d(9)-kke | 263 |
| 529693 | 62 | kdde-d(9)-kke | 263 |
| 529718 | 69 | eddk-d(9)-kke | 263 |
| 529911 | 66 | eeee-d(9)-kke | 263 |
| 529462 | 76 | eek-d(10)-keke | 419 |
| 529268 | 18 | eek-d(10)-keke | 420 |
| 529187 | 46 | eek-d(10)-keke | 421 |
| 529224 | 48 | eek-d(10)-kkke | 421 |
| 529130 | 34 | eee-d(10)-kkk | 422 |
| 529150 | 51 | kkk-d(10)-eee | 422 |
| 529549 | 85 | eek-d(10)-kke | 42 |
| 529574 | 81 | kee-d(10)-kke | 42 |
| 529599 | 64 | edk-d(10)-kke | 42 |
| 529624 | 68 | kde-d(10)-kke | 42 |
| 529649 | 77 | kddk-d(9)-kke | 42 |
| 529674 | 65 | kdde-d(9)-kke | 42 |
| 529699 | 63 | eddk-d(9)-kke | 42 |
| 529931 | 59 | eeee-d(9)-kke | 42 |
| 529810 | 80 | k-d(10)-kekee | 423 |
| 529829 | 67 | k-d(10)-kdkee | 423 |
| 529269 | 65 | eek-d(10)-keke | 424 |
| 529731 | 66 | ke-d(10)-keke | 425 |
| 529751 | 76 | ek-d(10)-keke | 425 |
| 529771 | 73 | ke-d(10)-kdke | 425 |
| 529791 | 65 | ek-d(10)-kdke | 425 |
| 529860 | 73 | kde-d(10)-kdke | 424 |
| 529880 | 74 | edk-d(10)-kdke | 424 |
| 529900 | 62 | k-(d4)-k-(d4)-k-(d4)-ke | 424 |
| 529270 | 69 | eek-d(10)-keke | 480 |
| 529550 | 81 | eek-d(10)-kke | 44 |
| 529575 | 88 | kee-d(10)-kke | 44 |
| 529600 | 78 | edk-d(10)-kke | 44 |
| 529625 | 74 | kde-d(10)-kke | 44 |
| 529650 | 81 | kddk-d(9)-kke | 44 |
| 529675 | 76 | kdde-d(9)-kke | 44 |
| 529700 | 73 | eddk-d(9)-kke | 44 |
| 529920 | 67 | eeee-d(9)-kke | 44 |
| 529271 | 43 | eek-d(10)-keke | 427 |
| 529272 | 0 | eek-d(10)-keke | 428 |
| 529273 | 62 | eek-d(10)-keke | 429 |
| 529274 | 78 | eek-d(10)-keke | 430 |
| 529275 | 70 | eek-d(10)-keke | 431 |
| 529276 | 73 | eek-d(10)-keke | 432 |
| 529277 | 71 | eek-d(10)-keke | 433 |
| 529278 | 72 | eek-d(10)-keke | 434 |
| 529279 | 10 | eek-d(10)-keke | 435 |
| 529280 | 11 | eek-d(10)-keke | 436 |
| 529281 | 82 | eek-d(10)-keke | 437 |
| 529282 | 87 | eek-d(10)-keke | 438 |
| 529803 | 71 | k-d(10)-kekee | 250 |
| 529822 | 72 | k-d(10)-kdkee | 250 |
| 529724 | 76 | ke-d(10)-keke | 439 |
| 529744 | 81 | ek-d(10)-keke | 439 |
| 529764 | 65 | ke-d(10)-kdke | 439 |
| 529784 | 68 | ek-d(10)-kdke | 439 |
| 529853 | 64 | kde-d(10)-kdke | 440 |
| 529873 | 69 | edk-d(10)-kdke | 440 |
| 529893 | 45 | k-(d4)-k-(d4)-k-(d4)-ke | 440 |
| 529937 | 81 | eek-d(10)-keke | 440 |
| 529551 | 88 | eek-d(10)-kke | 48 |
| 529576 | 71 | kee-d(10)-kke | 48 |
| 529601 | 74 | edk-d(10)-kke | 48 |
| 529626 | 72 | kde-d(10)-kke | 48 |
| 529651 | 85 | kddk-d(9)-kke | 48 |
| 529676 | 67 | kdde-d(9)-kke | 48 |
| 529701 | 82 | eddk-d(9)-kke | 48 |
| 529913 | 76 | eeee-d(9)-kke | 48 |
| 529811 | 56 | k-d(10)-kekee | 441 |
| 529830 | 46 | k-d(10)-kdkee | 441 |
| 529732 | 63 | ke-d(10)-keke | 442 |
| 529752 | 72 | ek-d(10)-keke | 442 |
| 529772 | 61 | ke-d(10)-kdke | 442 |
| 529792 | 68 | ek-d(10)-kdke | 442 |
| 529861 | 54 | kde-d(10)-kdke | 443 |
| 529881 | 78 | edk-d(10)-kdke | 443 |
| 529901 | 29 | k-(d4)-k-(d4)-k-(d4)-ke | 443 |
| 529939 | 67 | eek-d(10)-keke | 443 |
| 529283 | 70 | eek-d(10)-keke | 444 |
| 529552 | 72 | eek-d(10)-kke | 49 |
| 529577 | 80 | kee-d(10)-kke | 49 |
| 529602 | 64 | edk-d(10)-kke | 49 |
| 529627 | 56 | kde-d(10)-kke | 49 |
| 529652 | 57 | kddk-d(9)-kke | 49 |
| 529677 | 43 | kdde-d(9)-kke | 49 |
| 529702 | 54 | eddk-d(9)-kke | 49 |
| 529921 | 42 | eeee-d(9)-kke | 49 |
| 529284 | 76 | eek-d(10)-keke | 445 |
| 529285 | 77 | eek-d(10)-keke | 446 |
| 529286 | 68 | eek-d(10)-keke | 447 |
| 529287 | 65 | eek-d(10)-keke | 448 |
| 529719 | 73 | ke-d(10)-keke | 264 |
| 529739 | 83 | ek-d(10)-keke | 264 |
| 529759 | 63 | ke-d(10)-kdke | 264 |
| 529779 | 70 | ek-d(10)-kdke | 244 |
| 529848 | 60 | kde-d(10)-kdke | 449 |
| 529868 | 63 | edk-d(10)-kdke | 449 |
| 529888 | 53 | k-(d4)-k-(d4)-k-(d4)-ke | 449 |
| 529553 | 81 | eek-d(10)-kke | 265 |
| 529578 | 65 | kee-d(10)-kke | 265 |
| 529603 | 60 | edk-d(10)-kke | 265 |
| 529628 | 59 | kde-d(10)-kke | 265 |
| 529653 | 76 | kddk-d(9)-kke | 265 |
| 529678 | 56 | kdde-d(9)-kke | 265 |
| 529703 | 68 | eddk-d(9)-kke | 265 |
| 529908 | 69 | eeee-d(9)-kke | 265 |
| 529168 | 64 | eek-d(10)-keke | 450 |
| 529205 | 62 | eek-d(10)-kkke | 450 |
| 529290 | 53 | eek-d(10)-keke | 451 |
| 529802 | 57 | k-d(10)-kekee | 452 |
| 529821 | 61 | k-d(10)-kdkee | 452 |
| 529292 | 74 | eek-d(10)-keke | 453 |
| 529723 | 68 | ke-d(10)-keke | 454 |
| 529743 | 84 | ek-d(10)-keke | 454 |
| 529763 | 64 | ke-d(10)-kdke | 454 |
| 529783 | 72 | ek-d(10)-kdke | 454 |
| 529852 | 66 | kde-d(10)-kdke | 453 |
| 529872 | 62 | edk-d(10)-kdke | 453 |
| 529892 | 43 | k-(d4)-k-(d4)-k-(d4)-ke | 453 |
| 529554 | 80 | eek-d(10)-kke | 252 |
| 529579 | 83 | kee-d(10)-kke | 252 |
| 529604 | 73 | edk-d(10)-kke | 252 |
| 529629 | 64 | kde-d(10)-kke | 252 |
| 529654 | 69 | kddk-d(9)-kke | 252 |
| 529679 | 52 | kdde-d(9)-kke | 252 |
| 529704 | 63 | eddk-d(9)-kke | 252 |
| 529912 | 64 | eeee-d(9)-kke | 252 |
| 529294 | 74 | eek-d(10)-keke | 455 |
| 529296 | 52 | eek-d(10)-keke | 456 |
| 529298 | 60 | eek-d(10)-keke | 457 |
| 529300 | 71 | eek-d(10)-keke | 458 |
| 529188 | 79 | eek-d(10)-keke | 459 |
| 529225 | 78 | eek-d(10)-kkke | 459 |
| 529131 | 58 | eee-d(10)-kkk | 460 |
| 529151 | 71 | kkk-d(10)-eee | 460 |
| 529302 | 74 | eek-d(10)-keke | 461 |
| 529189 | 64 | eek-d(10)-keke | 222 |
| 529226 | 50 | eek-d(10)-kkke | 222 |
| 529132 | 78 | eee-d(10)-kkk | 462 |
| 529152 | 62 | kkk-d(10)-eee | 462 |
| 529190 | 76 | eek-d(10)-keke | 223 |
| 529227 | 88 | eek-d(10)-kkke | 250 |
| 529133 | 81 | eee-d(10)-kkk | 463 |
| 529153 | 68 | kkk-d(10)-eee | 463 |
| 529191 | 78 | eek-d(10)-keke | 224 |
| 529228 | 85 | eek-d(10)-kkke | 224 |

TABLE 34-continued

Inhibition of human Target-X mRNA levels by chimeric antisense oligonucleotides targeted to Target-X

| ISIS No | % inhibition | Chemistry | SEQ CODE |
|---|---|---|---|
| 529134 | 75 | eee-d(10)-kkk | 464 |
| 529154 | 61 | kkk-d(10)-eee | 464 |
| 529304 | 89 | eek-d(10)-keke | 465 |
| 529306 | 84 | eek-d(10)-keke | 466 |
| 529308 | 68 | eek-d(10)-keke | 467 |
| 529310 | 59 | eek-d(10)-keke | 468 |
| 529169 | 79 | eek-d(10)-keke | 469 |
| 529206 | 82 | eek-d(10)-kkke | 469 |
| 529312 | 68 | eek-d(10)-keke | 470 |
| 529314 | 61 | eek-d(10)-keke | 471 |
| 529316 | 62 | eek-d(10)-keke | 472 |
| 529555 | 78 | eek-d(10)-kke | 59 |
| 529580 | 73 | kee-d(10)-kke | 59 |
| 529605 | 71 | edk-d(10)-kke | 59 |
| 529630 | 64 | kde-d(10)-kke | 59 |
| 529655 | 63 | kddk-d(9)-kke | 59 |
| 529680 | 43 | kdde-d(9)-kke | 59 |
| 529705 | 63 | eddk-d(9)-kke | 59 |
| 529932 | 60 | eeee-d(9)-kke | 59 |
| 529318 | 82 | eek-d(10)-keke | 473 |
| 529170 | 85 | eek-d(10)-keke | 474 |
| 529207 | 88 | eek-d(10)-kkke | 474 |
| 529171 | 81 | eek-d(10)-keke | 475 |
| 529208 | 84 | eek-d(10)-kkke | 475 |
| 529805 | 40 | k-d(10)-kekee | 476 |
| 529824 | 32 | k-d(10)-kdkee | 476 |
| 529320 | 74 | eek-d(10)-keke | 477 |
| 529726 | 80 | ke-d(10)-keke | 478 |
| 529746 | 82 | ek-d(10)-keke | 478 |
| 529766 | 63 | ke-d(10)-kdke | 478 |
| 529786 | 69 | ek-d(10)-kdke | 478 |
| 529855 | 39 | kde-d(10)-kdke | 477 |
| 529875 | 40 | edk-d(10)-kdke | 477 |
| 529895 | 27 | k-(d4)-k-(d4)-k-(d4)-ke | 477 |
| 529556 | 72 | eek-d(10)-kke | 61 |
| 529581 | 68 | kee-d(10)-kke | 61 |
| 529606 | 54 | edk-d(10)-kke | 61 |
| 529631 | 29 | kde-d(10)-kke | 61 |
| 529656 | 74 | kddk-d(9)-kke | 61 |
| 529681 | 32 | kdde-d(9)-kke | 61 |
| 529706 | 41 | eddk-d(9)-kke | 61 |
| 529915 | 51 | eeee-d(9)-kke | 61 |
| 529172 | 88 | eek-d(10)-keke | 226 |
| 529209 | 87 | eek-d(10)-kkke | 226 |
| 529173 | 92 | eek-d(10)-keke | 227 |
| 529210 | 89 | eek-d(10)-kkke | 227 |
| 529183 | 85 | eek-d(10)-keke | 479 |
| 529220 | 92 | eek-d(10)-kkke | 479 |
| 529126 | 83 | eee-d(10)-kkk | 257 |
| 529146 | 84 | kkk-d(10)-eee | 257 |
| 529174 | 85 | eek-d(10)-keke | 480 |
| 529211 | 86 | eek-d(10)-kkke | 480 |
| 529322 | 71 | eek-d(10)-keke | 481 |
| 529324 | 79 | eek-d(10)-keke | 482 |
| 529326 | 85 | eek-d(10)-keke | 483 |
| 529175 | 92 | eek-d(10)-keke | 228 |
| 529212 | 92 | eek-d(10)-kkke | 228 |
| 529176 | 89 | eek-d(10)-keke | 229 |
| 529213 | 90 | eek-d(10)-kkke | 229 |
| 529804 | 89 | k-d(10)-kekee | 259 |
| 529823 | 89 | k-d(10)-kdkee | 259 |
| 529166 | 83 | eek-d(10)-keke | 230 |
| 529203 | 86 | eek-d(10)-kkke | 230 |
| 529725 | 92 | ke-d(10)-keke | 260 |
| 529745 | 91 | ek-d(10)-keke | 260 |
| 529765 | 88 | ke-d(10)-kdke | 260 |
| 529785 | 91 | ek-d(10)-kdke | 260 |
| 529799 | 89 | k-d(10)-kekee | 260 |
| 529818 | 88 | k-d(10)-kdkee | 260 |
| 529854 | 90 | kde-d(10)-kdke | 230 |
| 529874 | 81 | edk-d(10)-kdke | 230 |
| 529894 | 60 | k-(d4)-k-(d4)-k-(d4)-ke | 230 |
| 529167 | 71 | eek-d(10)-keke | 231 |
| 529204 | 70 | eek-d(10)-kkke | 231 |
| 529557 | 86 | eek-d(10)-kke | 69 |
| 529582 | 86 | kee-d(10)-kke | 69 |
| 529607 | 84 | edk-d(10)-kke | 69 |
| 529632 | 81 | kde-d(10)-kke | 69 |
| 529657 | 85 | kddk-d(9)-kke | 69 |
| 529682 | 78 | kdde-d(9)-kke | 69 |
| 529707 | 79 | eddk-d(9)-kke | 69 |
| 529720 | 75 | ke-d(10)-kke | 69 |
| 529740 | 70 | ek-d(10)-keke | 69 |
| 529760 | 78 | ke-d(10)-kdke | 69 |
| 529780 | 83 | ek-d(10)-kdke | 69 |
| 529849 | 80 | kde-d(10)-kdke | 231 |
| 529869 | 72 | edk-d(10)-kdke | 231 |
| 529889 | 49 | k-(d4)-k-(d4)-k-(d4)-ke | 231 |
| 529914 | 69 | eeee-d(9)-kke | 69 |
| 529328 | 68 | eek-d(10)-keke | 484 |
| 529558 | 71 | eek-d(10)-kke | 71 |
| 529583 | 81 | kee-d(10)-kke | 71 |
| 529608 | 68 | edk-d(10)-kke | 71 |
| 529633 | 73 | kde-d(10)-kke | 71 |
| 529658 | 63 | kddk-d(9)-kke | 71 |
| 529683 | 74 | kdde-d(9)-kke | 71 |
| 529708 | 70 | eddk-d(9)-kke | 71 |
| 529909 | 59 | eeee-d(9)-kke | 71 |
| 529192 | 51 | eek-d(10)-keke | 485 |
| 529229 | 69 | eek-d(10)-kkke | 485 |
| 529135 | 54 | eee-d(10)-kkk | 486 |
| 529155 | 56 | kkk-d(10)-eee | 486 |
| 529330 | 37 | eek-d(10)-keke | 487 | e = 2'-MOE, < = cEt, d = 2'-deoxyribonucleoside

Example 20

Design of Modified Oligonucleotides Comprising 2'-O-Methoxyethyl (2'-MOE) or 6'-(S)—CH₃ Bicyclic Nucleoside (e.g cEt) Modifications Based on the activity of the antisense oligonucleotides listed above, additional antisense oligonucleotides were designed targeting a Target-X nucleic acid targeting start positions 1147, 1154 or 12842 of Target-X.

The newly designed chimeric antisense oligonucleotides are 16 or 17 nucleotides in length and their motifs are described in Table 35. The chemistry column of Table 35 presents the sugar motif of each oligonucleotide, wherein "e" indicates a 2'-O-methoxyethyl (2'-MOE) nucleoside, "k" indicates a 6'-(S)—$CH_3$ bicyclic nucleoside (e.g cEt) and "d" indicates a 2'-deoxyribonucleoside. The internucleoside linkages throughout each gapmer are hosphorothioate (P=S) linkages. All cytosine residues throughout each oligonucleotide are 5-methylcytosine.

Each gapmer listed in Table 35 is targeted to the human Target-X genomic sequence.

TABLE 35

Chimeric antisense oligonucleotides targeted to Target-X

| ISIS No | Chemistry | SEQ CODE |
|---|---|---|
| 529544 | eek-d(10)-kke | 21 |
| 529569 | kee-d(10)-kke | 21 |
| 529594 | edk-d(10)-kke | 21 |
| 529619 | kde-d(10)-kke | 21 |
| 529644 | kddk-d(9)-kke | 21 |
| 529669 | kdde-d(9)-kke | 21 |

TABLE 35-continued

Chimeric antisense oligonucleotides targeted to Target-X

| ISIS No | Chemistry | SEQ CODE |
|---|---|---|
| 529694 | eddk-d(9)-kke | 21 |
| 529929 | eeee-d(9)-kke | 21 |
| 529809 | k-d(10)-kekee | 488 |
| 529828 | k-d(10)-kdkee | 488 |
| 529730 | ke-d(10)-keke | 489 |
| 529750 | ek-d(10)-keke | 489 |
| 529770 | ke-d(10)-kdke | 489 |
| 529790 | ek-d(10)-kdke | 489 |
| 529859 | kde-d(10)-kdke | 490 |
| 529879 | edk-d(10)-kdke | 490 |
| 529899 | k-d(4)-k-d(4)-k-d(4)-ke | 490 |
| 529545 | eek-d(10)-kke | 22 |
| 529570 | kee-d(10)-kke | 22 |
| 529595 | edk-d(10)-kke | 22 |
| 529620 | kde-d(10)-kke | 22 |
| 529645 | kddk-d(9)-kke | 22 |
| 529670 | kdde-d(9)-kke | 22 |
| 529695 | eddk-d(9)-kke | 22 |
| 529919 | eeee-d(9)-kke | 22 |
| 529548 | eek-d(10)-kke | 41 |
| 529573 | kee-d(10)-kke | 41 |
| 529598 | edk-d(10)-kke | 41 |
| 529623 | kde-d(10)-kke | 41 |
| 529648 | kddk-d(9)-kke | 41 |
| 529673 | kdde-d(9)-kke | 41 |
| 529698 | eddk-d(9)-kke | 41 |
| 529930 | eeee-d(9)-kke | 41 | e = 2'-MOE, k = cEt, d = 2'-deoxyribonucleoside

Example 21

Modified Oligonucleotides Comprising 2'-O-Methoxyethyl (2'-MOE) and 6'-(S)—CH₃ Bicyclic Nucleoside (e.g cEt) Modifications Targeting Human Target-X Additional antisense oligonucleotides were designed targeting a Target-X nucleic acid and were tested for their effects on Target-X mRNA in vitro. ISIS 472998 and ISIS 515554, described in the Examples above were also included in the screen.

The newly designed chimeric antisense oligonucleotides are 16 nucleotides in length and their motifs are described in Table 36. The chemistry column of Table 36 presents the sugar motif of each oligonucleotide, wherein "e" indicates a 2'-O-methoxyethyl (2'-MOE) nucleoside, "k" indicates a 6'-(S)—CH₃ bicyclic nucleoside (e.g cEt) and "d" indicates a 2'-deoxyribonucleoside. The internucleoside linkages throughout each gapmer are hosphorothioate (P=S) linkages. All cytosine residues throughout each oligonucleotide are 5-methylcytosine.

Each gapmer listed in Table 36 is targeted to the human Target-X genomic sequence.

Cultured Hep3B cells at a density of 20,000 cells per well were transfected using electroporation with 2,000 nM antisense oligonucleotide. After a treatment period of approximately 24 hours, RNA was isolated from the cells and Target-X mRNA levels were measured by quantitative real-time PCR. Human primer probe set RTS2927 was used to measure mRNA levels. Target-X mRNA levels were adjusted according to total RNA content, as measured by RIBOGREEN®. Results are presented as percent inhibition of Target-X, relative to untreated control cells.

TABLE 36

Inhibition of human Target-X mRNA levels by chimeric antisense oligonucleotides targeted to Target-X

| ISIS No | % inhibition | Chemistry | SEQ CODE |
|---|---|---|---|
| 472998 | 88 | kk-d(10)-kk | 74 |
| 515554 | 75 | eee-d(10)-kkk | 493 |
| 534530 | 92 | keke-d(9)-kek | 491 |
| 534563 | 92 | kek-d(9)-ekek | 491 |
| 534596 | 88 | ekee-d(9)-kke | 491 |
| 534629 | 89 | eke-d(9)-ekke | 491 |
| 534662 | 87 | eekk-d(9)-eke | 491 |
| 534695 | 92 | eek-d(9)-keke | 491 |
| 534732 | 90 | ekek-d(8)-keke | 491 |
| 534767 | 92 | keek-d(8)-keek | 491 |
| 534802 | 93 | ekk-d(10)-kke | 491 |
| 534832 | 83 | edk-d(10)-kke | 491 |
| 534862 | 72 | kde-d(10)-kke | 491 |
| 534892 | 82 | eek-d(10)-kke | 491 |
| 534922 | 80 | kddk-d(9)-kke | 491 |
| 534952 | 72 | kdde-d(9)-kke | 491 |
| 534982 | 77 | eddk-d(9)-kke | 491 |
| 535012 | 70 | eeee-d(9)-kke | 491 |
| 535045 | 84 | eeee-d(9)-kkk | 491 |
| 535078 | 87 | eeek-d(9)-kke | 491 |
| 535111 | 63 | eeeee-d(8)-kke | 491 |
| 535144 | 69 | ededk-d(8)-kke | 491 |
| 535177 | 68 | edkde-d(8)-kke | 491 |
| 534531 | 61 | keke-d(9)-kek | 492 |
| 534564 | 30 | kek-d(9)-ekek | 492 |
| 534597 | 67 | ekee-d(9)-kke | 492 |
| 534630 | 54 | eke-d(9)-ekke | 492 |
| 534663 | 94 | eekk-d(9)-eke | 492 |
| 534696 | 68 | eek-d(9)-keke | 492 |
| 534733 | 44 | ekek-d(8)-keke | 492 |
| 534768 | 55 | keek-d(8)-keek | 492 |
| 534803 | 73 | ekk-d(10)-kke | 492 |
| 534833 | 65 | edk-d(10)-kke | 492 |
| 534863 | 53 | kde-d(10)-kke | 492 |
| 534893 | 61 | eek-d(10)-kke | 492 |
| 534923 | 70 | kddk-d(9)-kke | 492 |
| 534953 | 54 | kdde-d(9)-kke | 492 |
| 534983 | 58 | eddk-d(9)-kke | 492 |
| 535013 | 52 | eeee-d(9)-kke | 492 |
| 535046 | 67 | eeee-d(9)-kkk | 492 |
| 535079 | 57 | eeek-d(9)-kke | 492 |
| 535112 | 42 | eeeee-d(8)-kke | 492 |
| 535145 | 41 | ededk-d(8)-kke | 492 |
| 535178 | 35 | edkde-d(8)-kke | 492 |
| 534565 | 87 | kek-d(9)-ekek | 493 |
| 534598 | 72 | ekee-d(9)-kke | 493 |
| 534631 | 70 | eke-d(9)-ekke | 493 |
| 534664 | 94 | eekk-d(9)-eke | 493 |
| 534697 | 90 | eek-d(9)-keke | 493 |
| 534734 | 74 | ekek-d(8)-keke | 493 |
| 534769 | 80 | keek-d(8)-keek | 493 |
| 534804 | 87 | ekk-d(10)-kke | 493 |
| 534834 | 76 | edk-d(10)-kke | 493 |
| 534864 | 56 | kde-d(10)-kke | 493 |
| 534894 | 67 | eek-d(10)-kke | 493 |
| 534924 | 71 | kddk-d(9)-kke | 493 |
| 534954 | 54 | kdde-d(9)-kke | 493 |
| 534984 | 48 | eddk-d(9)-kke | 493 |
| 535014 | 43 | eeee-d(9)-kke | 493 |
| 535047 | 60 | eeee-d(9)-kkk | 493 |
| 535080 | 64 | eeek-d(9)-kke | 493 |
| 535113 | 32 | eeeee-d(8)-kke | 493 |
| 535146 | 31 | ededk-d(8)-kke | 493 |
| 535179 | 28 | edkde-d(8)-kke | 493 |
| 534533 | 82 | keke-d(9)-kek | 494 |
| 534566 | 88 | kek-d(9)-ekek | 494 |
| 534599 | 65 | ekee-d(9)-kke | 494 |
| 534632 | 69 | eke-d(9)-ekke | 494 |
| 534665 | 87 | eekk-d(9)-eke | 494 |
| 534698 | 64 | eek-d(9)-keke | 494 |
| 534735 | 63 | ekek-d(8)-keke | 494 |
| 534770 | 66 | keek-d(8)-keek | 494 |
| 534805 | 87 | ekk-d(10)-kke | 494 |
| 534835 | 68 | edk-d(10)-kke | 494 |
| 534865 | 66 | kde-d(10)-kke | 494 |

TABLE 36-continued

Inhibition of human Target-X mRNA levels by chimeric antisense oligonucleotides targeted to Target-X

| ISIS No | % inhibition | Chemistry | SEQ CODE |
|---|---|---|---|
| 534895 | 57 | eek-d(10)-kke | 494 |
| 534925 | 82 | kddk-d(9)-kke | 494 |
| 534955 | 76 | kdde-d(9)-kke | 494 |
| 534985 | 71 | eddk-d(9)-kke | 494 |
| 535015 | 59 | eeee-d(9)-kke | 494 |
| 535048 | 69 | eeee-d(9)-kkk | 494 |
| 535081 | 67 | eeek-d(9)-kke | 494 |
| 535114 | 37 | eeeee-d(8)-kke | 494 |
| 535147 | 32 | ededk-d(8)-kke | 494 |
| 535180 | 31 | edkde-d(8)-kke | 494 |
| 534534 | 94 | keke-d(9)-kek | 234 |
| 534567 | 92 | kek-d(9)-ekek | 234 |
| 534600 | 92 | ekee-d(9)-kke | 234 |
| 534633 | 91 | eke-d(9)-ekke | 234 |
| 534666 | 89 | eekk-d(9)-eke | 234 |
| 534699 | 91 | eek-d(9)-keke | 234 |
| 534736 | 83 | ekek-d(8)-keke | 234 |
| 534771 | 80 | keek-d(8)-keek | 234 |
| 534806 | 96 | ekk-d(10)-kke | 234 |
| 534836 | 86 | edk-d(10)-kke | 234 |
| 534866 | 82 | kde-d(10)-kke | 234 |
| 534896 | 82 | eek-d(10)-kke | 234 |
| 534926 | 89 | kddk-d(9)-kke | 234 |
| 534956 | 91 | kdde-d(9)-kke | 234 |
| 534986 | 87 | eddk-d(9)-kke | 234 |
| 535016 | 83 | eeee-d(9)-kke | 234 |
| 535049 | 87 | eeee-d(9)-kkk | 234 |
| 535082 | 87 | eeek-d(9)-kke | 234 |
| 535115 | 77 | eeeee-d(8)-kke | 234 |
| 535148 | 73 | ededk-d(8)-kke | 234 |
| 535181 | 68 | edkde-d(8)-kke | 234 |
| 534535 | 66 | keke-d(9)-kek | 236 |
| 534568 | 85 | kek-d(9)-ekek | 236 |
| 534601 | 51 | ekee-d(9)-kke | 236 |
| 534634 | 80 | eke-d(9)-ekke | 236 |
| 534667 | 90 | eekk-d(9)-eke | 236 |
| 534700 | 88 | eek-d(9)-keke | 236 |
| 534737 | 65 | ekek-d(8)-keke | 236 |
| 534772 | 77 | keek-d(8)-keek | 236 |
| 534807 | 84 | ekk-d(10)-kke | 236 |
| 534837 | 78 | edk-d(10)-kke | 236 |
| 534867 | 44 | kde-d(10)-kke | 236 |
| 534897 | 82 | eek-d(10)-kke | 236 |
| 534927 | 61 | kddk-d(9)-kke | 236 |
| 534957 | 58 | kdde-d(9)-kke | 236 |
| 534987 | 49 | eddk-d(9)-kke | 236 |
| 535017 | 38 | eeee-d(9)-kke | 236 |
| 535050 | 32 | eeee-d(9)-kkk | 236 |
| 535083 | 43 | eeek-d(9)-kke | 236 |
| 535116 | 9 | eeeee-d(8)-kke | 236 |
| 535149 | 23 | ededk-d(8)-kke | 236 |
| 535182 | 18 | edkde-d(8)-kke | 236 |
| 534536 | 89 | keke-d(9)-kek | 238 |
| 534569 | 90 | kek-d(9)-ekek | 238 |
| 534602 | 85 | ekee-d(9)-kke | 238 |
| 534635 | 87 | eke-d(9)-ekke | 238 |
| 534668 | 90 | eekk-d(9)-eke | 238 |
| 534701 | 92 | eek-d(9)-keke | 238 |
| 534738 | 81 | ekek-d(8)-keke | 238 |
| 534773 | 79 | keek-d(8)-keek | 238 |
| 534808 | 90 | ekk-d(10)-kke | 238 |
| 534838 | 88 | edk-d(10)-kke | 238 |
| 534868 | 67 | kde-d(10)-kke | 238 |
| 534898 | 89 | eek-d(10)-kke | 238 |
| 534928 | 81 | kddk-d(9)-kke | 238 |
| 534958 | 78 | kdde-d(9)-kke | 238 |
| 534988 | 66 | eddk-d(9)-kke | 238 |
| 535018 | 78 | eeee-d(9)-kke | 238 |
| 535051 | 76 | eeee-d(9)-kkk | 238 |
| 535084 | 80 | eeek-d(9)-kke | 238 |
| 535117 | 58 | eeeee-d(8)-kke | 238 |
| 535150 | 51 | ededk-d(8)-kke | 238 |
| 535183 | 53 | edkde-d(8)-kke | 238 |
| 534537 | 91 | keke-d(9)-kek | 239 |
| 534570 | 85 | kek-d(9)-ekek | 239 |
| 534603 | 79 | ekee-d(9)-kke | 239 |
| 534636 | 72 | eke-d(9)-ekke | 239 |
| 534669 | 85 | eekk-d(9)-eke | 239 |
| 534702 | 85 | eek-d(9)-keke | 239 |
| 534739 | 73 | ekek-d(8)-keke | 239 |
| 534774 | 77 | keek-d(8)-keek | 239 |
| 534809 | 91 | ekk-d(10)-kke | 239 |
| 534839 | 86 | edk-d(10)-kke | 239 |
| 534869 | 71 | kde-d(10)-kke | 239 |
| 534899 | 82 | eek-d(10)-kke | 239 |
| 534929 | 83 | kddk-d(9)-kke | 239 |
| 534959 | 80 | kdde-d(9)-kke | 239 |
| 534989 | 79 | eddk-d(9)-kke | 239 |
| 535019 | 76 | eeee-d(9)-kke | 239 |
| 535052 | 79 | eeee-d(9)-kkk | 239 |
| 535085 | 81 | eeek-d(9)-kke | 239 |
| 535118 | 58 | eeeee-d(8)-kke | 239 |
| 535151 | 65 | ededk-d(8)-kke | 239 |
| 535184 | 60 | edkde-d(8)-kke | 239 |
| 534516 | 77 | keke-d(9)-kek | 495 |
| 534549 | 80 | kek-d(9)-ekek | 495 |
| 534582 | 73 | ekee-d(9)-kke | 495 |
| 534615 | 79 | eke-d(9)-ekke | 495 |
| 534648 | 67 | eekk-d(9)-eke | 495 |
| 534681 | 87 | eek-d(9)-keke | 495 |
| 534718 | 46 | ekek-d(8)-keke | 495 |
| 534753 | 68 | keek-d(8)-keek | 495 |
| 534788 | 84 | ekk-d(10)-kke | 495 |
| 534818 | 82 | edk-d(10)-kke | 495 |
| 534848 | 75 | kde-d(10)-kke | 495 |
| 534878 | 72 | eek-d(10)-kke | 495 |
| 534908 | 81 | kddk-d(9)-kke | 495 |
| 534938 | 69 | kdde-d(9)-kke | 495 |
| 534968 | 77 | eddk-d(9)-kke | 495 |
| 534998 | 76 | eeee-d(9)-kke | 495 |
| 535031 | 76 | eeee-d(9)-kkk | 495 |
| 535064 | 70 | eeek-d(9)-kke | 495 |
| 535097 | 57 | eeeee-d(8)-kke | 495 |
| 535130 | 69 | ededk-d(8)-kke | 495 |
| 535163 | 58 | edkde-d(8)-kke | 495 |
| 534538 | 71 | keke-d(9)-kek | 241 |
| 534571 | 64 | kek-d(9)-ekek | 241 |
| 534604 | 66 | ekee-d(9)-kke | 241 |
| 534637 | 74 | eke-d(9)-ekke | 241 |
| 534670 | 87 | eekk-d(9)-eke | 241 |
| 534703 | 72 | eek-d(9)-keke | 241 |
| 534740 | 56 | ekek-d(8)-keke | 241 |
| 534775 | 53 | keek-d(8)-keek | 241 |
| 534810 | 78 | ekk-d(10)-kke | 241 |
| 534840 | 73 | edk-d(10)-kke | 241 |
| 534870 | 65 | kde-d(10)-kke | 241 |
| 534900 | 69 | eek-d(10)-kke | 241 |
| 534930 | 67 | kddk-d(9)-kke | 241 |
| 534960 | 62 | kdde-d(9)-kke | 241 |
| 534990 | 66 | eddk-d(9)-kke | 241 |
| 535020 | 61 | eeee-d(9)-kke | 241 |
| 535053 | 47 | eeee-d(9)-kkk | 241 |
| 535086 | 61 | eeek-d(9)-kke | 241 |
| 535119 | 49 | eeeee-d(8)-kke | 241 |
| 535152 | 48 | ededk-d(8)-kke | 241 |
| 535185 | 57 | edkde-d(8)-kke | 241 |
| 534539 | 70 | keke-d(9)-kek | 496 |
| 534572 | 82 | kek-d(9)-ekek | 496 |
| 534605 | 59 | ekee-d(9)-kke | 496 |
| 534638 | 69 | eke-d(9)-ekke | 496 |
| 534671 | 89 | eekk-d(9)-eke | 496 |
| 534704 | 83 | eek-d(9)-keke | 496 |
| 534741 | 47 | ekek-d(8)-keke | 496 |
| 534776 | 46 | keek-d(8)-keek | 496 |
| 534811 | 71 | ekk-d(10)-kke | 496 |
| 534841 | 61 | edk-d(10)-kke | 496 |
| 534871 | 53 | kde-d(10)-kke | 496 |
| 534901 | 55 | eek-d(10)-kke | 496 |
| 534931 | 73 | kddk-d(9)-kke | 496 |
| 534961 | 53 | kdde-d(9)-kke | 496 |

TABLE 36-continued

Inhibition of human Target-X mRNA levels by chimeric antisense oligonucleotides targeted to Target-X

| ISIS No | % inhibition | Chemistry | SEQ CODE |
|---|---|---|---|
| 534991 | 56 | eddk-d(9)-kke | 496 |
| 535021 | 58 | eeee-d(9)-kke | 496 |
| 535054 | 59 | eeee-d(9)-kkk | 496 |
| 535087 | 0 | eeek-d(9)-kke | 496 |
| 535120 | 41 | eeeee-d(8)-kke | 496 |
| 535153 | 44 | ededk-d(8)-kke | 496 |
| 535186 | 35 | edkde-d(8)-kke | 496 |
| 534573 | 76 | kek-d(9)-ekek | 497 |
| 534606 | 55 | ekee-d(9)-kke | 497 |
| 534639 | 72 | eke-d(9)-ekke | 497 |
| 534672 | 89 | eekk-d(9)-eke | 497 |
| 534705 | 87 | eek-d(9)-keke | 497 |
| 534742 | 84 | ekek-d(8)-keke | 497 |
| 534777 | 79 | keek-d(8)-keek | 497 |
| 534812 | 76 | ekk-d(10)-kke | 497 |
| 534842 | 74 | edk-d(10)-kke | 497 |
| 534872 | 53 | kde-d(10)-kke | 497 |
| 534902 | 70 | eek-d(10)-kke | 497 |
| 534932 | 73 | kddk-d(9)-kke | 497 |
| 534962 | 60 | kdde-d(9)-kke | 497 |
| 534992 | 61 | eddk-d(9)-kke | 497 |
| 535022 | 38 | eeee-d(9)-kke | 497 |
| 535055 | 42 | eeee-d(9)-kkk | 497 |
| 535088 | 56 | eeek-d(9)-kke | 497 |
| 535121 | 5 | eeeee-d(8)-kke | 497 |
| 535154 | 22 | ededk-d(8)-kke | 497 |
| 535187 | 16 | edkde-d(8)-kke | 497 |
| 534541 | 86 | keke-d(9)-kek | 498 |
| 534574 | 89 | kek-d(9)-ekek | 498 |
| 534607 | 59 | ekee-d(9)-kke | 498 |
| 534640 | 76 | eke-d(9)-ekke | 498 |
| 534673 | 89 | eekk-d(9)-eke | 498 |
| 534706 | 86 | eek-d(9)-keke | 498 |
| 534743 | 79 | ekek-d(8)-keke | 498 |
| 534778 | 80 | keek-d(8)-keek | 498 |
| 534813 | 83 | ekk-d(10)-kke | 498 |
| 534843 | 82 | edk-d(10)-kke | 498 |
| 534873 | 83 | kde-d(10)-kke | 498 |
| 534903 | 78 | eek-d(10)-kke | 498 |
| 534933 | 83 | kddk-d(9)-kke | 498 |
| 534963 | 70 | kdde-d(9)-kke | 498 |
| 534993 | 78 | eddk-d(9)-kke | 498 |
| 535023 | 56 | eeee-d(9)-kke | 498 |
| 535056 | 59 | eeee-d(9)-kkk | 498 |
| 535089 | 73 | eeek-d(9)-kke | 498 |
| 535122 | 39 | eeeee-d(8)-kke | 498 |
| 535155 | 60 | ededk-d(8)-kke | 498 |
| 535188 | 41 | edkde-d(8)-kke | 498 |
| 534542 | 75 | keke-d(9)-kek | 499 |
| 534575 | 82 | kek-d(9)-ekek | 499 |
| 534608 | 72 | ekee-d(9)-kke | 499 |
| 534641 | 69 | eke-d(9)-ekke | 499 |
| 534674 | 84 | eekk-d(9)-eke | 499 |
| 534707 | 78 | eek-d(9)-keke | 499 |
| 534744 | 72 | ekek-d(8)-keke | 499 |
| 534779 | 75 | keek-d(8)-keek | 499 |
| 534814 | 81 | ekk-d(10)-kke | 499 |
| 534844 | 75 | edk-d(10)-kke | 499 |
| 534874 | 70 | kde-d(10)-kke | 499 |
| 534904 | 71 | eek-d(10)-kke | 499 |
| 534934 | 73 | kddk-d(9)-kke | 499 |
| 534964 | 72 | kdde-d(9)-kke | 499 |
| 534994 | 69 | eddk-d(9)-kke | 499 |
| 535024 | 56 | eeee-d(9)-kke | 499 |
| 535057 | 63 | eeee-d(9)-kkk | 499 |
| 535090 | 64 | eeek-d(9)-kke | 499 |
| 535123 | 40 | eeeee-d(8)-kke | 499 |
| 535156 | 47 | ededk-d(8)-kke | 499 |
| 535189 | 48 | edkde-d(8)-kke | 499 |
| 534515 | 52 | keke-d(9)-kek | 34 |
| 534548 | 85 | kek-d(9)-ekek | 34 |
| 534581 | 75 | ekee-d(9)-kke | 34 |
| 534614 | 83 | eke-d(9)-ekke | 34 |
| 534647 | 65 | eekk-d(9)-eke | 34 |
| 534680 | 88 | eek-d(9)-keke | 34 |
| 534717 | 76 | ekek-d(8)-keke | 34 |
| 534752 | 79 | keek-d(8)-keek | 34 |
| 534787 | 90 | ekk-d(10)-kke | 34 |
| 535030 | 77 | eeee-d(9)-kkk | 34 |
| 535063 | 75 | eeek-d(9)-kke | 34 |
| 535096 | 54 | eeeee-d(8)-kke | 34 |
| 535129 | 66 | ededk-d(8)-kke | 34 |
| 535162 | 49 | edkde-d(8)-kke | 34 |
| 534543 | 66 | keke-d(9)-kek | 500 |
| 534576 | 69 | kek-d(9)-ekek | 500 |
| 534609 | 77 | ekee-d(9)-kke | 500 |
| 534642 | 62 | eke-d(9)-ekke | 500 |
| 534675 | 80 | eekk-d(9)-eke | 500 |
| 534708 | 81 | eek-d(9)-keke | 500 |
| 534745 | 68 | ekek-d(8)-keke | 500 |
| 534780 | 69 | keek-d(8)-keek | 500 |
| 534815 | 85 | ekk-d(10)-kke | 500 |
| 534845 | 72 | edk-d(10)-kke | 500 |
| 534875 | 56 | kde-d(10)-kke | 500 |
| 534905 | 65 | eek-d(10)-kke | 500 |
| 534935 | 78 | kddk-d(9)-kke | 500 |
| 534965 | 48 | kdde-d(9)-kke | 500 |
| 534995 | 62 | eddk-d(9)-kke | 500 |
| 535025 | 58 | eeee-d(9)-kke | 500 |
| 535058 | 60 | eeee-d(9)-kkk | 500 |
| 535091 | 61 | eeek-d(9)-kke | 500 |
| 535124 | 51 | eeeee-d(8)-kke | 500 |
| 535157 | 55 | ededk-d(8)-kke | 500 |
| 535190 | 47 | edkde-d(8)-kke | 500 |
| 534517 | 71 | keke-d(9)-kek | 501 |
| 534550 | 80 | kek-d(9)-ekek | 501 |
| 534583 | 70 | ekee-d(9)-kke | 501 |
| 534616 | 84 | eke-d(9)-ekke | 501 |
| 534649 | 68 | eekk-d(9)-eke | 501 |
| 534682 | 87 | eek-d(9)-keke | 501 |
| 534719 | 90 | ekek-d(8)-keke | 501 |
| 534754 | 83 | keek-d(8)-keek | 501 |
| 534789 | 86 | ekk-d(10)-kke | 501 |
| 534819 | 69 | edk-d(10)-kke | 501 |
| 534849 | 62 | kde-d(10)-kke | 501 |
| 534879 | 69 | eek-d(10)-kke | 501 |
| 534909 | 73 | kddk-d(9)-kke | 501 |
| 534939 | 49 | kdde-d(9)-kke | 501 |
| 534969 | 47 | eddk-d(9)-kke | 501 |
| 534999 | 51 | eeee-d(9)-kke | 501 |
| 535032 | 51 | eeee-d(9)-kkk | 501 |
| 535065 | 64 | eeek-d(9)-kke | 501 |
| 535098 | 31 | eeeee-d(8)-kke | 501 |
| 535131 | 31 | ededk-d(8)-kke | 501 |
| 535164 | 40 | edkde-d(8)-kke | 501 |
| 534518 | 81 | keke-d(9)-kek | 502 |
| 534551 | 88 | kek-d(9)-ekek | 502 |
| 534584 | 78 | ekee-d(9)-kke | 502 |
| 534617 | 80 | eke-d(9)-ekke | 502 |
| 534650 | 83 | eekk-d(9)-eke | 502 |
| 534683 | 93 | eek-d(9)-keke | 502 |
| 534720 | 87 | ekek-d(8)-keke | 502 |
| 534755 | 82 | keek-d(8)-keek | 502 |
| 534790 | 89 | ekk-d(10)-kke | 502 |
| 534820 | 64 | edk-d(10)-kke | 502 |
| 534850 | 38 | kde-d(10)-kke | 502 |
| 534880 | 68 | eek-d(10)-kke | 502 |
| 534910 | 60 | kddk-d(9)-kke | 502 |
| 534940 | 37 | kdde-d(9)-kke | 502 |
| 534970 | 59 | eddk-d(9)-kke | 502 |
| 535000 | 30 | eeee-d(9)-kke | 502 |
| 535033 | 44 | eeee-d(9)-kkk | 502 |
| 535066 | 64 | eeek-d(9)-kke | 502 |
| 535099 | 22 | eeeee-d(8)-kke | 502 |
| 535132 | 54 | ededk-d(8)-kke | 502 |
| 535165 | 45 | edkde-d(8)-kke | 502 |
| 534544 | 80 | keke-d(9)-kek | 503 |
| 534577 | 83 | kek-d(9)-ekek | 503 |
| 534610 | 62 | ekee-d(9)-kke | 503 |
| 534643 | 66 | eke-d(9)-ekke | 503 |

TABLE 36-continued

Inhibition of human Target-X mRNA levels by chimeric antisense oligonucleotides targeted to Target-X

| ISIS No | % inhibition | Chemistry | SEQ CODE |
|---|---|---|---|
| 534676 | 95 | eekk-d(9)-eke | 503 |
| 534709 | 86 | eek-d(9)-keke | 503 |
| 534746 | 73 | ekek-d(8)-keke | 503 |
| 534781 | 71 | keek-d(8)-keek | 503 |
| 534816 | 83 | ekk-d(10)-kke | 503 |
| 534846 | 73 | edk-d(10)-kke | 503 |
| 534876 | 39 | kde-d(10)-kke | 503 |
| 534906 | 67 | eek-d(10)-kke | 503 |
| 534936 | 66 | kddk-d(9)-kke | 503 |
| 534966 | 48 | kdde-d(9)-kke | 503 |
| 534996 | 56 | eddk-d(9)-kke | 503 |
| 535026 | 39 | eeee-d(9)-kke | 503 |
| 535059 | 45 | eeee-d(9)-kkk | 503 |
| 535092 | 48 | eeek-d(9)-kke | 503 |
| 535125 | 26 | eeeee-d(8)-kke | 503 |
| 535158 | 44 | ededk-d(8)-kke | 503 |
| 535191 | 34 | edkde-d(8)-kke | 503 |
| 534545 | 83 | keke-d(9)-kek | 504 |
| 534578 | 81 | kek-d(9)-ekek | 504 |
| 534611 | 78 | ekee-d(9)-kke | 504 |
| 534644 | 72 | eke-d(9)-ekke | 504 |
| 534677 | 92 | eekk-d(9)-eke | 504 |
| 534710 | 78 | eek-d(9)-keke | 504 |
| 534747 | 85 | ekek-d(8)-keke | 504 |
| 534782 | 85 | keek-d(8)-keek | 504 |
| 534817 | 88 | ekk-d(10)-kke | 504 |
| 534847 | 73 | edk-d(10)-kke | 504 |
| 534877 | 66 | kde-d(10)-kke | 504 |
| 534907 | 73 | eek-d(10)-kke | 504 |
| 534937 | 85 | kddk-d(9)-kke | 504 |
| 534967 | 80 | kdde-d(9)-kke | 504 |
| 534997 | 74 | eddk-d(9)-kke | 504 |
| 535027 | 64 | eeee-d(9)-kke | 504 |
| 535060 | 68 | eeee-d(9)-kkk | 504 |
| 535093 | 73 | eeek-d(9)-kke | 504 |
| 535126 | 42 | eeeee-d(8)-kke | 504 |
| 535159 | 49 | ededk-d(8)-kke | 504 |
| 535192 | 51 | edkde-d(8)-kke | 504 |
| 534519 | 87 | keke-d(9)-kek | 505 |
| 534552 | 85 | kek-d(9)-ekek | 505 |
| 534585 | 76 | ekee-d(9)-kke | 505 |
| 534618 | 78 | eke-d(9)-ekke | 505 |
| 534651 | 79 | eekk-d(9)-eke | 505 |
| 534684 | 87 | eek-d(9)-keke | 505 |
| 534721 | 89 | ekek-d(8)-keke | 505 |
| 534756 | 90 | keek-d(8)-keek | 505 |
| 534791 | 84 | ekk-d(10)-kke | 505 |
| 534821 | 79 | edk-d(10)-kke | 505 |
| 534851 | 64 | kde-d(10)-kke | 505 |
| 534881 | 65 | eek-d(10)-kke | 505 |
| 534911 | 85 | kddk-d(9)-kke | 505 |
| 534941 | 66 | kdde-d(9)-kke | 505 |
| 534971 | 75 | eddk-d(9)-kke | 505 |
| 535001 | 62 | eeee-d(9)-kke | 505 |
| 535034 | 65 | eeee-d(9)-kkk | 505 |
| 535067 | 76 | eeek-d(9)-kke | 505 |
| 535100 | 5 | eeeee-d(8)-kke | 505 |
| 535133 | 30 | ededk-d(8)-kke | 505 |
| 535166 | 23 | edkde-d(8)-kke | 505 |
| 534520 | 87 | keke-d(9)-kek | 251 |
| 534553 | 79 | kek-d(9)-ekek | 251 |
| 534586 | 60 | ekee-d(9)-kke | 251 |
| 534619 | 62 | eke-d(9)-ekke | 251 |
| 534652 | 84 | eekk-d(9)-eke | 251 |
| 534685 | 84 | eek-d(9)-keke | 251 |
| 534722 | 75 | ekek-d(8)-keke | 251 |
| 534757 | 81 | keek-d(8)-keek | 251 |
| 534792 | 87 | ekk-d(10)-kke | 251 |
| 534822 | 80 | edk-d(10)-kke | 251 |
| 534852 | 38 | kde-d(10)-kke | 251 |
| 534882 | 75 | eek-d(10)-kke | 251 |
| 534912 | 74 | kddk-d(9)-kke | 251 |
| 534942 | 58 | kdde-d(9)-kke | 251 |
| 534972 | 59 | eddk-d(9)-kke | 251 |
| 535002 | 50 | eeee-d(9)-kke | 251 |
| 535035 | 57 | eeee-d(9)-kkk | 251 |
| 535068 | 67 | eeek-d(9)-kke | 251 |
| 535101 | 24 | eeeee-d(8)-kke | 251 |
| 535134 | 23 | ededk-d(8)-kke | 251 |
| 535167 | 26 | edkde-d(8)-kke | 251 |
| 534513 | 90 | keke-d(9)-kek | 252 |
| 534546 | 92 | kek-d(9)-ekek | 252 |
| 534579 | 78 | ekee-d(9)-kke | 252 |
| 534612 | 82 | eke-d(9)-ekke | 252 |
| 534645 | 73 | eekk-d(9)-eke | 252 |
| 534678 | 91 | eek-d(9)-keke | 252 |
| 534715 | 87 | ekek-d(8)-keke | 252 |
| 534750 | 88 | keek-d(8)-keek | 252 |
| 534785 | 89 | ekk-d(10)-kke | 252 |
| 535028 | 52 | eeee-d(9)-kkk | 252 |
| 535061 | 73 | eeek-d(9)-kke | 252 |
| 535094 | 61 | eeeee-d(8)-kke | 252 |
| 535127 | 59 | ededk-d(8)-kke | 252 |
| 535160 | 62 | edkde-d(8)-kke | 252 |
| 534521 | 86 | keke-d(9)-kek | 506 |
| 534554 | 87 | kek-d(9)-ekek | 506 |
| 534587 | 62 | ekee-d(9)-kke | 506 |
| 534620 | 68 | eke-d(9)-ekke | 506 |
| 534653 | 77 | eekk-d(9)-eke | 506 |
| 534686 | 90 | eek-d(9)-keke | 506 |
| 534723 | 88 | ekek-d(8)-keke | 506 |
| 534758 | 79 | keek-d(8)-keek | 506 |
| 534793 | 85 | ekk-d(10)-kke | 506 |
| 534823 | 81 | edk-d(10)-kke | 506 |
| 534853 | 59 | kde-d(10)-kke | 506 |
| 534883 | 69 | eek-d(10)-kke | 506 |
| 534913 | 76 | kddk-d(9)-kke | 506 |
| 534943 | 53 | kdde-d(9)-kke | 506 |
| 534973 | 61 | eddk-d(9)-kke | 506 |
| 535003 | 53 | eeee-d(9)-kke | 506 |
| 535036 | 35 | eeee-d(9)-kkk | 506 |
| 535069 | 62 | eeek-d(9)-kke | 506 |
| 535102 | 31 | eeeee-d(8)-kke | 506 |
| 535135 | 44 | ededk-d(8)-kke | 506 |
| 535168 | 34 | edkde-d(8)-kke | 506 |
| 534522 | 83 | keke-d(9)-kek | 507 |
| 534555 | 81 | kek-d(9)-ekek | 507 |
| 534588 | 72 | ekee-d(9)-kke | 507 |
| 534621 | 74 | eke-d(9)-ekke | 507 |
| 534654 | 78 | eekk-d(9)-eke | 507 |
| 534687 | 91 | eek-d(9)-keke | 507 |
| 534724 | 84 | ekek-d(8)-keke | 507 |
| 534759 | 86 | keek-d(8)-keek | 507 |
| 534794 | 78 | ekk-d(10)-kke | 507 |
| 534824 | 75 | edk-d(10)-kke | 507 |
| 534854 | 63 | kde-d(10)-kke | 507 |
| 534884 | 60 | eek-d(10)-kke | 507 |
| 534914 | 75 | kddk-d(9)-kke | 507 |
| 534944 | 69 | kdde-d(9)-kke | 507 |
| 534974 | 66 | eddk-d(9)-kke | 507 |
| 535004 | 56 | eeee-d(9)-kke | 507 |
| 535037 | 50 | eeee-d(9)-kkk | 507 |
| 535070 | 68 | eeek-d(9)-kke | 507 |
| 535103 | 55 | eeeee-d(8)-kke | 507 |
| 535136 | 51 | ededk-d(8)-kke | 507 |
| 535169 | 54 | edkde-d(8)-kke | 507 |
| 534523 | 89 | keke-d(9)-kek | 253 |
| 534556 | 91 | kek-d(9)-ekek | 253 |
| 534589 | 88 | ekee-d(9)-kke | 253 |
| 534622 | 93 | eke-d(9)-ekke | 253 |
| 534655 | 72 | eekk-d(9)-eke | 253 |
| 534688 | 92 | eek-d(9)-keke | 253 |
| 534725 | 87 | ekek-d(8)-keke | 253 |
| 534760 | 92 | keek-d(8)-keek | 253 |
| 534795 | 93 | ekk-d(10)-kke | 253 |
| 534825 | 82 | edk-d(10)-kke | 253 |
| 534855 | 73 | kde-d(10)-kke | 253 |
| 534885 | 82 | eek-d(10)-kke | 253 |
| 534915 | 88 | kddk-d(9)-kke | 253 |
| 534945 | 82 | kdde-d(9)-kke | 253 |

TABLE 36-continued

Inhibition of human Target-X mRNA levels by chimeric antisense oligonucleotides targeted to Target-X

| ISIS No | % inhibition | Chemistry | SEQ CODE |
|---|---|---|---|
| 534975 | 68 | eddk-d(9)-kke | 253 |
| 535005 | 69 | eeee-d(9)-kke | 253 |
| 535038 | 72 | eeee-d(9)-kkk | 253 |
| 535071 | 74 | eeek-d(9)-kke | 253 |
| 535104 | 61 | eeeee-d(8)-kke | 253 |
| 535137 | 67 | ededk-d(8)-kke | 253 |
| 535170 | 51 | edkde-d(8)-kke | 253 |
| 534524 | 95 | keke-d(9)-kek | 254 |
| 534557 | 98 | kek-d(9)-ekek | 254 |
| 534590 | 91 | ekee-d(9)-kke | 254 |
| 534623 | 91 | eke-d(9)-ekke | 254 |
| 534656 | 90 | eekk-d(9)-eke | 254 |
| 534689 | 92 | eek-d(9)-keke | 254 |
| 534726 | 57 | ekek-d(8)-keke | 254 |
| 534761 | 89 | keek-d(8)-keek | 254 |
| 534796 | 93 | ekk-d(10)-kke | 254 |
| 534826 | 89 | edk-d(10)-kke | 254 |
| 534856 | 87 | kde-d(10)-kke | 254 |
| 534886 | 85 | eek-d(10)-kke | 254 |
| 534916 | 87 | kddk-d(9)-kke | 254 |
| 534946 | 86 | kdde-d(9)-kke | 254 |
| 534976 | 77 | eddk-d(9)-kke | 254 |
| 535006 | 83 | eeee-d(9)-kke | 254 |
| 535039 | 86 | eeee-d(9)-kkk | 254 |
| 535072 | 87 | eeek-d(9)-kke | 254 |
| 535105 | 68 | eeeee-d(8)-kke | 254 |
| 535138 | 70 | ededk-d(8)-kke | 254 |
| 535171 | 65 | edkde-d(8)-kke | 254 |
| 534558 | 92 | kek-d(9)-ekek | 255 |
| 534591 | 91 | ekee-d(9)-kke | 255 |
| 534624 | 86 | eke-d(9)-ekke | 255 |
| 534657 | 90 | eekk-d(9)-eke | 255 |
| 534690 | 76 | eek-d(9)-keke | 255 |
| 534727 | 92 | ekek-d(8)-keke | 255 |
| 534762 | 91 | keek-d(8)-keek | 255 |
| 534797 | 94 | ekk-d(10)-kke | 255 |
| 534827 | 90 | edk-d(10)-kke | 255 |
| 534857 | 80 | kde-d(10)-kke | 255 |
| 534887 | 76 | eek-d(10)-kke | 255 |
| 534917 | 91 | kddk-d(9)-kke | 255 |
| 534947 | 91 | kdde-d(9)-kke | 255 |
| 534977 | 86 | eddk-d(9)-kke | 255 |
| 535007 | 80 | eeee-d(9)-kke | 255 |
| 535040 | 86 | eeee-d(9)-kkk | 255 |
| 535073 | 87 | eeek-d(9)-kke | 255 |
| 535106 | 70 | eeeee-d(8)-kke | 255 |
| 535139 | 73 | ededk-d(8)-kke | 255 |
| 535172 | 69 | edkde-d(8)-kke | 255 |
| 534514 | 90 | keke-d(9)-kek | 61 |
| 534547 | 92 | kek-d(9)-ekek | 61 |
| 534580 | 78 | ekee-d(9)-kke | 61 |
| 534613 | 80 | eke-d(9)-ekke | 61 |
| 534646 | 79 | eekk-d(9)-eke | 61 |
| 534679 | 93 | eek-d(9)-keke | 61 |
| 534716 | 94 | ekek-d(8)-keke | 61 |
| 534751 | 86 | keek-d(8)-keek | 61 |
| 534786 | 83 | ekk-d(10)-kke | 61 |
| 535029 | 45 | eeee-d(9)-kkk | 61 |
| 535062 | 81 | eeee-d(9)-kke | 61 |
| 535095 | 57 | eeeee-d(8)-kke | 61 |
| 535128 | 58 | ededk-d(8)-kke | 61 |
| 535161 | 49 | edkde-d(8)-kke | 61 |
| 534526 | 94 | keke-d(9)-kek | 256 |
| 534559 | 95 | kek-d(9)-ekek | 256 |
| 534592 | 93 | ekee-d(9)-kke | 256 |
| 534625 | 93 | eke-d(9)-ekke | 256 |
| 534658 | 93 | eekk-d(9)-eke | 256 |
| 534691 | 96 | eek-d(9)-keke | 256 |
| 534728 | 93 | ekek-d(8)-keke | 256 |
| 534763 | 93 | keek-d(8)-keek | 256 |
| 534798 | 97 | ekk-d(10)-kke | 256 |
| 534828 | 94 | edk-d(10)-kke | 256 |
| 534858 | 92 | kde-d(10)-kke | 256 |
| 534888 | 93 | eek-d(10)-kke | 256 |
| 534918 | 95 | kddk-d(9)-kke | 256 |
| 534948 | 93 | kdde-d(9)-kke | 256 |
| 534978 | 91 | eddk-d(9)-kke | 256 |
| 535008 | 88 | eeee-d(9)-kke | 256 |
| 535041 | 87 | eeee-d(9)-kkk | 256 |
| 535074 | 90 | eeek-d(9)-kke | 256 |
| 535107 | 78 | eeeee-d(8)-kke | 256 |
| 535140 | 81 | ededk-d(8)-kke | 256 |
| 535173 | 81 | edkde-d(8)-kke | 256 |
| 534527 | 95 | keke-d(9)-kek | 258 |
| 534560 | 96 | kek-d(9)-ekek | 258 |
| 534593 | 87 | ekee-d(9)-kke | 258 |
| 534626 | 85 | eke-d(9)-ekke | 258 |
| 534659 | 90 | eekk-d(9)-eke | 258 |
| 534692 | 91 | eek-d(9)-keke | 258 |
| 534729 | 91 | ekek-d(8)-keke | 258 |
| 534764 | 91 | keek-d(8)-keek | 258 |
| 534799 | 96 | ekk-d(10)-kke | 258 |
| 534829 | 91 | edk-d(10)-kke | 258 |
| 534859 | 87 | kde-d(10)-kke | 258 |
| 534889 | 81 | eek-d(10)-kke | 258 |
| 534919 | 92 | kddk-d(9)-kke | 258 |
| 534949 | 91 | kdde-d(9)-kke | 258 |
| 534979 | 84 | eddk-d(9)-kke | 258 |
| 535009 | 78 | eeee-d(9)-kke | 258 |
| 535042 | 76 | eeee-d(9)-kkk | 258 |
| 535075 | 83 | eeek-d(9)-kke | 258 |
| 535108 | 64 | eeeee-d(8)-kke | 258 |
| 535141 | 69 | ededk-d(8)-kke | 258 |
| 535174 | 65 | edkde-d(8)-kke | 258 |
| 534528 | 94 | keke-d(9)-kek | 260 |
| 534561 | 0 | kek-d(9)-ekek | 260 |
| 534594 | 92 | ekee-d(9)-kke | 260 |
| 534627 | 90 | eke-d(9)-ekke | 260 |
| 534660 | 92 | eekk-d(9)-eke | 260 |
| 534693 | 95 | eek-d(9)-keke | 260 |
| 534730 | 93 | ekek-d(8)-keke | 260 |
| 534765 | 92 | keek-d(8)-keek | 260 |
| 534800 | 93 | ekk-d(10)-kke | 260 |
| 534830 | 93 | edk-d(10)-kke | 260 |
| 534860 | 85 | kde-d(10)-kke | 260 |
| 534890 | 91 | eek-d(10)-kke | 260 |
| 534920 | 93 | kddk-d(9)-kke | 260 |
| 534950 | 90 | kdde-d(9)-kke | 260 |
| 534980 | 88 | eddk-d(9)-kke | 260 |
| 535010 | 88 | eeee-d(9)-kke | 260 |
| 535043 | 89 | eeee-d(9)-kkk | 260 |
| 535076 | 88 | eeek-d(9)-kke | 260 |
| 535109 | 76 | eeeee-d(8)-kke | 260 |
| 535142 | 86 | ededk-d(8)-kke | 260 |
| 535175 | 71 | edkde-d(8)-kke | 260 |
| 534529 | 70 | keke-d(9)-kek | 261 |
| 534562 | 86 | kek-d(9)-ekek | 261 |
| 534595 | 56 | ekee-d(9)-kke | 261 |
| 534628 | 73 | eke-d(9)-ekke | 261 |
| 534661 | 64 | eekk-d(9)-eke | 261 |
| 534694 | 75 | eek-d(9)-keke | 261 |
| 534731 | 47 | ekek-d(8)-keke | 261 |
| 534766 | 30 | keek-d(8)-keek | 261 |
| 534801 | 83 | ekk-d(10)-kke | 261 |
| 534831 | 84 | edk-d(10)-kke | 261 |
| 534861 | 71 | kde-d(10)-kke | 261 |
| 534891 | 73 | eek-d(10)-kke | 261 |
| 534921 | 55 | kddk-d(9)-kke | 261 |
| 534951 | 61 | kdde-d(9)-kke | 261 |
| 534981 | 48 | eddk-d(9)-kke | 261 |
| 535011 | 54 | eeee-d(9)-kke | 261 |
| 535044 | 46 | eeee-d(9)-kkk | 261 |
| 535077 | 29 | eeek-d(9)-kke | 261 |
| 535110 | 19 | eeeee-d(8)-kke | 261 |
| 535143 | 15 | ededk-d(8)-kke | 261 |
| 535176 | 37 | edkde-d(8)-kke | 261 | e = 2'-MOE, k = cEt, d = 2'-deoxynucleoside

Example 22

Modified Antisense Oligonucleotides Comprising 2'-O-Methoxyethyl (2'-MOE) and 6'-(S)—CH₃ Bicyclic Nucleoside (e.g cEt) Modifications Targeting Human Target-X Targeting Intronic Repeats Additional antisense oligonucleotides were designed targeting the intronic repeat regions of Target-X.

The newly designed chimeric antisense oligonucleotides and their motifs are described in Table 37. The internucleoside linkages throughout each gapmer are phosphorothioate linkages (P=S) and are designated as "s". Nucleosides followed by "d" indicate 2'-deoxyribonucleosides. Nucleosides followed by "k" indicate 6'-(S)—CH₃ bicyclic nucleosides (e.g cEt). Nucleosides followed by "e" indicate 2'-O-methoxyethyl (2'-MOE) nucleosides. "N" indicates modified or naturally occurring nucleobases (A, T, C, G, U, or 5-methyl C).

Each gapmer listed in Table 37 is targeted to the intronic region of human Target-X genomic sequence, designated herein as Target-X.

Cultured Hep3B cells at a density of 20,000 cells per well were transfected using electroporation with 2,000 nM antisense oligonucleotide. After a treatment period of approximately 24 hours, RNA was isolated from the cells and Target-X mRNA levels were measured by quantitative real-time PCR. Human primer probe set was used to measure mRNA levels. Target-X mRNA levels were adjusted according to total RNA content, as measured by RIBOGREEN®. Results are presented as percent inhibition of Target-X, relative to untreated control cells.

TABLE 37

Inhibition of human Target-X mRNA levels by chimeric antisense oligonucleotides targeted to Target-X

| Sequence (5' to 3') | ISIS No | % inhibition | SEQ CODE | SEQ ID NO |
| --- | --- | --- | --- | --- |
| Nks Nks Nds Nds Nds Nds Nds Nds Nds Nds Nds Nks Nk | 472998 | 90 | 508 | 7 |
| Nks Nks Nks Nds Nds Nds Nds Nds Nds Nds Nds Nes Nes Ne | 473327 | 88 | 30 | 6 |
| Nes Nes Nes Nds Nds Nds Nds Nds Nds Nds Nds Nks Nks Nk | 537024 | 74 | 509 | 6 |
| Nes Nes Nes Nds Nds Nds Nds Nds Nds Nds Nds Nks Nks Nk | 537025 | 79 | 510 | 6 |
| Nes Nes Nes Nds Nds Nds Nds Nds Nds Nds Nds Nks Nks Nk | 537026 | 76 | 511 | 6 |
| Nes Nes Nes Nds Nds Nds Nds Nds Nds Nds Nds Nks Nks Nk | 537028 | 37 | 512 | 6 |
| Nes Nes Nes Nds Nds Nds Nds Nds Nds Nds Nds Nks Nks Nk | 537029 | 45 | 513 | 6 |
| Nes Nes Nes Nds Nds Nds Nds Nds Nds Nds Nds Nks Nks Nk | 537030 | 67 | 514 | 6 |
| Nes Nes Nes Nds Nds Nds Nds Nds Nds Nds Nds Nks Nks Nk | 537031 | 59 | 515 | 6 |
| Nes Nes Nes Nds Nds Nds Nds Nds Nds Nds Nds Nks Nks Nk | 537032 | 9 | 516 | 6 |
| Nes Nes Nes Nds Nds Nds Nds Nds Nds Nds Nds Nks Nks Nk | 537033 | 65 | 517 | 6 |
| Nes Nes Nes Nds Nds Nds Nds Nds Nds Nds Nds Nks Nks Nk | 537034 | 71 | 518 | 6 |
| Nes Nes Nes Nds Nds Nds Nds Nds Nds Nds Nds Nks Nks Nk | 537035 | 68 | 519 | 6 |
| Nes Nes Nes Nds Nds Nds Nds Nds Nds Nds Nds Nks Nks Nk | 537036 | 74 | 520 | 6 |
| Nes Nes Nes Nds Nds Nds Nds Nds Nds Nds Nds Nks Nks Nk | 537038 | 69 | 521 | 6 |
| Nes Nes Nes Nds Nds Nds Nds Nds Nds Nds Nds Nks Nks Nk | 537039 | 67 | 522 | 6 |
| Nes Nes Nes Nds Nds Nds Nds Nds Nds Nds Nds Nks Nks Nk | 537040 | 68 | 523 | 6 |
| Nes Nes Nes Nds Nds Nds Nds Nds Nds Nds Nds Nks Nks Nk | 537041 | 76 | 524 | 6 |

TABLE 37-continued

Inhibition of human Target-X mRNA levels by chimeric antisense oligonucleotides targeted to Target-X

| Sequence (5' to 3') | ISIS No | % inhibition | SEQ CODE | SEQ ID NO |
|---|---|---|---|---|
| Nes Nes Nes Nds Nds Nds Nds Nds Nds Nds Nds Nds Nks Nks Nk | 537042 | 77 | 525 | 6 |
| Nes Nes Nes Nds Nds Nds Nds Nds Nds Nds Nds Nds Nks Nks Nk | 537043 | 70 | 526 | 6 |
| Nes Nes Nes Nds Nds Nds Nds Nds Nds Nds Nds Nds Nks Nks Nk | 537044 | 82 | 527 | 6 |
| Nes Nes Nes Nds Nds Nds Nds Nds Nds Nds Nds Nds Nks Nks Nk | 537045 | 69 | 528 | 6 |
| Nes Nes Nes Nds Nds Nds Nds Nds Nds Nds Nds Nds Nks Nks Nk | 537047 | 35 | 529 | 6 |
| Nes Nes Nes Nds Nds Nds Nds Nds Nds Nds Nds Nds Nks Nks Nk | 537049 | 62 | 530 | 6 |
| Nes Nes Nes Nds Nds Nds Nds Nds Nds Nds Nds Nds Nks Nks Nk | 537051 | 62 | 531 | 6 |
| Nes Nes Nes Nds Nds Nds Nds Nds Nds Nds Nds Nds Nks Nks Nk | 537055 | 16 | 532 | 6 |
| Nes Nes Nes Nds Nds Nds Nds Nds Nds Nds Nds Nds Nks Nks Nk | 537056 | 25 | 533 | 6 |
| Nes Nes Nes Nds Nds Nds Nds Nds Nds Nds Nds Nds Nks Nks Nk | 537057 | 49 | 534 | 6 |
| Nes Nes Nes Nds Nds Nds Nds Nds Nds Nds Nds Nds Nks Nks Nk | 537058 | 49 | 535 | 6 |
| Nes Nes Nes Nds Nds Nds Nds Nds Nds Nds Nds Nds Nks Nks Nk | 537059 | 53 | 536 | 6 |
| Nes Nes Nes Nds Nds Nds Nds Nds Nds Nds Nds Nds Nks Nks Nk | 537060 | 73 | 537 | 6 |
| Nes Nes Nes Nds Nds Nds Nds Nds Nds Nds Nds Nds Nks Nks Nk | 537061 | 70 | 538 | 6 |
| Nes Nes Nes Nds Nds Nds Nds Nds Nds Nds Nds Nds Nks Nks Nk | 537062 | 69 | 539 | 6 |
| Nes Nes Nes Nds Nds Nds Nds Nds Nds Nds Nds Nds Nks Nks Nk | 537063 | 68 | 540 | 6 |
| Nes Nes Nes Nds Nds Nds Nds Nds Nds Nds Nds Nds Nks Nks Nk | 537064 | 71 | 541 | 6 |
| Nes Nes Nes Nds Nds Nds Nds Nds Nds Nds Nds Nds Nks Nks Nk | 537065 | 67 | 542 | 6 |
| Nes Nes Nes Nds Nds Nds Nds Nds Nds Nds Nds Nds Nks Nks Nk | 537066 | 68 | 543 | 6 |
| Nes Nes Nes Nds Nds Nds Nds Nds Nds Nds Nds Nds Nks Nks Nk | 537067 | 71 | 544 | 6 |
| Nes Nes Nes Nds Nds Nds Nds Nds Nds Nds Nds Nds Nks Nks Nk | 537068 | 86 | 545 | 6 |
| Nes Nes Nes Nds Nds Nds Nds Nds Nds Nds Nds Nds Nks Nks Nk | 537069 | 82 | 546 | 6 |
| Nes Nes Nes Nds Nds Nds Nds Nds Nds Nds Nds Nds Nks Nks Nk | 537070 | 87 | 547 | 6 |
| Nes Nes Nes Nds Nds Nds Nds Nds Nds Nds Nds Nds Nks Nks Nk | 537792 | 36 | 548 | 6 |

TABLE 37-continued

Inhibition of human Target-X mRNA levels by chimeric antisense oligonucleotides targeted to Target-X

| Sequence (5' to 3') | ISIS No | % inhibition | SEQ CODE | SEQ ID NO |
|---|---|---|---|---|
| Nes Nes Nes Nds Nds Nds Nds Nds Nds Nds Nds Nds Nks Nks Nk | 537793 | 35 | 549 | 6 |
| Nes Nes Nes Nds Nds Nds Nds Nds Nds Nds Nds Nds Nks Nks Nk | 537794 | 35 | 550 | 6 |
| Nes Nes Nes Nds Nds Nds Nds Nds Nds Nds Nds Nds Nks Nks Nk | 537795 | 33 | 551 | 6 |
| Nes Nes Nes Nds Nds Nds Nds Nds Nds Nds Nds Nds Nks Nks Nk | 537796 | 49 | 552 | 6 |
| Nes Nes Nes Nds Nds Nds Nds Nds Nds Nds Nds Nds Nks Nks Nk | 537797 | 54 | 553 | 6 |
| Nes Nes Nes Nds Nds Nds Nds Nds Nds Nds Nds Nds Nks Nks Nk | 537798 | 68 | 554 | 6 |
| Nes Nes Nes Nds Nds Nds Nds Nds Nds Nds Nds Nds Nks Nks Nk | 537799 | 72 | 555 | 6 |
| Nes Nes Nes Nds Nds Nds Nds Nds Nds Nds Nds Nds Nks Nks Nk | 537800 | 69 | 556 | 6 |
| Nes Nes Nes Nds Nds Nds Nds Nds Nds Nds Nds Nds Nks Nks Nk | 537801 | 82 | 557 | 6 |
| Nes Nes Nes Nds Nds Nds Nds Nds Nds Nds Nds Nds Nks Nks Nk | 537802 | 72 | 558 | 6 |
| Nes Nes Nes Nds Nds Nds Nds Nds Nds Nds Nds Nds Nks Nks Nk | 537803 | 72 | 559 | 6 |
| Nes Nes Nes Nds Nds Nds Nds Nds Nds Nds Nds Nds Nks Nks Nk | 537804 | 67 | 560 | 6 |
| Nes Nes Nes Nds Nds Nds Nds Nds Nds Nds Nds Nds Nks Nks Nk | 537805 | 74 | 561 | 6 |
| Nes Nes Nes Nds Nds Nds Nds Nds Nds Nds Nds Nds Nks Nks Nk | 537806 | 70 | 562 | 6 |
| Nes Nes Nes Nds Nds Nds Nds Nds Nds Nds Nds Nds Nks Nks Nk | 537809 | 60 | 563 | 6 |
| Nes Nes Nes Nds Nds Nds Nds Nds Nds Nds Nds Nds Nks Nks Nk | 537810 | 71 | 564 | 6 |
| Nes Nes Nes Nds Nds Nds Nds Nds Nds Nds Nds Nds Nks Nks Nk | 537811 | 69 | 565 | 6 |
| Nes Nes Nes Nds Nds Nds Nds Nds Nds Nds Nds Nds Nks Nks Nk | 537812 | 80 | 566 | 6 |
| Nes Nes Nes Nds Nds Nds Nds Nds Nds Nds Nds Nds Nks Nks Nk | 537813 | 74 | 567 | 6 |
| Nes Nes Nes Nds Nds Nds Nds Nds Nds Nds Nds Nds Nks Nks Nk | 537814 | 54 | 568 | 6 |
| Nes Nes Nes Nds Nds Nds Nds Nds Nds Nds Nds Nds Nks Nks Nk | 537837 | 70 | 569 | 6 |
| Nes Nes Nes Nds Nds Nds Nds Nds Nds Nds Nds Nds Nks Nks Nk | 537838 | 76 | 570 | 6 |
| Nes Nes Nes Nds Nds Nds Nds Nds Nds Nds Nds Nds Nks Nks Nk | 537839 | 76 | 571 | 6 |
| Nes Nes Nes Nds Nds Nds Nds Nds Nds Nds Nds Nds Nks Nks Nk | 537840 | 80 | 572 | 6 |

TABLE 37-continued

Inhibition of human Target-X mRNA levels by chimeric antisense oligonucleotides targeted to Target-X

| Sequence (5' to 3') | ISIS No | % inhibition | SEQ CODE | SEQ ID NO |
|---|---|---|---|---|
| Nes Nes Nes Nds Nds Nds Nds Nds Nds Nds Nds Nds Nks Nks Nk | 537841 | 81 | 573 | 6 |
| Nes Nes Nes Nds Nds Nds Nds Nds Nds Nds Nds Nds Nks Nks Nk | 537842 | 75 | 574 | 6 |
| Nes Nes Nes Nds Nds Nds Nds Nds Nds Nds Nds Nds Nks Nks Nk | 537843 | 70 | 575 | 6 |
| Nes Nes Nes Nds Nds Nds Nds Nds Nds Nds Nds Nds Nks Nks Nk | 537844 | 73 | 576 | 6 |
| Nes Nes Nes Nds Nds Nds Nds Nds Nds Nds Nds Nds Nks Nks Nk | 537845 | 59 | 577 | 6 |
| Nes Nes Nes Nds Nds Nds Nds Nds Nds Nds Nds Nds Nks Nks Nk | 537846 | 51 | 578 | 6 |
| Nes Nes Nes Nds Nds Nds Nds Nds Nds Nds Nds Nds Nks Nks Nk | 537847 | 52 | 579 | 6 |
| Nes Nes Nes Nds Nds Nds Nds Nds Nds Nds Nds Nds Nks Nks Nk | 537848 | 41 | 580 | 6 |
| Nes Nes Nes Nds Nds Nds Nds Nds Nds Nds Nds Nds Nks Nks Nk | 537849 | 44 | 581 | 6 |
| Nes Nes Nes Nds Nds Nds Nds Nds Nds Nds Nds Nds Nks Nks Nk | 538160 | 69 | 582 | 6 |
| Nes Nes Nes Nds Nds Nds Nds Nds Nds Nds Nds Nds Nks Nks Nk | 538172 | 24 | 583 | 6 |
| Nes Nes Nes Nds Nds Nds Nds Nds Nds Nds Nds Nds Nks Nks Nk | 538173 | 23 | 584 | 6 |
| Nes Nes Nes Nds Nds Nds Nds Nds Nds Nds Nds Nds Nks Nks Nk | 538185 | 68 | 585 | 6 |
| Nes Nes Nes Nds Nds Nds Nds Nds Nds Nds Nds Nds Nks Nks Nk | 538187 | 69 | 585 | 6 |
| Nes Nes Nes Nds Nds Nds Nds Nds Nds Nds Nds Nds Nks Nks Nk | 538189 | 81 | 587 | 6 |
| Nes Nes Nes Nds Nds Nds Nds Nds Nds Nds Nds Nds Nks Nks Nk | 538191 | 66 | 588 | 6 |
| Nes Nes Nes Nds Nds Nds Nds Nds Nds Nds Nds Nds Nks Nks Nk | 538192 | 59 | 589 | 6 |
| Nes Nes Nes Nds Nds Nds Nds Nds Nds Nds Nds Nds Nks Nks Nk | 538193 | 16 | 590 | 6 |
| Nes Nes Nes Nds Nds Nds Nds Nds Nds Nds Nds Nds Nks Nks Nk | 538194 | 10 | 591 | 6 |
| Nes Nes Nes Nds Nds Nds Nds Nds Nds Nds Nds Nds Nks Nks Nk | 538195 | 15 | 592 | 6 |
| Nes Nes Nes Nds Nds Nds Nds Nds Nds Nds Nds Nds Nks Nks Nk | 538196 | 3 | 593 | 6 |
| Nes Nes Nes Nds Nds Nds Nds Nds Nds Nds Nds Nds Nks Nks Nk | 538197 | 36 | 594 | 6 |
| Nes Nes Nes Nds Nds Nds Nds Nds Nds Nds Nds Nds Nks Nks Nk | 538198 | 49 | 595 | 6 |
| Nes Nes Nes Nds Nds Nds Nds Nds Nds Nds Nds Nds Nks Nks Nk | 538199 | 47 | 596 | 6 |

TABLE 37-continued

Inhibition of human Target-X mRNA levels by chimeric antisense oligonucleotides targeted to Target-X

| Sequence (5' to 3') | ISIS No | % inhibition | SEQ CODE | SEQ ID NO |
|---|---|---|---|---|
| Nes Nes Nes Nds Nds Nds Nds Nds Nds Nds Nds Nds Nks Nks Nk | 538200 | 57 | 597 | 6 |
| Nes Nes Nes Nds Nds Nds Nds Nds Nds Nds Nds Nds Nks Nks Nk | 538201 | 71 | 598 | 6 |
| Nes Nes Nes Nds Nds Nds Nds Nds Nds Nds Nds Nds Nks Nks Nk | 538202 | 60 | 599 | 6 |
| Nes Nes Nes Nds Nds Nds Nds Nds Nds Nds Nds Nds Nks Nks Nk | 538203 | 55 | 600 | 6 |
| Nes Nes Nes Nds Nds Nds Nds Nds Nds Nds Nds Nds Nks Nks Nk | 538204 | 62 | 601 | 6 |
| Nes Nes Nes Nds Nds Nds Nds Nds Nds Nds Nds Nds Nks Nks Nk | 538205 | 68 | 602 | 6 |
| Nes Nes Nes Nds Nds Nds Nds Nds Nds Nds Nds Nds Nks Nks Nk | 538228 | 63 | 603 | 6 |
| Nes Nes Nes Nds Nds Nds Nds Nds Nds Nds Nds Nds Nks Nks Nk | 538229 | 26 | 604 | 6 |
| Nes Nes Nes Nds Nds Nds Nds Nds Nds Nds Nds Nds Nks Nks Nk | 538230 | 75 | 605 | 6 |
| Nes Nes Nes Nds Nds Nds Nds Nds Nds Nds Nds Nds Nks Nks Nk | 538231 | 75 | 606 | 6 |
| Nes Nes Nes Nds Nds Nds Nds Nds Nds Nds Nds Nds Nks Nks Nk | 538233 | 52 | 607 | 6 |
| Nes Nes Nes Nds Nds Nds Nds Nds Nds Nds Nds Nds Nks Nks Nk | 538235 | 26 | 608 | 6 |
| Nes Nes Nes Nds Nds Nds Nds Nds Nds Nds Nds Nds Nks Nks Nk | 538237 | 28 | 609 | 6 |
| Nes Nes Nes Nds Nds Nds Nds Nds Nds Nds Nds Nds Nks Nks Nk | 538239 | 54 | 610 | 6 |
| Nes Nes Nes Nds Nds Nds Nds Nds Nds Nds Nds Nds Nks Nks Nk | 538241 | 73 | 611 | 6 |
| Nes Nes Nes Nds Nds Nds Nds Nds Nds Nds Nds Nds Nks Nks Nk | 538242 | 68 | 612 | 6 |
| Nes Nes Nes Nds Nds Nds Nds Nds Nds Nds Nds Nds Nks Nks Nk | 538243 | 61 | 613 | 6 |
| Nes Nes Nes Nds Nds Nds Nds Nds Nds Nds Nds Nds Nks Nks Nk | 538245 | 75 | 614 | 6 |
| Nes Nes Nes Nds Nds Nds Nds Nds Nds Nds Nds Nds Nks Nks Nk | 538253 | 37 | 615 | 6 |
| Nes Nes Nes Nds Nds Nds Nds Nds Nds Nds Nds Nds Nks Nks Nk | 538254 | 45 | 616 | 6 |
| Nes Nes Nes Nds Nds Nds Nds Nds Nds Nds Nds Nds Nks Nks Nk | 538361 | 56 | 617 | 6 |
| Nes Nes Nes Nds Nds Nds Nds Nds Nds Nds Nds Nds Nks Nks Nk | 538378 | 70 | 618 | 6 |
| Nes Nes Nes Nds Nds Nds Nds Nds Nds Nds Nds Nds Nks Nks Nk | 538380 | 68 | 619 | 6 |

TABLE 37-continued

Inhibition of human Target-X mRNA levels by chimeric antisense oligonucleotides targeted to Target-X

| Sequence (5' to 3') | ISIS No | % inhibition | SEQ CODE | SEQ ID NO |
|---|---|---|---|---|
| Nes Nes Nes Nds Nds Nds Nds Nds Nds Nds Nds Nds Nds Nks Nks Nk | 538381 | 57 | 620 | 6 |
| Nes Nes Nes Nds Nds Nds Nds Nds Nds Nds Nds Nds Nds Nks Nks Nk | 540361 | 71 | 621 | 6 |
| Nes Nes Nes Nds Nds Nds Nds Nds Nds Nds Nds Nds Nds Nks Nks Nk | 540362 | 73 | 622 | 6 |
| Nes Nes Nes Nds Nds Nds Nds Nds Nds Nds Nds Nds Nds Nks Nks Nk | 540363 | 78 | 623 | 6 |
| Nes Nes Nes Nds Nds Nds Nds Nds Nds Nds Nds Nds Nds Nks Nks Nk | 540364 | 89 | 624 | 6 |
| Nes Nes Nes Nds Nds Nds Nds Nds Nds Nds Nds Nds Nds Nks Nks Nk | 540365 | 83 | 625 | 6 |
| Nes Nes Nes Nds Nds Nds Nds Nds Nds Nds Nds Nds Nds Nks Nks Nk | 540366 | 84 | 626 | 6 |
| Nes Nes Nes Nds Nds Nds Nds Nds Nds Nds Nds Nds Nds Nks Nks Nk | 540367 | 65 | 627 | 6 |
| Nes Nes Nes Nds Nds Nds Nds Nds Nds Nds Nds Nds Nds Nks Nks Nk | 540368 | 55 | 628 | 6 |
| Nes Nes Nes Nds Nds Nds Nds Nds Nds Nds Nds Nds Nds Nks Nks Nk | 540369 | 82 | 629 | 6 |
| Nes Nes Nes Nds Nds Nds Nds Nds Nds Nds Nds Nds Nds Nks Nks Nk | 540370 | 86 | 630 | 6 |
| Nes Nes Nes Nds Nds Nds Nds Nds Nds Nds Nds Nds Nds Nks Nks Nk | 540371 | 74 | 631 | 6 |
| Nes Nes Nes Nds Nds Nds Nds Nds Nds Nds Nds Nds Nds Nks Nks Nk | 540372 | 82 | 632 | 6 |
| Nes Nes Nes Nds Nds Nds Nds Nds Nds Nds Nds Nds Nds Nks Nks Nk | 540373 | 81 | 633 | 6 |
| Nes Nes Nes Nds Nds Nds Nds Nds Nds Nds Nds Nds Nds Nks Nks Nk | 540374 | 87 | 634 | 6 |
| Nes Nes Nes Nds Nds Nds Nds Nds Nds Nds Nds Nds Nds Nks Nks Nk | 540375 | 78 | 635 | 6 |
| Nes Nes Nes Nds Nds Nds Nds Nds Nds Nds Nds Nds Nds Nks Nks Nk | 540376 | 69 | 636 | 6 |
| Nes Nes Nes Nds Nds Nds Nds Nds Nds Nds Nds Nds Nds Nks Nks Nk | 540377 | 88 | 637 | 6 |
| Nes Nes Nes Nds Nds Nds Nds Nds Nds Nds Nds Nds Nds Nks Nks Nk | 540378 | 85 | 638 | 6 |
| Nes Nes Nes Nds Nds Nds Nds Nds Nds Nds Nds Nds Nds Nks Nks Nk | 540379 | 77 | 639 | 6 |
| Nes Nes Nes Nds Nds Nds Nds Nds Nds Nds Nds Nds Nds Nks Nks Nk | 540380 | 84 | 640 | 6 |
| Nes Nes Nes Nds Nds Nds Nds Nds Nds Nds Nds Nds Nds Nks Nks Nk | 540381 | 85 | 641 | 6 |
| Nes Nes Nes Nds Nds Nds Nds Nds Nds Nds Nds Nds Nds Nks Nks Nk | 540382 | 69 | 642 | 6 |

TABLE 37-continued

Inhibition of human Target-X mRNA levels by chimeric antisense oligonucleotides targeted to Target-X

| Sequence (5' to 3') | ISIS No | % inhibition | SEQ CODE | SEQ ID NO |
|---|---|---|---|---|
| Nes Nes Nes Nds Nds Nds Nds Nds Nds Nds Nds Nds Nks Nks Nk | 540383 | 85 | 643 | 6 |
| Nes Nes Nes Nds Nds Nds Nds Nds Nds Nds Nds Nds Nks Nks Nk | 540384 | 88 | 644 | 6 |
| Nes Nes Nes Nds Nds Nds Nds Nds Nds Nds Nds Nds Nks Nks Nk | 540385 | 87 | 645 | 6 |
| Nes Nes Nes Nds Nds Nds Nds Nds Nds Nds Nds Nds Nks Nks Nk | 540386 | 86 | 646 | 6 |
| Nes Nes Nes Nds Nds Nds Nds Nds Nds Nds Nds Nds Nks Nks Nk | 540387 | 77 | 647 | 6 |
| Nes Nes Nes Nds Nds Nds Nds Nds Nds Nds Nds Nds Nks Nks Nk | 540388 | 86 | 648 | 6 |
| Nes Nes Nes Nds Nds Nds Nds Nds Nds Nds Nds Nds Nks Nks Nk | 540389 | 86 | 649 | 6 |
| Nes Nes Nes Nds Nds Nds Nds Nds Nds Nds Nds Nds Nks Nks Nk | 540390 | 85 | 650 | 6 |
| Nes Nes Nes Nds Nds Nds Nds Nds Nds Nds Nds Nds Nks Nks Nk | 540391 | 83 | 651 | 6 |
| Nes Nes Nes Nds Nds Nds Nds Nds Nds Nds Nds Nds Nks Nks Nk | 540392 | 43 | 652 | 6 |
| Nes Nes Nes Nds Nds Nds Nds Nds Nds Nds Nds Nds Nks Nks Nk | 540393 | 88 | 653 | 6 |
| Nes Nes Nes Nds Nds Nds Nds Nds Nds Nds Nds Nds Nks Nks Nk | 540394 | 68 | 654 | 6 |
| Nes Nes Nes Nds Nds Nds Nds Nds Nds Nds Nds Nds Nks Nks Nk | 540395 | 87 | 655 | 6 |
| Nes Nes Nes Nds Nds Nds Nds Nds Nds Nds Nds Nds Nks Nks Nk | 540396 | 87 | 656 | 6 |
| Nes Nes Nes Nds Nds Nds Nds Nds Nds Nds Nds Nds Nks Nks Nk | 540397 | 59 | 657 | 6 |
| Nes Nes Nes Nds Nds Nds Nds Nds Nds Nds Nds Nds Nks Nks Nk | 540398 | 36 | 658 | 6 |
| Nes Nes Nes Nds Nds Nds Nds Nds Nds Nds Nds Nds Nks Nks Nk | 540399 | 81 | 659 | 6 |

Example 23

High Dose Tolerability of Modified Oligonucleotides Comprising 2'-O-Methoxyethyl (2'-MOE) and 6'-(S)—CH3 Bicyclic Nucleoside (e.g cEt) Modifications Targeting Human Target-X in BALB/c Mice BALB/c mice were treated at a high dose with ISIS antisense oligonucleotides selected from studies described above and evaluated for changes in the levels of various plasma chemistry markers.

Additionally, the newly designed antisense oligonucleotides were created with the same sequences as the antisense oligonucleotides from the study described above and were also added to this screen targeting intronic repeat regions of Target-X.

The newly designed modified antisense oligonucleotides and their motifs are described in Table 38. The internucleoside linkages throughout each gapmer are phosphorothioate linkages (P=S). Nucleosides followed by "d" indicate 2'-deoxyribonucleosides. Nucleosides followed by "k" indicate 6'-(S)—CH3 bicyclic nucleoside (e.g cEt) nucleosides. Nucleosides followed by "e" indicate 2'-O-methoxyethyl (2'-MOE) nucleosides. "N" indicates modified or naturally occurring nucleobases (A, T, C, G, U, or 5-methyl C).

Each gapmer listed in Table 38 is targeted to the intronic region of human Target-X genomic sequence, designated herein as Target-X. "Start site" indicates the 5'-most nucleoside to which the gapmer is targeted in the human gene sequence. "Stop site" indicates the 3'-most nucleoside to which the gapmer is targeted human gene sequence.

TABLE 38

Modified antisense oligonucleotides targeted to Target-X

| Sequence (5' to 3') | ISIS No | SEQ CODE | SEQ ID NO |
|---|---|---|---|
| Nks Nks Nks Nds Nds Nds Nds Nds Nds Nds Nds Nds Nds Nes Nes Ne | 537721 | 509 | 6 |
| Nks Nks Nks Nds Nds Nds Nds Nds Nds Nds Nds Nds Nds Nes Nes Ne | 537738 | 524 | 6 |
| Nks Nks Nks Nds Nds Nds Nds Nds Nds Nds Nds Nds Nds Nes Nes Ne | 537759 | 539 | 6 |
| Nks Nks Nks Nds Nds Nds Nds Nds Nds Nds Nds Nds Nds Nes Nes Ne | 537761 | 541 | 6 |
| Nks Nks Nks Nds Nds Nds Nds Nds Nds Nds Nds Nds Nds Nes Nes Ne | 537763 | 543 | 6 |
| Nks Nks Nks Nds Nds Nds Nds Nds Nds Nds Nds Nds Nds Nes Nes Ne | 537850 | 548 | 6 |
| Nks Nks Nks Nds Nds Nds Nds Nds Nds Nds Nds Nds Nds Nes Nes Ne | 537858 | 556 | 6 |
| Nks Nks Nks Nds Nds Nds Nds Nds Nds Nds Nds Nds Nds Nes Nes Ne | 537864 | 562 | 6 |
| Nks Nks Nks Nds Nds Nds Nds Nds Nds Nds Nds Nds Nds Nes Nes Ne | 537869 | 565 | 6 |
| Nks Nks Nks Nds Nds Nds Nds Nds Nds Nds Nds Nds Nds Nes Nes Ne | 537872 | 568 | 6 |
| Nks Nks Nks Nds Nds Nds Nds Nds Nds Nds Nds Nds Nds Nes Nes Ne | 537897 | 571 | 6 |
| Nks Nks Nks Nds Nds Nds Nds Nds Nds Nds Nds Nds Nds Nes Nes Ne | 540118 | 582 | 6 |
| Nks Nks Nks Nds Nds Nds Nds Nds Nds Nds Nds Nds Nds Nes Nes Ne | 540138 | 602 | 6 |
| Nks Nks Nks Nds Nds Nds Nds Nds Nds Nds Nds Nds Nds Nes Nes Ne | 540139 | 603 | 6 |
| Nks Nks Nks Nds Nds Nds Nds Nds Nds Nds Nds Nds Nds Nes Nes Ne | 540148 | 612 | 6 |
| Nks Nks Nks Nds Nds Nds Nds Nds Nds Nds Nds Nds Nds Nes Nes Ne | 540153 | 617 | 6 |
| Nks Nks Nks Nds Nds Nds Nds Nds Nds Nds Nds Nds Nds Nes Nes Ne | 540155 | 619 | 6 |
| Nes Nes Nks Nds Nds Nds Nds Nds Nds Nds Nds Nds Nds Nks Nks Ne | 540162 | 624 | 6 |
| Nes Nes Nks Nds Nds Nds Nds Nds Nds Nds Nds Nds Nds Nks Nks Ne | 540164 | 626 | 6 |
| Nes Nes Nks Nds Nds Nds Nds Nds Nds Nds Nds Nds Nds Nks Nks Ne | 540168 | 630 | 6 |
| Nes Nes Nks Nds Nds Nds Nds Nds Nds Nds Nds Nds Nds Nks Nks Ne | 540172 | 634 | 6 |
| Nes Nes Nks Nds Nds Nds Nds Nds Nds Nds Nds Nds Nds Nks Nks Ne | 540175 | 637 | 6 |
| Nes Nes Nks Nds Nds Nds Nds Nds Nds Nds Nds Nds Nds Nks Nks Ne | 540176 | 638 | 6 |
| Nes Nes Nks Nds Nds Nds Nds Nds Nds Nds Nds Nds Nds Nks Nks Ne | 540178 | 640 | 6 |
| Nes Nes Nks Nds Nds Nds Nds Nds Nds Nds Nds Nds Nds Nks Nks Ne | 540179 | 641 | 6 |
| Nes Nes Nks Nds Nds Nds Nds Nds Nds Nds Nds Nds Nds Nks Nks Ne | 540181 | 643 | 6 |
| Nes Nes Nks Nds Nds Nds Nds Nds Nds Nds Nds Nds Nds Nks Nks Ne | 540182 | 644 | 6 |
| Nes Nes Nks Nds Nds Nds Nds Nds Nds Nds Nds Nds Nds Nks Nks Ne | 540183 | 645 | 6 |
| Nes Nes Nks Nds Nds Nds Nds Nds Nds Nds Nds Nds Nds Nks Nks Ne | 540184 | 646 | 6 |
| Nes Nes Nks Nds Nds Nds Nds Nds Nds Nds Nds Nds Nds Nks Nks Ne | 540186 | 648 | 6 |
| Nes Nes Nks Nds Nds Nds Nds Nds Nds Nds Nds Nds Nds Nks Nks Ne | 540187 | 649 | 6 |
| Nes Nes Nks Nds Nds Nds Nds Nds Nds Nds Nds Nds Nds Nks Nks Ne | 540188 | 650 | 6 |
| Nes Nes Nks Nds Nds Nds Nds Nds Nds Nds Nds Nds Nds Nks Nks Ne | 540191 | 653 | 6 |
| Nes Nes Nks Nds Nds Nds Nds Nds Nds Nds Nds Nds Nds Nks Nks Ne | 540193 | 655 | 6 |
| Nes Nes Nks Nds Nds Nds Nds Nds Nds Nds Nds Nds Nds Nks Nks Ne | 540194 | 656 | 6 |
| Nes Nes Nks Nds Nds Nds Nds Nds Nds Nds Nds Nds Nds Nks Nks Ne | 544811 | 547 | 6 |
| Nes Nes Nks Nds Nds Nds Nds Nds Nds Nds Nds Nds Nds Nks Nks Ne | 544812 | 545 | 6 |
| Nes Nes Nks Nds Nds Nds Nds Nds Nds Nds Nds Nds Nds Nks Nks Ne | 544813 | 527 | 6 |

TABLE 38-continued

Modified antisense oligonucleotides targeted to Target-X

| Sequence (5' to 3') | ISIS No | SEQ CODE | SEQ ID NO |
|---|---|---|---|
| Nes Nes Nks Nds Nds Nds Nds Nds Nds Nds Nds Nds Nds Nks Nks Ne | 544814 | 557 | 6 |
| Nes Nes Nks Nds Nds Nds Nds Nds Nds Nds Nds Nds Nds Nks Nks Ne | 544815 | 546 | 6 |
| Nes Nes Nks Nds Nds Nds Nds Nds Nds Nds Nds Nds Nds Nks Nks Ne | 544816 | 573 | 6 |
| Nes Nes Nks Nds Nds Nds Nds Nds Nds Nds Nds Nds Nds Nks Nks Ne | 544817 | 572 | 6 |
| Nes Nes Nks Nds Nds Nds Nds Nds Nds Nds Nds Nds Nds Nks Nks Ne | 544818 | 566 | 6 |
| Nes Nes Nks Nds Nds Nds Nds Nds Nds Nds Nds Nds Nds Nks Nks Ne | 544819 | 510 | 6 |
| Nes Nes Nks Nds Nds Nds Nds Nds Nds Nds Nds Nds Nds Nks Nks Ne | 544820 | 525 | 6 |
| Nes Nes Nks Nds Nds Nds Nds Nds Nds Nds Nds Nds Nds Nks Nks Ne | 544821 | 567 | 6 |
| Nes Nes Nks Nds Nds Nds Nds Nds Nds Nds Nds Nds Nds Nks Nks Ne | 544826 | 537 | 6 |
| Nes Nes Nks Nds Nds Nds Nds Nds Nds Nds Nds Nds Nds Nks Nks Ne | 544827 | 538 | 6 |
| Nes Nes Nks Nds Nds Nds Nds Nds Nds Nds Nds Nds Nds Nks Nks Ne | 544828 | 539 | 6 |
| Nes Nes Nks Nds Nds Nds Nds Nds Nds Nds Nds Nds Nds Nks Nks Ne | 544829 | 540 | 6 |
| Nes Nes Nks Nds Nds Nds Nds Nds Nds Nds Nds Nds Nds Nks Nks Ne | 544830 | 541 | 6 |
| Nes Nes Nks Nds Nds Nds Nds Nds Nds Nds Nds Nds Nds Nks Nks Ne | 545471 | 542 | 6 |
| Nes Nes Nks Nds Nds Nds Nds Nds Nds Nds Nds Nds Nds Nks Nks Ne | 545472 | 543 | 6 |
| Nes Nes Nks Nds Nds Nds Nds Nds Nds Nds Nds Nds Nds Nks Nks Ne | 545473 | 544 | 6 |
| Nes Nes Nks Nds Nds Nds Nds Nds Nds Nds Nds Nds Nds Nks Nks Ne | 545474 | 558 | 6 |
| Nes Nes Nks Nds Nds Nds Nds Nds Nds Nds Nds Nds Nds Nks Nks Ne | 545475 | 559 | 6 |
| Nes Nes Nks Nds Nds Nds Nds Nds Nds Nds Nds Nds Nds Nks Nks Ne | 545476 | 560 | 6 |
| Nes Nes Nks Nds Nds Nds Nds Nds Nds Nds Nds Nds Nds Nks Nks Ne | 545477 | 561 | 6 |
| Nes Nes Nks Nds Nds Nds Nds Nds Nds Nds Nds Nds Nds Nks Nks Ne | 545478 | 562 | 6 |
| Nes Nes Nks Nds Nds Nds Nds Nds Nds Nds Nds Nds Nds Nks Nks Ne | 545479 | 556 | 6 |
| Nks Nks Nks Nds Nds Nds Nds Nds Nds Nds Nds Nds Nds Nes Nes Ne | 537727 | 514 | 6 |

Treatment

Male BALB/c mice were injected subcutaneously with a single dose of 200 mg/kg of ISIS 422142, ISIS 457851, ISIS 473294, ISIS 473295, ISIS 473327, ISIS 484714, ISIS 515334, ISIS 515338, ISIS 515354, ISIS 515366, ISIS 515380, ISIS 515381, ISIS 515382, ISIS 515384, ISIS 515386, ISIS 515387, ISIS 515388, ISIS 515406, ISIS 515407, ISIS 515408, ISIS 515422, ISIS 515423, ISIS 515424, ISIS 515532, ISIS 515533, ISIS 515534, ISIS 515538, ISIS 515539, ISIS 515558, ISIS 515656, ISIS 515575, ISIS 515926, ISIS 515944, ISIS 515945, ISIS 515948, ISIS 515949, ISIS 515951, ISIS 515952, ISSI 516003, ISIS 516055, ISIS 516057, ISIS 516060, ISIS 516062, ISIS 529126, ISIS 529146, ISIS 529166, ISIS 529170, ISIS 529172, ISIS 529173, ISIS 529174, ISIS 529175, ISSI 529176, ISIS 529182, ISIS 529183, ISIS 529186, ISIS 529282, ISIS 529304, ISIS 529306, ISIS 529360, ISIS 529450, ISIS 529459, ISIS 529460, ISIS 529461, ISIS 529547, ISIS 529550, ISIS 529551, ISIS 529553, ISIS 529557, ISIS 529562, ISIS 529563, ISIS 529564, ISIS 529565, ISIS 529575, ISIS 529582, ISIS 529589, ISIS 529607, ISIS 529614, ISIS 529632, ISIS 529650, ISIS 529651, ISIS 529657, ISIS 529663, ISIS 529725, ISIS 529745, ISIS 529765, ISIS 529785, ISIS 529804, ISIS 529818, ISIS 529823, ISIS 529854, ISIS 534528, ISIS 534534, ISIS 534594, ISIS 534660, ISIS 534663, ISIS 534664, ISIS 534676, ISIS 534677, ISIS 537679, ISIS 537683, ISIS 534693, ISIS 534701, ISIS 534716, ISIS 534730, ISIS 534765, ISIS 534795, ISIS 534796, ISIS 534797, ISIS 534798, ISIS 534799, ISIS 534800, ISIS 534802, ISIS 534806, ISSI 534830, ISIS 534838, ISIS 534888, ISIS 534890, ISIS 534898, ISIS 534911, ISIS 534920, ISIS 534926, ISIS 534937, ISIS 534950, ISSI 534956, ISIS 534980, ISIS 534986, ISIS 535010, ISIS 535043, ISIS 535049, ISIS 535076, ISIS 535082, ISSI 535142, ISIS 537024, ISIS 537030, ISIS 537041, ISIS 537062, ISIS 537064, ISIS 537066, ISIS 537721, ISIS 537727, ISIS 537738, ISIS 537759, ISIS 537761, ISIS 537763, ISIS 537792, ISIS 537800, ISIS 537806, ISIS 537811, ISIS 537814, ISIS 537839, ISIS 537850, ISSI 537858, ISIS 537864, ISIS 537869, ISIS 537872, ISIS 537897, ISIS 538160, ISIS 538196, ISIS 538205, ISIS 538228, ISIS 538242, ISIS 538361, ISIS 538380, ISIS 540118, ISIS 540138, ISIS 540139, ISIS 540148, ISIS 540153, ISIS 540155, ISIS 540162, ISIS 540164, ISIS 540168, ISIS 540172, ISIS 540175, ISIS 540176, ISIS 540178, ISIS 540179, ISIS 540181, ISIS 540182, ISIS 540183, ISIS 540184, ISIS 540186, ISIS 540187, ISIS 540188, ISIS 540191, ISIS 540193, ISIS 540194, ISIS 544811, ISIS 544812, ISIS 544813, ISIS 544814, ISIS 544815, ISIS 544816, ISIS 544817, ISIS 544818, ISIS 544819, ISIS 544820, ISIS 544821, ISIS 544826, ISIS 544827, ISIS 544828, ISIS 544829, ISIS 544830, ISIS 545471, ISIS 545472, ISIS 545473, ISIS 545474, ISIS 545475, ISIS 545476, ISIS 545477, ISIS 545478, and ISIS 545479. One set of male BALB/c mice was injected with a single dose of PBS. Mice were euthanized 96 hours later, and organs and plasma were harvested for further analysis.

Plasma Chemistry Markers

To evaluate the effect of ISIS oligonucleotides on liver and kidney function, plasma levels of transaminases, bilirubin, albumin, and BUN were measured using an automated clinical chemistry analyzer (Hitachi Olympus AU400e, Melville, N.Y.).

ISIS oligonucleotides that did not cause any increase in the levels of transaminases, or which caused an increase within three times the upper limit of normal (ULN) were deemed very tolerable. ISIS oligonucleotides that caused an increase in the levels of transaminases between three times and seven times the ULN were deemed tolerable. Based on these criteria, ISIS 529166, ISIS 529170, ISIS 529175, ISIS 529176, ISIS 529186, ISIS 529282, ISIS 529360, ISIS 529450, ISIS 529459, ISIS 529460, ISIS 529547, ISIS 529549, ISIS 529551, ISIS 529553, ISIS 529557, ISIS 529562, ISIS 529575, ISIS 529582, ISIS 529607, ISIS 529589, ISIS 529632, ISIS 529657, ISIS 529725, ISIS 529745, ISIS 529785, ISIS 529799, ISIS 529804, ISIS 529818, ISIS 529823, ISIS 534950, ISIS 534980, ISIS 535010, ISIS 537030, ISIS 537041, ISIS 537062, ISIS 537064, ISIS 537066, ISIS 537759, ISIS 537792, ISIS 537800, ISIS 537839, ISIS 538228, ISIS 473294, ISIS 473295, ISIS 484714, ISIS 515338, ISIS 515366, ISIS 515380, ISIS 515381, ISIS 515387, ISIS 515408, ISIS 515423, ISIS 515424, ISIS 515532, ISIS 515534, ISIS 515538, ISIS 515539, ISIS 515558, ISIS 515575, ISIS 515926, ISIS 515944, ISIS 515945, ISIS 515951, ISIS 515952, ISIS 529126, ISIS 529765, ISIS 534528, ISIS 534534, ISIS 534594, ISIS 534663, ISIS 534676, ISIS 534677, ISIS 534679, ISIS 534683, ISIS 534693, ISIS 534701, ISIS 534716, ISIS 534730, ISIS 534806, ISIS 534830, ISIS 534838, ISIS 534890, ISIS 534898, ISIS 534911, ISIS 534937, ISIS 534956, ISIS 534986, ISIS 535043, ISIS 535049, ISIS 535076, ISIS 535082, ISIS 535142, ISIS 538160, ISIS 538242, ISIS 538361, ISIS 538380, ISIS 534795, ISIS 534796, ISIS 534797, ISIS 540162, ISIS 540164, ISIS 540168, ISIS 540172, ISIS 540175, ISIS 540176, ISIS 540178, ISIS 540179, ISIS 540181, ISIS 540182, ISIS 540183, ISIS 540184, ISIS 540186, ISIS 540187, ISIS 540188, ISIS 540191, ISIS 540193, ISIS 540194, ISIS 544813, ISIS 544814, ISIS 544816, ISIS 544826, ISIS 544827, ISIS 544828, ISIS 544829, ISIS 545473, and ISIS 545474 were considered very tolerable in terms of liver function. Based on these criteria, ISIS 529173, ISIS 529854, ISIS 529614, ISIS 515386, ISIS 515388, ISIS 515949, ISIS 544817, and ISIS 545479 were considered tolerable in terms of liver function.

Example 24

Tolerability of Antisense Oligonucleotides Targeting Human Target-X in Sprague-Dawley Rats Sprague-Dawley rats are a multipurpose model used for safety and efficacy evaluations. The rats were treated with ISIS antisense oligonucleotides from the studies described in the Examples above and evaluated for changes in the levels of various plasma chemistry markers.

Treatment

Six-eight week old male Sprague-Dawley rats were maintained on a 12-hour light/dark cycle and fed ad libitum with Teklad normal rat chow. Groups of four Sprague-Dawley rats each were injected subcutaneously twice a week for 6 weeks with 25 mg/kg of ISIS 473286, ISIS 473547, ISIS 473567, ISIS 473589, ISIS 473630, ISIS 484559, ISIS 515636, ISIS 515640, ISIS 515641, ISIS 515655, ISIS 515657, ISIS 516046, ISIS 516048, ISIS 516051, ISIS 516052, and ISIS 516062. A group of four Sprague-Dawley rats was injected subcutaneously twice a week for 6 weeks with PBS. Forty eight hours after the last dose, rats were euthanized and organs and plasma were harvested for further analysis.

Liver Function

To evaluate the effect of ISIS oligonucleotides on hepatic function, plasma levels of transaminases were measured using an automated clinical chemistry analyzer (Hitachi Olympus AU400e, Melville, N.Y.). Plasma levels of ALT (alanine transaminase) and AST (aspartate transaminase) were measured. Plasma levels of Bilirubin and BUN were also measured using the same clinical chemistry analyzer.

ISIS oligonucleotides that did not cause any increase in the levels of transaminases, or which caused an increase within three times the upper limit of normal (ULN) were deemed very tolerable. ISIS oligonucleotides that caused an increase in the levels of transaminases between three times and seven times the ULN were deemed tolerable. Based on these criteria, ISIS 473286, ISIS 473547, ISSI 473589, ISIS 473630, ISIS 484559, ISIS 515636, ISIS 515640, ISIS 515655, ISIS 516046, and ISIS 516051 were considered very tolerable in terms of liver function. Based on these criteria, ISIS 473567, ISIS 515641, ISIS 515657, ISIS 516048, and ISIS 516051 were considered tolerable in terms of liver function.

Example 25

Tolerability of Chimeric Antisense Oligonucleotides Comprising 2'-O-Methoxyethyl (2'-MOE) Modifications Targeting Human Target-X in Sprague-Dawley Rats Sprague-Dawley rats were treated with ISIS antisense oligonucleotides from the studies described in the Examples above and evaluated for changes in the levels of various plasma chemistry markers.

Treatment

Six-eight week old male Sprague-Dawley rats were maintained on a 12-hour light/dark cycle and fed ad libitum with Purina normal rat chow. Groups of four Sprague-Dawley rats each were injected subcutaneously twice a week for 6 weeks with 50 mg/kg of ISIS 407936, ISIS 416507, ISIS 416508, ISIS 490208, ISIS 490279, ISIS 490323, ISIS 490368, ISIS 490396, ISIS 490803, ISIS 491122, ISIS 513419, ISIS 513446, ISIS 513454, ISIS 513455, ISIS 513456, ISIS 513504, ISIS 513507, and ISIS 513508. A group of four Sprague-Dawley rats was injected subcutaneously twice a week for 6 weeks with PBS. Forty eight hours after the last dose, rats were euthanized and organs and plasma were harvested for further analysis.

Liver Function

To evaluate the effect of ISIS oligonucleotides on hepatic function, plasma levels of transaminases were measured using an automated clinical chemistry analyzer (Hitachi Olympus AU400e, Melville, N.Y.). Plasma levels of Bilirubin and BUN were also measured using the same clinical chemistry analyzer.

ISIS oligonucleotides that did not cause any increase in the levels of transaminases, or which caused an increase within three times the upper limit of normal (ULN) were deemed very tolerable. ISIS oligonucleotides that caused an increase in the levels of transaminases between three times and seven times the ULN were deemed tolerable. Based on these criteria, ISIS 416507, ISIS 490208, ISIS 490368, ISIS 490396, ISIS 490803, ISIS 491122, ISIS 513446, ISIS 513454, ISIS 513455, ISIS 513456, ISIS 513504, and ISIS 513508 were considered very tolerable in terms of liver function. Based on these criteria, ISIS 407936, ISIS 416508, ISIS 490279, and ISIS 513507 were considered tolerable in terms of liver function.

Example 26

Tolerability of Chimeric Antisense Oligonucleotides Comprising 2'-O-Methoxyethyl (2'-MOE) Modifications Targeting Human Target-X in CD-1 Mice CD-1 mice are a multipurpose mice model, frequently utilized for safety and efficacy testing. The mice were treated with ISIS antisense oligonucleotides selected from studies described above and evaluated for changes in the levels of various plasma chemistry markers.
Treatment Groups of 3 male CD-1 mice each were injected subcutaneously twice a week for 6 weeks with 50 mg/kg of ISIS 473244, ISIS 473295, ISIS 484714, ISIS 515386, ISIS 515424, ISIS 515534, ISIS 515558, ISIS 515926, ISIS 515949, ISIS 515951, ISIS 515952, ISIS 529126, ISIS 529166, ISIS 529173, ISIS 529186, ISIS 529360, ISIS 529461, ISIS 529553, ISIS 529564, ISIS 529582, ISIS 529614, ISIS 529725, ISIS 529745, ISIS 529765, ISIS 529785, ISIS 529799, ISIS 529818, ISIS 529823, ISIS 534528, ISIS 534594, and ISIS 534664. One group of male CD-1 mice was injected subcutaneously twice a week for 6 weeks with PBS. Mice were euthanized 48 hours after the last dose, and organs and plasma were harvested for further analysis.
Plasma Chemistry Markers To evaluate the effect of ISIS oligonucleotides on liver and kidney function, plasma levels of transaminases, bilirubin, albumin, and BUN were measured using an automated clinical chemistry analyzer (Hitachi Olympus AU400e, Melville, N.Y.).

ISIS oligonucleotides that did not cause any increase in the levels of transaminases, or which caused an increase within three times the upper limit of normal (ULN) were deemed very tolerable. ISIS oligonucleotides that caused an increase in the levels of transaminases between three times and seven times the ULN were deemed tolerable. Based on these criteria, ISIS 473295, ISIS 473714, ISIS 515558, ISIS 515926, 515951, ISIS 515952, ISIS 529126, ISIS 529166, ISIS 529564, ISIS 529582, ISIS 529614, ISIS 529725, ISIS 529765, ISIS 529799, ISIS 529823, and ISIS 534594 were considered very tolerable in terms of liver function. Based on these criteria, ISIS 515424, ISIS 515534, ISIS 515926, ISIS 529785, and ISIS 534664 were considered tolerable in terms of liver function.

Example 27

Tolerability of Chimeric Antisense Oligonucleotides Comprising 2'-O-Methoxyethyl (2'-MOE) Modifications Targeting Human Target-X in CD-1 Mice CD-1 mice were treated with ISIS antisense oligonucleotides selected from studies described above and evaluated for changes in the levels of various plasma chemistry markers.
Treatment Groups of 3 male CD-1 mice each were injected subcutaneously twice a week for 6 weeks with 100 mg/kg of ISIS 490208, ISIS 490279, ISIS 490323, ISIS 490368, ISIS 490396, ISIS 490803, ISIS 491122, ISIS 513419, ISIS 513446, ISIS 513454, ISIS 513455, ISIS 513456, ISIS 513504, ISIS 513507, and ISIS 513508. Groups of 3 male CD-1 mice each were injected subcutaneously twice a week for 6 weeks with 100 mg/kg of ISIS 407936, ISIS 416507, and ISIS 416508, which are gapmers described in a previous publication. One group of male CD-1 mice was injected subcutaneously twice a week for 6 weeks with PBS. Mice were euthanized 48 hours after the last dose, and organs and plasma were harvested for further analysis.
Plasma Chemistry Markers To evaluate the effect of ISIS oligonucleotides on liver and kidney function, plasma levels of transaminases, bilirubin, and BUN were measured using an automated clinical chemistry analyzer (Hitachi Olympus AU400e, Melville, N.Y.).

ISIS oligonucleotides that did not cause any increase in the levels of transaminases, or which caused an increase within three times the upper limit of normal (ULN) were deemed very tolerable. ISIS oligonucleotides that caused an increase in the levels of transaminases between three times and seven times the ULN were deemed tolerable. Based on these criteria, ISIS 407936, ISIS 416507, ISIS 490279, ISIS 490368, ISIS 490396, ISIS 490803, ISIS 491122, ISIS 513446, ISIS 513454, ISIS 513456, and ISIS 513504 were considered very tolerable in terms of liver function. Based on these criteria, ISIS 490208, ISIS 513455, ISIS 513507, and ISIS 513508 were considered tolerable in terms of liver function.

Example 28

Efficacy of Modified Oligonucleotides Comprising 2'-O-Methoxyethyl (2'-MOE) and 6'-(S)—$CH_3$ Bicyclic Nucleoside (e.g cEt) Modifications Targeting Human Target-X in Transgenic Mice Transgenic mice were treated with ISIS antisense oligonucleotides selected from studies described above and evaluated for efficacy.
Treatment Groups of 2-3 male and female transgenic mice were injected subcutaneously twice a week for 3 weeks with 5 mg/kg/week of ISIS 473244, ISIS 473295, ISIS 484714, ISIS 515926, ISIS 515951, ISIS 515952, ISIS 516062, ISIS 529126, ISIS 529553, ISIS 529745, ISIS 529799, ISIS 534664, ISIS 534826, ISIS 540168, ISIS 540175, ISIS 544826, ISIS 544827, ISIS 544828, and ISIS 544829. One group of mice was injected subcutaneously twice a week for 3 weeks with PBS. Mice were euthanized 48 hours after the last dose, and organs and plasma were harvested for further analysis.

Protein Analysis

Plasma protein levels of Target-X were estimated using a Target-X ELISA kit (purchased from Hyphen Bio-Med). Results are presented as percent inhibition of Target-X, relative to control. As shown in Table 39, several antisense oligonucleotides achieved reduction of human Target-X over the PBS control. 'n.d.' indicates that the value for that particular oligonucleotide was not measured.

TABLE 39

Percent inhibition of Target-X plasma protein levels in transgenic mice

| ISIS No | % inhibition |
|---|---|
| 473244 | 2 |
| 473295 | 13 |
| 484714 | 19 |
| 515926 | 11 |
| 515951 | 13 |
| 515952 | 0 |
| 516062 | 62 |
| 529126 | 0 |
| 529553 | 0 |
| 529745 | 22 |
| 529799 | 26 |
| 534664 | 32 |
| 534826 | n.d. |
| 540168 | 94 |
| 540175 | 98 |
| 544813 | 0 |
| 544826 | 23 |
| 544827 | 60 |
| 544828 | 33 |
| 544829 | 53 |

Example 29

Efficacy of Modified Oligonucleotides Comprising 2'-Methoxyethyl (2'-MOE) and 6'-(S)—CH₃ Bicyclic Nucleoside (e.g cEt) Modifications Targeting Human Target-X in Transgenic Mice Transgenic mice were treated with ISIS antisense oligonucleotides selected from studies described above and evaluated for efficacy.

Treatment

Groups of 2-3 male and female transgenic mice were injected subcutaneously twice a week for 3 weeks with 1 mg/kg/week of ISIS 407936, ISIS 490197, ISIS 490275, ISIS 490278, ISIS 490279, ISIS 490323, ISIS 490368, ISIS 490396, ISIS 490803, ISIS 491122, ISIS 513446, ISIS 513447, ISIS 513504, ISIS 516062, ISIS 529166, ISIS 529173, ISIS 529360, ISIS 529725, ISIS 534557, ISIS 534594, ISIS 534664, ISIS 534688, ISIS 534689, ISIS 534915, ISIS 534916, ISIS 534917, and ISIS 534980. One group of mice was injected subcutaneously twice a week for 3 weeks with PBS. Mice were euthanized 48 hours after the last dose, and organs and plasma were harvested for further analysis.

Protein Analysis

Plasma protein levels of Target-X were estimated using a Target-X ELISA kit (purchased from Hyphen Bio-Med). Results are presented as percent inhibition of Target-X, relative to control. As shown in Table 40, several antisense oligonucleotides achieved reduction of human Target-X over the PBS control.

TABLE 40

Percent inhibition of Target-X plasm protein levels in transgenic mice

| ISIS No | % inhibition |
|---|---|
| 407936 | 28 |
| 490197 | 50 |
| 490275 | 21 |
| 490278 | 20 |
| 490279 | 59 |
| 490323 | 54 |
| 490368 | 22 |
| 490396 | 31 |
| 490803 | 30 |
| 491122 | 51 |
| 513446 | 29 |
| 513447 | 44 |
| 513504 | 45 |
| 516062 | 75 |
| 529166 | 37 |
| 529173 | 64 |
| 529360 | 43 |
| 529725 | 53 |
| 534557 | 76 |
| 534594 | 40 |
| 534664 | 14 |
| 534687 | 12 |
| 534688 | 48 |
| 534689 | 25 |
| 534915 | 40 |
| 534916 | 45 |
| 534917 | 66 |
| 534980 | 62 |

Example 30

Tolerability of Antisense Oligonucleotides Targeting Human Target-X in Sprague-Dawley Rats Sprague-Dawley rats were treated with ISIS antisense oligonucleotides from the studies described in the Examples above and evaluated for changes in the levels of various plasma chemistry markers.

Treatment

Six-eight week old male Sprague-Dawley rats were maintained on a 12-hour light/dark cycle and fed ad libitum with Teklad normal rat chow. Groups of four Sprague-Dawley rats each were injected subcutaneously twice a week for 4 weeks with ISIS 515380, ISIS 515381, ISIS 515387, ISIS 529175, ISIS 529176, ISIS 529575, ISIS 529804, and ISIS 537064. Doses 1, 5, 6, 7, and 8 were 25 mg/kg; dose 2 was 75 mg/kg; doses 3 and 4 were 50 mg/kg. One group of four Sprague-Dawley rats was injected subcutaneously twice a week for 4 weeks with PBS. Forty eight hours after the last dose, rats were euthanized and organs and plasma were harvested for further analysis.

Liver Function

To evaluate the effect of ISIS oligonucleotides on hepatic function, plasma levels of transaminases were measured using an automated clinical chemistry analyzer (Hitachi Olympus AU400e, Melville, N.Y.). Plasma levels of ALT (alanine transaminase) and AST (aspartate transaminase) were measured. Plasma levels of Bilirubin and BUN were also measured using the same clinical chemistry analyzer.

ISIS oligonucleotides that did not cause any increase in the levels of transaminases, or which caused increase in the levels within three times the upper limit of normal levels of transaminases were deemed very tolerable. ISIS oligonucleotides that caused increase in the levels of transaminases between three times and seven times the upper limit of normal levels were deemed tolerable. Based on these criteria, ISIS 515380, ISIS 515387, ISIS 529175, ISIS 529176, ISIS 529804, and ISIS 537064 were considered very tolerable in terms of liver function. Based on these criteria, ISIS 515381 was considered tolerable in terms of liver function.

Example 31

Efficacy of Antisense Oligonucleotides Targeting Human Target-X in Transgenic Mice Transgenic mice were treated with ISIS antisense oligonucleotides selected from studies described above and evaluated for efficacy.
Treatment Two groups of 3 male and female transgenic mice were injected subcutaneously twice a week for 2 weeks with 0.5 mg/kg/week or 1.5 mg/kg/week of ISIS 407935 and ISIS 513455. Another group of mice was subcutaneously twice a week for 2 weeks with 0.6 mg/kg/week or 2.0 mg/kg/week of ISIS 473286. Another 16 groups of mice were subcutaneously twice a week for 2 weeks with 0.1 mg/kg/week or 0.3 mg/kg/week of ISIS 473589, ISIS 515380, ISIS 515423, ISIS 529804, ISIS 534676, ISIS 534796, ISIS 540162, ISIS 540164, ISIS 540175, ISIS 540179, ISIS 540181, ISIS 540182, ISIS 540186, ISIS 540191, ISIS 540193, ISIS 544827, or ISIS 545474. Another 3 groups of mice were injected subcutaneously twice a week for 2 weeks with 0.3 mg/kg/week of ISIS 516062, ISIS 534528 or ISIS 534693. One group of mice was injected subcutaneously twice a week for 2 weeks with PBS. Mice were euthanized 48 hours after the last dose, and organs and plasma were harvested for further analysis.
Protein Analysis Plasma protein levels of Target-X were estimated using a Target-X ELISA kit (purchased from Hyphen Bio-Med). Results are presented as percent inhibition of Target-X, relative to control. As shown in Table 41, several antisense oligonucleotides achieved reduction of human Target-X over the PBS control.

TABLE 41

Percent inhibition of Target-X plasma protein levels in transgenic mice

| ISIS No | Dose (mg/kg/wk) | % inhibition |
| --- | --- | --- |
| 407935 | 1.5 | 65 |
|  | 0.5 | 31 |
| 513455 | 1.5 | 64 |
|  | 0.5 | 52 |
| 473286 | 2 | 67 |
|  | 0.6 | 11 |
| 473589 | 0.3 | 42 |
|  | 0.1 | 12 |
| 515380 | 0.3 | 64 |
|  | 0.1 | 32 |
| 515423 | 0.3 | 72 |
|  | 0.1 | 37 |
| 529804 | 0.3 | 36 |
|  | 0.1 | 24 |
| 534676 | 0.3 | 31 |
|  | 0.1 | 18 |
| 534796 | 0.3 | 54 |
|  | 0.1 | 43 |
| 540162 | 0.3 | 84 |
|  | 0.1 | 42 |
| 540164 | 0.3 | 25 |
|  | 0.1 | 17 |

TABLE 41-continued

Percent inhibition of Target-X plasma protein levels in transgenic mice

| ISIS No | Dose (mg/kg/wk) | % inhibition |
| --- | --- | --- |
| 540175 | 0.3 | 90 |
|  | 0.1 | 55 |
| 540179 | 0.3 | 29 |
|  | 0.1 | 24 |
| 540181 | 0.3 | 53 |
|  | 0.1 | 0 |
| 540182 | 0.3 | 78 |
|  | 0.1 | 21 |
| 540186 | 0.3 | 72 |
|  | 0.1 | 46 |
| 540191 | 0.3 | 62 |
|  | 0.1 | 35 |
| 540193 | 0.3 | 74 |
|  | 0.1 | 46 |
| 544827 | 0.3 | 28 |
|  | 0.1 | 19 |
| 545474 | 0.3 | 59 |
|  | 0.1 | 0 |
| 516062 | 0.3 | 33 |
| 534528 | 0.3 | 41 |
| 534693 | 0.3 | 34 |

Example 32

Tolerability of Antisense Oligonucleotides Targeting Human Target-X in Sprague-Dawley Rats Sprague-Dawley rats were treated with ISIS antisense oligonucleotides from the studies described in the Examples above and evaluated for changes in the levels of various plasma chemistry markers.
Treatment Five-six week old male Sprague-Dawley rats were maintained on a 12-hour light/dark cycle and fed ad libitum with Teklad normal rat chow. Groups of four Sprague-Dawley rats each were injected subcutaneously twice a week for 4 weeks with 50 mg/kg of ISIS 515423, ISIS 515424, ISIS 515640, ISIS 534676, ISIS 534796, ISIS 534797, ISIS 540162, ISIS 540164, ISIS 540172, ISIS 540175, ISIS 540179, ISIS 540181, ISIS 540182, ISIS 540183, ISIS 540186, ISIS 540191, and ISIS 545474. A group of four Sprague-Dawley rats was injected subcutaneously twice a week for 4 weeks with PBS. Forty eight hours after the last dose, rats were euthanized and organs and plasma were harvested for further analysis.
Liver Function To evaluate the effect of ISIS oligonucleotides on hepatic function, plasma levels of transaminases were measured using an automated clinical chemistry analyzer (Hitachi Olympus AU400e, Melville, N.Y.). Plasma levels of ALT (alanine transaminase) and AST (aspartate transaminase) were measured. Plasma levels of Bilirubin and BUN were also measured using the same clinical chemistry analyzer.

ISIS oligonucleotides that did not cause any increase in the levels of transaminases, or which caused an increase within three times the upper limit of normal (ULN) were deemed very tolerable. ISIS oligonucleotides that caused an increase in the levels of transaminases between three times and seven times the ULN were deemed tolerable. Based on these criteria, ISIS 540164, ISIS 540172, and ISIS 540175 were considered very tolerable in terms of liver function. Based on these criteria, ISIS 534676, ISIS 534796, ISIS 534797, ISIS 540162, and ISIS 540179 were considered tolerable in terms of liver function.

Example 33

Dose-Dependent Antisense Inhibition of Human Target-X in Hep3B Cells

Antisense oligonucleotides selected from the studies described above were tested at various doses in Hep3B cells. Cells were plated at a density of 20,000 cells per well and transfected using electroporation with 0.05 µM, 0.15 µM, 0.44 µM, 1.33 µM, and 4.00 µM concentrations of antisense oligonucleotide, as specified in Table 42. After a treatment period of approximately 16 hours, RNA was isolated from the cells and Target-X mRNA levels were measured by quantitative real-time PCR. Human Target-X primer probe set RTS2927 was used to measure mRNA levels. Target-X mRNA levels were adjusted according to total RNA content, as measured by RIBOGREEN®. Results are presented as percent inhibition of Target-X, relative to untreated control cells.

The half maximal inhibitory concentration ($IC_{50}$) of each oligonucleotide is also presented in Table 42. As illustrated in Table 42, Target-X mRNA levels were reduced in a dose-dependent manner in several of the antisense oligonucleotide treated cells.

TABLE 42

Dose-dependent antisense inhibition of human Target-X in Hep3B cells using electroporation

| ISIS No | 0.05 µM | 0.15 µM | 0.44 µM | 1.33 µM | 4.00 µM | $IC_{50}$ (µM) |
|---|---|---|---|---|---|---|
| 473286 | 0 | 1 | 13 | 12 | 15 | >4.0 |
| 457851 | 23 | 32 | 57 | 80 | 93 | 0.3 |
| 473286 | 3 | 20 | 43 | 71 | 88 | 0.5 |
| 473286 | 15 | 26 | 24 | 28 | 36 | >4.0 |
| 473286 | 6 | 3 | 10 | 26 | 29 | >4.0 |
| 473327 | 14 | 28 | 35 | 67 | 90 | 0.5 |
| 473589 | 29 | 53 | 76 | 89 | 95 | 0.1 |
| 515380 | 44 | 72 | 85 | 93 | 95 | <0.05 |
| 515423 | 43 | 64 | 87 | 95 | 98 | <0.05 |
| 515424 | 38 | 55 | 85 | 92 | 97 | 0.1 |
| 515636 | 21 | 33 | 74 | 82 | 93 | 0.2 |
| 516046 | 29 | 23 | 29 | 48 | 78 | 0.9 |
| 516048 | 35 | 24 | 41 | 67 | 87 | 0.4 |
| 516052 | 18 | 6 | 48 | 63 | 80 | 0.6 |
| 516062 | 24 | 14 | 21 | 47 | 68 | 1.6 |
| 529166 | 16 | 47 | 75 | 87 | 94 | 0.2 |
| 529173 | 14 | 49 | 77 | 91 | 96 | 0.2 |
| 529175 | 30 | 69 | 88 | 93 | 96 | 0.1 |
| 529176 | 34 | 63 | 85 | 93 | 96 | 0.1 |
| 529360 | 35 | 53 | 74 | 91 | 93 | 0.1 |
| 529725 | 53 | 69 | 85 | 92 | 95 | <0.05 |
| 529804 | 37 | 41 | 71 | 90 | 94 | 0.1 |
| 534528 | 50 | 68 | 78 | 93 | 97 | <0.05 |
| 534557 | 48 | 78 | 90 | 94 | 95 | <0.05 |
| 534594 | 39 | 47 | 76 | 87 | 94 | 0.1 |
| 534676 | 29 | 20 | 40 | 64 | 87 | 0.5 |
| 534687 | 41 | 37 | 56 | 80 | 93 | 0.2 |
| 534688 | 16 | 56 | 88 | 94 | 96 | 0.1 |
| 534689 | 21 | 59 | 82 | 94 | 95 | 0.1 |
| 534693 | 18 | 58 | 81 | 93 | 95 | 0.1 |
| 534795 | 19 | 43 | 68 | 90 | 94 | 0.2 |
| 534796 | 25 | 59 | 80 | 93 | 96 | 0.1 |
| 534890 | 31 | 55 | 77 | 90 | 96 | 0.1 |
| 534898 | 22 | 61 | 80 | 94 | 97 | 0.1 |
| 534915 | 19 | 26 | 51 | 77 | 94 | 0.3 |
| 534916 | 20 | 36 | 66 | 86 | 93 | 0.2 |
| 534917 | 34 | 53 | 82 | 89 | 94 | 0.1 |
| 540162 | 40 | 64 | 84 | 90 | 92 | <0.05 |
| 540164 | 34 | 60 | 83 | 91 | 92 | 0.1 |
| 540168 | 51 | 79 | 90 | 92 | 94 | <0.05 |
| 540172 | 40 | 66 | 80 | 88 | 92 | <0.05 |
| 540175 | 30 | 61 | 80 | 88 | 91 | 0.1 |
| 540176 | 7 | 17 | 50 | 75 | 85 | 0.5 |
| 540179 | 11 | 22 | 25 | 16 | 19 | >4.0 |
| 540181 | 19 | 46 | 72 | 86 | 91 | 0.2 |
| 540182 | 16 | 66 | 83 | 86 | 92 | 0.1 |
| 540183 | 39 | 74 | 87 | 92 | 93 | <0.05 |
| 540186 | 31 | 69 | 85 | 91 | 94 | 0.1 |
| 540191 | 38 | 54 | 80 | 88 | 91 | 0.1 |
| 540193 | 57 | 67 | 84 | 94 | 97 | <0.05 |
| 540194 | 30 | 45 | 62 | 77 | 91 | 0.2 |
| 544827 | 37 | 42 | 67 | 82 | 96 | 0.1 |
| 544829 | 26 | 41 | 42 | 71 | 93 | 0.3 |
| 545473 | 28 | 27 | 49 | 80 | 97 | 0.3 |
| 545474 | 23 | 27 | 55 | 84 | 96 | 0.3 |

Example 34

Tolerability of Antisense Oligonucleotides Targeting Human Target-X in CD-1 Mice CD-1 mice were treated with ISIS antisense oligonucleotides selected from studies described above and evaluated for changes in the levels of various plasma chemistry markers.

Treatment

Two groups of 4 male 6-8 week old CD-1 mice each were injected subcutaneously twice a week for 6 weeks with 50 mg/kg of ISIS 407935 and ISIS 490279. Another seven groups of 4 male 6-8 week old CD-1 mice each were injected subcutaneously twice a week for 6 weeks with 25 mg/kg of ISIS 473589, ISIS 529804, ISIS 534796, ISIS 540162, ISIS 540175, ISIS 540182, and ISIS 540191. One group of male CD-1 mice was injected subcutaneously twice a week for 6 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, bilirubin, albumin, and BUN were measured using an automated clinical chemistry analyzer (Hitachi Olympus AU400e, Melville, N.Y.). The results are presented in Table 43. Treatment with the newly designed antisense oligonucleotides were more tolerable compared to treatment with ISIS 407935 (disclosed in an earlier publication), which caused elevation of ALT levels greater than seven times the upper limit of normal (ULN).

TABLE 43

Effect of antisense oligonucleotide treatment on liver function in CD-1 mice

| | Motif | Dose (mg/kg/wk) | ALT (IU/L) | AST (IU/L) | BUN (mg/dL) | Bilirubin (mg/dL) |
|---|---|---|---|---|---|---|
| PBS | — | — | 37 | 47 | 28 | 0.2 |
| 407935 | e5-d(10)-e5 | 100 | 373 | 217 | 24 | 0.2 |
| 490279 | kdkdk-d(9)-ee | 100 | 96 | 82 | 24 | 0.2 |
| 473589 | e5-d(10)-e5 | 50 | 93 | 116 | 22 | 0.2 |
| 529804 | k-d(10)-kekee | 50 | 54 | 74 | 27 | 0.2 |
| 534796 | ekk-d(10)-kke | 50 | 60 | 63 | 27 | 0.2 |
| 540162 | eek-d(10)-kke | 50 | 43 | 55 | 29 | 0.2 |
| 540175 | eek-d(10)-kke | 50 | 113 | 78 | 24 | 0.3 |

TABLE 43-continued

Effect of antisense oligonucleotide treatment on liver function in CD-1 mice

|  | Motif | Dose (mg/kg/wk) | ALT (IU/L) | AST (IU/L) | BUN (mg/dL) | Bilirubin (mg/dL) |
|---|---|---|---|---|---|---|
| 540182 | eek-d(10)-kke | 50 | 147 | 95 | 26 | 0.1 |
| 540191 | eek-d(10)-kke | 50 | 79 | 88 | 28 | 0.2 | e = 2'-MOE, k = cEt, d = 2'-deoxynucleoside

Body and Organ Weights

Body weights, as well as liver, heart, lungs, spleen and kidney weights were measured at the end of the study, and are presented in Table 44. Several of the ISIS oligonucleotides did not cause any changes in organ weights outside the expected range and were therefore deemed tolerable in terms of organ weights.

TABLE 44

Body and organ weights (grams) of CD-1 mice

|  | Motif | Dose (mg/kg/wk) | Body weight | Liver | Spleen | Kidney |
|---|---|---|---|---|---|---|
| PBS | — | — | 42 | 2.2 | 0.12 | 0.64 |
| 407935 | e5-d(10)-e5 | 100 | 40 | 2.6 | 0.20 | 0.62 |
| 490279 | kdkdk-d(9)-ee | 100 | 42 | 2.8 | 0.17 | 0.61 |
| 473589 | e5-d(10)-e5 | 50 | 41 | 2.5 | 0.16 | 0.67 |
| 529804 | k-d(10)-kekee | 50 | 40 | 2.3 | 0.14 | 0.62 |
| 534796 | ekk-d(10)-kke | 50 | 37 | 2.6 | 0.15 | 0.51 |
| 540162 | eek-d(10)-kke | 50 | 42 | 2.4 | 0.15 | 0.60 |
| 540175 | eek-d(10)-kke | 50 | 39 | 2.2 | 0.11 | 0.62 |
| 540182 | eek-d(10)-kke | 50 | 41 | 2.6 | 0.16 | 0.61 |
| 540191 | eek-d(10)-kke | 50 | 40 | 2.4 | 0.13 | 0.60 | e = 2'-MOE, k = cEt, d = 2'-deoxynucleoside

Example 35

Tolerability of Antisense Oligonucleotides Targeting Human Target-X in Sprague-Dawley Rats Sprague-Dawley rats were treated with ISIS antisense oligonucleotides selected from studies described above and evaluated for changes in the levels of various plasma chemistry markers.

Treatment

Two groups of 4 male 7-8 week old Sprague-Dawley rats each were injected subcutaneously twice a week for 6 weeks with 50 mg/kg of ISIS 407935 and ISIS 490279. Another seven groups of 4 male 6-8 week old Sprague-Dawley rats each were injected subcutaneously twice a week for 6 weeks with 25 mg/kg of ISIS 473589, ISIS 529804, ISIS 534796, ISIS 540162, ISIS 540175, ISIS 540182, and ISIS 540191. One group of male Sprague-Dawley rats was injected subcutaneously twice a week for 6 weeks with PBS. The rats were euthanized 48 hours after the last dose, and organs and plasma were harvested for further analysis.

Plasma Chemistry Markers

To evaluate the effect of ISIS oligonucleotides on liver and kidney function, plasma levels of transaminases, bilirubin, albumin, and BUN were measured using an automated clinical chemistry analyzer (Hitachi Olympus AU400e, Melville, N.Y.). The results are presented in Table 45. Treatment with the all antisense oligonucleotides was tolerable in terms of plasma chemistry markers in this model.

TABLE 45

Effect of antisense oligonucleotide treatment on liver function in Sprague-Dawley rats

|  | Motif | Dose (mg/kg/wk) | ALT (IU/L) | AST (IU/L) | BUN (mg/dL) | Bilirubin (mg/dL) |
|---|---|---|---|---|---|---|
| PBS | — | — | 71 | 83 | 19 | 0.2 |
| 407935 | e5-d(10)-e5 | 100 | 74 | 96 | 22 | 0.2 |
| 490279 | kdkdk-d(9)-ee | 100 | 96 | 181 | 22 | 0.4 |
| 473589 | e5-d(10)-e5 | 50 | 57 | 73 | 21 | 0.2 |
| 529804 | k-d(10)-kekee | 50 | 54 | 78 | 21 | 0.2 |
| 534796 | ekk-d(10)-kke | 50 | 68 | 98 | 22 | 0.2 |
| 540162 | eek-d(10)-kke | 50 | 96 | 82 | 21 | 0.1 |
| 540175 | eek-d(10)-kke | 50 | 55 | 73 | 18 | 0.2 |
| 540182 | eek-d(10)-kke | 50 | 45 | 87 | 21 | 0.2 |
| 540191 | eek-d(10)-kke | 50 | 77 | 104 | 21 | 0.2 | e = 2'-MOE, k = cEt, d = 2'-deoxynucleoside

Body and Organ Weights

Body weights, as well as liver, heart, lungs, spleen and kidney weights were measured at the end of the study, and are presented in Table 46. Treatment with all the antisense oligonucleotides was tolerable in terms of body and organ weights in this model.

TABLE 46

Body and organ weights (grams) of Sprague-Dawley rats

|  | Motif | Dose (mg/kg/wk) | Body weight | Liver | Spleen | Kidney |
|---|---|---|---|---|---|---|
| PBS | — | — | 443 | 16 | 0.8 | 3.5 |
| ISIS 407935 | e5-d(10)-e5 | 100 | 337 | 14 | 1.8 | 3.2 |
| ISIS 490279 | kdkdk-d(9)-ee | 100 | 365 | 18 | 2.2 | 2.9 |
| ISIS 473589 | e5-d(10)-e5 | 50 | 432 | 18 | 1.3 | 3.3 |
| ISIS 529804 | k-d(10)-kekee | 50 | 429 | 18 | 2.2 | 3.4 |
| ISIS 534796 | ekk-d(10)-kke | 50 | 434 | 15 | 1.4 | 3.3 |
| ISIS 540162 | eek-d(10)-kke | 50 | 446 | 18 | 1.1 | 3.3 |
| ISIS 540175 | eek-d(10)-kke | 50 | 467 | 16 | 1.0 | 3.5 |
| ISIS 540182 | eek-d(10)-kke | 50 | 447 | 22 | 2.5 | 4.5 |
| ISIS 540191 | eek-d(10)-kke | 50 | 471 | 21 | 1.4 | 3.9 | e = 2'-MOE, k = cEt, d = 2'-deoxynucleoside

Example 36

Dose-Dependent Antisense Inhibition of Human Target-X in Cynomolgos Monkey Primary Hepatocytes Antisense oligonucleotides selected from the studies described above were tested at various doses in cynomolgous monkey primary hepatocytes. Cells were plated at a density of 35,000 cells per well and transfected using electroporation with 0.009 µM, 0.03 µM, 0.08 µM, 0.25 µM, 0.74 µM, 2.22 µM, 6.67 µM, and 20.00 µM concentrations of antisense oligonucleotide, as specified in Table 47. After a treatment period of approximately 16 hours, RNA was isolated from the cells and Target-X mRNA levels were measured by quantitative real-time PCR. Target-X primer probe set RTS2927 was used to measure mRNA levels. Target-X mRNA levels were adjusted according to total RNA content, as measured by RIBOGREEN®. Results are presented as percent inhibition of Target-X, relative to untreated control cells. As illustrated in Table 47, Target-X mRNA levels were reduced in a dose-dependent manner with some of the antisense oligonucleotides that are cross-reactive with the rhesus monkey genomic sequence.

TABLE 47

Dose-dependent antisense inhibition of Target-X in cynomolgous monkey primary hepatocytes using electroporation

| ISIS No | 0.009 μM | 0.03 μM | 0.08 μM | 0.25 μM | 0.74 μM | 2.22 μM | 6.67 μM | 20.00 μM |
|---|---|---|---|---|---|---|---|---|
| 407935 | 10 | 18 | 15 | 29 | 56 | 73 | 82 | 88 |
| 490279 | 19 | 12 | 13 | 0 | 6 | 18 | 27 | 22 |
| 473589 | 5 | 10 | 19 | 42 | 64 | 76 | 88 | 92 |
| 529804 | 10 | 3 | 23 | 25 | 57 | 80 | 86 | 91 |
| 534796 | 0 | 28 | 23 | 49 | 71 | 81 | 87 | 90 |
| 540162 | 9 | 14 | 9 | 6 | 13 | 13 | 11 | 31 |
| 540175 | 0 | 4 | 12 | 9 | 10 | 16 | 12 | 22 |
| 540182 | 0 | 7 | 0 | 6 | 36 | 12 | 10 | 0 |
| 540191 | 6 | 7 | 0 | 0 | 0 | 0 | 21 | 42 |

Example 37

Dose-Dependent Antisense Inhibition of Human Target-X in Hep3B Cells

Antisense oligonucleotides from the study described above were also tested at various doses in Hep3B cells. Cells were plated at a density of 20,000 cells per well and transfected using electroporation with 0.009 μM, 0.03 μM, 0.08 μM, 0.25 μM, 0.74 μM, 2.22 μM, 6.67 μM, and 20.00 μM concentrations of antisense oligonucleotide, as specified in Table 48. After a treatment period of approximately 16 hours, RNA was isolated from the cells and Target-X mRNA levels were measured by quantitative real-time PCR. Target-X primer probe set RTS2927 was used to measure mRNA levels. Target-X mRNA levels were adjusted according to total RNA content, as measured by RIBOGREEN®. Results are presented as percent inhibition of Target-X, relative to untreated control cells. As illustrated in Table 48, Target-X mRNA levels were reduced in a dose-dependent manner with several of the antisense oligonucleotides.

TABLE 48

Dose-dependent antisense inhibition of Target-X in Hep3B cells using electroporation

| ISIS No | 0.009 μM | 0.03 μM | 0.08 μM | 0.25 μM | 0.74 μM | 2.22 μM | 6.67 μM | 20.00 μM | IC$_{50}$ (μM) |
|---|---|---|---|---|---|---|---|---|---|
| 407935 | 3 | 9 | 11 | 35 | 64 | 83 | 87 | 93 | 4.5 |
| 473244 | 20 | 33 | 50 | 69 | 77 | 89 | 7 | 14 | 0.9 |
| 473589 | 0 | 14 | 23 | 44 | 74 | 88 | 90 | 94 | 2.7 |
| 490279 | 0 | 5 | 7 | 15 | 25 | 61 | 76 | 78 | 11.6 |
| 515533 | 0 | 12 | 21 | 36 | 63 | 78 | 88 | 94 | 3.6 |
| 515952 | 0 | 12 | 27 | 57 | 76 | 89 | 93 | 94 | 2.2 |
| 516066 | 6 | 0 | 12 | 26 | 52 | 70 | 81 | 86 | 6.0 |
| 529459 | 0 | 4 | 24 | 40 | 61 | 78 | 88 | 94 | 3.5 |
| 529553 | 9 | 7 | 17 | 40 | 58 | 74 | 87 | 93 | 4.6 |
| 529804 | 0 | 3 | 34 | 64 | 83 | 89 | 93 | 95 | 2.0 |
| 534796 | 8 | 18 | 43 | 67 | 82 | 89 | 95 | 96 | 1.4 |
| 537806 | 6 | 11 | 5 | 20 | 37 | 69 | 79 | 86 | 7.1 |
| 540162 | 18 | 33 | 63 | 75 | 87 | 91 | 91 | 92 | 0.7 |
| 540175 | 10 | 25 | 55 | 76 | 86 | 89 | 89 | 93 | 1.0 |
| 540182 | 13 | 36 | 61 | 75 | 84 | 88 | 90 | 93 | 0.7 |
| 540191 | 3 | 12 | 28 | 61 | 79 | 80 | 88 | 94 | 2.2 |

Example 38

Efficacy of Antisense Oligonucleotides Targeting Human Target-X in Transgenic Mice Transgenic mice were treated with ISIS antisense oligonucleotides selected from studies described above and evaluated for efficacy.

Treatment

Eight groups of 3 transgenic mice each were injected subcutaneously twice a week for 3 weeks with 20 mg/kg/week, 10 mg/kg/week, 5 mg/kg/week, or 2.5 mg/kg/week of ISIS 407935 or ISIS 490279. Another 24 groups of 3 transgenic mice each were subcutaneously twice a week for 3 weeks with 5 mg/kg/week, 2.5 mg/kg/week, 1.25 mg/kg/week, or 0.625 mg/kg/week of ISIS 473589, ISIS 529804, ISIS 534796, ISIS 540162, ISIS 540175, or ISIS 540191. One group of mice was injected subcutaneously twice a week for 3 weeks with PBS. Mice were euthanized 48 hours after the last dose, and organs and plasma were harvested for further analysis.

RNA Analysis

RNA was extracted from plasma for real-time PCR analysis of Target-X, using primer probe set RTS2927. The mRNA levels were normalized using RIBOGREEN®. As shown in Table 49, several antisense oligonucleotides achieved reduction of human Target-X over the PBS control. Results are presented as percent inhibition of Target-X, relative to control. Treatment with newly designed 2'-MOE gapmer, ISIS 490279, caused greater reduction in human Target-X mRNA levels than treatment with ISIS 407935, the 2'-MOE gapmer from the earlier publication. Treatment with several of the newly designed oligonucleotides also caused greater reduction in human Target-X mRNA levels than treatment with ISIS 407935.

TABLE 49

Percent inhibition of Target-X mRNA in transgenic mice

| ISIS No | Motif | Dose (mg/kg/wk) | % inhibition |
|---|---|---|---|
| 407935 | e5-d(10)-e5 | 20.0 | 85 |
|  |  | 10.0 | 57 |
|  |  | 5.0 | 45 |
|  |  | 2.5 | 28 |
| 490279 | kdkdk-d(9)-ee | 20.0 | 88 |
|  |  | 10.0 | 70 |
|  |  | 5.0 | 51 |
|  |  | 2.5 | 33 |
| 473589 | e5-d(10)-e5 | 5.00 | 80 |
|  |  | 2.50 | 62 |
|  |  | 1.25 | 44 |
|  |  | 0.625 | 25 |
| 529804 | k-d(10)-kekee | 5.00 | 55 |
|  |  | 2.50 | 41 |
|  |  | 1.25 | 0 |
|  |  | 0.625 | 1 |
| 534796 | ekk-d(10)-kke | 5.00 | 56 |
|  |  | 2.50 | 41 |
|  |  | 1.25 | 5 |
|  |  | 0.625 | 0 |
| 540162 | eek-d(10)-kke | 5.00 | 97 |
|  |  | 2.50 | 92 |
|  |  | 1.25 | 69 |
|  |  | 0.625 | 78 |
| 540175 | eek-d(10)-kke | 5.00 | 95 |
|  |  | 2.50 | 85 |
|  |  | 1.25 | 65 |
|  |  | 0.625 | 55 |
| 540182 | eek-d(10)-kke | 5.00 | 97 |
|  |  | 2.50 | 83 |
|  |  | 1.25 | 54 |
|  |  | 0.625 | 10 |
| 540191 | eek-d(10)-kke | 5.00 | 91 |
|  |  | 2.50 | 74 |
|  |  | 1.25 | 58 |
|  |  | 0.625 | 34 | e = 2'-MOE,
k = cEt,
d = 2'-deoxynucleoside

Protein Analysis

Plasma protein levels of Target-X were estimated using a Target-X ELISA kit (purchased from Hyphen Bio-Med). As shown in Table 50, several antisense oligonucleotides achieved reduction of human Target-X over the PBS control. Results are presented as percent inhibition of Target-X, relative to control.

TABLE 50

Percent inhibition of Target-X plasm protein levels in transgenic mice

| ISIS No | Motif | Dose (mg/kg/wk) | % inhibition |
|---|---|---|---|
| 407935 | e5-d(10)-e5 | 20 | 65 |
|  |  | 10 | 47 |
|  |  | 5 | 0 |
|  |  | 2.5 | 3 |
| 490279 | kdkdk-d(9)-ee | 20 | 91 |
|  |  | 10 | 75 |
|  |  | 5 | 31 |
|  |  | 2.5 | 23 |
| 473589 | e5-d(10)-e5 | 5 | 78 |
|  |  | 2.5 | 40 |
|  |  | 1.25 | 6 |
|  |  | 0.625 | 0 |
| 529804 | k-d(10)-kekee | 5 | 50 |
|  |  | 2.5 | 36 |
|  |  | 1.25 | 0 |
|  |  | 0.625 | 8 |
| 534796 | ekk-d(10)-kke | 5 | 45 |
|  |  | 2.5 | 26 |
|  |  | 1.25 | 0 |
|  |  | 0.625 | 8 |
| 540162 | eek-d(10)-kke | 5 | 98 |
|  |  | 2.5 | 96 |
|  |  | 1.25 | 78 |
|  |  | 0.625 | 74 |
| 540175 | eek-d(10)-kke | 5 | 93 |
|  |  | 2.5 | 83 |
|  |  | 1.25 | 49 |
|  |  | 0.625 | 24 |
| 540182 | eek-d(10)-kke | 5 | 97 |
|  |  | 2.5 | 71 |
|  |  | 1.25 | 50 |
|  |  | 0.625 | 0 |
| 540191 | eek-d(10)-kke | 5 | 97 |
|  |  | 2.5 | 74 |
|  |  | 1.25 | 46 |
|  |  | 0.625 | 25 | e = 2'-MOE,
k = cEt,
d = 2'-deoxynucleoside

Example 39

Effect of ISIS Antisense Oligonucleotides Targeting Human Target-X in Cynomolgus Monkeys Cynomolgus monkeys were treated with ISIS antisense oligonucleotides selected from studies described above, including ISIS 407935, ISIS 490279, ISIS 473589, ISIS 529804, ISIS 534796, ISIS 540162, ISIS 540175, ISIS 540182, and ISIS 540191. Antisense oligonucleotide efficacy was evaluated. ISIS 407935, from the earlier publication, was included in the study for comparison.

Treatment

Prior to the study, the monkeys were kept in quarantine for at least a 30-day period, during which the animals were observed daily for general health. Standard panels of serum chemistry and hematology, examination of fecal samples for ova and parasites, and a tuberculosis test were conducted immediately after the animals' arrival to the quarantine area. The monkeys were 2-4 years old at the start of treatment and weighed between 2 and 4 kg. Ten groups of four randomly assigned male cynomolgus monkeys each were injected subcutaneously with ISIS oligonucleotide or PBS using a stainless steel dosing needle and syringe of appropriate size into one of 4 sites on the back of the monkeys; each site used in clock-wise rotation per dose administered. Nine groups of monkeys were dosed four times a week for the first week (days 1, 3, 5, and 7) as loading doses, and subsequently once a week for weeks 2-12, with 35 mg/kg of ISIS 407935, ISIS 490279, ISIS 473589, ISIS 529804, ISIS 534796, ISIS 540162, ISIS 540175, ISIS 540182, or ISIS 540191. A control group of cynomolgus monkeys was injected with PBS subcutaneously thrice four times a week for the first week (days 1, 3, 5, and 7), and subsequently once a week for weeks 2-12. The protocols described in the Example were approved by the Institutional Animal Care and Use Committee (IACUC).

Hepatic Target Reduction

RNA Analysis

On day 86, RNA was extracted from liver tissue for real-time PCR analysis of Target-X using primer probe set RTS2927. Results are presented as percent inhibition of Target-X mRNA, relative to PBS control, normalized to RIBOGREEN® or to the house keeping gene, GAPDH. As shown in Table 52, treatment with ISIS antisense oligonucleotides resulted in reduction of Target-X mRNA in comparison to the PBS control.

TABLE 52

Percent Inhibition of cynomolgous monkey Target-X mRNA in the cynomolgus monkey liver relative to the PBS control

| ISIS No | Motif | RTS2927/Ribogreen | RTS2927/GAPDH |
|---|---|---|---|
| 407935 | e5-d(10)-e5 | 90 | 90 |
| 490279 | kdkdk-d(9)-ee | 72 | 66 |
| 473589 | e5-d(10)-e5 | 96 | 96 |
| 529804 | k-d(10)-kekee | 90 | 87 |
| 534796 | ekk-d(10)-kke | 80 | 78 |
| 540162 | eek-d(10)-kke | 66 | 58 |
| 540175 | eek-d(10)-kke | 68 | 66 |
| 540182 | eek-d(10)-kke | 0 | 0 |
| 540191 | eek-d(10)-kke | 34 | 14 | e = 2'-MOE,
k = cEt,
d = 2'-deoxynucleoside

Protein Levels and Activity Analysis

Plasma Target-X levels were measured prior to dosing, and on day 3, day 5, day 7, day 16, day 30, day 44, day 65, and day 86 of treatment. Target-X activity was measured using Target-X deficient plasma. Approximately 1.5 mL of blood was collected from all available study animals into tubes containing 3.2% sodium citrate. The samples were placed on ice immediately after collection. Collected blood samples were processed to platelet poor plasma and the tubes were centrifuged at 3,000 rpm for 10 min at 4° C. to obtain plasma.

Protein levels of Target-X were measured by a Target-X elisa kit (purchased from Hyphen BioMed). The results are presented in Table 53.

TABLE 53

Plasma Target-X protein levels (% reduction compared to the baseline) in the cynomolgus monkey plasma

| ISIS No | Day 3 | Day 5 | Day 7 | Day 16 | Day 30 | Day 44 | Day 65 | Day 86 |
|---|---|---|---|---|---|---|---|---|
| 407935 | 21 | 62 | 69 | 82 | 84 | 85 | 84 | 90 |
| 490279 | 0 | 29 | 35 | 30 | 38 | 45 | 51 | 58 |
| 473589 | 12 | 67 | 85 | 97 | 98 | 98 | 98 | 98 |
| 529804 | 19 | 65 | 76 | 87 | 88 | 89 | 90 | 90 |
| 534796 | 1 | 46 | 54 | 64 | 64 | 67 | 66 | 70 |
| 540162 | 0 | 24 | 26 | 37 | 45 | 49 | 49 | 50 |
| 540175 | 0 | 28 | 36 | 38 | 47 | 52 | 55 | 55 |
| 540182 | 0 | 17 | 8 | 0 | 0 | 0 | 5 | 0 |
| 540191 | 0 | 12 | 4 | 0 | 0 | 4 | 9 | 10 |

Example 40

Single Nucleotide Polymorphisms (SNPs) in the Huntingtin (HTT) Gene Sequence SNP positions (identified by Hayden et al, WO/2009/135322) associated with the HTT gene were mapped to the HTT genomic sequence, designated herein as SEQ ID NO: 1 (NT_006081.18 truncated from nucleotides 1566000 to 1768000). Table 56 provides SNP positions associated with the HTT gene. Table 56 provides a reference SNP ID number from the Entrez SNP database at the National Center for Biotechnology Information (NCBI, http://www.ncbi.nlm-.nih.gov/sites/entrez?db=snp), incorporated herein by reference. Table 56 furnishes further details on each SNP. The 'Reference SNP ID number' or 'RS number' is the number designated to each SNP from the Entrez SNP database at NCBI, incorporated herein by reference. 'SNP position' refers to the nucleotide position of the SNP on SEQ ID NO: 1. 'Polymorphism' indicates the nucleotide variants at that SNP position. 'Major allele' indicates the nucleotide associated with the major allele, or the nucleotide present in a statistically significant proportion of individuals in the human population. 'Minor allele' indicates the nucleotide associated with the minor allele, or the nucleotide present in a relatively small proportion of individuals in the human population.

TABLE 56

Single Nuclear Polymorphisms (SNPs) and their positions on SEQ ID NO: 1

| RS No. | SNP position | Polymorphism | Major allele | Minor allele |
|---|---|---|---|---|
| rs2857936 | 1963 | C/T | C | T |
| rs12506200 | 3707 | A/G | G | A |
| rs762855 | 14449 | A/G | G | A |
| rs3856973 | 19826 | G/A | G | A |
| rs2285086 | 28912 | G/A | A | G |
| rs7659144 | 37974 | C/G | C | G |
| rs16843804 | 44043 | C/T | C | T |
| rs2024115 | 44221 | G/A | A | G |
| rs10015979 | 49095 | A/G | A | G |
| rs7691627 | 51063 | A/G | G | A |
| rs2798235 | 54485 | G/A | G | A |
| rs4690072 | 62160 | G/T | T | G |
| rs6446723 | 66466 | C/T | T | C |
| rs363081 | 73280 | G/A | G | A |
| rs363080 | 73564 | T/C | C | T |
| rs363075 | 77327 | G/A | G | A |
| rs363064 | 81063 | T/C | C | T |
| rs3025849 | 83420 | A/G | A | G |
| rs6855981 | 87929 | A/G | G | A |

TABLE 56-continued

Single Nuclear Polymorphisms (SNPs) and their positions on SEQ ID NO: 1

| RS No. | SNP position | Polymorphism | Major allele | Minor allele |
|---|---|---|---|---|
| rs363102 | 88669 | G/A | A | G |
| rs11731237 | 91466 | C/T | C | T |
| rs4690073 | 99803 | A/G | G | A |
| rs363144 | 100948 | T/G | T | G |
| rs3025838 | 101099 | C/T | C | T |
| rs34315806 | 101687 | A/G | G | A |
| rs363099 | 101709 | T/C | C | T |
| rs363096 | 119674 | T/C | T | C |
| rs2298967 | 125400 | C/T | T | C |
| rs2298969 | 125897 | A/G | G | A |
| rs6844859 | 130139 | C/T | T | C |
| rs363092 | 135682 | C/A | C | A |
| rs7685686 | 146795 | A/G | A | G |
| rs363088 | 149983 | A/T | A | T |
| rs362331 | 155488 | C/T | T | C |
| rs916171 | 156468 | G/C | C | G |
| rs362322 | 161018 | A/G | A | G |
| rs362275 | 164255 | T/C | C | T |
| rs362273 | 167080 | A/G | A | G |
| rs2276881 | 171314 | G/A | G | A |
| rs3121419 | 171910 | T/C | C | T |
| rs362272 | 174633 | G/A | G | A |
| rs362271 | 175171 | G/A | G | A |
| rs3775061 | 178407 | C/T | C | T |
| rs362310 | 179429 | A/G | G | A |
| rs362307 | 181498 | T/C | C | T |
| rs362306 | 181753 | G/A | G | A |
| rs362303 | 181960 | T/C | C | T |
| rs362296 | 186660 | C/A | C | A |
| rs1006798 | 198026 | A/G | A | G |

Example 41

Modified Oligonucleotides Targeting Huntingtin (HTT) Single Nucleotide Polymorphism (SNP)

A series of modified oligonucleotides were designed based on the parent gapmer, ISIS 460209 wherein the central gap region contains nine 2'-deoxyribonucleosides. These modified oligonucleotides were designed by introducing various chemical modifications in the central gap region and were tested for their ability to selectively inhibit mutant (mut) HTT mRNA expression levels targeting rs7685686 while leaving the expression of the wild-type (wt) intact. The activity and selectivity of the modified oligonucleotides were evaluated and compared to the parent gapmer, ISIS 460209.

The modified oligonucleotides were created with a 3-9-3 motif and are described in Table 57. The internucleoside linkages throughout each gapmer are phosphorothioate (P=S) linkages. All cytosine nucleobases throughout each gapmer are 5-methyl cytosines. Nucleosides without a subscript are β-D-2'-deoxyribonucleosides. Nucleosides followed by a subscript "e", "k", "y", or "z" are sugar modified nucleosides. A subscript "e" indicates a 2'-O-methoxyethyl (MOE) modified nucleoside, a subscript "k" indicates a 6'-(S)—CH$_3$ bicyclic nucleoside (e.g. cEt), a subscript "y" indicates an α-L-LNA bicyclic nucleoside and a subscript "z" indicates a F-HNA modified nucleoside. $^P$U indicates a 5-propyne uridine nucleoside and $^x$T indicates a 2-thio-thymidine nucleoside.

The number in parentheses indicates the position on the modified oligonucleotide opposite to the SNP position, as counted from the 5'-terminus.

Cell Culture and Transfection

The modified oligonucleotides were tested in vitro. Heterozygous fibroblast GM04022 cell line was used (from Coriell Institute). Cultured GM04022 cells at a density of 25,000 cells per well were transfected using electroporation with 0.12, 0.37, 1.1, 3.3 and 10 µM concentrations of modified oligonucleotides. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN and the results are presented below.

Analysis of $IC_{50}$'s

The half maximal inhibitory concentration ($IC_{50}$) of each oligonucleotide is presented in Table 58 and was calculated by plotting the concentrations of oligonucleotides used versus the percent inhibition of HTT mRNA expression achieved at each concentration, and noting the concentration of oligonucleotide at which 50% inhibition of HTT mRNA expression was achieved compared to the control. The $IC_{50}$ at which each oligonucleotide inhibits the mutant HTT mRNA expression is denoted as 'mut $IC_{50}$'. The $IC_{50}$ at which each oligonucleotide inhibits the wild-type HTT mRNA expression is denoted as 'wt $IC_{50}$'. Selectivity was calculated by dividing the $IC_{50}$ for inhibition of the wild-type HTT versus the $IC_{50}$ for inhibiting expression of the mutant HTT mRNA.

The parent gapmer, ISIS 460209 is marked with an asterisk (*) in the table and was included in the study as a benchmark oligonucleotide against which the activity and selectivity of the modified oligonucleotides targeting nucleotides overlapping the SNP position could be compared.

As illustrated in Table 58, modified oligonucleotides having chemical modifications in the central gap region at the SNP position exhibited similar activity with an increase in selectivity comparing to the parent gapmer, wherein the central gap region contains full deoxyribonucleosides.

TABLE 57

Modified oligonucleotides targeting HTT rs7685686

| ISIS NO | Sequence (5' to 3') | Gap chemistry | Wing chemistry 5' | Wing chemistry 3' | SEQ ID NO. |
|---|---|---|---|---|---|
| 460209* (8) | $T_eA_kA_k$ATTGTCATCA$_kC_kC_e$ | Full Deoxy | ekk | kke | 10 |
| 539560 (8) | $T_eA_kA_k$ATTG$^p$UCATCA$_kC_kC_e$ | Deoxy/5-Propyne | ekk | kke | 11 |
| 539563 (8) | $T_eA_kA_k$ATTG$^x$TCATCA$_kC_kC_e$ | Deoxy/2-Thio | ekk | kke | 10 |
| 539554 (8) | $T_eA_kA_k$ATTGU$_y$CATCA$_kC_kC_e$ | Deoxy/α-L-LNA | ekk | kke | 11 |
| 542686 (8) | $T_eA_kA_k$ATTGT$_z$CATCA$_kC_kC_e$ | Deoxy/F-HNA | ekk | kke | 10 | e = 2-MOE, k = cEt

TABLE 58

Comparison of inhibition of HTT mRNA levels and selectivity of modified oligonucleotides with ISIS 460209 targeted to rs7685686 in GM04022 cells

| ISIS NO | Mut $IC_{50}$ (µM) | Wt $IC_{50}$ (µM) | Selectivity (mut vs wt) | Gap chemistry | Wing chemistry 5' | Wing chemistry 3' |
|---|---|---|---|---|---|---|
| 460209* (8) | 0.41 | 2.0 | 4.9 | Full Deoxy | ekk | kke |
| 539560 (8) | 0.29 | 1.1 | 3.8 | Deoxy/5-Propyne | ekk | kke |
| 539563 (8) | 0.45 | 3.1 | 6.9 | Deoxy/2-Thio | ekk | kke |
| 539554 (8) | 3.5 | >10 | >3 | Deoxy/α-L-LNA | ekk | kke |
| 542686 (8) | 0.5 | 3.1 | 6.0 | Deoxy/F-HNA | ekk | kke |

Example 42

Modified Oligonucleotides Comprising Chemical Modifications in the Gap Region Targeting Huntingtin (HTT) Single Nucleotide Polymorphism (SNP)

Additional modified oligonucleotides were designed in a similar manner as the antisense oligonucleotides described in Table 57. Various chemical modifications were introduced in the central gap region at the SNP position in an effort to improve selectivity while maintaining activity in reducing mutant HTT mRNA levels.

The modified oligonucleotides were created with a 3-9-3 motif and are described in Table 59. The internucleoside linkages throughout each gapmer are phosphorothioate (P=S) linkages. All cytosine nucleobases throughout each gapmer are 5-methyl cytosines. Nucleosides without a subscript are β-D-2'-deoxyribonucleosides. Nucleosides followed by a subscript "a", "e", "f", "h", "k", "l", "R", "w" are sugar modified nucleosides. A subscript "a" indicates a 2'-(ara)-F modified nucleoside, a subscript "e" indicates a 2'-O-methoxyethyl (MOE) modified nucleoside, a subscript "f" indicates a 2'-F modified nucleoside, a subscript "h" indicates a HNA modified nucleoside, a subscript "k" indicates a 6'-(S)—CH$_3$ bicyclic nucleoside (e.g. cEt), a subscript "l" indicates a LNA modified nucleoside, a subscript "R" indicates a 5'-(R)-Me DNA, a subscript "w" indicates an unlocked nucleic acid (UNA) modified nucleoside. $^n$T indicates an N3-ethylcyano thymidine nucleoside and $^b$N indicates an abasic nucleoside (e.g. 2'-deoxyribonucleoside comprising a H in place of a nucleobase). Underlined nucleoside or the number in parentheses indicates the position on the modified oligonucleotide opposite to the SNP position, as counted from the 5'-terminus.

Thermal Stability Assay

The modified oligonucleotides were evaluated in thermal stability ($T_m$) assay. The $T_m$'s were measured using the method described herein. A Cary 100 Bio spectrophotometer with the Cary Win UV Thermal program was used to measure absorbance vs. temperature. For the $T_m$ experiments, oligonucleotides were prepared at a concentration of 8 µM in a buffer of 100 mM Na+, 10 mM phosphate, 0.1 mM EDTA, pH 7. Concentration of oligonucleotides were determined at 85° C. The oligonucleotide concentration was 4 µM with mixing of equal volumes of test oligonucleotide and mutant or wild-type RNA strand. Oligonucleotides were hybridized with the mutant or wild-type RNA strand by heating duplex to 90° C. for 5 min and allowed to cool at room temperature. Using the spectrophotometer, $T_m$ measurements were taken by heating duplex solution at a rate of 0.5 C/min in cuvette starting @ 15° C. and heating to 85° C. $T_m$ values were determined using Vant Hoff calculations ($A_{260}$ vs temperature curve) using non self-complementary sequences where the minimum absorbance which relates to the duplex and the maximum absorbance which relates to the non-duplex single strand are manually integrated into the program.

Presented in Table 60 is the $T_m$ for the modified oligonucleotides when duplexed to mutant or wild-type RNA complement. The $T_m$ of the modified oligonucleotides duplexed with mutant RNA complement is denoted as "$T_m$ (° C.) mut". The $T_m$ of the modified oligonucleotides duplexed with wild-type RNA complement is denoted as "$T_m$ (° C.) wt".

Cell Culture, Transfection and Selectivity Analysis

The modified oligonucleotides were also tested in vitro. Heterozygous fibroblast GM04022 cell line was used. Cultured GM04022 cells at a density of 25,000 cells per well were transfected using electroporation with a single dose at 2 µM concentration of the modified oligonucleotide. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN. The results in Table 60 are presented as percent of HTT mRNA expression, relative to untreated control levels and is denoted as "% UTC". Selectivity as was also evaluated and measured by dividing the percent of wild-type HTT mRNA levels vs. the percent of mutant HTT mRNA levels.

The parent gapmer, ISIS 460209 is marked with an asterisk (*) in the table and was included in the study as a benchmark oligonucleotide against which the selectivity of the modified oligonucleotides targeting nucleotides overlapping the SNP position could be compared.

As illustrated in Table 60, improvement in selectivity was observed for antisense oligonucleotides comprising chemical modifications in the central gap region at the SNP site such as 5'-(R)-Me (ISIS 539558), HNA (ISIS 539559), and 2'-(ara)-F (ISIS 539565) in comparison to the parent full deoxy gapmer, ISIS 460209. Modified oligonucleotides comprising LNA (ISIS 539553) or 2'-F (ISIS 539570) showed comparable selectivity while UNA modification (ISIS 539556 or 543909) showed no selectivity. Modified oligonucleotides comprising modified nucleobase, N3-ethylcyano (ISIS 539564) or abasic nucleobase (ISIS 543525) showed little to no improvement in selectivity.

TABLE 59

Modified oligonucleotides comprising chemical modifications in the central gap region

| ISIS NO | Sequence (5' to 3') | Gap chemistry | Wing chemistry 5' | 3' | SEQ ID NO. |
|---|---|---|---|---|---|
| 460209* (8) | T$_e$A$_k$A$_k$ATTG<u>T</u>CATCA$_k$C$_k$C$_e$ | Full Deoxy | ekk | kke | 10 |
| 539553 (8) | T$_e$A$_k$A$_k$ATTGT$_l$CATCA$_k$C$_k$C$_e$ | Deoxy/LNA | ekk | kke | 10 |

TABLE 59-continued

Modified oligonucleotides comprising chemical modifications in the central gap region

| ISIS NO | Sequence (5' to 3') | Gap chemistry | Wing chemistry 5' | 3' | SEQ ID NO. |
|---|---|---|---|---|---|
| 539556 (8) | $T_eA_kA_k$ATTG$U_w$CATCA$_kC_kC_e$ | Deoxy/UNA | ekk | kke | 11 |
| 539558 (8) | $T_eA_kA_k$ATTG$T_R$CATCA$_kC_kC_e$ | Deoxy/5'-(R)-Me DNA | ekk | kke | 10 |
| 539559 (8) | $T_eA_kA_k$ATTG$T_h$CATCA$_kC_kC_e$ | Deoxy/HNA | ekk | kke | 10 |
| 539564 (8) | $T_eA_kA_k$ATTG"$T$CATCA$_kC_kC_e$ | Deoxy/deoxy with N3-Ethylcyano nucleobase | ekk | kke | 10 |
| 539565 (8) | $T_eA_kA_k$ATTG$T_a$CATCA$_kC_kC_e$ | Deoxy/2'-(ara)-F | ekk | kke | 10 |
| 539570 (8) | $T_eA_kA_k$ATTG$T_f$CATCA$_kC_kC_e$ | Deoxy/2'-F | ekk | kke | 10 |
| 543525 (8) | $T_eA_kA_k$ATTG$^b$NCATCA$_kC_kC_e$ | Deoxy/Deoxy-Abasic | ekk | kke | 12 |
| 543909 (5) | $T_eA_kA_kAU_w$TGTCATCA$_kC_kC_e$ | Deoxy/UNA | ekk | kke | 13 | e = 2'-MOE, k = cEt, d = 2'-deoxyribonucleoside

TABLE 60

Comparison of selectivity in inhibition of HTT mRNA levels and Tm of modified oligonucleotides with ISIS 460209 targeted to rs7685686 in GM04022 cells

| | Tm (° C.) | | % UTC | | Selectivity | | Wing chemistry | |
|---|---|---|---|---|---|---|---|---|
| ISIS NO | mutant | wt | mutant | wt | (wt vs mut) | Gap chemistry | 5' | 3' |
| 460209* (8) | 53.7 | 52.2 | 23 | 57 | 2.4 | Full Deoxy | ekk | kke |
| 539553 (8) | 57.7 | 55.3 | 54 | 102 | 1.9 | Deoxy/LNA | ekk | kke |
| 539556 (8) | 43.7 | 44.1 | 90 | 105 | 1.2 | Deoxy/UNA | ekk | kke |
| 539558 (8) | 51.2 | 49.7 | 25 | 83 | 3.3 | Deoxy/5'-(R)-Me DNA | ekk | kke |
| 539559 (8) | 55.4 | 50.5 | 18 | 62 | 3.5 | Deoxy/HNA | ekk | kke |
| 539564 (8) | 42.8 | 43.1 | 86 | 135 | 1.6 | Deoxy/Deoxy N3-ethylcyano nucleobase | ekk | kke |
| 539565 (8) | 53.8 | 52.5 | 14 | 46 | 3.4 | Deoxy/2'-(ara)-F | ekk | kke |
| 539570 (8) | 54.4 | 51.8 | 25 | 50 | 2.0 | Deoxy/2'-F | ekk | kke |
| 543525 (8) | 43.1 | 43.8 | 87 | 97 | 1.1 | Deoxy/Deoxy Abasic | ekk | kke |
| 543909 (5) | 44.7 | 42.1 | 68 | 79 | 1.2 | Deoxy/UNA | ekk | kke | e = 2'-MOE, k = cEt, d = 2'-deoxyribonucleoside

Example 43

Chimeric Oligonucleotides Comprising Self-Complementary Regions Targeting Huntingtin (HTT) Single Nucleotide Polymorphism (SNP)

Chimeric oligonucleotides were designed based on the parent gapmer, ISIS 460209. These gapmers comprise self-complementary regions flanking the central gap region, wherein the central gap region contains nine deoxyribonucleosides and the self-complementary regions are complementary to one another. The underlined nucleosides indicate the portion of the 5'-end that is self-complement to the portion of the 3'-end.

The gapmers and their motifs are described in Table 61. The internucleoside linkages throughout each gapmer are phosphorothioate (P=S) linkages. All cytosine nucleobases throughout each gapmer are 5-methyl cytosines. Nucleosides without a subscript are β-D-2'-deoxyribonucleosides. Nucleosides followed by a subscript "e" or "k" are sugar modified nucleosides. A subscript "e" indicates a 2'-O-methoxyethyl (MOE) modified nucleoside and a subscript "k" indicates a 6'-(S)—CH$_3$ bicyclic nucleoside (e.g. cEt).

The modified oligonucleotides were tested in vitro. Heterozygous fibroblast GM04022 cell line was used. Cultured GM04022 cells at a density of 25,000 cells per well were transfected using electroporation with a single dose at 2 μM concentration of the modified oligonucleotide. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. HTT mRNA levels were adjusted according to total RNA content, as measured by RIBOGREEN. The results in Table 62 are presented as percent of HTT mRNA expression, relative to untreated control levels and is denoted as "% UTC". Selectivity was also evaluated and measured by dividing the percent of wild-type HTT mRNA levels vs. the percent of the mutant HTT mRNA levels.

The parent gapmer, ISIS 460209 is marked with an asterisk (*) in the table and was included in the study as a benchmark oligonucleotide against which the selectivity of the modified oligonucleotides targeting nucleotides overlapping the SNP position could be compared.

As illustrated in Table 62, improvement in selectivity was observed for chimeric oligonucleotides comprising 5-9-5 (ISIS 550913), 6-9-6 (ISIS 550912), 6-9-3 (ISIS 550907) or 3-9-7 (ISIS 550904) in comparison to the parent gapmer motif, 3-9-3 (ISIS 460209). The remaining gapmers showed moderate to little improvement in selectivity.

TABLE 61

Chimeric oligonucleotides comprising various wing motifs targeted to HTT rs7685686

| ISIS NO | Sequence (5' to 3') | Motif | Wing chemistry 5' | 3' | SEQ ID NO. |
|---|---|---|---|---|---|
| 460209* | T$_e$A$_k$A$_k$ATTGTCATCA$_k$C$_k$C$_e$ | 3-9-3 | ekk | kke | 10 |
| 544838 | T$_e$A$_k$A$_k$ATTGTCATCA$_k$C$_k$C$_e$A$_k$ | 3-9-4 | ekk | kkek | 14 |
| 544840 | T$_e$A$_k$A$_k$ATTGTCATCA$_k$C$_k$C$_e$T$_k$T$_k$A$_k$ | 3-9-6 | ekk | kkekkk | 15 |
| 544842 | T$_e$A$_k$A$_k$ATTGTCATCA$_k$C$_k$C$_e$A$_k$T$_k$T$_k$T$_k$A$_k$ | 3-9-8 | ekk | kkekkkkk | 16 |
| 550903 | T$_e$A$_k$A$_k$ATTGTCATCA$_k$C$_k$C$_e$T$_k$A$_k$ | 3-9-5 | ekk | kkekk | 17 |
| 550904 | T$_e$A$_k$A$_k$ATTGTCATCA$_k$C$_k$C$_e$T$_k$T$_k$T$_k$A$_k$ | 3-9-7 | ekk | kkekkkk | 18 |
| 550905 | G$_k$T$_e$A$_k$A$_k$ATTGTCATCA$_k$C$_k$C$_e$ | 4-9-3 | kekk | kke | 19 |
| 550906 | G$_k$G$_k$T$_e$A$_k$A$_k$ATTGTCATCA$_k$C$_k$C$_e$ | 5-9-3 | kkekk | kke | 20 |
| 550907 | G$_k$G$_k$T$_k$T$_e$A$_k$A$_k$ATTGTCATCA$_k$C$_k$C$_e$ | 6-9-3 | kkkekk | kke | 21 |
| 550908 | G$_k$G$_k$T$_k$G$_k$T$_e$A$_k$A$_k$ATTGTCATCA$_k$C$_k$C$_e$ | 7-9-3 | kkkkekk | kke | 22 |
| 550909 | G$_k$G$_k$T$_k$G$_k$A$_k$T$_e$A$_k$A$_k$ATTGTCATCA$_k$C$_k$C$_e$ | 8-9-3 | kkkkkekk | kke | 23 |
| 550910 | G$_k$G$_k$C$_k$T$_e$A$_k$A$_k$ATTGTCATCA$_k$C$_k$C$_e$G$_k$C$_k$C$_k$ | 6-9-6 | kkkekk | kkekkk | 24 |
| 550911 | G$_k$C$_k$T$_e$A$_k$A$_k$ATTGTCATCA$_k$C$_k$C$_e$G$_k$C$_k$ | 5-9-5 | kkekk | kkekk | 25 |
| 550912 | T$_k$A$_k$A$_k$T$_e$A$_k$A$_k$ATTGTCATCA$_k$C$_k$C$_e$T$_k$T$_k$A$_k$ | 6-9-6 | kkkekk | kkekkk | 26 |
| 550913 | A$_k$A$_k$T$_e$A$_k$A$_k$ATTGTCATCA$_k$C$_k$C$_e$T$_k$T$_k$ | 5-9-5 | kkekk | kkekk | 27 |
| 550914 | T$_k$C$_k$T$_k$T$_e$A$_k$A$_k$ATTGTCATCA$_k$C$_k$C$_e$A$_k$G$_k$A$_k$ | 6-9-6 | kkkekk | kkekkk | 28 |
| 550915 | C$_k$T$_k$T$_e$A$_k$A$_k$ATTGTCATCA$_k$C$_k$C$_e$A$_k$G$_k$ | 5-9-5 | kkekk | kkekk | 29 | e = 2'-MOE, k = cEt

TABLE 62

Comparison of selectivity in inhibition of HTT mRNA levels of chimeric oligonucleotides with ISIS 460209 targeted to rs7685686 in GM04022 cells

| | % UTC | | Selectivity | | wing chemistry | |
|---|---|---|---|---|---|---|
| ISIS NO | mut | wt | (wt vs. mut) | Motif | 5' | 3' |
| 460209* | 23 | 57 | 2.4 | 3-9-3 | ekk | kke |
| 544838 | 13 | 25 | 2.0 | 3-9-4 | ekk | kkek |
| 544840 | 17 | 31 | 1.8 | 3-9-6 | ekk | kkekkk |
| 544842 | 55 | 102 | 1.9 | 3-9-8 | ekk | kkekkkkk |
| 550903 | 13 | 36 | 2.7 | 3-9-5 | ekk | kkekk |
| 550904 | 23 | 67 | 3.0 | 3-9-7 | ekk | kkekkkk |
| 550905 | 21 | 51 | 2.4 | 4-9-3 | kekk | kke |
| 550906 | 23 | 67 | 2.9 | 5-9-3 | kkekk | kke |
| 550907 | 30 | 93 | 3.1 | 6-9-3 | kkkekk | kke |
| 550908 | 60 | 80 | 2.4 | 7-9-3 | kkkkekk | kke |
| 550909 | 42 | 101 | 2.4 | 8-9-3 | kkkkkekk | kke |
| 550910 | 57 | 102 | 1.8 | 6-9-6 | kkkekk | kkekkk |
| 550911 | 18 | 40 | 2.2 | 5-9-5 | kkekk | kkekk |
| 550912 | 14 | 51 | 3.6 | 6-9-6 | kkkekk | kkekkk |
| 550913 | 8 | 36 | 4.5 | 5-9-5 | kkekk | kkekk |
| 550914 | 29 | 45 | 1.5 | 6-9-6 | kkkekk | kkekkk |
| 550915 | 13 | 28 | 2.1 | 5-9-5 | kkekk | kkekk | e = 2'-MOE, k = cEt

Example 44

Chimeric Antisense Oligonucleotides Comprising Non-Self-Complementary Regions Targeting Huntingtin (HTT) Single Nucleotide Polymorphism (SNP)

Additional gapmers are designed based on the most selective gapmers from studies described in Tables 61 and 62 (ISIS 550912 and 550913). These gapmers are created such that they cannot form self-structure in the effort to evaluate if the increased activity simply is due to higher binding affinity. Gapmers are designed by deleting two or three nucleotides at the 3'-terminus and are created with 6-9-3 or 5-9-3 motif.

The chimeric oligonucleotides and their motifs are described in Table 63. The internucleoside linkages throughout each gapmer are phosphorothioate (P=S) linkages. All cytosine nucleobases throughout each gapmer are 5-methyl cytosines. Nucleosides without a subscript are β-D-2'-deoxyribonucleosides. Nucleosides followed by a subscript "e" or "k" are sugar modified nucleosides. A subscript "e" indicates a 2'-O-methoxyethyl (MOE) modified nucleoside and a subscript "k" indicates a 6'-(S)—CH₃ bicyclic nucleoside (e.g. cEt).

The gapmers, ISIS 550912 and ISIS 550913, from which the newly designed gapmers are derived from, are marked with an asterisk (*) in the table.

These gapmers were evaluated for thermal stability ($T_m$) using methods described in Example 42. Presented in Table 65 are the $T_m$ measurements for chimeric antisense oligonucleotides when duplexed to mutant or wild-type RNA complement. The $T_m$ of chimeric antisense oligonucleotides duplexed with mutant RNA complement is denoted as "$T_m$ (° C.) mut". The $T_m$ of chimeric antisense oligonucleotides duplexed with wild-type RNA complement is denoted as "$T_m$ (° C.) wt".

These gapmers were also tested in vitro. Heterozygous fibroblast GM04022 cell line was used. Cultured GM04022 cells at a density of 25,000 cells per well were transfected using electroporation with a single dose at 2 µM concentration of the modified oligonucleotide. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. HTT mRNA levels were adjusted according to total RNA content, as measured by RIBOGREEN. The results in Table 65 are presented as percent of HTT mRNA expression, relative to untreated control levels and is denoted as "% UTC". Selectivity was also evaluated and measured by dividing the percent of wild-type HTT mRNA levels vs. the percent of mutant HTT mRNA levels.

TABLE 63

Non-self-complementary chimeric oligonucleotides targeting HTT SNP

| ISIS NO | Sequence (5' to 3') | Motif | Wing chemistry 5' | Wing chemistry 3' | SEQ ID NO. |
|---|---|---|---|---|---|
| 550912* | $T_kA_kA_kT_eA_kA_k$ATTGTCATCA$_kC_kC_eT_kT_kA_k$ | 6-9-6 | kkkekk | kkekkk | 26 |
| 550913* | $A_kA_kT_eA_kA_k$ATTGTCATCA$_kC_kC_eT_kT_k$ | 5-9-5 | kkekk | kkekk | 27 |
| 556879 | $T_kA_kA_kT_eA_kA_k$ATTGTCATCA$_kC_kC_e$ | 6-9-3 | kkkekk | kke | 30 |
| 556880 | $A_kA_kT_eA_kA_k$ATTGTCATCA$_kC_kC_e$ | 5-9-3 | kkekk | kke | 31 | e = 2'-MOE, k = cEt

Example 45

Chimeric Oligonucleotides Containing Mismatches Targeting Huntingtin (HTT) Single Nucleotide Polymorphism (SNP)

A series of chimeric antisense oligonucleotides were designed based on the parent gapmer, ISIS 460209, wherein the central gap region contains nine 2'-deoxyribonucleosides. These gapmers were designed by introducing modified nucleosides at both 5' and 3' termini. Gapmers were also created with a single mismatch shifted slightly upstream and downstream (i.e. "microwalk") within the central gap region and with the SNP position opposite position 5 of the parent gapmer, as counted from the 5'-gap terminus.

The gapmers and their motifs are described in Table 64. The internucleoside linkages throughout each gapmer are phosphorothioate (P=S) linkages. All cytosine nucleobases throughout each gapmer are 5-methyl cytosines. Nucleosides without a subscript are β-D-2'-deoxyribonucleosides. Nucleosides followed by a subscript "e" or "k" are sugar modified nucleosides. A subscript "e" indicates a 2'-O-methoxyethyl (MOE) modified nucleoside and a subscript "k" indicates a 6'-(S)—CH₃ bicyclic nucleoside (e.g. cEt). Underlined nucleosides indicate the mismatch position, as counted from the 5'-gap terminus.

The parent gapmer, ISIS 460209 is marked with an asterisk (*) in the table and was included in the study as a benchmark oligonucleotide against which the selectivity of the modified oligonucleotides targeting nucleotides overlapping the SNP position could be compared.

As illustrated in Table 65, improvement in selectivity was observed for gapmers comprising a 4-9-4 motif with a central deoxy gap region (ISIS 476333) or a single mismatch at position 8 within the gap region (ISIS 543531) in comparison to the parent gapmer. The remaining gapmers showed moderate to little improvement in selectivity.

TABLE 64

Chimeric oligonucleotides containing a single mismatch targeting mutant HTT SNP

| ISIS NO | Sequence (5' to 3') | Mismatch position | Motif | Wing chemistry 5' | 3' | SEQ ID NO. |
|---|---|---|---|---|---|---|
| 460209* | $T_eA_kA_k$ATTGTCATCA$_kC_kC_e$ | — | 3-9-3 | ekk | kke | 10 |
| 476333 | $A_eT_eA_eA_k$ATTGTCATCA$_kC_eC_kA_e$ | — | 4-9-4 | ekek | keke | 32 |
| 543526 | $A_eT_eA_eA_k$ATT<u>C</u>TCATCA$_kC_eC_kA_e$ | 4 | 4-9-4 | ekek | keke | 33 |
| 543527 | $A_eT_eA_eA_k$AT<u>A</u>GTCATCA$_kC_eC_kA_e$ | 3 | 4-9-4 | ekek | keke | 34 |
| 543529 | $A_eT_eA_eA_k$ATTGT<u>G</u>ATCA$_kC_eC_kA_e$ | 6 | 4-9-4 | ekek | keke | 35 |
| 543530 | $A_eT_eA_eA_k$ATTGTC<u>TT</u>CA$_kC_eC_kA_e$ | 7 | 4-9-4 | ekek | keke | 36 |
| 543531 | $A_eT_eA_eA_k$ATTGTCA<u>A</u>CA$_kC_eC_kA_e$ | 8 | 4-9-4 | ekk | keke | 37 |
| 543532 | $T_eA_kA_k$ATT<u>C</u>TCATCA$_kC_kC_e$ | 4 | 3-9-3 | ekk | kke | 38 |
| 543534 | $T_eA_kA_k$A<u>A</u>TGTCATCA$_kC_kC_e$ | 2 | 3-9-3 | ekk | kke | 39 |
| 543535 | $T_eA_kA_k$ATTGT<u>G</u>ATCA$_kC_kC_e$ | 6 | 3-9-3 | ekk | kke | 40 |
| 543536 | $T_eA_kA_k$ATTGTC<u>TT</u>CA$_kC_kC_e$ | 7 | 3-9-3 | ekk | kke | 41 |
| 543537 | $T_eA_kA_k$ATTGTCA<u>A</u>CA$_kC_kC_e$ | 8 | 3-9-3 | ekk | kke | 42 | e = 2'-MOE, k = cEt

TABLE 65

Comparison of selectivity and $T_m$ of chimeric oligonucleotides with ISIS 460209 targeted to rs7685686 in GM04022 cells

| | Tm (° C.) | | % UTC | | Selectivity | Mismatch | | Wing chemistry | |
|---|---|---|---|---|---|---|---|---|---|
| ISIS NO | mut | wt | mut | wt | (wt vs mut) | position | Motif | 5' | 3' |
| 460209* | 53.7 | 52.2 | 23 | 57 | 2.4 | — | 3-9-3 | ekk | kke |
| 476333 | 60.2 | 58.4 | 10 | 37 | 3.6 | — | 4-9-4 | ekek | keke |
| 543526 | 47.9 | 46.6 | 70 | 86 | 1.2 | 4 | 4-9-4 | ekek | keke |
| 543527 | 52.6 | 49.9 | 40 | 103 | 2.6 | 3 | 4-9-4 | ekek | keke |
| 543529 | 50.3 | 49.0 | 66 | 102 | 1.5 | 6 | 4-9-4 | ekek | keke |
| 543530 | 52.9 | 50.9 | 67 | 110 | 1.6 | 7 | 4-9-4 | ekek | keke |
| 543531 | 53.3 | 50.3 | 46 | 136 | 3.0 | 8 | 4-9-4 | ekk | keke |
| 543532 | 43.6 | 42.8 | 127 | 151 | 1.2 | 4 | 3-9-3 | ekk | kke |
| 543534 | 45.9 | 43.8 | 67 | 95 | 1.4 | 2 | 3-9-3 | ekk | kke |
| 543535 | 44.0 | 43.3 | 96 | 113 | 1.2 | 6 | 3-9-3 | ekk | kke |
| 543536 | 46.8 | 44.6 | 106 | 104 | 1.0 | 7 | 3-9-3 | ekk | kke |
| 543537 | 45.9 | 44.3 | 77 | 81 | 1.1 | 8 | 3-9-3 | ekk | kke | e = 2'-MOE, k = cEt

Example 46

Chimeric Oligonucleotides Comprising Mismatches Targeting Huntingtin (HTT) Single Nucleotide Polymorphism (SNP)

Additional chimeric antisense oligonucleotides are designed based on two gapmers selected from studies described in Tables 64 and 65 (ISIS 476333 and ISIS 460209) wherein the central gap region contains nine 2'-deoxyribonucleosides. These gapmers are designed by introducing a single mismatch, wherein the mismatch will be shifted throughout the antisense oligonucleotide (i.e. "microwalk"). Gapmers are also created with 4-9-4 or 3-9-3 motifs and with the SNP position opposite position 8 of the original gapmers, as counted from the 5'-terminus.

The gapmers and their motifs are described in Table 66. The internucleoside linkages throughout each gapmer are phosphorothioate (P=S) linkages. All cytosine nucleobases throughout each gapmer are 5-methyl cytosines. Nucleosides without a subscript are β-D-2'-deoxyribonucleosides. Nucleosides followed by a subscript "e" or "k" are sugar modified nucleosides. A subscript "e" indicates a 2'-O-methoxyethyl (MOE) modified nucleoside and a subscript "k" indicates a 6'-(S)—CH$_3$ bicyclic nucleoside (e.g. cEt). Underlined nucleosides indicate the mismatch position, as counted from the 5'-terminus.

The gapmers, ISIS 476333 and ISIS 460209, in which the newly designed antisense oligonucleotides are derived from, are marked with an asterisk (*) in the table.

TABLE 66

Chimeric oligonucleotides comprising mismatches targeting HTT SNP

| ISIS NO | Sequence (5' to 3') | Mismatch position | Motif | Wing chemistry 5' | 3' | SEQ ID NO |
|---|---|---|---|---|---|---|
| 476333* | $A_eT_kA_eA_k$ATTGTCATCA$_kC_eC_kA_e$ | — | 4-9-4 | ekek | keke | 32 |
| 554209 | $\underline{T}_eT_kA_eA_k$ATTGTCATCA$_kC_eC_kA_e$ | 1 | 4-9-4 | ekek | keke | 43 |
| 554210 | $A_e\underline{A}_kA_eA_k$ATTGTCATCA$_kC_eC_kA_e$ | 2 | 4-9-4 | ekek | keke | 44 |
| 554211 | $A_eT_k\underline{T}_eA_k$ATTGTCATCA$_kC_eC_kA_e$ | 3 | 4-9-4 | ekek | keke | 45 |
| 554212 | $A_eT_kA_e\underline{T}_k$ATTGTCATCA$_kC_eC_kA_e$ | 4 | 4-9-4 | ekek | keke | 46 |
| 554213 | $A_eT_kA_eA_k\underline{T}$TTGTCATCA$_kC_eC_kA_e$ | 5 | 4-9-4 | ekek | keke | 47 |
| 554214 | $A_eT_kA_eA_k$ATTGTCAT$\underline{GA}_kC_eC_kA_e$ | 13 | 4-9-4 | ekek | keke | 48 |
| 554215 | $A_eT_kA_eA_k$ATTGTCATC$\underline{T}_kC_eC_kA_e$ | 14 | 4-9-4 | ekek | keke | 49 |
| 554216 | $A_eT_kA_eA_k$ATTGTCATCA$_k\underline{G}_eC_kA_e$ | 15 | 4-9-4 | ekek | keke | 50 |
| 554217 | $A_eT_kA_eA_k$ATTGTCATCA$_kC_e\underline{G}_kA_e$ | 16 | 4-9-4 | ekek | keke | 51 |
| 554218 | $A_eT_kA_eA_k$ATTGTCATCA$_kC_eC_k\underline{T}_e$ | 17 | 4-9-4 | ekek | keke | 52 |
| 460209* | $T_eA_kA_k$ATTGTCATCA$_kC_kC_e$ | — | 3-9-3 | ekk | kke | 10 |
| 562481 | $T_eA_kA_k\underline{G}$TTGTCATCA$_kC_kC_e$ | 4 | 3-9-3 | ekk | kke | 53 |
| 554482 | $T_eA_kA_kA\underline{G}$TGTCATCA$_kC_kC_e$ | 5 | 3-9-3 | ekk | kke | 54 |
| 554283 | $T_eA_kA_kAT\underline{GG}$TCATCA$_kC_kC_e$ | 6 | 3-9-3 | ekk | kke | 55 | e = 2'-MOE, k = cEt

Example 47

Short-Gap Chimeric Oligonucleotides Targeting Huntingtin (HTT) Single Nucleotide Polymorphism (SNP)

Chimeric antisense oligonucleotides were designed based on the parent gapmer, ISIS 460209, wherein the central gap region contains nine 2'-deoxyribonucleosides. These gapmers were designed by shortening the central gap region to seven 2'-deoxyribonucleosides. Gapmers were also created with 5-7-5 motif and with the SNP position opposite position 8 or 9 of the parent gapmer, as counted from the 5'-terminus.

The gapmers and their motifs are described in Table 67. The internucleoside linkages throughout each gapmer are phosphorothioate (P=S) linkages. All cytosine nucleobases throughout each gapmer are 5-methyl cytosines. Nucleosides without a subscript are β-D-2'-deoxyribonucleosides. Nucleosides followed by a subscript "e" or "k" are sugar modified nucleosides. A subscript "e" indicates a 2'-O-methoxyethyl (MOE) modified nucleoside and a subscript "k" indicates a 6'-(S)—CH₃ bicyclic nucleoside (e.g. cEt). Underlined nucleoside or the number in parentheses indicates the position on the modified oligonucleotide opposite to the SNP position, as counted from the 5'-terminus.

The chimeric antisense oligonucleotides were tested in vitro. ISIS 141923 was included in the study as a negative control and is denoted as "neg control". A non-allele specific antisense oligonucleotide, ISIS 387916 was used as a positive control and is denoted as "pos control". ISIS 460209 was included in the study for comparison. Heterozygous fibroblast GM04022 cell line was used. Cultured GM04022 cells at a density of 25,000 cells per well were transfected using electroporation with 0.12, 0.37, 1.1, 3.3, and 10 μM concentration of the modified oligonucleotide. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. HTT mRNA levels were adjusted according to total RNA content, as measured by RIBOGREEN and the results are presented in Table 68.

The $IC_{50}$ and selectivity were calculated using methods described previously in Example 41. As illustrated in Table 68, no improvement in potency and selectivity was observed for the chimeric antisense oligonucleotides as compared to ISIS 460209.

TABLE 67

Chimeric antisense oligonucleotides targeting HTT rs7685686

| ISIS NO | Sequence (5' to 3') | Motif | Wing Chemistry 5' | 3' | SEQ ID NO. |
|---|---|---|---|---|---|
| 460209* (8) | $T_eA_kA_k$ATTG$\underline{T}$CATCA$_kC_kC_e$ | 3-9-3 | ekk | kke | 10 |
| 460085 (9) | $A_eT_eA_eA_e$TTG$\underline{T}$CATC$_eA_eC_eC_eA_e$ | 5-7-5 | eeeee | eeeee | 32 |
| 540108 (9) | $A_eT_eA_eA_kA_k$TTG$\underline{T}$CATC$_kA_kC_eC_eA_e$ | 5-7-5 | eeekk | kkeee | 32 |
| 387916 (pos control) | $T_eC_eT_eC_eT_e$ATTGCACATTC$_eC_eA_eA_eG_e$ | 5-10-5 | eeeee | eeeee | 56 |
| 141923 (neg control) | $C_eC_eT_eT_eC_e$CCTGAAGGTTC$_eC_eT_eC_eC_e$ | 5-10-5 | eeeee | eeeee | 57 | e = 2'-MOE, k = cEt

TABLE 68

Comparison of inhibition of HTT mRNA levels and selectivity of chimeric antisense oligonucleotides with ISIS 460209 targeted to rs7685686 in GM04022 cells

| ISIS NO | Mut IC$_{50}$ (μM) | Wt IC$_{50}$ (μM) | Selectivity (mut vs wt) | Motif | Wing chemistry 5' | 3' |
|---|---|---|---|---|---|---|
| 460209* (8) | 0.41 | 2.0 | 4.9 | 3-9-3 | ekk | kke |
| 460085 (9) | 3.5 | >10 | >3 | 5-7-5 | eeeee | eeeee |
| 540108 (9) | 0.41 | — | — | 5-7-5 | eeekk | kkeee |
| 387916 (pos control) | 0.39 | 0.34 | 1.0 | 5-10-5 | eeeee | eeeee |
| 141923 (neg control) | >10 | >10 | — | 5-10-5 | eeeee | eeeee | e = 2'-MOE,
k = cEt

Example 48

Short-Gap Chimeric Oligonucleotides Targeting Huntingtin (HTT) Single Nucleotide Polymorphism (SNP)

Additional chimeric antisense oligonucleotides were designed based on the parent gapmer, ISIS 460209, wherein the central gap region contains nine 2'-deoxyribonucleosides. These gapmers were designed with the central gap region shortened or interrupted by introducing various modifications either within the gap or by adding one or more modified nucleosides to the 3'-most 5'-region or to the 5'-most 3'-region. Gapmers were created with the SNP position opposite position 8 of the parent gapmer, as counted from the 5'-terminus.

The gapmers and their motifs are described in Table 69. The internucleoside linkages throughout each gapmer are phosphorothioate (P=S) linkages. All cytosine nucleobases throughout each gapmer are 5-methyl cytosines. Nucleosides without a subscript are β-D-2'-deoxyribonucleosides. Nucleosides followed by a subscript "e" or "k" are sugar modified nucleosides. A subscript "e" indicates a 2'-O-methoxyethyl (MOE) modified nucleoside and a subscript "k" indicates a 6'-(S)—CH$_3$ bicyclic nucleoside (e.g. cEt).

The chimeric antisense oligonucleotides were tested in vitro. Heterozygous fibroblast GM04022 cell line was used. Cultured GM04022 cells at a density of 25,000 cells per well were transfected using electroporation with 2 μM concentration of the modified oligonucleotide. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. HTT mRNA levels were adjusted according to total RNA content, as measured by RIBOGREEN. The results in Table 70 are presented as percent of HTT mRNA expression, relative to untreated control levels and is denoted as "% UTC". Selectivity was also evaluated and measured by dividing the percent of wild-type HTT mRNA levels vs. the percent of mutant HTT mRNA levels. ISIS 460209 marked with an asterisk (*) in the table was included in the study for comparison.

As illustrated in Table 70, modifications to the 3'-most 5'-region nucleosides that shorten the gap from 9 to 7 or 8 nucleotides (ISIS 551429 and ISIS 551426) improved selectivity and potency comparing to the parent gapmer (ISIS 460209). The remaining chimeric antisense oligonucleotides showed moderate to little improvement in selectivity.

TABLE 69

Short-gap antisense oligonucleotides targeting HTT rs7685686

| ISIS NO | Sequence (5' to 3') | Motif | Wing Chemistry 5' | 3' | SEQ ID NO. |
|---|---|---|---|---|---|
| 460209* | $T_eA_kA_k$ATTGTCATCA$_kC_kC_e$ | 3-9-3 | ekk | kke | 10 |
| 551426 | $T_eA_kA_eA_k$TTGTCATCA$_kC_kC_e$ | 4-8-3 | ekek | kke | 10 |

TABLE 69-continued

Short-gap antisense oligonucleotides targeting HTT rs7685686

| ISIS NO | Sequence (5' to 3') | Motif | Wing Chemistry 5' | 3' | SEQ ID NO. |
|---|---|---|---|---|---|
| 551427 | $T_eA_kA_eAT_k$TGTCATCA$_kC_kC_e$ | 3-9-3 or 5-7-3 | eke or ekedk | kke | 10 |
| 551428 | $T_eA_kA_eATT_k$GTCATCA$_kC_kC_e$ | 3-9-3 or 6-6-3 | eke or ekeddk | kke | 10 |
| 551429 | $T_eA_kA_kA_kT_k$TGTCATCA$_kC_kC_e$ | 5-7-3 | eeekk | kke | 10 | e = 2'-MOE, k = cEt, d = 2'-deoxyribonucleoside

TABLE 70

Comparison of selectivity in inhition of HTT mRNA levels of antisense oligonucleotides with ISIS 460209 targeted to rs7685686 in GM4022 cells

| | % UTC | | Selectivity | | Wing chemistry | |
|---|---|---|---|---|---|---|
| ISIS NO | mut | wt | (wt vs. mut) | Motif | 5' | 3' |
| 460209* | 23 | 57 | 2.4 | 3-9-3 | ekk | kke |
| 551426 | 14 | 66 | 4.8 | 4-8-3 | ekek | kke |
| 551427 | 35 | 97 | 2.8 | 3-9-3 or 5-7-3 | eke or ekedk | kke |
| 551428 | 61 | 110 | 1.8 | 3-9-3 or 6-6-3 | eke or ekeddk | kke |
| 551429 | 19 | 94 | 5.0 | 5-7-3 | eeekk | kke | e = 2'-MOE,
k = cEt,
d = 2'-deoxyribonucleoside

Example 49

Modified Oligonucleotides Targeting HTT SNP

A series of modified antisense oligonucleotides are designed based on the parent gapmer, ISIS 460209, wherein the central gap region contains nine 2'-deoxynucleosides and is marked with an asterisk (*) in the table. These modified oligonucleotides are designed by shortening or interrupting the gap with a single mismatch or various chemical modifications within the central gap region. The modified oligonucleotides are created with the SNP position opposite position 8 of the parent gapmer, as counted from the 5'-terminus.

The gapmers and their motifs are described in Table 71. The internucleoside linkages throughout each gapmer are phosphorothioate (P=S) linkages, except for the internucleoside linkage with a subscript "p", "pz" or "pw". Subscript "p" indicates methyl phosphonate internucleoside linkage. Subscript "pz" indicates (R)-methyl phosphonate internucleoside linkage. Subscript "pw" indicates (S)-methyl phosphonate internucleoside linkage. All cytosine nucleobases throughout each gapmer are 5-methyl cytosines. $^xT$ indicates a 2-thio thymidine nucleoside. Nucleosides without a subscript are β-D-2'-deoxyribonucleosides. Nucleosides followed by a subscript "e", "k" or "b" are sugar modified nucleosides. A subscript "e" indicates a 2'-O-methoxyethyl (MOE) modified nucleoside, a subscript "k" indicates a 6'-(S)—$CH_3$ bicyclic nucleoside (e.g. cEt) and a subscript "b" indicates a 5'-Me DNA modified nucleoside. Underlined nucleosides indicate the position of modification. Bold and underlined nucleosides indicate the mismatch position.

TABLE 71

Short-gap chimeric oligonucleotides targeting HTT SNP

| ISIS NO | Sequence (5' to 3') | Motif | Gap Chemistry | Wing Chemistry 5' | 3' | SEQ ID NO. |
|---|---|---|---|---|---|---|
| 460209* | $T_eA_kA_k$ATTGTCATCA$_kC_kC_e$ | 3-9-3 | — | ekk | kke | 10 |
| XXXX16 | $T_eA_kA_kA^xTTGT$CATCA$_kC_kC_e$ | 3-9-3 | Deoxy/2-thio | ekk | kke | 10 |
| XXXX17 | $T_eA_kA_kAT^xTGT$CATCA$_kC_kC_e$ | 3-9-3 | Deoxy/2-thio | ekk | kke | 10 |
| XXXX18 | $T_eA_kA_kA^xT^xTGT$CATCA$_kC_kC_e$ | 3-9-3 | Deoxy/2-thio | ekk | kke | 10 |
| XXXX19 (558257) | $T_eA_kA_kATT_p$GTCATCA$_kC_kC_e$ | 3-9-3 | Deoxy/Methyl phosphonate | ekk | kke | 10 |
| XXXX20 (558256) | $T_eA_kA_kAT_p$TGTCATCA$_kC_kC_e$ | 3-9-3 | Deoxy/Methyl phosphonate | ekk | kke | 10 |
| XXXX20a | $T_eA_kA_kAT_{pz}$TGTCATCA$_kC_kC_e$ | 3-9-3 | Deoxy/(R)-Methyl phosphonate | ekk | kke | 10 |

TABLE 71-continued

Short-gap chimeric oligonucleotides targeting HTT SNP

| ISIS NO | Sequence (5' to 3') | Motif | Gap Chemistry | Wing Chemistry 5' | Wing Chemistry 3' | SEQ ID NO. |
|---|---|---|---|---|---|---|
| XXXX20b | $T_eA_kA_kAT_{pw}TG$ $TCATCA_k\overline{C}_kC_e$ | 3-9-3 | Deoxy/(S)-Methyl phosphonate | ekk | kke | 10 |
| XXXX21 (558255) | $T_eA_kA_kA_pTTGT$ $CATCA_k\overline{C}_kC_e$ | 3-9-3 | Methyl phosphonate | ekk | kke | 10 |
| XXXX22 | $T_eA_kA_kATT_bGT$ $CATCA_kC_k\overline{C}_e$ | 3-9-3 | 5'-Me-DNA | ekk | kke | 10 |
| XXXX23 | $T_eA_kA_kAT_bTGT$ $CATCA_k\overline{C}_kC_e$ | 3-9-3 | 5'-Me-DNA | ekk | kke | 10 |
| XXXX24 | $T_eA_kA_kA_bTTGT$ $CATCA_{\overline{k}}C_kC_e$ | 3-9-3 | 5'-Me-DNA | ekk | kke | 10 |
| XXXX25 | $T_eA_kA_k\underline{G}TTGTC$ $ATCA_kC_kC_e$ | 4-8-3 | Mismatch at position 4 | ekk | kke | 53 |
| XXXX26 | $T_eA_kA_k\underline{A}GTGT$ $CATCA_kC_kC_e$ | 5-7-3 | Mismatch at position 5 | ekk | kke | 54 |
| XXXX27 | $T_eA_kA_kAT\underline{G}GT$ $CATCA_kC_kC_e$ | 6-6-3 | Mismatch at position 6 | ekk | kke | 55 | e = 2'-MOE, k = cEt

Example 50

Short-Gap Chimeric Oligonucleotides Comprising Modifications at the Wing Regions Targeting Huntingtin (HTT) Single Nucleotide Polymorphism (SNP)

Additional chimeric antisense oligonucleotides were designed based on the parent gapmer, ISIS 460209, wherein the central gap region contains nine 2'-deoxynucleosides. These gapmers were designed by shortening the central gap region to seven 2'-deoxynucleosides and introducing various modifications at the wing regions.

The gapmers and their motifs are described in Table 72. The internucleoside linkages throughout each gapmer are phosphorothioate (P=S) linkages. All cytosine nucleobases throughout each gapmer are 5-methyl cytosines. Nucleosides without a subscript are β-D-2'-deoxyribonucleosides. Nucleosides followed by a subscript "e" or "k" are sugar modified nucleosides. A subscript "e" indicates a 2'-O-methoxyethyl (MOE) modified nucleoside and a subscript "k" indicates a 6'-(S)—CH₃ bicyclic nucleoside (e.g. cEt).

The number in parentheses indicates the position on the chimeric oligonucleotide opposite to the SNP position, as counted from the 5'-terminus.

These gapmers were evaluated for thermal stability ($T_m$) using methods described in Example 42. Presented in Table 73 is the $T_m$ measurements for chimeric antisense oligonucleotides when duplexed to mutant or wild-type RNA complement. The $T_m$ of chimeric antisense oligonucleotides duplexed with mutant RNA complement is denoted as "$T_m$ (° C.) mut". The $T_m$ of chimeric antisense oligonucleotides duplexed with wild-type RNA complement is denoted as "$T_m$ (° C.) wt".

These gapmers were also tested in vitro. Heterozygous fibroblast GM04022 cell line was used. Cultured GM04022 cells at a density of 25,000 cells per well were transfected using electroporation with a single dose at 2 μM concentration of the modified oligonucleotide. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. HTT mRNA levels were adjusted according to total RNA content, as measured by RIBOGREEN. The results in Table 73 are presented as percent of HTT mRNA expression, relative to untreated control levels and is denoted as "% UTC". Selectivity was also evaluated and measured by dividing the percent of wild-type HTT mRNA levels vs. the percent of mutant HTT mRNA levels. ISIS 460209 marked with an asterisk (*) in the table was included in the study for comparison.

As illustrated in Table 73, improvement in selectivity was observed for gapmers comprising 2-7-8 or 5-7-5 motifs having cEt subunits at the wing regions in comparison to the parent gapmer, ISIS 460209. The remaining gapmers showed moderate to little improvement in selectivity.

TABLE 72

Short-gap chimeric oligonucleotides comprising wing modifications

| ISIS NO | Sequence (5' to 3') | Motif | wing chemistry 5' | 3' | SEQ ID NO. |
|---|---|---|---|---|---|
| 460209* (8) | $T_eA_kA_k$ATTGTCATCA$_kC_kC_e$ | 3-9-3 | ekk | kke | 10 |
| 540103 (6) | $A_kA_k$TTGTCATC$_eA_eC_eC_eA_eG_eA_eA_e$ | 2-7-8 | kk | e8 | 58 |
| 540104 (6) | $A_eA_e$TTGTCATC$_eA_eC_eC_eA_eG_eA_eA_e$ | 2-7-8 | ee | e8 | 59 |
| 540105 (7) | $A_eA_eA_e$TTGTCATC$_eA_eC_eC_eA_eG_eA_e$ | 3-7-7 | eee | e7 | 60 |
| 540106 (8) | $T_eA_eA_eA_e$TTGTCATC$_eA_eC_eC_eA_eG_e$ | 4-7-6 | eeee | e6 | 61 |
| 540107 (9) | $A_eT_eA_eA_eA_k$TTGTCATC$_kA_eC_eC_eA_e$ | 5-7-5 | eeeek | keeee | 32 |
| 540109 (10) | $A_eA_eT_eA_eA_eA_e$TTGTCATC$_eA_eC_eC_e$ | 6-7-4 | e6 | e4 | 62 |
| 540110 (11) | $T_eA_eA_eT_eA_eA_eA_e$TTGTCATC$_eA_eC_e$ | 7-7-3 | e7 | eee | 63 |
| 540111 (12) | $T_eT_eA_eA_eT_eA_eA_eA_e$TTGTCATC$_eA_e$ | 8-7-2 | e8 | ee | 64 |
| 540112 (12) | $T_eT_eA_eA_eT_eA_eA_eA_e$TTGTCATC$_kA_k$ | 8-7-2 | e8 | kk | 64 | e = 2'-MOE (e.g. e6 = eeeeee), and k = cEt

TABLE 73

Comparison of selectivity in inhibition of HTT mRNA levels of antisense oligonucleotides with ISIS 460209 targeted to RS7685686 in GM04022 cells

| | Tm (° C.) | | % UTC | | Selectivity (wt vs mut) | Motif | wing chemistry 5' | 3' |
|---|---|---|---|---|---|---|---|---|
| ISIS NO | mut | wt | mut | wt | | | | |
| 460209* (8) | 53.7 | 52.2 | 23 | 57 | 2.4 | 3-9-3 | ekk | kke |
| 540103 (6) | 57.6 | 56.4 | 23 | 74 | 3.3 | 2-7-8 | kk | e8 |
| 540104 (6) | 54.8 | 52.8 | 36 | 91 | 2.5 | 2-7-8 | ee | e8 |
| 540105 (7) | 54.2 | 52.2 | 53 | 135 | 2.6 | 3-7-7 | eee | e7 |
| 540106 (8) | 52.4 | 50.8 | 30 | 77 | 2.6 | 4-7-6 | eeee | e6 |
| 540107 (9) | 56.6 | 54.7 | 19 | 62 | 3.3 | 5-7-5 | eeeek | keeee |
| 540109 (10) | 49.1 | 47.3 | 78 | 127 | 1.6 | 6-7-4 | e6 | e4 |
| 540110 (11) | 42.8 | 41.2 | 89 | 112 | 1.3 | 7-7-3 | e7 | eee |
| 540111 (12) | 39.0 | 36.9 | 111 | 128 | 1.1 | 8-7-2 | e8 | ee |
| 540112 (12) | 44.2 | 42.4 | 86 | 102 | 1.2 | 8-7-2 | e8 | kk |

Example 51

Chimeric Oligonucleotides with SNP Site Shifting within the Central Gap Region

Chimeric antisense oligonucleotides were designed based on the parent gapmer, ISIS 460209 wherein the SNP site aligns with position 5 of the parent gapmer, as counted from the 5'-gap terminus. These gapmers were designed by shifting the SNP site upstream or downstream (i.e. microwalk) within the central gap region of the parent gapmer.

The gapmers and their motifs are described in Table 74. The internucleoside linkages throughout each gapmer are phosphorothioate (P=S) linkages. All cytosine nucleobases throughout each gapmer are 5-methyl cytosines. Nucleosides without a subscript are β-D-2'-deoxyribonucleosides. Nucleosides followed by a subscript "e" or "k" are sugar modified nucleosides. A subscript "e" indicates a 2'-O-methoxyethyl (MOE) modified nucleoside and a subscript "k" indicates a 6'-(S)—CH$_3$ bicyclic nucleoside (e.g. cEt). Underline nucleosides indicate the position on the chimeric oligonucleotide aligns with the SNP site.

The SNP site indicates the position on the chimeric antisense oligonucleotide opposite to the SNP position, as counted from the 5'-gap terminus and is denoted as "SNP site".

The chimeric oligonucleotides were tested in vitro. Heterozygous fibroblast GM04022 cell line was used. Cultured GM04022 cells at a density of 25,000 cells per well were transfected using electroporation with 0.12, 0.37, 1.1, 3.3 and 10 µM concentrations of modified oligonucleotides. After a treatment period of approximately 16 hours, RNA was isolated from the cells and mRNA levels were measured by quantitative real-time PCR using ABI assay C_2229297_10 which measures at dbSNP rs362303. The HTT mRNA levels were adjusted according to total RNA content, as measured by RIBOGREEN. ISIS 460209 marked with an asterisk (*) in the table was included in the study for comparison.

The IC$_{50}$ and selectivity were calculated using the methods previously described in Example 41. As illustrated in Table 75, chimeric oligonucleotides comprising 4-9-2 (ISIS 540082) or 2-9-4 (ISIS 540095) motif with the SNP site at position 1 or 3 showed comparable activity and 2.5 fold selectivity as compared to their counterparts.

TABLE 74

Chimeric oligonucleotides designed by microwalk

| ISIS NO | Sequence (5' to 3') | Motif | SNP site | Wing chemistry 5' | 3' | SEQ ID NO. |
|---|---|---|---|---|---|---|
| 460209* | $T_eA_kA_k$ATTGTCATCA$_kC_kC_e$ | 3-9-3 | 5 | ekk | kke | 10 |
| 540082 | $A_eT_kT_kG_k\underline{T}$CATCACCAG$_kA_e$ | 4-9-2 | 1 | ekkk | ke | 65 |
| 540089 | $T_eT_kA_kA_k$TAAATTG$\underline{T}$CA$_kT_e$ | 4-9-2 | 8 | ekkk | ke | 66 |
| 540095 | $A_eT_k$TG$\underline{T}$CATCACC$_kA_kG_kA_e$ | 2-9-4 | 3 | ek | kkke | 65 | e = 2'-MOE, and k = cEt

TABLE 75

Comparison of inhibition of HTT mRNA levels and selectivity of chimeric oligonucleotides with ISIS 460209 targeted to HTT SNP

| ISIS NO | Mut IC$_{50}$ (µM) | Wt IC$_{50}$ (µM) | Selectivity (wt vs mut) | Motif | SNP site | Wing chemistry 5' | 3' |
|---|---|---|---|---|---|---|---|
| 460209 | 0.41 | 2.0 | 4.9 | 3-9-3 | 5 | ekk | kke |
| 540082 | 0.45 | 5.6 | 12 | 4-9-2 | 1 | ekkk | ke |
| 540089 | >10 | >10 | — | 4-9-2 | 8 | ekkk | ke |
| 540095 | 0.69 | 8.4 | 12 | 2-9-4 | 3 | ek | kkke | e = 2'-MOE, and k = cEt

Example 52

Chimeric Oligonucleotides with SNP Site Shifting at Various Positions

Chimeric antisense oligonucleotides were designed based on the parent gapmer, ISIS 460209 wherein the SNP site aligns with position 8 of the parent gapmer, as counted from the 5'-terminus. These gapmers were designed by shifting the SNP site upstream or downstream (i.e. microwalk) of the original oligonucleotide.

The gapmers and their motifs are described in Table 76. The internucleoside linkages throughout each gapmer are phosphorothioate (P=S) linkages. All cytosine nucleobases throughout each gapmer are 5-methyl cytosines. Nucleosides without a subscript are β-D-2'-deoxyribonucleosides. Nucleosides followed by a subscript "e" or "k" are sugar modified nucleosides. A subscript "e" indicates a 2'-O-methoxyethyl (MOE) modified nucleoside and a subscript "k" indicates a 6'-(S)—CH$_3$ bicyclic nucleoside (e.g. cEt). Underline nucleosides indicate the SNP site.

The SNP site indicates the position on the chimeric antisense oligonucleotide opposite to the SNP position, as counted from the 5'-terminus and is denoted as "SNP site".

The chimeric oligonucleotides were tested in vitro. Heterozygous fibroblast GM04022 cell line was used. Cultured GM04022 cells at a density of 25,000 cells per well were transfected using electroporation with 0.12, 0.37, 1.1, 3.3 and 10 µM concentrations of modified oligonucleotides. After a treatment period of approximately 16 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. HTT mRNA levels were adjusted according to total RNA content, as measured by RIBOGREEN. The results in Table 77 are presented as percent of HTT mRNA expression, relative to untreated control levels and is denoted as "% UTC". Selectivity was also evaluated and measured by dividing the percent of wild-type HTT mRNA levels vs. the percent of mutant HTT mRNA levels.

The parent gapmer, ISIS 460209 is marked with an asterisk (*) in the table and was included in the study as a benchmark oligonucleotide against which the selectivity of the modified oligonucleotides targeting nucleotides overlapping the SNP position could be compared.

As illustrated in Table 77, improvement in potency and selectivity was observed for chimeric oligonucleotides comprising 4-9-2 or 2-9-4 motif having the target SNP site at positions 3, 4, 6, 7 and 8 (ISIS540083, ISIS540084, ISIS 540085, ISIS 540094, ISIS 540096, ISIS 540097 and ISIS 540098) in comparison to position 8 of the parent gapmer (ISIS 460209). The remaining gapmers showed little to no improvement in potency or selectivity.

TABLE 76

Chimeric oligonucleotides designed by microwalk

| ISIS NO | Sequence (5' to 3') | SNP site | Motif | SEQ ID NO. |
|---|---|---|---|---|
| 460209* | $T_eA_kA_k$ATTG$\underline{T}$CATCA$_kC_kC_e$ | 8 | 3-9-3 (ekk-d9-kke) | 10 |
| 543887 | $T_eT_kG_kT_k$CATCACCAGA$_kA_e$ | 4 | 4-9-2 (ekkk-d9-ke) | 67 |
| 540083 | $A_eA_kT_kT_k$G$\underline{T}$CATCACCA$_kG_e$ | 6 | 4-9-2 (ekkk-d9-ke) | 68 |

TABLE 76-continued

Chimeric oligonucleotides designed by microwalk

| ISIS NO | Sequence (5' to 3') | SNP site | Motif | SEQ ID NO. |
|---|---|---|---|---|
| 540084 | $A_eA_kA_kT_k$TGTCATCACC$_k$A$_e$ | 7 | 4-9-2 (ekkk-d9-ke) | 69 |
| 540085 | $T_eA_kA_kA_k$TTG$\underline{T}$CATCAC$_k$C$_e$ | 8 | 4-9-2 (ekkk-d9-ke) | 10 |
| 540087 | $A_eA_kT_kA_k$AATTG$\underline{T}$CATC$_k$A$_e$ | 10 | 4-9-2 (ekkk-d9-ke) | 70 |
| 540090 | $A_eT_kT_kA_k$ATAAATTG$\underline{T}$C$_k$A$_e$ | 13 | 4-9-2 (ekkk-d9-ke) | 71 |
| 540091 | $T_eA_kT_kT_k$AATAAATTGT$_k$C$_e$ | 14 | 4-9-2 (ekkk-d9-ke) | 72 |
| 540092 | $G_eT_k$CATCACCAGA$_kA_kA_k$A$_e$ | 2 | 2-9-4 (ek-d9-kkke) | 73 |
| 540093 | $T_eG_k\underline{T}$CATCACCAG$_kA_kA_k$A$_e$ | 3 | 2-9-4 (ek-d9-kkke) | 74 |
| 540094 | $T_eT_k$G$\underline{T}$CATCACCA$_kG_kA_k$A$_e$ | 4 | 2-9-4 (ek-d9-kkke) | 67 |
| 540096 | $A_eA_k$TTG$\underline{T}$CATCAC$_kC_kA_k$G$_e$ | 6 | 2-9-4 (ek-d9-kkke) | 68 |
| 540097 | $A_eA_k$ATTGTCATCA$_kC_kC_k$A$_e$ | 8 | 2-9-4 (ek-d9-kkke) | 69 |
| 540098 | $T_eA_k$AATTGTCATC$_kA_kC_k$C$_e$ | 8 | 2-9-4 (ek-d9-kkke) | 10 |
| 540099 | $A_eT_k$AAATTGTCAT$_kC_kA_k$C$_e$ | 9 | 2-9-4 (ek-d9-kkke) | 75 |
| 540100 | $A_eA_k$TAAATTGTCA$_kT_kC_k$A$_e$ | 10 | 2-9-4 (ek-d9-kkke) | 70 |
| 540101 | $T_eA_k$ATAAATTGT$\underline{C}_kA_kT_k$C$_e$ | 11 | 2-9-4 (ek-d9-kkke) | 76 |
| 540102 | $T_eT_k$AATAAATTGT$_kC_kA_k$T$_e$ | 12 | 2-9-4 (ek-d9-kkke) | 66 | e = 2'-MOE; k = cEt; d = 2'-deoxyribonucleoside

TABLE 77

Comparison of selectivity in HTT SNP inhibition of chimeric oligonucleotides with ISIS 460209

| ISIS NO | % UTC mut | % UTC wt | Selectivity (wt vs. mut) | SNP site | Motif |
|---|---|---|---|---|---|
| 460209* | 23 | 57 | 2.4 | 8 | 3-9-3 (ekk-d9-kke) |
| 543887 | 18 | 43 | 2.3 | 4 | 4-9-2 (ekkk-d9-ke) |
| 540083 | 18 | 67 | 3.7 | 6 | 4-9-2 (ekkk-d9-ke) |
| 540084 | 10 | 49 | 4.9 | 7 | 4-9-2 (ekkk-d9-ke) |
| 540085 | 21 | 86 | 4.1 | 8 | 4-9-2 (ekkk-d9-ke) |
| 540087 | 60 | 98 | 1.6 | 10 | 4-9-2 (ekkk-d9-ke) |
| 540090 | 129 | 137 | 1.1 | 13 | 4-9-2 (ekkk-d9-ke) |
| 540091 | 93 | 105 | 1.1 | 14 | 4-9-2 (ekkk-d9-ke) |
| 540092 | 28 | 55 | 2.0 | 2 | 2-9-4 (ek-d9-kkke) |
| 540093 | 18 | 62 | 3.4 | 3 | 2-9-4 (ek-d9-kkke) |
| 540094 | 13 | 45 | 3.4 | 4 | 2-9-4 (ek-d9-kkke) |
| 540096 | 17 | 68 | 4.0 | 6 | 2-9-4 (ek-d9-kkke) |
| 540097 | 8 | 35 | 4.2 | 8 | 2-9-4 (ek-d9-kkke) |
| 540098 | 12 | 45 | 3.9 | 8 | 2-9-4 (ek-d9-kkke) |
| 540099 | 62 | 91 | 1.5 | 9 | 2-9-4 (ek-d9-kkke) |

TABLE 77-continued

Comparison of selectivity in HTT SNP inhibition of chimeric oligonucleotides with ISIS 460209

| ISIS NO | % UTC mut | % UTC wt | Selectivity (wt vs. mut) | SNP site | Motif |
|---|---|---|---|---|---|
| 540100 | 80 | 106 | 1.3 | 10 | 2-9-4 (ek-d9-kkke) |
| 540101 | 154 | 152 | 1.0 | 11 | 2-9-4 (ek-d9-kkke) |
| 540102 | 102 | 106 | 1.0 | 12 | 2-9-4 (ek-d9-kkke) | e = 2'-MOE;
k = cEt;
c = 2'-deoxyribonucleoside

Example 53

Selectivity in Inhibition of HTT mRNA Levels Targeting SNP by Chimeric Oligonucleotides Designed by Microwalk A series of modified oligonucleotides were designed based on the parent gapmer, ISIS 460209, wherein the central gap region comprises nine 2'-deoxyribonucleosides. These gapmers were created with various motifs and modifications at the wings and/or the central gap region.

The modified oligonucleotides and their motifs are described in Table 78. The internucleoside linkages throughout each gapmer are phosphorothioate (P=S) linkages. All cytosine nucleobases throughout each gapmer are 5-methyl cytosines. Nucleosides without a subscript are β-D-2'-deoxyribonucleosides. Nucleosides followed by a subscript "e", "k", "y", or "z" are sugar modified nucleosides. A subscript "e" indicates a 2'-O-methoxyethyl (MOE) modified nucleoside, a subscript "k" indicates a 6'-(S)—CH$_3$ bicyclic nucleoside (e.g. cEt), a subscript "y" indicates an α-L-LNA modified nucleoside, and a subscript "z" indicates a F-HNA modified nucleoside. $^P$U indicates a 5-propyne uridine nucleoside and $^X$T indicates a 2-thio-thymidine nucleoside. Underlined nucleosides indicate the mismatch position.

These gapmers were evaluated for thermal stability ($T_m$) using methods described in Example 42. Presented in Table 79 are the $T_m$ measurements for chimeric antisense oligonucleotides when duplexed to mutant or wild-type RNA complement. The $T_m$ of chimeric antisense oligonucleotides duplexed with mutant RNA complement is denoted as "$T_m$ (° C.) mut". The $T_m$ of chimeric antisense oligonucleotides duplexed with wild-type RNA complement is denoted as "$T_m$ (° C.) wt".

These gapmers were also tested in vitro. ISIS 141923 was included in the study as a negative control and is denoted as "neg control". The non-allele specific antisense oligonucleotides, ISIS 387916 was used as a positive control and is denoted as "pos control". Heterozygous fibroblast GM04022 cell line was used. Cultured GM04022 cells at a density of 25,000 cells per well were transfected using electroporation with a single dose at 2 μM concentration of the modified oligonucleotide. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. HTT mRNA levels were adjusted according to total RNA content, as measured by RIBOGREEN. ISIS 460209 marked with an asterisk (*) in the table was included in the study for comparison. The results in Table 79 are presented as percent of HTT mRNA expression, relative to untreated control levels and is denoted as "% UTC". Selectivity was also evaluated and measured by dividing the percent of wild-type HTT mRNA levels vs. the percent of mutant HTT mRNA levels.

As illustrated, several of the newly designed antisense oligonucleotides showed improvement in potency and/or selectivity in inhibiting mut HTT mRNA levels comparing to ISIS 460209.

TABLE 78

Modified oligonucleotides comprising various modifications targeting HTT SNP

| ISIS NO | Sequence (5' to 3') | Modification | Wing Chemistry 5' | Wing Chemistry 3' | SEQ ID NO. |
|---|---|---|---|---|---|
| 460209* | T$_e$A$_k$A$_k$ATTGTCATCA$_k$C$_k$C$_e$ | 3-9-3 (ekk-d9-kke) | ekk | kke | 10 |
| 539560 | T$_e$A$_k$A$_k$ATTG$^P$UCATCA$_k$C$_k$C$_e$ | 5-propyne in gap | ekk | kke | 11 |
| 539563 | T$_e$A$_k$A$_k$ATTG$^X$TCATCA$_k$C$_k$C$_e$ | 2-thio in gap | ekk | kke | 10 |
| 539554 | T$_e$A$_k$A$_k$ATTGU$_y$CATCA$_k$C$_k$C$_e$ | α-L-LNA in gap | ekk | kke | 11 |
| 542686 | T$_e$A$_k$A$_k$ATTGT$_z$CATCA$_k$C$_k$C$_e$ | F-HNA in gap | ekk | kke | 10 |
| 540108 | A$_e$T$_e$A$_e$A$_k$A$_k$TTGTCATC$_k$A$_k$C$_e$C$_e$A$_e$ | 5-7-5 (eeekk-d7-kkeee) | eeekk | kkeee | 23 |
| 544840 | T$_e$A$_k$A$_k$ATTGTCATCA$_k$C$_k$C$_e$T$_k$T$_k$A$_k$ | 3-9-6 (ekk-d9-kkekkk) | ekk | kkekkk | 15 |
| 550904 | T$_e$A$_k$A$_k$ATTGTCATCA$_k$C$_k$C$_e$T$_k$T$_k$T$_k$A$_k$ | 3-9-7 (ekk-d9-kkekkkk) | ekk | kkekkkk | 18 |

TABLE 78-continued

Modified oligonucleotides comprising various modifications targeting HTT SNP

| ISIS NO | Sequence (5' to 3') | Modification | Wing Chemistry 5' | 3' | SEQ ID NO. |
|---|---|---|---|---|---|
| 540082 | $A_eT_kT_kG_k$TCATCACCAG$_kA_e$ | 4-9-2 (ekkk-d9-ke) | ekkk | ke | 65 |
| 540089 | $T_eT_kA_kA_k$TAAATTGTCA$_kT_e$ | 4-9-2 (ekkk-d9-ke) | ekkk | ke | 66 |
| 540095 | $A_eT_k$TGTCATCACC$_kA_kG_kA_e$ | 2-9-4 (ek-d9-kkke) | ek | kkke | 67 |
| 543528 | $A_eT_kA_kA_k$A<u>A</u>TGTCATCA$_kC_eC_kA_e$ | Mismatch at position 2 counting from 5' gap | ekek | keke | 77 |
| 543533 | $T_eA_kA_k$AT<u>A</u>GTCATCA$_kC_kC_e$ | Mismatch at position 3 counting from 5' gap | ekk | kke | 78 |
| 387916 (pos control) | $T_eC_eT_eC_eT_e$ATTGCACATTC$_eC_eA_eA_eG_e$ | 5-10-5 | eeeee | eeeee | 56 |
| 141923 (neg control) | $C_eC_eT_eT_eC_e$CCTGAAGGTTC$_eC_eT_eC_eC_e$ | 5-10-5 | eeeee | eeeee | 57 | e = 2'-MOE; k = cEt; d = 2'-deoxyribonucleoside

TABLE 79

Comparison of selectivity in inhibition of HTT mRNA levels, and Tm of modified oligonucleotides with ISIS 460209 targeted tors7685686 in GM04022 cells

| | Tm (° C.) | | % UTC | | Selectivity | | Wing Chemistry | |
|---|---|---|---|---|---|---|---|---|
| ISIS NO | mutant | wt | mut | wt | (wt vs mut) | Modification | 5' | 3' |
| 460209* | 53.7 | 52.2 | 23 | 57 | 2.7 | 3-9-3 (ekk-d9-kke) | ekk | kke |
| 539560 | 54.1 | 50.8 | 13 | 32 | 2.4 | 5-propyne in gap | ekk | kke |
| 539563 | 53.8 | 49.1 | 13 | 40 | 3.2 | 2-thio in gap | ekk | kke |
| 539554 | 56.5 | 54.5 | 54 | 89 | 1.7 | α-L-LNA in gap | ekk | kke |
| 542686 | 56.1 | 50.4 | 26 | 62 | 2.4 | F-HNA in gap | ekk | kke |
| 540108 | 60.0 | 57.9 | 27 | 63 | 2.3 | 5-7-5 (eeekk-d7-kkeee) | eeekk | kkeee |
| 544840 | — | — | 19 | 40 | 2.1 | 3-9-6 (ekk-d9-kkekkk) | ekk | kkekkk |
| 550904 | — | — | 39 | 65 | 1.7 | 3-9-7 (ekk-d9-kkekkkk) | ekk | kkekkkk |
| 540082 | — | — | 21 | 62 | 3.0 | 4-9-2 (ekkk-d9-ke) | ekkk | ke |
| 540089 | — | — | 78 | 86 | 1.1 | 4-9-2 (ekkk-d9-ke) | ekkk | ke |
| 540095 | — | — | 22 | 66 | 3.1 | 2-9-4 (ek-d9-kkke) | ek | kkke |
| 543528 | 50.5 | 49.1 | 44 | 90 | 2.1 | Mismatch at position 2 counting from 5' gap | ekek | keke |
| 543533 | 47.0 | 44.8 | 83 | 97 | 1.2 | Mismatch at position 3 counting from 5' gap | ekk | kke |
| 387916 (pos control) | — | — | 21 | 19 | 0.9 | 5-10-5 | eeeee | eeeee |
| 141923 (neg control) | — | — | 95 | 99 | 1.0 | 5-10-5 | eeeee | eeeee | e = 2'-MOE;
k = cEt;
d = 2'-deoxyribonucleoside

Example 54

Chimeric Oligonucleotides Comprising Modifications at the SNP Site of HTT Gene

Additional gapmers are designed based on the gapmer selected from studies described in Tables 73 and 74 (ISIS 540108) and is marked with an asterisk (*). These gapmers are designed by introducing modifications at the SNP site at position 9 of the oligonucleotides, as counted from the 5'-terminus and are created with a 5-7-5 motif.

The gapmers are described in Table 80. The internucleoside linkages throughout each gapmer are phosphorothioate (P=S) linkages. All cytosine nucleobases throughout each gapmer are 5-methyl cytosines. Nucleosides without a subscript are β-D-2'-deoxyribonucleosides. Nucleosides followed by a subscript "a", "b", "e", or "k" are sugar modified nucleosides. A subscript "a" indicates 2'-(ara)-F modified nucleoside, a subscript "b" indicates a 5'-Me DNA modified nucleoside, a subscript "e" indicates a 2'-O-methoxyethyl (MOE) modified nucleoside, and a subscript "k" indicates a 6'-(S)—CH$_3$ bicyclic nucleoside (e.g. cEt). $^x$T indicates a 2-thio-thymidine nucleoside. Underline nucleoside or the number in parentheses indicates the position on the oligonucleotides opposite to the SNP position, as counted from the 5'-terminus.

TABLE 80

Modified oligonucleotides targeting HTT SNP

| ISIS NO | Sequence (5' to 3') | Gap Chemistry | Wing chemistry 5' | 3' | SEQ ID NO. |
|---|---|---|---|---|---|
| 540108* (9) | A$_e$T$_e$A$_e$A$_k$A$_k$TTG<u>T</u>CATC$_k$A$_k$C$_e$C$_e$A$_e$ | Deoxy | eeekk | kkeee | 32 |
| XXXX28 (9) | A$_e$T$_e$A$_e$A$_k$A$_k$TTG$^x$<u>T</u>CATC$_k$A$_k$C$_e$C$_e$A$_e$ | Deoxy/2-thio | eeekk | kkeee | 32 |
| XXXX29 (9) | A$_e$T$_e$A$_e$A$_k$A$_k$TTGT$_a$CATC$_k$A$_k$C$_e$C$_e$A$_e$ | Deoxy/2'-(ara)-F | eeekk | kkeee | 32 |
| XXXX30 (9) | A$_e$T$_e$A$_e$A$_k$A$_k$TTGT$_b$CATC$_k$A$_k$C$_e$C$_e$A$_e$ | Deoxy/5'-Me-DNA | eeekk | kkeee | 32 | e = 2'-MOE, k = cEt

Example 55

Chimeric Oligonucleotides Comprising Modifications at the Wing Regions Targeting HTT SNP Additional gapmers are designed based on the gapmer selected from studies described in Tables 89 and 21 (ISIS 540107) and is marked with an asterisk (*). These gapmers are designed by introducing bicyclic modified nucleosides at the 3' or 5' terminus and are tested to evaluate if the addition of bicyclic modified nucleosides at the wing regions improves the activity and selectivity in inhibition of mutant HTT SNP.

The gapmers comprise a 5-7-5 motif and are described in Table 81. The internucleoside linkages throughout each gapmer are phosphorothioate (P=S) linkages. All cytosine nucleobases throughout each gapmer are 5-methyl cytosines. Nucleosides without a subscript are β-D-2'-deoxyribonucleosides. Nucleosides followed by a subscript "e", or "k" are sugar modified nucleosides. A subscript "e" indicates a 2'-O-methoxyethyl (MOE) modified nucleoside, and a subscript "k" indicates a 6'-(S)—CH$_3$ bicyclic nucleoside (e.g. cEt).

TABLE 81

Modified oligonucleotides targeting HTT SNP

| ISIS NO | Sequence (5' to 3') | Motif | wing chemistry 5' | wing chemistry 3' | SEQ ID NO. |
|---|---|---|---|---|---|
| 540107* | $A_eT_eA_eA_kA_k$TTGTCATC$_kA_eC_eC_eA_e$ | 5-7-5 (eeeek-d7-keeee) | eeeek | keeee | 32 |
| XXXX31 | $A_eT_eA_kA_kA_k$TTGTCATC$_kA_kC_kC_eA_e$ | 5-7-5 (eekkk-d7-kkkee) | eekkk | kkkee | 32 |
| XXXX32 | $A_eT_eA_eA_kA_k$TTGTCATC$_eA_eC_eC_eA_e$ | 5-7-5 (eeeek-d7-eeeee) | eeeek | eeeee | 32 |
| XXXX33 | $A_eT_eA_eA_kA_k$TTGTCATC$_eA_eC_eC_eA_e$ | 5-7-5 (eeekk-d7-eeeee) | eeekk | eeeee | 32 |
| XXXX34 | $A_eT_eA_kA_kA_k$TTGTCATC$_eA_eC_eC_eA_e$ | 5-7-5 (eekkk-d7-eeeee) | eekkk | eeeee | 32 |
| XXXX35 | $A_eT_eA_eA_eA_e$TTGTCATC$_kA_eC_eC_eA_e$ | 5-7-5 (eeeee-d7-keeee) | eeeee | keeee | 32 |
| XXXX36 | $A_eT_eA_eA_eA_e$TTGTCATC$_kA_kC_eC_eA_e$ | 5-7-5 (eeeee-d7-kkeee) | eeeee | kkeee | 32 |
| XXXX37 | $A_eT_eA_eA_eA_e$TTGTCATC$_kA_kC_kC_eA_e$ | 5-7-5 (eeeee-d7-kkkee) | eeeee | kkkee | 32 | e = 2'-MOE; k = cEt; d = 2'-deoxyribonucleoside

Example 56

Chimeric Oligonucleotides Comprising Wing and Central Gap Modifications Targeting HTT SNP Additional gapmers are designed based on the parent gapmer, ISIS 460209, wherein the central gap region comprises nine 2'-deoxyribonucleosides and is marked with an asterisk (*) in the table. These gapmers were designed by introducing modifications at the wings or the central gap region and are created with a 3-9-3 motif.

The gapmers are described in Table 82. The internucleoside linkages throughout each gapmer are phosphorothioate (P=S) linkages. All cytosine nucleobases throughout each gapmer are 5-methyl cytosines. Nucleosides without a subscript are β-D-2'-deoxyribonucleosides. Nucleosides followed by a subscript "e", or "k" are sugar modified nucleosides. A subscript "e" indicates a 2'-O-methoxyethyl (MOE) modified nucleoside, and a subscript "k" indicates a 6'-(S)—CH$_3$ bicyclic nucleoside (e.g. cEt). $^P$T indicates a 5-propyne thymidine nucleoside. $^P$C indicates a 5-propyne cytosine nucleoside. Underline nucleoside or the number in parentheses indicates the position on the oligonucleotides opposite to the SNP position, as counted from the 5'-terminus.

TABLE 82

Modified oligonucleotides targeting HTT SNP

| ISIS NO | Sequence (5' to 3') | Modification | wing chemistry 5' | wing chemistry 3' | SEQ ID NO |
|---|---|---|---|---|---|
| 460209* (8) | $T_eA_kA_k$ATTG$\underline{T}$CATCA$_kC_kC_e$ | Deoxy gap (3-9-3) | ekk | kke | 10 |
| 552103 (8) | $T_eA_eA_e$ATTG$\underline{T}$CATCA$_kC_kC_k$ | Deoxy gap (3-9-3) | eee | kkk | 10 |
| 552104 (8) | $T_kA_kA_k$ATTG$\underline{T}$CATCA$_eC_eC_e$ | Deoxy gap (3-9-3) | kkk | eee | 10 |
| 552105 (8) | $T_eA_kA_k$ATTG$^P\underline{T}^P$CATCA$_kC_kC_e$ | Deoxy/5-Propyne | ekk | kke | 10 |
| 552106 (8) | $T_eA_kA_k$A$^P$T$^P$TG$^P\underline{T}^P$CA$^P$T$^P$CA$_kC_kC_e$ | Deoxy/5-Propyne | ekk | kke | 10 | e = 2'-MOE; k = cEt

Example 57

Modified Oligonucleotides Comprising F-HNA Modification at the Central Gap or Wing Region Targeting HTT SNP A series of modified oligonucleotides were designed based on ISIS 460209, wherein the central gap region contains nine 2'-deoxyribonucleosides. These modified oligonucleotides were designed by incorporating one or more F-HNA(s) modification within the central gap region or on the wing regions. The F-HNA containing oligonucleotides were tested for their ability to selectively inhibit mutant (mut) HTT mRNA expression levels targeting rs7685686 while leaving the expression of the wild-type (wt) intact. The activity and selectivity of the modified oligonucleotides were evaluated and compared to ISIS 460209.

The modified oligonucleotides and their motifs are described in Table 83. The internucleoside linkages throughout each modified oligonucleotide are phosphorothioate linkages (P=S). Nucleosides without a subscript are β-D-2'-deoxyribonucleosides. Nucleosides followed by a subscript "e" indicate 2'-O-methoxyethyl (MOE) modified nucleosides. Nucleosides followed by a subscript "k" indicate 6'-(S)—CH$_3$ bicyclic nucleosides (e.g. cEt). Nucleosides followed by a subscript "z" indicate F-HNA modified nucleosides. $^m$C indicates a 5-methyl cytosine nucleoside. Underlined nucleoside indicates the position on the oligonucleotides opposite to the SNP position, which is position 8 as counted from the 5'-terminus.

The gap-interrupted antisense oligonucleotides were tested in vitro. Heterozygous fibroblast GM04022 cell line was used. Cultured GM04022 cells at a density of 25,000 cells per well were transfected using electroporation with 0.12, 0.37, 1.1, 3.3 and 10 μM concentrations of modified oligonucleotides. After a treatment period of approximately 16 hours, RNA was isolated from the cells and mRNA levels were measured by quantitative real-time PCR using ABI assay C_2229297_10 which measures at dbSNP rs362303. The HTT mRNA levels were adjusted according to total RNA content, as measured by RIBOGREEN and the results are presented in Table 84.

The IC$_{50}$ and selectivity were calculated using methods previously described in Example 41. The IC$_{50}$ at which each oligonucleotide inhibits the mutant HTT mRNA expression is denoted as 'mut IC$_{50}$'. The IC$_{50}$ at which each oligonucleotide inhibits the wild-type HTT mRNA expression is denoted as 'wt IC$_{50}$'. Selectivity was calculated by dividing the IC$_{50}$ for inhibition of the wild-type HTT versus the IC$_{50}$ for inhibiting expression of the mutant HTT mRNA.

The parent gapmer, 460209 is marked with an asterisk (*) in the table and was included in the study as a benchmark oligonucleotide against which the activity and selectivity of antisense oligonucleotides targeting nucleotides overlapping the SNP position could be compared.

As illustrated in Table 84, oligonucleotides comprising F-HNA modification(s) showed improvement in selectivity while maintaining activity as compared to the parent gapmer, ISIS 460209.

TABLE 83

Gap-interrupted antisense oligonucleotides targeting HTT SNP

| ISIS NO. | Sequence (5' to 3') | Motif | Gap chemistry | Wing chemistry 5' | 3' | SEQ ID NO. |
|---|---|---|---|---|---|---|
| 460209* | T$_e$A$_k$A$_k$ATTGT $^m$CAT$^m$CA$_k$$^m$C$_k$$^m$C$_e$ | 3-9-3 | Full deoxy | ekk | kke | 10 |
| 566266 | T$_e$A$_k$A$_k$A$_z$TTGT $^m$CAT$^m$CA$_k$$^m$C$_k$$^m$C$_e$ | 3-9-3 or 4-8-3 | Deoxy/F-HNA | ekk or ekkz | kke | 10 |
| 566267 | T$_e$A$_k$A$_k$AT$_z$TGT $^m$CAT$^m$CA$_k$$^m$C$_k$$^m$C$_e$ | 3-9-3 or 5-7-3 | Deoxy/F-HNA | ekk or ekkdz | kke | 10 |
| 566268 | T$_e$A$_k$A$_k$ATT$_z$GT $^m$CAT$^m$CA$_k$$^m$C$_k$$^m$C$_e$ | 3-9-3 or 6-6-3 | Deoxy/F-HNA | ekk or ekkddz | kke | 10 |
| 566269 | T$_e$A$_k$A$_k$ATTG$_z$T $^m$CAT$^m$CA$_k$$^m$C$_k$$^m$C$_e$ | 3-9-3 or 7-5-3 | Deoxy/F-HNA | ekk or ekkdddz | kke | 10 |
| 567369 | T$_e$A$_k$A$_k$A$_z$T$_z$TGT $^m$CAT$^m$CA$_k$$^m$C$_k$$^m$C$_e$ | 3-9-3 or 5-7-3 | Deoxy/F-HNA | ekk or ekkzz | kke | 10 | e = 2'-MOE, k = cEt, d = 2'-β-deoxyribonucleoside, z = F-HNA

TABLE 84

Comparison of inhibition of HTT mRNA levels and selectivity of gap-interrupted antisense oligonucleotides with ISIS 460209 targeting HTT SNP

| | IC$_{50}$ (μM) | | Selectivity | Gap | Wing Chemistry | |
|---|---|---|---|---|---|---|
| ISIS NO | Mut | Wt | (wt vs mut) | Motif | chemistry 5' | 3' |
| 460209* | 0.28 | 3.1 | 11 | 3-9-3 | Full deoxy ekk | kke |
| 566266 | 0.20 | >10 | >50 | 3-9-3 or 4-8-3 | Deoxy/F-HNA ekk or ekkz | kke |

TABLE 84-continued

Comparison of inhibition of HTT mRNA levels and selectivity of gap-interrupted antisense oligonucleotides with ISIS 460209 targeting HTT SNP

| ISIS NO | IC$_{50}$ (µM) Mut | IC$_{50}$ (µM) Wt | Selectivity (wt vs mut) | Motif | Gap chemistry | Wing Chemistry 5' | Wing Chemistry 3' |
|---|---|---|---|---|---|---|---|
| 566267 | 0.90 | >9.9 | >11 | 3-9-3 or 5-7-3 | Deoxy/F-HNA | ekk or ekkdz | kke |
| 566268 | 1.0 | >10 | >10 | 3-9-3 or 6-6-3 | Deoxy/F-HNA | ekk or ekkddz | kke |
| 566269 | 1.7 | >10.2 | >6 | 3-9-3 or 7-5-3 | Deoxy/F-HNA | ekk or ekkdddz | kke |
| 567369 | 0.82 | >9.8 | >12 | 3-9-3 or 5-7-3 | Deoxy/F-HNA | ekk or ekkzz | kke | e = 2'-MOE,
k = cEt,
d = 2'-β-deoxyribonucleoside,
z = F-HNA

Example 58

Modified Oligonucleotides Comprising cEt Modification(s) at the Central Gap Region Targeting HTT SNP A series of modified oligonucleotides were designed in the same manner as described in Example 57. These modified oligonucleotides were designed by replacing F-HNA(s) with cEt modification(s) in the central gap region while maintaining the wing configuration. The modified oligonucleotides were tested for their ability to selectively inhibit mutant (mut) HTT mRNA expression levels targeting rs7685686 while leaving the expression of the wild-type (wt) intact. The activity and selectivity of the modified oligonucleotides were evaluated and compared to ISIS 460209.

The modified oligonucleotides and their motifs are described in Table 85. The internucleoside linkages throughout each modified oligonucleotide are phosphorothioate linkages (P=S). Nucleosides without a subscript are β-D-2'-deoxyribonucleosides. Nucleosides followed by a subscript "e" indicate 2'-O-methoxyethyl (MOE) modified nucleosides. Nucleosides followed by a subscript "k" indicate 6'-(S)—CH$_3$ bicyclic nucleosides (e.g. cEt). IT indicates a 5-methyl cytosine nucleoside. Underlined nucleoside indicates the position on the oligonucleotides opposite to the SNP position, which is position 8 as counted from the 5'-terminus.

The gap-interrupted antisense oligonucleotides were tested in vitro. Heterozygous fibroblast GM04022 cell line was used. Cultured GM04022 cells at a density of 25,000 cells per well were transfected using electroporation with 0.12, 0.37, 1.1, 3.3 and 10 µM concentrations of modified oligonucleotides. After a treatment period of approximately 16 hours, RNA was isolated from the cells and mRNA levels were measured by quantitative real-time PCR using ABI assay C_2229297_10 which measures at dbSNP rs362303. The HTT mRNA levels were adjusted according to total RNA content, as measured by RIBOGREEN and the results are presented below.

The IC$_{50}$ and selectivity were calculated using methods previously described in Example 41. The IC$_{50}$ at which each oligonucleotide inhibits the mutant HTT mRNA expression is denoted as 'mut IC$_{50}$'. The IC$_{50}$ at which each oligonucleotide inhibits the wild-type HTT mRNA expression is denoted as 'wt IC$_{50}$'. Selectivity was calculated by dividing the IC$_{50}$ for inhibition of the wild-type HTT versus the IC$_{50}$ for inhibiting expression of the mutant HTT mRNA.

As illustrated in Table 86, some of the newly designed antisense oligonucleotides (ISIS 575006, 575007, and 575008) showed improvement in potency and/or selectivity in inhibiting mut HTT mRNA levels comparing to ISIS 460209.

TABLE 85

Gap-interrupted antisense oligonucleotides targeting HTT SNP

| ISIS NO. | Sequence (5' to 3') | Motif | Gap chemistry | Wing chemistry 5' | Wing chemistry 3' | SEQ ID NO. |
|---|---|---|---|---|---|---|
| 460209* | T$_e$A$_k$A$_k$ATTGT $^m$CAT$^m$CA$_k^m$C$_k^m$C$_e$ | 3-9-3 | Full deoxy | ekk | kke | 10 |
| 575006 | T$_e$A$_k$A$_k$A$_k$TTGT $^m$CAT$^m$CA$_k^m$C$_k^m$C$_e$ | 4-8-3 | Full deoxy | ekkk | kke | 10 |
| 575007 | T$_e$A$_k$A$_k$AT$_k$TGT $^m$CAT$^m$CA$_k^m$C$_k^m$C$_e$ | 3-9-3 or 5-7-3 | Full deoxy or Deoxy/cEt | ekk or ekkdk | kke | 10 |
| 575133 | T$_e$A$_k$A$_k$ATT$_k$GT $^m$CAT$^m$CA$_k^m$C$_k^m$C$_e$ | 3-9-3 or 6-6-3 | Full deoxy or Deoxy/cEt | ekk or ekkddk | kke | 10 |

TABLE 85-continued

Gap-interrupted antisense oligonucleotides targeting HTT SNP

| ISIS NO. | Sequence (5' to 3') | Motif | Gap chemistry | Wing chemistry 5' | 3' | SEQ ID NO. |
|---|---|---|---|---|---|---|
| 575134 | $T_eA_kA_k$ATTGk$\underline{T}$ $^mCAT^mCA_k{}^mC_k{}^mC_e$ | 3-9-3 or 7-5-3 | Full deoxy or Deoxy/cEt | ekk or ekkdddk | kke | 10 |
| 575008 | $T_eA_kA_kA_kT_k$TG$\underline{T}$ $^mCAT^mCA_k{}^mC_k{}^mC_e$ | 5-7-3 | Deoxy | ekkkk | kke | 10 | e = 2'-MOE, k = cEt, d = 2'-β-deoxyribonucleoside

TABLE 86

Comparison of inhibition of HTT mRNA levels and selectivity of gap-interrupted antisense oligonucleotides with ISIS 460209 targeting HTT SNP

| | $IC_{50}$ (μM) | | Selectivity | Gap | | Wing Chemistry | |
|---|---|---|---|---|---|---|---|
| ISIS NO | Mut | Wt | (wt vs mut) | Motif | chemistry | 5' | 3' |
| 460209* | 0.28 | 3.1 | 11 | 3-9-3 | Full deoxy | ekk | kke |
| 575006 | 0.27 | 3.8 | 14 | 4-8-3 | Full deoxy | ekkk | kke |
| 575007 | 0.67 | >10.1 | >15 | 3-9-3 or 5-7-3 | Full deoxy or Deoxy/cEt | ekk or ekkdk | kke |
| 575133 | 3.0 | >9 | >3 | 3-9-3 or 6-6-3 | Full deoxy or Deoxy/cEt | ekk or ekkddk | kke |
| 575134 | 2.6 | >10.4 | >4 | 3-9-3 or 7-5-3 | Full deoxy or Deoxy/cEt | ekk or ekkdddk | kke |
| 575008 | 0.18 | >9.9 | >55 | 5-7-3 | Full deoxy | ekkkk | kke | e = 2'-MOE,
k = cEt,
d = 2'-β-deoxyribonucleoside

Example 59

Modified Oligonucleotides Comprising F-HNA Modification at the 3'-End of Central Gap Region Targeting HTT SNP A series of modified oligonucleotides were designed based on ISIS 460209, wherein the central gap region contains nine 2'-deoxyribonucleosides. These modified oligonucleotides were designed by incorporating one F-HNA modification at the 3'-end of the central gap region. The F-HNA containing oligonucleotides were tested for their ability to selectively inhibit mutant (mut) HTT mRNA expression levels targeting HTT SNP while leaving the expression of the wild-type (wt) intact. The activity and selectivity of the modified oligonucleotides were evaluated and compared to ISIS 460209.

The modified oligonucleotides and their motifs are described in Table 87. The internucleoside linkages throughout each modified oligonucleotide are phosphorothioate linkages (P=S). Nucleosides without a subscript are β-D-2'-deoxyribonucleosides. Nucleosides followed by a subscript "e" indicate 2'-O-methoxyethyl (MOE) modified nucleosides. Nucleosides followed by a subscript "k" indicate 6'-(S)—CH₃ bicyclic nucleosides (e.g. cEt). Nucleosides followed by a subscript "z" indicate F-HNA modified nucleosides. $^mC$ indicates a 5-methyl cytosine nucleoside. Underlined nucleoside indicates the position on the oligo-nucleotides opposite to the SNP position, which is position 8 as counted from the 5'-terminus.

The modified oligonucleotides were tested in vitro. Heterozygous fibroblast GM04022 cell line was used. Cultured GM04022 cells at a density of 25,000 cells per well were transfected using electroporation with 0.12, 0.37, 1.1, 3.3 and 10 μM concentrations of modified oligonucleotides. After a treatment period of approximately 16 hours, RNA was isolated from the cells and mRNA levels were measured by quantitative real-time PCR using ABI assay C_2229297_10 which measures at dbSNP rs362303. The HTT mRNA levels were adjusted according to total RNA content, as measured by RIBOGREEN and the results are presented in Table 88.

The $IC_{50}$ and selectivity were calculated using methods previously described in Example 41. The $IC_{50}$ at which each oligonucleotide inhibits the mutant HTT mRNA expression is denoted as 'mut $IC_{50}$'. The $IC_{50}$ at which each oligonucleotide inhibits the wild-type HTT mRNA expression is denoted as 'wt $IC_{50}$'. Selectivity was calculated by dividing the $IC_{50}$ for inhibition of the wild-type HTT versus the $IC_{50}$ for inhibiting expression of the mutant HTT mRNA.

As illustrated in Table 88, a couple of the newly designed antisense oligonucleotides (ISIS 575833 and 575834) showed improvement in selectivity while maintaining potency as compared to ISIS 460209. ISIS 575836 showed an increase in potency without improvement in selectivity while ISIS 575835 showed comparable selectivity without improvement in potency.

TABLE 87

Modified oligonucleotides targeting HTT SNP

| ISIS NO. | Sequence (5' to 3') | Gap Motif | Gap chemistry | Wing chemistry 5' | Wing chemistry 3' | SEQ ID NO. |
|---|---|---|---|---|---|---|
| 460209* | $T_eA_kA_k$ATTGT $^mCA T^mCA_k{}^mC_k{}^mC_e$ | 3-9-3 | Full deoxy | ekk | kke | 10 |
| 575833 | $T_eA_kA_k$ATTGT $^mC_zAT^mCA_k{}^mC_k{}^mC_e$ | 3-9-3 or 3-5-7 | Deoxy/F-HNA | ekk | kke or zdddkke | 10 |
| 575834 | $T_eA_kA_k$ATTGT $^mCA_zT^mCA_k{}^mC_k{}^mC_e$ | 3-9-3 or 3-6-6 | Deoxy/F-HNA | ekk | kke or zddkke | 10 |
| 575835 | $T_eA_kA_k$ATTGT $^mCAT_z{}^mCA_k{}^mC_k{}^mC_e$ | 3-9-3 or 3-7-5 | Deoxy/F-HNA | ekk | kke or zdkke | 10 |
| 575836 | $T_eA_kA_k$ATTGT $^mCAT^mC_zA_k{}^mC_k{}^mC_e$ | 3-9-3 or 3-8-4 | Deoxy/F-HNA | ekk | kke or zkke | 10 | e = 2'-MOE, k = cEt, d = 2'-β-deoxyribonucleoside, z = F-HNA

TABLE 88

Comparison of inhibition of HTT mRNA levels and selectivity of modified oligonucleotides with ISIS 460209 targeting HTT SNP

| ISIS NO | $IC_{50}$ (μM) Mut | $IC_{50}$ (μM) Wt | Selectivity (wt vs mut) | Motif | Gap chemistry | Wing Chemistry 5' | Wing Chemistry 3' |
|---|---|---|---|---|---|---|---|
| 460209* | 0.28 | 3.1 | 11 | 3-9-3 | Full deoxy | ekk | kke |
| 575833 | 0.22 | 4.2 | 19 | 3-9-3 or 3-5-7 | Deoxy/F-HNA | ekk | kke or zdddkke |
| 575834 | 0.30 | 6.3 | 21 | 3-9-3 or 3-6-6 | Deoxy/F-HNA | ekk | kke or zddkke |
| 575835 | 0.89 | 9.8 | 11 | 3-9-3 or 3-7-5 | Deoxy/F-HNA | ekk | kke or zdkke |
| 575836 | 0.09 | 0.4 | 4.6 | 3-9-3 or 3-8-4 | Deoxy/F-HNA | ekk | kke or zkke | e = 2'-MOE,
k = cEt,
d = 2'-β-deoxyribonucleoside,
z = F-HNA

Example 60

Short-Gap Chimeric Oligonucleotides Targeting Huntingtin (HTT) Single Nucleotide Polymorphism (SNP)

Additional chimeric antisense oligonucleotides were designed based on ISIS 460209 and ISIS 540094 wherein the central gap region contains nine 2'-deoxynucleosides. These gapmers were designed with the central gap region shortened by introducing cEt modifications to the wing regions, or interrupted by introducing cEt modifications at the 3'-end of the central gap region. The modified oligonucleotides were tested for their ability to selectively inhibit mutant (mut) HTT mRNA expression levels targeting HTT SNP while leaving the expression of the wild-type (wt) intact. The activity and selectivity of the modified oligonucleotides were evaluated and compared to ISIS 460209 and 540094.

The gapmers and their motifs are described in Table 89. The internucleoside linkages throughout each modified oligonucleotide are phosphorothioate linkages (P=S). Nucleosides without a subscript are (3-D-2'-deoxyribonucleosides. Nucleosides followed by a subscript "e" indicate 2'-O-methoxyethyl (MOE) modified nucleosides. Nucleosides followed by a subscript "k" indicate 6'-(S)—CH₃ bicyclic nucleosides (e.g. cEt). $^mC$ indicates a 5-methyl cytosine nucleoside. Underlined nucleoside indicates the position on the oligonucleotides opposite to the SNP position, which is position 4 or 8 as counted from the 5'-terminus.

The modified oligonucleotides were tested in vitro. Heterozygous fibroblast GM04022 cell line was used. Cultured GM04022 cells at a density of 25,000 cells per well were transfected using electroporation with 0.12, 0.37, 1.1, 3.3 and 10 μM concentrations of modified oligonucleotides. After a treatment period of approximately 16 hours, RNA was isolated from the cells and mRNA levels were measured by quantitative real-time PCR using ABI assay C_2229297_10 which measures at dbSNP rs362303. The HTT mRNA levels were adjusted according to total RNA content, as measured by RIBOGREEN and the results are presented in Table 90.

The $IC_{50}$ and selectivity were calculated using methods previously described in Example 41. The $IC_{50}$ at which each oligonucleotide inhibits the mutant HTT mRNA expression is denoted as 'mut $IC_{50}$'. The $IC_{50}$ at which each oligonucleotide inhibits the wild-type HTT mRNA expression is denoted as 'wt $IC_{50}$'. Selectivity was calculated by dividing the $IC_{50}$ for inhibition of the wild-type HTT versus the $IC_{50}$ for inhibiting expression of the mutant HTT mRNA.

As illustrated in Table 90, the newly designed antisense oligonucleotides (ISIS 575003) showed improvement in selectivity while maintaining potency as compared to ISIS 460209.

TABLE 89

Short-gap antisense oligonucleotides targeting HTT SNP

| ISIS NO. | Sequence (5' to 3') | Gap Motif | Gap chemistry | Wing chemistry 5' | Wing chemistry 3' | SEQ ID NO. |
|---|---|---|---|---|---|---|
| 460209* | $T_eA_kA_k$ATTG$\underline{T}$ $^mCAT^mCA_k^mC_k^mC_e$ | 3-9-3 | Full deoxy | ekk | kke | 10 |
| 540094* | $T_eT_k\underline{GT}^mCAT^mCA$ $^mC^mCA_kG_kA_kA_e$ | 2-9-4 | Full deoxy | ek | kkke | 67 |
| 575003 | $T_eT_k\underline{GT}^mCAT^mCA$ $^mC^mC_kA_kG_kA_kA_e$ | 2-8-5 | Full deoxy | ek | kkkke | 67 |
| 575004 | $T_eT_k\underline{GT}^mCAT^mCA$ $^mC^mCA_kG_kA_kA_e$ | 2-9-4 or 2-7-6 | Full deoxy or Deoxy/cEt | ek | kkke or kdkkke | 67 |
| 575005 | $T_eT_k\underline{GT}^mCAT^mCA$ $^mC_k^mC_kA_kG_kA_kA_e$ | 2-7-6 | Full deoxy | ek | kkkkke | 67 | e = 2'-MOE, k = cEt, d = 2'-deoxyribonucleoside

TABLE 90

Comparison of inhibition of HTT mRNA levels and selectivity of modified oligonucleotides with ISIS 460209 targeting HTT SNP

| ISIS NO | IC$_{50}$ (μM) Mut | IC$_{50}$ (μM) Wt | Selectivity (wt vs mut) | Motif | Gap chemistry | Wing Chemistry 5' | Wing Chemistry 3' |
|---|---|---|---|---|---|---|---|
| 460209* | 0.34 | 3.3 | 9.7 | 3-9-3 | Full deoxy | ekk | kke |
| 540094* | 0.17 | 2.4 | 14 | 2-9-4 | Full deoxy | ek | kkke |
| 575003 | 0.40 | 10 | 25 | 2-8-5 | Full deoxy | ek | kkkke |
| 575004 | 1.2 | >9.6 | >8 | 2-9-4 or 2-7-6 | Full deoxy or Deoxy/cEt | ek | kkke or kdkkke |
| 575005 | >10 | >100 | >10 | 2-7-6 | Full deoxy | ek | kkkkke | e = 2'-MOE,
k = cEt,
d = 2'-deoxyribonucleoside

Example 61

Short-Gap Chimeric Oligonucleotides Targeting Huntingtin (HTT) Single Nucleotide Polymorphism (SNP)

Additional chimeric antisense oligonucleotides were designed based on 15-mer, ISIS 460209 and 17-mer, ISIS 476333 wherein the central gap region contains nine 2'-deoxynucleosides. These gapmers were designed with the central gap region shortened at the 5'-end of the central gap region. The gapmers were tested for their ability to selectively inhibit mutant (mut) HTT mRNA expression levels targeting HTT SNP while leaving the expression of the wild-type (wt) intact. The activity and selectivity of the gapmers were evaluated and compared to ISIS 460209 and ISIS 476333.

The gapmers and their motifs are described in Table 91. The internucleoside linkages throughout each modified oligonucleotide are phosphorothioate linkages (P=S). Nucleosides without a subscript are (3-D-2'-deoxyribonucleosides. Nucleosides followed by a subscript "e" indicate 2'-O-methoxyethyl (MOE) modified nucleosides. Nucleosides followed by a subscript "k" indicate 6'-(S)—CH$_3$ bicyclic nucleosides (e.g. cEt). $^mC$ indicates a 5-methyl cytosine nucleoside. Underlined nucleoside indicates the position on the oligonucleotides opposite to the SNP position, which is position 8 or 9 as counted from the 5'-terminus.

The modified oligonucleotides were tested in vitro. Heterozygous fibroblast GM04022 cell line was used. Cultured GM04022 cells at a density of 25,000 cells per well were transfected using electroporation with 0.12, 0.37, 1.1, 3.3 and 10 μM concentrations of modified oligonucleotides. After a treatment period of approximately 16 hours, RNA was isolated from the cells and mRNA levels were measured by quantitative real-time PCR using ABI assay C_2229297_10 which measures at dbSNP rs362303. The HTT mRNA levels were adjusted according to total RNA content, as measured by RIBOGREEN and the results are presented in Table 92.

The IC$_{50}$ and selectivity were calculated using methods previously described in Example 41. The IC$_{50}$ at which each oligonucleotide inhibits the mutant HTT mRNA expression is denoted as 'mut IC$_{50}$'. The IC$_{50}$ at which each oligonucleotide inhibits the wild-type HTT mRNA expression is denoted as 'wt IC$_{50}$'. Selectivity was calculated by dividing the IC$_{50}$ for inhibition of the wild-type HTT versus the IC$_{50}$ for inhibiting expression of the mutant HTT mRNA.

As illustrated in Table 92, a couple of the newly designed antisense oligonucleotides (ISIS 571036 and 571037) showed improvement in potency and selectivity in inhibiting mut HTT mRNA levels as compared to ISIS 460209 and 476333.

TABLE 91

Short-gap antisense oligonucleotides targeting HTT SNP

| ISIS NO. | Sequence (5' to 3') | Motif | Gap chemistry | Wing chemistry 5' | Wing chemistry 3' | SEQ ID NO. |
|---|---|---|---|---|---|---|
| 460209* | $T_eA_kA_k$ATTG$\underline{T}$ $^mCA T^mCA_k{}^mC_k{}^mC_e$ | 3-9-3 | Full deoxy | ekk | kke | 10 |
| 476333* | $A_eT_eA_eA_k$ATTG$\underline{T}$ $^mCA T^mCA_k{}^mC_e{}^mC_kA_e$ | 4-9-4 | Full deoxy | ekek | keke | 32 |
| 571036 | $A_eT_eA_eA_kA_eT_k$TG$\underline{T}$ $^mCA T^mCA_k{}^mC_e{}^mC_kA_e$ | 6-7-4 | Full deoxy | ekekek | keke | 32 |
| 571037 | $A_eT_eA_eA_eA_kT_k$TG$\underline{T}$ $^mCA T^mCA_k{}^mC_e{}^mC_kA_e$ | 6-7-4 | Full deoxy | eeeekk | keke | 32 |
| 571038 | $A_eT_eA_kA_kA_eT_e$TG$\underline{T}$ $^mCA T^mCA_k{}^mC_e{}^mC_kA_e$ | 6-7-4 | Full deoxy | ekekee | keke | 32 | e = 2'-MOE, k = cEt, d = 2'-deoxyribonucleoside

TABLE 92

Comparison of inhibition of HTT mRNA levels and selectivity of modified oligonucleotides with ISIS 460209 targeting HTT SNP

| | $IC_{50}$ (µM) | | Selectivity (wt vs | | Gap | Wing Chemistry | |
|---|---|---|---|---|---|---|---|
| ISIS NO | Mut | Wt | mut) | Motif | chemistry | 5' | 3' |
| 460209* | 0.34 | 3.3 | 9.7 | 3-9-3 | Full deoxy | ekk | kke |
| 476333* | 0.32 | 1.5 | 4.7 | 4-9-4 | Full deoxy | ekek | keke |
| 571036 | 0.17 | >10.0 | >59 | 6-7-4 | Full deoxy | ekekek | keke |
| 571037 | 0.11 | >9.9 | >90 | 6-7-4 | Full deoxy | eeeekk | keke |
| 571038 | 1.5 | >10.5 | >7 | 6-7-4 | Full deoxy | ekekee | keke | e = 2'-MOE,
k = cEt,
d = 2'-deoxyribonucleoside

Example 62

Short-Gap Chimeric Oligonucleotides Targeting Huntingtin (HTT) Single Nucleotide Polymorphism (SNP)

Additional chimeric antisense oligonucleotides were designed based on 15-mer, ISIS 460209 wherein the central gap region contains nine 2'-deoxynucleosides. These gapmers were designed by having the central gap region shortened to seven 2'-deoxynucleosides. The gapmers were tested for their ability to selectively inhibit mutant (mut) HTT mRNA expression levels targeting HTT SNP while leaving the expression of the wild-type (wt) intact. The activity and selectivity of the gapmers were evaluated and compared to ISIS 460209.

The gapmers and their motifs are described in Table 93. The internucleoside linkages throughout each modified oligonucleotide are phosphorothioate linkages (P=S). Nucleosides without a subscript are 13-D-2'-deoxyribonucleosides. Nucleosides followed by a subscript "e" indicate 2'-O-methoxyethyl (MOE) modified nucleosides. Nucleosides followed by a subscript "k" indicate 6'-(S)—$CH_3$ bicyclic nucleosides (e.g. cEt). $^mC$ indicates a 5-methyl cytosine nucleoside. Underlined nucleoside indicates the position on the oligonucleotides opposite to the SNP position, which is position 8 or 9 as counted from the 5'-terminus.

The modified oligonucleotides were tested in vitro. Heterozygous fibroblast GM04022 cell line was used. Cultured GM04022 cells at a density of 25,000 cells per well were transfected using electroporation with 0.12, 0.37, 1.1, 3.3 and 10 µM concentrations of modified oligonucleotides. After a treatment period of approximately 16 hours, RNA was isolated from the cells and mRNA levels were measured by quantitative real-time PCR using ABI assay C_2229297_10 which measures at dbSNP rs362303. The HTT mRNA levels were adjusted according to total RNA content, as measured by RIBOGREEN and the results are presented in Table 94.

The $IC_{50}$ and selectivity were calculated using methods previously described in Example 41. The $IC_{50}$ at which each oligonucleotide inhibits the mutant HTT mRNA expression is denoted as 'mut $IC_{50}$'. The $IC_{50}$ at which each oligonucleotide inhibits the wild-type HTT mRNA expression is denoted as 'wt $IC_{50}$'. Selectivity was calculated by dividing the $IC_{50}$ for inhibition of the wild-type HTT versus the $IC_{50}$ for inhibiting expression of the mutant HTT mRNA.

As illustrated in Table 94, each of the newly designed antisense oligonucleotides (ISIS 540108 and 571069) showed improvement in potency and/or selectivity in inhibiting mut HTT mRNA levels as compared to ISIS 460209.

TABLE 93

Short-gap antisense oligonucleotides targeting HTT SNP

| ISIS NO. | Sequence (5' to 3') | Motif | Gap chemistry | Wing chemistry 5' | Wing chemistry 3' | SEQ ID NO. |
|---|---|---|---|---|---|---|
| 460209 | $T_eA_kA_k$ATTG$\underline{T}$ $^mCA T^mCA_k{}^mC_k{}^mC_e$ | 3-9-3 | Full deoxy | ekk | kke | 10 |
| 540108 | $A_eT_eA_eA_kA_k$TTG$\underline{T}$ $^mCA T^mC_kA_k{}^mC_e{}^mC_eA_e$ | 5-7-5 | Full deoxy | eeekk | kkeee | 32 |

TABLE 93-continued

Short-gap antisense oligonucleotides targeting HTT SNP

| ISIS NO. | Sequence (5' to 3') | Gap Motif | Gap chemistry | Wing chemistry 5' | Wing chemistry 3' | SEQ ID NO. |
|---|---|---|---|---|---|---|
| 571069 | $A_eT_eA_eA_kA_kT_kTGT$ $^mCA T^mCA_k{}^mC_k{}^mC_eA_e$ | 6-7-4 | Full deoxy | eeeekk | kkee | 32 |
| 571173 | $A_eT_eA_kA_kATTGT$ $^mCAT_k{}^mC_kA_e{}^mC_e{}^mC_eA_e$ | 4-7-6 | Full deoxy | eekk | kkeeee | 32 |
| 572773 | $T_eA_eA_kA_kTTGT$ $^mCAT^mC_kA_k{}^mC_e{}^mC_e$ | 4-7-4 | Full deoxy | eekk | kkee | 10 | e = 2'-MOE, k = cEt, d = 2'-deoxyribonucleoside

TABLE 94

Comparison of inhibition of HTT mRNA levels and selectivity of modified oligonucleotides with ISIS 460209 targeting HTT SNP

| ISIS NO | $IC_{50}$ (μM) Mut | $IC_{50}$ (μM) Wt | Selectivity (wt vs mut) | Gap Motif | Gap chemistry | Wing Chemistry 5' | Wing Chemistry 3' |
|---|---|---|---|---|---|---|---|
| 460209 | 0.34 | 3.3 | 9.7 | 3-9-3 | Full deoxy | ekk | kke |
| 540108 | 0.20 | >10 | >50 | 5-7-5 | Full deoxy | eeekk | kkeee |
| 571069 | 0.29 | >9.9 | >34 | 6-7-4 | Full deoxy | eeeekk | kkee |
| 571173 | 1.0 | >10 | >10 | 4-7-6 | Full deoxy | eekk | kkeeee |
| 572773 | 0.71 | >7.8 | 11 | 4-7-4 | Full deoxy | eekk | kkee | e = 2'-MOE,
k = cEt,
d = 2'-deoxyribonucleoside

Example 63

Short-Gap Chimeric Oligonucleotides Targeting Huntingtin (HTT) Single Nucleotide Polymorphism (SNP)

Additional chimeric antisense oligonucleotides were designed based on 15-mer, ISIS 460209 and 17-mer, ISIS 540108 wherein the central gap region contains nine and seven 2'-deoxynucleosides, respectively. These gapmers were designed by introducing one or more cEt modification(s) at the 5'-end of the central gap region. The gapmers were tested for their ability to selectively inhibit mutant (mut) HTT mRNA expression levels targeting HTT SNP while leaving the expression of the wild-type (wt) intact. The activity and selectivity of the gapmers were evaluated and compared to ISIS 460209 and ISIS 540108.

The gapmers and their motifs are described in Table 95. The internucleoside linkages throughout each modified oligonucleotide are phosphorothioate linkages (P=S). Nucleosides without a subscript are (3-D-2'-deoxyribonucleosides. Nucleosides followed by a subscript "e" indicate 2'-O-methoxyethyl (MOE) modified nucleosides. Nucleosides followed by a subscript "k" indicate 6'-(S)—CH$_3$ bicyclic nucleosides (e.g. cEt). $^mC$ indicates a 5-methyl cytosine nucleoside. Underlined nucleoside indicates the position on the oligonucleotides opposite to the SNP position, which is position 8 or 9 as counted from the 5'-terminus.

The modified oligonucleotides were tested in vitro. Heterozygous fibroblast GM04022 cell line was used. Cultured GM04022 cells at a density of 25,000 cells per well were transfected using electroporation with 0.12, 0.37, 1.1, 3.3 and 10 μM concentrations of modified oligonucleotides. After a treatment period of approximately 16 hours, RNA was isolated from the cells and mRNA levels were measured by quantitative real-time PCR using ABI assay C_2229297_10 which measures at dbSNP rs362303. The HTT mRNA levels were adjusted according to total RNA content, as measured by RIBOGREEN and the results are presented in Table 96.

The $IC_{50}$ and selectivity were calculated using methods previously described in Example 41. The $IC_{50}$ at which each oligonucleotide inhibits the mutant HTT mRNA expression is denoted as 'mut $IC_{50}$'. The $IC_{50}$ at which each oligonucleotide inhibits the wild-type HTT mRNA expression is denoted as 'wt $IC_{50}$'. Selectivity was calculated by dividing the $IC_{50}$ for inhibition of the wild-type HTT versus the $IC_{50}$ for inhibiting expression of the mutant HTT mRNA.

As illustrated in Table 96, most of the newly designed oligonucleotides showed improvement in selectivity while maintaining potency as compared to 460209.

TABLE 95

Short-gap antisense oligonucleotides targeting HTT SNP

| ISIS NO. | Sequence (5' to 3') | Gap Motif | Gap chemistry | Wing chemistry 5' | Wing chemistry 3' | SEQ ID NO. |
|---|---|---|---|---|---|---|
| 460209 | $T_eA_kA_kATTGT$ $^mCAT^mCA_k{}^mC_k{}^mC_e$ | 3-9-3 | Full deoxy | ekk | kke | 10 |
| 540108 | $A_eT_eA_kA_kA_kTTGT$ $^mCAT^mC_kA_k{}^mC_e{}^mC_eA_e$ | 5-7-5 | Full deoxy | eeekk | kkeee | 32 |
| 556872 | $A_eT_eA_eA_eA_kTTGT$ $^mCAT^mC_eA_e{}^mC_e{}^mC_eA_e$ | 5-7-5 | Full deoxy | eeeek | eeeee | 32 |

TABLE 95-continued

Short-gap antisense oligonucleotides targeting HTT SNP

| ISIS NO. | Sequence (5' to 3') | Gap Motif | Gap chemistry | Wing chemistry 5' | Wing chemistry 3' | SEQ ID NO. |
|---|---|---|---|---|---|---|
| 556873 | $A_eT_eA_kA_kA_k$TTGT$^mCAT^mC_eA_e^mC_e^mC_eA_e$ | 5-7-5 | Full deoxy | eeekk | eeeee | 32 |
| 556874 | $A_eT_eA_kA_kA_k$TTGT$^mCAT^mC_eA_e^mC_e^mC_eA_e$ | 5-7-5 | Full deoxy | eekkk | eeeee | 32 |
| 568877 | $A_eT_kA_kA_kA_k$TTGT$^mCAT^mC_eA_e^mC_e^mC_eA_e$ | 5-7-5 | Full deoxy | ekkkk | eeeee | 32 |
| 568878 | $A_kT_kA_kA_kA_k$TTGT$^mCAT^mC_eA_e^mC_e^mC_eA_e$ | 5-7-5 | Full deoxy | kkkkk | eeeee | 32 | e = 2'-MOE, k = cEt, d = 2'-deoxyribonucleoside

TABLE 96

Comparison of inhibition of HTT mRNA levels and selectivity of modified oligonucleotides with ISIS 460209 targeting HTT SNP

| ISIS NO | $IC_{50}$ (μM) Mut | $IC_{50}$ (μM) Wt | Selectivity (wt vs mut) | Gap Motif | Gap chemistry | Wing Chemistry 5' | Wing Chemistry 3' |
|---|---|---|---|---|---|---|---|
| 460209 | 0.45 | 2.3 | 5.1 | 3-9-3 | Full deoxy | ekk | kke |
| 540108 | 0.25 | 9.5 | 38 | 5-7-5 | Full deoxy | eeekk | kkeee |
| 556872 | 1.0 | 9.9 | 9.9 | 5-7-5 | Full deoxy | eeeek | eeeee |
| 556873 | 0.67 | 3.4 | 5.1 | 5-7-5 | Full deoxy | eeekk | eeeee |
| 556874 | 0.38 | 1.9 | 5.0 | 5-7-5 | Full deoxy | eekkk | eeeee |
| 568877 | 0.44 | 6.2 | 14 | 5-7-5 | Full deoxy | ekkkk | eeeee |
| 568878 | 0.41 | 8.6 | 21 | 5-7-5 | Full deoxy | kkkkk | eeeee | e = 2'-MOE,
k = cEt,
d = 2'-deoxyribonucleoside

Example 64

Short-Gap Chimeric Oligonucleotides Targeting Huntingtin (HTT) Single Nucleotide Polymorphism (SNP)

Additional chimeric antisense oligonucleotides were designed based on 15-mer, ISIS 460209 and 17-mer, ISIS 540108 wherein the central gap region contains nine and seven 2'-deoxynucleosides, respectively. These gapmers were designed by introducing one or more cEt modification(s) at the 3'-end of the central gap region. The gapmers were tested for their ability to selectively inhibit mutant (mut) HTT mRNA expression levels targeting HTT SNP while leaving the expression of the wild-type (wt) intact. The activity and selectivity of the gapmers were evaluated and compared to ISIS 460209 and ISIS 540108.

The gapmers and their motifs are described in Table 97. The internucleoside linkages throughout each modified oligonucleotide are phosphorothioate linkages (P=S). Nucleosides without a subscript are (3-D-2'-deoxyribonucleosides. Nucleosides followed by a subscript "e" indicate 2'-O-methoxyethyl (MOE) modified nucleosides. Nucleosides followed by a subscript "k" indicate 6'-(S)—$CH_3$ bicyclic nucleosides (e.g. cEt). $^mC$ indicates a 5-methyl cytosine nucleoside. Underlined nucleoside indicates the position on the oligonucleotides opposite to the SNP position, which is position 8 or 9 as counted from the 5'-terminus.

The modified oligonucleotides were tested in vitro. Heterozygous fibroblast GM04022 cell line was used. Cultured GM04022 cells at a density of 25,000 cells per well were transfected using electroporation with 0.12, 0.37, 1.1, 3.3 and 10 μM concentrations of modified oligonucleotides. After a treatment period of approximately 16 hours, RNA was isolated from the cells and mRNA levels were measured by quantitative real-time PCR using ABI assay C_2229297_10 which measures at dbSNP rs362303. The HTT mRNA levels were adjusted according to total RNA content, as measured by RIBOGREEN and the results are presented in Table 98.

The $IC_{50}$ and selectivity were calculated using methods previously described in Example 41. The $IC_{50}$ at which each oligonucleotide inhibits the mutant HTT mRNA expression is denoted as 'mut $IC_{50}$'. The $IC_{50}$ at which each oligonucleotide inhibits the wild-type HTT mRNA expression is denoted as 'wt $IC_{50}$'. Selectivity was calculated by dividing the $IC_{50}$ for inhibition of the wild-type HTT versus the $IC_{50}$ for inhibiting expression of the mutant HTT mRNA.

As illustrated in Table 98, each of the newly designed oligonucleotides showed improvement in selective inhibition of mutant HTT mRNA levels compared to ISIS 460209. Comparable potency was observed for ISIS 568879 and 568880 while a slight loss in potency was observed for ISIS 556875, 556876 and 556877.

TABLE 97

Short-gap antisense oligonucleotides targeting HTT SNP

| ISIS NO. | Sequence (5' to 3') | Gap Motif | Gap chemistry | Wing chemistry 5' | Wing chemistry 3' | SEQ ID NO. |
|---|---|---|---|---|---|---|
| 460209 | $T_kA_kA_k$ATTGT$^m$CAT$^m$CA$_k^m$C$_k^m$C$_e$ | 3-9-3 | Full deoxy | ekk | kke | 10 |
| 540108 | $A_eT_eA_eA_kA_k$TTGT$^m$CAT$^m$C$_kA_k^m$C$_e^m$C$_eA_e$ | 5-7-5 | Full deoxy | eeekk | kkeee | 32 |
| 556875 | $A_eT_eA_eA_eA_e$TTGT$^m$CAT$^m$C$_kA_e^m$C$_e^m$C$_eA_e$ | 5-7-5 | Full deoxy | eeeee | keeee | 32 |
| 556876 | $A_eT_eA_eA_eA_e$TTGT$^m$CAT$^m$C$_kA_k^m$C$_e^m$C$_eA_e$ | 5-7-5 | Full deoxy | eeeee | kkeee | 32 |
| 556877 | $A_eT_eA_eA_eA_e$TTGT$^m$CAT$^m$C$_kA_k^m$C$_k^m$C$_eA_e$ | 5-7-5 | Full deoxy | eeeee | kkkee | 32 |
| 568879 | A.TA,A,A,TTGT$^m$CAT$^m$C$_kA_k^m$C$_k^m$C$_kA_e$ | 5-7-5 | Full deoxy | eeeee | kkkke | 32 |
| 568880 | A.T.A.A.A.TTGT$^m$CAT$^m$C$_kA_k^m$C$_k^m$C$_kA_k$ | 5-7-5 | Full deoxy | eeeee | kkkkk | 32 | e = 2'-MOE, k = cEt, d = 2'-deoxyribonucleoside

TABLE 98

Comparison of inhibition of HTT mRNA levels and selectivity of modified oligonucleotides with ISIS 460209 targeting HTT SNP

| ISIS NO | IC$_{50}$ (µM) Mut | IC$_{50}$ (µM) Wt | Selectivity (wt vs mut) | Gap Motif | Gap chemistry | Wing Chemistry 5' | Wing Chemistry 3' |
|---|---|---|---|---|---|---|---|
| 460209 | 0.45 | 2.3 | 5.1 | 3-9-3 | Full deoxy | ekk | kke |
| 540108 | 0.25 | 9.5 | 38 | 5-7-5 | Full deoxy | eeekk | kkeee |
| 556875 | 1.9 | >9.5 | >5 | 5-7-5 | Full deoxy | eeeee | keeee |
| 556876 | 0.99 | >9.9 | >10 | 5-7-5 | Full deoxy | eeeee | kkeee |
| 556877 | 1.0 | >10 | >10 | 5-7-5 | Full deoxy | eeeee | kkkee |
| 568879 | 0.44 | >10.1 | >23 | 5-7-5 | Full deoxy | eeeee | kkkke |
| 568880 | 0.59 | >10 | >17 | 5-7-5 | Full deoxy | eeeee | kkkkk | e = 2'-MOE,
k = cEt,
d = 2'-deoxyribonucleoside

Example 65

Modified Oligonucleotides Targeting Huntingtin (HTT) Single Nucleotide Polymorphism (SNP)

A series of modified oligonucleotides were designed based on the parent gapmer, ISIS 460209 wherein the central gap region contains nine 2'-deoxyribonucleosides. These modified oligonucleotides were designed by introducing various chemical modifications in the central gap region and were tested for their ability to selectively inhibit mutant (mut) HTT mRNA expression levels targeting SNP while leaving the expression of the wild-type (wt) intact. The activity and selectivity of the modified oligonucleotides were evaluated and compared to the parent gapmer, ISIS 460209.

The modified oligonucleotides were created with a 3-9-3 motif and are described in Table 99. The internucleoside linkages throughout each gapmer are phosphorothioate (P=S) linkages, except for the internucleoside linkage having a subscript "p" which indicates a methyl phosphonate internucleoside linkage (—O—P(CH$_3$)(=O)—O—).

Nucleosides without a subscript are β-D-2'-deoxyribonucleosides. Nucleosides followed by a subscript "e" indicates a 2'-O-methoxyethyl (MOE) modified nucleoside. Nucleosides followed by a subscript "k" indicates a 6'-(S)—CH$_3$ bicyclic nucleoside (e.g. cEt). $^m$C indicates a 5-methyl cytosine nucleoside. $^x$T indicates a 2-thio-thymidine nucleoside. Underlined nucleoside indicates the position on the oligonucleotides opposite to the SNP position, which is position 8 as counted from the 5'-terminus.

The modified oligonucleotides were tested in vitro. Heterozygous fibroblast GM04022 cell line was used (from Coriell Institute). Cultured GM04022 cells at a density of 25,000 cells per well were transfected using electroporation with 0.12, 0.37, 1.1, 3.3 and 10 µM concentrations of modified oligonucleotides. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN and the results are presented in Table 100.

The IC$_{50}$ and selectivity were calculated using methods previously described in Example 41. The IC$_{50}$ at which each oligonucleotide inhibits the mutant HTT mRNA expression is denoted as 'mut IC$_{50}$'. The IC$_{50}$ at which each oligonucleotide inhibits the wild-type HTT mRNA expression is denoted as 'wt IC$_{50}$'. Selectivity was calculated by dividing the IC$_{50}$ for inhibition of the wild-type HTT versus the IC$_{50}$ for inhibiting expression of the mutant HTT mRNA.

As illustrated in Table 100, improvement in selectivity with a slight decrease in potency was observed for the newly designed oligonucleotides as compared to ISIS 460209.

TABLE 99

Short-gap antisense oligonucleotides targeting HTT SNP

| ISIS NO. | Sequence (5' to 3') | Gap chemistry | Wing chemistry 5' | 3' | SEQ ID NO. |
|---|---|---|---|---|---|
| 460209 | $T_eA_kA_k$ATTGT $^mCA T^mCA_k{}^mC_k{}^mC_e$ | Full deoxy | ekk | kke | 10 |
| 556845 | $T_eA_kA_kA^x$TTGT $^mCA T^mCA_k{}^mC_k{}^mC_e$ | Deoxy/2-Thio | ekk | kke | 10 |
| 556847 | $T_eA_kA_kA^xT^x$TGT $^mCA T^mCA_k{}^mC_k{}^mC_e$ | Deoxy/2-Thio | ekk | kke | 10 |
| 558257 | $T_eA_kA_k$ATT$_p$GT $^mCA T^mCA_k{}^mC_k{}^mC_e$ | Deoxy/Methyl Phosphonate | ekk | kke | 10 |
| 571125 | $T_eA_kA_kA^x$TT$_p$GT $^mCA T^mCA_k{}^mC_k{}^mC_e$ | Deoxy/2-Thio/Methyl Phosphonate | ekk | kke | 10 | e = 2'-MOE, k = cEt, d = 2'-deoxyribonucleoside

TABLE 100

Comparison of inhibition of HTT mRNA levels and selectivity of modified oligonucleotides with ISIS 460209 targeting HTT SNP

| | $IC_{50}$ (μM) | | Selectivity | | Wing Chemistry | |
|---|---|---|---|---|---|---|
| ISIS NO | Mut | Wt | (wt vs mut) | Gap chemistry | 5' | 3' |
| 460209 | 0.56 | 3.8 | 6.8 | Full deoxy | ekk | kke |
| 556845 | 0.98 | >9.8 | >10 | Deoxy/2-Thio | ekk | kke |
| 556847 | 1.3 | >10.4 | >8 | Deoxy/2-Thio | ekk | kke |
| 558257 | 1.7 | >10.2 | >6 | Deoxy/Methyl Phosphonate | ekk | kke |
| 571125 | 1.8 | >10.8 | >6 | Deoxy/2-Thio/Methyl Phosphonate | ekk | kke | e = 2'-MOE,
k = cEt,
d = 2'-deoxyribonucleoside

Example 66

Modified Oligonucleotides Comprising Chemical Modifications in the Central Gap Region Targeting Huntingtin (HTT) Single Nucleotide Polymorphism (SNP)

Additional chimeric antisense oligonucleotides were designed in the same manner as the antisense oligonucleotides described in Example 65. These gapmers were designed by introducing various modifications in the central gap region and were tested for their ability to selectively inhibit mutant (mut) HTT mRNA expression levels targeting SNP while leaving the expression of the wild-type (wt) intact. The activity and selectivity of the modified oligonucleotides were evaluated and compared to the parent gapmer, ISIS 460209.

The modified oligonucleotides and their motifs are described in Table 101. The internucleoside linkages throughout each gapmer are phosphorothioate (P=S) linkages, except for the internucleoside linkage having a subscript "p" which indicates a methyl phosphonate internucleoside linkage (—O—P(CH₃)(=O)—O—). Nucleosides without a subscript are β-D-2'-deoxyribonucleosides. Nucleosides followed by a subscript "e" indicates a 2'-O-methoxyethyl (MOE) modified nucleoside. Nucleosides followed by a subscript "k" indicates a 6'-(S)—CH₃ bicyclic nucleoside (e.g. cEt). IT indicates a 5-methyl cytosine nucleoside. $^xT$ indicates a 2-thio-thymidine nucleoside. Underlined nucleoside indicates the position on the oligonucleotides opposite to the SNP position, which is position 8 as counted from the 5'-terminus.

The modified oligonucleotides were tested in vitro. Heterozygous fibroblast GM04022 cell line was used (from Coriell Institute). Cultured GM04022 cells at a density of 25,000 cells per well were transfected using electroporation with 0.12, 0.37, 1.1, 3.3 and 10 μM concentrations of modified oligonucleotides. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN and the results are presented in Table 102.

The $IC_{50}$ and selectivity were calculated using methods previously described in Example 41. The $IC_{50}$ at which each oligonucleotide inhibits the mutant HTT mRNA expression is denoted as 'mut $IC_{50}$'. The $IC_{50}$ at which each oligonucleotide inhibits the wild-type HTT mRNA expression is denoted as 'wt $IC_{50}$'. Selectivity was calculated by dividing the $IC_{50}$ for inhibition of the wild-type HTT versus the $IC_{50}$ for inhibiting expression of the mutant HTT mRNA.

As illustrated in Table 102, some of the newly designed oligonucleotides showed improvement in selectivity while maintaining potency as compared to 460209.

TABLE 101

Short-gap antisense oligonucleotides targeting HTT SNP

| ISIS NO. | Sequence (5' to 3') | Motif | Gap chemistry | Wing chemistry 5' | 3' | SEQ ID NO. |
|---|---|---|---|---|---|---|
| 460209 | $T_eA_kA_k$ATTGT$^m$CAT$^m$CA$_k^m$C$_k^m$C$_e$ | 3-9-3 | Full deoxy | ekk | kke | 10 |
| 551429 | $T_eA_eA_eA_kT_k$TGT$^m$CAT$^m$CA$_k^m$C$_k^m$C$_e$ | 5-7-3 | Full deoxy | eeekk | kke | 10 |
| 571122 | $T_eA_eA_eA_k^x$TTGT$^m$CAT$^m$CA$_k^m$C$_k^m$C$_e$ | 4-8-3 | Deoxy/2-Thio | eeek | kke | 10 |
| 571123 | Te$A_eA_kT_k$TpGT$^m$CAT$^m$CA$_k^m$C$_k^m$C$_e$ | 5-7-3 | Deoxy/Methyl Phosphonate | eeekk | kke | 10 |
| 571124 | $T_eA_eA_eA_k^x$TT$_p$GT$^m$CAT$^m$CA$_k^m$C$_k^m$C$_e$ | 4-8-3 | Deoxy/2-Thio/Methyl Phosphonate | eeek | kke | 10 |
| 579854 | $T_eA_eA_eA_k$TT$_p$GT$^m$CAT$^m$CA$_k^m$C$_k^m$C$_e$ | 4-8-3 | Deoxy/Methyl Phosphonate | eeek | kke | 10 |
| 566282 | $T_eA_kA_kA_{dx}T_{dx}T_dG_dT_d^mC_dA_dT_d^mC_dA_k^mC_k^mC_e$ | 3-9-3 | Deoxy/Methyl Phosphonate | ekk | kke | 10 | e = 2'-MOE, k = cEt, d = 2'-deoxyribonucleoside

TABLE 102

Comparison of inhibition of HTT mRNA levels and selectivity of modified oligonucleotides with ISIS 460209 targeting HTT SNP

| ISIS NO | IC$_{50}$ (μM) Mut | Wt | Selectivity (wt vs mut) | Motif | Gap chemistry | Wing Chemistry 5' | 3' |
|---|---|---|---|---|---|---|---|
| 460209 | 0.56 | 3.8 | 6.8 | 3-9-3 | Full deoxy | ekk | kke |
| 551429 | 0.50 | >10 | >20 | 5-7-3 | Full deoxy | eeekk | kke |
| 571122 | 1.8 | >10.8 | >6 | 4-8-3 | Deoxy/2-Thio | eeek | kke |
| 571123 | 0.96 | >9.6 | >10 | 5-7-3 | Deoxy/Methyl Phosphonate | eeekk | kke |
| 571124 | 2.3 | >9.2 | >4 | 4-8-3 | Deoxy/2-Thio/Methyl Phosphonate | eeek | kke |
| 579854 | 0.63 | >10.1 | >16 | 4-8-3 | Deoxy/Methyl Phosphonate | eeek | kke |
| 566282 | 0.51 | 6.3 | 12.4 | 3-9-3 | Deoxy/Methyl Phosphonate | ekk | kke | e = 2'-MOE,
k = cEt

Example 67

Modified Oligonucleotides Comprising Chemical Modifications in the Central Gap Region Targeting Huntingtin (HTT) Single Nucleotide Polymorphism (SNP)

Additional chimeric antisense oligonucleotides were designed in the same manner as the antisense oligonucleotides described in Example 65. These gapmers were designed by introducing various modifications in the central gap region and were tested for their ability to selectively inhibit mutant (mut) HTT mRNA expression levels targeting SNP while leaving the expression of the wild-type (wt) intact. The activity and selectivity of the modified oligonucleotides were evaluated and compared to the parent gapmer, ISIS 460209.

The modified oligonucleotides and their motifs are described in Table 103. The internucleoside linkages throughout each gapmer are phosphorothioate (P=S) linkages, except for the internucleoside linkage having a subscript "p" which indicates a methyl phosphonate internucleoside linkage (—O—P(CH$_3$)(=O)—O—). Nucleosides without a subscript are β-D-2'-deoxyribonucleosides. Nucleosides followed by a subscript "e" indicates a 2'-O-methoxyethyl (MOE) modified nucleoside. Nucleosides followed by a subscript "k" indicates a 6'-(S)—CH$_3$ bicyclic nucleoside (e.g. cEt). IT indicates a 5-methyl cytosine nucleoside. $^x$T indicates a 2-thio-thymidine nucleoside. Underlined nucleoside indicates the position on the oligonucleotides opposite to the SNP position, which is position 8 or 9 as counted from the 5'-terminus.

The modified oligonucleotides were tested in vitro. Heterozygous fibroblast GM04022 cell line was used (from Coriell Institute). Cultured GM04022 cells at a density of 25,000 cells per well were transfected using electroporation with 0.12, 0.37, 1.1, 3.3 and 10 μM concentrations of modified oligonucleotides. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN and the results are presented in Table 104.

The IC$_{50}$ and selectivity were calculated using methods previously described in Example 41. The IC$_{50}$ at which each oligonucleotide inhibits the mutant HTT mRNA expression is denoted as 'mut IC$_{50}$'. The IC$_{50}$ at which each oligonucleotide inhibits the wild-type HTT mRNA expression is denoted as 'wt IC$_{50}$'. Selectivity was calculated by dividing the IC$_{50}$ for inhibition of the wild-type HTT versus the IC$_{50}$ for inhibiting expression of the mutant HTT mRNA.

As illustrated in Table 104, all but one of the newly designed oligonucleotides showed improvement in selectivity while maintaining potency as compared to ISIS 460209.

script "e" indicates a 2'-O-methoxyethyl (MOE) modified nucleoside. Nucleosides followed by a subscript "k" indicates a 6'-(S)—CH$_3$ bicyclic nucleoside (e.g. cEt). $^m$C indicates a 5-methyl cytosine nucleoside. $^x$T indicates a 2-thio-thymidine nucleoside. Underlined nucleoside indicates the

TABLE 103

Short-gap antisense oligonucleotides targeting HTT SNP

| ISIS NO. | Sequence (5' to 3') | Motif | Gap chemistry | Wing chemistry 5' | 3' | SEQ ID NO. |
|---|---|---|---|---|---|---|
| 460209 | T$_e$A$_k$A$_k$ATTGT $^m$CAT$^m$CA$_k$$^m$C$_k$$^m$C$_e$ | 3-9-3 | Full deoxy | ekk | kke | 10 |
| 476333 | A$_e$T$_k$A$_e$A$_k$ATTGT $^m$CAT$^m$CA$_k$$^m$C$_e$$^m$C$_k$A$_e$ | 4-9-4 | Full deoxy | ekek | keke | 32 |
| 571039 | A$_e$T$_k$A$_e$A$_k$A$^x$TTGT $^m$CAT$^m$CA$_k$$^m$C$_e$$^m$C$_k$A$_e$ | 4-9-4 | Deoxy/2-Thio | ekek | keke | 32 |
| 571171 | A$_e$T$_k$A$_e$A$_k$ATT$_p$GT $^m$CAT$^m$CA$_k$$^m$C$_e$$^m$C$_k$A$_e$ | 4-9-4 | Deoxy/Methyl Phosphonate | ekek | keke | 32 |
| 571041 | A$_e$T$_k$A$_e$A$_k$A$^x$TT$_p$GT $^m$CAT$^m$CA$_k$$^m$C$_e$$^m$C$_k$A$_e$ | 4-9-4 | Deoxy/2-Thio/Methyl Phosphonate | ekek | keke | 32 | e = 2'-MOE, k = cEt, d = 2'-deoxyribonucleoside

TABLE 104

Comparison of inhibition of HTT mRNA levels and selectivity of modified oligonucleotides with ISIS 460209 targeting HTT SNP

| ISIS NO | IC$_{50}$ (μM) Mut | Wt | Selectivity (wt vs mut) | Gap chemistry | Wing Chemistry 5' | 3' |
|---|---|---|---|---|---|---|
| 460209 | 0.56 | 3.8 | 6.8 | Full deoxy | ekk | kke |
| 476333 | 0.56 | 3.4 | 6.1 | Full deoxy | ekek | keke |
| 571039 | 0.34 | >9.9 | >29 | Deoxy/2-Thio | ekek | keke |
| 571171 | 0.54 | >10.3 | >19 | Deoxy/Methyl Phosphonate | ekek | keke |
| 571041 | 0.75 | >9.8 | >13 | Deoxy/2-Thio/Methyl Phosphonate | ekek | keke | e = 2'-MOE, k = cEt, d = 2'-deoxyribonucleoside

Example 68

Selectivity in Inhibition of HTT mRNA Levels Targeting SNP by Gap-Interrupted Modified Oligonucleotides Additional modified oligonucleotides were designed based on the parent gapmer, ISIS 460209 wherein the central gap region contains nine 2'-deoxyribonucleosides. These modified oligonucleotides were designed by introducing one or more modified nucleobase(s) in the central gap region and were tested for their ability to selectively inhibit mutant (mut) HTT mRNA expression levels targeting SNP while leaving the expression of the wild-type (wt) intact. The activity and selectivity of the modified oligonucleotides were evaluated and compared to ISIS 460209.

The modified oligonucleotides were created with a 3-9-3 motif and are described in Table 105. The internucleoside linkages throughout each gapmer are phosphorothioate (P=S) linkages. Nucleosides without a subscript are β-D-2'-deoxyribonucleosides. Nucleosides followed by a subposition on the oligonucleotides opposite to the SNP position, which is position 8 as counted from the 5'-terminus.

The modified oligonucleotides were tested in vitro. Heterozygous fibroblast GM04022 cell line was used (from Coriell Institute). Cultured GM04022 cells at a density of 25,000 cells per well were transfected using electroporation with 0.12, 0.37, 1.1, 3.3 and 10 μM concentrations of modified oligonucleotides. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN.

The IC$_{50}$ and selectivity were calculated using methods previously described in Example 41. The IC$_{50}$ at which each oligonucleotide inhibits the mutant HTT mRNA expression is denoted as 'mut IC$_{50}$'. The IC$_{50}$ at which each oligonucleotide inhibits the wild-type HTT mRNA expression is denoted as 'wt IC$_{50}$'. Selectivity was calculated by dividing the IC$_{50}$ for inhibition of the wild-type HTT versus the IC$_{50}$ for inhibiting expression of the mutant HTT mRNA.

As illustrated in Table 106, ISIS 556845 showed improvement in selectivity and potency as compared to ISIS 460209. ISIS 556847 showed improvement in selectivity with comparable potency while ISIS 556846 showed improvement in potency with comparable selectivity.

TABLE 105

Gap-interrupted modified oligonucleotides targeting HTT SNP

| ISIS NO. | Sequence (5' to 3') | Gap chemistry | Wing chemistry 5' | 3' | SEQ ID NO. |
|---|---|---|---|---|---|
| 460209 | $T_eA_kA_k$ATTGT $^mCAT^mCA_k{}^mC_k{}^mC_e$ | Full deoxy | ekk | kke | 10 |
| 556845 | $T_eA_kA_kA^x$TTGT $^mCAT^mCA_k{}^mC_k{}^mC_e$ | Deoxy/2-Thio | ekk | kke | 10 |
| 556846 | $T_eA_kA_kAT^x$TGT $^mCAT^mCA_k{}^mC_k{}^mC_e$ | Deoxy/2-Thio | ekk | kke | 10 |
| 556847 | $T_eA_kA_kA^xT^x$TGT $^mCAT^mCA_k{}^mC_k{}^mC_e$ | Deoxy/2-Thio | ekk | kke | 10 | e = 2'-MOE, k = cEt, d = 2'-deoxyribonucleoside

TABLE 106

Comparison of inhibition of HTT mRNA levels and selectivity of gap-interrupted modified oligonucleotides with ISIS 460209 targeting HTT SNP

| ISIS NO | $IC_{50}$ (μM) Mut | Wt | Selectivity (wt vs mut) | Gap chemistry | Wing Chemistry 5' | 3' |
|---|---|---|---|---|---|---|
| 460209 | 0.30 | 0.99 | 3.3 | Full deoxy | ekk | kke |
| 556845 | 0.13 | 10.01 | >77 | Deoxy/2-Thio | ekk | kke |
| 556846 | 0.19 | 0.48 | 2.5 | Deoxy/2-Thio | ekk | kke |
| 556847 | 0.45 | 9.9 | >22 | Deoxy/2-Thio | ekk | kke | e = 2'-MOE, k = cEt, d = 2'-deoxyribonucleoside

Example 69

Evaluation of Modified Oligonucleotides Targeting HTT SNP—In Vivo Study

Additional modified oligonucleotides were selected and tested for their effects on mutant and wild type HTT protein levels in vivo targeting various SNP sites as illustrated below.

The gapmers and their motifs are described in Table 107. The internucleoside linkages throughout each gapmer are phosphorothioate (P=S) linkages. All cytosine nucleobases throughout each gapmer are 5-methyl cytosines. Nucleosides without a subscript are β-D-2'-deoxyribonucleosides. Nucleosides followed by a subscript "e" or "k" are sugar modified nucleosides. A subscript "e" indicates a 2'-O-methoxyethyl (MOE) modified nucleoside and a subscript "k" indicates a 6'-(S)—CH₃ bicyclic nucleoside (e.g. cEt).

The gapmer, ISIS 460209 was included in the study as a benchmark oligonucleotide against which the potency and selectivity of the modified oligonucleotides could be compared. A non-allele specific oligonucleotide, ISIS 387898, was used as a positive control.

Hu97/18 mice, the first murine model of HD that fully genetically recapitulates human HD were used in the study. They were generated in Hayden's lab by cross bred BACHD, YAC18 and Hdh (−/−) mice.

Hu97/18 mice were treated with 300 μg of modified oligonucleotides by a single unilateral intracerebroventricular (ICV) bolus injection. This treatment group consisted of 4 animals/oligonucleotide. The control group received a 10 μM bolus injection of sterile PBS and consisted of 4 animals.

Animals were sacrificed at 4 weeks post-injection. The second most anterior 2 mm coronal slab for each brain hemisphere was collected using a 2 mm rodent brain matrix. The remaining portion of the brain was post-fixed in 4% paraformaldehyde, cryoprotected in 30% sucrose and sectioned into 25 μm coronal sections for immunohistochemical analysis.

The HTT protein levels were analyzed by high molecular weight western blot (modified from Invitrogen's NuPAGE Bis-Tris System Protocol). The tissue was homogenized in ice cold SDP lysis buffer. 40 μg of total protein lysate was resolved on 10% low-BIS acrylamide gels (200:1 acrylamide:BIS) with tris-glycine running buffer (25 mM Tris, 190 mM Glycince, 0.1% SDS) containing 10.7 mM β-mercaptoethanol added fresh. Gels were run at 90V for 40 min through the stack, then 190V for 2.5 h, or until the 75 kDa molecular weight marker band was at the bottom of the gel. Proteins were transferred to nitrocellulose at 24V for 2 h with NuPage transfer buffer (Invitrogen: 25 mM Bicine, 25 mM Bis-Tris, 1.025 mM EDTA, 5% MeOH, pH 7.2). Membranes were blocked with 5% milk in PBS, and then blotted for HTT with MAB2166 (1:1000, millipore). Anti-calnexin (Sigma C4731) immunoblotting was used as loading control. Proteins were detected with IR dye 800CW goat anti-mouse (Rockland 610-131-007) and AlexaFluor 680 goat anti-rabbit (Molecular Probes A21076)-labeled secondary antibodies, and the LiCor Odyssey Infrared Imaging system.

The results in Table 108 are presented as the average percent of HTT protein levels for each treatment group, normalized to PBS-treated control and is denoted as "% UTC". The percent of mutant HTT protein levels is denoted as "mut". The percent of wild-type HTT protein levels is denoted as "wt". Selectivity was also evaluated and measured by dividing the percent of wild-type HTT protein levels vs. the percent of the mutant HTT protein levels.

As illustrated in Table 108, treatment with the newly designed oligonucleotides, ISIS 476333 and 460085 showed improvement in potency and selectivity in inhibiting mutant HTT protein levels as compared to the parent gapmer, 460209. Comparable or a slight loss in potency and/or selectivity was observed for the remaining oligonucleotides.

TABLE 107

Modified oligonucleotides targeting HTT rs7685686, rs4690072 and rs363088 in Hu97/18 mice

| ISIS NO | Sequence (5' to 3') | Motif | Wing Chemistry 5' | Wing Chemistry 3' | SEQ ID NO. |
|---|---|---|---|---|---|
| 387898 | $C_eT_eC_eG_eA_e$CTAAAGCAGGA$_eT_eT_eT_eC_e$ | 5-10-5 | e5 | e5 | 79 |
| 460209 | $T_eA_kA_k$ATTG$\underline{T}$CATCA$_kC_kC_e$ | 3-9-3 | ekk | kke | 10 |
| 435879 | $A_eA_eT_eA_eA_e$ATTGTCATCA$_eC_eC_eA_eG_e$ | 5-9-5 | e5 | e5 | 80 |
| 476333 | $A_eT_kA_kA_k$ATTGTCATCA$_kC_eC_kA_e$ | 4-9-4 | ekek | keke | 32 |
| 435874 | $C_eA_eC_eA_eG_e$TGCTACCCAA$_eC_eC_eT_eT_e$ | 5-9-5 | e5 | e5 | 81 |
| 435871 | $T_eC_eA_eC_eA_e$GCTATCTTCT$_eC_eA_eT_eC_e$ | 5-9-5 | e5 | e5 | 82 |
| 460085 | $A_eT_eA_eA_eA_e$TTG$\underline{T}$CATC$_eA_eC_eC_eA_e$ | 5-7-5 | e5 | e5 | 32 | e = 2'-MOE (e.g. e5 = eeeee), k = cEt

TABLE 108

Effects of modified oligonucleotides on mutant and wild type HTT protein levels in Hu97/18 mice

| ISIS NO | SNP site | Dosage (µg) | % UTC mut | % UTC wt | Selectivity (wt vs mut) |
|---|---|---|---|---|---|
| PBS | — | 300 | 100 | 100 | 1 |
| 387898 | — | 300 | 23.76 | 25.66 | 1 |
| 460209 | rs7685686 | 300 | 18.16 | 48.99 | 2.7 |
| 435879 | rs7685686 | 300 | 41.48 | 73.11 | 1.8 |
| 476333 | rs7685686 | 300 | 6.35 | 22.05 | 3.5 |
| 460085 | rs7685686 | 300 | 2.9 | 40.1 | 13.8 |
| 435874 | rs4690072 | 300 | 44.18 | 76.63 | 1.7 |
| 435871 | rs363088 | 300 | 33.07 | 89.30 | 2.7 |

Example 70

Evaluation of ISIS 435871 in Central Nervous System (CNS) Targeting HTT rs363088—In Vivo Study A modified oligonucleotide from Example 68, ISIS 435871 was selected and tested for its effects on mutant and wild type HTT protein levels in the CNS in vivo targeting rs363088.

Hu97/18 mouse was treated with 300 µg of ISIS 435871 by a single unilateral intracerebroventricular (ICV) bolus injection. The animal was sacrificed at 4 weeks post-injection. Regional CNS structures were then micro-dissected including bilateral samples from the most anterior portion of cortex (Cortex 1), an intermediate section of cortex (Cortex 2), the most posterior section of cortex (Cortex 3), the striatum, the hippocampus, the cerebellum, and a 1 cm section of spinal cord directly below the brain stem. Tissue was homogenized and assessed for mutant and wild-type HTT levels by Western blotting using the procedures as described in Example 69. The results are presented below. As no untreated or vehicle treated control is shown, HTT intensity of each allele is expressed as a ratio of calnexin loading control intensity. The ratio of the mutant HTT to the wt HTT in the treated animal was determined and is denoted as "wt/mut". Having a ratio higher than 1 is indicative of allele-specific silencing.

As illustrated in Table 109, a single unilateral ICV bolus injection of the modified antisense oligonucleotide showed selective HTT silencing throughout the CNS except in the cerebellum, where the antisense oligonucleotide did not distribute evenly.

TABLE 109

Effects of ISIS 435871 on mutant and wild type HTT protein levels in CNS targeting rs363088 in Hu97/18 mice

| Tissue | HTT intensity/calnexin intensity wt | HTT intensity/calnexin intensity mut | wt/mut |
|---|---|---|---|
| Cortex 1 | 0.032 | 0.014 | 2.29 |
| Cortex 2 | 0.027 | 0.009 | 3 |
| Cortex 3 | 0.023 | 0.007 | 3.29 |
| Striatum | 0.030 | 0.012 | 2.5 |
| Hippocampus | 0.016 | 0.006 | 2.67 |
| Cerebellum | 0.023 | 0.019 | 1.21 |
| Spinal Cord | 0.014 | 0.007 | 2 |

Example 71

Evaluation of Modified Oligonucleotides Targeting HTT rs7685686—In Vivo Study

Several modified oligonucleotides from Examples 43, 51, 52, 53 and 66 were selected and tested for their effects on mutant and wild type HTT protein levels in vivo targeting HTT rs7685686.

The gapmer, ISIS 460209 was included in the study as a benchmark oligonucleotide against which the potency and selectivity of the modified oligonucleotides could be compared.

Hu97/18 mice were treated with 300 µg of modified oligonucleotides by a single unilateral intracerebroventricular (ICV) bolus injection. This treatment group consisted of 4 animals/oligonucleotide. The control group received a 10 µl bolus injection of sterile PBS and consisted of 4 animals.

Animals were sacrificed at 4 weeks post-injection. The second most anterior 2 mm coronal slab for each brain hemisphere was collected using a 2 mm rodent brain matrix. The HTT protein levels were analyzed in the same manner as described in Example 69 and the results are presented below.

The results in Table 110 are presented as the average percent of HTT protein levels for each allele and treatment group, normalized to PBS-treated control and is denoted as "% UTC". The percent of mutant HTT protein levels is denoted as "mut". The percent of wild-type HTT protein levels is denoted as "wt".

As shown in Table 110, each of the newly designed oligonucleotides showed improvement in selective inhibition of mutant HTT protein levels as compared to ISIS 460209. ISIS 550913 and 540095 showed improvement in potency while the remaining modified oligonucleotides showed comparable or a slight decrease in potency as compared to the parent gapmer.

TABLE 110

Effects of modified oligonucleotides on mutant and wild type HTT protein levels targeting rs7685686 in Hu97/18 mice

| ISIS NO | % UTC mut | % UTC wt | Motif | Wing chemistry 5' | Wing chemistry 3' | Gap chemistry | SEQ ID NO |
|---|---|---|---|---|---|---|---|
| PBS | 100 | 100 | — | — | — | — | — |
| 460209 | 18.16 | 48.99 | 3-9-3 | ekk | kke | Full deoxy | 10 |
| 550913 | 9.31 | 34.26 | 5-9-5 | kkekk | kkekk | Full deoxy | 27 |
| 540095 | 12.75 | 106.05 | 2-9-4 | ek | kkke | Full deoxy | 65 |
| 551429 | 19.07 | 108.31 | 5-7-3 | eeekk | kke | Full deoxy | 10 |
| 540094 | 24.68 | 87.56 | 2-9-4 | ek | kkke | Full deoxy | 67 |
| 540096 | 24.89 | 98.26 | 2-9-4 | ek | kkke | Full deoxy | 68 |
| 540108 | 28.34 | 85.62 | 5-7-5 | eeekk | kkeee | Full deoxy | 23 | e = 2'-MOE, k = cEt

Example 72

Evaluation of Modified Oligonucleotides Targeting HTT rs7685686—In Vivo Study

Several modified oligonucleotides selected from Examples 57, 58, 61 and 62 were tested and evaluated for their effects on mutant and wild type HTT protein levels in vivo targeting HTT rs7685686.

Hu97/18 mice were treated with 300 μg of modified oligonucleotides by a single unilateral intracerebroventricular (ICV) bolus injection and the control group received a 10 μl bolus injection of sterile PBS. Each treatment group consisted of 4 animals.

Animals were sacrificed at 4 weeks post-injection. The second most anterior 2 mm coronal slab for each brain hemisphere was collected using a 2 mm rodent brain matrix. The HTT protein levels were analyzed in the same manner as described in Example 69. The in vivo study for ISIS 575008 and 571069 marked with an asterisk (*) was performed independently and the results are presented below.

The results in Table 111 are presented as the average percent of HTT protein levels for each allele and treatment group, normalized to PBS-treated control and is denoted as "% UTC". The percent of mutant HTT protein levels is denoted as "mut". The percent of wild-type HTT protein levels is denoted as "wt".

As illustrated in Table 111, selective inhibition of mut HTT protein levels was achieved with the newly designed oligonucleotide treatment as compared to PBS treated control.

TABLE 111

Effects of modified oligonucleotides on mutant and wild type HTT protein levels targeting rs7685686 in Hu97/18 mice

| ISIS NO | % UTC mut | % UTC wt | Motif | Wing chemistry 5' | Wing chemistry 3' | Gap chemistry | SEQ ID NO |
|---|---|---|---|---|---|---|---|
| PBS | 100 | 100 | — | — | — | — | — |
| 575007 | 26.9 | 104.5 | 3-9-3 | ekk | kke | Deoxy/cEt | 10 |
| 575008* | 21.7 | 105.9 | 5-7-3 | ekkkk | kke | Deoxy/cEt | 10 |
| 566267 | 32.8 | 109.3 | 3-9-3 | ekk | kke | Deoxy/F-HNA | 10 |
| 571036 | 30.3 | 103.3 | 6-7-4 | ekekek | keke | Full deoxy | 32 |
| 571037 | 32.8 | 111.9 | 6-7-4 | eeeekk | keke | Full deoxy | 32 |
| 571069* | 29.4 | 109.8 | 6-7-4 | eeeekk | kkee | Full deoxy | 32 | e = 2'-MOE, k = cEt

Example 73

Evaluation of Modified Oligonucleotides Targeting HTT rs7685686—In Vivo Dose Response Study ISIS 476333, 435871, 540108, 575007 and 551429 from previous examples were selected and evaluated at various doses for their effect on mutant and wild type HTT protein levels in vivo targeting HTT rs7685686.

Hu97/18 mice were treated with various doses of modified oligonucleotides as presented in Table 112 by a single unilateral intracerebroventricular (ICV) bolus injection. This treatment group consisted of 4 animals/oligonucleotide. The control group received a 10 μl bolus injection of sterile PBS and consisted of 4 animals.

Animals were sacrificed at 4 weeks post-injection. The second most anterior 2 mm coronal slab for each brain hemisphere was collected using a 2 mm rodent brain matrix. The HTT protein levels were analyzed in the same manner as described in Example 69. The dose response study was performed independently for each modified oligonucleotide and the results are presented below.

The results in Table 112 are presented as the average percent of HTT protein levels for each allele and treatment group, normalized to PBS-treated control and is denoted as "% UTC". The percent of mutant HTT protein levels is denoted as "mut". The percent of wild-type HTT protein levels is denoted as "wt".

As illustrated in Table 112, selective inhibition of mut HTT protein levels was achieved in a dose-dependent manner for the newly designed oligonucleotides.

TABLE 112

Dose-dependent effect of modified oligonucleotides on mutant and wild type HTT protein levels targeting rs7685686 in Hu97/18 mice

| ISIS NO | Dosage (μg) | % UTC mut | % UTC wt | Motif | SEQ ID NO. |
|---|---|---|---|---|---|
| PBS | 0 | 100 | 100 | — | |
| 476333 | 50 | 48.7 | 115 | 4-9-4 (ekek-d9-keke) | 32 |
| | 150 | 23.1 | 53.3 | | |
| | 300 | 8.8 | 36.7 | | |
| 435871 | 75 | 114 | 118 | 5-9-5 (e5-d9-e5) | 82 |
| | 150 | 47.3 | 80.3 | | |
| | 300 | 33 | 89.3 | | |
| | 500 | 36 | 97.5 | | |
| 540108 | 75 | 30.5 | 71.7 | 5-7-5 (eeekk-d7-kkeee) | 32 |
| | 150 | 22 | 81 | | |
| | 300 | 8.6 | 59.6 | | |

TABLE 112-continued

Dose-dependent effect of modified oligonucleotides on mutant and wild type HTT protein levels targeting rs7685686 in Hu97/18 mice

| ISIS NO | Dosage (μg) | % UTC mut | % UTC wt | Motif | SEQ ID NO. |
|---|---|---|---|---|---|
| 575007 | 150 | 41.5 | 110.7 | 3-9-3 | 10 |
|  | 300 | 29 | 119.4 | (ekk-d-k-d7-kke) |  |
|  |  |  |  | (deoxy gap interrupted with cEt) |  |
| 551429 | 75 | 58 | 101.3 | 5-7-3 | 10 |
|  | 150 | 36.2 | 110.4 | (eeekk-d7-kke) |  |
|  | 300 | 19.7 | 107.8 |  |  | e = 2'-MOE (e.g. e5 = eeeee),
k = cEt,
d = 2'-deoxyribonucleoside

Example 74

Modified Oligonucleotides Targeting Huntingtin (HTT) Single Nucleotide Polymorphism (SNP)

A series of modified oligonucleotides was designed based on a parent gapmer, ISIS 460209, wherein the central gap region contains nine β-D-2'-deoxyribonucleosides. The modified oligonucleotides were designed by introducing a 5'-(R)-Me DNA modification within the central gap region. The 5'-(R)-Me DNA containing oligonucleotides were tested for their ability to selectively inhibit mutant (mut) HTT mRNA expression levels targeting rs7685686 while leaving the expression of the wild-type (wt) intact. The potency and selectivity of the modified oligonucleotides were evaluated and compared to ISIS 460209.

The position on the oligonucleotides opposite to the SNP position, as counted from the 5'-terminus is position 8.

The modified oligonucleotides were created with a 3-9-3 motif and are described in Table 113. The internucleoside linkages throughout each gapmer are phosphorothioate (P=S) linkages. Nucleosides followed by a subscript "d" are β-D-2'-deoxyribonucleosides. Nucleosides followed by a subscript "e" indicates a 2'-O-methoxyethyl (MOE) modified nucleoside. Nucleosides followed by a subscript "k" indicates a 6'-(S)—CH$_3$ bicyclic nucleoside (e.g. cEt). Nucleosides followed by a subscript "z" indicates a 5'-(R)-Me DNA. "$^m$C" indicates a 5-methyl cytosine nucleoside.

The modified oligonucleotides were tested in vitro. Heterozygous fibroblast GM04022 cell line was used. Cultured GM04022 cells at a density of 25,000 cells per well were transfected using electroporation with a single dose at 2 μM concentration of the modified oligonucleotide. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2xPCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN.

The IC$_{50}$s and selectivities as expressed in "fold" were measured and calculated using methods described previously in Example 41. As illustrated in Table 114, treatment with the newly designed oligonucleotides showed comparable or a slight increase in potency and/or selectivity as compared to ISIS 460209.

TABLE 113

Gap-interrupted oligonucleotides comprising 5'-(R)-Me DNA targeting HTT SNP

| ISIS NO. | Sequence (5' to 3') | Gap chemistry | Wing chemistry 5' | Wing chemistry 3' | SEQ ID NO. |
|---|---|---|---|---|---|
| 460209 | T$_e$A$_k$A$_k$A$_d$T$_d$T$_d$G$_d$T$_d$$^m$C$_d$A$_d$T$_d$$^m$C$_d$A$_k$$^m$C$_k$$^m$C$_e$ | Full deoxy | ekk | kke | 10 |
| 556848 | T$_e$A$_k$A$_k$A$_z$T$_d$T$_d$G$_d$T$_d$$^m$C$_d$A$_d$T$_d$$^m$C$_d$A$_k$$^m$C$_k$$^m$C$_e$ | Deoxy/5'-(R)-Me DNA | ekk | kke | 10 |
| 556849 | T$_e$A$_k$A$_k$A$_d$T$_z$T$_d$G$_d$T$_d$$^m$C$_d$A$_d$T$_d$$^m$C$_d$A$_k$$^m$C$_k$$^m$C$_e$ | Deoxy/5'-(R)-Me DNA | ekk | kke | 10 |
| 556850 | T$_e$A$_k$A$_k$A$_d$T$_d$T$_z$G$_d$T$_d$$^m$C$_d$A$_d$T$_d$$^m$C$_d$A$_k$$^m$C$_k$$^m$C$_e$ | Deoxy/5'-(R)-Me DNA | ekk | kke | 10 | e = 2'-MOE, k = cEt

TABLE 114

Comparison of inhibition of HTT mRNA levels and selectivity of gap-interrupted oligonucleotides with ISIS 460209 targeting HTT SNP

| ISIS NO. | $IC_{50}$ (µM) Mut | $IC_{50}$ (µM) Wt | Selectivity (wt vs mut) | Gap chemistry | Wing chemistry 5' | Wing chemistry 3' |
|---|---|---|---|---|---|---|
| 460209 | 0.30 | 0.99 | 3.3 | Full deoxy | ekk | kke |
| 556848 | 0.15 | 0.6 | 4.0 | Deoxy/5'-(R)-Me DNA | ekk | kke |
| 556849 | 0.16 | 0.46 | 2.9 | Deoxy/5'-(R)-Me DNA | ekk | kke |
| 556850 | 0.33 | 0.96 | 2.9 | Deoxy/5'-(R)-Me DNA | ekk | kke | e = 2'-MOE, k = cEt

Example 75

Modified Oligonucleotides Comprising 5'-(R)- or 5'-(S)-Me DNA Modification Targeting HTT SNP A series of modified oligonucleotides was designed based on a parent gapmer, ISIS 460209, wherein the central gap region contains nine β-D-2'-deoxyribonucleosides. The modified oligonucleotides were designed by introducing 5'-(S)- or 5'-(R)-Me DNA modification slightly upstream or downstream (i.e. "microwalk") within the central gap region. The gapmers were created with a 3-9-3 motif and were tested for their ability to selectively inhibit mutant (mut) HTT mRNA expression. The potency and selectivity of the modified oligonucleotides were evaluated and compared to ISIS 460209.

The position on the oligonucleotides opposite to the SNP position, as counted from the 5'-terminus is position 8.

The modified oligonucleotides and their motifs are described in Table 115. The internucleoside linkages throughout each gapmer are phosphorothioate (P=S) linkages. Nucleosides followed by a subscript "d" are β-D-2'-deoxyribonucleosides. Nucleosides followed by a subscript "e" indicates a 2'-O-methoxyethyl (MOE) modified nucleoside. Nucleosides followed by a subscript "k" indicates a 6'-(S)—$CH_3$ bicyclic nucleoside (e.g. cEt). Nucleosides followed by a subscript "v" indicates a 5'-(S)-Me DNA. Nucleosides followed by a subscript "z" indicates a 5'-(R)-Me DNA. "$^mC$" indicates a 5-methyl cytosine nucleoside.

The modified oligonucleotides were tested in vitro. Heterozygous fibroblast GM04022 cell line was used. Cultured GM04022 cells at a density of 25,000 cells per well were transfected using electroporation with 0.1, 0.4, 1.1, 3.3 and 10 µM concentrations of modified oligonucleotides. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN and the results are presented below.

The $IC_{50}$s and selectivities as expressed in "fold" were measured and calculated using methods described previously in Example 41. The results in Table 116 demonstrated that each of the newly designed oligonucleotides comprising 5'-(S)- or 5'-(R)-Me DNA within the central gap region achieved improvement in potency and selectivity as compared to the parent gapmer, ISIS 460209.

TABLE 115

Gap-interrupted oligonucleotides comprising +-(S)- or 5'-(R)-Me DNA targeting HTTSNP

| ISIS NO | Sequence (5' to 3') | Motif | Gap Chemistry | Wing Chemistry 5' | Wing Chemistry 3' | SEQ ID NO |
|---|---|---|---|---|---|---|
| 460209 | $T_eA_kA_kA_dT_dG_dT_d{}^mC_dA_dT_d{}^mC_dA_k{}^mC_k{}^mC_e$ | 3-9-3 | Full deoxy | ekk | kke | 10 |
| 589429 | $T_eA_kA_kA_dT_vT_dG_dT_d{}^mC_dA_dT_d{}^mC_dA_k{}^mC_k{}^mC_e$ | 3-9-3 | Deoxy/5'-(S)-Me DNA | ekk | kke | 10 |
| 589430 | $T_eA_kA_kA_dT_dG_dT_v{}^mC_dA_dT_d{}^mC_dA_k{}^mC_k{}^mC_e$ | 3-9-3 | Deoxy/5'-(S)-Me DNA | ekk | kke | 10 |
| 589431 | $T_eA_kA_kA_dT_dG_dT_v{}^mC_dA_dT_d{}^mC_dA_k{}^mC_k{}^mC_e$ | 3-9-3 | Deoxy/5'-(S)-Me DNA | ekk | kke | 10 |
| 589432 | $T_eA_kA_kA_dT_dG_dT_d{}^mC_dA_dT_v{}^mC_dA_k{}^mC_k{}^mC_e$ | 3-9-3 | Deoxy/5'-(S)-Me DNA | ekk | kke | 10 |
| 594588 | $T_eA_kA_kA_dT_vT_vG_dT_d{}^mC_dA_dT_d{}^mC_dA_k{}^mC_k{}^mC_e$ | 3-9-3 | Deoxy/5'-(S)-Me DNA | ekk | kke | 10 |
| 556848 | $T_eA_kA_kA_zT_dG_dT_d{}^mC_dA_dT_d{}^mC_dA_k{}^mC_k{}^mC_e$ | 3-9-3 | Deoxy/5'-(R)-Me DNA | ekk | kke | 10 |
| 556849 | $T_eA_kA_kA_dT_zG_dT_d{}^mC_dA_dT_d{}^mC_dA_k{}^mC_k{}^mC_e$ | 3-9-3 | Deoxy/5'-(R)-Me DNA | ekk | kke | 10 |
| 556850 | $T_eA_kA_kA_dT_zG_dT_d{}^mC_dA_dT_d{}^mC_dA_k{}^mC_k{}^mC_e$ | 3-9-3 | Deoxy/5'-(R)-Me DNA | ekk | kke | 10 |

TABLE 115-continued

Gap-interrupted oligonucleotides comprising +-(S)- or 5'-(R)-Me DNA targeting HTTSNP

| ISIS NO | Sequence (5' to 3') | Motif | Gap Chemistry | Wing Chemistry 5' | 3' | SEQ ID NO |
|---|---|---|---|---|---|---|
| 539558 | $T_eA_kA_kA_dT_dT_dG_dT_z{}^mC_dA_dT_d{}^mC_dA_k{}^mC_k{}^mC_e$ | 3-9-3 | Deoxy/5'-(R)-Me DNA | ekk | kke | 10 |
| 594160 | $T_eA_kA_kA_dT_dT_dG_dT_d{}^mC_zA_dT_d{}^mC_dA_k{}^mC_k{}^mC_e$ | 3-9-3 | Deoxy/5'-(R)-Me DNA | ekk | kke | 10 |
| 594161 | $T_eA_kA_kA_dT_dT_dG_dT_d{}^mC_dA_zT_d{}^mC_dA_k{}^mC_k{}^mC_e$ | 3-9-3 | Deoxy/5'-(R)-Me DNA | ekk | kke | 10 |
| 589433 | $T_eA_kA_kA_dT_dT_dG_dT_d{}^mC_dA_dT_z{}^mC_dA_k{}^mC_k{}^mC_e$ | 3-9-3 | Deoxy/5'-(R)-Me DNA | ekk | kke | 10 |
| 594162 | $T_eA_kA_kA_dT_dT_dG_dT_d{}^mC_dA_dT_d{}^mC_zA_k{}^mC_k{}^mC_e$ | 3-9-3 | Deoxy/5'-(R)-Me DNA | ekk | kke | 10 |
| 594589 | $T_eA_kA_kA_dT_zT_zG_dT_d{}^mC_dA_dT_d{}^mC_dA_k{}^mC_k{}^mC_e$ | 3-9-3 | Deoxy/5'-(R)-Me DNA | ekk | kke | 10 | e = 2'-MOE; k = cEt

TABLE 116

Comparison of inhibition of HTT mRNA levels and selectivity of gap-interrupted oligonucleotides with ISIS 460209 targeting HTT SNP

| ISIS NO. | IC$_{50}$ (μM) Mut | Wt | Selectivity (wt vs. mut) | Motif | Gap Chemistry | Wing Chemistry 5' | 3' |
|---|---|---|---|---|---|---|---|
| 460209 | 1.2 | 1.4 | 1.2 | 3-9-3 | Full deoxy | ekk | kke |
| 589429 | 0.22 | 3.3 | 15 | 3-9-3 | Deoxy/5'-(S)-Me DNA | ekk | kke |
| 589430 | 0.22 | >10 | >45.5 | 3-9-3 | Deoxy/5'-(S)-Me DNA | ekk | kke |
| 589431 | 0.16 | 1.9 | 11.9 | 3-9-3 | Deoxy/5'-(S)-Me DNA | ekk | kke |
| 589432 | 0.23 | >10 | >43.5 | 3-9-3 | Deoxy/5'-(S)-Me DNA | ekk | kke |
| 594588 | 0.81 | >10 | >12.3 | 3-9-3 | Deoxy/5'-(S)-Me DNA | ekk | kke |
| 556848 | 0.16 | 1.8 | 11.3 | 3-9-3 | Deoxy/5'-(R)-Me DNA | ekk | kke |
| 556849 | 0.14 | 1.1 | 7.9 | 3-9-3 | Deoxy/5'-(R)-Me DNA | ekk | kke |
| 556850 | 0.22 | 1.7 | 7.7 | 3-9-3 | Deoxy/5'-(R)-Me DNA | ekk | kke |
| 539558 | 0.38 | 3.8 | 10 | 3-9-3 | Deoxy/5'-(R)-Me DNA | ekk | kke |
| 594160 | 0.28 | 3.3 | 11.8 | 3-9-3 | Deoxy/5'-(R)-Me DNA | ekk | kke |
| 594161 | 0.28 | >10 | >35.7 | 3-9-3 | Deoxy/5'-(R)-Me DNA | ekk | kke |
| 589433 | 0.27 | 4.4 | 16.3 | 3-9-3 | Deoxy/5'-(R)-Me DNA | ekk | kke |
| 594162 | 0.27 | 3.5 | 13.0 | 3-9-3 | Deoxy/5'-(R)-Me DNA | ekk | kke |
| 594589 | 0.48 | 4.4 | 9.2 | 3-9-3 | Deoxy/5'-(R)-Me DNA | ekk | kke | e = 2'-MOE; k = cEt

Example 76

Inhibition of HTT mRNA Levels Targeting SNP by Modified Oligonucleotides

Additional modified oligonucleotides were designed in a similar manner as the antisense oligonucleotides described in Example 75. Various chemical modifications were introduced slightly upstream or downstream (i.e. "microwalk") within the central gap region. The gapmers were created with a 3-9-3 motif and were tested for their ability to selectively inhibit mutant (mut) HTT mRNA expression. The position on the oligonucleotides opposite to the SNP position, as counted from the 5'-terminus is position 8. The potency and selectivity of the modified oligonucleotides were evaluated and compared to ISIS 460209.

The modified oligonucleotides and their motifs are described in Table 117. The internucleoside linkages throughout each gapmer are phosphorothioate (P=S) linkages. Nucleosides followed by a subscript "d" are β-D-2'-deoxyribonucleosides. Nucleosides followed by a subscript "e" indicates a 2'-O-methoxyethyl (MOE) modified nucleoside. Nucleosides followed by a subscript "k" indicates a 6'-(S)—CH$_3$ bicyclic nucleoside (e.g. cEt). Nucleosides followed by a subscript "b" indicates a 5'-(R)-allyl DNA. Nucleosides followed by a subscript "c" indicates a 5'-(S)-allyl DNA. Nucleosides followed by a subscript "g" indicates a 5'-(R)-hydroxyethyl DNA. Nucleosides followed by a subscript "i" indicates a 5'-(S)-hydroxyethyl DNA. "$^m$C" indicates a 5-methyl cytosine nucleoside.

The modified oligonucleotides were tested in vitro using heterozygous fibroblast GM04022 cell line. The transfection method and analysis of HTT mRNA levels adjusted according to total RNA content, as measured by RIBOGREEN were performed in the same manner as described in Example 76. The IC$_{50}$s and selectivities as expressed in "fold" were measured and calculated using methods described previously and the results are shown below. As presented in Table 118, several modified oligonucleotides achieved greater than 4.5 fold selectivity in inhibiting mutant HTT mRNA levels and, therefore, are more selective than ISIS 460209.

TABLE 117

Gap-interrupted oligonucleotides comprising 5'-substituted DNA targeting HTT SNP

| ISIS NO | Sequence (5' to 3') | Motif | Gap Chemistry (mod position) | Wing Chemistry 5' | Wing Chemistry 3' | SEQ ID NO |
|---|---|---|---|---|---|---|
| 460209 | $T_e A_k A_k A_d T_d T_d G_d T_d {}^m C_d A_d T_d {}^m C_d A_k {}^m C_k {}^m C_e$ | 3-9-3 | Full deoxy | ekk | kke | 10 |
| 589414 | $T_e A_k A_k A_d T_b T_d G_d T_d {}^m C_d A_d T_d {}^m C_d A_k {}^m C_k {}^m C_e$ | 3-9-3 | Deoxy/5'-(R)-allyl DNA (pos 5) | ekk | kke | 10 |
| 589415 | $T_e A_k A_k A_d T_d T_b G_d T_d {}^m C_d A_d T_d {}^m C_d A_k {}^m C_k {}^m C_e$ | 3-9-3 | Deoxy/5'-(R)-allyl DNA (pos 6) | ekk | kke | 10 |
| 589416 | $T_e A_k A_k A_d T_d T_d G_d T_b {}^m C_d A_d T_d {}^m C_d A_k {}^m C_k {}^m C_e$ | 3-9-3 | Deoxy/5'-(R)-allyl DNA (pos 8) | ekk | kke | 10 |
| 589417 | $T_e A_k A_k A_d T_d T_d G_d T_d {}^m C_d A_d T_b {}^m C_d A_k {}^m C_k {}^m C_e$ | 3-9-3 | Deoxy/5'-(R)-allyl DNA (pos 11) | ekk | kke | 10 |
| 589418 | $T_e A_k A_k A_d T_c T_d G_d T_d {}^m C_d A_d T_d {}^m C_d A_k {}^m C_k {}^m C_e$ | 3-9-3 | Deoxy/5'-(S)-allyl DNA (pos 5) | ekk | kke | 10 |
| 589419 | $T_e A_k A_k A_d T_d T_c G_d T_d {}^m C_d A_d T_d {}^m C_d A_k {}^m C_k {}^m C_e$ | 3-9-3 | Deoxy/5'-(S)-allyl DNA (pos 6) | ekk | kke | 10 |
| 589420 | $T_e A_k A_k A_d T_d T_d G_d T_c {}^m C_d A_d T_d {}^m C_d A_k {}^m C_k {}^m C_e$ | 3-9-3 | Deoxy/5'-(S)-allyl DNA (pos 8) | ekk | kke | 10 |
| 589421 | $T_e A_k A_k A_d T_d T_d G_d T_d {}^m C_d A_d T_c {}^m C_d A_k {}^m C_k {}^m C_e$ | 3-9-3 | Deoxy/5'-(S)-allyl DNA (pos 11) | ekk | kke | 10 |
| 589422 | $T_e A_k A_k A_d T_g T_d G_d T_d {}^m C_d A_d T_d {}^m C_d A_k {}^m C_k {}^m C_e$ | 3-9-3 | Deoxy/5'-(R)-hydroxyethyl DNA (pos 5) | ekk | kke | 10 |
| 589423 | $T_e A_k A_k A_d T_d T_g G_d T_d {}^m C_d A_d T_d {}^m C_d A_k {}^m C_k {}^m C_e$ | 3-9-3 | Deoxy/5'-(R)-hydroxyethyl DNA (pos 6) | ekk | kke | 10 |
| 589424 | $T_e A_k A_k A_d T_d T_d G_d T_g {}^m C_d A_d T_d {}^m C_d A_k {}^m C_k {}^m C_e$ | 3-9-3 | Deoxy/5'-(R)-hydroxyethyl DNA (pos 8) | ekk | kke | 10 |
| 589437 | $T_e A_k A_k A_d T_d T_d G_d T_d {}^m C_d A_d T_g {}^m C_d A_k {}^m C_k {}^m C_e$ | 3-9-3 | Deoxy/5'-(R)-hydroxyethyl DNA (pos 11) | ekk | kke | 10 |
| 589426 | $T_e A_k A_k A_d T_i T_d G_d T_d {}^m C_d A_d T_d {}^m C_d A_k {}^m C_k {}^m C_e$ | 3-9-3 | Deoxy/5'-(S)-hydroxyethyl DNA (pos 5) | ekk | kke | 10 |
| 589427 | $T_e A_k A_k A_d T_d T_i G_d T_d {}^m C_d A_d T_d {}^m C_d A_k {}^m C_k {}^m C_e$ | 3-9-3 | Deoxy/5'-(S)-hydroxyethyl DNA (pos 6) | ekk | kke | 10 |
| 589428 | $T_e A_k A_k A_d T_d T_d G_d T_i {}^m C_d A_d T_d {}^m C_d A_k {}^m C_k {}^m C_e$ | 3-9-3 | Deoxy/5'-(S)-hydroxyethyl DNA (pos 8) | ekk | kke | 10 |
| 589425 | $T_e A_k A_k A_d T_d T_d G_d T_d {}^m C_d A_d T_i {}^m C_d A_k {}^m C_k {}^m C_e$ | 3-9-3 | Deoxy/5'-(S)-hydroxyethyl DNA (pos 11) | ekk | kke | 10 | e = 2'-MOE; k = cEt

TABLE 118

Comparison of inhibition of HTT mRNA levels and selectivity of gap-interrupted oligonucleotides with ISIS 460209 targeting HTT SNP

| ISIS NO | IC$_{50}$ (µM) Mut | IC$_{50}$ (µM) Wt | Selectivity (wt vs. mut) | Gap Chemistry (mod position) | Motif | Wing Chemistry 5' | Wing Chemistry 3' |
|---|---|---|---|---|---|---|---|
| 460209 | 0.47 | 2.1 | 4.5 | Full deoxy | 3-9-3 | ekk | kke |
| 589414 | 1.0 | 7.6 | 7.6 | Deoxy/5'-(R)-Allyl DNA (pos 5) | 3-9-3 | ekk | kke |
| 589415 | 1.4 | >10 | >7.1 | Deoxy/5'-(R)-Allyl DNA (pos 6) | 3-9-3 | ekk | kke |
| 589416 | 2.7 | >10 | >3.7 | Deoxy/5'-(R)-Allyl DNA (pos 8) | 3-9-3 | ekk | kke |
| 589417 | 5.4 | >10 | >1.9 | Deoxy/5'-(R)-Allyl DNA (pos 11) | 3-9-3 | ekk | kke |
| 589418 | 1.2 | >10 | >8.3 | Deoxy/5'-(S)-Allyl DNA (pos 5) | 3-9-3 | ekk | kke |
| 589419 | 1.1 | >10 | >9.1 | Deoxy/5'-(S)-Allyl DNA (pos 6) | 3-9-3 | ekk | kke |
| 589420 | 3.2 | >10 | >3.1 | Deoxy/5'-(S)-Allyl DNA (pos 8) | 3-9-3 | ekk | kke |
| 589421 | 2.0 | >10 | >5.0 | Deoxy/5'-(S)-Allyl DNA (pos 11) | 3-9-3 | ekk | kke |
| 589422 | 0.73 | 3.2 | 4.4 | Deoxy/5'-(R)-Hydroxyethyl DNA (pos 5) | 3-9-3 | ekk | kke |
| 589423 | 0.92 | 9.2 | 10 | Deoxy/5'-(R)-Hydroxyethyl DNA (pos 6) | 3-9-3 | ekk | kke |
| 589424 | 0.21 | 4.4 | 21 | Deoxy/5'-(R)-Hydroxyethyl DNA (pos 8) | 3-9-3 | ekk | kke |
| 589437 | 0.73 | >10.2 | >14 | Deoxy/5'-(R)-Hydroxyethyl DNA (pos 11) | 3-9-3 | ekk | kke |
| 589426 | 0.91 | 5.1 | 5.6 | Deoxy/5'-(S)-Hydroxyethyl DNA (pos 5) | 3-9-3 | ekk | kke |
| 589427 | 0.91 | >10 | >11 | Deoxy/5'-(S)-Hydroxyethyl DNA (pos 6) | 3-9-3 | ekk | kke |
| 589428 | 1.1 | >11 | >10 | Deoxy/5'-(S)-Hydroxyethyl DNA (pos 8) | 3-9-3 | ekk | kke |
| 589425 | 1.5 | >10.5 | >7 | Deoxy/5'-(S)-Hydroxyethyl DNA (pos 11) | 3-9-3 | ekk | kke | e = 2'-MOE; k = cEt

Example 77

Modified Oligonucleotides Comprising 5'-(R)-Me DNA(s) Targeting Human C-Reactive Protein (hCRP)

A series of modified oligonucleotides were designed based on ISIS 353512, wherein the central gap region contains fourteen β-D-2'-deoxyribonucleoside. These modified oligonucleotides were designed by replacement of two or three β-D-2'-deoxyribonucleoside in the 14 nucleoside gap region with 5'-(R)-Me DNA(s). The thermal stability ($T_m$) and potency of these modified oligonucleotides targeting hCRP was evaluated. The 3-14-3 MOE gapmer, ISIS 353512 and 5-10-5 MOE gapmer, ISIS 330012 were included in the study for comparison.

The modified oligonucleotides and their motifs are described in Table 119. Each internucleoside linkage is a phosphorothioate (P=S) except for nucleosides followed by a subscript "o" which are phosphodiester internucleoside linkages (P=O). Nucleosides followed by a subscript "d" indicates a β-D-2'-deoxyribonucleoside. Nucleosides followed by a subscript "e" indicates a 2'-O-methoxyethyl (MOE) modified nucleoside. Nucleosides followed by a subscript "z" indicates a 5'-(R)-Me DNA. "$^m$C" indicates a 5-methyl cytosine modified nucleoside. Underlined nucleosides indicate a region comprising 5'-(R)-Me DNA modification.

Thermal Stability Assay

The modified oligonucleotides were evaluated in thermal stability ($T_m$) assay. The $T_m$'s were measured using the method described herein. A Cary 100 Bio spectrophotometer with the Cary Win UV Thermal program was used to measure absorbance vs. temperature. For the $T_m$ experiments, oligonucleotides were prepared at a concentration of 8 µM in a buffer of 100 mM Na+, 10 mM phosphate, 0.1 mM EDTA, pH 7. Concentration of oligonucleotides were determined at 85° C. The oligonucleotide concentration was 4 µM with mixing of equal volumes of test oligonucleotide and complimentary RNA strand. Oligonucleotides were hybridized with the complimentary RNA strand by heating duplex to 90° C. for 5 min and allowed to cool to room temperature. Using the spectrophotometer, $T_m$ measurements were taken by heating duplex solution at a rate of 0.5 C/min in cuvette starting @ 15° C. and heating to 85° C. $T_m$ values were determined using Vant Hoff calculations (A$_{260}$ vs temperature curve) using non self-complementary sequences where the minimum absorbance which relates to the duplex and the maximum absorbance which relates to the non-duplex single strand are manually integrated into the program. The results are presented below.

Cell Culture and Transfection

The modified oligonucleotides were tested in vitro. Hep3B cells were plated at a density of 40,000 cells per well and transfected using electroporation with 0.009 μM, 0.027 μM, 0.082 μM, 0.25 μM, 0.74 μM, 2.2 μM, 6.7 μM and 20 μM concentrations of antisense oligonucleotides. After a treatment period of approximately 16 hours, RNA was isolated from the cells and hCRP mRNA levels were measured by quantitative real-time PCR. Human CRP primer probe set RTS1887 was used to measure mRNA levels. hCRP mRNA levels were adjusted according to total RNA content, as measured by RIBOGREEN®.

Analysis of $IC_{50}$'s

The half maximal inhibitory concentration ($IC_{50}$) of each oligonucleotide is presented below and was calculated by plotting the concentrations of oligonucleotides used versus the percent inhibition of hCRP mRNA expression achieved at each concentration, and noting the concentration of oligonucleotide at which 50% inhibition of hCRP mRNA expression was achieved compared to the control.

As illustrated in Table 120, treatment with the newly designed oligonucleotides showed no improvement in potency as compared to the controls, ISIS 353512 and 330012.

TABLE 120-continued

Effect of gap-interrupted oligonucleotide treatment on Tm and hCRP inhibition

| ISIS NO | Tm (° C.) | $IC_{50}$ (μM) | Gap Motif | Chemistry | Wing Chemistry 5' | Linkage 3' | backbone |
|---|---|---|---|---|---|---|---|
| 544810 | 64.3 | 2.4 | 3-14-3 | Deoxy/5'-(R)-Me DNA | eee | eee | Mixed PS/PO |
| 544806 | 62.8 | 2.8 | 3-14-3 | Deoxy/5'-(R)-Me DNA | eee | eee | Mixed PS/PO |
| 544807 | 65.1 | 2.7 | 3-14-3 | Deoxy/5'-(R)-Me DNA | eee | eee | Mixed PS/PO |
| 544809 | 64.2 | 5.0 | 3-14-3 | Deoxy/5'-(R)-Me DNA | eee | eee | Mixed PS/PO |
| 330012 | 71.7 | 0.6 | 5-10-5 | Full deoxy | e5 | e5 | Full PS | e = 2'-MOE (e.g. e5 = eeeee), PS/PO = phosphorothioate/phosphodiester internucleoside linkage Example 78

Human Peripheral Blood Mononuclear Cells (hPBMC) Assay Protocol—In Vitro

The hPBMC assay was performed using BD Vautainer CPT tube method. A sample of whole blood from volunteered donors with informed consent at US HealthWorks clinic (Faraday & El Camino Real, Carlsbad) was obtained

TABLE 119

Gap-interrupted oligonucleotides comprising 5'-(R)-Me DNA targeting hCRP

| ISIS NO | Sequence (5' to 3') | Gap Motif | Chemistry | Wing Chemistry 5' | Linkage 3' | backbone | SEQ ID NO |
|---|---|---|---|---|---|---|---|
| 353512 | $T_e{}^mC_e{}^mC_e{}^mC_dA_dT_dT_dT_d{}^mC_dA_d$ $G_dG_dA_dG_dA_d{}^mC_d{}^mC_dT_eG_eG_e$ | 3-14-3 | Full deoxy | eee | eee | Full PS | 83 |
| 546127 | $T_e{}^mC_e{}^mC_e{}^mC_dA_dT_dT_dT_d{}^mC_{do}A_{zo}$ $\underline{G_z}G_dA_dG_dA_d{}^mC_d{}^mC_dT_eG_eG_e$ | 3-14-3 | Deoxy/5'-(R)-Me DNA | eee | eee | Mixed PS/PO | 83 |
| 544810 | $T_e{}^mC_e{}^mC_e{}^mC_dA_dT_dT_dT_d{}^mC_dA_d$ $G_dG_dA_dG_dA_{do}{}^mC_{zo}{}^mC_zT_eG_eG_e$ | 3-14-3 | Deoxy/5'-(R)-Me DNA | eee | eee | Mixed PS/PO | 83 |
| 544806 | $T_e{}^mC_e{}^mC_{eo}{}^mC_{zo}A_{zo}T_zT_dT_d{}^mC_dA_d$ $G_dG_dA_dG_dA_d{}^mC_d{}^mC_dT_eG_eG_e$ | 3-14-3 | Deoxy/5'-(R)-Me DNA | eee | eee | Mixed PS/PO | 83 |
| 544807 | $T_e{}^mC_e{}^mC_e{}^mC_dA_dT_{do}T_{zo}T_{zo}{}^mC_zA_d$ $G_dG_dA_dG_dA_d{}^mC_d{}^mC_d\overline{T_e}G_eG_e$ | 3-14-3 | Deoxy/5'-(R)-Me DNA | eee | eee | Mixed PS/PO | 83 |
| 544809 | $T_e{}^mC_e{}^mC_e{}^mC_dA_dT_dT_dT_d{}^mC_dA_d$ $G_dG_{do}A_{zo}G_{zo}A_z{}^mC_d{}^mC_dT_eG_eG_e$ | 3-14-3 | Deoxy/5'-(R)-Me DNA | eee | eee | Mixed PS/PO | 83 |
| 330012 | $T_e{}^mC_e{}^mC_e{}^mC_dA_eT_dT_dT_d{}^mC_dA_d$ $G_dG_dA_dG_dA_d{}^mC_e{}^mC_eT_eG_eG_e$ | 5-10-5 | Full deoxy | e5 | e5 | Full PS | 83 | e = 2'-MOE (e.g. e5 = eeeee)

TABLE 120

Effect of gap-interrupted oligonucleotide treatment on Tm and hCRP inhibition

| ISIS NO | Tm (° C.) | $IC_{50}$ (μM) | Gap Motif | Chemistry | Wing Chemistry 5' | Linkage 3' | backbone |
|---|---|---|---|---|---|---|---|
| 353512 | 66.7 | 1.1 | 3-14-3 | Full deoxy | eee | eee | Full PS |
| 546127 | 65.9 | 2.5 | 3-14-3 | Deoxy/5'-(R)-Me DNA | eee | eee | Mixed PS/PO | and collected in 4-15 BD Vacutainer CPT 8 ml tubes (VWR Cat. #BD362753). The approximate starting total whole blood volume in the CPT tubes for each donor was recorded using the PBMC assay data sheet.

The blood sample was remixed immediately prior to centrifugation by gently inverting tubes 8-10 times. CPT tubes were centrifuged at rt (18-25° C.) in a horizontal (swing-out) rotor for 30 min. at 1500-1800 RCF with brake off (2700 RPM Beckman Allegra 6R). The cells were retrieved from the buffy coat interface (between Ficoll and polymer gel layers); transferred to a sterile 50 ml conical tube and pooled up to 5 CPT tubes/50 ml conical tube/donor.

The cells were then washed twice with PBS (Ca++, Mg++ free; GIBCO). The tubes were topped up to 50 ml and mixed by inverting several times. The sample was then centrifuged at 330×g for 15 minutes at rt (1215 RPM in Beckman Allegra 6R) and aspirated as much supernatant as possible without disturbing pellet. The cell pellet was dislodged by gently swirling tube and resuspended cells in RPMI+10% FBS+pen/strep (~1 ml/10 ml starting whole blood volume). A 60 μl sample was pipette into a sample vial (Beckman Coulter) with 600 μl VersaLyse reagent (Beckman Coulter Cat #A09777) and was gently vortexed for 10-15 sec. The sample was allowed to incubate for 10 min. at rt and being mixed again before counting. The cell suspension was counted on Vicell XR cell viability analyzer (Beckman Coulter) using PBMC cell type (dilution factor of 1:11 was stored with other parameters). The live cell/ml and viability were recorded. The cell suspension was diluted to $1\times10^7$ live PBMC/ml in RPMI+10% FBS+pen/strep.

The cells were plated at $5\times10^5$ in 50 μl/well of 96-well tissue culture plate (Falcon Microtest). 50 μl/well of 2× concentration oligos/controls diluted in RPMI+10% FBS+pen/strep. was added according to experiment template (100 μl/well total). Plates were placed on the shaker and allowed to mix for approx. 1 min. After being incubated for 24 hrs at 37° C.; 5% $CO_2$, the plates were centrifuged at 400×g for 10 minutes before removing the supernatant for MSD cytokine assay (i.e. human IL-6, IL-10, IL-8 and MCP-1).

Example 79

Evaluation of the Proinflammatory Effects in hPBMC Assay for 5'-(R)-Me DNA Containing Modified Oligonucleotides—In Vitro Study The modified oligonucleotides targeting hCRP from Example 77 were tested and evaluated for the proinflammatory response in hPBMC assay using methods described previously in Example 78. The hPBMCs were isolated from fresh, volunteered donors and were treated with modified oligonucleotides at 0, 0.0128, 0.064, 0.32, 1.6, 8, 40 and 200 μM concentrations using the hPBMC assay protocol described herein. After a 24 hr treatment, the cytokine levels were measured.

IL-6 was used as the primary readout. The resulting IL-6 level was compared to the positive control, ISIS 353512 and negative control, ISIS 104838. The results are presented in Table 121. As illustrated, reduction in proinflammatory response was achieved with the newly designed oligonucleotides at doses evaluated as compared to the positive control, ISIS 353512.

ISIS 104838 designated herein as SEQ ID NO: 84, is a 5-10-5 MOE gapmer with the following sequence, $G_e{}^mC_e T_e G_e A_e T_d T_d A_d G_d A_d G_d A_d G_d A_d G_d G_e T_e{}^mC_e{}^mC_e{}^mC_e$. Each internucleoside linkage is a phosphorothioate (P=S). Each nucleoside followed by a subscript "d" is a β-D-2'-deoxyribonucleoside. Each "$^mC$" is a 5-methyl cytosine modified nucleoside and each nucleoside followed by a subscript "e" is a 2'-O-methoxyethyl (MOE) modified nucleoside.

TABLE 121

Effect of gap-interrupted oligonucleotide treatment on proinflammatory response in hPBMC

| ISIS NO | Conc. (uM) | IL-6 (pg/mL) | Motif | Gap Chemistry | Wing Chemistry 5' | 3' | Linkage backbone |
|---|---|---|---|---|---|---|---|
| 353512 (pos control) | 0 | 26.9 | 3-14-3 | Full deoxy | eee | eee | Full PS |
| | 0.0128 | 10.6 | | | | | |
| | 0.064 | 73.3 | | | | | |
| | 0.32 | 219.8 | | | | | |
| | 1.6 | 200.1 | | | | | |
| | 8 | 287.8 | | | | | |
| | 40 | 376.9 | | | | | |
| | 200 | 181.5 | | | | | |
| 546127 | 0 | 11.5 | 3-14-3 | Deoxy/5'-(R)-Me DNA | eee | eee | Mixed PS/PO |
| | 0.0128 | 15.1 | | | | | |
| | 0.064 | 19.0 | | | | | |
| | 0.32 | 37.3 | | | | | |
| | 1.6 | 67.5 | | | | | |
| | 8 | 86.3 | | | | | |
| | 40 | 111.2 | | | | | |
| | 200 | 83.1 | | | | | |
| 544810 | 0 | 11.5 | 3-14-3 | Deoxy/5'-(R)-Me DNA | eee | eee | Mixed PS/PO |
| | 0.0128 | 13.9 | | | | | |
| | 0.064 | 15.1 | | | | | |
| | 0.32 | 24.9 | | | | | |
| | 1.6 | 34.0 | | | | | |
| | 8 | 66.2 | | | | | |
| | 40 | 96.8 | | | | | |
| | 200 | 76.5 | | | | | |
| 06/544806 | 0 | 11.3 | 3-14-3 | Deoxy/5'-(R)-Me DNA | eee | eee | Mixed PS/PO |
| | 0.0128 | 10.8 | | | | | |
| | 0.064 | 25.8 | | | | | |
| | 0.32 | 15.6 | | | | | |
| | 1.6 | 25.4 | | | | | |
| | 8 | 52.3 | | | | | |
| | 40 | 69.3 | | | | | |
| | 200 | 341.7 | | | | | |
| 06/544807 | 0 | 13.3 | 3-14-3 | Deoxy/5'-(R)-Me DNA | eee | eee | Mixed PS/PO |
| | 0.0128 | 13.7 | | | | | |
| | 0.064 | 18.4 | | | | | |

TABLE 121-continued

Effect of gap-interrupted oligonucleotide treatment on proinflammatory response in hPBMC

| ISIS NO | Conc. (uM) | IL-6 (pg/mL) | Motif | Gap Chemistry | Wing 5' | Wing 3' | Linkage backbone |
|---|---|---|---|---|---|---|---|
| | 0.32 | 53.3 | | | | | |
| | 1.6 | 18.4 | | | | | |
| | 8 | 164.9 | | | | | |
| | 40 | 202.7 | | | | | |
| | 200 | 606.5 | | | | | |
| 06/544809 | 0 | 10.8 | 3-14-3 | Deoxy/5'-(R)-Me DNA | eee | eee | Mixed PS/PO |
| | 0.0128 | 13.3 | | | | | |
| | 0.064 | 14.3 | | | | | |
| | 0.32 | 34.8 | | | | | |
| | 1.6 | 62.3 | | | | | |
| | 8 | 100.9 | | | | | |
| | 40 | 213.1 | | | | | |
| | 200 | 225.0 | | | | | |
| 06/330012 | 0 | 10.9 | 5-10-5 | Full deoxy | e5 | e5 | Full PS |
| | 0.0128 | 12.9 | | | | | |
| | 0.064 | 10.8 | | | | | |
| | 0.32 | 25.3 | | | | | |
| | 1.6 | 44.2 | | | | | |
| | 8 | 87.5 | | | | | |
| | 40 | 80.2 | | | | | |
| | 200 | 82.3 | | | | | |
| 07/104838 (neg control) | 0 | 9.3 | 5-10-5 | Full deoxy | e5 | e5 | Full PS |
| | 0.0128 | 10.4 | | | | | |
| | 0.064 | 17.6 | | | | | |
| | 0.32 | 30.1 | | | | | |
| | 1.6 | 53.9 | | | | | |
| | 8 | 124.8 | | | | | |
| | 40 | 94.5 | | | | | |
| | 200 | 89.3 | | | | | | e = 2'-MOE (e.g. e5 = eeeee)

Example 80

Evaluation of the Proinflammatory Effects in hPBMC Assay for a Modified Oligonucleotide Comprising Methyl Thiophosphonate Internucleoside Linkages—In Vitro Study A modified oligonucleotide was designed based on the 3/14/3 MOE gapmer, ISIS 353512. This modified oligonucleotide was created by having alternating methyl thiophosphonate (—P($CH_3$)(=S)—) internucleoside linkages throughout the gap region. The proinflammatory effect of the modified oligonucleotide targeting hCRP was evaluated in hPBMC assay using the protocol described in Example 78. The modified oligonucleotide and its motif are described in Table 122. Each internucleoside linkage is a phosphorothioate (P=S) except for nucleosides followed by a subscript "w". Each nucleoside followed by a subscript "w" indicates a methyl thiophosphonate internucleoside linkage (—P($CH_3$)(=S)—). Nucleosides followed by a subscript "d" is a β-D-2'-deoxyribonucleoside. Nucleosides followed by a subscript "e" indicates a 2'-O-methoxyethyl (MOE) modified nucleoside. "$^m$C" indicates a 5-methyl cytosine modified nucleoside.

The hPBMCs were isolated from fresh, volunteered donors and were treated with modified oligonucleotides at 0, 0.0128, 0.064, 0.32, 1.6, 8, 40 and 200 μM concentrations. After a 24 hr treatment, the cytokine levels were measured.

IL-6 was used as the primary readout. The resulting IL-6 level was compared to the positive control oligonucleotide, ISIS 353512 and negative control, ISIS 104838. The results from two donors denoted as "Donor 1" and "Donor 2" are presented in Table 123. As illustrated, reduction in proinflammatory response was achieved with the newly designed oligonucleotide at doses evaluated as compared to the positive control, ISIS 353512.

TABLE 122

Modified oligonucleotide comprising alternating methyl thiophosphonate internucleoside linkages throughout the gap region

| ISIS NO | Sequence (5' to 3') | Motif | Gap Chemistry | Wing 5' | Wing 3' | SEQ ID NO |
|---|---|---|---|---|---|---|
| 353512 | $T_e{}^mC_e{}^mC_e{}^mC_dA_dT_dT_dT_d{}^mC_dA_dG_d$ $G_dA_dG_dA_d{}^mC_d{}^mC_dT_eG_eG_e$ | 3-14-3 | Full deoxy | eee | eee | 83 |
| 560221 | $T_e{}^mC_e{}^mC_eC_{dw}A_dT_{dw}T_dT_{dw}{}^mC_dA_{dw}G_dG_{dw}$ $A_dG_{dw}A_dC_{dw}{}^mC_dT_eG_eG_e$ | 3-14-3 | Deoxy/methyl thiophosphonate | eee | eee | 83 |

TABLE 122-continued

Modified oligonucleotide comprising alternating methyl thiophosphonate internucleoside linkages throughout the gap region

| ISIS NO | Sequence (5' to 3') | Motif | Gap Chemistry | Wing Chemistry 5' | Wing Chemistry 3' | SEQ ID NO |
|---|---|---|---|---|---|---|
| 104838 | $G_e{}^mC_eT_eG_eA_eT_dT_dA_dG_dA_dG_dA_d$ $G_dA_dG_dG_eT_e{}^mC_e{}^mC_e{}^mC_e$ | 5-10-5 | Full deoxy | e5 | e5 | 84 | e = 2'-MOE (e.g. e5 = eeeee)

TABLE 123

Effect of modified oligonucleotide treatment on proinflammatory response in hPBMC assay

| ISIS NO | Conc. (µM) | IL-6 (Donor 1) (pg/mL) | IL-6 (Donor 2) (pg/mL) | Motif | Gap Chemistry | Wing Chemistry 5' | Wing Chemistry 3' |
|---|---|---|---|---|---|---|---|
| 353512 | 0 | 6.3 | 7.8 | 3-14-3 | Full deoxy | eee | eee |
|  | 0.0128 | 8.3 | 10.2 |  |  |  |  |
|  | 0.064 | 77.2 | 118.2 |  |  |  |  |
|  | 0.32 | 151.9 | 394.3 |  |  |  |  |
|  | 1.6 | 152.4 | 395.3 |  |  |  |  |
|  | 8 | 147.6 | 337.2 |  |  |  |  |
|  | 40 | 122.5 | 228.4 |  |  |  |  |
|  | 200 | 119.7 | 193.5 |  |  |  |  |
| 560221 | 0 | 5.6 | 7.6 | 3-14-3 | Deoxy/methyl thiophosphonate | eee | eee |
|  | 0.0128 | 6.4 | 6.9 |  |  |  |  |
|  | 0.064 | 6.7 | 7.6 |  |  |  |  |
|  | 0.32 | 7.6 | 8.9 |  |  |  |  |
|  | 1.6 | 9.1 | 11.8 |  |  |  |  |
|  | 8 | 17.5 | 24.3 |  |  |  |  |
|  | 40 | 65.8 | 50.2 |  |  |  |  |
|  | 200 | 60.0 | 100.4 |  |  |  |  |
| 104838 | 0 | 5.8 | 7.3 | 5-10-5 | Full deoxy | e5 | e5 |
|  | 0.0128 | 7.7 | 7.9 |  |  |  |  |
|  | 0.064 | 7.5 | 11.6 |  |  |  |  |
|  | 0.32 | 15.1 | 22.0 |  |  |  |  |
|  | 1.6 | 73.1 | 112.8 |  |  |  |  |
|  | 8 | 29.6 | 51.5 |  |  |  |  |
|  | 40 | 41.6 | 69.5 |  |  |  |  |
|  | 200 | 55.4 | 4018 |  |  |  |  | e = 2'-MOE (e.g. e5 = eeeee)

Example 81

Modified Oligonucleotides Comprising Methyl Phosphonate Internucleoside Linkage Targeting HTT SNP—In Vitro Study ISIS 558255 and 558256 from Example 49 were selected and evaluated for their effect on mutant and wild type HTT mRNA expression levels targeting rs7685686. ISIS 46020 was included in the study for comparison. The position on the oligonucleotides opposite to the SNP position, as counted from the 5'-terminus is position 8.

Heterozygous fibroblast GM04022 cell line was used for the in vitro assay (from Coriell Institute). Cultured GM04022 cells at a density of 25,000 cells per well were transfected using electroporation with 0.12, 0.37, 1.1, 3.3 and 10 µM concentrations of modified oligonucleotides. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 µL 2×PCR buffer, 101 µL primers (300 µM from ABI), 1000 µL water and 40.4 µL RT MIX. To each well was added 15 µL of this mixture and 5 µL of purified RNA. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN.

The $IC_{50}$s and selectivities as expressed in "fold" were measured and calculated using methods described previously in Example 41. As illustrated in Table 124, improvement in selectivity and potency was achieved with modified oligonucleotides comprising methyl phosphonate internucleoside linkage as compared to ISIS 460209.

TABLE 124

Comparison of selectivity in inhition of HTT mRNA levels of antisense oligonucleotides with ISIS 460209 targeted to rs7685686 in GM4022 cells

| ISIS NO | $IC_{50}$ ($\mu$M) Mut | $IC_{50}$ ($\mu$M) Wt | Selectivity (wt vs mut) | Motif | Gap Chemistry | Wing Chemistry 5' | Wing Chemistry 3' | SEQ ID NO |
|---|---|---|---|---|---|---|---|---|
| 460209 | 0.30 | 0.99 | 3.3 | 3-9-3 | Full deoxy | ekk | kke | 10 |
| 558255 | 0.19 | 1.3 | 6.8 | 3-9-3 | Deoxy/Methyl phosphonate | ekk | kke | 10 |
| 558256 | 0.20 | 1.3 | 6.5 | 3-9-3 | Deoxy/Methyl phosphonate | ekk | kke | 10 | e = 2'-MOE (e.g. e5 = eeeee), k = cEt

Example 82

Modified Oligonucleotides Comprising Methyl Phosphonate or Phosphonoacetate Internucleoside Linkage(s) Targeting HTT SNP A series of modified oligonucleotides were designed based on ISIS 460209 wherein the gap region contains nine β-D-2'-deoxyribonucleosides. The modified oligonucleotides were synthesized to include one or more methyl phosphonate or phosphonoacetate internucleoside linkage modifications within the gap region. The oligonucleotides with modified phosphorus containing backbone were tested for their ability to selectively inhibit mutant (mut) HTT mRNA expression levels targeting rs7685686 while leaving the expression of the wild-type (wt) intact. The potency and selectivity of the modified oligonucleotides were evaluated and compared to ISIS 460209.

The position on the oligonucleotides opposite to the SNP position, as counted from the 5'-terminus is position 8.

The modified oligonucleotides and their motifs are described in Table 125. Each internucleoside linkage is a phosphorothioate (P=S) except for the internucleoside linkage having a subscript "x" or "y". Each nucleoside followed by a subscript "x" indicates a methyl phosphonate internucleoside linkage (—P(CH$_3$)(=O)—). Each nucleoside followed by a subscript "y" indicates a phosphonoacetate internucleoside linkage (—P(CH$_2$CO$_2$—)(=O)—). Nucleosides followed by a subscript "d" is a β-D-2'-deoxyribonucleoside. Nucleosides followed by a subscript "e" indicates a 2'-O-methoxyethyl (MOE) modified nucleoside. Nucleosides followed by a subscript "k" indicates a 6'-(S)—CH$_3$ bicyclic nucleoside (e.g. cEt). "$^m$C" indicates a 5-methyl cytosine modified nucleoside.

The modified oligonucleotides were tested in vitro. Heterozygous fibroblast GM04022 cell line was used (from Coriell Institute). Cultured GM04022 cells at a density of 25,000 cells per well were transfected using electroporation with 0.12, 0.37, 1.1, 3.3 and 10 μM concentrations of modified oligonucleotides. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 μL 2×PCR buffer, 101 μL primers (300 μM from ABI), 1000 uL water and 40.4 μL RT MIX. To each well was added 15 μL of this mixture and 5 μL of purified RNA. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN.

The $IC_{50}$s and selectivities as expressed in "fold" were measured and calculated using methods described previously in Example 41. As illustrated in Table 126, most of the newly design oligonucleotides achieved improvement in selectivity while maintaining potency as compared to ISIS 460209.

TABLE 125

Modified oligonucleotides comprising methyl phosphonate or phosphonoacetate internucleoside linkage(s) targeting HTT SNP

| ISIS NO | Sequence (5' to 3') | Motif | Gap Chemistry | Wing Chemistry 5' | Wing Chemistry 3' | SEQ ID NO |
|---|---|---|---|---|---|---|
| 460209 | T$_e$A$_k$A$_k$A$_d$T$_d$T$_d$G$_d$T$_d$$^m$C$_d$A$_d$T$_d$$^m$C$_d$A$_k$$^m$C$_k$$^m$C$_e$ | 3-9-3 | Full deoxy | ekk | kke | 10 |
| 566276 | T$_e$A$_k$A$_k$A$_d$T$_d$T$_d$G$_{dx}$T$_d$$^m$C$_d$A$_d$T$_d$$^m$C$_d$A$_k$$^m$C$_k$$^m$C$_e$ | 3-9-3 | Deoxy/Methyl phosphonate | ekk | kke | 10 |
| 566277 | T$_e$A$_k$A$_k$A$_d$T$_d$T$_d$G$_d$T$_{dx}$$^m$C$_d$A$_d$T$_d$$^m$C$_d$A$_k$$^m$C$_k$$^m$C$_e$ | 3-9-3 | Deoxy/Methyl phosphonate | ekk | kke | 10 |
| 566278 | T$_e$A$_k$A$_k$A$_d$T$_d$T$_d$G$_d$T$_d$$^m$C$_{dx}$A$_d$T$_d$$^m$C$_d$A$_k$$^m$C$_k$$^m$C$_e$ | 3-9-3 | Deoxy/Methyl phosphonate | ekk | kke | 10 |
| 566279 | T$_e$A$_k$A$_k$A$_d$T$_d$T$_d$G$_d$T$_d$$^m$C$_d$A$_{dx}$T$_d$$^m$C$_d$A$_k$$^m$C$_k$$^m$C$_e$ | 3-9-3 | Deoxy/Methyl phosphonate | ekk | kke | 10 |
| 566280 | T$_e$A$_k$A$_k$A$_d$T$_d$T$_d$G$_d$T$_d$$^m$C$_d$A$_d$T$_{dx}$$^m$C$_d$A$_k$$^m$C$_k$$^m$C$_e$ | 3-9-3 | Deoxy/Methyl phosphonate | ekk | kke | 10 |
| 566283 | T$_e$A$_k$A$_k$A$_d$T$_{dx}$T$_{dx}$G$_d$T$_d$$^m$C$_d$A$_d$T$_d$$^m$C$_d$A$_k$$^m$C$_k$$^m$C$_e$ | 3-9-3 | Deoxy/Methyl phosphonate | ekk | kke | 10 |
| 573815 | T$_e$A$_k$A$_k$A$_d$T$_{dy}$T$_d$G$_d$T$_d$$^m$C$_d$A$_d$T$_d$$^m$C$_d$A$_k$$^m$C$_k$$^m$C$_e$ | 3-9-3 | Deoxy/Phosphonoacetate | ekk | kke | 10 |

TABLE 125-continued

Modified oligonucleotides comprising methyl phosphonate or phosphonoacetate internucleoside linkage(s) targeting HTT SNP

| ISIS NO | Sequence (5' to 3') | Motif | Gap Chemistry | Wing Chemistry 5' | Wing Chemistry 3' | SEQ ID NO |
|---|---|---|---|---|---|---|
| 573816 | $T_eA_kA_kA_dT_dT_{dy}G_dT_d{}^mC_dA_dT_d{}^mC_dA_k{}^mC_k{}^mC_e$ | 3-9-3 | Deoxy/Phosphonoacetate | ekk | kke | 10 |
| 573817 | $T_eA_kA_kA_dT_dT_dG_dT_{dy}{}^mC_dA_dT_d{}^mC_dA_k{}^mC_k{}^mC_e$ | 3-9-3 | Deoxy/Phosphonoacetate | ekk | kke | 10 |
| 573818 | $T_eA_kA_kA_dT_dT_dG_dT_d{}^mC_dA_dT_{dy}{}^mC_dA_k{}^mC_k{}^mC_e$ | 3-9-3 | Deoxy/Phosphonoacetate | ekk | kke | 10 | e = 2'-MOE, k = cEt

TABLE 126

Comparison of selectivity in inhition of HTT mRNA levels of antisense oligonucleotides with ISIS 460209 targeted to rs7685686 in GM4022 cells

| ISIS NO | Mut IC$_{50}$ (μM) | Selectivity (wt vs mut) | Motif | Gap Chemistry | Wing Chemistry 5' | Wing Chemistry 3' | SEQ ID NO |
|---|---|---|---|---|---|---|---|
| 460209 | 0.15 | 9.4 | 3-9-3 | Full deoxy | ekk | kke | 10 |
| 566276 | 0.76 | 12.8 | 3-9-3 | Deoxy/Methyl phosphonate | ekk | kke | 10 |
| 566277 | 0.20 | 17 | 3-9-3 | Deoxy/Methyl phosphonate | ekk | kke | 10 |
| 566278 | 0.25 | 8.9 | 3-9-3 | Deoxy/Methyl phosphonate | ekk | kke | 10 |
| 566279 | 0.38 | — | 3-9-3 | Deoxy/Methyl phosphonate | ekk | kke | 10 |
| 566280 | 0.27 | 47 | 3-9-3 | Deoxy/Methyl phosphonate | ekk | kke | 10 |
| 566283 | 0.8 | >100 | 3-9-3 | Deoxy/Methyl phosphonate | ekk | kke | 10 |
| 573815 | 0.16 | 18.8 | 3-9-3 | Deoxy/Phosphonoacetate | ekk | kke | 10 |
| 573816 | 0.55 | 18.1 | 3-9-3 | Deoxy/Phosphonoacetate | ekk | kke | 10 |
| 573817 | 0.17 | 22.5 | 3-9-3 | Deoxy/Phosphonoacetate | ekk | kke | 10 |
| 573818 | 0.24 | 13.5 | 3-9-3 | Deoxy/Phosphonoacetate | ekk | kke | 10 | e = 2'-MOE, k = cEt

Example 83

Modified Oligonucleotides Comprising Methyl Phosphonate Internucleoside Linkages Targeting PTEN and SRB-1—In Vivo Study Additional modified oligonucleotides were designed based on ISIS 482050 and 449093 wherein the gap region contains ten β-D-2'-deoxyribonucleosides. The modified oligonucleotides were designed by introducing two methyl phosphonate internucleoside linkages at the 5'-end of the gap region with a 3/10/3 motif. The oligonucleotides were evaluated for reduction in PTEN and SRB-1 mRNA expression levels in vivo. The parent gapmers, ISIS 482050 and 449093 were included in the study for comparison.

The modified oligonucleotides and their motifs are described in Table 127. Each internucleoside linkage is a phosphorothioate (P=S) except for the internucleoside linkage having a subscript "x". Each nucleoside followed by a subscript "x" indicates a methyl phosphonate internucleoside linkage (—P(CH$_3$)(=O)—). Nucleosides followed by a subscript "d" is a β-D-2'-deoxyribonucleoside. Nucleosides followed by a subscript "k" indicates a 6'-(S)—CH$_3$ bicyclic nucleoside (e.g. cEt). "$^m$C" indicates a 5-methyl cytosine modified nucleoside.

Treatment

Six week old BALB/C mice (purchased from Charles River) were injected subcutaneously twice a week for three weeks at dosage 10 mg/kg or 20 mg/kg with the modified oligonucleotides shown below or with saline control. Each treatment group consisted of 3 animals. The mice were sacrificed 48 hrs following last administration, and organs and plasma were harvested for further analysis.

mRNA Analysis

Liver tissues were homogenized and mRNA levels were quantitated using real-time PCR and normalized to RIBOGREEN as described herein. The results in Table 128 are listed as PTEN or SRB-1 mRNA expression for each treatment group relative to saline-treated control (% UTC). As illustrated, reduction in PTEN or SRB-1 mRNA expression levels was achieved with the oligonucleotides comprising two methyl phosphonate internucleoside linkages at the 5'-end of the gap region, ISIS 582073 and 582074.

Plasma Chemistry Markers

Plasma chemistry markers such as liver transaminase levels, alanine aminotranferase (ALT) in serum were measured relative to saline injected mice and the results are presented in Table 128. Treatment with the oligonucleotides resulted in reduction in ALT level compared to treatment with the parent gapmer, ISIS 482050 or 449093. The results suggest that introduction of methyl phosphonate internucleoside linkage(s) can be useful for reduction of hepatotoxicity profile of otherwise unmodified parent gapmers.

Body and Organ Weights

Body weights, as well as liver, kidney and spleen weights were measured at the end of the study. The results below are presented as the average percent of body and organ weights for each treatment group relative to saline-treated control. As illustrated in Table 129, treatment with ISIS 582073 resulted in a reduction in liver and spleen weights compared to treatment with the parent gapmer, ISIS 482050. The remaining oligonucleotide, ISIS 582074 did not cause any changes in body and organ weights outside the expected range as compared to ISIS 449093.

TABLE 127

Modified oligonucleotides comprising methyl phosphonate internucleoside linkages

| ISIS NO | Sequence (5' to 3') | Motif | Gap Chemistry | Wing Chemistry 5' | 3' | SEQ ID NO. |
|---|---|---|---|---|---|---|
| 482050 | $A_k T_k {}^m C_k A_d T_d G_d G_d {}^m C_d T_d G_d {}^m C_d A_d G_d {}^m C_k T_k T_k$ | 3-10-3 | Full deoxy | kkk | kkk | 85 |
| 582073 | $A_k T_k {}^m C_k A_{dx} T_{dx} G_d G_d {}^m C_d T_d G_d {}^m C_d A_d G_d {}^m C_k T_k T_k$ | 3-10-3 | Deoxy/Methyl phosphonate | kkk | kkk | 85 |
| 449093 | $T_k T_k {}^m C_k A_d G_d T_d {}^m C_d A_d T_d G_d A_d {}^m C_d T_d T_k {}^m C_k {}^m C_k$ | 3-10-3 | Full deoxy | kkk | kkk | 86 |
| 582074 | $T_k T_k {}^m C_k A_{dx} G_{dx} T_d {}^m C_d A_d T_d G_d A_d {}^m C_d T_d T_k {}^m C_k {}^m C_k$ | 3-10-3 | Deoxy/Methyl phosphonate | kkk | kkk | 86 | k = = cEt

TABLE 128

Effect of modified oligonucleotide treatment on target reduction and liver function in BALB/C mice

| ISIS NO. | Target | Dosage (mg/kg/wk) | % UTC | ALT (IU/L) | Motif | Gap Chemistry | Wing Chemistry 5' | 3' | SEQ ID NO. |
|---|---|---|---|---|---|---|---|---|---|
| Saline | — | 0 | 100 | 30 | — | — | — | — | — |
| 482050 | PTEN | 10 | 50 | 228 | 3-10-3 | Full deoxy | kkk | kkk | 85 |
| 482050 | | 20 | 36.1 | 505 | | | | | |
| 582073 | | 10 | 72.2 | 47.7 | | Deoxy/Methyl phosphonate | kkk | kkk | 85 |
| 582073 | | 20 | 57.4 | 46 | | | | | |
| 449093 | SRB-1 | 10 | 48 | 543 | 3-10-3 | Full deoxy | kkk | kkk | 86 |
| 449093 | | 20 | 18.5 | 1090 | | | | | |
| 582074 | | 10 | 51.3 | 58.3 | | Deoxy/Methyl phosphonate | kkk | kkk | 86 |
| 582074 | | 20 | 30.3 | 126.3 | | | | | | k = cEt

TABLE 129

Effect of modified oligonucleotide treatment on body and organ weights in BALB/C mice

| ISIS NO. | Target | Dosage (mg/kg/wk) | Body wt rel to predose (%) | Liver/Body Wt (%) | Spleen/Body Wt (%) | Kidney/Body Wt (%) | SEQ ID NO. |
|---|---|---|---|---|---|---|---|
| Saline | — | 0 | 108.4 | 100 | 100 | 100 | |
| 482050 | PTEN | 10 | 107.4 | 154.9 | 141.8 | 115.7 | 85 |
| 482050 | | 20 | 111.3 | 176.7 | 142.3 | 112.5 | |
| 582073 | | 10 | 108.9 | 122.9 | 111.7 | 100.0 | 85 |
| 582073 | | 20 | 107.9 | 133.8 | 114.6 | 102.9 | |
| 449093 | SRB-1 | 10 | 101.3 | 105.9 | 117.9 | 89.3 | 86 |
| 449093 | | 20 | 95.3 | 118.6 | 129.6 | 93.0 | |
| 582074 | | 10 | 107.1 | 92.2 | 116.4 | 89.2 | 86 |
| 582074 | | 20 | 103.8 | 95.5 | 128.8 | 91.9 | |

Example 84

Modified Oligonucleotides Comprising Methyl Phosphonate Internucleoside Linkages Targeting Target-Y—In Vivo Study Additional modified oligonucleotides were designed in the same manner as the antisense oligonucleotides described in Example 24, wherein two methyl phosphonate internucleoside linkages are introduced at the 5'-end of the gap region. The modified oligonucleotides were designed based on ISIS 464917, 465178, 465984 and 466456 with a 3/10/3 motif. The oligonucleotides were evaluated for reduction in Target-Y mRNA expression levels in vivo. The parent gapmers, ISIS 464917, 465178, 465984 and 466456 were included in the study for comparison.

The modified oligonucleotides and their motifs are presented in Table 130. Each internucleoside linkage is a phosphorothioate (P=S) except for the internucleoside linkage having a subscript "x". Each nucleoside followed by a subscript "x" indicates a methyl phosphonate internucleoside linkage (—P(CH$_3$)(=O)—). Each nucleoside followed by a subscript "d" is a β-D-2'-deoxyribonucleoside. Nucleosides followed by a subscript "e" indicates a 2'-O-methoxyethyl (MOE) modified nucleoside. Nucleosides followed by a subscript "k" indicates a 6'-(S)—CH$_3$ bicyclic nucleoside (e.g. cEt). "N" indicates modified or naturally occurring nucleobases (A, T, C, G, U, or 5-methyl C).

Treatment

Six week old BALB/C mice (purchased from Charles River) were injected subcutaneously twice a week for three weeks at dosage 10 mg/kg or 20 mg/kg with the modified oligonucleotides shown below or with saline control. Each treatment group consisted of 3 animals. The mice were sacrificed 48 hrs following last administration, and organs and plasma were harvested for further analysis.

mRNA Analysis

Liver tissues were homogenized and mRNA levels were quantitated using real-time PCR and normalized to RIBOGREEN as described herein. The results below are listed as Target-Y mRNA expression for each treatment group relative to saline-treated control (% UTC). As illustrated in Table 131, reduction in Target-Y mRNA expression levels was achieved with the oligonucleotides comprising two methyl phosphonate internucleoside linkages at the 5'-end of the gap region, ISIS 582071, 582072, 582069 and 582070.

Plasma Chemistry Markers

Plasma chemistry markers such as liver transaminase levels, alanine aminotranferase (ALT) in serum were measured relative to saline treated mice and the results are presented in Table 131. Treatment with the oligonucleotides resulted in reduction in ALT level compared to treatment with the parent gapmer, ISIS 464917, 465178, 465984 or 466456. The results suggest that introduction of methyl phosphonate internucleoside linkage(s) can be useful for reduction of hepatoxicity profile of otherwise unmodified parent gapmers.

Body and Organ Weights

Body weights, as well as liver, kidney and spleen weights were measured at the end of the study. The results in Table 132 are presented as the average percent of body and organ weights for each treatment group relative to saline-treated control. As illustrated, treatment with ISIS 582070 resulted in a reduction in liver and spleen weights compared to treatment with the parent gapmer, ISIS 466456. An increase in body and organ weights was observed for ISIS 582071 as compared to ISIS 464917. The remaining oligonucleotides, ISIS 582072 and 582069 did not cause any changes in body and organ weights outside the expected range as compared to ISIS 465178 and 465984.

TABLE 130

Modified oligonucleotides comprising methyl phosphonate internucleoside linkages

| ISIS NO | Sequence (5' to 3') | Motif | Gap Chemistry | Wing Chemistry 5' | Wing Chemistry 3' | SEQ ID NO. |
|---|---|---|---|---|---|---|
| 464917 | $N_kN_kN_kN_dN_dN_dN_dN_dN_dN_dN_dN_dN_kN_kN_k$ | 3-10-3 | Full deoxy | kkk | kkk | 6 |
| 582071 | $N_kN_kN_kN_{dx}N_dN_dN_dN_dN_dN_dN_dN_dN_kN_kN_k$ | 3-10-3 | Deoxy/Methyl phosphonate | kkk | kkk | |
| 465178 | $N_kN_kN_kN_dN_dN_dN_dN_dN_dN_dN_dN_dN_kN_kN_k$ | 3-10-3 | Full deoxy | kkk | kkk | 6 |
| 582072 | $N_kN_kN_{dx}N_dN_dN_dN_dN_dN_dN_dN_dN_dN_kN_kN_k$ | 3-10-3 | Deoxy/Methyl phosphonate | kkk | kkk | |
| 465984 | $N_kN_kN_kN_dN_dN_dN_dN_dN_dN_dN_dN_dN_eN_eN_e$ | 3-10-3 | Full deoxy | kkk | eee | 6 |
| 582069 | $N_kN_kN_kN_{dx}N_dN_dN_dN_dN_dN_dN_dN_dN_kN_kN_k$ | 3-10-3 | Deoxy/Methyl phosphonate | kkk | kkk | |
| 466456 | $N_kN_dN_kN_dN_kN_dN_dN_dN_dN_dN_dN_dN_dN_eN_e$ | 5-9-2 or 3-11-2 | Full deoxy or deoxy/cEt | kdkdk or kdk | ee | 6 |
| 582070 | $N_kN_dN_kN_{dx}Nd_xN_dN_dN_dN_dN_dN_dN_dN_dN_eN_e$ | 3-11-2 | Deoxy/Methyl phosphonate | kdk | ee | | e = 2'-MOE, k = cEt, d = 2'-deoxyribonucleoside

TABLE 131

Effect of modified oligonucleotide treatment on Target-Y reduction and liver function in BALB/C mice

| ISIS NO. | Dosage (mg/kg/wk) | % UTC | ALT (IU/L) | Motif | Gap Chemistry | Wing Chemistry 5' | Wing Chemistry 3' |
|---|---|---|---|---|---|---|---|
| Saline | 0 | 100 | 30 | — | — | — | — |
| 464917 | 10 | 29 | 1244 | 3-10-3 | Full deoxy | kkk | kkk |
| 464917 | 20 | 30.1 | 2335 | | | | |
| 582071 | 20 | 10.2 | 274 | 3-10-3 | Deoxy/Methyl phosphonate | kkk | kkk |
| 465178 | 10 | 4.9 | 1231 | 3-10-3 | Full deoxy | kkk | kkk |
| 465178 | 20 | 10.6 | 6731 | | | | |
| 582072 | 10 | 36.7 | 44.7 | 3-10-3 | Deoxy/Methyl phosphonate | kkk | kkk |
| 582072 | 20 | 23.6 | 43.7 | | | | |
| 465984 | 10 | 4.7 | 61 | 3-10-3 | Full deoxy | kkk | eee |
| 465984 | 20 | 0.9 | 57 | | | | |
| 582069 | 10 | 11.1 | 39.7 | 3-10-3 | Deoxy/Methyl phosphonate | kkk | kkk |
| 582069 | 20 | 3.3 | 27.7 | | | | |

TABLE 131-continued

Effect of modified oligonucleotide treatment on Target-Y reduction and liver function in BALB/C mice

| ISIS NO. | Dosage (mg/kg/wk) | % UTC | ALT (IU/L) | Motif | Gap Chemistry | Wing Chemistry 5' | 3' |
|---|---|---|---|---|---|---|---|
| 466456 | 10 | 9.5 | 692 | 5-9-2 or | Full deoxy or | kdkdk | ee |
| 466456 | 20 | 10.5 | 2209 | 3-11-2 | deoxy/cEt | or kdk | |
| 582070 | 10 | 73.9 | 24 | 3-11-2 | Deoxy/Methyl | kdk | ee |
| 582070 | 20 | 51.3 | 36.7 | | phosphonate | | | e = 2'-MOE, k = cEt, d = 2'-deoxyribonucleoside

TABLE 132

Effect of modified oligonucleotide treatment on body and organ weights in BALB/C mice

| ISIS NO. | Dosage (mg/kg/wk) | Body wt rel to predose (%) | Liver/Body Wt (%) | Spleen/Body Wt (%) | Kidney/Body Wt (%) |
|---|---|---|---|---|---|
| Saline | 0 | 108 | 100 | 100 | 100 |
| 464917 | 10 | 92.9 | 125 | 106.2 | 102.3 |
| 464917 | 20 | 71.1 | 110.9 | 67.2 | 107.3 |
| 582071 | 20 | 104.6 | 135.2 | 142.8 | 89.8 |
| 465178 | 10 | 94.9 | 131.3 | 108.1 | 85.3 |
| 465178 | 20 | 79.5 | 147.5 | 112 | 95.3 |
| 582072 | 10 | 109.2 | 117.3 | 111.7 | 104.8 |
| 582072 | 20 | 107.1 | 130.1 | 107.2 | 99.8 |
| 465984 | 10 | 111.4 | 117.6 | 110.1 | 98.8 |
| 465984 | 20 | 111.3 | 122.6 | 134.5 | 96.1 |
| 582069 | 10 | 107.8 | 106.2 | 97 | 100.6 |
| 582069 | 20 | 105.4 | 115.8 | 106.2 | 100.4 |
| 466456 | 10 | 109.7 | 148.6 | 198.7 | 105.9 |
| 466456 | 20 | 101.2 | 182.3 | 213.7 | 101.9 |
| 582070 | 10 | 111.2 | 100.3 | 116.7 | 100.8 |
| 582070 | 20 | 111.1 | 108.9 | 115.6 | 95.7 |

Example 85

Short-Gap Chimeric Oligonucleotides Targeting Target-Y

A series of chimeric antisense oligonucleotides was designed based on ISIS 464917 or 465178, wherein the central gap region contains ten 2'-deoxyribonucleosides. These gapmers were designed by introducing 2'-MOE modified nucleoside(s) at the wing(s) and/or shortening the central gap region to nine, eight, or seven 2'-deoxyribonucleosides.

The gapmers and their motifs are described in Table 133. The internucleoside linkages throughout each gapmer are phosphorothioate (P=S) linkages. All cytosine nucleobases throughout each gapmer are 5-methyl cytosines. Nucleosides without a subscript are β-D-2'-deoxyribonucleosides. Nucleosides followed by a subscript "e" or "k" are sugar modified nucleosides. A subscript "e" indicates a 2'-O-methoxyethyl (MOE) modified nucleoside and a subscript "k" indicates a 6'-(S)—CH$_3$ bicyclic nucleoside (e.g. cEt).

TABLE 133

Short-gap antisense oligonucleotides targeting Target-Y

| ISIS NO | Sequence (5' to 3') | Motif | SEQ ID NO. |
|---|---|---|---|
| 464917 | N$_k$N$_k$N$_k$NNNNNNNNNNN$_k$N$_k$N$_k$ | 3-10-3 (kkk-d10-kkk) | 6 |
| 465977 | N$_k$N$_k$N$_k$NNNNNNNNNNN$_e$N$_e$N$_e$ | 3-10-3 (kkk-d10-eee) | 6 |
| 573331 | N$_e$N$_k$N$_k$NNNNNNNNNNN$_k$N$_k$N$_e$ | 3-10-3 (ekk-d10-kke) | 6 |
| 573332 | N$_e$N$_e$N$_k$N$_k$NNNNNNNNNN$_k$N$_k$N$_e$ | 4-9-3 (eekk-d9-kke) | 6 |
| 573333 | N$_e$N$_e$N$_e$N$_k$N$_k$NNNNNNNNN$_k$N$_k$N$_e$ | 5-8-3 (eeekk-d8-kke) | 6 |

TABLE 133-continued

Short-gap antisense oligonucleotides targeting Target-Y

| ISIS NO | Sequence (5' to 3') | Motif | SEQ ID NO. |
|---|---|---|---|
| 573334 | $N_e N_e N_e N_k N_k NNNNNNNN N_k N_e$ | 6-7-3 (eeeekk-d7-kke) | 6 |
| 573335 | $N_e N_k N_k NNNNNNNNN N_k N_e N_e$ | 3-9-4 (ekk-d9-kkee) | 6 |
| 573336 | $N_e N_k N_k NNNNNNNN N_k N_e N_e N_e$ | 3-8-5 (ekk-d8-kkeee) | 6 |
| 573361 | $N_e N_k N_k NNNNNNN N_k N_e N_e N_e N_e$ | 3-7-6 (ekk-d7-kkeeee) | 6 |
| 573338 | $N_e N_e N_k N_k NNNNNNNN N_k N_e N_e$ | 4-8-4 (eekk-d8-kkee) | 6 |
| 573339 | $N_e N_e N_e N_k N_k NNNNNNN N_k N_e N_e$ | 5-7-4 (eeekk-d7-kkee) | 6 |
| 573340 | $N_e N_e N_k N_k NNNNNNN N_k N_e N_e N_e$ | 4-7-5 (eekk-d7-kkeee) | 6 |
| 573779 | $N_k N_k N_k NNNNNNNN N_k N_e N_e N_e N_e$ | 3-8-5 (kkk-d8-keeee) | 6 |
| 573780 | $N_k N_k N_k NNNNNNNN N_k N_e N_e N_e N_e$ | 3-8-5 (kkk-d8-keeee) | 6 |
| 573806 | $N_k N_k N_k NNNNNNNN N_k N_e N_e N_e N_e$ | 3-8-5 (kkk-d8-keeee) | 6 |
| 573782 | $N_k N_k N_k NNNNNNNN N_k N_e N_e N_e N_e$ | 3-8-5 (kkk-d8-keeee) | 6 |
| 573783 | $N_k N_k N_k NNNNNNNN N_k N_e N_e N_e N_e$ | 3-8-5 (kkk-d8-keeee) | 6 |
| 573784 | $N_k N_k N_k NNNNNNNN N_k N_e N_e N_e N_e$ | 3-8-5 (kkk-d8-keeee) | 6 |
| 573785 | $N_k N_k N_k NNNNNNNN N_k N_e N_e N_e N_e$ | 3-8-5 (kkk-d8-keeee) | 6 |
| 573786 | $N_k N_k N_k NNNNNNNN N_k N_e N_e N_e N_e$ | 3-8-5 (kkk-d8-keeee) | 6 |
| 573787 | $N_k N_k N_k NNNNNNNN N_k N_e N_e N_e N_e$ | 3-8-5 (kkk-d8-keeee) | 6 |
| 465178 | $N_k N_k N_k NNNNNNNNNN N_k N_k N_k$ | 3-10-3 (kkk-d10-kkk) | 6 |
| 466140 | $N_k N_k N_k NNNNNNNNNN N_e N_e N_e$ | 3-10-3 (kkk-d10-eee) | 6 |
| 573341 | $N_e N_k N_k NNNNNNNNNN N_k N_k N_e$ | 3-10-3 (ekk-d10-kke) | 6 |
| 573342 | $N_e N_e N_k N_k NNNNNNNNN N_k N_k N_e$ | 4-9-3 (eekk-d9-kke) | 6 |
| 573343 | $N_e N_e N_e N_k N_k NNNNNNNN N_k N_k N_e$ | 5-8-3 (eeekk-d8-kke) | 6 |
| 573344 | $N_e N_e N_e N_k N_k N_k NNNNNNN N_k N_k N_e$ | 6-7-3 (eeeekk-d7-kke) | 6 |
| 573345 | $N_e N_k N_k NNNNNNNNN N_k N_k N_e$ | 3-9-4 (ekk-d9-kkee) | 6 |
| 573346 | $N_e N_k N_k NNNNNNNN N_k N_e N_e N_e$ | 3-8-5 (ekk-d8-kkeee) | 6 |
| 573347 | $N_e N_k N_k NNNNNNN N_k N_e N_e N_e N_e$ | 3-7-6 (ekk-d7-kkeeee) | 6 |

TABLE 133-continued

Short-gap antisense oligonucleotides targeting Target-Y

| ISIS NO | Sequence (5' to 3') | Motif | SEQ ID NO. |
|---|---|---|---|
| 573348 | $N_eN_eN_kN_k$NNNNNNNNN$N_kN_eN_e$ | 4-8-4 (eekk-d8-kkee) | 6 |
| 573349 | $N_eN_eN_eN_kN_k$NNNNNNN$N_kN_kN_eN_e$ | 5-7-4 (eeekk-d7-kkee) | 6 |
| 573350 | $N_eN_eN_kN_k$NNNNNNN$N_kN_eN_eN_e$ | 4-7-5 (eekk-d7-kkeee) | 6 |
| 573788 | $N_kN_kN_k$NNNNNNNN$N_kN_eN_eN_eN_e$ | 3-8-5 (kkk-d8-keeee) | 6 |
| 573789 | $N_kN_kN_k$NNNNNNNN$N_kN_eN_eN_eN_e$ | 3-8-5 (kkk-d8-keeee) | 6 |
| 573790 | $N_kN_kN_k$NNNNNNNN$N_kN_eN_eN_eN_e$ | 3-8-5 (kkk-d8-keeee) | 6 |
| 573791 | $N_kN_kN_k$NNNNNNNN$N_kN_eN_eN_eN_e$ | 3-8-5 (kkk-d8-keeee) | 6 |
| 573792 | $N_kN_kN_k$NNNNNNNN$N_kN_eN_eN_eN_e$ | 3-8-5 (kkk-d8-keeee) | 6 |
| 573793 | $N_kN_kN_k$NNNNNNNN$N_kN_eN_eN_eN_e$ | 3-8-5 (kkk-d8-keeee) | 6 |
| 573794 | $N_kN_kN_k$NNNNNNNN$N_kN_eN_eN_eN_e$ | 3-8-5 (kkk-d8-keeee) | 6 |
| 573795 | $N_kN_kN_k$NNNNNNNN$N_kN_eN_eN_eN_e$ | 3-8-5 (kkk-d8-keeee) | 6 |
| 573796 | $N_kN_kN_k$NNNNNNNN$N_kN_eN_eN_eN_e$ | 3-8-5 (kkk-d8-keeee) | 6 |
| 141923 (neg control) | $C_eC_eT_eT_eC_e$CCTGAAGGTTC$C_eC_eT_eC_eC_e$ | 5-10-5 (e5-d10-e5) | 9 | e = 2'-MOE (e.g. e5 = eeeee), k = cEt, d = 2'-deoxyribonucleoside

Example 86

Short-Gap Chimeric Oligonucleotides Targeting Target-Y—In Vitro Study

Several short-gap chimeric oligonucleotides from Table 133 were selected and evaluated for their effects on Target-Y mRNA in vitro. The parent gapmer, ISIS 464917 and 465178 were included in the study for comparison. ISIS 141923 was used as a negative control.

The newly designed gapmers were tested in vitro. Primary mouse hepatocytes at a density of 35,000 cells per well were transfected using electroporation with 0.0625, 0.25, 1, 4 and 16 µM concentrations of chimeric oligonucleotides. After a treatment period of approximately 24 hours, RNA was isolated from the cells and Target-Y mRNA levels were measured by quantitative real-time PCR. Primer probe set RTSXXXX was used to measure mRNA levels. Target-Y mRNA levels were adjusted according to total RNA content, as measured by RIBOGREEN.

The half maximal inhibitory concentration ($IC_{50}$) of each oligonucleotide is presented in Table 134 and was calculated by plotting the concentrations of oligonucleotides used versus the percent inhibition of Target-Y mRNA expression achieved at each concentration, and noting the concentration of oligonucleotide at which 50% inhibition of Target-Y mRNA expression was achieved compared to the control. As illustrated in Table 134 and 135, several short-gap oligonucleotides showed comparable inhibition of Target-Y mRNA levels as compared to the parent gapmers, ISIS 464917 or 465178.

TABLE 134

Comparison of inhibition of Target-Y mRNA levels of short-gap oligonucleotides with ISIS 464917

| ISIS NO | Motif | $IC_{50}$ (µM) | SEQ ID NO. |
|---|---|---|---|
| 464917 | 3-10-3 (kkk-d10-kkk) | 0.5 | 6 |
| 573331 | 3-10-3 (ekk-d10-kke) | 0.5 | 6 |
| 573332 | 4-9-3 (eekk-d9-kke) | 0.6 | 6 |
| 573333 | 5-8-3 (eeekk-d8-kke) | 0.5 | 6 |
| 573335 | 3-9-4 (ekk-d9-kkee) | 0.4 | 6 |
| 573336 | 3-8-5 (ekk-d8-kkeee) | 0.5 | 6 |
| 573361 | 3-7-6 (ekk-d7-kkeeee) | 0.6 | 6 |

TABLE 134-continued

Comparison of inhibition of Target-Y mRNA levels of short-gap oligonucleotides with ISIS 464917

| ISIS NO | Motif | IC$_{50}$ (μM) | SEQ ID NO. |
|---|---|---|---|
| 573340 | 4-7-5 (eekk-d7-kkeee) | 2.3 | 6 |
| 141923 (neg control) | 5-10-5 (e5-d10-e5) | >16 | 9 | e = 2'-MOE (e.g. e5 = eeeee),
k = cEt,
d = 2'-deoxyribonucleoside

TABLE 135

Comparison of inhibition of Target-Y mRNA levels of short-gap oligonucleotides with ISIS 465178

| ISIS NO | Motif | IC$_{50}$ (μM) | SEQ ID NO. |
|---|---|---|---|
| 465178 | 3-10-3 (kkk-d10-kkk) | 0.2 | 6 |
| 573341 | 3-10-3 (ekk-d10-kke) | 0.2 | 6 |
| 573342 | 4-9-3 (eekk-d9-kke) | 0.4 | 6 |
| 573345 | 3-9-4 (ekk-d9-kkee) | 0.2 | 6 |
| 573346 | 3-8-5 | 0.4 | 6 |
| 573348 | (ekk-d8-kkeee) | 0.5 | 6 |
| 573350 | 4-8-4 (eekk-d8-kkee) | 0.9 | 6 |
| 573806 | 4-7-5 (eekk-d7-kkeee) | 0.8 | 6 |
| 573783 | 3-8-5 (kkk-d8-keeee) | 1.0 | 6 |
| 573784 | 3-8-5 (kkk-d8-keeee) | 1.3 | 6 |
| 573785 | 3-8-5 (kkk-8-keeee) | 1.0 | 6 |
| 573792 | 3-8-5 (kkk-8-keeee) | 0.5 | 6 |
| 573794 | 3-8-5 (kkk-d8-keeee) | 0.4 | 6 |
| 573795 | 3-8-5 (kkk-d8-keeee) | 0.5 | 6 |
| 573796 | 3-8-5 (kkk-d8-keeee) | 0.8 | 6 |
| 141923 (neg control) | 5-10-5 (e5-d10-e5) | >16 | 6 | e = 2'-MOE (e.g. e5 = eeeee),
k = cEt,
d = 2'-deoxyribonucleoside

Example 87

Short-Gap Chimeric Oligonucleotides Targeting Target-Y—In Vivo Study

Several short-gap oligonucleotides described in Example 85 were selected and evaluated for efficacy in vivo and for changes in the levels of various plasma chemistry markers targeting Target-Y. The parent gapmer, ISIS 464917 was included in the study for comparison.

Treatment

Six week male BALB/C mice (purchased from Charles River) were injected subcutaneously with a single dose of antisense oligonucleotide at 10 mg/kg or 20 mg/kg or with saline control. Each treatment group consisted of 4 animals. The mice were sacrificed 96 hrs following last administration, and organs and plasma were harvested for further analysis.

mRNA Analysis

Liver tissues were homogenized and mRNA levels were quantitated using real-time PCR and normalized to Cyclophilin A as described herein. The results below are listed as Target-Y mRNA expression for each treatment group relative to saline-injected control (% UTC). As illustrated in Table 136, Target-Y mRNA expression levels were reduced in a dose-dependent manner with the newly designed oligonucleotides.

Plasma Chemistry Markers

Plasma chemistry markers such as liver transaminase levels, alanine aminotranferase (ALT) in serum were measured relative to saline treated mice and the results are presented in Table 136. Treatment with the newly designed oligonucleotides resulted in reduction in ALT levels compared to treatment with the parent gapmer, ISIS 464917. The results suggest that shortening the central gap region and introducing 2'-MOE modified nucleoside(s) at the wing(s) can be useful for the reduction of hepatoxicity profile of ISIS 464917.

Body and Organ Weights

Body weights, as well as liver, kidney and spleen weights were also measured at the end of the study. The results showed that treatment with the newly designed oligonucleotides did not cause any changes in body and organ weights outside the expected range as compared to ISIS 464917 (data not shown).

TABLE 136

Effect of short-gap antisense oligonucleotide treatment on Target-Y reduction and liver function in BALB/C mice

| ISIS NO | Dosage (mg/kg/wk) | % UTC | ALT (IU/L) | Motif | SEQ ID NO. |
|---|---|---|---|---|---|
| Saline | 0 | 99 | 23 | — | |
| 464917 | 10 | 11.5 | 1834 | 3-10-3 (kkk-d10-kkk) | 6 |
| | 20 | 5.1 | 8670 | | |
| 573333 | 10 | 32.8 | 79 | 5-8-3 (eeekk-d8-kke) | 6 |
| | 20 | 21.2 | 370 | | |
| 573334 | 10 | 79.5 | 26 | 6-7-3 (eeeekk-d7-kke) | 6 |
| | 20 | 69.4 | 29 | | |
| 573336 | 10 | 23.2 | 179 | 3-8-5 (ekk-d8-kkeee) | 6 |
| | 20 | 12.0 | 322 | | |
| 573339 | 10 | 47.9 | 35 | 5-7-4 (eeekk-d7-kkee) | 6 |
| | 20 | 32.8 | 199 | | |
| 573340 | 10 | 81.3 | 63 | 4-7-5 (eekk-d7-kkeee) | 6 |
| | 20 | 66.2 | 33 | | |
| 573361 | 10 | 33.6 | 150 | 3-7-6 (ekk-d7-kkeeee) | 6 |
| | 20 | 19.2 | 722 | | |
| 573783 | 10 | 16.5 | 734 | 3-8-5 (kkk-d8-keeee) | 6 |
| | 20 | 6.3 | 1774 | | |
| 573785 | 10 | 20.2 | 61 | 3-8-5 (kkk-d8-keeee) | 6 |
| | 20 | 14.2 | 40 | | |
| 573806 | 10 | 19.3 | 346 | 3-8-5 (kkk-d8-keeee) | 6 |
| | 20 | 15.4 | 1389 | | | e = 2'-MOE,
k = cEt,
d = 2'-deoxyribonucleoside

Example 88

Short-Gap Chimeric Oligonucleotides Targeting PTEN

A series of chimeric antisense oligonucleotides was designed based on ISIS 482050, wherein the central gap region contains ten 2'-deoxyribonucleosides. These gapmers were designed by introducing 2'-MOE modified nucleoside(s) at the wing(s) and/or shortening the central gap region to nine, or eight 2'-deoxyribonucleosides.

The gapmers and their motifs are described in Table 137. The internucleoside linkages throughout each gapmer are phosphorothioate (P=S) linkages. All cytosine nucleobases throughout each gapmer are 5-methyl cytosines. Nucleosides without a subscript are β-D-2'-deoxyribonucleosides. Nucleosides followed by a subscript "e" or "k" are sugar modified nucleosides. A subscript "e" indicates a 2'-O-methoxyethyl (MOE) modified nucleoside and a subscript "k" indicates a 6'-(S)—CH$_3$ bicyclic nucleoside (e.g. cEt).

TABLE 137

Short-gap antisense oligonucleotides targeting PTEN

| ISIS NO. | Sequence (5' to 3') | Motif | SEQ ID NO. |
|---|---|---|---|
| 482050 | $A_kT_kC_k$ATGGCTGCAGC$_kT_kT_k$ | 3-10-3 (kkk-d10-kkk) | 85 |
| 508033 | $A_kT_kC_k$ATGGCTGCAGC$_eT_eT_e$ | 3-10-3 (kkk-d10-eee) | 85 |
| 573351 | $A_eT_kC_k$ATGGCTGCAGC$_kT_kT_e$ | 3-10-3 (ekk-d10-kke) | 85 |
| 573352 | $A_eT_eC_kA_k$TGGCTGCAGC$_kT_kT_e$ | 4-9-3 (eekk-d9-kke) | 85 |
| 573353 | $A_eT_eC_eA_kT_k$GGCTGCAGC$_kT_kT_e$ | 5-8-3 (eeekk-d8-kke) | 85 |
| 573354 | $A_eT_eC_eA_eT_kG_k$GCTGCAGC$_kT_kT_e$ | 6-7-3 (eeeekk-d7-kke) | 85 |
| 573355 | $A_eT_kC_k$ATGGCTGCAG$C_kC_kT_eT_e$ | 3-9-4 (ekk-d9-kkee) | 85 |
| 573356 | $A_eT_kC_k$ATGGCTGCA$G_kC_eT_eT_e$ | 3-8-5 (ekk-d8-kkeee) | 85 |
| 573357 | $A_kT_kC_k$ATGGCTGC$_kA_kG_eC_eT_eT_e$ | 3-7-6 (ekk-d7-kkeeee) | 85 |
| 573358 | $A_eT_eC_kA_k$TGGCTGCAG$_kC_kT_eT_e$ | 4-8-4 (eekk-d8-kkee) | 85 |
| 573359 | $A_eT_eC_kA_kT_k$GGCTGCAG$_kC_kT_eT_e$ | 5-7-4 (eeekk-d7-kkee) | 85 |
| 573360 | $A_eT_eC_kA_k$TGGCTGCA$G_kC_eT_eT_e$ | 4-7-5 (eekk-d7-kkeee) | 85 |
| 573797 | $T_kG_kG_k$CTGCAGCTT$_kC_eC_eG_eA_e$ | 3-8-5 (kkk-d8-keeee) | 87 |
| 573798 | $A_kT_kG_k$GCTGCAGCT$_kT_eC_eC_eG_e$ | 3-8-5 (kkk-d8-keeee) | 88 |
| 573799 | $C_kA_kT_k$GGCTGCAGC$_kT_eT_eC_eC_e$ | 3-8-5 (kkk-d8-keeee) | 89 |
| 573800 | $T_kC_kA_k$TGGCTGCAG$_kC_eT_eT_eC_e$ | 3-8-5 (kkk-d8-keeee) | 90 |
| 573801 | $A_kT_kC_k$ATGGCTGCA$_kG_eC_eT_eT_e$ | 3-8-5 (kkk-d8-keeee) | 85 |
| 573802 | $C_kA_kT_k$CATGGCTGC$_kA_eG_eC_eT_e$ | 3-8-5 (kkk-d8-keeee) | 91 |
| 573803 | $C_kC_kA_k$TCATGGCTG$_kC_eA_eG_eC_e$ | 3-8-5 (kkk-d8-keeee) | 92 |
| 573804 | $T_kC_kC_k$ATCATGGCT$_kG_eC_eA_eG_e$ | 3-8-5 (kkk-d8-keeee) | 93 |
| 573805 | $T_kT_kC_k$CATCATGGC$_kT_eG_eC_eA_e$ | 3-8-5 (kkk-d8-keeee) | 94 | e = 2'-MOE, k = cEt, d = 2'-deoxyribonucleoside

Example 89

Short-Gap Chimeric Oligonucleotides Targeting PTEN—In Vitro Study

Several short-gap chimeric oligonucleotides from Table 137 were selected and evaluated for their effects on PTEN mRNA in vitro. The parent gapmer, ISIS 482050 were included in the study for comparison. ISIS 141923 was used as a negative control.

The newly designed gapmers were tested in vitro. Primary mouse hepatocytes at a density of 35,000 cells per well were transfected using electroporation with 0.0625, 0.25, 1, 4 and 16 µM concentrations of chimeric oligonucleotides. After a treatment period of approximately 24 hours, RNA was isolated from the cells and PTEN mRNA levels were measured by quantitative real-time PCR. Primer probe set RTS186 was used to measure mRNA levels. PTEN mRNA levels were adjusted according to total RNA content, as measured by RIBOGREEN.

The half maximal inhibitory concentration ($IC_{50}$) of each oligonucleotide was calculated in the same manner as described previously and the results are presented in Table 138. As illustrated, most short-gap oligonucleotides showed comparable inhibition of PTEN mRNA levels as compared to ISIS 482050.

TABLE 138

Comparison of inhibition of PTEN mRNA levels of short-gap oligonucleotides with ISIS 482050

| ISIS NO | Motif | $IC_{50}$ (µM) | SEQ ID NO. |
|---|---|---|---|
| 482050 | 3-10-3 (kkk-d10-kkk) | 1.9 | 85 |
| 573351 | 3-10-3 (ekk-d10-kke) | 2.8 | 85 |
| 573353 | (ekk-d10-kke) | 6.1 | 85 |
| 573355 | 3-9-4 (ekk-d9-kkee) | 2.6 | 85 |
| 573798 | 3-8-5 (kkk-d8-keeee) | 1.6 | 88 |
| 573799 | 3-8-5 (kkk-d8-keeee) | 1.9 | 89 |
| 573803 | 3-8-5 (kkk-d8-keeee) | 1.4 | 92 |
| 141923 (neg control) | 5-10-5 (e5-d10-e5) | >16 | 9 | e = 2'-MOE (e.g. e5 = eeeee),
k = cEt,
d = 2'-deoxyribonucleoside

We claim:

1. An oligomeric compound comprising a modified oligonucleotide having a modification motif comprising:
   a 5'-region consisting of three linked 5'-region nucleosides, wherein the 5'-region has an ABB motif;
   a 3'-region consisting of four linked 3'-region nucleosides, wherein the 3'-region has a BBAB motif; and
   a central region between the 5'-region and the 3'-region consisting of 6-12 linked central region nucleosides, each independently selected from a nucleoside comprising a modified sugar moiety and a nucleoside comprising an unmodified deoxyribosyl sugar moiety, wherein the 5'-most central region nucleoside comprises an unmodified deoxyribosyl sugar moiety and the 3'-most central region nucleoside comprises an unmodified deoxyribosyl sugar moiety;
   wherein each A is a nucleoside comprising a non-bicyclic modified sugar moiety, each B is a bicyclic nucleoside.

2. The oligomeric compound of claim 1, wherein each B comprises a bicyclic sugar moiety independently selected from cEt, cMOE, LNA, α-LNA, ENA, and 2'-thio LNA.

3. The oligomeric compound of claim 2, wherein each B comprises a bicyclic sugar moiety independently selected from cEt and LNA.

4. The oligomeric compound of claim 2, wherein each B comprises a cEt sugar moiety.

5. The oligomeric compound of claim 1, wherein each A comprises a non-bicyclic 2'-substituted sugar moiety.

6. The oligomeric compound of claim 5, wherein each A is a nucleoside comprising a 2'-substituent independently selected from a halogen, $OCH_3$, $OCF_3$, $OCH_2CH_3$, $OCH_2CF_3$, $OCH_2$—$CH$=$CH_2$, $O(CH_2)_2$—$OCH_3$ (MOE), $O(CH_2)_2$—$O(CH_2)_2$—$N(CH_3)_2$, $OCH_2C$(=O)—$N(H)CH_3$, $OCH_2C$(=O)—$N(H)$—$(CH_2)_2$—$N(CH_3)_2$, and $OCH_2$—$N(H)$—$C$(=$NH$)$NH_2$.

7. The oligomeric compound of claim 5, wherein each A is a nucleoside comprising a 2'-substituent independently selected from F, $OCH_3$, and $O(CH_2)_2$—$OCH_3$ (MOE).

8. The oligomeric compound of claim 1, wherein each A is a nucleoside comprising a 2'-$O(CH_2)_2$—$OCH_3$ (MOE) substituent.

9. The oligomeric compound of claim 4, wherein each A is a nucleoside comprising a 2'-$O(CH_2)_2$—$OCH_3$ (MOE) substituent.

10. The oligomeric compound of claim 1, wherein the central region consists of 6-10 linked nucleosides.

11. The oligomeric compound of claim 1, wherein the central region consists of 7 linked nucleosides.

12. The oligomeric compound of claim 1, wherein the central region consists of 8 linked nucleosides.

13. The oligomeric compound of claim 1, wherein the central region consists of 9 linked nucleosides.

14. The oligomeric compound of claim 1, wherein each central region nucleoside comprises an unmodified deoxyribosyl sugar moiety.

15. The oligomeric compound of claim 1, wherein at least one central region nucleoside comprises a modified sugar moiety.

16. The oligomeric compound of claim 15, wherein one central region nucleoside comprises a modified sugar moiety and each of the other central region nucleosides comprises an unmodified deoxyribosyl sugar moiety.

17. The oligomeric compound of claim 1, wherein the modified oligonucleotide comprises at least one modified internucleoside linkage.

18. The oligomeric compound of claim 17, wherein each internucleoside linkage of the modified oligonucleotide is a modified internucleoside linkage.

19. The oligomeric compound of claim 17, wherein at least one modified internucleoside linkage is a phosphorothioate internucleoside linkage.

20. The oligomeric compound of claim 17, wherein at least one modified internucleoside linkage is a methylphosphonate internucleoside linkage.

* * * * *

SEQUENCE LISTING

<160> NUMBER OF SEQ ID NOS: 94

<210> SEQ ID NO 1
<211> LENGTH: 202001
<212> TYPE: DNA
<213> ORGANISM: Homo sapiens

<400> SEQUENCE: 1

```
gcccagcagg tgtcagcctc attttacccc gcccctattc aagatgaagt tgttctggtt      60
ccaacgcctc tgacatatta gctgcatcat tttacatttc tttttttttt ttccttttaa     120
atggggtctt gctctgtcac ccaggctgga gtgctgtggt atgatctcgg ctcactgcaa     180
tctccacctc cgaggttcca gcgattctct tgcctcagcc tcccgagtag ctgggactac     240
aggcacccac catcatactg ggctaatttt tgtgttttta gtagagatgg ggtttcccca     300
tgttgcccag gctgatctca aactcctggg cttaagcaat acagccgcgt tggcctccca     360
aagtgttggg attacaagca tgagctaccc cacccagctc attttacatt tccacttgtt     420
aaactgaaaa ctggcccgag aaagcttctg tactgccatc cttgcgtcct tgcagatgaa     480
tcgtaaccta gcatagtagg taggcagact gaaaacctaa cttagcagta ggcttctgta     540
acaacagctg tgtctcagcc agttcctgca gccagacttc aaccactcac aggccgcaaa     600
ctgttcaaac tgtgttcgga gaaggcgaat tcatctggct gttaacgtgc ctcacttctg     660
ctttctgtgg ccactttccc ttttctgtcc ataaatttgc tttgaccaca cagcatccct     720
agagtctccc tgaatctgct gtgattctgg gacctgcacc atttgtgaat tgttttttt     780
ttccttgatc agctaaactc tgttcaattc aatttgttgg aagtttttaa cataccaatg     840
gtgcaccaag gttccaattt ctccacttcc tcataaataa gtcattttaa atggcttttc     900
agtattccaa tatttggaag tattaatgtt tctaccaatt ttctattttt ggacattgag     960
gttgtttcat ttttttttc tttttttgag acagagtctc gctccgtcac ccaggctgga    1020
gtgcagtggc ctgatcccgg cccactgcaa cctccacctc cctcctcagc ctcctgagta    1080
```

```
gctgggatta caggtgcatg caccaccaca cccagctaat ttttgtattt ttagtagaga    1140
tggggtttca ccatgttggt caggctggtc tcaaactcct gacctcaggt ggtccacctg    1200
ccttggcctc ccaaaatgct gggattacag gcctgagcca ctgcgcctgg cctcatcttc    1260
ttgatattaa tgttgcttta acatctttgt ccctgtgttt tttgtttttt ttttgagac    1320 ggagtctcat tcattctgtc acccaggctg gagttcagtg gcgtgatctc agctcactgc    1380
aacctctgtc tcctgggttc cagtgattct cctgcgtcgg tctcctgagt agctgtgttc    1440
ctgggtcttt cgatggttat ttaatacttc cctacagtaa tgccctgtgc gtacatgcta    1500
agtgtgatga aatggttggc acagttaaat cttttgaaag acattgccaa gtcactcttc    1560
agaaaagtga taggaggtca tagcaatttt aagaagtcct catttctaca tttccttact    1620
aatctcggtt ggtgtctctt caatctttcc tcacactttt cttgggtttt tcctgaatca    1680
tgagtctact acatttacac attttaaagc atctttagaa acaggatctc attttgttgc    1740
ccaggctaga gtttggtggc atgattatag ctcctcatac tcctgggctc aagtgatcct    1800
tccacctctg aaacccccaaa atttgagaaa ggtctcattt aatttagaaa gtttattttg    1860
ccaaggttga gggtgcacac ctgtgatgat atacgagtta aaagaaatt atttaggcag    1920 atactgaggg taagaaagtc ctcggtaagg ttttctttc aatgaaaagc agcccccaag    1980
catttctttt tctaacaaag agcagcctgt aaaatcgagc tgcagacata cacaagcaag    2040
ctggaagctt gcacaggtga atgctggcag ctgtgccaat aagaaaaggc tacctggggc    2100
caggcagatc caacatggcg gctccatctt ccctttcctt gtcaaccatg tgcacagtaa    2160
ggagcaggca acatagtgtc ccccgagtag agaccaattt gcataataaa aggtgagggt    2220
agggtgggca gcttctttgc atgctatgta acattatgc ctggtccaac caatctttgg    2280
gccctgtgta aattagacac cacctcctca agcctgtcta taaaaccctg tccattctgc    2340
cgcaggctgg aagacccact ggggcacccc tctctctcta taggagacag ctattcattt    2400
ttctctttct ttcacctatt aaagctccac tcttaacccc actccgtgtg tatctatgtt    2460
cttgatttcc ttggcatgag gcaatgaacc ttgggtatta ccccagaacc ttgggtatta    2520
tgccacttca gtgacacagc ctcaggaaat cctgatgaca tgttcccaag atggtcgggg    2580
cacagcttgg ttttatacat tttagggaga catgagacgt caattcatat atgtaagaag    2640
tacattggtt ccgtccagaa aggcggggac aacttgaggc agggagagag cttctaggtc    2700
acaggtagac aaatggttgc attcttttga atctccgata agccttccca aaggaggcaa    2760
tcagaatatg cgtctattga ctgggcgcag tggctcatgc ctgtaatgcc agcactttgg    2820
gaggcggagg tgggtggatc acctgaggtc aggagtttga gagcagcccg gccaacatgg    2880
tgaaaccctg tctctactaa aaatacaaaa aattagctgg gcgtggtggc gggcgcctgt    2940
aatcccagct actcgggagg ctgaggcagg agaatagctt gaacccagaa ggaagaggtt    3000
gcagtgagct gagatggtgc cattgcactc cagcctgggc aacaagagtg aaactccatc    3060
tcagaaaaaa aaaaaaaagg cctgggcaaa gtggctcacg cctgtaatcc cagcactttg    3120
ggaagccgag gcgggcaggt cacaaagtca ggagattgag accatcctgg ctaacatgat    3180
gaaaccccat ctctactaaa aaatacaaaa aactagctgg gtgtggtggc gagcacctgt    3240
agtcccagct actcggcagg ctgaggcagg agaatggcgt gaaccgggga ggcggagctt    3300
gcagtgagcc gagatcacac cactgcactc cagcccggac gacagggcaa gactctatct    3360
caaattaaaa aaaaaaaaa aaaaaaaaaa aagagagag agaatatgca tctatctcag    3420
tgagcagaag gatgactttg aatggaatgg gagcagttcc tagcttgaac ttccccttta    3480
```

```
gcttcagtga tttgggggct caaggtatgt tcctttcaca tacctcagcc tcccaagtag    3540
ctgggaccac aagtgcatgc caccacacgt ggctaatgtt ttattttttt tgtaggaata    3600
gggtctcact atgtgtccag gctggtctaa accccctgag ctcaaatggt cctcccgcct    3660
cagcctcccg aaatgctggg attacaggca tgagccagca tgcccggcct agtctacatt    3720
tttataaatt gctaattcaa agttccctct ccaaaacctc atggttttcc ctgttctcat    3780
cccctgcacc ctcccttccc ctggagtact cacctggcct tggaggtctg gtgtgagccc    3840
ggacttcgat tctaggcaca gcatgtgatg agcgccccca ggtcaaacac ctcccctctg    3900
cggcctgtgc ttcaccgcct tgacagtgag aaaggtctcc cttcggctca ttctcgaagt    3960
ctcaaacttc acttctcctg tgcgctgatt ctgaattcag ccccgtcca aggtcctggc    4020 cccttctct tctgcttggc gtgttgttca tcaccactgt gcactgctga gggtaagtgc    4080
ggttctctgg acctctgctt tatcattaga acagactctt gcggtttccc acgacattcc    4140
tttcacttct cacttggaag atgagccgtg aggaaatcct gtgttgtgtg gtatgtgggc    4200
tgtgcttctg cttgacttga gggccaagca gcattgcaag ccatggtttt aaataagaaa    4260
gaacatttct aaccttcatc ttctagtaag gaaacaagtg ggctttagag ttcttgctca    4320
ggaaagacct atgtcccagt ccaaccggac cttttactaa agagatcttc ctgatcctcc    4380
tccccaggcc aggggagggg tcctccctgg ggttggagcc tttagtaggg ggtcggagac    4440
acgacgtagc cttcatgaca ttcatagtct agttacacga tccctgtaag ggtcagttga    4500
agtaagtgct acaaaggaag ggaggtgctc agtggagagg gctctctttt atgtattata    4560
tttctttcat ggggagggat atggatcagg gatcagcaga ggtgtttcag tcccgaggga    4620
aagaaagtca gcgtggcttg ggagttggga gcagcaagac agtggctcaa gatatcttaa    4680
gactagtgga gtacaccttg catgttaaaa gccttgctca gggctgcctg gttcttgtag    4740
gacgacagag atggcctagc tctgcatact gcaccccag gggctcagaa cagtgcaaat    4800
gtcagtctat ctgtcagtgg cagagccagc cttggagcag gggtgcaagg aggtctctgc    4860
actggccagg catgcagaac attctgttca gtagcactgg acagaaggcc ccatctagat    4920
gagacagagc tggtggggca ggacaaagac tcctggcagc tcaaacgcc tggcagatgc    4980 ttggagagag ggggcttctt gagacagcac catttctggg aagagagtca cctgggaggg    5040
atgaggccac gctccggctt ggaggtgaag agaggggctg ctgcaagaaa gaattagaga    5100
catgccagcc tttgctgtgt tgcccaggct ggtcatgaac tcttggcctc aagcaatctt    5160
cccacctcag cctccccaag cgctgggatt atagacatga gccccatgc tggccaataa    5220 aagatgattt tatggagggg atggtggtga aggttgtggg tggtatgaaa tagtaagaaa    5280
tatatattgg tctgcaccca gttcctgcca cagagctcct aaaatcctga aacttcctg    5340 ggtgagcatc ttttgttcta atgaggtgac tcttggtggc tcctggatag gagtgaatca    5400
ccagaaagat caagccagag ttagaagcag aaagtgctgg ctataacaca ggaaagctgt    5460
aacacaaata ataaagtttt tttttttttt tttgagatgg agcctcactc tgttgcccag    5520
gctggagtgc aatggtgcaa tctcagctca ctacaagctc tgcctcccag gttcaagtga    5580
ttctcctgcc tcagcctcct gagcagttgg gactacaggt gtgtgccacc acatctggct    5640
aatttttgta ttttagcag agacggggtt tcaccatatt aaccaggctg gcctcaaact    5700
ccttaccttg tgatccgcct gcctcagcct cccaaagtgc tgggattaca ggcatgagcc    5760
accgtgcctg gccaaaagac attgttctta aaagaatcaa ctaactaacc aaataaataa    5820
```

```
aaatctaacc taattaagaa actaaaaata cacaaaaatt aatttcaagg ggagaaaaat    5880
catgtaaaga gagaaagata atgaatactt tgcagaaatt tatgaacata aacataaaac    5940
ttggatgaaa tgcatttcta ggaaaacata atttatcaaa actaaccaca agtaaaatag    6000
aagcctaaat aggatatttt caagagaaga agtaaagttg tcaaagtgct acccttcaaa    6060
aaaacaccag gctcaaacaa tctgacatgg gaatgttagc acaccttaga gagcaaataa    6120
aactttgaat gggcttgaaa tattccagac tctagaaaaa caaaacttcc caattctttt    6180
tataaagcaa gtataaattg ataccaaaat cttataaaga ccttatacaa aacttcatac    6240
caatctcttt tatgaataca aaacccttaa taaagtatta ccagacagaa cccaacaata    6300
cataaaaatg tcacatcata acatagtggg gtttatttca ataatgcatg gatggttcaa    6360
tacaaggaaa ttcagtaaca caatataata gatcatgtga atatacccaa agaaaaaata    6420
gattattttc atagatgctg taaaggcatt tgaccaaatt caacacctac ttttttaggtg    6480
gtcaataaaa taaattagtt actccttctt tagcatgata aatatatttt atcagcccag    6540
aaggcatcat tttacccgat aagggcacac gctggaggga ataatgttaa aattaggaat    6600
aagaggatag ctagttttctt tcttcttttt tttttttgag acggagtctt gctctgttgc    6660
caggctggag tgcagtggtg caatgttggc tcactgcacg ccccccgcct cccaggttca    6720
agcgattctc ctgcctcagc ctcccgagta gctgggacta caggcgcgca ccaccatgcc    6780
cggctaattt tttttttgtat tttagtagag atggggtttc accatgttgg tcaggctggt    6840
cttgaactcc caacctcacg tactgggatt accggtgtga gccaccacgc cagcccaact    6900
actttcaaca ttatccttaa tactgatgct tattgactta ctatggggtt acctctagat    6960
aaatccataa taagttgaaa atataagtaa aaaatgccct taatacacct aacctaccaa    7020
acatcatagc tgagcccagc ctgccttagc tatgctcaga cactgacgtc agcctacaat    7080
tggcaaaatc acacagcagc acagtctact gcagagcatc tgctgtttgc ccttgtgact    7140
gcgtggctgc ctgggagctt cccagcttca caagacagta ttacgtagca catcactagc    7200
ctggggaaag atcaaagttg aaaatttgaa gtgtggtttc cattgaatgt gtactgctttt   7260
tgcaccatca tcaagtcaaa aaattttagt tgaaccagcc taagtttggg accatcttta    7320
ttttcaggag gaacttccat gtacattgat gacggacgat agaatccgtt tctatcatcc    7380
taatgaacat aatgaataaa tccagacaaa cataaacatt aacagagtaa gcagctttcg    7440
gggctggaag ccagaagagg gtgggagcgc agagagagag gccaaacacc agggctgctt    7500
ctgctttgcg ggtatttgct gatctgggaca aggtatctgg aaggctgagc taagcctcct    7560
tttttttttga ggtggcgtct cactctgttg ccaggctgga gtgcaatggt gcgatctcag    7620
ctcactgcaa cctccacctc cctggttcaa gcgattctcc tgcctcagcc tcccgagtag    7680
ctgggattac aggctcccgc cactacaccc agctgatttt tgtaattttta gtagagacgg    7740
ggtttcacca tgttggccag gatggtctcg atctcttgac gtcatgatct gtccacctcg    7800
gcctcccaaa gtgctgggat tataggcgtg acccaccgtg cccgtctga gctaagcctc     7860
ttgagcatag gggactaaaa atgaaatcta gcgcatgcca gtttagggt cccaggcaat     7920
tcctttccac tttggggtcc actttgggg ccacccacc caagaagaag gatgacttgg      7980
aagtaaacca gctctgaaat atggatggtc ctctgggacc ataccaatcc cttcatatca    8040
accacatcca gttcctcaaa actggaactt ggattaagat ggcctaggac ttctagtgtc    8100
ccaggagcct ggcattgcaa acaaaaatcc tctccggaag aagataatac cttaagcttc    8160
aaatgactct ctaataaatt tcaaatacaa tgtccagcac acaaacacaa attaccagga    8220
```

```
acgtgatatg aggcctgatg gatgggaatt agcagaaact tcaggcatga gaaacatacc    8280
ctcagaggcc tagaatctat ctagtgtcta gataatggag atatgaaata cagacactta    8340
aacaactatg tttcccatgt tcaaagagga aatttgcaaa acttgaaagt gttggcagga    8400
aatcagaaac tataaaatgt gacaacagca tactttagag tcagtataaa ttacggtccc    8460
gaaaactgca gaattccaga acttaatggt aaagcaaggg tttaacagca gaatagaaat    8520
agccagagag aactaggaag taagtcagat gacactaccc agaataaggc actgagaggc    8580
caaggaatgg aaaatgcaga agaaaggata tggtgagagg atctaatata catttatttg    8640
gagtaccagg gagagagaga aggagaagaa cagaagccgt gtttcaagga cggtgactga    8700
gaggcttcga aactgatgaa agccatcagt tcacaaattc aaagcccagt gaattccaag    8760
gagaaaaaaa gaaatcccata ctgtgaaagc aagtccagac aatgacaaac accatcaaca    8820
atacacagga caggcataag atgcatttaa tggggacact cagaggcaga gggttatcag    8880
aaggaggcac ttctctccca agttctcatc atcccagggc cagggacagc tggtcacacc    8940
ttagggagtt cactaggaga gggatctggc ttcttgtcat tctgggtatt tgtagggaaa    9000
ttggaaggga accgagagca cctagccaat cgcatagcaa tgggagattt caggctgtgg    9060
ggaatgtctt tgctggtgaa aagaacatcc tgaccttaga aatctttcac cgaggggat    9120
ctgcgttcca gaacttctgg agctggtata ggtaaggctt tgagctttcc tactgagcca    9180
gcctgttgct aggttaccaa aggggacctc gagggccatc tggccaacaa gcagacttgt    9240
ctctccttac acccccagac gtatcactgc aaaactacag aaaaccaaag acagagaaaa    9300
tcttaaaagc agccagattt aaaaaatggc atattagttt caaagcagca gccatgaaat    9360
tgacagctga tgtctcaaca gcaagaatga aaagtggaag acaggccagg tgtggtggct    9420
caggcctgta atcccagcac tttgggaggc cgaggcgggt ggatcacgag gtcaggagac    9480
caagaccatc ctggctaaca tggtgaaacc ccgtctctac taaaaataca aaaaattag    9540
tcgggcatgg tggtgggtgc ctgtagtccc agctactcgg gaggctgagg caggagaatg    9600
gcgtgaaccc gggaggcgga gcttgcagtg agccgagatt gtgccactgc actccagcct    9660
gggtgacaga gcaagactct gtctcaaaaa aaaaaaaaa aaaaaaaaa aaagggtgac    9720
gaagcttcaa tctcctgaaa ggaagcaact gccgcctttg attcgatacc caccaaaatc    9780
cgtgaagaag gaaggcaaaa taaaacact tcctgattga actggaaaga tttccgcaat    9840
agaagaccca ctgtccaagg aattctaaag gatgctttcc aggcagaaga aaatgacccc    9900
agaggaagat cagagattca ggaaagaaat ggagagtgat aaaaatggaa aattcggggg    9960
ccaatttaaa caaagctga ctgctctaca actgttgtgt ctctatcttt tgtaacatat   10020
atgtgtgtgt agcttttttt tttttttttg tcaagatgga ttctcactct gtcgcccagg   10080
ctacagtgaa atggcacggt ctcggctcac tgcaacctct gccccttggg ctcaaatgat   10140
tctcttgcct cagcctcctg agtagctgag attacaggtg cctggcacaa tgcctggcta   10200
atttttgtat ttttactaga gatgggattt ctccatgttg gccaggctgg tcttgaacac   10260
ctgacctcag gtgatccacc tgcctgggcc tcccaaagtg ctaggattac aggcgcgagc   10320
cactgcatct ggcctatgtg tgtgtttata tggaattaaa acacatggca ataatacccct   10380
ccaaattggg agaaaccaaa aatagcattt aaatgttgta agctccctgc ataatcaaga   10440
agagaataga tttacgttag atttgatac ctggaggatg aatgttgtaa tttctagggt   10500
gaccatgaaa agaggagaca acggtgtatg ttttttttttt tttgagatgg agtctcactt   10560
```

```
tgtcacccag gctggagtgt tgtggtgtga tcttggctca ctgcaacctc ctcctcttgg    10620
gttcaggcca tcctcccacc taggcctcca gagtaggtgg gatcacaggc acctgccacc    10680
acacctggct aatttttttt tttttttaaa tatttagtag agatgggggtt tcaccatgtt    10740
ggccaggctg gtcttgaact cctgacctca ggcgatctgc ctacctctgc ctctcaaagt    10800
gctgggatta caggtgtgag ccatcgcgcc cggccaacag tgatcacttt caaactaaca    10860
gaggttcaaa ataaaatca gacttaacca aaaaccaggt aacagagctg gtaggatata    10920
cagaaagact gacctcacgt atatcaacga ttacagttaa tattaatgaa ggaaatgctc    10980
tagtttaaaa acgagggttg tcaaagaccc cacataagaa gctccttacc agcggtgcac    11040
ctagaaccta aggaaacagg acagatgaag gaggacgcgc ccccgccgct gtcctgcgcc    11100
tcagccatcc tatgagacgg gaaaggtttc tgtctgcagc tgggcccgtg ctctttacca    11160
gctcctggct ttcttctctg gaaggttcct gcctgttttg ccctcacacc tgctcctctc    11220
tcagccctct caggggtggg gctggaggcc accaaagagc ctcctctgct ctccagttgc    11280
tcgactgctc ctcatttccc cctggggtct gcgtcagggt ttccttcttt tccagcccca    11340
ccccgcgtgc atcccacctg gtctcgggtc ggggctgctc ccgcttactg cccccctgccc    11400
aggctggtgt gcacccccctc tggctgcttt caaggcctct tctctcttct cggcaggaca    11460
ggcacaggca ggtggccagg tgtcatgctt agctccccgc ccagtgagat tctttcattt    11520
aacaatcttc ccctgaatag ttcatgttca ttgctgaaaa tttgaaaaat atggaaaagc    11580
acaaagatta agatataaac cgccctcaat tcccctgccc agagagagtc actgctatga    11640
cttggtgact aggaacccta tttctctctc gctcttttt ttttttttga cacagagtct    11700
tgctctgtca cccaggctgg agtgcagtgg ctcgatctca gctcactgca acctccgcct    11760
cctgggttca agcgattctc ctgcctcagc ctcttgagta gctgggatta caggcacctg    11820
ccaccatgcc cggctaattt ttgtattttt agttgagaga gggtttcatc ttgttggtca    11880
ggcggacttg aactcctgac ctcaggtgat cagcccacct cggcctccca aagtgctggg    11940
attacaggtg tgagccactg cgccttcatc tctcttctgt gtatgtgtac gctgtttttt    12000
ctttagaatg ggggacgtta tcaggctcta catggtgtgt agtcggctag catgttgtaa    12060
gcctttccct gtgtcacaag tgctcatctg gaacaggatt ctaatgactg cctgtggcta    12120
tgttgggatt cctttaactc agctccttct gcccagcatc tatctttttt ccatcttttg    12180
tcctaagtgt tgctataata aatcattgat cacacatgcc tgactgtttg cataggataa    12240
attacgggaa atgttttttgc tgttcaggga ctgtgcccat ttttaggcct cagagacacc    12300
atgccagact gcccagtatt gatctttact cttttttagat gatgccaaac ttttctgtga    12360
actttaaaaa cctgtgtctt gacagtccat ttctgtaagt cttttcacatt agatttcctg    12420
tcaggatgat agtcaattct aggcagatga tgttttctca gccatggctg aagcagttgt    12480
gatttgttgt ggccatgtaa agtcccgatg atccattgcc tccctggatg ggttggaata    12540
atttggtttg ggagcatata acagaatgac ctggagtcac agcagctcag acggaagtgt    12600
atttctcccct tacagatgaa agaattccag gccaggctgg aatgacaact gcacacagtc    12660
atctgggccc cctccttcca gctcccatca ccccaggatg tggctttttat gcagatgatc    12720
caaaatggct gctcaagtcc cagccaacac atcccattcc agggagcagg aaaaaggtgt    12780
gtctttccct tcattttatg tgattccttt ctagaagtac tactcattac ttctgcttgc    12840
atctccctgg ctagcactta cttagttata tggccatagc tagctgaagg aaggacaggg    12900
actgtcatac actagctaag aggcaaactg cttagataaa aaggtctcta aagaaggtca    12960
```

```
gagcggctgc tagggtgcaa ctctattact tattgttatg ggacgaactg tgtccctcat  13020
tcaggttgat gtcctaagcc ccagaacctc agaatgggat tgtatttgga dacaggttct  13080
ttaaggaggt aaggaggcta aaatgagatc attagggtgg gccataatcc gactgatgtc  13140
ttacaagaag agattaggac acggacatgc tcagaggac ggccacgtga ggacaccaag  13200
aaaggcagct gtctgcaagt caaggacagg gctcagggga aaccaaccTT gccaacacct  13260
tcatctcgga cttctagcct ctaggaccat gagaagatac atttctgttg tttaagctgc  13320
ccggtctgtg gtactttgtt atggcagccc aagtaaacaa atacagtcat ctgctgctgg  13380
aacaaatcac cccagcactg tggcttggca gcacacatgt ctagtcatag agttatatgt  13440
agttacgtgt agagccatat gtatcgtcac acgttctgtg ggtcaggaat ttggacccag  13500
cttaaccagc tccacttctc gccagggttc agtcaaatac cagctgcctc ccacctgaga  13560
gctcagccgg ggaagggtcc ctttccaatc tcacgtggtg ttggcaggat ccagttcctc  13620
atggcctgct ggactgagaa cctcagttct cactgcctgt tggccagagg ccgcctttat  13680
gtcctcgcca tgtgggcctc tccaacatgg cagctgactt catcagagca tccatgccaa  13740
gaaggcaaca gagagggcca gggagactga agtcataccc ttttgcgacc tagtcatggg  13800
gtgacattcc atcacctttg cccattggtt agaagcaggc caccaggtac agcccaagct  13860
cacggggagg ggtcatacaa gggtgtcaat accaggaggt gaggggtgct ggggccatct  13920
tatgagtctg cccactgagg taactaacaa ccttgaggcc tgacacagtg gacaaaggcc  13980
cttattaaca gcagagaact gggaacttta tttatttatt tattttgag acagagtctc  14040 actcttgtca cccaggctgg agtgcaatgg catgatcttg gctcactgca acctccacct  14100
cccaggttca gcaattctg cctcagcctc cggaatagct gggactacag gcatgcacca  14160
ctacacccgg ctaattttg tattttagt agagacaggg tttcgccatg ttggccaggc  14220
tggtctcgaa ctcctgacct ctggtgatct gcctgcttg gcctcccaaa gtgctgggat  14280
tacaggcgtg agccaccgca cctcgctgga acttaatttt tttagagaca gtgtcgctct  14340
atcacccaag ctggagtgca gtggtgcaat cctagctcac ttgcagcctc aaattcctgg  14400
gttcaggtga tcctcccaca tcagcctccc aagaactggg aactaacagc tgtttctctg  14460
ctgtccttct caagaaaagg gaggctactg ctaccccact ggggacaatg ctgggtttcc  14520
ctttaggaca ggctctgaga caaggcgagg gtgctgtttg tggccacaga gcaggggact  14580
ctgggttgca ggtgtggcct ggctaaagta ggctttactg ggctcctctc tgcctgcatc  14640
accccccggc tgggcggttg tctctgaggc caaccttact ccctgctggg caggctggac  14700
agctgccctc tccgtttgcc cctctaccac ccaaaaggca ggaggctctg gagaccagga  14760
ccctgcccgc cacggcctgt gtcccaggcg tgaggggtg ccccacagac ctctgctgag  14820
ctgctgctga atgacgcccc ttgggggtcc tgccggaagg tcagagcagg ggtgcactcc  14880
cataaagaaa cgcccccagg tcgggactca ttcctgtggg cggcatcttg tggccatagc  14940
tgcttctcgc tgcactaatc acagtgcctc tgtgggcagc aggcgctgac cacccaggcc  15000
tgccccagac cctctcctcc cttccggggc gctgcgctgg gaccgatggg gggcgccagg  15060
cctgtggaca ccgccctgca ggggcctctc cagctcactg ggggtggggt gggggtcaca  15120
cttggggtcc tcaggtcgtg ccgaccacgc gcattctctg cgctctgcgc aggagctcgc  15180
ccaccctctc cccgtgcaga gagccccgca gctggctccc cgcagggctg tccgggtgag  15240
tatggctctg gccacgggcc agtgtggcgg gagggcaaac cccaaggcca cctcggctca  15300
```

```
gagtccacgg ccggctgtcg ccccgctcca ggcgtcggcg ggggatcctt tccgcatggg   15360
cctgcgcccg cgctcggcgc cccctccacg gccccgcccc gtccatggcc ccgtccttca   15420
tgggcgagcc cctccatggc cctgcccctc cgcgcccac  ccctccctcg ccccacctct   15480
caccttcctg ccccgccccc agcctcccca ccctcaccg  gccagtcccc tcccctatcc   15540
cgctccgccc ctcagccgcc ccgcccctca gccggcctgc ctaatgtccc cgtccccagc   15600
atcgccccgc cccgccccg  tctcgcccg  ccctcaggc  ggcctccctg ctgtgccccg   15660
ccccggcctc gccacgcccc tacctcacca cgccccccgc atcgccacgc ccccgcatc   15720 gccacgcctc ccttaccatg cagtcccgcc ccgtcccttc ctcgtcccgc ctcgccgcga   15780
cacttcacac acagcttcgc ctcaccccat tacagtctca ccacgccccg tccctctcc   15840 gttgagcccc cgcgccttcg ccgggtgggg cgctgcgctg tcagcggcct tgctgtgtga   15900
ggcagaacct gcggggggcag gggcgggctg gttccctggc cagccattgg cagagtccgc   15960
aggctagggc tgtcaatcat gctggccggc gtggccccgc ctccgccggc gcggccccgc   16020
ctccgccggc gcagcgtctg ggacgcaagg cgccgtgggg gctgccggga cgggtccaag   16080
atggacggcc gctcaggttc tgcttttacc tgcggcccag agccccattc attgccccgg   16140
tgctgagcgg cgccgcgagt cggcccgagg cctccgggga ctgccgtgcc gggcgggaga   16200
ccgccatggc gaccctggaa aagctgatga aggccttcga gtccctcaag tccttccagc   16260
agcagcagca gcagcagcag cagcagcagc agcagcagca gcagcagcag cagcaacagc   16320
cgccaccgcc gccgccgccg ccgccgcctc ctcagcttcc tcagccgccg ccgcaggcac   16380
agccgctgct gcctcagccg cagccgcccc cgccgccgcc ccgccgcca  ccggcccgg   16440 ctgtggctga ggagccgctg caccgaccgt gagtttgggc ccgctgcagc tccctgtccc   16500
ggcgggtccc aggctacggc ggggatggcg gtaaccctgc agcctgcggg ccggcgacac   16560
gaacccccgg ccccgcagag acagagtgac ccagcaaccc agagcccatg agggacaccc   16620 gcccctcct  ggggcgaggc cttcccccac ttcagccccg ctccctcact tgggtcttcc   16680
cttgtcctct cgcgagggga ggcagagcct tgttggggcc tgtcctgaat tcaccgaggg   16740
gagtcacggc ctcagccctc tcgcccttcg caggatgcga agagttgggg cgagaacttg   16800
tttcttttta tttgcgagaa accagggcgg gggttctttt aactgcgttg tgaagagaac   16860
ttggaggagc cgagatttgc tcagtgccac ttccctcttc tagtctgaga gggaagaggg   16920 ctggggcgc  gggacacttc gagaggaggc ggggtttgga gctggagaga tgtgggggca   16980
gtggatgaca taatgctttt aggacgcctc ggcgggagtg gcggggcagg ggggggcgg   17040 ggagtgaggg cgcgtccaat gggagatttc ttttcctagt ggcacttaaa acagcctgag   17100
atttgaggct cttcctacat tgtcaggaca tttcatttag ttcatgatca cggtggtagt   17160
aacacgattt taagcaccac ctaagagatc tgctcatcta agcctaagtt ggtctgcagg   17220
cgtttgaatg agttgtggtt gccaagtaaa gtggtgaact tacgtggtga ttaatgaaat   17280
tatcttaaat attaggaaga gttgattgaa gttttttgcc tatgtgtgtt gggaataaaa   17340
ccaacacgtt gctgatgggg aggttaattg ccgagggatg aatgaggtgt acattttacc   17400
agtattccag tcaggcttgc cagaatacgg ggggtccgca gactccgtgg gcatctcaga   17460
tgtgccagtg aaagggtttc tgtttgcttc attgctgaca gcttgttact ttttggaagc   17520
taggggtttc tgttgcttgt tcttggggag aattttgtaa acaggaaaag agagaccatt   17580
aaaacatcta gcggaacccc aggactttcc ctggaagtct gtgtgtcgag tgtacagtag   17640
gagttaggaa gtactctggt gcagttcagg cctttctctt acctctcagt attctatttc   17700
```

```
cgatctggat gtgtcccaga tggcatttgg taagaatatc tctgttaaga ctgattaatt   17760
tttagtaata tttcttgttc tttgtttctg ttatgatcct tgtctcgtct tcaaagttta   17820
attagaaaat gattcggaga gcagtgttag cttatttgtt ggaataaaat ttaggaataa   17880
attattctaa aggatggaaa aactttttgg atatttggag aaattttaaa acaatttggc   17940
ttatctcttc agtaagtaat ttctcatcca gaaatttact gtagtgcttt tctaggaggt   18000
aggtgtcata aaagttcaca cattgcatgt atcttgtgta aacactaaac agggctcctg   18060
atgggaagga agacctttct gctgggctgc ttcagacact tgatcattct aaaaatatgc   18120
cttctctttc ttatgctgat ttgacagaac ctgcatttgc ttatcttcaa aatatgggta   18180
tcaagaaatt tcctttgctg ccttgacaaa ggagatagat tttgtttcat tactttaagg   18240
taatatatga ttaccttatt taaaaaattt aatcaggact ggcaaggtgg cttacacctt   18300
taatccgagc actttgggag gcctaggtgg acgaatcacc tgaggtcagg agtttgagac   18360
cagcctggct aacatggtga aaccctgtct ctactaaaaa tacaaaaatt agctggtcat   18420
ggtggcacgt gcctgtaatc caagctacct gggaggctga ggcaggaaaa tcgcttgaac   18480 ccggaggca gagtctgcag tgagttgaga tcacgccact gcactccagc ctgggtgaca   18540
gagcgagact ctatctcaaa aaaaatttt tttaatgtat tattttgca taagtaatac   18600 attgacatga tacaaattct gtaattacaa aagggcaata attaaaatat cttccttcca   18660
cccctttcct ctgagtacct aactttgtcc ccaagaacaa gcactatttc agttcctcat   18720
gtatcctgcc agatataacc tgttcatatt gtaagataga tttaaaatgc tctaaaaaca   18780
aaagtagttt agaataatat atatctatat attttttgag atgtagtctc acattgtcac   18840
ccaggctgga gtgcagtgat acaatctcgg ctcactgcag tctctgcctc ccaggttcaa   18900
atgcttctcc tgcctcagcc ttctgagtag ctgggattac aggcgcccac caccatgtcc   18960
agctaatttt tgtatttta gtagagatgg ggtttcacca tgttggccag gctggtcttg   19020
aactcctgac cttgtgatct gtccacctcg gcctcccaaa gtgctgggat tacaggtgtg   19080
agccaccatg cctggctaga ataataactt ttaaaggttc ttagcatgct ctgaaatcaa   19140
ctgcattagg ttttatttata gttttatagt tatttttaaat aaaatgcata tttgtcatat   19200
ttctctgtat tttgctgttg agaaaggagg tattcactaa ttttgagtaa caaacactgc   19260
tcacaaagtt tggattttgg cagttctgtt cacgtgcttc agccaaaaaa tcctcttctc   19320
aaagtaagat tgatgaaagc aatttagaaa gtatctgttc tgtttttatg gctcttgctc   19380
tttggtgtgg aactgtggtg tcacgccatg catgggcctc agtttatgag tgtttgtgct   19440
ctgctcagca tacaggatgc aggagttcct tatgggctg gctgcaggct cagcaaatct   19500
agcatgcttg ggagggtcct cacagtaatt aggaggcaat taatacttgc ttctggcagt   19560
ttcttattct ccttcagatt cctatctggt gtttccctga ctttattcat tcatcagtaa   19620
atatttacta aacatgtact atgtgcctgg cactgttata ggtgcagggc tcagcagtga   19680
gcagacaaag ctctgccctc gtgaagcttt cattctaatg aaggacatag acagtaagca   19740
agatagataa gtaaaatata cagtacgtta atacgtggag gaacttcaaa gcagggaagg   19800 ggataggaa atgtcagggt taatcgagtg ttaacttatt tttattttta aaaaaattgt   19860
taagggcttt ccagcaaaac ccagaaagcc tgctagacaa attccaaaag agctgtagca   19920
ctaagtgttg acattttat tttattttgt tttgttttgt tttttttgag acagttcttg   19980
ctctatcagc caggctggag tgcactagtg tgatcttggc tcactgcaac ctctgcctct   20040
```

-continued

```
tgggttcaag tgattctcat gcctcagcct cctgtttagc tgggattata gacatgcact    20100
gccatgcctg ggtaattttt ttttttttccc ccgagacgga gtcttgctct gtcgcccagg   20160
ctggagtgca gtggcgcgat ctcagctcac tgcaagctcc gcttcccgag ttcacgccat    20220
tctcctgcct cagtctccca agtagctggg actacaggcg cctgccacca cgtccagcta    20280
atttttttgt attttttaata gagacggggt ttcaccgtgt tagccaggat gatcttgatc   20340
tcctgacctc gtcatccgcc gaccttgtga tccgcccacc tcggcctccc aaagtgctgg    20400
gattacaggc atgagccact gtcccggcc acgcctgggt aattttttgta ttttttagtag   20460 agatggggtt ttgccatgat gagcaggctg gtctcgaact cccggcctca tgtgatctgc    20520
ctgccttggc ctcccaaagt gctaggatta caggcatgag ccaccatacc tggccagtgt    20580
tgatatttta aatacggtgt tcagggaagg tccactgaga agacagcttt tttttttttt    20640
tttttggggg ttgggggca aggtcttgct ctttaaccca ggctggaatg cagtatcact     20700
atcgtagctc acttcagcct tgaactcctg ggctcaagtg atcctcccac ctcaacctca    20760
caatgtgttg ggactatagg tgtgagccat cacacctggc cagatgatgg cttttgagta    20820
aagacctcaa gcgagttaag agtctagtgt aagggtgtat gaagtagtgg tattccagat    20880
ggggggaaca ggtccaaaat cttcctgttt caggaatagc aaggatgtca ttttagttgg    20940
gtgaattgag tgaggggac atttgtagta agaagtaagg tccaagaggt caagggagtg     21000
ccatatcaga ccaatactac ttgccttgta gatggaataa agatattggc atttatgtga    21060
gtgagatggg atgtcactgg aggattagag cagaggagta gcatgatctg aatttcaatc    21120
ttaagtgaac tctggctgac aacagagtga aggggaacac cggcaaaagc agaaaccagt    21180
taggaagcca ctgcagtgct cagataagca tggtgggttc tgtcagggta ccggctgtcg    21240
gctgtgggca gtgtgaggaa tgactgactg gattttgaat gcggaaccaa ctgcacttgt    21300
tgaactctgc taagtataac aatttagcag tagcttgcgt tatcaggtttt gtattcagct   21360 gcaagtaaca gaaaatcctg ctgcaatagc ttaaactggt aacaagcaag agcttatcag    21420
aagacaaaaa taagtctggg gaaattcaac aataagttaa ggaacccagg ctctttcttt    21480
tttttttttt tgaaacggag tttcgctctt gtcacccggg ctggagtgca atgatgtgat    21540
ctcagctcac taaaacctct acctcctggg ttcaagtgat tcttctgcct cagcctccca    21600
agtaactggg attacaggcg tataccacca tgcccagcta attttgtgt tttagtaga     21660 gatggggttt caccatgttg gccaggctgg tctcgaactt ctgacctcag gtgatccact    21720
cgcctcagcc tgccaaagtg ctgggattac aggtttgggc cactgcaccc ggtcagaacc    21780
caggctcttt cttatactta ccttgcaaac ccttgttctc attttttccc tttgtatttt    21840
tattgttgaa ttgtaatagt tctttatata ttctggatac tggattctta tcagatagat    21900
gatttgtaaa aactctccct tcctttggat tgtcttttta ctttcttgat agtgtcttttt   21960 gaagtgtaaa agttttttaat tttgatgaag tcgagtttat ctattttgtc tttggttgct   22020
gtgcttcaag tgtcatatct aagaaatcat tgtctaatcc aaagtcaaaa aggtttactc    22080
ctatgttttc ttctaagaat tttagagtttt tacatttaag tctgatccat tttgagttaa   22140
tttttatata tggttcaggt agaagtccaa ctttattctt ttccatgtgg ttattcagtt    22200
gtcccagcac tgtttgttga agagactatt cttttcccat ggaattatct tagtaccctt    22260
gttgaaaatt aatcgtccctt aattgtataa atttatttct agactgtcag ttctacctgt   22320
tggtctttat gtcgatcctg tgccagtacc atacagtctt gattactgaa gtttgtgtca    22380
cagtttaaat tcatgaaatg tgagttctcc aactttgttc cttttcaaga ttgatttggc    22440
```

```
catgctgggt cccttgcatt tccgtacgaa ttgtaggatc agcttgtcag tttcaacaaa   22500
gaagccaagt aggattctga gagggattgt gttgaatctg tagatcaact tggggagtat   22560
tcgcatctta acaatattgt cttccaccta tgaacatggg caaactttgt gtaaatggtc   22620
agattgtaag tatttcgggc tgtgtgggca cagtgtctct gtcacagcta cgcggctctg   22680
ccattgtagc atgaaagtag ccataagcaa tatgtatgag tgtctgtgtt ccaatagaat   22740
tttattaatg acaaggaagt ttgaatttca tataattttc acctgtcatg agatagtatt   22800
tgattatttt ggtcaaccat ttaaaaatgt aaaaacattt cttagcttgt gaactagcca   22860
aaaatatgca ggttatagtt ttcccactcc taggttaaaa tatgatagga ccacatttgg   22920
aaagcatttc tttttttttt tttttttttt tttttgagac ggagtttcac tcttgttgcc   22980
caggctggag tgcagtggcg cgatctcggc tcactgcaac ctctgcctcc caggttcaag   23040
acattctcct gcacggcctc cctagtagct gggattacag gcatgcgcca ccacacccag   23100
ctaattttgt attttagta gagacggggg ttctccatgt tggtcaggct ggtcttgaac   23160
tcctgacctc aggtgatcca cccgcctcag cctcccaaag tgctgggatt acagggtgtg   23220
agccaccaca ccctgctgga aagcatttct tttttggctg ttttttgtttt ttttttaaac   23280 tagttttgaa aattataaaa gttacacata tacattataa aaatatcttc aagcagcaca   23340
gatgaaaaac aaagcccttc ttgcaagtct gtcatctttg tctaacttcc taagaacaaa   23400
agtgtttctt gtgtcttctt cccagatttt aatatgcata tacaagcatt taaatgtgtc   23460 atttttttgtt tgcttgactg agatcacatt acatatgtat ttttttactt aacaatgtgt   23520
catagatatt gttccatagc agtacctgta attcttatta attgctatgt aatatttag    23580 aattctttt taaagagga cttttggaga tgtaaaggca aaggtctcac attttttgtgg   23640 ctgtagaatg tgctggtgac atattctctc taccttgaga agtccccatc cccatcacct   23700
ccatttcctg taaataagtc aaccacttga taaactacct ttgaatggat ccacactcaa   23760
aacatttagt cttattcaga caacaaggag gaaaaataaa ataccttata aagcactgtt   23820
taatattgta ttaaattgga tcaatttggg ggctagaatg tatgttagag acatgatatg   23880
tccataggtc cttgctatca cagtgaggtc tcagggacac tcgtttggta tcatttggga   23940
tctcataagc agactctctc tgcttgacct gacaaatcag agtctgtgtt ttaacaggtt   24000
cagtgagtga cttacatgca cattggagtt tgggaagctc cactgtaggt gcttagacct   24060
tacctttgtt gttgctaata acaatgcaag catttgggag gaagacctgt gttgctcata   24120
tgtgtccagg tgtagctgag gtggccttgc ttatctgctg tagggccgtt gagcatttct   24180
gtagctgtga tgagtgagct gaggtgagcc tgcggagagc tcccagccat tggtagtggg   24240
actcgcttag atgaactgga aggaccctt catctgagca gccactatgg agaaaaacaa   24300
ccgaatgagg ggagagacaa tgtgcaattt tatttagggc acaaaggaga gctgtggtta   24360
gaaggtgaca tttgagtgga aaggggggcaa gccatgtgta tagcgggaga agagaggtcc   24420
aggcagagtt aacagaaggc agaaatgctt tccatgtttg agaaccagta aggaggccag   24480
tggctgaagt aaggtgaagg gcagaaataa ggatgaggct gcgagagatg agaggttaga   24540
gacgagcgtc ttgtgcacca agataagctt gtgtggtcaa acaagtagt ttaatttatg    24600 tttttaaaag atcatttgg ctgggcacaa tggttcatgc ctgtaatacc agtagtttga    24660
gacggtgtgg tgggaggatt gcctgaggcc agacgaccag catagccaac atagcagcac   24720
ctataaggtc tctacaaaaa actttaaaaa attagctggg catagtggtg tgtgcctgta   24780
```

```
gtcccagcta ctcaggaggc tgaggaggct ggaggattgc ttgagtccag gagtttgagg    24840
ctgcagtgag ctatgattat gccactacac tacaacctgg gcaagagagt gagaccctgt    24900
ctctaaatat acacacacac acacacacac acacacacac acacacacac acacacacac    24960
acacacatat atatgtatat atatgcattt agatgaaaag atcactttga caataccaca    25020
tgctggtgag gatttagaaa aactaggtca cttattgctg gtgggaatat aatatagtac    25080
ggccactctg gaaaacagtt tggcagtttg tcataaaact gaacataccg ttagtataca    25140
gcccagcagc aactacaatc ctgggcatta atcctagaga aatgaaacct taatgttcac    25200
ataaaaacct atactcaagt atgcatagca gctttaccca taatatctaa gaactggaat    25260
cagctcagat gtccttcaac aggtgaatgg ttaaactact cagtaataaa aaggaatgag    25320
ctactgatag catgcaacag tttaggtgaa gttatgctaa tgaaaaaagc caatcccaaa    25380
aggttataca tactgtatga ttctatgttt ttttgcaatg gcacagtttt agggatggag    25440
aatagattag tggttgcctg gggttagaga tggggtagta gagtaggtta gtggtggcag    25500
aggagagaaa agagagggag gtgaatgtgg ttataaaagg acaacacagg gaatacttg     25560 taatggaaat gctttgtctt ttttttttt ttttttttt tggcgacaga gtcttgctct     25620
gttgcccagg ctggagtgca gtggcatgat cttttctcac tgcaacctct gcctcctggg    25680
ttcaagtgat acttgtgtct cagtctccca tgttcagagt gaaacaaacc agaggtaatg    25740
ttcatccaaa taatccaaca cacatgacat taaaacatca agatcaggtc ggacgtggtg    25800
gctcatgcct gtaatcccag cacttttggg aggccaaggt gggcagatca cttgaggtca    25860
ggagttcgag accagccggg ccaacatgat gaaacccat cttgactaaa aatacaaaaa     25920
ttagccgggc atggtggtgt gcacctgtag tcccagctac ttgggaggct gaggcaagag    25980
aactgcttga acccgagggg cagaggttgc agtgagctga gagtgcgcca ttgcacttca    26040
gcctgtgtga cagagtaaga ctccatctcc aaaaaaaaaa aaccaagatc aattaaaata    26100
cagcattact gggccgggtg tggtggctca cacctgtaat cccagcactt tgggaggccg    26160
agatgggcag atcacgaggt caggagatcc agaccatccc ggctaacacg gtgaaacccc    26220
gtctctacta aaaatacaa aaaattagcc gggtatagtg gtgggtgcct gtagtcccag     26280
ctacttggga ggctgaagca ggagaatggt gtgaacccgg gaggcagagc tggcagtgag    26340
ctgagatcgc gccactgcac tccagcctgg gcgacagagc aagactccgt ctcggggaa     26400 aaaaaaaat aaataaatag aatgctgtag tgtccttgag tttacatgcc cctccttacg     26460
cttgtgtgcc cgtgcagatt gcttgattac acaattagag gaggctggcg gaggattgtt    26520
ttaatttttt ttttttgag acagtctggc tctgttcccc aggctagagt gcaatggcgc    26580
aatcttggtg cactgcaacc tctgcctcct gggttcaagc agttcttctg ccgcagcctc    26640
ccgagtagct gggattatag gcgcccgcca ccacgcccaa ctattttttg tattttagt     26700 agagcagcgt ttcaccatgc tggccaggct ggtctcgaac tcctgacctc agatgatctg    26760 ctgcccagc ctcccaaagt gctgggatta caggcgtgag ccacacctgg ccgtttgttt     26820
taattttgaa ggtgaagtga aagtgactac atttaccaaa agtgattgaa aagccaggac    26880
tgttcttacc ctgttttcc agttcttgct cagagcaagg tggtttcttt ttcacttaat     26940
caccatactt actttcatg tagaacaagt cagtttgagt tatcagttca tcatcttaac     27000
taaattccat gggggaagga attagtttta gtttcttaaa cttccaggtt tgcttattgg    27060
acaaaatgag atagcaaggc agtgttttta agttagattt tttatttctt tggtaataca    27120
attttctcag aaacttagta gtctttttagt ttagttgttt ttagttggtc ctatgttttg    27180
```

```
gatcacccct ctctacttta ttttgatagt gccaactgtg aagacatctg aagccatagg   27240
tttggatggg aaggaggcat ctttagcctg atcatcttcg ccaggctgtt tatctccttt   27300
tgcttggctg agaagtctta ataggaggct tattcccagc tatttgggga catagaagca   27360
gttagccatt gcttatattt tactgaggtc tgtgtggtat gttgattgta gtcagttaac   27420
gattttgaga actgaaggca gcctggtata tatagagtag gtattagact gtgtttcttc   27480
taattgaatt tcccatctct tgtaatctat gccatcatct tctgtactgc tgagaaagaa   27540
agaaagtttc taatcaaact ataccactgg ttgtaagatg cagtttggct ttagtgatgt   27600
taacacatga ttcaaacgtg aaattgattg agtattggtg aaatacagag gagatttaaa   27660
gccagaagac ctgggtttaa atgctggctg tatgacttca tatctgtgtg atctttgggca  27720
tgtcatggtt ggcacttcaa tttcttctct ctataatggg ggaagtgagg ccagtcatgg   27780
tggctcatac ctataatccc agtgctttgg gaggccaaga tgggaagatc gcttgaggcc   27840
aggagtttga gcaattgggc aacatcgtga ggccccgtct ctacaaaata ttttgaaaaa   27900
attagccagg cccagtggtg cgtgcctgtg gtccgcgcca ctcaggaggc tgagacggga   27960
ggatcctttc agcctaggag tttaaggcta aagtgagcca tgattgtgct atcgtactcc   28020
agcctgggca gcagagcaag atcctgactc taaaaaaaag taaaataaag taaaatgggg   28080
gaaatgaact gctttagtaa catcatctgt ttttctgtg agcagcgtag cttgacagcc    28140
attggtgaac tcgtgccctg tgcttccctg tccagatccc cattctgccc gcaacatgga   28200
gtataacggt ttattcatag tagtcgagaa acactcactg aatgaatgaa tgaggtgtag   28260
aactaagtgg agtgggtaat tcaacacata ttaatttcct tcttttttt attttagaa     28320
agaaagaact ttcagctacc aagaaagacc gtgtgaatca ttgtctgaca atatgtgaaa   28380
acatagtggc acagtctgtc aggtaattgc actttgaact gtctagagaa aataagaact   28440
ttgtatattt tcagtcttaa tgggctagaa tattctttgt gtcccagcta ttttaaatgg   28500
attcagaaat ccatttaaga tgaagaagga cccttttccc atatttctgg ctatatacaa   28560
ggatatccag acactgaaat gaataatgtt cccttttgt aatctttat gcaaaaatta     28620
aaaccattat ggtaattgaa caacatgttt atgtttagtt aacaccctta gcaactatag   28680
ttatttaaa accatctatg gtttgatatt tttgcatttg ttgcaatagt aggaacagca    28740
caagacagtt cagtttgtct ctcttatttg cttttcttg gcagtttgct gtcctattgt    28800
acctctgctc ctagcagtgg ctggagccca ctcctctgtg cttcgggatt agtggggatc   28860
gtggggcatt gactgtaggt cagcttcct tgcttgatct ttctcactgg gatgaactag    28920
cagcaccttc ttttgtagct gctttgcttt tgactatctt tctgaccgtt gttcctagta   28980
gctgtagatg gtaaatatat ttaggcctgt ttccaatggc tcagtaggag acatattcac   29040
ctatgatatc tgaattctgt tacccacatg ggcatgcgtg aaatagttgc cttgccttac   29100
tttcccttgg aataaataat tcatgttatt ctcctggtag aagctagaaa aagccttat    29160
agtcagtcag aaaaaaattt ttagacaaat aatcttgatt ttagtactga caaaaacgtg   29220
tggtgattct ttttttaatt tttttttgag acggagtttc actcttgttg cccaggctgg   29280
agtgcaatgc cgtgatctcg gctcactgca acctctgcct cctgggttca agtgattctc   29340
ctgcctcagc ctcccaagta gctggagtta caggcatgtg ctactgtgcc cagctaattt   29400
tgtatttta gtagagatgt tggtcaggct gatctcgaac tcccaacctt aggtgatctg    29460
cccgcctcag cctcccaaag tgctgggatt acaggcgtga gccagggcgc ccggtgattc   29520
```

```
atttgttttt tcaaaaaatt tcctcttggc cattgctttt cacttttgtt tttttttttt    29580
ttttgagacg gagtcacgat ctgtcaccca ggctggagtg cagtggcatg atcttggctt    29640
actgcaagct ctgcctccca ggttcacgcc attctcctgc ttcagcctgg cgagtagctg    29700
ggactacagg tgctcgccac cacacccggc taatttttg tattttagt agagatgggg      29760 tttcaccgtg gtcttgatct cctgacctca tgacccgctc aactcagcct cccaaagtgc    29820
tgggattaca ggcgtgagcc accgcgcccg gccctctctt gtcttttat tgtggtaaaa     29880 tgcacataaa attgactgtc ttaaccattt ttaggggtac agttcagtat atatattcgt    29940
aatgttgtac agccatcact gccatctact tcataagttt ttcttctgtc aaaactgaac    30000
atctgtcttc attaaactcc ctatcatcca ttctttcctg tagtcccttt ctactttctg    30060
tctgtatgag tgtaactgct ctggagacct catgtaagtg gattcctaca ggatttgtgt    30120
tttttttttg gtgatctgct tattttaat gcctctgtgc atttgtatta tatactttca     30180
aagtgatttc acaaaaccgt ttcattttag gttaactcat ttctgttgtt tgtgaaatac    30240
tgtgtatgat tctgttctgt ttctgtctaa tttgtgaaaa tgttgtggga agaaaatgaa    30300
ataacaaatg agcatatgtc ctgaaaataa aaatatataaaa attctaagtt agcatgctat  30360
tgtagaatac aacgctatga taaaagtagg aaaaaaaaag gtttgaattc tatctctgct    30420
acctgtgtaa gctgggtgac tttagataag ctgtaacgtg tttgagcctt actggctcat    30480
ttttgaaatg taatccctag ttacacagtt cttgtgggat cagatggtac atgtgaaaca    30540
ctgtgaaaaa gcaactgcat agatatgttc attagccacc tgagcgggaa gcgtatccca    30600
ttgcgatgcc catcatccaa agctatatgt tatctttact ttttttttt tgagacagag     30660 tcttgctctg ttgcccaggc tagagtgcag tggtgcaatc tcagctcact gcaagctcca    30720
cctcccgggt tcacgctatt ctcctgcccc agcctcccaa gtagctggga ctacaggcac    30780
ccgccaccat gcctggctaa attttgtat ttttagtaga gatggggttt caccgtgtta     30840
gccaggatgg tcttgatctc ctgacctcgt gatccgcccg cctcggcctc ccaaagtgct    30900
gggattacag gcgtgagcca ctgcccctgg ccatctttac tttttttgtg aaatgacttt    30960
aaatacttgg caaacatttg gtcattgttc atctgatctc caccatccag gtctcagaga    31020
acataatttc tctctgaaag cttattgacc caggaaataa gatctctttc aatctgagtg    31080
cgtcaggctt tattcttgtc atttttgtctt tgataatttt tcaaatggaa ttcatggaat   31140
gttggcttat attcatatat tagtaaagta tgttgagaca tcttaagatt gatttgtggt    31200
tctatatgcc atattaaatc aaaataatag ctgttaatgg ttttcacatt agtctgtctc    31260
ttgtttttat ggagtaatgc tgagagttca ttatgcttgt tctacagaag agcatgttaa    31320
aaggagtttt tggagtcaga gaggttattc ttggtttcat aggatacact ctatactttt    31380
tagggatttc agagtatata gctgaaggtg atattttatg taaatatgtt ttatggaaac    31440
ttattgctca tcgctgtttc ctgttaactc tcctaaaata taattaaaact tttgaaactt   31500 ttttatagct tttgtgctag actaattttt gtctctaatg aggttatata aatggcagct    31560
tctgacgttt tcaatgtagg aagtcattta aaacttcatg tatattgtga aaatgtagtc    31620
tgctttaagc tctctaaagt ggtctaagtt actggttcct aagtatggat gagcatcaaa    31680
atcatctgga aaatttgtta aaaatacagt aatgaaggca cctcactgtc cttttccca    31740 aacatacttc tgcattctgt ttgagtaggt agggactaca cattttttcac aagtatcctc    31800 ttgggaatac ccaggaatgc ttacttgagc aacctcttac taatatgtac cttgataagg   31860
tggctaggta aacataaata tacaaaaatc catagatctc ccatatatta gcataaatca    31920
```

```
gctagaaaat ataacgttta aagatctagt tcacagtagc accaatatat cgaactctaa    31980
ggaatcgata aatatgcaaa aactttataa aaacttctgt taatgtttct gaaagatata    32040
ggtgaccact ttctagatag gaagatttta tattactaag ttgaattttc tctaaattaa    32100
cacagaaatt taaaataatc ttgatcaaaa ttctagtaga ggtatttttg aacttgttca    32160
ctgcaagaat aaatacataa ttgcaaagaa tatctcaaaa tcatcaccag gcctggtgtg    32220
gtggcccatg cctgtaatcc cagcactttg ggaggctgag gcaggcagat cacctgaggt    32280
caagagtttg agaccagctg gaccagtgcg gtgaaacact gcctctacta aaaatacaaa    32340
aattagctgg gtgtggtggt gcatgcctgt agtcccagct acttgggagg ctgaggcagg    32400
agaattgctt gaacccagga ggtacaggtt gcggtgagcc tagatcgcac cactgcattc    32460
cagcctgggc gacaagagca aaattctgtc tcaagaaaaa agagaaaaaa gaaaagaaa    32520 tcaacactaa tatggtgaga cttaatgtat gtgacattaa aatagtgatt ggatgttaaa    32580
acaggtatag aacagaaaga agagtgtatg tgtgtatctg tatgaattta tgatgggtgt    32640
aacatatatg tattagggaa atgagggaaa tgatacattt ctctgacttt gggagaacat    32700
tatatctcta cctcatattg caaacaaaca taaagttcag attaattacc taaatgtgaa    32760
aaaatgaaat aatttcttta aaaaatgtaa tcttagtttg aggaaggtta acattataaa    32820
ggaaaaaact gttttgagtg gaatatagtt caatatgtca aaatccacct tcaacaaaat    32880
tgaaagtaaa ttgaacttgg ggaaagtatt gacagcatat agatcaaagg ttactagcct    32940
gtgtaaagag cagttataaa tatcgttaag aaaaacactg tcgacctgtc ggcaccttgt    33000
tctccgactc ccagcctcca gaactgtgac gagtaagtgc ttattgttta aaccacccag    33060
tctgtatgtg gtattttgtt atagaaactc aagctgatta ggacactagt aatcagtaga    33120
ctgaaactga aacaaaaata agaacctttt ttacctgtca aattggcaaa cattaagaat    33180
attcagattt ttgtcagagg tgatacaacc ttctaagaag gcaatttggg aaaatataaa    33240
gctttagatt attatatgtc tgacctagca gttttacctc tagggtgctt accctagga    33300 aagtgtgtaa tgatattggt gcagtgccct tcatcccatt agaaaattaa aaataacctt    33360
aatggcctac cactaaaagg ggattgaaaa tttaagatat atttatttat gtgtttattg    33420
agatggagtc ttgcactgtc cgcctgggcc agagtgcaat ggtgcgatct cggctcactg    33480
caacctctgc ttcccgggtt catgtgattc tcctgcctca gcctcctgag tagctgggat    33540
tacaggctca caccaccgca cccggctaat ttttttgtatt tttagtagag atggggtttc    33600
actgtgttgg ccagactggt ctcgaactcc tgacctcatg atccgcgccc ctcggcctcc    33660
cagtgttggg attacaggtg tgagccactg cgcctggcca gatacattta tacaagagaa    33720
tgttagttaa cattcataga tatttatatt ttgtttactt tttattaaaa aaattttttt    33780
tagagacagg atcttactct gtcacccagg caggatgcag ttgcacaatc atagcccact    33840
gcagcctgaa ctcctgggct taagtgatcc ttctgcctca gccttttgag tacctggggg    33900
actttaggca gtgctactat acctggctaa ttttttaaatg ttttatagat gagatcttgc    33960
tgtattgccc aggctggtct agaattcctg ggcccaagtg atcctcccac cttggcctcc    34020
caaagcgctg agattacagg catgagccac cacttctgac caatagatat ttatatttgt    34080
gactggaaaa tatattaaca atgtgttaaa aaattcagtt aaaaaataat gaaagatttt    34140
tgcttctggc taagatagaa taacaaggac agcatttatc ttcttgcctt gaaatagttg    34200
aaaacggaag aaatatatgt aacagtggtt ttcaagttat tgggcatcag gcaaagaaga    34260
```

```
atagttatcc caggaaaatg aatgtggaga gccctacaat ttccttacat tactgcctgg    34320
tcatggcaag aggaaaaact gagaggagac tgaggctgag ccagtggttt gctgggttga    34380
ggaggcagag ctgggagtgc agagatgcaa ggtggtgaga gcccatatgg aagaatacca    34440
gggaagagag ctgcagaggg agctccggag acctgcaccc tgccctctca gtaccctgtc    34500
atgtgtgtag ctgagtactg acgagcactt gcttgtgcgg aaatgaccca gggctggagg    34560
tagagccacc tgaaaggatt agaaggaaca gttgctgaaa gtcacacagg gccaggaaga    34620
atttctaatc acaccagttg gagtggaaaa cctcagctct catagagcag gtagggtact    34680
cagaagggtt tgcccaccta gccccagact aagtttcgtt actctgaccc tacctaatat    34740
taaaaagaga ttaattaaat tgttcgcaac aaaaataata tatttcagtg tttgtaacac    34800
gtagaagtga attgtatgac aatagcataa aggctggaag agcagaaatt gacatgtatt    34860
tgcgctgggc agaataatgc tcccctcttt ccccaaaaga tatcaagtcc taatccctgg    34920
agcctgtaaa tattacttta tatggaaaat tgttttatga tgtgattaaa ttcaggatct    34980
tgagatgagg gggctatctt ggatgatctg gtaggcact aaatgcaatc acatatatat     35040
aaaaaggagg cagagggaga ttttacacac agagagaagg ccctgtgaag atggaacaga    35100
aagatttgaa ggtgctggcc ttgaaaattg gagtgatgaa gctataagcc aaggaatgca    35160
gcagccacca aagctggaag aggcacggag cagttctcat ttagagccta ctccagaggg    35220
aatgtggtgc tgccaattcc tttttttttt ttttttttaa gatatcattt ccccttttaa    35280
gttggttttt tttttttttt ttttttttta gtatttattg atcattcttg ggtgtttctt    35340 ggagagggggg atttggcagg gtcataggac aatagtggag ggaaggtcag cagataaaca   35400
tgtaaacaaa ggtctctggt tttcctaggc agagggccct gccacgttct gcagtgtttg    35460
tgtccctggg tacttgagat tagggagtgg tgatgactct taacgagtat gctgccttca    35520
agcatctgtt taacaaagca catcttgcac cgcccttaat ccatttaacc cttagtggac    35580
acagcacatg tttcagagag cacggggttg ggggtaaggt tatagattaa cagcatccca    35640
aggcagaaga attttctta gtacagaaca aaatggagtg tcctatgtct acttcttttct    35700 acgcagacac agtaacaatc tgatctctct ttcttttccc acatttcctc cttttctatt    35760
cgacaaaact gccaccgtca tcatggactg ttctcaatga gctattgggt acacctccca    35820
gatggggtgg cggccgggca gaggggctcc tcacttccca gatggggcgg ccgggcagag    35880
gcgcccccca acctcccaga cggggcggcg gctgggcggg ggctgccccc cacctcccgg    35940
acggggcggg tggccgggcg ggggctgccc accacctccc ggacggggcg gctgccgggc    36000
cgggggctgc cccccacctc ccggacgggg cgggtggccg gcgggggct gcccccacc     36060 tcccggacgg ggcggctggc cgggcggggg ctgccccccca cctcccggac ggagcggctg    36120
ccgggcggag gggctcctca cttcccggac ggggcggctg ctgggcggag gggctcctca    36180
cttctcagac ggggcggctg gtcagagacg ctcctcacct cccagacggg gtggcagtgg    36240
ggcagagaca ttcttaagtt cccagacgga gtcacgccg gcagaggtg ctcttcacat      36300 ctcagacggg gcggcgggc agaggtgctc cccacttccc agacgatggg cggccgggca     36360
gagatgctcc tcacttccta gatgggatga cagccgggaa gaggcgctcc tcacttccca    36420
gactgggcag ccaggcagag gggctcctca catcccagac gatgggcggc caggcagaaa    36480
cgctcctcac ttcctagacg gggtggcggc tgggcagagg ccgcaatctt ggcactttgg    36540
gaggccaagg caggcggctg ggaggtgaag gttgtagtga cccgagatca cgccactgca    36600
ctccagcctg ggcaacactg agcactgagt gagcgagact ccgtctgcaa tcccggcacc    36660
```

```
tcgggaggcc gaggctggca gatcacttgc agtcaggagc tggagaccag cccggccaac    36720
acggcgaaac cccgtctcca ccaaaaaaca cgaaaaccag tcagacatgg cggtgcgtgc    36780
ctgcaatccc aggcacttgg caggctgagg caggagaatc aggtagggag gttgcagtga    36840
gtagagatgg tggcagtaca gtccagcctt ggctcggcat cagagggaga ctgtgcgagg    36900
gcgagggcga gggcgaggga attccttaat ttcagtttag tgatactaat tttggactct    36960
ggcctctaaa actgtgaaag aaaaaatttt ttgtttgttt gtttctttta agccacatag    37020
tttgtggtaa tttgttacag cagctgcagg aaactaattt atgctgcatg tgaaatggtg    37080
taataaggta gattgtgatg aagatacata gtataaacaa ttaagcaaca actaaaagca    37140
caacaaggaa ttatagctaa tgaaccaaaa aaggagatta gaataataaa aatggtgaat    37200
cccaaagaag ccagaaatag gggaagaggc aaataaagga agaaagagc ttgatggtag    37260
atttcaacct aactatgtca aaaggacat tacatgtaaa aggcagcgat ttttcagatt    37320
gaatggaaaa gtaagactcg gtatatgctg ctgcctgcaa gaaacacatt ctaaatataa    37380
aggcaaaaat aacctacagg taacagaacg gaaagaagtt cactgtgctt acaagaatta    37440
gatgcaagct agactggttc tgttaatatc agacaaagtg gatttcaaag caaaggctct    37500
tgcccaggat gagatggtca tttcataatg atgaagggga ttcgttcatc agcctggcat    37560
agcaagctga aatgtttatg caccggacta cagagctaaa atacatgaag caaagcctga    37620
cagaactaca agtagaaaca gacaaatcca cagtgataga gatttcagta gccgctctca    37680
atgatttgta gaacacgtag ccataatatc tggatctaga acacttgacc aacactgtcc    37740
cctgtgcaac ctcattggca tttacaggac actccaccca gcaccagcag aagagacact    37800
ctctcaagtg ctcacagaat gtttgccaag atagagcaga tgctgggcca taaacaagt    37860
ctctaaatta aaagcattca aattattcag agtatgtttt ctgacctcag tatcattaag    37920
ttggaatata ttataggaag ataacctgga aaagcctcag atatgtggaa aaacccattt    37980
ccacatggcc catgggtcag aagtgaagtc aaaagggaaa tttgaaagtc ttttggattg    38040
actgatataa aaacaataga tttctaaact tgtggggtgc tgttacagca tagtaaatgg    38100
aaatttctag cattaaatgc ctgttttagg aaagaaagat ttcaaatcaa tgacctcagc    38160
ttctacctttt ggaaacttga aaatgacaag caaatggaat ccagagttac cagaagggcc    38220
aggtacggtg gcttatgcct gcagttctgc cactttggga ggccgaggca ggtggattgt    38280
ttgagactgg cagttgaaga ccagcctggg cagcctaggg agaccccata tctacaaaaa    38340
acaaaaaaat tagccaggtg tggtggcatg tgcctgtagt cccagctaac caggagtcta    38400
aggtgggagg attgcttgag tctgggaggt tgaggctgca gtgaactgtg attgtgccac    38460
tgtgttccat cctgggcaac agaatgagac cctgtctcaa aaacaaaaac agttactaga    38520
agaatggaca tcataaagat aggagcagaa gtcagtaaaa tagaaaacaa aaatacatag    38580
gaaatcaata aaaccaaaag ctggttcatc aagaacatca ataaattggt aaagctgata    38640
ggaaaaacag tgaagtcaca aattagcaat atcaggaatg agggagatga cagtagtata    38700
gattatatag atattaaaag gactgtatga ggcaggtgtg gtggttcacg cctgtaatcc    38760
cagcaccttg ggaggccgag gtggacagat cacctgaggt caggagtttg gaccagcct    38820
ggccaacatg gtgaaactct gtctctacta aaaatacaaa aattagttgg tcgtggtgct    38880
gtgtgcctgt aatcccagct acttgggagg ctgaggcagg agaattgctt gaacctggga    38940
ggcggaggtt gcagtgagct gagattgtgc cgttgcactc cagcctgggt gacagagcaa    39000
```

-continued

```
gactccatct caaaacaaat aaataaataa aaaggactat atggtaatat tatgaacaac    39060
tttatgccaa taaatttgac aacttataga tgaaatggat gagttccttg aaagacacag    39120
aaactattaa agctctctca agaagatata gataagctga ttagccctat atctatttta    39180
ttgaatttaa atgtaaaaat caatatttag ttactggaaa acttttaagt gtggttggaa    39240
atggtatacg aacttttca actgaatttt atgaagtcta atcacaggta aaggttttct    39300
gatgaaaatt tagtgtctga attgagatat actgtaaaaa atgttatata tcttaattat    39360
ttcttcacat taattacatg ttgaaataat actttgggtg tattgggtta aattaaatat    39420
tatgaaaatc ttgcctgttt tcttttact tttgatgcgt cagctaggaa atataaaagt    39480
gtagctcaca ttctgtttct gttgacagta ctgctttgga gcacagtgtt tgaatgatct    39540
atcatttcaa agacctttcc tcagttcgtt attcatggct gtctgtattc cacatagata    39600
aggtctgaaa tactgctaag tggcatgttt tgttttatgc ttttataagt ttgttgatca    39660
ttactgatgt ggacttttgg tgcctcttag gctcattgct atcttccaac cattgtttgc    39720 aattttacc tagagataaa gagaaagaga catttggttt cagagtagtt agattgggat    39780
catgaaagag caacctcatt ttgatgcttc aaaaatagca catccccgt attactggga    39840 tttgctattc ttgggattac ttcaagaaca tccttgtgtt actggtttgg atgcttctga    39900
atgctgtgaa gtcagtttca tgtacatggc tcatcagttt agctctctct tggctttgtt    39960
tagacagttg gagcatgatg gcctaaacag cttctttcaa ttaaacattt taaaatagtt    40020
tacaaatagt aaacaaactc cagttttgt gactctttgt ctcgcacaac aaaaacacaa    40080
tctgaccatg atcatctggc atcttagggt gaaatatggt tatactttgg cccataccga    40140
aagcaagatt aaaagggc aggagagata gactgctgaa ctgattttca aggttccaag    40200
aatattgtag gttaagagta aaagtaaact tttggtagaa agcagtgggt tgtctaggat    40260
tgaagtatct gaagtttta aacgaaaatt taaaagaaa aatgagaatt gccttacaag    40320
tacaatctct tcttttttaa aaaataaact ttattttgaa atagttttag atttatagaa    40380
aaaaattaga tagggtagga agttttcata taccctacat ccagttaccc cagttattat    40440
catcctaatt tagtgtgaga cattttcatg tttaatgaat caatattgat atgctattaa    40500
cttaagtcca gactttattc agattttctt aatttctatg taatgtcctt tttctgttcc    40560
agaattccat gcaggacacc ggatacctca ttacatttca ttgtcatgtc accttaggct    40620
cctcttgaca gtttctcttc ttttttttgct tagaaattct ccagaatttc agaaacttct    40680
gggcatcgct atggaacttt ttctgctgtg cagtgatgac gcagagtcag atgtcaggat    40740
ggtggctgac gaatgcctca acaaagttat caaagtaaga accgtgtgga tgatgttctc    40800
ctcagagcta tcattgttgt aggctgagag aagaagcgat cattgagtgt tcttctgttt    40860
tgagtccctg aggatgtctg cactttttc ctttctgatg tatggtttgg aggtgctctg    40920
ttgtatggtt tggaggtgct ctgttgtatg gtttggaggt gctctattgt atggtttgga    40980
ggtgctctgt tgtatggttt ggaggtgctc ttgtatggtt tggaggtgct cttgtatggt    41040
ttggaggtgc tctgttgtat ggtttggagg tggtcttgta tggtttgcag gtgctctatt    41100
gcatggtttg caggtgctct attgtatggt tggaagtgc tcttgtatgg tttgaggtg    41160 ctcttgtatg gtttggagat gctctattgt atggtttgca ggtgctctat tgtatggttt    41220
ggaagtgctc ttgtatggtt tggaggtgct cttgtatggt ttggaggtgc tctgttgtat    41280
ggtttggagg tgctctgttg tatggtttgg aggtgctctt gtatggtttg gaggtgctct    41340
attgtatggt ttggagatgc tctggtatct gcctgcattg cttgccacac ctgcccggtc    41400
```

```
agaaggcgct atgttgacaa ttgtgcctgc acggtgccta ggtcaatgaa gggaaccgat    41460
ggtagccact ggatgctcct gggaaaatgt cactacaggc accagagaag ccagagctat    41520
gcccaaattt ctatgagtct cagttttctt aaccataaaa tgggatcaat gttttttgtgg   41580 catgtgtatg agtgtgtgtc tgtgtatgtg tgaggattaa attgtgtatg tgtgaggact    41640
aattgccact actggatcct caaagtggta agaagtgttc ttattaataa tgacatcctt    41700
acactcttac ccagcaagat tgatgggtgt ggcactgctt ctcttttttcc atcacatggt   41760 ttccatggta tccttttgcc cagggaatct ttgctttgtg gctagcactt tgttgtttgg    41820
ctaatcacgc tttctgtggt caggacgctg gcttctctgg agccatggga ttctagctcc    41880
ctgtcttgtc cctagagtgg tcactgtctt ctctctccgc ttgcaattcc tgctttgctc    41940
gcatctcact tatgcagtga cgtatatcag tttcaccttg ttctccgtgc ctgctgatca    42000
ttggcaccac ttgcatggtg ccatttaggg cctgcttcca gttaagcttg cttctccaca    42060
ggcctaaata tccttgcttg cttcttttat tctcactggc aggaccaggg cggtctgtct    42120
ttgcatgaga cagggtctcg ctcagtcacc caggctggag tgcagtggct gatcacggct    42180
cattgcagcc ttgagctacc gggctcaagc tatcctcctg gcttggcccc ttgagtagct    42240
gggactacag gcgtgcacca ccatgcccag ctaattttta aaattatttg tagagatggg    42300
atctcgccag gttgcccagg ctggtcttga acgcctgggc tcaagtgatc ctccctcctt    42360
ggtttcccaa agtgctggga tcacaggtgt gagccactgt gcctggccct tgatgtttca    42420
gttcttgata tttgatcctc agagtcagaa aatctaaaaa gagggctatc ccaggttgcc    42480
ttggttcatg gcaaatggga cgttaagagg gcagagagaa tatgaacaga aactgttcta    42540
atattggtca tttaatgtgt aagtattgtt cttttttaaa cctccttcat ttttttttcca   42600 ggaattgctg gacacagtgg cttggtgtgt gtctgaggac tgtaggccat ggccctaggt    42660
tgtggtttta ggtctcaggt gctcttcctg gctgtctcct tgcttctttc ccatgtcctc    42720
ttctttgttt ccagccattt ctcccttatg cttaagtttg gtgcagcagg gtttggctgc    42780
tctcagattc ctgcttcctc agatgctgta gttgtcaggc ccagcgggct ggcagcggga    42840
tcaggatctg gctaggtttg ctctcactgt ggcagagtag ggggaggcgt gggagagcac    42900 gtgtgaccccc aggccagctg tagggagcat aggcatggtc acgtagcctt caggtcctag   42960
actttgtctt tcatgagta tggctgtgtg tgtatggtga aaactaggtt ctacttagcc     43020
caagaaaatg ggcacatttt gcatgtggtt tctgtagaga aatgcactgg gtatctgaca    43080
tagcctggca gcatgcctcc ctcaggtagg ttagtctcag gcggtgaagc acgtgtgtcc    43140
agcaagaact tcatatgtgg cataaagtct ccgttctgtg aggtgctggc aaatcaccac    43200
caccgtcaag aggctgaagt gattttttgtc taggaggca ggaaaggctt cctggagtca    43260
gcagccagta ggtgaaagag tagattggag accttcttaa tcatcaccgc tcttgtctc    43320 aagggggtgcc aggaagctgt ggaggctgaa cccatcttat gctgccagag agtgggacac   43380
catgagggtc aggtcaaggg gttgtacctt gtttggtaga gaattagggg ctcttgaaga    43440
ctttggatgt ggtcagggga gtgtatcatt taggaagagt gacccggtga ggacgtgggg    43500
tagaggagga caggtgggag ggagtccagg tgggagtgag tagacccagc aggagtgcag    43560
ggcctcgagc caggatggtg gcagggctgt gaggagaggc agccaccgtt gtgtctgcgg    43620
aagcaggggc aagagggaag aggccagcag cgtgctgcca tcacccagcg actggcgtag    43680
attgtgagag accattccct gctcttagga ggggctgagt tttagttttc tcttgttata    43740
```

-continued

| | | | | | |
|---|---|---|---|---|---|
| caataagctt | ggtatttgtt | tacaaaacat | ttgtaaagct | aaatcaaggt | ttgataaggc | 43800 |
| ttctagtttt | atttaagaag | taatgttgaa | ataaatgttt | gtccaattcg | ctttgctcat | 43860 |
| ttaaggactt | tcagtacaaa | ctgcaacaac | aggattagga | tttaaacgtt | tctgagatgt | 43920 |
| ttttactcct | cagaatttcc | cagaatgtga | tctggttttg | attttcaagc | ttgctgaccc | 43980 |
| aataggttaa | cccacaagtt | ttacgaagac | catctcagtc | cacttacatc | aactgcccat | 44040 |
| gccacggtta | aagagatcat | cgactgatgt | ttggcacagc | ttcctccctc | ttgggtgggc | 44100 |
| aagcatttgg | aagagaaggc | tcctatgggt | gagagtgggg | caccaaagtc | ttccctgtcc | 44160 |
| catcccctag | cttgagaagc | ccttctctaa | tgtggacttt | gtgccgttag | catcgttact | 44220 |
| agcttgaagt | tgaccatctg | gacgtacttt | ctggtttagc | ctcacaagtg | agcaaggagg | 44280 |
| gttgagagat | gtgctgtgag | gaatgtgggg | ccccagctgg | cagcaggctc | tgggtcaggg | 44340 |
| gggcagggac | cacgggcata | cctgacagtg | aggaggggcc | acacctgcag | aaaaggatgc | 44400 |
| aggactccgc | cttgggaagt | gttctaggcc | agagcgaggg | tctgtggttt | ataagtacac | 44460 |
| ccacagtgct | cgggaccctg | cagatgtcca | gggtgccgtc | tgagcccgta | tcatccaaca | 44520 |
| gaatgttctg | ctagtgaaga | ttaaagattt | actccagggg | ctttaggatt | tattatatat | 44580 |
| atataaatcc | tatatatata | attttttttt | tttttttttt | tgagatggag | tttcgctctt | 44640 |
| gttgcccagg | ctggagtgca | atggcgtgat | cttggctcac | tgcaacctcc | gcctcccggg | 44700 |
| ttcaaactat | tctcctgcct | cagcctctcg | agtagctggg | attacaggcg | cccaccacca | 44760 |
| cacccggcta | attttgtat | tttttagtag | agacggagtt | tctccatgtt | ggtcaggctg | 44820 |
| gtcttgaact | cctgacctca | ggtgatctgc | ccgccttggc | ctcccaaagt | gctgggatta | 44880 |
| caggcatgag | ccaccccacc | tggccaggat | ttattgtatt | tgaaccatct | accattttaa | 44940 |
| ttttgatgtt | atgtagtatt | tgatgataat | gaaagttaaa | ttgttttct | ttccattttt | 45000 |
| ctgtttaagt | gaatgacctg | tatctagttt | attcagtaac | ttcctgcata | tatttgtttc | 45060 |
| tttcattctt | aatgaatata | ttcttaattt | agttgctatt | atgttttgct | ttgccccaaa | 45120 |
| attgaaatct | tagtttcctt | ttagctcgtt | ttagaactag | tgatgggatg | tgtcttccat | 45180 |
| aaatctcttg | tgatttgttg | taggcttga | tggattctaa | tcttccaagg | ttacagctcg | 45240 |
| agctctataa | ggaaattaaa | aaggtgggcc | ttgctttct | tttttaaaaa | tgttttaaat | 45300 |
| tttaaatttt | tataggtaca | cgtatttgt | aggtacatgt | aaatgtatat | atttatgggg | 45360 |
| tacatgagat | attttgatac | aggtatacaa | tacataataa | tcacaccatg | gaaagttgga | 45420 |
| tatccatgcc | ctcaagcatt | tatcctttgt | gttacaaaca | atccagttac | atgctttact | 45480 |
| tattttattt | tattttgag | acagagtctt | gctttcaccc | atgctagagt | acagtggcat | 45540 |
| gaccttggct | cactgcaacc | tccgcctccc | gggttcaacc | gaactttggg | ctggtctcaa | 45600 |
| actcctgacc | tcaggtgatc | cgcccgcctc | ggcctcccaa | agtgttggga | ttacaggcgt | 45660 |
| gagccactgt | gccgggcctg | attgtacatt | ttaaaataac | taaaacagtc | agggcacagt | 45720 |
| ggctcatgcc | tgtaatccca | gcattttggg | aggctgagg | aggtgatcac | ctgagatcag | 45780 |
| gagttcgaga | ccagcctggc | caacatggag | aaaccctgtc | tctactaaaa | atacaaaaat | 45840 |
| tagccaagtg | tggtggcggg | cgcctgtaat | cctggctact | cggaggctg | aggtagggga | 45900 |
| atcgcttgaa | cctgggggtg | gaggttgcag | tgagccgaga | tcacgccact | gcattccagc | 45960 |
| ctgagcgaca | gagtgagact | ttgtctcaaa | aaataaaaat | gaaataaaat | tgggccgggt | 46020 |
| gtggtggctc | acaccttagt | cccagcactt | tgggaacctg | aggcaggtgg | atgcttgaga | 46080 |
| ccaggagttt | gagaccagca | tgggcaacat | ggcaaaacgc | tgtctgtaca | gaaattagct | 46140 |

```
gggtgtggtg gtgcacaact atagtctcag ctacttggga gattgaggtg ggaggattaa    46200
ttgagcctgg aaggttgaat ctataggtag ctgagattgt gccactgccc ttcagcctgg    46260
gcgaccaagt gagaccctgt ctcaaaagaa aaacaaaaaa acaaaaaaca aaccactatt    46320
atcgactata tattattgtc tatgatccct ctgctgtgct gtcgaatacc aggtcttggg    46380
cccttatttc catcactgag caaacttcac tctgttaagc agcaggtgtg ggatttcatc    46440
gttattcagt aattcacaat gttagaagga aatgctgttt ggtagacgat tgctttactt    46500
ttcttcaaaa ggttactctt tattagatga gatgagaatt aaaaatggta acttacttta    46560
tatctttata attgaagccc actagacctt aaagtagtta ccagatgttt tatgcattta    46620
aatggccttt tctctaaaat tagaaagtaa caaggaaaga aaatgcttcg tttctatgca    46680
accctcttgg tgactagtat gtgactctta atgcaaccct cattgcaccc cctcagaatg    46740
gtgcccctcg gagtttgcgt gctgccctgt ggaggtttgc tgagctggct cacctggttc    46800
ggcctcagaa atgcaggtaa gttgtacact ctggatgttg gttttttgtcg ggggccagct    46860 gctactgatc ctttatgtct cagctcagat gtcatttcaa aagtctgctc tgccctctcc    46920
aaattgcagt cgaccttgcc ctgtttatgt ttccctcata gcactaatcc atgtcagaaa    46980
ttgtcacgta cagtctatct gtgtgcttgt ttattttcta tcccacccctt ccgcaagaga    47040 cttatgggat gtgtgcccca ggacagcagg ggtcttactg tcttatgctc tgttgcagcc    47100
cagcagcgat aacagtgtct gcacatagta cttgcttaaa agatacttgc caaattgttg    47160
aaggttgagg taccaatttc attattgctg actataggag ttatagcaaa atatccattt    47220
gtctgttaca tgagttaaaa atatggttgt tgcactgtga atagtttggt ttagtcaaaa    47280
cagttgtatc ttaacggatt gagaaacaaa agcaggacca cttttcatca gctccctcct    47340
tctccttaac cagcaataca tgctgatgct gatatcccat agaccctcag ctccatcctg    47400
agtcactggg aatgtggtct aaaccctcac tattaatatg aactgagttt caataagaat    47460
cttatatggg tcgggcatag tggctcatac ctttgatccc agcacttcag gaggccaagg    47520
caggtggatt gcttgaccca gactaggcaa catggtgaaa cgccgcctct acaaaaaata    47580
caaaacttag ccaggcatgg tggtgcgtgc ctgtggtcac agccactcga gaggctgagg    47640
tgggaggatc acttgagcct gggaggtgga ggtcgtgttg agccaagatc gcaccactgc    47700
actccagcct gggcaacaga gtgagacctg tctcaaaaaa accaaaatcc agaaaagaac    47760
ttatatggct gcagaggtat aatcactaag gaaatttcct tttgtataat cttttttctt    47820
ttactatcat ttaaaaaaat gtgttatatt tctgaagcaa cacatccagg ttctgcacat    47880
agcagccaaa gtgaccttaa agaatataac tgggtcttgt cattcccttta tttaaactct    47940 tgtacccatt tccagtgcc gtttagatag agattccaga ctcgtcaatg gctctgtcac    48000
ctcagacacc ctgcattgac tcattagtct gattagagtc aggttttttct tcctcctgat    48060 ggttttttt tccccttag ttctcagcgg aacagtcact tccttaggga ggtttcccca    48120 gccacccttct gaggccgtgc ttgttgccag actctgccac tagagggcag ggctgcacca    48180
ctcctggcac ctcgcacccg gcctgccctg tcactctgtg tgttgggtga attcctgtga    48240
tctgtgactc actgctctgt gtcctacaca ttcggctttt cttctctccc cacaacccca    48300
ttttataatt ctccttttttc aggaaagctt tattcccatt taaaaatttt tgttttttaaa    48360 atggtatttt cttacactta ttttctaatt aaaaatgagt gttttaagaa gtattatgat    48420
ttactgcaaa taattttttaa acccagcctt ttagatcctc tgtgatcata agagaaatga    48480
```

```
aggatgtctc ccaacacttg agcttcatcc acatttcatc ctcctgttct ttcagctgag    48540
tttccccat  cccattaggg actgttggaa tataaaactg gcttttccct aacagggaat    48600
gaattgcttc tgtttctcct gaaggagagc tggaagaatg acttgcgttc ttttgcatac    48660
acaggcctta cctggtgaac cttctgccgt gcctgactcg aacaagcaag agacccgaag    48720
aatcagtcca ggagaccttg gctgcagctg ttcccaaaat tatggcttct tttggcaatt    48780
ttgcaaatga caatgaaatt aaggtatgat tgttgcctca ggtcacaaac atgcgagtga    48840
tgctgtgagt gagtctgtgg agggtgaggg cttctgaaca gggagtcctg tgggagtgct    48900
tcttggggta tgttgtatgt cgtaatttag actaccatca tttgtgttat ttttgaggca    48960
cctaaggact tctttccact tctcatttct tactgtgggg tgaagagttg aattgggaga    49020
tggtttctag atgcaaattg aaaaggcatt tttccagagc agatttgttt tcggcgtact    49080
agagtgactc tttaacctag ctgcgggaag atgactgtgc caagactgca ggtaggagaa    49140
agctcactga cgaggccttg tgggtctgaa cgtcctgcag ctatcagagc ctgttggctt    49200
cctgttgtgc attccaacaa atcatcttca aacccacttt agtgttttgt ttataatgtc    49260
cagaaatagt gaccctgtca catgctctac agattacagg attcttagcc tcttcctttt    49320
tggtaggtca gtcctgggtt tgagcccaag tgaccctcct gggaggtgat gatacacact    49380
gggtagagtg gaatcagatg gacttggatt agaattctgt cctctttact agttattttc    49440
ctctaggcaa actgcccaac agctctaagc tatttccttc gtattctgaa aaataagcct    49500
taatgggacc catatagggc aactctgaga gtaaaataaa ggaatatgtg ttagagtgta    49560
gcatagtcac ccacgggaag ggcttagatg ttagctgcta ctgctcttat tagctgaatg    49620
atttggaata aactgttagc ctctctcatg ttttttctct tgagcttcga agttttcttg    49680
ttaatactaa ggagatattc aaactagtca tggggttttg gaatgacgaa gggagatgat    49740
gaatctaaag aatttagtgt aatatttctt catgctcagt aaatggtagt ttctgctgct    49800
gttattttta ttaccatctc tttggaatgg gagtaggtgc tcctttgtgg tcagaggctg    49860
tgagagctcc acagcgccag tttgcccatc tgtacactgg ggtctgttga aggcagtccc    49920
ctctgtgata tctctggctg tcagagctca gatgatagat ggtattttg  tactcttagt    49980
tctcatcatt ttcatgattt cgatcaccat ttgagtatga tgatgctaac actttgttga    50040
acgtagaatc cgttaattac ttccttcctg aacctttggc attaaaaaaa atctattctg    50100
ctacctctct gctcatttat ggttattcaa atttattatc aagagcctgg tacagtggct    50160
tgtgcctata attgtagcta cttgggaggc tgaggtagga ggattgcttg aggccaggag    50220
tttgagacca gcctgggcaa gatagtgaga ccctatctct aaaaaaactg aaaaaaaatt    50280
agctggacat gatggcatgt gcctgtggtc ctagctactc aggaggctga cacaggaggc    50340
tcggttgagc ccaggagttg gagttcgagg ctacactgag ctgtgattgt gccaccacac    50400
tccagcatgg gtggtaaaac aagatgccat ttcttaaaaa aaaaaaatat atatatat     50460
attatcaatg aaattcagta gtaccaacag gattataaac aaagatagta gttcccttcc    50520
tacttttct  cttaatcctt gtgtctcaca ggcaaacata actcttagta tttcttccaa    50580
tatttacttt catgtttctt tctttctttc tttttttttc tttgagatgg agttttgctc    50640
ttgttgccaa ggctggagtg caatgacgca atcttggctc accacaacct ctgtctcccg    50700
ggttcaagcg attctcctgc ctcagcctcc tagtagctgg gattacaggc atgcatcacc    50760
acgctcggct aattttgtac ttttagtaga tgggggttt  ccgggttg  gtcaggctgg    50820
tctcgaactc ctgacctcag gtgatcctcc cacctcagcc tcccaaagtg ctgggattac    50880
```

| | | | | | |
|---|---|---|---|---|---|
| aggcgtgagc | cactgcgccc | agcaacttcc | acatttctaa | ataacatgct | tctactgcta | 50940 |
| tttttttttt | caattttaga | cattttttta | ctttcactat | agttctatca | gaattcagtg | 51000 |
| tgtacgttat | tatgcctaag | taaatagtca | tggttgctta | cgtattatat | ttctttgatt | 51060 |
| gtgtttctta | tttgatgaga | aagctgtgtt | ttttgctctg | ggttgaaact | ggagagagga | 51120 |
| cctggggagg | aggaggagga | cagatgaagt | tggtgactgt | accttcatgg | ccatagctgg | 51180 |
| gttctcagca | cccgggatc | tgctgatcac | ctactcatag | gccaggcccc | tatcgaagtt | 51240 |
| ctaggtgacc | cagtgctggg | gacggggggg | ccacctgcaa | ggtctaatca | tggaggtggg | 51300 |
| ggctacagtg | ttggcttgtg | ctggggccag | catccttagg | aaggcatctt | ggaggtggag | 51360 |
| gagacagccg | cccacttctt | gattgggcc | ttcagcagca | ccagcttctt | gggcaggctg | 51420 |
| gtgctggctt | tcatcaccat | gtcgtgttca | atcttcttcc | agatcctgac | ttctaggttc | 51480 |
| agctttcctc | agaccctggt | tcctttcaga | ggccattgct | gctgccttgc | tctttgctgg | 51540 |
| cttgtgcctt | gattatatgt | ctttgtacaa | cttttgttt | tcctggagtt | aatcttcaca | 51600 |
| tctgttttct | tggagttaat | cgttacctct | atatcgcttg | cttattattc | tttggccttt | 51660 |
| ttgtcttctc | acaccttcca | acttctttgt | aatatgtgtt | tagtacaatt | tttcatgaca | 51720 |
| ggtagtttac | tgaatcagtt | tttccccagt | gtggtcatcc | aacttgagtt | atccagctct | 51780 |
| ctgccccagt | ctgggcaggt | tgatcttcag | gtctgtagta | cacttgtatc | ctaggacttc | 51840 |
| tctttgccat | tagcctggaa | tttcctttgc | agttctcccg | ttggatgccc | agttcctaga | 51900 |
| tgccatatgt | ttttctatcg | tctagtagct | tcctgagaga | agatgaatgg | gagggaaatt | 51960 |
| gtatgaggtt | ttgcattcat | aaaaatgcca | ttttttttcc | tgtacacttg | gctgggtatg | 52020 |
| gtgttctggg | gtagaaatca | ttttccctca | gaaatgcaaa | gtctttgccc | tgttgtctta | 52080 |
| aaatctccaa | cgtgacccga | ttccttaacc | tatgaatgta | cttttctttg | gaagctttcc | 52140 |
| attttggggg | aggtgaagtg | ctaggtactt | agtaggcctt | ttaatttgga | aacttacatc | 52200 |
| ccttcagttc | tgggaaaatt | ttcttaacat | ttctctgaga | agttcttgcc | ttttattttc | 52260 |
| tgtgttctct | cctgaaattg | gttagttgga | tgttggtcct | cctagattga | ctcacatctt | 52320 |
| accttttct | tttcttttc | tggtactttt | tagatatcca | tctcaaactc | ttctattcat | 52380 |
| tgttatgttt | ttaacttctt | tcttttcttt | gtctcttgat | ggggtcttgc | cctgttgccc | 52440 |
| aggttgtggt | gcagtggtgc | gatcatagct | cactgcagcc | tcaaattcct | gggctcaagc | 52500 |
| agctgttctg | cctcacccctc | ccaagtagtt | gggactacag | gtatgcacca | ccacgtccag | 52560 |
| ctatttctt | tactttttt | tttttttt | tgagatggag | tcctactctg | tcgcccaggc | 52620 |
| tagagtgcgg | tggtgggatt | ttggctcact | taagcctctg | cctcccaggt | tcaagcagtt | 52680 |
| ctcctgcctc | agcctctcaa | gtagctggga | ttacaggtgt | gcaccaccat | gcccggctaa | 52740 |
| tttttgtatt | tttagtagag | ccagagtttc | accatgttgg | ccaggctggt | ctcgaacgcc | 52800 |
| tgacctcagg | tgatccgcct | gccttggcct | ccgaaagtgc | cgggattaca | ggcgtgagcc | 52860 |
| catcattaga | tctttaaata | ccagtatcta | taagtctttt | cctcttgagt | cagctagtat | 52920 |
| ccctggaagg | aaattactca | ttttcctgct | tggaggctat | aagcttggct | atgtttatcc | 52980 |
| tgcaaccggg | gactggaagg | gagggactg | acagtgttgc | tggtcagggt | gccctcttac | 53040 |
| tttttgtttt | ctgtgtgcat | ctcacgtctg | tcctcagcct | atgtaaacac | ctcttgagat | 53100 |
| tatccctctc | aatctttgcc | ggaggtgggg | gagggctgc | ttcctgggct | gccttggatt | 53160 |
| ggagggaaga | cctcaggtga | gtgggtggga | atttgcccaa | ggagccatga | gaccagccac | 53220 |

```
tatttcaccc tctccatccc tccactttca gatgtatgtg gcgcctccaa agcccgagct   53280
cttcttggcg tctgtggctt caataagctt gcttttttgct ggtatccctc ctaccctccc   53340
ctgtccccag caaagcttgc atttgaactt cttcctacgg gctaacaaat cagtcagtta   53400
tgtagctctt gttacttttt agcttccgaa gttttgttga cacccgtagt ctgctaatgt   53460
ccctgttctg ttctttctgt tcgtgtaaat atatgcttta tacaacttct ttacatgatt   53520
tttgtggggt ttctgggtag cagagcttca caagttcaat ccagcgtgtt ggattagaaa   53580
tctcccaccc tctggtttat tcttattctc aaaattacct gccaaacact gatactccct   53640 tgttttttcct tttcctgaca ggaaatgtac ataccataca ggacagaaat cattagtgta   53700
tcccttggtg aataaccaca aagtgaactt aacccttgta accgccaccc aggtcaagac   53760
agaatattac caagcactca gaagcctctc ccctattccc ccgtcactgc tcctgccttc   53820
ctccccaagg tcatgactgc tggcttctaa ttccagagtc tgttttttaaa ttctgtgtac   53880 atagaccatg gattaagtgt tctttttgtc tggtttattt tggtcgacat taagttcatg   53940
agagtcttct atattatcgt gtgtattagt attcctgtag ttttaggagc ttcatagcat   54000
tccattgtag ggatatacca cagtttattc attgtattat cactgggttg tttctagttc   54060
ttggctattg cgagcagtgc tactgtgacc actcttaggt gtgtcttttg gagtacatgt   54120
gcaggtttcc atcttgcaca gctagaggtg gagttgttgg gtgatagggt gtgtgcatct   54180
cagctgcagt agaaactgcc aaatagcttt ccttgagtgc ttgtaccagc tcacccttt   54240 gccactgtgt atgggattc caggagctct ggtcctcgct agcacttgga attgctgatg   54300
cttttactct tagccttcct gatgggtgtt ttctggaatc acattatgat tttaatttcc   54360
attccttaaa gtaccttgg ctctgaagtt taatgattca tgcatctctt cccttttgaa   54420
gtactcttac aggtatgttg tgcatgtgtt gaaaagtggc actatctatt ctaaaataca   54480
gtatgcctcc tctgtgtttg aacagttgta gcgtggcctt ggggcctcct gttagctggc   54540
ttggagaagg gattcttggg attgtagaga ttagacctga ggaggcccct tggagctctc   54600
tgactaaatt ttattcttta ttattccaaa ctatttaagc tcaccgtgtg ctgactcatc   54660
ataataatga gtagctctca ttgtgcttgt ctatttggac tcatacaatg attttttttt   54720
tttctttgag acagagtctt gctctgttgc ctaggctgga gtgcagtggc acaatctcgg   54780
ctcactgcag cctccacctc ccaggttcaa gtgattcttg tgcctcagct tctcaagtag   54840
ctgagactgc aggtgcgtac caccatgcct ggctaatgtt tgtattttta gtagagacgg   54900
ggtttcacca tgttggccag gttggtctca aactcctgac ctcaagtgat ctgccttctt   54960
cagcctccca aagtgctggg attacaggtg tgagccactg agcttggcca aagtagtttt   55020
ttaagatgtt agtatctttt cttgcagcta aaaaagtttg tcagagatga ttctactttg   55080
ttctccaggt gttttctcag ggagaaattg gaggcagtaa gccactgggg gagtcctgtg   55140 gctgggggt ggggtagtcc tgtggctcct tgtcagggag tcctgtggct ggcaaggaga   55200
gaagtcctgt ggctgggttg ggagggagtc ctgtggctgg ggtctcatcc tgtgcctaac   55260
agtgtccaga ggtgccgaga ccagctcagt cggggagacc ctaacccagc agcgctagag   55320
gaattaaaga cacacacaca gaaatataga ggtgtgaagt gggaaatcag gggtctcaca   55380
gcctttagag ctgagagccc tgaacagaga tttacccaca tatttattaa tagcaaacca   55440
gtcattagca ttgtttctat agatgttaaa ttaactaaaa gtatccctta tgggaaacga   55500
ggggatgggc cgaattaaaa gaagaggttg ggctagttaa ccgcagcagg agcatgtcct   55560
taaggcacag atcgctcatg ctattgtttg tggcttaaga atgcctttaa gcggttttcc   55620
```

```
accctgggtg ggccaggtgt tccttgccct cattcctgtc aacccacaac cttccagtgt   55680
gggcattagg gccattatga acatgttaca gtgcttcaga gattttgttt atggccagtt   55740
ttggggccag tttatggcca gattttgggg ggcctgctcc caatacagag gtctcgtgta   55800
aattccctgg gaggcgataa gcctctgaga aacagactat gctaaccacg ccatgaaaga   55860
gaaacttatt tataaatcag atgccagtta ctagtttact gcttatttgc ccaggcgtag   55920
ctctgacaga gtccccgact catagtgctt gctcagtgca tgctgaacaa tgattggaat   55980
caagtcatgg ctcagagcat agttttgaat aatgggaaat ggatgttctt aagtaacata   56040
gtcaccaaga taatgcgact agctgggtca cccctttca atttaggat attttatca    56100 agatttaaat ggccatcatt agagttatag cactttctcc tttggattgt cctagaggcc   56160
catgagaaag tattccctaa tttcttagga gaacagtttg tgggtagtat gcggtcatgt   56220
ccagttaaat tgcagatatt tccgatcgaa gatgttccag tcctgagaac ttcgtgacat   56280
tagcaggact tctacaagcc atctcttagg gtggggcatt tactgcagtt ggctagtact   56340
cttttctcct taactttgtc atttgttgat ttttttttaa ctgtccccaa atactgtggg   56400
cagagtgtat ctagaattga ggcctccacc attgcggaga ggacatggat gctgagcagt   56460
cccctgagtg aaggttataa agaagcaaat agactacaca tgtctgtaaa ctgctcttga   56520
gtgtcccaaa tttggggtac ttcagttcag ctgtaggaaa agcctcaaac tgtttatact   56580
ttgcaagaat tggaaacttc taattcacgt taagttttat gtaatacatg ataagcttca   56640
taggagcttc atctttatc tacttggact tttgcttccg taggttttgt taaaggcctt    56700
catagcgaac ctgaagtcaa gctcccccac cattcggcgg acagcggctg gatcagcagt   56760
gagcatctgc cagcactcaa gaaggacaca atatttctat agttggctac taaatgtgct   56820
cttaggtaag gtggaggcat atgagtggaa gagtctccag catgtactca agatagacct   56880
ttgaaataaa taaaaccaga tgatccctca gcttctagac caggctattt ggcactggtt   56940
gattgaatgt gaactgcact ggggctgctg tgagcccgca tgggtctctg tgaccctgca   57000
gatgcagccg tgcccaggga ctgggcagtg ggtgtgggct ggtgtgagcc ctgtctgcca   57060
cccagggcct ggccctctgt ctgtgtcggc catgactatg gtgagtcttg taggcttgag   57120
actgtgcctc gggttcctgc gggttctctg taggtcagtt gacagtttct cctgttgttt   57180
gggtaactgt ggaaacgaac actggcaagt gctgaagcga gcatgtggac gtgcgatatg   57240
aaataacgac ctggctttca aaggcagtga ggctctctgg aaaggaccct gctgagctag   57300
ggatgtgggt gtgtagccat tcccagtggg cctcatggcg tactcgttca tgatcatgtt   57360
tgtgccatct tgatctctca ggatctcttc tttttaaca gattaagccg ggaatctcca   57420
aacagtgagt cagatgttaa gatgtcttgc ttccacccc acaggcttac tcgttcctgt   57480
cgaggatgaa cactccactc tgctgattct tggcgtgctg ctcaccctga ggtatttggt   57540
gcccttgctg cagcagcagg tcaaggacac aagcctgaaa ggcagcttcg gagtgacaag   57600
gaaagaaatg gaagtctctc cttctgcaga gcagcttgtc caggtaggag cacagggttt   57660
actctaggcc ctgcatgtga atgactgaca ttcaaagaac cgattaattt ggaagagaag   57720
cggcagaacc gagagttaga ggtgtggact ctggagctgc gctgctcgtt tccacccta    57780 ggtgctgacc tctagctgtc ttccctctgt atgtccctgt caccgtgagt caaatgcggg   57840
tgatgcctcc tcaggtgccg tgttacctaa gcctctcaga gaccactgct accctgtttc   57900
taaaaccaga ggtcacgata tgtgttcatc cacccagtaa atactgattg agcacccact   57960
```

```
gtgtgctagg ctctgggata ggggctgggt atacaatggt gagtatttca gctgcagctt    58020
ctgccccgtg gaggctgtgg cctagcacac tggtctaggc acgtggtat atgctcactc    58080 aaggagatag ggacgtggtc gtttggggtg tcggaacaaa atgtcggaac ttctctttcc    58140
aatgcagaga aaccttgcag taattctaat gtactgtgat tggcagttga cttcagttct    58200
ttgtagcacg cttactcagg ttatttcact aactatgtaa ccatgcagcc tcattttaag    58260
caattggatt ttttgaactt tacttaaaat gttatgtcag ggttttatt gtgcttaatg     58320 tgtgccattt agctaagttt tgtaggatac gaaattgtaa gtggcttaaa atgattctta    58380
atagaatcat gaattgaaga taatgctaat aatttaagca ctgagttagg tagtgtttgt    58440
aaaatgctta gaatgcttcc tggcacatgt taaggccatg taagtgctgc gtgttgataa    58500
acagctgagc aaaagtggac tcttaagaaa gtattgggc tgagagttct gttccaacca    58560
gctgcccttt ggttattttt cagaataaaa gcagagtctc atgggatatg acatttatat    58620
ttccttcaca aaaacactg ctgagtgttt tgttgagtaa aaagggtgta gccatggtaa     58680
taatacattt aaaatatagt ttatttcatc tttaccttgc cttgttttt ttttaagcta     58740 gcttttattt gagaattcca cacatacaaa agtatcaact catgaccagt tatatttcat    58800
ttataatcct acttctccct tttttttatta tttgaaagca accccaatt atcctcttat    58860 ttcatctata agtatttcag tatctctata gatgaggact cttctttatt tttaaaactt    58920 tattttaaa atgatggtca gatgcagtgt tcatgcctgt aatcccagaa ctttgggagg    58980
ccaagctggg cggatcactt gaacctggga gtttgagacc agcccgggaa acatggcgaa    59040
accccatgtc ttaaagaaaa aaatcagcca agtgtggtga tgcatgcctg tagtcccagc    59100
tacttgggag gctgagatgg gagggtcaca tgagcctgga agatcaaggc tgcagtgatc    59160
catgattgta ccactgcact ccatcctggg tgatggagca agattctgtc tcaaaaaaac    59220
aaaactgcaa acaacgtca caaaacagtg ccattgttag acctgaaaat attaaacatt    59280
tcctacatca aataccacc aactcattat caatttttct ctctactctt ttggaatcag     59340
catctaaata aaattggtcg ataaggattg taaatctctt tgatgaactg gttccctcc    59400 atcccagttt ttttcccctta gagttcattt attgagaaac cagattgttt gtcttctaag    59460
ttttcctgtg gtctgatata ctgcttccat ctccactgtg taaattaaca ccttttctc     59520 ttctctgtat ttcctgtaaa tcaataattg gaggaaagc cttgtcagat ttagtgtata     59580
ttttatatct gagtccagta tttcttatat aatatttaa gataagtgta ctcttttaaa     59640
aagtattgaa actatatgct caattttttt taactgatgc ttttaagaag gctgcttgat    59700
cataaaagtt tagagatcat tggtctgatg ggaaaagcaa ataattacta aaccgtttag    59760
caaggttgag gtgcacatgg tggggcctgg agaagttcag tcatgagccg tcacttatgg    59820
gcacgtggaa tctgacccgg cacagagttg ggagaagaca ggagctttat agacagaaaa    59880
tgtggtcttt gctaagtccc aggagtgaaa gggtgagaca gtgctcacag cacacgagtg    59940
tgggtgcgta gacagagcaa gggtgggtcc tgaaaaggcc tgcaggcttt ctcatagatt    60000
agcaagagtg ctggttacgg aggtttctaa catttgtgaa cagatcgaaa ctgtgttaaa    60060
ttgggattgc agtaatcctg gaaggacagg gatagaggt gaaggggaaa aagggtatg     60120 gatgtgagac ttaattgctg attttcttaa gacctttctc caaagtaaat aaatgatgtg    60180
gcacattttt gaactggcaa attctaaact ctagatatga ttatctctat aacatatctt    60240
actccatctt cttttgacta aaaactgttc ttaattaaat taccatgaga cgttcaattc    60300
agcaaatgta gtttggctaa ccatatttaa ttagaattta atataatcct aggcctggcc    60360
```

```
aaactattaa gcaagtgtgg gcaaaatatt gataatttta gatatgcagg aacttagttt    60420
gctttccatg tgtgcttttc gaaaaaggaa taaattgaaa aatagaggaa gccctgaaat    60480
ccaagaagca aactctctca cctaggcatg cagtaaaagc aattctagga tgattgctgt    60540
ttggcgcgta gttcgtatta gaaaccattc ttcttgaata aatagtatgt ttaagaagct    60600
gggcagaggg aaggcatatg catatattat caacaaggag ggagaaaaag gcaattagta    60660
accatccata ggagggtcag caagatttat aaaggaaatt tgtgatccaa gtatgaagca    60720
aaataaggtg cagaataaat tttaagcaag taatagatta gagtaagaga acccatttga    60780
ccattaacct tgggacattc tctttcaaat gacatggagt agtactgaaa tctttctttc    60840
tttctgagtc taggttattg tgactggact cagaagaaaa tatttcatta ttgcagtgaa    60900
taacatttgt gaacattatt gttcataaat tatgcagtga ataacattta tgaacacgtg    60960
atgtgtaaga tacatactgt ttatttttag ttaagttttt tggctcaact tctaggcaga    61020
gaacattaaa tgtaaatagt gttacctagg agcatgtaaa tggaaatctc catagtatga    61080
aagcagtgct gttgctaaca gaatttagga gggggcagat gaggtgaagg aaatgtgggt    61140
gctgatttcc ttattacatt gagaggagcc aggagattct ttgttcaaaa tggatggctt    61200
aagaagtcaa agtataagct gattacgtag agcaggtacc caaaaatgtt ttgtgtaagg    61260
ggccagatag taaatatttt cagtcttgca ggccatccca agtctgtggc agctactcaa    61320 cactacctt gtagcatgaa agcagccaca ggcagcccat aaatgtggct ctgttccggt    61380
gaaactttag gtacaaaagc aggtgcaggc cagacctgac ctgtgcactg tggtttgctg    61440
acctgggatt caggggtata gaagttacca tcagaagagc taaaagtgag acttttact    61500 ttatactctt ctacactgtc tgattttgaa aaaagaaac atgtatttta taatattaaa    61560
gatagggttg gcaaatagca aataaaaata cagaatacca gtgaaatttg aacttcagat    61620
acattatgag taattttatg gtgtaagtat attccaaatc atgtgggaca tacttacact    61680
acaaaattat ttgttgtttg tttacagttt aaatttgagt gccttgtatt ttatctggca    61740
actgtaatta aagggaaaaa gaataaaattc attatgttca tataatgtga tatagcaggg    61800
gtccccaacc cccaggctgc agagtggtac tggtccatgg gtccccaacc cccaggctgc    61860
agagcggtat tggtccatgg cctgttagga accaggctgc ccagcaggaa gtgagcagca    61920
ggtgagctgg cattcccacc tgagcaccgc ctcctgtcag atcagtggca gcattagatt    61980
cccataggag tgcaaaccct attgtgaact gcacatgtga ggggtctagg ttgtgcgctc    62040
cttatgagaa tctaatgcct gatgatctga ggtggaacag tctcgtcttg aaaccatccc    62100
ctggccctgt ggaaaaattg tctcccatga aaccagtctc tggtgccaga aaggttgggt    62160
agcactgtga tatagtatta aaagtgctaa taaatatggc atactgcctt taaaatgtct    62220
ggtagctctt tctcagtggc actcataata gtgttttttg attttaaat gtgtgtcaag    62280 ctgactctcc cctccgtgta tgctgggctt tattttccct ttcctagtca ccagttttgg    62340
gaaatagaga tcttcattct catgctgctc ctctagtgca agtgctccat ttatttttaa    62400
ggaattaata taacaaaaaa tcatgggaat ttagaaaaca acatggaagc taatgatcac    62460
attggtggaa gtgatagggga aatatttagg gggagaagtt aaggtataaa ctttgtcaat    62520
gaagtcctat taaaaacaac aaaaagtgaa agcttaggat gcatttata aactctgacc    62580 agaacacctg tgtttctctg tttctaggtt tatgaactga cgttacatca tacacagcac    62640
caagaccaca atgttgtgac cggagccctg gagctgttgc agcagctctt cagaacgcct    62700
```

```
ccacccgagc ttctgcaaac cctgaccgca gtcgggggca ttgggcagct caccgctgct    62760
aaggaggagt ctggtggccg aagccgtagt gggagtattg tggaacttat aggcaagtta    62820
ttagcaaggt ctactcttac aattaacttt gcagtaatac tagttacact ctattgatta    62880
tgggcctgcc ctgtgctaag cagtctgcat tccatcttcc ttgccaaaac ttataataca    62940
aatttcatct ttattttata aataggggag ttgggctggg tgtggtggct cacgcctgta    63000
atttcagcac tttggaagga tcgcttcagc ccaggagttt gagacaacct ggccaagtga    63060
gaccctgtct ctacaaaaaa aaaaaaaaa aaaaaattag ctgggcatgg tggcacatgc    63120
ctgtagtccc agctgctttg gaggctgagg tggtaggatt gcttaagccc aagaggttga    63180
ggctgcagtg aatcttgatg gcagctgcac tgagcctggt gacagagcaa gatgctgtct    63240
caaaataaat ttaaaaataa aataagagaa ttaaagttta gcaggttggg tgcaaaatg    63300 aggccacaca tttaaagccc ctcctcctga ttcttttctc tgccttggct gcctcctgtg    63360
gcattttagg tgctgagaaa tgaaaacagt agggaaaata gttccaggat cctcatgtta    63420
atttgccaga aatggcatct tcaagtcgtc agagggatct gagagttcct tcctggcctg    63480
acttgagaaa atccgtctgt ccccagctct gcgtctgcct ccactgccca gtcacctcct    63540
ctccatgctc ttggggctgg gccctacccc accatgcagt gctgcctgg agcagtgagc    63600 ttggtgggtc ctgtctggca tgagagctgc ctttgggagc tggatcccag cctctaccac    63660
tgggtctggt gcctagcagg ctatggataa acttctgctg actccggcct ctcctaagcc    63720
actgcaacgt ggtcggtgta gtgcacagtg tgtgtgcagc gtggccttac tcacagcctc    63780
cacattagag agaatctgac tgaagtctta ctgctgcctc gtgtgaacat aaatgtttgc    63840
cagaaccatg agcaggaaat gttaatctgc cttgtttcct gtcctttaca cggaagaatt    63900 ttttttctgta tggaatgcgt gccttacaaa taatgagtgg aaatacccat cgctaatgaa    63960
aagttatact tgactgttag tcagctaaat aatctgagat ttctaatact tttaatttgg    64020
cttttacaat gcaattatc ttagctttt tgatttctta ggtcatatct ttagaactat    64080
atatttgaat gttaatgtaa ttttcatatt gaaattaaaa tgttgaactg cgatgttaag    64140
tgtttcctgt ggaaaaacgt tcacattttc tctagtttta aagttgaatc aagctgtttg    64200
aagattttca catttcttct agattttatc agcttgttac tttatctgtc actttctgtg    64260
atttgcagct ggaggggtt cctcatgcag ccctgtcctt tcaagaaaac aaaaaggtga    64320
ttatttcaga aatcagagtc ttgtgttgaa tcttactgat tttcttgtat ttctgtaatg    64380
taatgtatct tgtatttctt gtaatactgt attggactct gtgtatatct cttctcagat    64440
gagtgattat atgtgtgaat gttgctggaa tctgataacc aggcctgaat agttttgtag    64500
ggtggctttt aaaaattact ttcatatcag aattgctttg tcataaattt tgaacgcatc    64560
ataaatttct aatgttcggg gtcagcagac ttttttttgta aagggacaga gtgtaaacat    64620
cttagcttta tgggccatat ggtctctttt gcaacattca gctctgccct gtgacaggaa    64680
tgcagttgta aagacatgag ctactggcca gctatgttcc agtagaactt tacttacaga    64740
aacagacagg ctgtagtttg ccaatacctg ccttagggaa tgtgttgtta tattttgtga    64800
gttaccttct cagtaaattt tatttagtat tagtcaggaa tattattaag tagcttcttt    64860
tccagcctgg tcaacatagt gagacccggt ctctaccaaa acaaaacaaa acaaaaaaac    64920
agccacgcat gtggcatgtg cctgtagcct cagctgctgc tcaggggct gaggcaagag    64980 gattgtttga gcccaggagt ttgaggtcac agtgagctgt agtcatgcca ctgcactcca    65040
gcctaggcaa cagaatgaga ccttgtgtct taaaaaaaa aagtttcctt tgttgggtta    65100
```

```
ttttaatttg gacctggtta tcattttcca gccatattta actttgtaca tatcagaatg   65160
ttctgataaa acttaacttt tattaaagtg tttgtgatat aatctgctag ttttggtaca   65220
cattatcttt tgcaatgcca gttattttct tttccagtgt gggtttgcat aggaaaagaa   65280
ttgctgtcac tttctatttt gaaatcttaa aagactgatc cttttttgtg tcatgatttg   65340
agtatttaat tgagagccta atgcctaata ttatttgcag tattaaatgg gatcttaaca   65400
ggaatagcat tctagccttc attgaattaa gtaaacattt cttaagagaa cttggaatct   65460
ataatatttg cgtcatcata gtatgagata cttaatcaag tttgagattt tagtgaaaca   65520
ttgtttagaa gccaaaagga ttctaggaaa aattaatgtc tatattcttg aattaggaga   65580
gattttggga cgtgtgacta agttacgctg acacttgttt gtttcttagt cgcttttcc    65640 agtggcggtg agaacgaaga tgactgattc acattgctca gatgagttta tcctcttctg   65700
gctgggacat gggatatatc ctgtctcttt taagcctttt tggtattttt cccccattga   65760
gagctgtgtc ttcaaactct tctgttatag ctggaaaatc cttttaagt gaaatctgcc    65820 caaattataa gacagatgaa ggtagagttg tgttggatat aggattaggg tgaaagtagt   65880
gggggtgtcc tggagcctct cttctggtgg cagcctagct cttgtgcctt tgaggaaatt   65940
accctgggga cggctctgtg gaacatattt gcaaaccact gatttggaag atagagatgg   66000
cttttgttaa gatctgaatt cacctttttg gcatttatt tgatttctca aggtaaagaa    66060 cttatttgt aataaagttt cctattattt agtagatagg ccaagttgct gtgttaattc    66120
catgtagatt ttgggtttcc tttgctcatt ttttcactct taatctcaca tcattgtaag   66180
tttatggaag ttatcatact tctgactttt tctttgaaga gcagaaatta gaaattccca   66240
ataattattt tgatagtgtc atttaatgac actcacatgt gatgtagcca caagatttta   66300
atgagttcag ttttaaatca tattaagact gttggtttca tttgttctca ttaatgtaat   66360
tctgaagatg aacaataaaa tgtattttta gaactttcaa atgaaatatt atttcatcct   66420
tccagatcat ataatgctta agttctgatt gttaatcata aagtctagaa aattaaaaga   66480
taataaaatg aaagtgactt ttaggtatta gagttttatt ataaattctg gtgtgtcatt   66540
ggagctatga catgaatatt tcaaaggcca atagcattgg atctttacag ttataactta   66600
ccatttttaa gtttaagtag taatatagat tatttaataa tcaaaatcaa taaatattaa   66660
ttattaaaat gttttgtggt atagtttgag aatcattgct tttaactttt tccatatagg   66720
tttattgact ttaatagcat tctaaacata acatctctac attctttgtg tttaatactg   66780
tggaggtata aaaatactta tatatgatga taaactatat tagagtaaat taaatattct   66840
tatgagtttc attttagagt gcatttactt aattttgaag tccttatttt tagcaaacta   66900
aaaggaatgt tggtacatta tttactaggc aaagtgctct taggagaaga agaagccttg   66960
gaggatgact ctgaatcgag atcggatgtc agcagctctg ccttaacagg tagttctcac   67020
tagttagccg ctggtgtgga ccttcactgt ctgccttcca ccccttgccc ttcctgctcg   67080 tcccctgca cctggtggac agcacgactg ggggcagcag tggagccagg ttgcttaaat    67140
ggggcatatt cgggcttctt ttataatact tactctgaag cttgtgtgtc tgtggtgttt   67200
gcatcatata tttgttgttt tccatggttt aggctgtttt aaaattaggt ttatggcttg   67260
agcatagggc tttgtgagta ggggatggca ggtcgaaaca tctcatgagt tggatgggtt   67320
atgctggggg ttgggaaatg ggatgaaaaa ttatgggatg aaaaattgcc tatggatagt   67380
ttaacttgaa agaatctgcc tttgtttaca gatagttatc ttttttcttt tttgagatag   67440
```

```
agtctcacac tgtcacccag tgcagatacc cagtgtcact ggagtgcagt ggtgtgctct    67500
tggtgcactg cagcctccgc cttctgggtt ccagcgattc tcctgcctca gcctcccaag    67560
tagctgggac tacaggtgcc cgccaccacg cttggctaat ttttgtattt ttttgtggag    67620
acgggttttt gccatgttgg tcaggctggt cttgaactcc tgacctcaag tgatctgcct    67680
gcctcagcct cccacagtgc cgggattaca ggagtgagcc actgtgcccg ccagttaca     67740 gatacttatc taatgaaatt ctctgtgtac tttataaaag atgaggatta actgaaggta    67800
ctaataactg gattatatga gggtggtttt ggttgtataa tcctatctaa aagaatattt    67860
tagctataac tgaaagtaag acttaaatat ttagagagga aaatctgaat aattctagta    67920
gtaattattt atttacaaaa taaaaataga ttttttttg attacacaaa ttaaacaaca     67980
ataaaacatc acagcaatcc ggatactata aagctcacat gcttaccgac ccaactgccc    68040
caggagtgac cactgccaac agcttcatgt cgacctttt gccataattt ttatatagcc     68100
ttttttgttt ttaaatggta atttagaaag tcaactagga aatgtgtta caggtttatc     68160 ttccaggaga ataggactgg agtcgagatc ttgaatgtgg cttggaagaa ggcaagccca    68220
ccccagagag atgagttgac agttgtttct gaccactgct tgcttagagg gcctgcgtgt    68280
ctgtgaccgc ctagctttgc gcccctgact aggctgcccc ttaattacaa atgtcttat     68340 atattgctcc agctaaggct tggagtagtc ggttaagaac ttgaacttcg gttttttgcag  68400 tgaaacagca tttgagaata tccaccttctg ataagcctta ttttataagg tgggtactgt   68460
agtgggaggc agtgtgagag atgcttgaag gatgcactgc tgtcctgcat ttcagcatct    68520
tcaggatgct gtgcagctga acatttgat aacggtggaa ctgttcgtta ttttgcaagc     68580
ctgtgattcc ctattgaatg ttttctctcg ccatttgaca aatgagtgtt tctctgtctt    68640
cagcctcagt gaaggatgag atcagtggag agctggctgc ttcttcaggg gtttccactc    68700
cagggtcagc aggtcatgac atcatcacag aacagccacg gtcacagcac acactgcagg    68760
cggactcagt ggatctggcc agctgtgact tgacaagctc tgccactgat ggggatgagg    68820
aggatatctt gagccacagc tccagccagg tcagcgccgt cccatctgac cctgccatgg    68880
acctgaatga tgggacccag gcctcgtcgc ccatcagcga cagctcccag accaccaccg    68940
aagggcctga ttcagctgtt acccccttcag acagttctga aattgtaagt gggcagaggg    69000
gcctgacatc tttttttta tttttattt gagacagagt ctcactccat agtgcagtgg      69060
aggccgggca caggggctca tgcctgtaat cccagcactt gggagactg aggcaggcgg     69120 atcacttgag gtcaggagtt cgagaccagc ctggccaaca tggtgaaacc ctgtctctac    69180
taaaaataca aaattagtt gggcgtggtg gcacatgtct gtagtcccag ctgttaggga     69240
ggctgaggca ggagaattgc ttgagcctgg gaggcagagg ttgcaatgag ccgagatcgt    69300
gacactgcac tccagcccgg gcaacagagc aagactccat ttcaaaaaaa ataaaaaaat    69360
aaagtgcagt ggctcgttct cagcccactg caacttctgc ctcccaggct cgagcgattc    69420
tcccgcctca gcctcctgag taggtgggat tacaggtggg caccaccaca ctcagctaat    69480
gtttgtattt tcagtagaga cagggttca ccatgttggc caggctggtc tcaaactcct     69540
gaccttagat gatccaccca ccttggcctc ctaaagtatt gggattatag ttgtgagcca    69600
ccatgcccgg ccctgccacc tgccatcttt tgagttcttc cctggagacc tagacctgaa    69660
ccctcctgct tgttctcttg ttatctaata cccctattga cagcgcagct tagatcatta    69720
atggagagct tgacctcatc tgataccttc actgaaggaa caacttagt gtcttttgtg     69780 ttgaacactg aggtaaaaaa ttggaatagt tgattatatg aactctgcta aaattgagtg    69840
```

```
catttacat ttttaaggc cttgttgggc cctggttaaa taattatttt taaaaatcct    69900
taaggagcct attataaaca gatctgtggt cttaatgaaa tgtgattaat actgtgcatt   69960
attttaagaa cttttgactt ttcaaaaaac ttttacaaca tttcccattt gatagcggca   70020
taggtttaag cacttctcat ctctaagtta gtggacaaaa aaccctcatg gatagtctaa   70080
taatgtttgc tacaagtcca tgttgagttt tatactccat tttattttca gttttaaaaa   70140
ctgtggttaa atatgtgtaa cataaaattt atgttcttaa ccattttttg cgtatacagt   70200
tcgctggtat taaatacatt taaataatgt catggaatca ttgctaccac ccatctctgt   70260
aaccttttga tcatgtaaca ctgaagctct gttcccattg aactctattc ctcctttccc   70320
gccaagtccc tggcaaccac gattcttctt tctgtcttct gaatttgact actttgggtt   70380
ctcatatact ttaggagtca cacagtattt gttttactta gcataatgtc cccaaagctc   70440
atgcatgttg tagcctatgt tagaacttcc taatgtttca ggccaaatac tattccattg   70500
tatggatagg ccacattttg cttttccatt cctctgtcca tggacacttg tattgcttca   70560
tgttttagcc attgtgaatc atgctgttat gaacgtgggt gtacagatag ctcctggaga   70620
ctctgctttc cattttttg gctaaatacc cagaaatgga gttgcttta cattccaatt   70680 ttaatttaaa acattcatat cattgagtgt tttacttaat agtatagtag ttaacaaact   70740
taataaaata gtattttggt aataatttgc tggtagtcca ttgttcagtt ttttttaggta   70800 aattacacag gacatttcaa gtggacatga acatcttgt gatgtggaat catgccccaa    70860
gctgatggct aaacatatga aataccatac cctaaattta gtagatttag tctttgcaat   70920
ttaggagata acctgttata ttgttaggtt tttgtcgaaa agctttgtcc tcatatttcc    70980
aacttgctgt aaaatttgtt tgtgaagaca aatattttg tatgggtttt ttcttttca    71040 tattaaaaag aaatgtccac attggaattt ttttggagtt tttagagcta atagagcttt   71100
tcataatgta gtgggaatga gtgatcagta agctcttagc agtttccatg cgtgcatttc   71160
tgtgccttga aataaatgac agatgagtac atttgtgttc tgtgtgtaaa atgtgctctt   71220
tcctcattgc acttccatgt tggagggctt gtctcttggt gatcacactt caaaattctc   71280
acagcccccc ttgaaccgtt taggtgttag acggtaccga caaccagtat ttgggcctgc   71340
agattggaca gccccaggat gaagatgagg aagccacagg tattcttcct gatgaagcct   71400
cggaggcctt caggaactct tccatgggta tgtggactac aggtgatgcg ctacaaagtg   71460
gtttgtattc agacctggac atcttaatta tatctttgct tccaagaaga agtcctttga   71520
tactgttttc tgagttctga atagctgatg aaaatgacca attgaggaat aatcatactt   71580
tttcttgatc taaatcttat acttttgagt tatcttagca taaatgtata attgtatttt   71640
aagtggaaat ttgtcactta atcttgattt ctctgttttt aaagcccttc aacaggcaca   71700
tttattgaaa aacatgagtc actgcaggca gccttctgac agcagtgttg ataaatttgt   71760
gttgagagat gaagctactg aaccgggtga tcaagaaaac aaggtgaggg acataggctt   71820
gagacgactt ggtgtttctg agcttgtgtg aggatttaaa atcgccctgg ctactgtcta   71880
ctttattgct ttcccatccc tgggcccttta aatttcccct ttaaatacca gctcttccca   71940
ggcctgttgt tttctgcctt tccaggtact acccacagcc ttgagaattg cctgagttct   72000
gcctcctttg agagtgtgcc ccagacaaat ctattctgta ctgaatgttt ccttgtctga   72060
tttcttggat cattcatttg atggttgcgt atggcctgca acgtttcttg ttttggttct   72120
actgaactgt tctaaaagtc tctcttcata ttatcttttt acatgtaaat gtaactgtct   72180
```

```
tcactttaa ttcctcaagg acaaggaata gcgtttcaca gttcgtccca tcaatcagaa   72240
ttatagcctt tggcatctcc ctatctacca ggcccactc ctcttagatt tgggcttccc    72300
caggctgttg cctttcccca agtagcttct gcttgtcctg tagaagacct ttcatgcttt   72360
gcttctgcag cagccgttcc tgaatgccta gtgtcaactg ccttcttacc acgcccaccc   72420
tccctgcatg ctgcatttat cccctgccac agccctgtga ccctgtgtcc tgctgcctct   72480
gacttgtctg tttctgcttg gccatggtct ctgtgaggtc aggtgtgcat atgggcacaa   72540
accagggcat ctcttatcc ccagcacctg gcttaagtgc tgctctggaa ctatctgttg    72600
aatgaactaa tgcatgaatg tattgttgag tatgagacaa acaagtgtca ttgtctcctt   72660
tctagccttg ccgcatcaaa ggtgacattg gacagtccac tgatgatgac ctgcacctc    72720 ttgtccattg tgtccgcctt ttatctgctt cgttttgct  aacaggggga aaaaatggtg    72780
agtacaaaag gggatgtgca cagttgaagg aaataactag gtttcagagg tcagcttggt   72840
ggcctgtttt tgccttgcgt gcagcagagg aagtagaatc tgaggatgag tttggttttc   72900
actagccgag gggagggagg aaatgatggg agcaggtagg ttattgggtc tggttttgtt   72960
catttgaaaa caatctgttg tttgaggctg aaggtggctt gggtgatttc ttggcagtgc   73020
tggttccgga cagggatgtg agggtcagcg tgaaggccct ggccctcagc tgtgtgggag   73080
cagctgtggc cctccacccg gaatctttct tcagcaaact ctataaagtt cctcttgaca   73140
ccacggaata ccctggtatg ttaaaagttc acatcttatt ttctcagatt taatcattat   73200
tgtaaaaact atttcagtat tgactatttt agttttagag cagtaagtgt tttgagttca   73260
tttgggatat ttgacctgcg ttgtagctct tcagaaaaca catgaatagt gaagttcttc   73320
gtttcatggg ttccctttag atgaaaccca tagaggagaa aagtagaaac ctcagcacgt   73380
aagagccaac atatatacac atcggattta aacctaaagc acaaattgtg cctggtcgca   73440
gtggcgctga gtcgcactca gccaggccag gcattcacac tcagggtgag tgggaaccag   73500
gactggctga ggcagcagtg gacccaagtc tccatcgcgc ccatgcttac tatggagcct   73560
tctcgttctc tctttttctt tgggtgagag ggtacacttg tgtttttgaa tttatatgag   73620
gtaagtgtgt aatagggttt tttctaatct ttttaagtg  gaatctggaa ttttaatcag    73680
atttattatc tgcaaaccta gaattataat ccagaaagtc tgtggtattg aggacatatt   73740
ggcaatatga tgaatctcta attcttaaat cctgaaactt tttttttttt aatcacttag   73800
ggttattata gtgaagtcat ttctgaattt ggatcttctc ttcacacctc tttttctctt   73860
tcctgagaat taagcttttg tttcgagtta gaaagttgat agtagggaat tgttccatgg   73920
ctgagcaatt tatctccaca gaggaacagt atgtctcaga catcttgaac tacatcgatc   73980
atggagaccc acaggttcga ggagccactg ccattctctg tgggaccctc atctgctcca   74040
tcctcagcag gtcccgcttc cacgtgggag attggatggg caccattaga accctcacag   74100
gtaacggcca gttttttcagc tgtgtttttt ctagttatgc ttactaaggt ttaagtttag   74160
atgatgatgt ttgttgcttg ttcttctggt taggaaatac atttcttg  gcggattgca    74220 ttcctttgct gcggaaaaca ctgaaggatg agtcttctgt tacttgcaag ttagcttgta   74280
cagctgtgag ggtgagcata atcttctgtg gaaccatttc ttcacttagt ggacattta    74340 tcattgctac aattaaaatt ggagcttaat aggaaatatt tccatgcact ctaaagctgt   74400
aaccagtaat acccaccatg tatccatctc tcagctttag aaagaaaacg ttgccagtaa   74460
agttaatgct tcataaactt cagtttaagt tctaattctc agaatatttg tttgaaatag   74520
acctcttcct aaaggatata tttagaaata acctatcatt aagtgtaaag tctgttgaat   74580
```

```
atgctgggca cggtgactca cacctgtaat ctgaccactt tgggaggcca aggtggaagg   74640
attgcttgag cccaggagtt caagactatg ggcaacatag ttgaccctgt ccctacagaa   74700
aattaaaaaa aaaaaaaaaa aaagtagctg ggtatggtgg tgcatacctg tagtctcagc   74760
tactcgggaa gctgaggtgg aggggggatt gcttgagccc cagagatcaa ggctgcagta   74820
aggcgtggtt acaccactgc cctctagcct gggcaacaga gtgagactgt ctcaaaaata   74880
atagtaataa taatcagttg aattaaaaaa aaaaaaaaa aaaccactgt gctaggccca    74940
tagtatggta agagttaaag tgagccttag ggattattta ctcaacctct gtttctgtat   75000
aaagtggaat aggctcaatt ctttaagtga tagcatgttg aacctttcca taccaactgg   75060
ctcataagtc acaactggcc agtcaacaag agtaaaaatt aactggtaaa aatcaaagca   75120
aaaaacctac aattgtcaaa tttgtgggat aactccccct tttaaaatgt catgcctgac   75180
agtaatttct ctctagtttc caggttttca gtcagttgtg tcttttttga gcagaaggaa   75240
gcatgctaag agctcaatct tgtggctagc tgggggtctt tgtgtcagcc atgcatgtga   75300
tggtgcccct gggtgcttgg ggctgcaggg gaggggtaca gcagtagggg cctgttctgt   75360
tctctcgtgc tgtggagtac atagtgacat agtggggtgg tccttggtgt aggtcccttg   75420
ttcctacccc tgggtctgag atttatttag aagtggtgtt ggggctgtgc ggcaggcccc   75480
tctgtaactg atcaatgttt gtgaagttgc tgtttgagag ttgaaaccat gacataagca   75540
gaaatggaag gaagaaagaa ccagttatgt gaaagggaca catttacttt taagcttgta   75600
tttactgaga taaagtattc ttaatcaatg ttcttgagag gtgtgggaaa aatgcaacat   75660
cctggttgca gttaaaccca gaacattgtg tgttgaagag tgacggttct caaaccgtca   75720
agacgcgggt actgagtggg actaacctgc tgtcctcttg ccttggacct tgtgttccag   75780
aactgtgtca tgagtctctg cagcagcagc tacagtgagt taggactgca gctgatcatc   75840
gatgtgctga ctctgaggaa cagttcctat tggctggtga ggacagagct tctggaaacc   75900
cttgcagaga ttgacttcag gtaagtgagt cacatccatt agatttcatg aactaagctc   75960
aattgaaagt tctgggatca cttgatgcaa ggaatgatgt tatcaagtac cctgtccatc   76020
agaaatccga gtggtttagg tagatgacag tgattttctc ctcccagtgg cttttgctg    76080 aactttgccc tatgcttgga atttattttt attttattat ttatttagag acaagatctt   76140
gctctgtcgc ccaggcttga atgcagtagc acaatcatag ctcactgaag ctttgaactc   76200
taggactcaa gtggtcctcc tgcctcagcc tcccgattag ctaggagaat aggtgtgtgc   76260
cgtcacactg gctaatattt tttgtagaaa tggggtcttg ctatgttgcc caggctggtc   76320
tcaaactcct gggcttgatt gatcctccat cttggcctcc caaagtgctg ggattacagg   76380
catgagccac tgtgcctggc ctagaatttt aaaatataag tagaagagta gatttttttt   76440
tttggtagtc ctcgtcattt aagtattctg gatagtggga ataaaagagc ttagaatttt   76500
tcatctttgt cttaaacttt taaaaaaatg tagcttatat taattctgct tgtttaaaaa   76560
gaatatactc ttcattatac tgaacctagg taagacagct ggtttatatt ttgttgcaat   76620
taaaaaacgt gagctgtggt tgcagtgagc caagattgtg gccattgcac ttcagcctgg   76680
caacagagtg agacttggcc tcaaaaaaaa aaaataaca tgagctgtgt tggcactttc    76740 atttctaag agtagttttg gctggagaag ttttctttca gtactttctt ttagaaggga    76800
aattttcctt tataatttag ggtttgtttt ttttttttcc aagccaccttt ttatagagcc  76860 cttgtgggtt atttcattta atccttagaa tgtttataaa tctgggcttg ttctcggctc   76920
```

```
cacccacaga tagggacgct gagcgtgcat gagtgggcag caagatagca ggttatggag    76980
ggcccagctc accccttctg tggcttgagc caatttttata gggcacttac agagtctttt    77040
gaaatagtat ttattttgaa gaaaaagaaa aacagtttac tgagtactgt cttattgagt    77100
ctggaattgt gagaggaatg ccacctctat ttatttaaag ccattggcct tttttgttgt    77160
tttgagtaag tgctgcccaa ggtccttcca gggcacctgg atgagcctgc tctggagcaa    77220
gctggcggta agtgtttact gagtaactaa atgatttcat tgttaaatgt gctcttttgt    77280
taggctggtg agcttttttgg aggcaaaagc agaaaactta cacagagggg ctcatcatta    77340
tacaggggta agcggtttat ttttgtgaga tgctgttttta ccttcaagaa ggtgaaagtg    77400 aggcttttcct tgtggaattt ctctaaatgc attcgtcatg ttttagatgt ttatttcaca    77460
gtttatatca tgaaagttat aatcttgtca tatggattta agtctagtaa tgttgagttc    77520
tttctcacta gctttccaaa atatcttacc taaaatttag tcaaatacaa gattatgttt    77580
atttttatta tccttctctc taaagctttt aaaactgcaa gaacgagtgc tcaataatgt    77640
tgtcatccat ttgcttggag atgaagaccc cagggtgcga catgttgccg cagcatcact    77700
aattaggtat ttaccaatat tttatctctt ttcctttttt ggttgaagta ctaaaagata    77760
cgagaatgga aagagaggga agaattcaaa ggatgtagag cagtattcct gaatctgagc    77820
tcatttcagc cattctattc ttaaactata atgaaaaaaa aatccaaaaa agtctaaaat    77880
tataattaaa aaaacaacaa aatactaact gtccattgta aaaagtaatg cactttcatt    77940
gtaaaatttt tggactatag agaatagtac taagaagaaa aaaaaaatca ccttcaattc    78000
tgctgccacc tggaggtaat cactgttaat attttgctat atactctatg agtttcttgt    78060
tcaaaatcag gtcaaaatta catgcaattt tgtaatctga caatttccac ttaatatttt    78120
attagcattt tcctgttatg aaacagtaat tttagttatg ggtcgttgtt ttgctatgcg    78180
gttgggataa aatttttatat acttttttttg gcaattactt attatacata aatgtttgtg    78240
tatagttttc ttttctctgag aattcctgga agttgagtta ccaggcccgg ctttgaattt    78300 ttttttttttat tttttttttttg agacagagtc ctgctctatt gtccaggtgc tatctcggct    78360
cactgcaacc tctgtctccc tggttcaagc gattctcctg cctcagcctc ccgagtagct    78420
gggattacag gggcacacca ccacgcccaa ttaattttttg tattttttagt agagacaggg    78480 tttcacgata ttggccaggc tggtctcgaa cttctgaccc cgtgatccac ctgcattggc    78540
ctcccaaagt gctgggatta caggcgtgag ccatggcgcc tggccaggct ttaaatttaa    78600
aacaaatctt ctaatagctt tatggaggtt ataatttaca tttcttgaaa tgtactcact    78660
ttgagtgtat agtaaactcc aatttttatca catttctgtc accccaaatg tatccttgtg    78720
cccatttgct gtaacctccg gttcctgccc caactcctag gcagccactc atctattttc    78780
tgtcccttaa gatttgtgtt ttcgccaggc gctcatgcct gtaatcccag cactttggga    78840
ggccgaggtt ggtggatcac ttgaggtcag gagttcgaga ccagcctggc caacatggtg    78900
aaaccttgtc tctactaaaa atacaaaaat tagtcggatg tggtggcaca cgcctgtaat    78960
cccagctact cgggaggctg aggcaggaga atcacttgaa cctgggaggc ggaggttgca    79020
gtgagcagag atcgcgccac tgccttccaa cctgggcaac agagagagac tgtctcaaaa    79080
caaacaaaga tttgtatttt ctggacattt tatagtactg gggtcatagt atagatggac    79140
ttttgcattt ggcttctttt acttaattgt gagattggtt cttgttgtag catgtatcag    79200
tagtttgttc attttttattg gcgaaagtat tctattatat gaataatacc atattttatc    79260
tatccatcag atggatatta tagagttcat gttttggcta atttatgaat tatggtactg    79320
```

```
tgaacatttg cctgcaagat tttgtgtaga catgtcttca tttctcttga gtagatcacc   79380
tagaagtgga tttttaaata attttggtac ttactgtgaa actgctcttc aaaaacatac   79440
cattgttcct tccttccttc cttccttcct tccttccttc tttccttcct cccttcctcc   79500
ctcccttccc tacttccctc tcccttccc tttcccttcc ccttttccct tccccttccc   79560
gcctgcctgc ctgcctgcct tccttccttc cttccttcgt ttctttctac atatacacat   79620
ttttttaaat ttcaatggtt tttggggtac aagtggtttt tggttacatg gctgaatttt   79680
ggttacatgg tgaagtctga gattttagta cacctgtcac ccgagtagtg taccttgtac   79740
ccaatatgta gttttttgtc cctccacttc cagccttccg ccttgtgagt ctccaatgtc   79800
cattatacca cactgtatgc ccttgcgtac ccacagctca gctcccactt ctgagaacat   79860
atagcagaaa catgccaaag tatactccca ctaccagaat gtgattgtgc ctgattcttc   79920
tcaccagtac aaatatttca aaaaagtta aatatgtatc agttttttgg gcagaagttg   79980
atacttctct ttatttattt atttttttg agatagggtc tcattctatg atgcccaggc   80040
tggagtgtgg tggtgcgatc tcggctcact gcagtctctg cctcccaggt tcaagtgatt   80100
cccacgtcag cctcccagga agctggaatt acaggcgagg gccaccactg ccagctaatt   80160
tttgtatttt ttggtagaga tggggtttca ccatgttggc cagactggtc tcaagctcct   80220
gacctcaagt gatccacctg ccttggcctt ccaaagtgct gggattacag gcgtgagcta   80280
ccacacccgg ctgatatttc tttttaaaat aacttacctt cttttgaaag taatacatgt   80340
ttaatgaaca gaatttaagg aaaatataaa aaaacgaaat aatctttgta atcaaactac   80400
tgaaaagaaa accaaagtta cattttggtg catattcttt ttcattttca tcattgtaat   80460
ttgcatttct ttgattactt gtgagacact cctttcattt acttaatagg tttatatgac   80520
ttgcctattc agagattttg cagctttacc attttctgca aatgatagca acttcttttt   80580
gtttgtttgt ttgtggagac agagtctcgc tctgtcactc aggcaggaat gcagtggtgg   80640
aatcttggct cattgcaact attgcctcct gggttcaagc gattttcctg cctcagcctc   80700
ccaagtagct gggattacag gagtgtgcca ccatgcccgg ctaattttg tatctttagt   80760 agagatgggg ttttgccatg ttggccgggc tgatcttgaa ctcctggcct caagcggtcc   80820
ccctgtctcg gcctcccaaa gtgctgggat tacaggcgtg agccaccgta cccagccagt   80880
agttacttct tatattctag aaaaaattct actcatgatc aagtctccat gaggaaagag   80940
actttaattg aagatcatgg ggcttgcaga ccaatatgat aaaatagttc attgtttcta   81000
aaagtattac tgagtgttga tggcagatat gaacccttt gttttgtag aaaatgtta   81060 cccgtattct ccatttgaat tcagtttaga tttgttagga atcgcagctt aagctttgcc   81120
atctgggagt gtttgggaca gttttgcaga caaaattgca aaagtgccta aggaatgcag   81180
ctggcattca gacctgctct gtgctcagta ctctgtggac agacactgtt cagcacttgt   81240
tgatcagaag gtttagaaag agaactttca aagttggttt ttaattaaag catttaatag   81300
tgtaaataga aagggattaa attttatgac agacaaaaga aagtacagca cccagctggg   81360
cgtgggggct cacgcctgta atcccagcact atgggggggct gaggtgggtg gatcacgagg   81420
tcaggagttc aagagttcaa gaacagcctg gccaaggtga tgaaccctg tctctactaa   81480 aactacaaaa attagccggg cgcggtggca ggcgcctgta atcccagcta ctcaggaggc   81540
tgaggcagga gaatcacttg aacctggacg gcagaggttg cagtgagcca agattgcacc   81600
attgtactcc ggcctgggcc acagagtgac attctgtctc aaaaaaaaaa aaaaagaaa   81660
```

```
aaaagaaagt acagcaccca gttatgtccg agtgggtgca tgagagtgac cctgagattg   81720
gagacaacgc tgtcacgtgc ttgaagaacg ccacctgaga aaggggggcga gaagtggtgt   81780 ccgctggtaa ccagaggtgt tggcttagcc atctgcaggg aggagggtgg tctatcacag   81840
gtgagtttca tctactttct taagcaaatt aaccttactt ttgtgttagg cttgtcccaa   81900
agctgtttta taaatgtgac caaggacaag ctgatccagt agtggccgtg gcaagagatc   81960
aaagcagtgt ttacctgaaa cttctcatgc atgagacgca gcctccatct catttctccg   82020
tcagcacaat aaccaggtat gctgacccag tggcatcttc acattgtcgg gaaaatgccc   82080
tttcctgatg cctttcttta ggctttaatt gaaaacattt tattttctag aaaaaagctt   82140
cagctcagga tgtttgagtg taggtcagtc ctttgatagg atattatcat tttgaggatt   82200
gaccacacca cctctgtatt taagctctgc acaatcact cagctgtgac actgtaaatc    82260
tcttaatagt ttattacatt ccatgtgctg acagttgtat ttttgtttgt gacacttacg    82320
tattatctgt taaaacattt tcactttagt tgtgttacct ttaaagagga ttgtattcta    82380
tcatgcctgt tgattttttg gtgagcgggc tattaaagtc agtgttattt agggttatcc    82440
actagttcag tgatttgcga gattatcatt cacatttatt gtggagcttt tgaatatcgt    82500
gtcaaatggc cacatatatc ccattcttat ctgcttctta ggtgagtggg acacagtgct    82560
ttaatgaagc tataatcttc agaattctag cttgcagaga agattgcaga agtgataaga    82620
cttgtgcttt ttaattttgt ctttttaaatg ttattttaaa aattggcttt atatgatact   82680 cttttttttct gctgagtaac agtgttttac aaaacttgga ctaaatgact tctaagctta   82740
aatgatcact tgatgctttt tttctgaatt aggaactcag cttatcaaat atcaaagtca    82800
taattcctga ataaataacg tcttttttca tgtaaagact gctttaaaaa acacatggaa    82860
ggctgggtgc ggtggctcac gcctgtaatc ctaacacttt gggaggccca ggtgggcagg    82920
tcgcttgagc tcagggggttc aagaccaccc agggcaacat ggcaaaaccc acctctactc    82980 aaaatacaaaa aattagccag gcgtggtggc gggcccctgt aatcccagct actcgggagg    83040
ctgagggatg agaatcactt gagccccgga ggcagaggtt gcagtgagcc aagattgtgc    83100
cattgcactc ccagcttggg ctacagagtg agactctgtc tcaaaaaaag acacacacac    83160
aaacaaaaaa aacatggaga cattttttttg gccaccttaa tatttcccct cagataattt    83220
cctttgttta aactcagaac tggcattttc tctcttggag aagattcagg acaaatactc    83280
ctttaagata agtagaagca gtgaaagagg atttgattat caggaatttg ataagcttag    83340
aataaattgt tgcttcttaa tgtcatttca gaagatgaat atttattaat agatgccaac    83400
tgagatatca ttaaaattga ttactaacta ctacttggaa aagtctccca gttccaaact    83460
tcagcaggcc tcttgacaat tcagctgtgg tcaattgggt cttgcgtgat agatacaatg    83520
accaattgtg cagcagagtg tgctgcttag ctgcctattc tgttagcatt catgtgttaa    83580
cttaaaatca taatctcctt agttttgttg agtgtctccg tggacaagac actgtgaggg    83640
atacaaaatc agattggctt tattcaaacc actggggtat tataattcat ttataattta    83700
ttttattttt tgcctttttt ccatgtgttc taaaggaatt agagtttgta tataactata    83760 atggggggata gaaattgaca tgtgccatga agggaatgca aaaagtgcc gtgggagatg     83820 agaagtggag aaaggaattt ctttttttctt ggaagcagga ataacttcat gaagcatgta    83880
tttcaactta aacagatagt aggcaacgct gtaaggggag tatggctgca gcaaaagtgt    83940
tcggggcaga ctgggaggaa gggagggaat aaattcagcc attgttatgg aataatgatc    84000
aaaatttatt ttcagcccgt ttcacttaaa agttgagact gcttaacttt ttttaatctt    84060
```

```
taatcttaaa cttttaaatg ccatttgatc tttaaaaata tatgttttaa tagtgtattt    84120
taagtctcta tattttgtt attagaatat atagaggcta taacctacta ccaagcataa    84180
cagacgtcac tatggaaaat aacctttcaa gagttattgc agcagtttct catgaactaa    84240
tcacatcaac caccagagca ctcacagtaa gtctctttct tgatcggtct tactgacatt    84300
gtaatagttt ttggtagctt gtatggccag ttagttgtat ggtcatctta cggtgaggtg    84360
cttgtcttac agctcttact tatccatgag gcttgctaag aaattgtgct tctgtgaaaa    84420
gaatctcagc ttactccagg aatgtaaatg actatgtttt ttctgattat taaagtaata    84480
cacgcccaaa ataaaaaaat tcagccaatt taggaagaca caacaattaa aataagccag    84540
gcatggtggc tcatgcctgt aatcccagca ctttgggagg ccaaggttgg gggctcactt    84600
gaggtcagga gtcggatacc agcctggcca acgtggtgaa accccatctc tactaaaaat    84660
acaaaaatta gctgggcgtg gtggcgggcg cctgtaatcc cagctactca ggaggctgag    84720
gcaggagaat cgcttgaacc tgggaggtag aggttgcagt gagctgaggt caagccactg    84780
cactccagcc tgtgcaatag agcgagactc tgtctcaaaa aaaaaaaaa aaaagaaaa    84840 gaaaaaagta aactactgtc acctgcattg gtaatgtatc agaagtttaa aatgtctaga    84900
ttataattaa ctcagtgacc tggtaatata tactaaggga aaaatattta taatttacat    84960
ttttacattt ttattttttt aatttttatta tttttttttt gagacagagt tttgctcttg    85020
ttgcccaggc tggagtgcaa tggcatgatc tcagctcacc acaacctcca cctcccgggt    85080
tcaagcaatt ctcctgcctc agcctcctga gtagctggga ttacaggcat gcaccaccat    85140
gcccggctaa ttttgtattt ttagtagaga cagggtttct ccatgttggt caggctggtc    85200
tcaaactccc aacctcaggt gatccgcccct cctcgacccc ccaaagtgct gggattacag    85260
gtgtgagcca ccatgcctgg ccttacattt ttataataag aatttatgtt gctgacatta    85320
gaaaagaacc ataatatcca agaatccaag aataattaaa ttatgtacat atgctagtat    85380
atagtgtgat gctttggaga attttttaaca atatggagat gtataatctg gattgtaata    85440
ttgagtgaaa aaaggcagaa tacaaacctg gtgggggtat agtcggattt cagttaagaa    85500
aaataatatt tacatatata catttctcac actggcagat aatcaccaag ataaattttg    85560
ggattgtgga tgatttttt cttctttata tttttcagat attctcaaat tttctaaaat    85620
gagcaagtat aacttttgtt atcagaaaaa aataatatac aaaagtaatg ttaatttgct    85680
ggtgaccagg ttaaaccttt ttattttttat tttttgagat ggaatctcac tctgttgccc    85740
aggctagagc acagtggcat gatcttggct cactgcagcc tccgcttcct gggttcaaat    85800
gattctctgg ccccagcctc ctgagtggct ggaattacag gcgtgtggca ccacctgg    85860 ctaattttg tatttttagt agaggtaggg tttcaccagg ttggtcaggc tggtctcgaa    85920
ctcctgacct cgtgatccac ccacctcggc ctcccaaagt gctgggatta caggcgtgag    85980
ctactgcgcc cagccagacc ttttattttt atttgacaaa agaaatactt ccatgttata    86040
gaagactaaa tattgtttgg gctgtctgca gtatggtctt cccttgattt gttcaaaata    86100
tcgtaaactt tgcttattta ttttattgt ggccgactgt gtcgggcact gttgtaggct    86160
tgggatggaa aaacaggatt cctgccctta gggtttctgc aggctggtca gggagacgat    86220
gtggtaagct ggagctcagc tcctaaggat gtgcaggggc agttgagagg cggaagggtg    86280
ggagatcatt ccagggtgtg ggcagcacag gaacctctct tcattgggat ataattgcca    86340
ttctgataac acgtgtttga ggtgtctaaa gtaggaagtt gtaccatggt gggacagata    86400
```

```
tcctgtggtt atcatacaca gatctcagtt ttcttctcat tgtttgtact ttttataaag   86460
ggtaacagga gatataattc aataaacctt tgtggtgttt gggtgtgatt ttattgtttc   86520
tttcttctca gtttggatgc tgtgaagctt tgtgtcttct ttccactgcc ttcccagttt   86580
gcatttggag tttaggttgg cactgtgggt atgtattttc ctcagtatat attaatagtt   86640
gtctacaaca gtatgacata aacatagtta ttaggatgcc ctttttcttt cttttttaagt  86700 cttttatcaa tttggctttt tggaaaaata tctgatggaa tacttgtttc tgctatatta   86760
gctgtgtgag actagtgaca ggagctgtgg gaaatgaatg ccaaatgttc ttaggcattg   86820
atgggaattt cagggtgtgg tcttcaagtt catttaaggg aattttcata tgctggcaaa   86880
aggcttttct cattagcttg actctttcca aaattatttg ctgtgaatta aagtttagg    86940 aacctttttt cacttaattg tgacctagca tacgaaatgg tgatgattta ggaactactg   87000
ttcttgtatt aacagctttt atttaaaaat gattttcctc cagtagatgg ccctactagc   87060
atctgggaaa taatttcaag tcttctccag cattcaggaa taggcttttca ttttgtgtat   87120 caattactga gaatgatttt ggtgactcac atcacatttg agaagtaaac ctgcagattt   87180
cttgtgtgtg tcagcaaatg accaactgat atttgcttga agtggattac attatctgct   87240
ctagaatgat tgctttccca ccttcctcac atacagactg agcagctacg gtttctaatc   87300
ataggtctgg cactagactt cacttctggg caactttggc attggagtaa aatgtattaa   87360
tttaaagaaa gttaaaaatc cgttcaagta aacatacagt tctaatactt tttacaattt   87420
aaaatataga tttaaatgat aaaataaaaa agaaaatatg ggtagacacc ataatcctcg   87480
tttctgcatc tgttcacaag gggttgatat ttatgagttc tattctccat atccattcta   87540
tgttctctta atgctcagtc agcacctcag gtggttggag ttcaatgctt ggtagtttga   87600
cttacactgt cttttctagg ggattgagcc ctgggtagtc ctgcttattt gaggttgcaa   87660
tttgtctttc aataactttt actacaagat atggcgtgtt aaaggatacc attggggaac   87720
caacataata atatcaggaa aactaaccac gtcagacctg ccccattgtg tatcaagtac   87780 actattttc catagtaata aagagttcac cccagccaat tctcttttat tttgtgcctg   87840
tttactcaat ggcattaaca tgcccaaatg tctgggtagc tgtctcatct ccagttcagc   87900
agaaccattg tcatatgccc tagtaaaagc attccttcat tggacactta ggccccaata   87960
ctttcattca gatctactac ctgatttcat ttctcaaatg attttttatgg agctctgatt   88020 tataggaaag atgttagttg attaaaaata aaacaatttc tgagctggta taaaatgtat   88080
tgtgacatgc cttcctcttg gaattgcaag agaaaggaag actgttgttt gcttaaaaat   88140
tgtctataat ttgactttgc aaatgtctgc ttccagagtg cctccactga gtgcctcaga   88200
tgagtctagg aagagctgta ccgttgggat ggccacaatg attctgaccc tgctctcgtc   88260
agcttggttc ccattggatc tctcagccca tcaagatgct ttgattttgg ccggaaactt   88320
gcttgcaggt actggtactg agttgaaaca gggactccag gacttggatt ttgatttcct   88380 taggggaat gggggtggtg agcatatgag gggaaaatac tataaggtca ttgccagtga    88440
tggcttgtcc cttttagtcaa atttcagatg ttacctatat gcataaacac atgcagttgg   88500
cagctgttct gtgctgagta tttttaaagta gcctcttccc aatatagccc ctcagttaac   88560
tacaagtaaa ctcattttga atttcatttt aatgggcacc atatgccagt actccctcgg   88620
gcactgggat gttaagaaag tataatgtat ggacttcatt ctcaagttag ttttagatta   88680
gagggggata cacgtaaaca aaagtgcagt ggtcacacag agtggcccta atcactctcc   88740
ttgggcagat ttatgggctg gtaggaaaga gcacaacacg gagagggtgt agcaccttgg   88800
```

```
cgatgataat ggaggatgtg gccagcaagg aagacggagt ccattgaaat tgattttggg   88860
agaagttgcc aatctccatg aaagaattgg ggcctgtgct atttgcttca gggggctata   88920
ggagagtttc gtgaaaggga ctaaaagatg agtattttaa taagatcatt catccaactt   88980
gaacatgggc tggaggagaa ggtagggaga ctcaggagat taatgttgat gctaaggcaa   89040
gataatggct ttgggactgt agggaagaca ctgattgtaa gagaatgaag gaggcagaat   89100
tgccaggcct ggttcaccaa ctgaacttcg gttgtgaaga caaagaaacc tgggatgact   89160
tcacatcctg ggcaggtgtg tggtggtgac agtcatggaa attgggaaca cagatttgtg   89220
cgggaaacat cagtttcagt ttgagtttgg cttatcagtt gaatatcagg cacagatgtc   89280
tggccaactc tcaacatagg gtcttaaatg acttcagttc cccaagcaat ttgtccttcc   89340
catgctattg gggtggagag gtaatgtctg tgcccatatc acagccagtg ctcccaaatc   89400
tctgagaagt tcatgggcct ctgaagaaga agccaaccca gcagccacca agcaagagga   89460
ggtctggcca gccctggggg accgggccct ggtgccatg gtggagcagc tcttctctca   89520
cctgctgaag gtgattaaca tttgtgccca cgtcctggat gacgtggctc ctggacccgc   89580
aataaaggta atgtcccact tgggtgctgg attcatacag ccttaatgac tatgggtttc   89640
cagactacct ttgtttagta atctgtccct tctttattct cttttttgctt taaatgaaca   89700 aaattgctca gattgtgaca ctaaatttaa catcaaaatg tgaccatgtg gatgggtgca   89760
gtggctcgtg cctgttattc cagcactttg ggagactgag gcaagtggat cacttgaggc   89820
caagagttcg agaccagcct gggcaacatc acgaaacccc ctctctacta aaaatacaaa   89880
aaattagatg ggttgggccg ggcgtggtgg ctcaagcctg taatcccagc actttgggag   89940
gccgaggtgg gcggatcacg aggtcaagag atcaagacca tcctggctaa cacagtgaaa   90000
ccccgtctct actaaaaata caaaaaaatt atctgagcat ggtggcgggc gcctgtagtc   90060
ccagctgctc gggaggctga ggcaggagaa tggcgtgaat ccgggaggcg gagcttgcag   90120
tgagccgaga tcgtgccact gcactccagc ctgggtgaca gagcgagact ccgtctcaaa   90180
aaaaaaatta gatgggcatg gtggtgcgtg cctgtaatcc cagctacttg ggaggctgag   90240
gcaagagagt tgcttgaacc tgggaggcgg agtttgcagt aagccttgat tgtgccgctg   90300
cactccagcc tgggtgacag agtcagactc tttccaaaag aagaaaaaaa tgtgaccatg   90360
tgttttatag ctcttttagt atcatcagtc actgttatcc ctaagaggga aatacctagc   90420
tttagtttta ggtttccagc attagccaag aaagctcaga attgatgttc ctggccaagt   90480
acctcattgc tgtctcctta aatcttggtt aatggctact gtcctggcta gcatagttat   90540
ggagcatttc catggttgta gaatgttctg ccaatctcag ggacagtttt gcttttctgt   90600
gaagcaataa aatcaacttc aaaacaaatg ttaactattt gtacaatgga tttaagatag   90660
accagttcac atactttttt tttttttttt ttttgagatg gagtttcatt cttgttgcct   90720
gggctggagt gcaatggtgt gatctcagct cactgcaact tctgcctcct gggttcaaac   90780
gattcttctg cctcagcctc tcgaggcaga ttacagctgg gattacaggc atgcaccacc   90840
acacccagct aatttttttg tagtttagt agagacgggg tttcaccatg ttggtcaggt   90900
tggtctcaaa ctcctgacct gaagtgatct atccgcttcg gcctcccaaa gtgttgggat   90960
tacgggcatg agccaccacg cccagcctaa gatagaccag ttcacttact gtttatatct   91020
gattactctc tcttttgcctt gtcttctacc tttaaaaatc tccctactaa cttcccattc   91080
tcctttagct gccatcagtc ttctcccttc tctgcaaaca tctctggaga gtcccagcct   91140
```

| | | | | | |
|---|---|---|---|---|---|
| cagcccacag | agcttcccac | tgctctgagg | tggaccttgt | ttgcaaggct | tctttggctc | 91200 |
| tcttggcctg | gaccctgtct | actacttcag | ccatccttcc | ttaaccctg | ctggtggttt | 91260 |
| ctgttgccac | actccatagc | agcgtttccc | gcccagatca | tgtctttaca | tctctgggca | 91320 |
| ctgctctggt | cctgcctgcc | tttccctctt | tgtatcctgc | aggctgctac | ccccatcttg | 91380 |
| agtgtcctct | tcagttggct | ttcagagggc | ctcctgggtg | ttcccttacc | cacttgccac | 91440 |
| tccccagtca | ctgggttcag | tccttcctgc | ccaccagcac | atgctttcta | ggctctgtcc | 91500 |
| taggccgtct | tctctctttg | tagtctctgg | gccagtgctg | ttctagagag | tggcagaatt | 91560 |
| ttctataacc | atggcagtgc | tccatagcta | tgccaggcaa | gacagtagcc | actaaacaca | 91620 |
| tatagctgtt | gagcccttga | aatgcagcta | gtgtgactga | agaactgaac | cccgattcgg | 91680 |
| tttaattttc | attaaattta | aatttaaata | accttatgtg | ggtagtggct | ccagtattgg | 91740 |
| gcagggcagc | ctgagagtcg | gggctgttct | cctgtcttca | gtgtctagat | gagggacctc | 91800 |
| agaggacctg | tctctggagc | tgcagttcaa | tgtagccagc | tgccccgtga | cacttacata | 91860 |
| tagctgattt | gtggatatgt | cagacacggt | gtgatgagct | cagcttttctg | tcctcctccc | 91920 |
| cacatctgcc | cctgccccat | ttaccccact | ttgtgtctta | tcaagctaga | aacaggtcac | 91980 |
| cacaagtctt | catttccact | caccaagtct | tttgtttccc | ctactaaata | ttttgcgaga | 92040 |
| agaaagtgtg | tacctttgta | ttcacataca | tgtacatgca | catatacatg | cacatatgca | 92100 |
| ggggtcccca | acctctgtta | aaaaccggac | tgcaggccgt | gcgtggtggc | tcacgcctgt | 92160 |
| aattccagaa | ctttgggagg | ccgagaccag | tgcatcacaa | ggtcaggaga | tcgagaccat | 92220 |
| tccggctcac | acggtgaaac | cccgtctcta | ctaaaaatac | aaaaaaaaat | tagccgggtg | 92280 |
| tggtggcggg | cgcccatagt | cccagctacc | tgggaggctg | atgcaggaga | acggcgtgaa | 92340 |
| cctggggaggc | ggagcttgca | gtgagccgag | attgtgccat | tgcactccag | cctgggcgac | 92400 |
| agagcgagac | tctgtctcaa | aaacaaaaca | aaacaaaaaa | aaaaaaaacc | aggctgcaca | 92460 |
| ggaagaagtg | agcaagcatt | accatctgag | ctctatctcc | tctcaggcca | gtggtggcat | 92520 |
| tagattctca | taggagcgtg | tatgagttcg | ttctcacact | tctgtaaaga | catacctgag | 92580 |
| acatataaag | aaaagaggtt | taattggctc | acagttctgc | aggctgtaca | ggcttctgtt | 92640 |
| tctgggaagg | cctcaggaaa | cttgcagtca | tggcagaagg | tgaaggggaa | gtaggcacat | 92700 |
| cttcacatgg | cccacaggaa | aaagagagaa | ggagagagag | agagagacag | agagagagag | 92760 |
| agaaaaagaa | agattgagag | ggagagagga | gggagaaagg | agagtgcctg | taggggagt | 92820 |
| tgctacacaa | aggagcacca | gggggatggt | gctcaaccat | tagaaactac | ccccatgatc | 92880 |
| caatcacctc | ccaccaggcc | ccacctccga | cactggagat | tacaattcag | catgagattt | 92940 |
| gggtggggac | acagagccaa | accatatcag | agcatgaacc | ctattgtgaa | ctgcacattt | 93000 |
| gagggatcta | ggttgcatgc | tccttatgag | aatctaatgc | ctgatgatga | tttgaggtgg | 93060 |
| aacagtttca | tcccgaaacc | atcccccgcc | aaccctggtt | tgtggaaaaa | ttgtcttcca | 93120 |
| cagaaccggt | ccctggtgcc | aaaaagtttg | gggacctctg | cacatatgca | tgcacctgta | 93180 |
| catggacaca | taatacatgt | acatatgcat | actttatatt | ctctgccact | tctggtccag | 93240 |
| actgatatac | tatctcattt | ggattactgc | actagccttt | tgttttggaa | acagcatttt | 93300 |
| ttaaaaaatt | taatttaatt | tttttgagat | agggtgtcat | tctgttgccc | agcttggagt | 93360 |
| gcagtgtcat | gatcatagct | cactgcggcc | tcgatctccc | aggctcaagt | gatccttctg | 93420 |
| cctcagcctt | ctcagtagtt | gggactacag | gcatacccac | catgcccagc | taatttttg | 93480 |
| atttttttt | tttttttgaga | cagagtctca | gcctgtcgcc | caggctggag | tgggttggcg | 93540 |

```
cgatctcagc tcactgcaac ttctgcctcc caggttcaag tgattctcct gcctcagcct   93600
cccgagtagt tgggattaca ggcgcctgcc accacaccca gctaactttt tgtatttta    93660 gtagagacgg ggtttcacca tgttggccag gctggtctcg aacttgtgac ctcgtgatta   93720
gcccgcctcg gcctcccaaa gtgctgggat tacaggcgtg agctaccgct cccagccagg   93780
aaacagcatt cttgagataa ttcatataat tcacccattt aaagtatata attcattctc   93840
tttagtatgc ccacagagtt gtacagccat caccagaatc agttttagaa cccataaagg   93900
aactctgtac tctttaccca aaacctccat gcctccagct gcaggcagcc actaacctgc   93960
cttctgtctc tgtgactcta cgtcttctgg acattactgt ggatgggctc atacagtcag   94020
tgagcttgtg actggtgcct tctaccaagc agggttttca gtgtagcagc ctctctgttt   94080
ttcttttttt tttaaattgt gacggaactt ctgcctcccg ggttcaagcg attctcctgc   94140
ctcagcctcc cgagtggctg ggactacagg cccatgtcac catgcctggc taattttttt   94200
tttttttttt tttagtagag atgggtttca acatgttagc cagggtggtc tcgatctcct   94260
gacttcatga tccgcctgcc tcggcctccc aaagtgctgg gattacaggc gtgagccacc   94320
atgcccggct aacctttcat ttactgtctg catttcttcc ctgatgcctt ccagtccatg   94380
cacccgattg tagccattca tcctattatg gtttaaggtg actgtcttag tcagcatggg   94440
ttgccataac aaaataccat agcctgggtg gcttcaacaa cagaatttac ttctcacact   94500
tctggaggtt gggaagtcca agatccagga cttttcgcctt gccctcatgt ggtgagggg   94560 tgaggaagct ctgtggggcc tcttatatat ggatgctaat ctcattcatg agggtctgc   94620 cctcatgacc cagtcacctc ccaaaggccc cacctcctaa taccatcacc ctggtaatta   94680
agtttcagtg tataaatttg ggggactata gacattgaaa ccataacaag cacttttcta   94740
agatcaggga gtgagtaagt agcagagcta ggacctcaat tccacatgtc agtcatcttg   94800
ccttcactct gctccatgat ggctgcctcc tagagcattg ggagtctcga tgttctatat   94860
gctctcatgt gttgtgtatt ggagatagtt gaggctttat gaatacatct ggatttgttg   94920
acttctagct ttgctggtaa ccagctgtga ccttgaataa gttacttcat ctctgagcct   94980
gtttcctctt ttagaaacag gagtttaaaa tgctgctttg ggttgggcac ggtggctcat   95040
gcctgtaatt ccagcacttt gggaggctga gatgggagga tcactggagc ttggagttcg   95100
agaccagcct gggcatcata gtgtgagatc ctgtctcctc aagaaattaa aaaattagct   95160
gggtgatgtg gcgtgtgcct gtggtcccat ctactctgga ggctgaggtg ggaggattgc   95220
ttgagcccag gaggttgagg ctacaatgaa atatgattgc accccatcct gggtgacgag   95280
tgagaccctg tctcaaaaaa gaaaaaaaaa atgctgcttt gtaccccttt catgtcatgg   95340
cgtcatggcc aacatagaat gccctggttg tttgctgttg gagggcatgg gcctgggggc   95400
tccctgaggg ctccttccat cttcaactca ttctctgtgc acctgttagg aagttgtggg   95460
ccagtcccta ccatgtatca ttgtgtgggt aaaagtaaat aaaatgtgta cagtgtctga   95520
actgtacata tcagggtcca agaacaaaat gagtgacatg ggttagctct ttttaataaa   95580
tggtaaaacc aaatattcta attttcagtt ttgttatact tccatcacat gttttttgttt   95640 ttttgttttt tgttttttgtt tttctatttt aggcagcctt gccttctcta acaaccccc   95700 cttctctaag tcccatccga cgaaagggga aggagaaaga accaggagaa caagcatctg   95760
taccgttgag tccaagaaa ggcagtgagg ccagtgcagg taggaaacag cgtggggaag   95820
ggagggacat gagtgcagca tctgtcatgt agaaacatag gatttaagta acttggtgtt   95880
```

| | |
|---|---|
| ttagagaaat aaatataata cacatcagta aagtgagaga aagtttctcc aggtgcggtt | 95940 |
| caagatatta gaaactaatg actgatgtac acagaccacc ttttggtctg aagcatttct | 96000 |
| aagtgccact ggctgacatg cagcccctac agcctccagg cttccagccc tagcatggag | 96060 |
| catcactctc ctatgcttcc ctggttgcag gtgatggctg gagaggcctc ctgattttca | 96120 |
| gtaagggaag tggtgtagat gcttaggaat agatgtagtg agtgaaaaaa ctgattctga | 96180 |
| tatgtcaaaa attctgattg gaaatggaat atttacattt ggaagagcta aaggcgagag | 96240 |
| aaagtgggga taaagtcatc tgagttggag gagcttaaac cattcacaag tttggaggac | 96300 |
| cttttttttac ccatgaaaag gtcagaacag aaggggctag gatttaggtg tgactgcagt | 96360 |
| ttattgaatt cccatccata ctgctctcgg tgggcagtgg caggggcagg agaggagcct | 96420 |
| ggcaaagcat gaagtgactg ctgctgcctc tgctatctgg gacgcctggc cacctgtctg | 96480 |
| tacagtctcc ctccagaccc attctcacgc tgtctcttgg cacccagggg ccagtgatgg | 96540 |
| ttctcccatt tgttttgtgt atatagcatt tatatcaagg ctattttattt atttatttat | 96600 |
| tttatttatt tattttttttg agacagagtc tcactctgtc acccaggctg gagtgcagtg | 96660 |
| gtgcaatctc ggctcagtgc aagctctgcc tcctgggttc aagcaattct cctgcctcag | 96720 |
| cctcctgagt agctgggact acaggtgtgc accaccacac ctggctaatt ttttgtattt | 96780 |
| tttattagtg gagacggggt ttcaccttgt tggccaggat ggtcttgatc tcctgacctc | 96840 |
| gtgatccgtc cacctcagcc tctcaaagtg ctgggattac aggcatgagt cactgtaccc | 96900 |
| ggcctattta tttattttta attgacaaaa ttgtatatat ctgtaatata caacatgatg | 96960 |
| tttgaaatat gtgtacattg gccaggcgtg gtggctcaca cctgtaatcc cagcactttg | 97020 |
| ggaggctgag gtgggcggat cacgaggtcg ggagttcaag accaaactgg ccagcatggt | 97080 |
| gaaatcctgt ctctactaaa aataccacaa aaaaaaaaa aaaaaaaaa agccgggcat | 97140 |
| ggtggctcgc gccagtcgtc ccagctactt gggaggctga ggcaggagaa ttgcttgaat | 97200 |
| ctggcaggtg gaggttgcag tgagctgagt tcatgccact gcactctagc ctgggcgata | 97260 |
| gagcgagact ccgtctcaaa aaaaaaaaa aaagaagaaa tacatatgca ttgtggaatg | 97320 |
| gctaattaac ctgtgcatca cctcacgtat cattgttttg tggtgagaac acttaaaatc | 97380 |
| tactctttca gtgattttct tgcatatggt acattgctat taactgcagt caccatgcta | 97440 |
| tacagtagat ctcttgaact cattcctcct gtctataaat gaaattttgt atccttgacc | 97500 |
| aacacattca aggttttttt tgagatggag tcttcttcac ccaggctgga gtaccatggc | 97560 |
| acgatctcat ctcactgcaa cctccgcctc ccaggttcaa gcaattctcc tgcctcagcc | 97620 |
| tcctgagtag ctgggattac aggcacatgc tactgcacct ggctaatttt tgtattttta | 97680 |
| gtagaagtgg agtttcacca tgttggccag gctggtctcg aactcctgac ctcaagtgat | 97740 |
| ccgcctgcct tggcctgcca aagtgctggg attacaggtg tgagccactg cacccggcct | 97800 |
| caagcgtttt aaaagatgct ctttttctaag gattgactgt agtacaggag gaagattgac | 97860 |
| ctgttgaaaa gcctcagcct ttacaagtgt aaaattatca gtatattact atcatctttc | 97920 |
| tgatgaatta aataaactaa ggactccaag tcaaagtct tcaaactgaa gtagaatagt | 97980 |
| tgtatatagt gcttggcact ttaatattta gtatcggttt aatgataatg tttgtgccttt | 98040 |
| tgccgtcttt aaaacatttt tacatcatcc ctgtttgatt acttggtgtg ctcatgaagt | 98100 |
| tgttggccac taaggaatct taggctcaga gaggttctgg aattggccag tggtccttga | 98160 |
| atcagctgct cctatgattc tctaactgat ttctcacaaa gcaaacaagc aatcataaca | 98220 |
| aaacaactgt gcacactgct cttcttattt tgttatttaa aaagtactta ggctctactt | 98280 |

```
atgtttgtta gtcaatttct cattacttct agttaatcaa aaggtcagag gaaatacttg   98340
aatattttca tactagaata ctttaaaaaa tcatgatttc cagtaatctc tttaaaactt   98400
ggcaagttat tttgatctaa aagtttatct tttgtgtgca tatttttaaa gcttctagac   98460
aatctgatac ctcaggtcct gttacaacaa gtaaatcctc atcactgggg agtttctatc   98520
atcttccttc atacctcaaa ctgcatgatg tcctgaaagc tacacacgct aactacaagg   98580
tatgggcctc tgcatctttt aaaaatatat atgcacacat acttacgtct aatggatagt   98640
tgatgttttt cttatgattt gtaggatgta taagccctt gagatatgag ttacatttag   98700 tttttttcaag tttgtttgtc tttcagcttt gtttatgata gcttctatca tacaggtgtt   98760
ttggattttc atattgtttg tactcacagc taagattgat tacagtgaca gagctaggat   98820
gtgcagccag gttataggg gaagtggccc tggtggagtc tggagggatc cgtgtacagg   98880
cttccttccc tcccgtgagg ctcacacaaa aatacagcaa catgctggtc ctgcaggtac   98940
cctctgccta acatgagcca caattccaga ctcacagaag aaaagcaggt gttcggcata   99000
aaccatgtgt ttcaaatagt ctgggcatgg tgagccactt gttatcagct agggaaagtt   99060
tatgtcagcg taagaaactg ttcaccagat accccccaaga gccagccttt ctgtctaggg   99120
atgttttagt ttttttagttc atttttttttt ttaacttttaa aattttctgt tcatctgcaa   99180
tttgttagat atgaagtatg tgtctaattt aattttttgtt tttggttgtc cccaataatg   99240
tttacagaag aattttttctg cactaattgg cttgagttac ttacattctc atagttctct   99300
agtttcagta gtttcatttta ttattttgtt atatcaatct atctgtctgc tcatctatta   99360
gaagcatcct tgtttttttt ttttctttttt tagacagagt cttgctctgt ccccaggttg   99420
gagtgcagtg gtgcaaccat gcctcctgc agtctcaggg ctcaagtgat cctcccacct   99480
cagctcctga gtacctggga ctaccggcat gtgccaccac acccagctaa ttttttacatt   99540 tttttgtagag acagggtctc cctaagttgc ctgggctggt ctcaagctcc tggcttaagt   99600
aatcctccct ccttggcctc ccaaagtgct gggattacag gtgtgagcaa ctgcacccgg   99660
ctacaagtat acttcttaat tattgtagct taatggtatt tatgagggga tcagttcccc   99720
tgttgttctt tagaattttc tggatattct tctttattga ttttgggatg tgaacaatag   99780
aatcaacttc tacttgtaga ttgatttagg gagaacttat acctcagatg ttaagtcacc   99840
ctgtccagaa tgtgggatgc tttcctattt gttcagaact ttttaaatta cctcagaagc   99900
acatgaaatt taaggatttt taaaaaaaac ttaaagatta tttcacatag ctcttgcaca   99960
tttcttgata aatgaatcct caggtattcc tctgtttttg ttactaatag ttacttctta  100020 tgggttttt ttcccctgaa aatcatttat caaacgtatg tggcttattt tctgaaggat  100080
gtttgataat tttggaagat atgaaagtct tcatattttta caaggtttga ggtctcttta  100140
agctgcatgg ttctcatgtc agctcccaaa gcagaagacg gcatgttgaa aaatgccgta  100200
gagaagatac ttcttttcca cctgttttca actcatatca tcttgaattt cagggcacct  100260
ttccatgctc ctagtgcttg ctatctgttt attattttcc ttcctgaata ccctgaactc  100320
cagcatgttc tgctgtaatt ctggcctccc tggcatcttg gactcctgtt tcctttgctc  100380
tgtcatcccc gcggtcagct cctgctgcgc agcttctcag ctgaagtgcg tttggagtgc  100440
ctggcgtgtc ttgctggatc tttgagtatt gcctctggtt tccttggttc cttctgctga  100500
gttgctcagc gtctccactc cccatttctt gtgtggccct tcctgcactc ctctgattcc  100560
ttttgtcttc cctggtttct tgctttggtt tcgagtctcc acagaacttt tgcagctctt  100620
```

-continued

```
ctgaagacct ggaagctttt tcatcttaat tctcatctca tgacctcttt tcccttcttt 100680
gagagctaga acttcccatg gtgaacttct cttccagaa ttccatgcct tcttttcct 100740 cccacttacc tgttgtccag gagaggtcag attgctgtgc atattggagg agaacccttt 100800
cttccctggg ctcttcatct cacatgacat caccacatca cctcgttcct tggaccctca 100860
gtggtgtcac tgctggattt ttcttttcctt tggctggcct tagggcacac ccaggttgac 100920
tagcgtagtc atggtattta gatccactca cattttcagt ttctgtgtct gtctcttgcc 100980
tgcttctgac ttcgcccaga gaaagcttct ctttcacaag ggttcttaga tttatgttca 101040
ctgagcacct tcttttctga ggcagtgttt taccaatatt tattttccta gtcagtctcg 101100
ccttaccttt cttgttatgc atgtctttgg tcctgaccca ttctctgagt ctgtaaaata 101160
gaattgctgt ataatttaat tacatgaaat cctttagaat cttaacacat cttacacctg 101220
atttaatatt ttattgtatc caaattgaac caaccctatg tgaatttgac agtgattcct 101280
cccagggatc ctagtgtata aggaatagga cttagtattt tctatttttt gatataccac 101340
ataccagata ctgattatga tggacattta acccttttt ctcattatga aagaaagtta 101400
ggaattattt cttccagtag cgccagtgta acctgaaagc ctttgaaaga gtagttttg 101460 tatagctatc tgaaaggaat ttcttccaa aatattttc cagtgctgac aacaaacacg 101520
cagacacacc ctgcaaggtg agtgtacggc ccgcacagt ggaggcatct gctgcagccg 101580
tcgatgtttg tgtctttggt tgtacattat gagatcgtga cagggccagt aaccgtgtgt 101640
tctctccttc accttcccaa ggtcacgctg gatcttcaga acagcacgga aaagtttgga 101700
gggtttctcc gctcagcctt ggatgttctt tctcagatac tagagctggc cacactgcag 101760
gacattggga aggtttgtgt cttgttttt ctccttgggt tgtggctggc acacttgatg 101820
tgcgtcttct gggctgagtt catctaggat ggagcctggt tctccagggt gcctccggga 101880
gactcctccc tgccccacgt gcttgcgtca caggacccaa gtctgactct gccttagcca 101940
tgaagtttag ggggaagttt ctatttgtat tctattttg tctgttatca tgtattagct 102000
tagacccagt ttagtttgga aaatcagtgg gtttcaaaat gtgtttgtag agtcctttat 102060
ttcttaactt gacctttca agtggaaagg ggcaaaacag acgggtaagg gggcggggcg 102120
ggaggtgtga cttgctcttt tgtgcctgag gaagtaacag agctggggtt gacagtcata 102180
ttctctgaca cagatagtct ctgacttatc tcacagaaag tcagcggcag agcctgagtt 102240
aaaagtctcg tagattttct ttttcttttt tttggtggct aatttcagtt ttatttatat 102300
ttgtttattt atttattata ctttaagttc tgggttacat gtgcagaatg tgcagttttg 102360
ttacataggt atacacgtgc catgatggtt tgctgcaccc atcaacccat cacctacatt 102420
aggtatttct cctaatgtta tccctccccc agtcccctca ctcccatgg ccccggtgt 102480 gtgatgttct cctccctgtg cccatgtgtt ctcattgttc aatttccact tgtgagtgag 102540
aacatgcggt gtttggtttt ctgatcttgt gatagtttgc tgagaatgat ggtttccagc 102600
atcatccatg tgcctgcaaa ggacatgaac tcatcctttt ttatggctgt atagtattcc 102660
atggtgtata tgtgccacat tttcttaatc cagtctatca ttgatggaca ttcgggttgg 102720
ttccaagtct ttgctattgt gactagtgcc acaataaaca tacatgtgca tgtgtcttta 102780
tcgtagaatg atttataatc ctttgggtat atgcccagta atgggattgc tgggtcaaat 102840
ggtatttcta gttctagacc tttgaggaat cgccagactg tcttccacaa tagttgaact 102900
aatttacact cccaccaaca gtgtaaaagt gttcctattt ttccacaacc tctccagcat 102960
ctgttgtttc gtgacttttt aacgatcgcc atcctaactg gcgtgagatg gtatctcatt 103020
```

```
gtgattttga tctgcatttc tctaatgacc agtggtgatg agcattttt  cgtatgtctg 103080
ttggctgcat aaatgtcttc ttttgcgaag tgtctgttca tatcctttgt ccattttttg 103140
atggggttgt ttgctttttt ttcgtaaatt tgtttaagtt ctttgtagat tctggatgtt 103200
aatcttttgt cagatgggta gattgcaaaa attttatccc attctgtagg ttgcctgttc 103260
actctgatga tagtttcttt tgctatgcag aagctcttta gtttaattag atcccgtttg 103320
tcaattttgg cttttgttgc cattgctttt ggtgttttag acatgaagtc tttgcctatg 103380
cctatgtcct gaatgttatg gcccaggttt tcttctagga tttttatggt cctaggtctt 103440
atgtttaagt ctttgatcca tcttgagttg atttttgtgt aaggtataag gaagggtcc  103500
agtttcagtt ttctgcatgt ggctagccag tttcccaac  accatttatt aaatagggaa 103560
tctttttcccc attgcttatg tgtgtcaggt tgtcaaaga tcagatgatt gtagatgtgt 103620
ggtggtattt ctgaggcctc tgttctgttc cattggtcta tatatctgtt ttggtaccag 103680
taccatgcag ttttggttac tgtagtgttg tagtatagtt tgaagtcagg tagtgtgatg 103740
cctccagctt tgttcttcta gcccaggatt gtcttggcta tgcaggctct tttttggttc 103800
catatgaagt ttaaaatagt tttttccaat tctgtgaaga aagtcagtga tagcttgatg 103860
gggggatagc attgaatcta taaattactt tgggcagcaa ggccatttc  acgatattga 103920
ttcgtcctat ccatgaacat ggaatgtttt tctatttgtt tgtgtcctct cttatttcct 103980
tgagcagtgg tttgtagttc tccttgaaga ggtccttcac atcccttgta agttgtcttc 104040
ctaggtgttt cattcccta  gtagcatttg tgaatgggag ttcactcatg atttggctct 104100
ctgtttgtct gttattggtg tataggaatg cttgtgattt ttgcacattg attttgtatc 104160
ctgagacttt gctgaagttg ctaatcagct taaggagatt ttgagctgaa ccaatagggt 104220
tttctaaata tacaatcatg tcatctgcaa acagggacag ttttacttcc tctcttccta 104280
tttgaatacc cttttattgct ttctcttgcc tgattgcgct ggccagaact tccaatacta 104340
tgttgaatag gagtggtgag agagggcatc cttgtcttgt gccggttttc gaagggaatg 104400
cttccagttt ttgcccattc agtatgatat tagctgtggg tttgtcataa atagctctta 104460
ctatgttgag atacgttcca tcgataccta gtttattgag agttttttagc atgaaaggct 104520
gttgaatttt gtcaaaggcc ttttctgcat ctgttgagat aatcatatgg ttttgttgt  104580
tggttctgtt tatgtgatgg attacgttta ttgatttgcg tatgttgaac cagccttgca 104640
ttccagggat gaagctgact tgattgtggt ggataagctt tttgatgtgc tgctggattc 104700
agtttgccag tattttattg aggattttca catcgatgtt catcagggat attggcctaa 104760
aattctcttt ttttgttgtg tctctgccag gctttggtat caggatgatg ctggcctcat 104820
aaaatgagtt agggaggatt ctctctttt  ctattgattg gaatagtttc agaaggaatg 104880
gtaccatctc ctctttgtac ctctggtaga attcggctgt gaatccatcc tggactttt  104940
ttggttagta ggctattaac tattgcctca gtttagaac  ctgttatcag tctattcaga 105000
gattcagctt ttttctggtt tagtcttggg agggtgtatg tgtccaggaa tttatccatt 105060
tcttctagat tttctagttt atttgggtag agatgtttat agtattctct gatggtagtt 105120
tgtatttctg tgggatcggt ggtgatatcc cctttatcgt ttttattgag tctatttgat 105180
tcttctctct tttcttcttt attagtcttg ctagcggtct acctatttta ttgatctttt 105240
caaaaaacca gcacctggat tcattgattt ttttggagg  gttttttttc gtgtctctat 105300
ctccttcagt tctgctctga tcttagttat ttttgtgtctt ctgctagctt ttgaatttgt 105360
```

```
ttgctcttgc tttttctagtt cttttaattg tgatgttagg gtgttaattt tagatctttt    105420
ctgctttctc ttgtgggcat ttagtgctat aaatttccct ctacacactg ctttaaatgt    105480
gtcccagaga ttctggtatg ttgtgtcttc gttctcattg gtttccaaga aaattttat     105540
ttctgccttc atttcgttat ttacccagta gtcattcaag agcaggttgt tcagtttcca    105600
tgtagttgtg tggttttgag tgagattctc aatcctgagt tctaatttga ttgcactgtg    105660
gtctgacaga cagtttgttg tgatttctgt tcttttacat ttgctgagga gtgttttact    105720
tccaactatg tggtcagttt tagaataagt gcaatgtggt gctgagaaga atgtatgttc    105780
tgttgatttg gggtgcagag ttctgtagat gtctattagg tccgcttggt ccagtgctga    105840
gttcaagtcc tggatatcct tgttaatttt ctggctcatt gatctgccta atattgacag    105900
tggggtgtta aagtctccca ctattaccgg gtgggagtct cttttgtaggt ctctaagaac   105960
ttgcttcatg aatctgggtg ctcctgtatt gggggcgtgt atatttagga tagttagctc    106020
ttcttgttga attgatccct ttaccattat gtaatggcct tctttgtctc ctttgaactt    106080
tgttgattta aagtctgttt tatcagagac taggattgca atccctgctt tttttttgct    106140
ttccatttgc ttgttagatc ttcctccatc ccttttatttt gagccaatga gtgtctttgc   106200
atgtgagatg ggtctcctga atacagcaca ccaatgggtc ttgactcttt atccaatttg    106260
ccagtctgtg tcttttaatt ggggcattta gcccatttac atttaaggtt aatattgcta    106320
tgtgtgaatt tgatcctgtc attatgatcc tagttggtta ttttgcccgt taactgatgc    106380
agtttcttca tagcgtcagt agtctttaca atttggcatg tttttgcagt ggctggtact    106440
ggttgttcct ttccatgttt agtgcttcct tcaggagctc ttgtaaggca ggcctggtgg    106500
tgacaaaatc tctgcatttg cttgtctgta aaggatttta tttctcgttc acttatgaag    106560
cttagtttgg ctggatatga aattctgggt tgaaaatact ttttttaaag aatgttgaat    106620
attggctccc actctttttct ggcttgtagg atttctgcag agagatctgc tgttagtctg   106680
atgggcttcc ctttgtgggt aacccgacct ttctctctgg ctgcccttc cttcatttca    106740
atcttggtgg atctgatgat tatgtgtctt ggggttgctc ttctcgagga gtatctttgt    106800
ggtgttctct gtatttcctg aatttgaatg ttggtctgcc ttgctaggtt ggggaagttc    106860
tcctggataa tatcctgaag agtgtttttct aacttggttc tattctcccc atcactttca   106920
ggtacaccaa tcaaacgtag atttggtctt ttcacatagt cccatatttc ttggaggctt    106980
ggttcatttc ttttcactct tttttctcta atcttgtctt ctcgctttat ttcattaatt    107040
tgatcttcaa tcactgatat cctttcttct gcttgattga atcggctgtc gaagcttgtg    107100
tatacttcac aaaattctcg ttctgtggtt tttagctcca tcaggtcatt taagctcttc    107160
tctacactgg ttattctagc cattagtcta acatttttttt caaggttttt agcttccttg    107220
tgatgggtta gaacatgctc ctttagctcg gagaagtttg ttattaccga ccttctgaag    107280
cctacttctg tcaattcatc aaactcattc tccatccagt tttgttccct tgctggtgag    107340
gagttgtgat cctttggagg agaagaggtg ttctggtttt tggaatttc agcctttctg    107400
ctatggtttc tccccatcat tgtggtttta tctacctttg gtctttgatg ttggtgacct    107460
acggatgggg tttggtgtg ggtgtccttt tgttgatgt tgatgctatt cctttctgtt     107520
tgttagtttt ccttctaaca gacaggcccc tcagctgcag gtctgttgga gtttgctgga    107580
ggtccactcc aggccctgtt tgcctgggca tcaccagcag aggctgcaga acagcaaata    107640
ttgctgccta atccttcctc tggaaacatc gtcccagagc acgaaggtgt ctgcctgtat    107700
gaggtgtttg ttggccccta ctgggaggtg tctcccagtc aggctacatg ggggtcaggg    107760
```

```
acccacttga ggcagtctgt tcattatcgg agcttgaatg ccgtaccggg agaaccactg   107820
ctctcttcag agctgtcagg cacgtatgtt taaatctgga gaagctgtct gctgcctttt   107880
gttcagatgt gcccttcccc cagaggtgga atctagagag gcagtaggcc ttgctgagct   107940
gcagtgggct ctgcccagtt cgagcttccc tgctgctttg tttacactgt gagcatagaa   108000
ccacctactc tagcctcagc agtggtggac acccctcccc cagccaagct cctgcatccc   108060
aggtcgattt cagagtgctg cgctagcagt gagcaaggcc ccatgggcgt gggacccgct   108120
gagccaggca caggagagaa tctcctggtc tgctggttgt gaagactgtg ggaaaagtgc   108180
agtatttggg caggagtgta ctgctccttc aggtacagtc actcatggct tcctttggct   108240
tggaaaggga agtcccccga ccccttgtgc ttcccaggtg aggcaacacc ccgccctgct   108300
tcggcttgcc ctccgtgggc tgcacccact gtccagcaag tcccagtgag atgaactagg   108360
tacctcagtt ggaaatgcag aaatcacctg tcttctgtgt cgatctcact gggagctgta   108420
gactggagct gttcctattc ggccatttg gaagcatccc ttgttttttg aggtggagtc   108480
ttgctctgtc gcccaggctg acgtgcatcg gcacaatctc ggcccactgc aacctttgcc   108540
tcctggtttc aagcgattct cctacctcag cctccggagt agctgggatt acaggcacct   108600
gccaccatgc ctggctaatt ttttgtattt ttagtggaga tggggtttca ccacattggc   108660
caggctagtc tcgaactcct gaccttgtga tccacccacc tcagcctcct agagtgctgg   108720
gatcacaggt gtcagccacc acgcccagcc atatttcag atctccctct ctttgcccta   108780
aaccactgtg cttaataagt agttttagt ggccagcagt ctccatgtat aacacatttt   108840
agcaaaatgg aaaatactat atgttttaaa tttgaacgtg agattatact gaaataaaaa   108900
tcatctaact gggattcttt aaatagtaag attttctttt ttgtatgtgg gttttttttt   108960
aaccttatta ttatgactgt catatataga aatggctgtt tttcagttac agtcagtgaa   109020
tgtatcaaat gctgccttat ccaaataata aaagtaaatt attaataagt cacaatttaa   109080
tgaagattga tgttagttga tctttatatt cttgaaatca gccatggtt tgtgtgtgta   109140
tgtatatatt tttaaaggta cataaagata ataagctcat ctctgaaaat ttttacattt   109200
ggcataagaa taactggata attaagcatc ttattctctg gcctgtgtct ttacagttaa   109260
aggtagattt actcacctct cctttttgt ttttctaagt tcatcttttt tgctgtttca   109320
agacagaggc ccatttagc tttctcgcat atccttttgt ttgtactttg gaagcctcac   109380
ctgcttaatt gttgagtttt tatccgtggt cttttagagg gggatatgta gggtagaagc   109440
tttcacaggt tcttgtttgc acttggcccc tgactgtttt gaggaatctc cctcactgac   109500
tcacagcatg gcaaggtttc agatctcttt ctgccacaca gcagttctga ggcagctgga   109560
aagatatcca gatgcttaga ttgtcaggcc aggcttgaga tatacaaact attgagcctt   109620
atctgtgacc ttgcttaggt gaaggcatca gagcccctgc accaacatgc ataggcctct   109680
gcatgtgtgc ggggctgggt gttgaggtct gagcacaagt gtagctggag aggtgagctt   109740
gatgtggcga cgggtatgag caggttttct tcagacttct gtgagtttac ctagttccag   109800
gatttaaagg cacagagact ttagaattaa aatagaatca ttttcttttt ctaaatagca   109860
acactaggaa taaaaaataa taattccaca ttccttgacag gtaatgtttt ttcttgtctt   109920
ctaatcctta tttattccat actcattttt atacataatt gaaatgtatt atgcattgga   109980
tttttctttt gcattatatt atagacgatt tttcatgtaa ctccttactg ttccatttta   110040
tatgttttgt ctggtttaag actttatctg caaaccggga aactgtctct acaaaaagaa   110100
```

-continued

```
aaacaaaaat agttggccgc agtggcatgc gtctgtggtc ccagctactc ggggctgagg 110160
tgggaggatt gcttgagcct tgggaggttg aggctgcaaa gagccatgat catgccattg 110220
cactccagca tgggtgacag actttatact gtctgttttg ggtgatttga taatgatatg 110280
ccctgatgta gttttttttat atcttgtgtt tcttgtgcct gggtttattg aggttgggtc 110340
tgtggcttca tagtattttt aaagtttgga aaattttagg ccattctttc tttctttctt 110400
tctttttttt tttttttgaga cagtgtctcg ctctgtcgcc tgcgttggag tgcagtgaca 110460
ctatcttggc tcactgcaag ctctgcctcc tgggttcacg ccattctcct gcctcagcct 110520
cctgagtagc tgggactaca ggcgcctgcc accacgcctg gctaattttt tgtattttta 110580
gtagagacga ggtttcactg tgttagccag gatggtctca atctcctgac ctcgtgatct 110640
gcccgcctgg gcctcccaaa gtgctgggat tacaggcgtg agccactgca cccagctagg 110700
ccattatttc ttcaaagatt tttttttctgc cctgcctccc tccttttttc cctctcttaa 110760
aggggctgtg atttcctgaa tgattgctta gtgttgtccc atagcttact gatgctcttt 110820
tcagtgtttg attgttttat gtgttttctg ttttgtatag tttctattat tgtgttttca 110880
agttctctga tcttttcttc tacagtgtct actctgttgt taatctgtta atctgttgtt 110940
aatcctgtcc agcgtatttt ttttttttgtt tttgaaacag tctcactctg ttgcccaggc 111000
tggagtttag tggtgcgata tcagctcact gcaacctcca cctcccaggc tcaagcaatt 111060
cttctgcctc agcctcccga gtagctggga ctataggcac gtgccaccac acctggctaa 111120
tttgtgtatt tttattagag atggggtttc accatgttgg ccaaactggc cttgaactcc 111180
tgacctcagg tgattcatcc gcctcggtct cccaaagtgt tgggattata ggcatgagcc 111240
accgtgtctg gcccctgttc agtgtatatc actaattttg tttttatctc tagaagtttg 111300
atttaggtct tttaaaaatg tctccctgtg tttctgttta gctttgtgaa cacaattgta 111360
ataactgttt taatatcctt ctctgctagt tctaagatct tctaataact cccagttct 111420
tggtgttttct cattggttga ttgatactcc tcgtttttggg ttgtattttc ctgcctcttt 111480
gtatggctgc caattttttta ttggatgccc aaccttgtga attttacttt gttggatgct 111540
atatatttttt gtgttcccat agatcttctt gagctttgtt ctgaggttag ttgagttaca 111600
tatagatggt ttactctttt gggtcttgct ttataatttg tcagatgggt tggagcagtg 111660
cttagtttag gactaatttt ttttttggac taattattcc tctttaggaa taattaggta 111720
ccatgcttag gaggcaagac catcctgagt actctaccta atgaaccaga aagtttgggt 111780
tttccagtcc gcctgctgag aacagtgact ttctagccct gtgtgagcgc tgagctctgc 111840
tccttctaat ccttttccaat gcttctttcc ctggcctcag ggagttttct cacacacata 111900
tctctgctga gtactcgaga gggaccttcc ccagatctcc agagctctct ctgtcttgtt 111960
ttctcttctc tggtgctctg tcttatgaac tgtggctgtc ttggtctcct tagattctca 112020
gcacctcttc aattcagagg gttgcctgtc cctcctcctt gtgccacagc ctaggaactc 112080
tctcaaagca gcgagttggg gcagccatag ggctgactta gtctctcgtc tcccagggat 112140
cactgtcctt cattgctcat gtccagtgtc ttgaggactc tgggttttgt ctgttttgtt 112200
ttttggtttg ctttggttgt ctcaggcagg agggtaaacc cagtccctca ccctcattgt 112260
gctcagtagt ggaagtctca ctctattaca ttagatatta gtatttgtag cagagccctg 112320
gttccctggt acttggggag ctcttgaaag gccagaaaca gcatgctttc tcaccttttc 112380
cagggcttca gttctggtg cacatcaagc attccataca catttgttaa agtcccttgt 112440
tagacaagta gtgattcaca ggttctattt gtaatttttt cagttaacat gtattgggta 112500
```

```
tctgctggga gctagtaaaa acaaaaagtg gtgtgtgaca aattcaattc tgacaagaac  112560
aaccttaaac acttagaata tactttgagc atatcagaat tttaaaaatg tgtggccctt  112620
gagtatttga aaccaacaag aatctattgc ttattagtag aggatatttt gttaaacaag  112680
tggagagaga ggcattttca gtctaattgg tgttggcttt tagcagctga tggaaaccag  112740
ttcgtgatta gccaggcagt ggtgaaacag gctgtgcatt ctgaatgcct aggtatctag  112800
gcattcagaa tggtggcgct cttttgagtta gcatcttctt cttcttgat tctttttttt  112860 ttttttttga gatggacttt cgctcttgtt gcccaggtaa caactccagt gcaatggcgc  112920
catctcggct cactgtaacc tctgcctccc tggttcaagc gattctcctg cctcagcctc  112980
tcaagtagct gggattacag gtgtgcgcca ccacgcctgg ctaattttgt atttttggta  113040
gagatggggg ttcactatat tggtcaggct ggtcttgaac tcctgacctc aagtgatgca  113100
cctgcctcga tctcccaaaa tgctgggatt acaggcgtga gccaccactc ccagcccctt  113160
cttgattctt gaaaaggaca ttgggtgctg tacatctcgt tatagatgtt gataaaaatg  113220
cttgtgagaa gagtaacatt aaggtagtta tttggtcatt tttgcagatt attttaagac  113280
aattctagga ctgatttgtg gtaaatcaca cattgctgta tcatagttgt gttcactgaa  113340
catattcagg ggctctacag atgcagggct cttagctgct ttgcacactt ctgaattcct  113400
gccctgcgaa caggactgga tacctaatag acaacaggta cttgataaca gtttattgaa  113460
ttaatgagtg aatgaacaga tacataaatg catgaaagaa tggttgtaat gtatataact  113520
tggatttcaa gactttttac tgactgttca aaataagaaa ttgaaaactt tcctctgatt  113580
ttcctctact atttacacaa tttaaatgga agttatcttg taccttcaat ttctgtctag  113640
gattcgtaca ataacgggtc atctctgagt cgcttaatgt ctcacttgtc tttctacagt  113700
gtgttgaaga gatcctagga tacctgaaat cctgctttag tcgagaacca atgatggcaa  113760
ctgtttgtgt tcaacaagta agagcttcat tcttttcctc ttctgttaag acgttcgggt  113820
atgacagcaa aacgctgcta ctccttaaga ggcaggcgct gttggcataa tcagctggga  113880
ggattgtggg gtccagcgca gcacttttg gctcagtcca tgattgagcc aagaggccat  113940
ccttcccttc actcccagg aggacgaggt ctgtcactgt ggagggcaga ggacaccaga  114000
agctcctctg caacctcgct agttaacttc cagtccctcg gagtttctgt ttagaatgct  114060
caatctcatt tagaattgca aggaaaccca aaacgcctat ttaaggtaca aacagcactt  114120
catacaatat ctcatgaggt attaatagtg attcacagga agaatttcac gctgtgagtc  114180
tttgctaaca tatccagtta tttacagatg gatttgatat ttgtgtggga gattcttaaa  114240
agtgttgttc acgccacatt gttgatgcct cattttttc actgtagttg ttgaagactc  114300
tctttggcac aaacttggcc tcccagtttg atggcttatc ttccaacccc agcaagtcac  114360
aaggccgagc acagcgcctt ggctcctcca gtgtgaggcc aggcttgtac cactactgct  114420
tcatggcccc gtacacccac ttcacccagg ccctcgctga cgccagcctg aggaacatgg  114480
tgcaggcgga gcaggagaac gacacctcgg ggtaacagtt gtggcaagaa tgctgtcgtt  114540
ggtggaagca cgaaagagca agcaggaaat actttgtaaa agaataaaaa cgaaaaatgt  114600
tagcgaacat cttctaatag tctgctgtat tcagagaact ctaggagata tatatggttg  114660
atgcaaagat gatttaaggc atagcccggc cttccaagaa gtgtgtggcc agtgagtgag  114720
atgggcttgg gacttacaca tctcagaggt ggggtagag gaggaggaac actgagtggg  114780
ctgagaagca gccagctctc attgccaaag tgtgtcagca aaccagaatg cagttcataa  114840
```

```
tgtccccacc cattcaaagc acaggacctg tagagtggtg tggcatgtgt tggtggcact   114900
tttcaggcct gtaacaagga tgaaagaaca gcttcatagc agcacagtag tgctggtgtt   114960
cagaggtgtg tgaaggccat agaagcatct tggatatatt accttgtgtt ttgtcagctt   115020
tatgactaga agtctctttt cacttaaatt tgtttttttt tttttgaga cggagtcttg    115080 ctctgtcgcc caggctggag tgcagtggtg caatctcagc tcactgcaag ctctgcatcc   115140
tgggttcatg ccattctcct gcctcagcct cccgagtagc tgggactaca ggcgcctgcc   115200
atcacgcctg gctaactttt ttttgtattt ttagtagaga cggggtttca ccatgttagc   115260
caggatggtc tcgatctcct gacctcgtga tctgcccgtc ccggcctccc aaagtgctgg   115320
gattacaggc gtgagccacc gcgcccggcc tcttttcact taaatttatg tttgtgtttt   115380
taatgcctag tatacaggac ttcttaaatt gccttaagta tgaacaggta tttgagttgc   115440
taatctgtat agtagcaata atagaatccc ttgttttttcc ttttataaat ttagcgatta  115500
aatagctaca attaaaacac tagagtcagg agtcaaggaa aatacccatg ttccaggctg   115560
tatgttagtg atgtacttac tatatattgg agtttcagga gtaagtctgt ttcaatgctt   115620
tctgtaacca tttggggtat taataagcat gtgagtgtgt gcatgtttgg gttaatttca   115680
tatatgtttc ttagaaggga tatcattgat gtaaatattt taaaggcttg tcctccaaaa   115740
aaatcatgta atttcttcta aattactgat cttttaaatg accttcacct ttctctcaaa   115800
tctcacttaa gactgggctg agtagtcagt ttcctgtagc agaaaaaagc tcagacttga   115860
gtagccttct gcgagtgagg agacttgatg gctgtcaggc agctgtaaac tctaaataga   115920
gtgtcattat ctgaagaggg cgatgctgcc acactgagtg gcctttcaag ttgtttctca   115980
atctgacacg ttctgatcgt gtgaatgtga aattggtttg agcaggagta tatctgagtg   116040
cagaggagat tatttaaaga tattctcatt ctctgcttcc cttttattcc catttggcag   116100
atggtttgat gtcctccaga aagtgtctac ccagttgaag acaaacctca cgagtgtcac   116160
aaagaaccgt gcagataagg taatggtgc cgtttgtggc atgtgaactc aggcgtgtca   116220
gtgctagaga ggaaactgga gctgagactt tccaggtatt tgcttgaag cttttagttg    116280 aaggcttact tatggattct ttctttcttt ttttctttt tatagaatgc tattcataat    116340
cacattcgtt tgtttgaacc tcttgttata aaagctttaa aacagtacac gactacaaca   116400
tgtgtgcagt tacagaagca ggttttagat ttgctggcgc agctggttca gttacgggtt   116460
aattactgtc ttctggattc agatcaggtt tgtcacttt atctttcatc catcatacct    116520
gttcctaatt tagtacaaat taccctaaaa gacactgaaa tctactttaa agaaatgtgg   116580
tctgcatgtt tccctcatca gttgctgctg cttatctttt tcatgcacct agctggtgca   116640
gaaggcctgg ggcatagcca gcctcagcaa gtcagcatcc ttgccccagc tccctggact   116700
caaggctaac ctggggttgg ctgttaggga tttccaaagg tttgtcccat ccacttgcct   116760
cccctccaaa ataagtttga atttaaattg tgagatacaa ttaagattta ttgtttgggg   116820 aacattttg caaaatctag agttagttta aacagattat caattattac cataattgat    116880
catctgcagt ttcaagctat ctaacaggtt cacttacctc tttaaaaagg aatggaattt   116940
agcaggacag taactgagac ccgtgctcct ggagtccatg tgggagctgt gtggctctgc   117000
acaagcattt gcacgcttcc cctcttgact gcattacctt cctcctatag ttgctgtggg   117060
caccagattc tggctagtcc tgtcccttca tgatgcacat tttcctcaag attcgtccca   117120
gttaaatcac tgcagatgaa actgcctttt catcgtcaaa atttaactgt catttttgag   117180
ccgtgatctt gggctacttt cttatgtggg gtaggaatat ttgtgagtta gaaatattac   117240
```

```
acttctctat ttccttctag acgtaaatct gttaatcctg tcagcactgt tactcacctg   117300
aaagggtctg tttccctagg agaactgagg gcactcggtc aacactgatt ttccacagtg   117360
ggtattgggg tggtatctgc ttgttttttt tgttgttgtt gtttgttttt ttttgttttt   117420
tttttgagat ggagtctcgc tctgtcaccc aggctggagt gcaggggtgc gatctcggct   117480
cactgccagc tccgcctcag aggttcacgc cattctcctg cctcagcctc ccgagtagct   117540
gggactacag gcacccacca ctacgccagg ctaattttt gtattttag tagagacgag    117600
gtttcactgt gttagccagg atggtctcca tctcctgacc tcgtgatctg cccgcctcgg   117660
cctcccaaag tgctgggatg acaggcgtga gccaccgcgc ccggcctggg gtctgctttt   117720
aatgaaggag gcatcaaggg gtgggctttg cgttggcctg atgctttcat ctttctttca   117780
caaaacctgt ccgaagaaaa tccgtctaaa tgggccattg ctctcctcag gaaatagtca   117840
ttgggaactt cttttccttt cctttgacac taggaggctg actggggaga gccctggtc   117900
tatggctgtg ggcagcaggg gctgagagga gcaggctctc agggggcac gggtaccca    117960
agggaagcca gagccctgat ttgttccatt ctagtaagaa caaagactgc tctggtttca   118020
tgtttgttct gattgccttt catcaaccgg tccccttcct cccagttctt aagattcagt   118080
acagtgacag ttttatgaac aagaatagaa cactagaaca gacaaaccat tgaactctat   118140
gctgataaag atttattgag ctcctgctgt atgtttgcat tctgcccaga ggctctgaga   118200
aaaccaggcc atatgctcca tgctttatcc atggaagctc cccgtcaggt tgggaaagct   118260
gacagctgca gggaatacag tgtgacacaa aactggctcc catgcagccc ttacgtgtcg   118320
cctctcagat ggttggggga cgaaggtcga ctccctttggg tatcttatta ctaaaccagt   118380
ttcagggaat ctgtgccacc ctatctgcca ttaacgtgaa cagatgagtc cccaaggtgt    118440
aatttttgggt attgtctgat gtctcttgga atttattatt tgttttttcca atgagatttc   118500
acctcagggt atagtaaagt tgttgagggg attcctggat gtgttctgca attatctagg    118560
ctgatttcag aatagagtta tgcttatagt caaatttatc agctgtcaag aattttattt    118620
aaaatttatg cagataagca ggaggaaaag aagcctggtt tttacatttt aatcctatta    118680
ttgatgtgaa attttatttt ccttcctgta ggtgtttatt ggctttgtat tgaaacagtt    118740
tgaatacatt gaagtgggcc agttcaggta atagcatttt attatttag atttttttct     118800
tcttcttgtg tacttacatg taatttaggt tattaagtga atgtttaaac tactgttagg   118860
cattttttgct gttttctta aatggaaatc tgactaacat actgtgcatt tttgcttctc    118920
ttaaaaatta atgtatatct caagacttgt ttggaagtag ttatgtatct gaaaattcca    118980
tatgttgtca gtattcattg cacatttcaa agcatttaat tgtgttgaca gatggtggaa    119040
tgaaatcttg tggtggagca ctagttttta aatcttctta gagaaagcag ttttatataa    119100
tgttgtctttt agtaattatt atgcatttgt attctctgca gcttttttctt gctagatgtt    119160
gaggttttaa tacttcttgc tagtccatta caggtttata attattaaaa gttaaaattc    119220
ttttagtacc taaaatgctt aataaacatt gtaattagga aaatttagtg cagaaggaaa   119280
gtgttcccag attccctggg gtctggaaac atagtgttta ttctaattac atgacacctc    119340
cactgtgttt tggggcaagt tactgttct cttttgagtt tcaatttctt caagagcaaa    119400
gaggcagagg agagctagga agatcgtagc tgctgtgccc ctgtgccgtc gggtgccttc    119460
tacctgctgc ctccgaacct ttacacatgt ccctgctctg cgcgagggca cagatgggat    119520
gcactgtggc aggggtgggg ttagagtaga tcacggacac ctgttagctt gatgtgtgct    119580
```

```
tgctgtcaag gttgaatcat gaattatttt atgttgctta tattgatatg tatcttaatt  119640
ttaaaagaaa ggtctaaatg gatgtttttg tttttaggga atcagaggca atcattccaa  119700 acatctttttt cttcttggta ttactatctt atgaacgcta tcattcaaaa cagatcattg  119760
gaattcctaa aatcattcag ctctgtgatg gcatcatggc cagtggaagg aaggctgtga  119820
cacatggtaa cgggacacac ctttcactgt cgtcttcggt gtcgtgatgt gcttggcagt  119880
gttcgttttc atatacccac tttgaacgtt gtcagtggca gccatgtgct tctcaggctc  119940
tgcatgtgtg tctgtgtatg tgaaggtact ggttagagac gtttcaaaag agaagagagc  120000
atattcttta ctctcagcaa tttgtaatct tctcagggaa aaaaattcaa gaaacagtaa  120060
gataacctaa ggtacagata gattctgaat ataaagttcc tgttcattca catgaaacgc  120120
taaaagttct tcacttgatc ttagccaaaa ggccaagaag cgatgcaaca ctaaaaattc  120180
ttaaatcgaa cttgccgtga attaaatttt gatctctcat ccagtggtat tggagatata  120240
gtttgacttg ggttcagggc tttctgtttt gcctgatgat tttgctggag cttaaataag  120300
gaacccagga gatggccagc tgtgcaagcc cccagcctgt ggaaggagct agtgtggttt  120360
tatgaatgag ttgcaaatct ttcttgagc ttttgaact gatcttccag cattgcccta  120420
ttgacccctc cctgactcct ttgctggaat ctgtaggctt ttgaactttg acagggacac  120480
atcctaagac ccttgcaaac tcccagatgt gagaatggca ctactactta gagtcttttc  120540
gactcagcgt gtgtgcagaa gagcatcaac cgggctgtgt tgcgaggcag ggccttggct  120600
gacctctcag tgtttacata gctaagccag ttagtgtttg ccacggcctc acaagggctt  120660
cagattcaca cagccaaagt atagattatt aaaggcatag gtgtttggtt tcctggactt  120720
ggagggtctt tggacagaaa atcagtaggc aaccacaccc agtactttgt gctgggaagc  120780
ttggtcatct gtgagagggt cagagagtat acccatgcgt gcatgccacc gaagggtcag  120840
tgagtattcc tgtgtgtgca tgtctcaggg ccggagagag tatgtgtcac tgagaggtca  120900 gagtgttttgt gtgtgtgtca aagagggttg cattgtgccc ttcactgagg ggtcagaggg  120960
tgcctcgcgt gtgtgtgtgt gtacgtgtgt gtgtgtcact gaggggtcag agtgtgcctg  121020
tgtgtgtgct tgtgtgtgcg tacatgtcac tgagggtca gagtgtgcct ctgtgtgtgt  121080
gctcatgtgt gtgcatacgt gtcactgagg ggtcagagtg tgcctctgtg tgtgctcatt  121140
tgtgagcgta tgtgtcactg agggggtcag agtgtgcctc tgtgtgtgtg ctcatgtgtg  121200
agcgtatgtg tcactgaggg ggtcagagtg tgcctctgtg tgtgctca tgtgtgagcg  121260 tatgtgtcac tgagggtca gtgttcctat gtgctcatga cattgagggt cagagtgtgc  121320
ctgtgtgcca atgaaaggca tttcttatat ttttttatat gtggtcatag tagaccagtt  121380
aatttatttt gactcctgtg ttagaccaaa ataagacttg ggggaaagtc ccttatctat  121440
ctaatgacag agtgagttta cttaaaaaag cataataatc cagtggcttt gactaaatgt  121500
attatgtgga agtctttatt gtcttttcag atgaatcaag tagattattc ttgagaccag  121560
gaatgttgct gttttggtta tttggaaagt tttatcattt tcaaattgac ttttgaattt  121620
gagtcacctt ttttcagaag tggtgttaaa ttataggagc cctaggtttt ttttctttt  121680 ttagaagtca tcacaaaatg atcagtgttc agaggaagag ctttgacctt ccacatggta  121740
taatgattga taaccttaat tcatctctta ccataaacca agtatgtgta agggttttct  121800
ttatttcttg aaagcatttt gtagatgttg agagcagttt tccaaatgta atttccatga  121860
aatgcctgat aagggtaccc ttttgtcccc acagccatac cggctctgca gcccatagtc  121920
cacgacctct ttgtattaag aggaacaaat aaagctgatg caggaaaaga gcttgaaacc  121980
```

```
caaaaagagg tggtggtgtc aatgttactg agactcatcc agtaccatca ggtaagagga   122040
atgtatgttg gaactgtcgt ggatacttta ttgacccgtg cagatggaag gaagtgccat   122100
gtggtaacgc tcactgttaa ctgtgttact ttgaaccagg tttgggcttt ctggggcctg   122160
ggtagatgcc ggtgcagggg gatggggagg gaggcggggg gtgggggggt gtggtggagt   122220
tggggaggtg cagtggcagg aggtgttgtt ggtgtgtatc cttttttttt ttttgagatg   122280
gagtctctct ccgtcgccca ggctggagtg tggtggcacg atcttggctc attgcaagct   122340
ccacctcccg ggtttaagca attctcctgc ctccacctcc cgagtagctg ggattacagg   122400
catgcaccac catgcccagc aaatttttt ttttgtattt ttagtagaga tggggtttca   122460
ccatgatggc caagctgttt cgaactcctg acctcaagtg atcctcctgc cttggcctcc   122520
caaagtgcta ggattacagg cgtgagccac catgcccagc ctggtgttta tctttaaagt   122580
gggcacagcc acaggagttc acctgactcc tggtctgaga gtcacgagat cgttcaagat   122640
agtgaggccc tcttttccaa aacgaggacc aaaaatcaat tgacagtgtt ggtcaagatg   122700
gtagaaacct taaaatgata gaaatctcaa ctctgaaata aaaactttat ttgtatattt   122760
atttaccact atttttgacat agggctaagg tcttttttctt tgagctgatt tctggttttg   122820
ttttcttaaa gtggcataag aattcaaaga cattttgagg aaggctgagt gcagaaatct   122880 ctcttttttaa atgacttctc ctttcttttta acttgcactg ttgtctagcc ctcacttatt   122940
ttgtcaattc ttttttagctg tttgtctttg aatcttcata aagccatagc ttttctcata   123000
agaagcagca ctttctttgt tcattcatat tttaatgaac ccctgtagta tttaattaaa   123060
tacttaatgc ctaattaaat cacataattg caatgcaaaa gtacatgtat cataaagagg   123120
tctgaaaatg agcaactggc aagcaggtgg tggcaggcag agctgcttgg gtgggtgggt   123180
gtcatggaga ggagttcatc agccacatgt tcagtgagct ctggatatgt ctgtttagaa   123240
atgatcacta ataaacttgt gctcaaccat gtatacctct gggaagcagg tgctcttcag   123300
tagattgcct ctgcagagaa cacagaattg aagtgaatgt ccacaaaggc aatgagccac   123360
ctgcagaata gtttagtcaa ggctgtgttt gaagtttgcc aaagattaat atacatttga   123420
ttttcatgtt gtgccttttc tctgattgtg aaatattaca aattctatac aaataacaat   123480
gatggcaaat cctcctgagc aaagtgtgca ccttgtatgt gccctagagg aacttgtgtt   123540
tcgttctgat tcccctacat ttctcatgtc atagagtggg ggttgcatta gtgtccccct   123600
gtcctcgctg ggatcacatc tgtttggatc ctagagtctt ccagctgaac tgggacaagt   123660
ataacagacg gacacgtagg ggtggaaagg cgtctcttgg cagcagactt tctaattgtg   123720
cacgctctta taggtgttgg agatgttcat tcttgtcctg cagcagtgcc acaaggagaa   123780
tgaagacaag tggaagcgac tgtctcgaca gatagctgac atcatcctcc caatgttagc   123840
caaacagcag gtttgtcccc gcagccttgg cttgttgttg catagtgatg gtagcttaag   123900
gtccttgtga aaggtgggtg gctggaatca gctcttcctt cagtcctaat ctgtgccttg   123960
atagcagttc tccgtgctag tcatgggaca gctgacttca tttcttctca caatgccatc   124020
tcaggttggt attgcccacc tactttacag gggggatccc acagctccga gaggttatgg   124080
aggtgatcag gcagcacaca gctttagagt gctggggtga gggcgggcca aggctaactc   124140
taaagcccga accccttacct cctacactgc ctcctgcatt ctggtcaacc cagtgtttta   124200
tttggtggtt agattttttgt ttttgttacc ttactgcttg taatttagca gttttccttt   124260
cctttccctt cctttccttt ccgacagggt ctcactctgt cacccaggct agagtgcagt   124320
```

```
cgtgtaatct cactgcaaca acctctgcct cccaggttca accaattctc ccacctcagc  124380
ctcctgagta gcaaggacca caggtgtgca ccactacgcc tggctagttt tttgtatttt  124440
tagtagagat gaggtctcgc tgtgttgccc aggctggttt taaactcctg ggcgcaagtg  124500
atccaccaac cttggcctgc caaagtgctg gcattacagg tgtgagccac ctcgcctggc  124560
ctattcatca ctaatcagaa tttctatgat caaatgacat gaatcattgt ttccacaact  124620
gcagtggaag gaaatggcct ggcagtgcca gtttcagaag cagcctgccc ccagtcaggc  124680
acaggccact gtgccccag tgtagcagca cctctgtagc tcacagagaa gggtggtggg  124740
gacctccttg aggcagctct gccagaaaat ctcatgagct gcctggcaca gcttgaggtt  124800
gcctttaag tggactcagc aaatacatgt ttgttcatct tgattataca caataaacaa  124860
ctactctgta tagtacgagt agtccgtggt ttttggcatt tgatttaaac ttagaggcat  124920
gtgatattga tgttactgcc ttcatgactg caccccatt ctgatttcat aatggaatgt  124980
tatcttgaga ccagttagac aacaggacag ggatcttggc ttctggtgag attgacagca  125040
gttttagtgt ggtcagggtc tccctgccta cagatggttt tagaatggtg ccctggaagc  125100
tttatcccat tcttttctgt gcgtaatctg agtagagtgg agatcgaagg cctgaataca  125160
tagtaaatac ctgacttaat atctgccgca atggaaattg tgtgatacaa catttatgaa  125220
acgcttagtg cagcacctgc caggtagctc accacaggtg catgttgcat tcagaagtag  125280
tgctagatac tatcctgtta ctggcagtgc atacatcagt gatcaaagca gattaaagaa  125340
agaccccctg ccttcttgga gtgaagattt tgttgggatg cgggtaaggg gacagacaat  125400
agaaaagcaa gtgagtgaag tctataccat ggcggctgat caggaacacc gtacagaaga  125460
atccaggagg gaagagagtt aggtggtgtc tgcggtggga gtggcattgt tcagctggtg  125520
atgagaagaa gctttggtga tctggtgaca tttgagtgaa tttgcagaaa ggaaagatac  125580
aagcctagga gatacctggg gaaggaacat tccaggcaga gcaaatagca gtgcaaaggc  125640
cctggcgggg ggcggacatg ctgttagggt acaagcaatg agggtggagg agtggggcag  125700
ccatggggag ggaagggagt gaggcctggt ggggtgaggc cagtgtggag gagccttgag  125760
agggtttgcg ctgatgtggt gtaggtttta gcaggatcat tcttattcct gagttgaaa  125820
tagccttgag ggggaggtga gggcagagca gggccaccca tgtgagaccc ggcactggag  125880
tggaatggcc caagtcagca tcccttggca gcatgaaagc aaaaccagca aggtttgctg  125940
gtggcttaga tgtggcatgt gagagagagc agggctttgg gggtgatttc agggtgagga  126000
cagggtggct gtggacaagg tagggcagac attgggggca gcaggaggtc agagcctgtc  126060
tggatgtagc agttgagacc ccataggtgc ctaatgaggt gaggccagca tcaggtgtat  126120
gagcctggag ttgtcgagag actgtggggc aggggtcag catctgagat gtccactcac  126180
agtggaccca gactggctgg agaggaggag gagcttgaat accgagcctg ctgagtccca  126240
gctccaaggt caggtaggtg aggggagcca gtgctgggc aggggagta ggcaggtgtg  126300
gggttcctaa agccaagatt tttttaagg cattttgtgc aggagggcga catctgctgt  126360
cagcaccttg ggaacttggc ccaggtttgg cagcaccgag ggcactgatg agtgcttttg  126420
gaggagcaaa gggagccaaa ccctaatggg aatgtgttcc tgaaaggaca ggagagagac  126480
ttgggaaaag gttttacttg aagagggaac ggagaaatag ggcagtagcc agaggaggag  126540
aggagtcggc aatgggttaa gttggcagaa atgaaggcct gtttacgcac tgagggcaga  126600
agcaacaggg aggatcagtt catgacacag gagacacaaa tcgccgttgt ggtgttcaca  126660
gacatgggtt aggattggct gcatggatga cagagcactg tgggttctcc cagagttgct  126720
```

```
ggggaggagg cagagttggt gagcacaggc gagggtccag gatgcaggaa tcctggagct   126780
caagtcagtt gttcccttgt tgtaagatgt ggccagtgtt gtgagcttca catctgtgcc   126840
ttgaaaaaca ccacatctgt ttgcagagtt gtttactatg tatacacact cagtagaaac   126900
aaaaattgga aacagtcagt gcccaccatc aataagtaat ggttgaacac actgtggtat   126960
aagcttagac tattttagct tgggctattt tgcatgatta aaaatgttct ggccaggtgt   127020
ggtggctcat gcctgtaatc ccagcacttt gggaggccaa gcaggcaga  ttgcttgagc   127080 tcaggagttt gagaccagcc tgggcaacat ggtgaaaccc tgtctctact agaaatacaa   127140
aaagtagctg ggtgtggtgg tgtgcgcctg tagtcctggc taactcagga ggctgaggtg   127200
ggaggatcac ttgagcccat tcgtgcgcca ctgcactcct ggggcacaga gtgagactct   127260
gttagaaaga gagagagaga aagaagagag agggagggag gaaggaagga aggaaataaa   127320
tggaagaaat ggaagggagg aaggggaggg aggaaggaag aaaggaagtt cagccagttg   127380
ccttgggagt tctccattgc actgggttaa gtgagaagag cagagacgtt tatgatttt   127440 caaaacaact aaaacaaaac ctctgtgggt gagggggcaa ggatatggct ataggaacat   127500
ggggcagatt aagaaaggga tatacacaca ccacttagca tttgttacaa ctgttgtggg   127560
agggatggag tgcagaaaaa gaaaaaaaaa agtgcacacc atcccatgta tgtgtataca   127620
aagggacgct tggaagactg gtccccaaaa tgttggtaat gattgtgtca gggtgctgca   127680
gtgctagttg atttttttc acacttttgt atatttgagt cttttacaga aagcatttat   127740
tatttatgta ataaaaatct aaatgacaag atttctgtta tgggaaaaat gtagctatac   127800
agtgttgttg taaaaatgtt tgcttggttc accactgaac ttaaaatgct tttaaatgag   127860
ggaaggtgac gatgagatga ttatgatgat ttgcccttga gttacatagc tggtgtacag   127920
gaagctgtcg tttcttttgg cttacgtaga aatgtttgtg gtgtctaatt ccacagatgc   127980
acattgactc tcatgaagcc cttggagtgt taaatacatt atttgagatt ttggccccctt   128040 cctccctccg tccggtagac atgctttac ggagtatgtt cgtcactcca aacacaatgg   128100
tgagtctctc gcctggctca gcagatgaat ctggacggct tgttcaggct ctgattactg   128160
ggaccacccc cagaatgtct gagtcagtca gtttgggtag ggcttcttga gagttttgctt  128220 ttttttttt tttttttttt ggtgtggggg tggtgcggaa cagagtctca ctctgtcgcc   128280
caggctggag tacagtgtca tgatctcggc tcactgcaag ctctgccttc cagcttcaca   128340
ccattctcct gcctcagcct cccgagttgc tgggactaca agcgcccacc accacgcccg   128400
gctaattttt ttgtattttt agtagagatg gggtttcacc gtgttagcca ggatggtctt   128460
gatctcctga cctcgtgacc cgcccatctc agcctcccaa agtgctggga ttacaggcgt   128520
gagccaccgc acccggcctt tttatttttt ttggagatgg agccttgctc tgtcacccag   128580
gctggagtac agtggcgcta cctcgactca ctgcaacctc cgcctccgg  gttcaagcaa   128640 ttttcctgcc tcagcctccc gagtagctgg gactacaggt gcgtgccact gtgcccggct   128700 aatttttttgt atttttagta gagacggggt ttcactgtgt tagccaggat ggtcgcgatc   128760
tcctgacctt gtgatccgcc cgcctcggcc tcccaaagtg ttgggattac aggtggctct   128820
cgcaccaagc caagagtttg catttttagc aaattcccag gtgaaactaa tgcctgcttt   128880
tctgggagca cactttggga ctcagtgata gagaggttta ttggtaggat agtaaaatag   128940
gagttatttt ctttcacaaa attggcaatt gggggaaatt taatcttcct ttttcttca    129000 gctgtgactt atgtattatg tttatttag  gcgtccgtga gcactgttca actgtggata   129060
```

```
tcgggaattc tggccatttt gagggttctg atttcccagt caactgaaga tattgttctt    129120
tctcgtattc aggagctctc cttctctccg tatttaatct cctgtacagt aattaatagg    129180
ttaagagatg gggacagtac ttcaacgcta gaagaacaca gtgaagggaa acaaataaag    129240
aatttgccag aagaaacatt ttcaaggtat gctttctatc tgagcctata actaacccat    129300
gccttttggg aagtcacgtg atgtttcaca gtcagtaagt ctggaataat acctggtctt    129360
gcttcacttc tgagttgggt aaagaagtct gtatcagtgt aattttctaa tccgtcctgc    129420
attatctatg gctcttggtt catacctgtc ttgaagttct gtcatgttct gtctcttgtc    129480
ctcagtagag atgctacagc agtggctcgc ctcaggcagg gcagggcagt ggggtggctg    129540
tcctggggggc aggcagtagg ggcacgctga cgtcagggaa gttgaaaccc aagagaagcc   129600
agtaaaagtg agtctcagat tgtcaccatg tgctggcagt tttacacgct gtcagtaata    129660
aaagtcttct ccctgcaggg cagcctgcct ccaataaata cgtgtagtat caaatcctgt    129720
cttccctcat aaattgtttg gaagctcccc aaggacagtg atgaggcact cgtaagtgct    129780
tgctgcctag atgggtccct ctccaccttt gctagattct gagcattcac tgagttagag    129840
ctgcttctgc aaatgtgctg cttctgctaa gtggctgtga cttcatgcag ccttcacttg    129900
gtttgtcatc agtggagatg ccctgtgttg tcgaaggaga taagcccagt aagcctgctg    129960
ggcaccttt ggtttgcagg ttcagcaggc agcccatggc tttccctgtg tcgcattgaa     130020
gcagctggct aaaattgatg atacattaaa ttcctgtgac agatgatcag cttgtatttg    130080
tgtaatggtg tacagttcac aaagcttaaa aaaatgctac ctgccatttc atcctcagtg    130140
aggaaggtga tacacagaga gaccaagtga ctgtgtccac ggcgacggcg ctctgcattt    130200
cactttagcg gttaatgtac tctacctata ttttactttt atatttacca tatatctttt    130260
catgtatact tggcgtaagt gctttatagt agtcacctaa ttcactgtca tcttttttgt    130320
ttcttggaag gtttctatta caactggttg gtattctttt agaagacatt gttacaaaac    130380
agctgaaggt ggaaatgagt gagcagcaac atactttcta ttgccaggaa ctaggcacac    130440
tgctaatgtg tctgatccac atcttcaagt ctggtaggtg aatcacatta gtcttcctgg    130500
agtgtctcgt tccccattct gcactataca ctctcagagt gtaggagctg tgctgcccgg    130560
tagaaactct gccttgccca gtgtgccagt tgaaaatatt tgttgctgta agagtacacc    130620
tgataccatg tgacccagca gttccactct tgggtatata cccaaaagaa tggaaagcag    130680
ggtggtgaaa agatatttgc atgccagcat tcatagcagc attattcacg atagctaaaa    130740
tgtgaaacca actgaagtgt ccctcgatgg atgaatggat aagcaaaatc tggtgtatat    130800
ttacagtgga atattattca gccttaaaaa aaggacattc tgacacatgc tacaacatgg    130860
gtgaccctta aggacattat gctaaatgaa ataagccagt cacaaaagga caaatactat    130920
gtgattccac ttcatgagg gacctggagt agttaattca tagatataga aagtagaatg    130980
gtggttgcca ggggctgcag gggaggggag ttattttttac aagatgaaga gagttattct   131040
agaaatgaat ggtggtgatg gttgtataac attatgaatg tacttaatgc tactgaactg    131100
tacagttaaa aatagttaag aggaccaggt gtcatggctc atgcctgaaa tccaagcact    131160
ttgagaggcc aaggcaggag gattgcttga gccaaggagt tgagaccag cctcagcaac     131220
atggtaggac cccatctgta caaacaaact agccggggat agtggtgtgc atgtggtccc    131280
agctactcag gagactgagg ctggaggatc gcttgagccc aggaggttaa gtctctagtg    131340
agatgtgttc atgccactgc actccagcct cggctataga gtaagaccct gcctcaaaaa    131400
aacaaaacaa aacaagacaa gagccaaaaa tggttaagat gggccaatca cagtggctta    131460
```

```
tgcctgtaat cccaacactt tgggaggtca aggtaaaagg atcacttgaa gccaggagct    131520
tgggaccagc ctgagcaaca tatcgagacc cctatctcta caaagaaaat caaaaactag    131580
ctagatatgg tgggcacatg cctgtagtcc cagctacttg ggaggctgag gtgggaggat    131640
ctcttgagct caggagttcg aggctgcagg gagctattat tgcactccag cctgggctac    131700
agaatgatac cctgcctctt attaaaaaaa aatccaaaaa aaaaaaaaag taaacctgag    131760
agcttcctcc tcctgtgtta aatttggagg ccaagatgtt tttgttactt ttacaaatga    131820
tcaaggacgg tgaaggttgg gcatggtagc tcacacctga atcccagca ctttgggagg    131880 ctgaggcggg gtgatcgctt gagcttgaga ccagcctgga caacatagca agagacccca    131940
tctccacaaa aataaaaaaa taaaaaaaaa tagccaggag tagtggcatg agcctgagcc    132000
caggaggtca agctgtagtg agccatgatc atgccactgc actccagcct gggcgagatc    132060
gagaccatgt ctctagagaa agaaaatgac aaggacagtg aacccaagaa agtcataaga    132120
tgccagctgt gcagcaagca tggaaagcag ccagtccaaa ttaggacagt gtgttttcca    132180
agaagaacga tcgtttgtaa tgagaatgct ttgctttaaa taaatgacta aatagctaga    132240
agcctagttc taggggatag gcacgtcttt cttctctcaa gaaatagaaa aggcaattct    132300
aatttctagt aacagcaaac agcattaagt catggtccaa atatgaggca aaccaaaatg    132360
tggcttgatt gttcagcagt tgatctgttg gaagcccttg atattaaaaa ggttctcctt    132420
taagcggctt aggagtcacg atcaaagacc tatagaaaga gatgccatcc ttctaggatc    132480
cttggctctc ttgggaacta gattcagata gtcataatgt aaatactgct tgagcttcct    132540
ttctttcttt cttcttctc ttttttttt gagacagagt ttcactcttg ttgcccatcc    132600
tggagtgcaa tggtgccatc tcggctcacc gcaacctctg cctcccaggt tcaagcaatt    132660
ctcctgcctc agcctcccga gtagctggga ttacgggcat gcaccaccac gcctggctaa    132720
ttttttgtat ttttagtaga gacagggttt ctccatgttg aggctggtct cgaactcctg    132780
acctcaggtg atccacccgc ctcggcctcc caaagtgctg ggattacagg tgtgagccac    132840
cgcacccggc ccgagctttc atttttgaaa tcaatgtatg actgaaacac tgaagactta    132900
ctgacttaat tatggtttca gaacagaatg aaaatgtctt cggttctgat gaatataaaa    132960
ggaaaactaa ccaagttaat ttggcaagta gatggtagag atagaggtgg ggagtggaag    133020
gggaactaaa atcttcacct agcattgttg ggattatatg gttacatcat ctgaagttga    133080
cagaccaaaa tatagaggct tcagaggtct ccaaatagaa ctaaacatgt aattcagatt    133140
gttaggaggt agtataaatg agctaaatct catctttatt acggtagagt taatgggtga    133200
tgtctaaagt tgtctgaagt ctataaatca tgacaaatta tgatgtggtg attgtattca    133260
acagtctttc agttgcaggg ataaaacccc agtttaaact agagtaagag aaagaatgtg    133320
ttggtttaag ctcctggaaa gtgcaggcaa gggtagttgg taggactgca tctagtgttg    133380
taattctgtg gtctgcattg tatatttatg catctcagct ctgctttctt cttttcattt    133440
atataatttt taaattttat tttaaagata gggtctcact ttgtcgccta ggctgaagtg    133500
cagtggcatg aagtgcagtg cgaggctcac tctagcctcg aactcctggg ctctagagtt    133560
cttcctgcct cagccttcta agtagctgag acaataggca tgtaccaaca tgcctggata    133620
ggttttaaaa tttttttgta gaaatggaag tcttgctgtg ttgcccaggc gggtctttaa    133680
ctcttagctt caggcgatcc tcctgcctct gcctcccaaa atgctgaggt tataggtgtc    133740
acccaccacg cccagtctca tctctgcttc ctgtgttagt tttgttctct ggtgggctgt    133800
```

```
tttcacatga ccgaagatga cctctagcag gctgtgttct cagcccctca agtaggccta 133860
tgtgattggc cttgcatgag taatatgggt gaccataaac ccctgaatgc tctggtccac 133920
atgggccaaa tgggagactg gacagcattc cattgatgag gaggtggggc tggtctccgg 133980
gagtaaggga gaggagcaca tgcagtaact gatggtctgc tgcaagggat agcagcacag 134040
cagttagaat tttggaggta actaccagaa ctgaaaacag aaatgataac aagtagttgc 134100
cttaaaaagg gatgggagca gggtgctttt gtgatcaaag ctccttctc ttactggatt 134160 tttgtacaca ttttgcatac atatcttaga gtaaagata gcattttcag ccttggtcca 134220
tttgaggata ctcttggcgt ggcccgcctc catgctagca ggctctggtt gtgccaagtt 134280
cagttgagca tcctggctct tgcctgcacg gaacttccag tcagtgcgtc agtatcacaa 134340
gtcttgatat ttcctatgaa gaagaacagt agtgcagtga cagacgaaat gggtgggcag 134400
gcagaggcag gatttctgag ggagagaagt agctagcttt ttgcagagaa gagttccggc 134460
acccaagaga gcagctgaga gtacaggcag gcaggcagga tgccggtagg gcccggccgc 134520
acggcgccac agaatcctgg agaaaggggc ctcttcatgg cctctgcatt cagctgctgt 134580
caccctccgc acaggccatg gccaaaattt aattttcata gtggactcta gttttgagc 134640 cttacttgct attattgaaa taattttctt gtttctttt aaagatcttc ggattatgct 134700
tcactgacca ctgtaataag tttaaagttg agaaaatatg gcttgttaat gaatgatagg 134760
tcaattttag tatgttggtc attttaatat tttgccacca gttggtttgg atttgatgcc 134820
aggaggagac agcctcattt ctaaggacta gtcttgcctt tgtgggataa gggtggtgtg 134880
ttctgtgtcc ttctacatgt ccgagcgatc tctgtgcagc tcaaatgtgg tcactgtctt 134940
attgcgctga tttcctctcc ttccatctca caattgaggc aaaatattgt tactgttgaa 135000
gtgttgtcca ataggacttc cagcagagac aggatgtctg cactgtctaa tttagttgcc 135060
tttagccaca tgtggtgttc tgtacctgaa atgtggctgg tctgattgga tagcttaatt 135120
tataatttta tttaattta attaacttaa atttaaacag ctctgtgtgg atagtggctc 135180
ctgtatgaga cagtgcaggt ctgttgagaa gcagctttac tggtgggagt ggagggcttg 135240
gagagggcac gtgggtttcc tgctggtatc ttttgacctt atttaatctg cccaacattt 135300
gcaagtaagt tgtgtgtgtg tgtatatata aatgtgtgtt tctgtcttct tgtttccttt 135360
gactgcattt atttgaaaga cactaggtgg cagaattact gtatttgatt ggtttcaaga 135420
taagagttga ataattcat ctcgtgtttt tatataagta aggtgtgttt agcatgtaaa 135480
attggtaata tgtattcacg tactgcttaa acaaaggcta tgaattccac ccataaaccg 135540
aaaatgaaga cctttaaatt tgtccatttc aggcgtgggt acttcttaaa taatacctgg 135600
ttcaggaact agtcagaatg gcacccttga ctttttgttt cctgcttttc ctcttgttgg 135660
gagaggaggg tattcatccc aaagtggttt gcctatttca cattccatct aggataagca 135720
gaatagccaa gaaagatagc tgtcctcctg tttacaacat tgggggtaac cagcatccct 135780
ctcttttggt ccaagataga ctggtttaga aacagatgat ggcaccagag gcccaggagg 135840
tggaaacatc agctttgttt gttgtccatg tggctgaatt agagctgtct ggccttgtag 135900
cctcaacacg gccttccagc tttgctcacc gtgattttca aggacacatc ttgtgctctt 135960
ccctgcctgc catccagact atacccagtc agggtggcag gagctgctgc cccttcctcc 136020
ctgagtcctg gtcgtgggtg gtggagatgt gccatgacgc tcacggaggc atgctcaccc 136080
cttcctctgt ggcagagggg atggctgcac gacagctctt ccctgtcctt tccaaagcgt 136140
ctgtggttcc acttttgggg gcaaagcagg aatactggaa gagagagaaa gtggtccttt 136200
```

```
ctatagtaat aaagttgaca ttgattcaag ttcatgcttg gggaaaggac agggctacta  136260
acaattataa tgctgggagc aatggaattt tctcatgggt atgtggtagg tttaatttta  136320
attatcccag ttaattctta gaactgctct gtgaagtatt tcccgctttg tgcttaagtt  136380
ctaaaagatc ctgtgccaaa accaagaatg aaaacccaag cattctttct tgcccatcga  136440
tctttctctc atcaggccac ttcttgggtt gatagtggtg agtgtagccg ctgccacttt  136500
cagaataccc accatgggcc ccagtcactg tgtggcgtgg agaagagatg gttctctctg  136560
tgtcatagct gaacaagccc agcccagaga ggtttctgcc ctaggagctc tcgatggtgg  136620
aattgggatg cgatcccaca tcctgcctgt tttgaaaaca gcattcttta tttccaattc  136680
ctgcttccat tgttcctttt aatatttctt tgtttagctc acaaaaacac ggcttgcgga  136740
gctgctgcgt gcagctgtag ctgtttctct gggtgcagcc tgcatccgcc ttcctgcccg  136800
cctcctttcc tgcactgcca tcgtggtctc cgggcacttg gtccctttct cttccctga   136860 gtcccttggg ctcccctgtg ccacccttgt gatccacagg ctctgccttc tttctgtctc  136920
agactgctgc tcatcactac tcgggaccct aggaagggag gttccaccga aagcatctt   136980 ctcatctcag ccacgttctc agtgccactg ttgtctttgt taggtaatgg tagctactgt  137040
aacaaataaa ccaacatttc catggcttca caccagagaa ggttgtttct tggttttatg  137100
acaatgtatt gagggtgttc ttggttcacg gatggttttc ctccatgtgg aattcgggg   137160 acccaggctc ctttccttct tttggttctg ttctccaggc cttcacatcc tctgtgtctg  137220
gttggggaca aggagaggga aggtaaagaa ggctttgtgg ccttggataa gtgacaggca  137280
tgcctttgct ggtgttctct cgtggtgaca ggtcacagcc ccaccctgta aaggggact   137340 gagagacgtc gtcctgctgc ttcccagcag cagcactgtg gtctctgatg tgttttctgt  137400
gaggataaaa acaggtgatt ccaggatgag gaaagtcagg gaaacccttg gaaggagggg  137460
accaggcggg tgtcaccatg ggattagtgg tggcttcaga atgagctgca gcgagtgcca  137520
tgccttctaa agcttttgct attctgatat gcccacacca tgcccagcag gtgtctgcct  137580
tgctctccgc agagagagtg atgaatcctt ctcatgagcc tctgtccagt tgttcctccc  137640
tccacctgga agggaccctg ggttcctcat aacatcccag cggaacaggg gaccttctat  137700
cctgtcccca agttcatcct catcctcctg ccggcttcct ggcccctctt atgtctgctt  137760
cctgacgcca catccttctg gattctctgg aattgaattt tgcctttgat gcttatttaa  137820
aaatatccat tgcaggccag gtgtggtggc tcacacctgt aatcctgtgc actttgggaa  137880
gccaaggtgg gcagattgct tgagcccagg agtttgagat tagcctgagc aacatgttga  137940
aatcctgttt ctatagaaaa tacaaaaatt agctgggcat ggtggcgcac acctatactc  138000
ccagctactc aggaacctga gacaggagga tcaattgagc cccggaggcc aaagctcag   138060 tgggctgtga tcgtgccact gtactccagt ctggtcaaac agagtgagac cctgtctgaa  138120 aaaaaaaaa aaatccattg catacttcac cgtagcgaaa catgtatgtc ttacctttcc   138180
tttcctgcct gtagctgctc ttttacactt aacagccaca ctaagccagc cttaaatgaa  138240
aaacaaacca gcacttcctg tgccctcctg cttccttcat gaggggtccc tccctctgtg  138300
tacactccat tctcattgcc catggtggtt tgtttccctc ttgttctca agccatggca   138360 gcctgcctct tgccctcttt actaaaaagg cctttgcaga ggctgcctgt gttctttctt  138420
tctaggtctc tctcatccta ggccctccag cttgattctg tggagctgcc ctcttgtcac  138480
tcagtagctt gtggggtctt ctctgtctag ccacttaatt gattgtgttc ctcgagttgc  138540
```

```
tgtccatggt ctctcgttac tgttttctct gtgtttctgc ctctctcctt ggccttggta 138600
ggtccatccc ctttgtgacc ttggctgttg ctctcatgga caactttctc ttgctggtcc 138660
ttgtagtcct ggcatccagc ttctcgacac gggacttgtc ctgccagtac ctcagacttg 138720
cacttaaaat tgaactagca ccactgtcac tctccagggc ctcttcttgt taattagatc 138780
attagggatg ttcagaatcc cagcatcata gtatgttcct cctcccgcta ccccaggaac 138840
cctaacctta cctcctcctc tctatctact aggaggtggc cctcagagtc cgtctcatct 138900
tccacctgaa cttccctaat aggctccagc agctgccacc ccggggggctg agtacttcct 138960 ccatgccttg tgcagtgctg agcccttttac ctgggttctc ctgtttgctc cttattacag 139020
ccctgcgaac agatactgct cttaattcca tcttacacct aaggaagctg aggccccagg 139080
taaggtgcat ccaaggtcac ccaggtagta gacagtagag ccacgatctg aaccaggcag 139140
tctgattcag agcctgtgtt gacactcagc cacctagaac acagcttgga ttgtgggttt 139200
ctattacctg ttcaaaaccc ctacatcccg ggtctgtccc tgcacgtgct ctgtggcctg 139260
gctgcatctt ccttgaaggc agtgcatgcc tcttcactca gggggccat gcaggaacag 139320 agggccccac agaaggatga ggccagtgca gaatgggctg gaggggacaa tgctgaccag 139380
gaagcaagtg tagagaaatc ccaggaaacc tggaggagcc agagacaagg cattagaact 139440
cctcgtcgtg acctggtctg cattctctga gtgtgctgct tctgttagct cgcttccttg 139500
gtctcaggtt atagtttaag gcattgtgga gccctaaaaa gcctgtactc tgttttacc 139560 tgttttagga cccttcact ttggggatgt gttgatttt tttttttttt ttttttttt 139620 tttgagatag agtctcgctc cattgcccag gctagagtgc agtggcacga tcttggccac 139680
tgctgcccct gcctcctggg ttcaagcaat tcttgtgctc ccgcctccca atacctggg 139740 attacaggca cccgccacca cactcggcca attttttgtat ttttagtgga dagggttt 139800 taccatgttg gtcaggctgg tctcgaactc ctgacctcaa gtgatctgcc caccttggcc 139860
tcccaaagtg ctgtgattat aggcgtgagc caccacaccc ggcctgaaat ttaaatcaga 139920
aataaaattt tgatcccaac agtgatgcca ggcagcccag atctggggga gagggtggcc 139980
ttggccagct gggccttttct ctgtttccca agtcttgctg cctctccctg ctgggctttg 140040
cagcctgtgc atgtctctgt gcctttgacc ttgtttatcc aaaggagagg atagaatgaa 140100
gtcatgattc ctggagccct gagaaggatg ctgtggagaa atttgccggt agaatctagc 140160
tgagtgtgtt gctgaggtgc cagcattgtg tgtggggagg ctgaccgctt ggcctgccta 140220
ggcccaggat gctccatggc cgggcacaga ggccacttgg ctgtcaggtg tcaggagcct 140280
gcagagggca cacagagcct ggaccgcagg ggggtcctgc tttctcacct ggcctccttc 140340
agcatttctg tccctcagtc cttagcaagc ccaggagctg ttgagtttgg caggtgccga 140400
gtgctgttcc tgcctgtgta gctgtggctc agtcctgtgg gggccccgct gtggcccgag 140460
tgcagtgatt cgaggcgctg agtgttccct gactccttct ccaggagctg tgttcagact 140520
ttcgcagctc ttggcttgga gctcctggag ggcttggcat tgccgaccaa tgtggaggtc 140580
gacagtgaga gaggaggaat gctagctttc ttgaccagtc cattaaataa gtgggatatt 140640
ggccaggcac ggcggctcac gccttaatcc cagcactttg ggaggctgag gcgggtggat 140700
cacgagctca ggagttcaag accagcctgg ccaacatggt gaaacccct ctatactaaa 140760 aatacaaata ttagctgggc gtggtggcag gcgcctgtaa tcctagctac ttgggaggct 140820
gaggcaggag aacagcttga aaccggaagg tggagtttgc agtgagccaa gattgcgcca 140880
ctgcactcca acctgggcaa caagagcaaa actctatctc aaaaaaaaaa aaaaaagtag 140940
```

```
gatatctgtt tctgcttaga aaaatcagaa ttttctaaat gccaggtgtt ctgaatacgt    141000
aagtatggga gacgactcag cctgtttcat ttttatgtaa aatcttcgcg tagccatgtg    141060
gcactggacc gagatgaaag caaagacatt tctccttaac tttgtttcta ggaatgttcc    141120
ggagaatcac agcagctgcc actaggctgt tccgcagtga tggctgtggc ggcagtttct    141180
acaccctgga cagcttgaac ttgcgggctc gttccatgat caccacccac ccggccctgg    141240
tgctgctctg gtgtcagata ctgctgcttg tcaaccacac cgactaccgc tggtgggcag    141300
aagtgcagca gaccccgaag taggttcata atgccccaca gcccagggcg ccagcccagc    141360
accctgtcct gagactccca gtaacctgag ctttggccac cgttaaagca tttttcatttt    141420 ccatttttg tgagggcttg tgaaatttct gctgcatatt aatattcctt tcatggacag    141480
catattattg ggacaaacat gcggtccagc taaaggcatt caaaatagca gttgctttct    141540
aaatgcgatt ttctttggca ggttctttga caccattgca tcttgtggga tatgcttgtc    141600
atgctctgtg gctcctacta agttctagtc cttaaattgg ttccatagcc agacatgttg    141660
caatgtctta acctcattat aaagtaaatg tggttctggt tatccttaga taatgaagta    141720
acagtgtagc aaatttcaaa acctcttgga aatgttattt taccattcaa aaaggcttac    141780
taaggttctc gttatgggtg gccctctttt tgcaaaaggt tttcaggctt aagctccatt    141840
tctaggtgct ccaacactcc attatttgta tatgtatgga aataaaagct gtgaccaccc    141900
ccaaccctgg cccccgccca gctgaatcct cagcacagta tttctggaag gctcaagatc    141960
ccacgctggg gaaagaagt tctggagaca aagagggca ggtgctgccg tgcctctctg    142020
ctcagtatgg atactggacc ttgtgctgcc agggctccca gtagggccag ttcatggcac    142080
tcagctggaa agtccactgt tgggaggcat tcttaaccat ccactctgtg ccgtatgtag    142140
tggggtctgg tcattctgtt ggaggagaca gaccagtgac gacatttgaa atgcttggtg    142200
gatgtcttag gcctgttacg atgactgagc actgtggggg caggagacag aaagtcagtg    142260
tctcctagtt ctgtgctgct ttaacgtgca tagaaatcag ctgcggattc agcagatcac    142320
tccttttctg acagatgggc ctgcttactc tgatgttata tcagaaagct ctgaatctgg    142380
gaattgtgtc ccctgaattg gagtaacaga aatgcttaga tgatgagtgt ttaaaagaaa    142440
taaaccaaag gtaaatttag tttggaattc agcaagcgtc ttcattcagc cctctgaggg    142500
caaactacag cttttttgtaa atgtaggtaa attctgtgac tgtttcgtga cccccctctga    142560 tccagtttc ctttataacc ttctgtattg ttccttctat tatcctgaaa taacattaat    142620
agattaggct gggcgtggtg gctcatgcct ataatcccag caccttggga agccaaggcg    142680
ggcagatcac ctgaggccag gacttcgaga ccagcctggc caacatgatg aaatgctgtc    142740
tctactgaaa ataacaaaaa ttagccgagc atggtgacag gtgcctgtag tccctgctac    142800
tcagaaggct gaggcgggag aatcgcttga acctaggagg aaaaggttgc agtgagctga    142860
gatcgcgcca ctgcactcta gcctgggtga cagagtgaga ctccatctca aaaaaaaaa    142920 aaaaaaaaa aaattaatgg atcaatggat ttttaaccta ataattaaat ttcaaaaaat    142980
atcgttcttt aatggtaatg taaaggtaaa attaagataa tatgtaacaa gcatgtgagt    143040
gtctaaggtg tccccgtggt ggaaggaaaa aataaatccc cataagtgtc caagatgccc    143100
atagagagca gagctgttct ggtttaaacc cctgctctta gcactgtgtt tttccagctg    143160
tgggtggtgg gggatgagta tctttttatt tccatgagat gagaaaaatg aattactaga    143220
agtgtgaaat acaaaacaca gctgctcttt ttttagccat agactcagca gccataaaat    143280
```

```
tgctgtatcc agttgcagaa attcctgctg cttactcttg accctctctc ggtttgtgtg 143340
catctcctct caggctggct cccagatggg agctggctcc aggcgacact gggtgctctg 143400
ctccaggagg tccttatgtg ggtcctgccc tagcctagcc cctctcttat ggactctgtc 143460
actgtgggtt tatgattcac tctcaatctg tcttacctct tggtgaactg ttagagtcct 143520
gcctatactt tggcgcttgt gggtgtgttg tggtacacat gatgtgttgg tcacttccca 143580
gctcatcttg ttctgagtca ccctagattt gggacattca ttcgccacca gtaccgggcg 143640
gtgtatggcc tgagatttgg gggggcttgt gctgctacaa attggggctg aatttgagtt 143700
gacagtggac cttctttatg tctactgctc atatttgaat tgcaaatact gcctcttctc 143760
tttcagaggc tcattaccct atagctgtat tattgcaaag tgcacaatta cagcttgagt 143820
gtaagtcaca ctgcgctggc aggacggccc actgagaaag ggcacgtttc ctgttcgtta 143880
gttttcacat tgacacataa tttacaatac agtaaaatgt acttttctat caactgtagt 143940
cagtaacagc ccccctcccc caaccacatc aagatataga ggagtgctgt cacttcaaac 144000
agttccctct tcctctgcca catcctgccc ctccccaggt ctaaccacca atccgtgctc 144060
tgtccctctg ttcagcccat tgcagaaggc catagaaata gaatctatag ctaggtgtg 144120
gtggctcatg cctgtaatcc cagtattttg agaggctgaa gtgggaggat gacttgaggc 144180
tgggagttca agactagcct gggctgccta gcaagacccc atctccagaa aaaaaaatt 144240
taaaaattac aatcacgtcc ctgtagttca gctgcttggg aggctgaggc aggaggatca 144300
cttgagctca ggagttagag gttacagtga gctatgatcg tgccactgtg ctccagccta 144360
ggtgacacag caagacgttg tctctgggga aaaagaaag aaacggaacc acgcggtgtg 144420
cagccttctg agtctggccc ctttcggtga gcagtgtcta agttctgtc gcgtgttgcc 144480
cacgcgtcgg tggctcgctc cttgcaactg ctgagcattg tatggctagg ctgtagtttg 144540
ttttcacttc accagttggg aaacagagaa aaggcacttt ttaaaaagtt taaatctgta 144600
gaatttggt ttttaccagt tctcttctaa atcctgaggg attacaggaa aagttgttgt 144660
atttcagaat attcttagct tgatgtgacc tctgtccccg ttaaggccct ttgccgcaat 144720
gggaaggacg tcgctcggtc agaccctgaa ggtcagaggg gcagtttggg agtgtgtcaa 144780
cattttaact gtatggacta gagccaagag tctcaaggtt tataattccc acgtattcaa 144840
aaagaaaaaa acaataaagt gagaagtcag tgtagagtga ataacctgt gttagtgggg 144900
aagaagtgtt tttaaacagg atttccataa cgtataacat caacatgttt agagtggtga 144960
tgtttcattg ggaaacgaac agtaaaacat gaaagcaggg aggttttcat tctggcagtt 145020
ggcaactttc acggcagatg gagaatttca aaagcaattg ctcaattatc aaacatagcc 145080
agtgtgagtt ctgaaataaa ggtgctgatt gaatgtgcag cttatggtg gattttgcta 145140
ttcaggcaag cattttaatt ttctgcctgt taaattctgt tttctttagt ttttcatatg 145200
tggtttattg tagcttagga atagataact gagagtatat attacacata caacattctg 145260
atatggcaat atttaaaaca acttgtctgt tttagaacta gaattaaaca taatcatctt 145320
cagtattttg caaataagct cactgccatc cagaaacatt gtcaatgcat ctgttgctcc 145380
ttctagaaga cacagtctgt ccagcacaaa gttacttagt ccccagatgt ctggagaaga 145440
ggaggattct gacttggcag ccaaacttgg aatgtgcaat agagaaatag tacgaagagg 145500
ggctctcatt ctcttctgtg attatgtcgt aagtttgaaa tgcctgtaaa cggggttgag 145560
ggaggtgggg accaggagaa catcctgtgt agatgacact tgcatggacc ctctggaacc 145620
cagaccgccc ggtgtcctgc caagctccat cgaaactaaa tctagaatga atgtttactt 145680
```

```
ctgctgtgac atataattgg agaccaggcc tggccttcca gtcactggat tctaagttgg  145740
actgtgagag ttttttgcagc tgactcattt atcaaatgcc cggctattgg ctcacgccta  145800
catgatgctg ggtatgtttg ttaatttgag ggaagcaatg gaataataat aactaatgat  145860
ttaaaaaaca aagtaagtgc attgactgta gtggggttct gattttaaat ttttttaaaa  145920
attaatacca ggagcagtgg cttatgccta aattccagca actcgagagg ctgaggtagg  145980
aagatcactt gagcccagga gtttgagaca agcctgggct atggtgtgag acacccatct  146040
ctaaaaaaat aaaaaataaa aaattatcca agtgtggtgg ctcgtgcctg taatcacagc  146100
tctttgagaa gctgagggcg gaggatggct tgagcctggg agttcgagac cagcctggca  146160
acacagagaa accctgcctc taccaaaaaa agaaagagag gaagaaagaa aaattagcct  146220
ggcgtggtgg tgcatgcctg tggtcccagc cacctgagag actgagaagg gaggattgct  146280
tgagcccaga agtttgaggc tgcagtgagc tgtgactgtg tcactgcact ccggcctggg  146340
tgacaaggcg agacccctgc tctaaaataa tttttttaag ttaatttgta gaaaggtgt  146400
tagatgttct ttgtcacatt ttatgatgga ttcctgttta aatgccgttc tctttaaaga  146460
aaaaaaaata acttgtggga gttttttaacc ataaaactag catcacatat ttaccatgga  146520
gaatttacaa aaaaacaaat aaacggagga aaataaaacc tcctgtaatc atactactca  146580
gagataactt gctgttagat tttggtctag atttaatact ttttctatat ttatattaaa  146640
aatatttaaa acatatgcat ttctttgtca caaacatggt atcttataga tactactgtc  146700
acatagcaaa acagtgttaa atattctgaa tcagaaaagg aagccgactc tccaactgaa  146760
agaggtgtta tcctagagac ttttttctggt gatgacaatt tattaatagt cacttttgc  146820
tttactttct ctattgaagt agttttttcta ttttgttcta cttttaagga taatataatt  146880
tataatgctg tttttcacag aaatataaga aaaagatac taatttttata agttaataaa  146940
gtttgatcat cccaaatcca aaaatctgaa atccaaaatg ctccaaattc tgaagctttt  147000
tgagtgctga cattatgttc aaaggaaatg ttcattggaa ggtttcagat tttcggattt  147060
agggagctca acaaataagt ataatgcaca tatttcaaaa cctgaaaaaa atcctaaatt  147120
cagaatactt ctgatcccaa acatttcaga taagggttat tcaacctgta ctgtcagatg  147180
atcccaaatg aaaaatatta atcgttaacc aaatatcaag gaattgatca cattttacag  147240
tttctgccta ggattatgaa tcaagatgaa aaggctctgc atgttaaaa atatatattt  147300
ttattttctt ataaatctta aatatctaca cttaagattt atttgatatg tgggatccat  147360
tcatattttg gattcaacag ttctgtcaaa actgtggcag tgataggga ttcttttttt  147420
cccactgaac tatcacaaaa ttggaaaaag agtaattgga gaacccccact ggcttagccg  147480
gcccgaagcc cgggagaggg caggcagtgc tgtggatggg gtcatcccag cgcaacgctg  147540
cccctgctac ctgcggatct cgctgaggcc tgcctttgtc ctttgaccct tggccatttg  147600
ttagtgtctc tgagagctgg actgctgtac cctacttccc caggggggcct aacttcacac  147660
agcctctgcc gcagtgcgtg gttggaggtg acggccttgg taaatcgagt ttcctacctc  147720
ctcaattatt tgtgctcata cactgtatat ttttagtgag gtttatattt gggatgtgtt  147780
ttctccttct tacccttttct ggcctttcta tggcattaat acctggtctc ttcttgtgta  147840
cttgaaaatg aatctctcat catatttttc cttagtgtca gaacctccat gactccgagc  147900
acttaacgtg gctcattgta aatcacattc aagatctgat cagcctttcc cacgagcctc  147960
cagtacagga cttcatcagt gccgttcatc ggaactctgc tgccagcggc ctgttcatcc  148020
```

```
aggcaattca gtctcgttgt gaaaaccttt caactgtacg tcttcatcct gccgactatt   148080
gccagttgca gttttccctg ccttaaaaat ggagtattga aattttttaac tttaatttct   148140 gatttgcaaa atagtcatct tttgttcttt tccttcttgc tgttagccaa ccatgctgaa   148200
gaaaactctt cagtgcttgg aggggatcca tctcagccag tcgggagctg tgctcacgct   148260
gtatgtggac aggcttctgt gcaccccttt ccgtgtgctg gctcgcatgg tcgacatcct   148320
tgcttgtcgc cgggtagaaa tgcttctggc tgcaaattta caggtattgg gaagagaaac   148380
cctgatattg atttatattg aaaatttagc aggccaagca aaacaggtgg ctggcttttt   148440
cctccgtaag tatggtcttg acatggtcac cgatagaaac atggaaacat ctgcaaactt   148500
gccgttactc gtgtgtccga tctgactgtt tcttgtattt ttttctagtc tgcccttact   148560
aggatgaact gtacacatca gttcatcctt tttaaatgag catgaggtta ttttgggttg   148620
ttaggtgtta caaacacact aatgtgtttt tgtctattag agcagcatgg cccagttgcc   148680
aatggaagaa ctcaacagaa tccaggaata ccttcagagc agcgggctcg ctcagaggta   148740
atgctggaaa cacaggtcgt ccttgtgtta ggacaaccca ggatataaag gatatagatt   148800
tgtacgggaa taaattcaca ggacaagaaa tcgatgtgcc ttataggtgg gtttactgca   148860
gaagtgccat aatagaacct tcctactttt aaaacaacca gatctcactt tctaaagagt   148920
aaaggatgac cggcaggatc acgtctgtga cgtgagtgga ggcagtttgc actcctggtg   148980
gctgtttgag aggtagcatt tagaatgcct gtattcactg tcctgtgatg agtgggaaaa   149040
taggttatca ggtttatctt agcaaaatca aagcatgtca tctaattgct aaacaagagt   149100
tggcaaatct gagagacatt actcaatcct tggcatgcag gacttacatc tgcatcctgt   149160 tgccattta tgtcttcaaa gcatttaatc atttagttgt gtttgcaaag tctttgagaa   149220
gcctttgtca gaaatcccta catctcctat gtgagtgtat ttccatgact gcagaataag   149280
ttaaactttt acctttttcc ttcccttgcg gggcggggtg ggggcaggg attgtgtgtg   149340 tgagagggag agagagacag cagagaagga gaatataatt atcatgctgt gtactttgag   149400
ctgaaactgc aaaaaaggaa aaacacacaa aaattattat gcttttcagt ctttagagta   149460
ccttgtctat tatgcttttc agtctttaga gtaccttgtt gatggtgttt ttaaatggga   149520
ttgggcacaa ttaggtggac agtttgggat gattttttcag tctgtagggc caagctcttt   149580
tgtaatttgc attatgaagt tgtcactctc atagcagatg gcgggagata aactattatt   149640 acttttgac cctagactta gtcttcagtc cagatgaggg agattaaaag attataaata   149700
tcttgtgcca gatgaggtga ttttattttg aaatgaccat gaattcctat cagttgtctt   149760
actgggatat ttgatagtgg aatttgtgca tttgagtctt agatgatctg ttttacattt   149820
attaagaaag cctttattag ctttttatact gtgtattgcc tgttgcagtg tttgagtata   149880
aatgaaattt ctggaaaata ttaatggagt acaaactgtg atacttaaaa gtaaactagg   149940
gcctgcattt gtatcatgac ctgtttgagt attgatgaga atagctgt gaagaaaaag   150000 gtttaaacaa gtgtattttc ctttaagaag ccactaatag tgcatctcct tagagtgtat   150060
atttctagaa tcctagtgtg cagagtttag actaagacta aaaaaaaaa aaaacaaatt   150120 atactgtaat tcatttttta tttgtatttt agacaccaaa ggctctattc cctgctggac   150180
aggtttcgtc tctccaccat gcaagactca cttagtccct ctcctccagt ctcttcccac   150240
ccgctggacg gggatgggca cgtgtcactg gaaacagtga gtccggacaa agtaagtgtc   150300
cagcgtgtct gcatgggagg cacagggcgc tgagtgcctc tgtcacctgt ggcagataca   150360
gagagtgcag aggaggtgcc gtggacccaa ggagttctgg cgctcggctc ggctcagtga   150420
```

```
agctgtggtt agagacgtgg ggggccatca aggtctgagg gagccaagca gtgctgatgt    150480
gggacccttt tggtaggagt gtggggtgag tagttagtgg gtgaatcaag gaatagtcgg    150540
ccgtggcctg caggcccctg actgcacagg ccttcaagca catgtcaatg ccgttagcct    150600
ccctccatct cctcatacct tctgccacc tgtgagttgc actgccactg ccagccattc    150660
tggtatgttg tcagcacctc cactgctcat acctcatggt tagggaccac ctggagcctt    150720
ggtagagcct tggtagagcc ttggtactct actttcctgg acaaagttca gcttatgaat    150780
atgaatttag atttcaaaaa ccagcagccc aagtataaga aagcgaaggt tcagtcctgc    150840
cttcttaggc tctattcgct aagcacctgc cctgccctgg ttgctgggga gagatgagta    150900
aagcagacaa cccaggagag gatggcaaag gggccgctaa cccttagtgg tttagctata    150960
tttgaaggc ctattggaag ttcaccaggt gaaggggag gctgtgaggg tgcccaggca    151020
ggtaacagaa gtccaaaggg gaaaacctgt ggtgtggtga gccgtatagc cacagcctgc    151080
cggccggcag ccctctcagc ctagtgcggt gttcccaagc actggcctag gcctgtagct    151140
ccagggatgt gaagtcccct tgaacgccgc ccatcatgtt cccctatcc attttttct    151200
tcccaggact ggtacgttca tcttgtcaaa tcccagtgtt ggaccaggtc agattctgca    151260
ctgctggaag gtgcagagct ggtgaatcgg attcctgctg aagatatgaa tgccttcatg    151320
atgaactcgg tacgggggga gcagtggagg caaggaatcc tcagcttttc ttgtgacttc    151380
caagtgggat ttgtctcatc atcatgtgac ccacttgttg acaacacatg ttgggactc    151440
cagtctgggc agggacggga tgtcggagag actccactct gaatgggcc gggaagtggg    151500
gaggactcca tttcagatgg ggtcgggaca tgggggttat gctgatcgag acagaaaagc    151560
acattgtttc agccacatta gaatccacgg aggtgttgtt ttgaaatcca gctggcccca    151620
aggctgggtg tatggtttgg gatgagaact atctggcctc cactggagga acaaacacag    151680
gatgttatca tctaagctcc atggccaaga cagaatggaa gtcaaggttg cgtatttgcc    151740
gtagacttca acacagtgtc gtaatgcgtg acgtcaataa cttgtttcta gtgtcttgga    151800
agttgatctt tagtcgtaaa agagacccctt ggatgcagcg agatttcctc tactcacacc    151860
tctgttagat gtagtgaggt tcttcacccc ccaaccccag atgtcagagg gcaccctgcg    151920
cagagctagg aggccatgca aagccttggt gtccctgtcc ctcacccgtg ggcaggtcct    151980
gtgagcagtg ggggggccac ctcttgggta tggtgcagcc atggcccaag cagggcttct    152040
tctcagacct actaggacgg gagaaacctc ctggtgcttt agccctgcgt tgatatgcag    152100
caaatgggag ggaagtgggc acctgggagg acaaatgcct gtagaggccg ggagtgacgg    152160
caggtgttca tgaaaagaga ccttgtgggg agggcaacac aacagtgtgt tctgatgtac    152220
tgaagagctc aactgaaaac aacaggagaa ttagcccaaa atccatttac taaaattgtt    152280
tatctttttt tttttttttg agacaaagtc tcgctgttgt cccccaggct ggagtgcaat    152340
ggcgctatct tggctcactg caacctccgc ctcctgggtt catacgattc tcctgcctca    152400
gcctcccaaa tagctggtat taacaggcat gcaccaccac gcccggctaa tttttgtatt    152460
tttagtagag acgggatttc accatgttgg ccaggctggt ctcaaactcc tgacctcagg    152520
tgatccgccc acctcggcct cccaaagtgc tgggattata ggcctgagcc accacgcccg    152580
gcctaaaatt gtttatctta agattcatgc agtgaaagct aacttactga gtgataaatt    152640
tgcttagtga tctgttttatt aggttttcca aatttgctaa ttgggctttg aacagctgta    152700
aaagttctga ctgtaaaaga aagcttcaac ttttggcatt catgatgctt ttctgagtat    152760
```

```
taaactaaga tagatgtttt acctgaagga tcggccacca atctttaaat ggctaaacaa   152820
aagggttgct aaaacataat ccaaattgac ataagaaata ccattttttcc aaccaaaatt   152880
ttggcattca tatggctact tttacgtatt tcagctgcat ttgaacatct ttttcaaact   152940
ttagggtggt tggtgtatca ctgaggtctt ggatgacact ttagctttga ttttgttttt   153000
atgaattaaa attgtcatac caaattttt atttcaagca aatccaagag cataaaaat   153060
taaaatatta cttaaaatac taagagagaa cagatatata ttttactaag catatgttga   153120
atgaaattgt tcaaatattt ataacaggca tagagtagaa ttttcttaaa aatattttg   153180
atggtatacc aatttgtatt ttctcagaaa catttgcctt attcttttt ctgttgtgtt   153240
tttcttacct gattgaaagc tcataatctg ttgttattgt ttgttaacct ttaatgctct   153300
gatttcagga gttcaaccta agcctgctag ctccatgctt aagcctaggg atgagtgaaa   153360
tttctggtgg ccagaagagt gcccttttg aagcagcccg tgaggtgact ctggcccgtg   153420
tgagcggcac cgtgcagcag ctccctgctg tccatcatgt cttccagccc gagctgcctg   153480
cagagccggc ggcctactgg agcaagttga atgatctgtt tggtaattaa aattaaaatt   153540
tatcttattt ttaaaaagca ttccagggcc agtatagtac tttgcaccaa gtaaatgtac   153600
aataaaggca gtggatctaa tacattgaaa gcgtttacag aggtagctaa agagcagcac   153660
gggtgtcctc ggctcagaat ttcttcctgt gtgtttgcca cttttgccatt cattgacatg   153720
gtcatggaca tagggctcta agcccttgag gaaggctggg ccagacctca ggggagatgc   153780
agccccaaac cacgtgcagt cctgtggacg gatgtgtaga tgtgccactg aggaacaatg   153840
tcttgagctt tcatcagatt tcagagaat tgcttgactg cctttcgaag ttgatgcatc   153900
tgtgctcacg tttgcaccca cccacgaggt ccttctgttt caggggatgc tgcactgtat   153960
cagtccctgc ccactctggc ccgggccctg gcacagtacc tggtggtggt ctccaaactg   154020
cccagtcatt tgcaccttcc tcctgagaaa gagaaggaca ttgtgaaatt cgtggtggca   154080
acccttgagg taagaggcag ctcgggagct cagtgttgct gtggggaggg gcatgggc   154140
tgacactgaa gagggtaaag cagttttatt tgaaaagcaa gatctctgac cagtccagtc   154200
acttttccat ctcagcctgg cagtaagtct tgtcaccgtc aagttattgt agccatcctt   154260
caccctcacc tcgccactcc tcatggtggc ctgtgaggtc agccaggtcc ccttctcatc   154320
tgcacctacc atgttaggtg gatcctaatt ttagagacat gaaaaataat catctggaag   154380
tactttatgt cttaagttgg cctggacatg tcagccaagg aatacttact tggtttgtgt   154440
tagtgcttgt aattcgcccc cagaatgtgt acacgttctg gatgcattaa agtctggcct   154500
gtatccttaa agggccatcg ctgtgctgcc tgccctcagc aaggacacac tttgcagacc   154560
cacagaggct ccgcctccac ctcacaccaa agaaagggag gagtccaaag gcatcagtg   154620
ccattactca caaaatgata aatacaccct tattctgaac cacgtggagt catatggttt   154680
gtgatccctg tccttcaggt ttcagcttag tggggaagtg ggaaagtcag cgtgtgatca   154740
cagcacaggg tgattgctgc tgattatatt atgtgcctgc tgtatgcagg atgaaatact   154800
ttatatgcgt catcttattt gactctcaca accccctgtg atataggctc tgttactccc   154860
atttgacagg tgaggaaagc aaggcttaga gaatttcagt gacttgccca ggtcctctga   154920
gctaggaagt agccattctg gcatttgaac ccaaggcctg ctatccctag aacccacgct   154980
ctcaaattca acctatgaca gaggcaagcc ctggtgctgt gggagcccca aggaagagcc   155040
tctggcctgg tggccacgta gcccaggaga gatttctaca ggagcccaca gcgctgaagg   155100
agagagaggc agcagagtaa gggggctttg tggcagagag gggactggca ctttggggaa   155160
```

```
taggtgggtc aggactgaat gtaatggagc catgtcagag ctgtccttct ggaagggcaa 155220
gggcacctgg acgcgctgcc cctcagtgct ttggacggtt ccacaactgt gattcacacg 155280
gcttccccaa acgaaggtac acgagtgggc attctgtgac tcggtacttc cctttaggcc 155340
ctgtcctggc atttgatcca tgagcagatc ccgctgagtc tggatctcca ggcagggctg 155400
gactgctgct gcctggccct gcagctgcct ggcctctgga gcgtggtctc ctccacagag 155460
tttgtgaccc acgcctgctc cctcatctac tgtgtgcact tcatcctgga ggccggtgag 155520
tccccgtcca tgaacggtgg gttcctatca tagttcctgt ctgcttcacc atgttttat 155580
tttgtgctgc ctgtttgcca ggtactaagc taggaattgg ggatggagag gtagataaaa 155640
tatgcatcag gaagggctgg gccccatctc ttactctcca atatattgga gtctacactg 155700
gaatttaact ggaatttgct tttttagtca ttttatttag attttgaagt ttcagctttc 155760
atcaaaaata cctctaaact ttatgtctct gtgatctttg gtcttagctg ttttatgtat 155820
ttagtcttat atgatcataa gattaataac attacattca gaagattatt tgttttctgt 155880
cagagttaaa atgtttgttt ttatactgca ttgtaatatt aacgtactgt aaaataaaag 155940
tggcttgttc ttttcaagga acagtatcct caacaagggt cattagccac aattttaaa 156000
aaattggacg tcatagttta catgttagag ggcgttttga agctttgtat ttttaaatta 156060
aatgttatag agtgatgttt tcatgtttca taattgtttt catctgtgca tttgtagcca 156120
acttgaaaac aaagatccag ggattactac ttaaaagcca gacttcttgg aggttatagt 156180
gatgattttg atagtatctt gagccgtctc ataataacct cagggtgaga gatggccaac 156240
aggagacagt cgagggactt agaaatctga atgaaatctg aagttcaaat cttcagacat 156300
ataccactaa ccaagagatt ggtacctcag tctagtattg tctgtttgtc taaaattggt 156360
tctaaggaat ctaggctagt ctgtctatcc cttcaactt ttgtgaggct gcacaaatgt 156420
aaaatgttga ataaaagca ctgatggaag tgtgtagaaa ttcttctctt tgttctgttg 156480
taattttagt tgcagtgcag cctggagagc agcttcttag tccagaaaga aggacaaata 156540
ccccaaaagc catcagcgag gaggaggagg aagtagatcc aaacacacag agtaagtctc 156600
aggacccatt ttttcttac atgttgttcc tccaggactt aaaaatcatt cacagagacg 156660
tgcaccgcgg tgagtgtgga ctcctggaag cgcaccgtag ctccgctgtg tcctgctgct 156720
cctccctagc tgtcagggag gctgtagtcc attgcttgc cagctctttt gtttccgagt 156780
gaacacctta tccgtacaca tgcggctgtc tctgaccta cagaccagct gggatgccac 156840
tggggagcg ctcccttccc cccgcacttc ccacactctg cagttattct gagatccttg 156900
agggcaggga acaggtttgt cttctttgtg ttctcagaaa ttaatgctcg gcctctggtc 156960
agcaagcaac aaccttttgt tgagtgataa tgaataaata aatgtttccc acatgagtat 157020
tcagtaacct cagtgtcagg ttcagccatc tgttttggtg gatatttaaa agaaaattcc 157080
gcttttccta cagaaaaaaa aaaaaatcca aatcccagtg atttaagcca gttatagact 157140
tagacatata ctacggcttt tcatgcactt tcctcccaat tctagagtag gtattttact 157200
aggaaaatgg tggcagtgcc tgttgggagg aagattcttt ggccaagtgt cttttgttct 157260
tgccagggcc cctaggctgc tggggtgctt cagcttcttt agcccagtgt ctggtgggga 157320
atggcccctg ttgcctgtcc cacagaggtg ggggtgcctc acctggagcc tgtccacaca 157380
ttttacacag cacgcttacc tggagcatca ggcatctttt ccatgctctg tggctcagga 157440
aacacgcctt ttcaatcatg agtgcaccag tgcttttggg cttttctcc ccgcttttgt 157500
```

```
gcaatcctgg ttgtggatgg agttttcctg tctttagtct tctgcatagt acttttctct 157560
tctggttccc ggttcaaggt tttgtaatta gagaatgacc cagaagcaat ggcattttaa 157620
tgcacagcca aggacttctc tgaatttgta tctcaaacct ctgtgggtcc ttcaggcttc 157680
agtttgtgat ttcatgattt cttgttgcta cctaaggaat atgaaaacac ccacctccct 157740
actctgcatc ttccagccga gtggcacctc aggctgtgga tcctgtgctt ctgtggtgag 157800
gataagaata gtgccaaccg tgtggattga aatcaatcag ttaatccctc catgtaaagc 157860
acctggaacg gatgacagtc ttgttatgaa tactcaacaa atgctatcat gattttttagt 157920
tagatttcca ttgctttaaa acagttgaga catcttggcg gtttgagtta gagcaacggg 157980
ccctgaagtg ggttctgttt gggtgaagat gattatgctt attccccatg gccctcttta 158040
ggcaagagtg ggaagctttc tttgttttttt taatcacctc gataggacgt tacttcttaa 158100
aggtcatcca ataaatatta ataggccggg cgcggtggct cacgcctgta atcccagcac 158160
tttgggaggc cgaggcgggc ggatcacgag gtcaggagat cgagaccatc ccagctaaaa 158220
cggtgaaacc ccgtctctac taaaaataca aaaaattagc cgggcgtagt ggcgggcgcc 158280
tgtagtccca gctacttggg aggctgaggc aggagaatgg cgtgaacccg ggaggcggag 158340
cttgcagtga gccgagatcc cgccactgca ctccagcctg ggcgacagag caagactccg 158400
tctcaaaaaa aaaaaaaaat attaataaag ccaactcgtt agcgtggggc ttaattgctt 158460
aagtccaatg agaagtcctt ctctatccta ggaagttgcc caaactgtag aatctcgtgg 158520
cctgtgggta atagccacgt aatacacact cactgcctca acaaatcata ttttagtagg 158580
tatgatattc tagactcaag acaccattct gtggatcttc ccaagggtgt gaagtgtcca 158640
cagcgtctgc cttgggagtt tccatgccca ccagaaccat gccccaagcc cctcaagcac 158700
tctgacctag gaaagccagt gaagcaagga tgacaacatg gcccttttgat actagctgag 158760
ggacagacac aggtcctggg agaccagaga aagacgaggg gcagaggagg tgtcctaaag 158820
gaagtctgag gctgaggagc cacaggatgg cttccagctg tcacaggctg ctgctggcct 158880
tatcacagag agtgggccag agggctggga accaaggcca gagctcaggt tcaggaccat 158940
tccagcaatc ccagcagaaa atggggagaa ttgtatggta taggcggata tgaaggtaga 159000
atctgcaggc cttcagtggc caactcagag tctaagtgga ttccacagtt acagcttgag 159060
cagctggttg taggtcatgc tttctacact gggcatatag gatgtgtttt ttaaaaagtc 159120
ctctcttaac cgttgcttgt ttagatccta agtatatcac tgcagcctgt gagatggtgg 159180
cagaaatggt ggagtctctg cagtcggtgt tggccttggg tcataaaagg aatagcggcg 159240
tgccggcgtt tctcacgcca ttgctaagga acatcatcat cagcctggcc cgcctgcccc 159300
ttgtcaacag ctacacacgt gtgccccccac tggtgagtct gctcgttcct tgcagaagac 159360
caagtacggt gaaaggcacc ggtaggccct gggctgggca cacgtgagag ggcgggacag 159420
aatccccgca gcccagaggc tgcctgctgt ggttctggtg cccactgtgg ttctggtgcc 159480
aggctgcttt cctcaggcac cacgtgtgga ggtcgctagt agaaatactg ggttttctaa 159540
aatgaactga ggccctacat ccctaagaga ttagtgttag acctgattct agagcaacta 159600
gaccactttg cttaatagca gaccagaaac cacaccccct cgagtgagtg agattttcct 159660
ttggagataa ttcatgtttt tctacacagt tttgcagttg tcttcagaat tggtttaaag 159720
taggtgttat tgccaggcgc agtagctcat gcctgtaatc ccagcacttt gggaagccaa 159780
ggtgggcgga tcacttgagg tcaggatttc gagaccagcc tggccaacat ggtgaaaccc 159840
catctctact aaaaatataa aaattagcca ggtgtggtgg tgtacgcctg taatcccagc 159900
```

```
tactcaggag actgagacag gagaatcgct tgaacccagg aggcgaaggt tgcagtaagc   159960
cgagatcgcg ccactgcact ctagcctggg caacagagca agactccgtc tcaaaaaaaa   160020
aaaaggtagg tgttattgat cagaacccct tgtttcagata acatgaggag cttagcttga   160080
ggagagtgag ggttgatgga gggggactga cttctgccca gtgaaatggc atcatctccc   160140
accagcccgc tgaaataaga tgatgggggcc tgttccttag ggcctgcagc atcctcaggc   160200
aggaaagaaa ggccgacctg gcagggtgtg agccagcagg tgtaggtcag ggagaatgga   160260
gccaggtccc agggaagagg cttgtggctg cctgagaagg gtgcgtgcct gcctgtgtgt   160320
gtgtgtgcac gtgtgtgtat gtatgctgga gagtctaggg aggcttgctc caaggacgca   160380
gtattgtttg atcctgagag ataaggattc tgccgcaggg aatgaaggta ttccagatgg   160440
cgggcttatt ccgaagaaga ggccagtgcc tggcggtgct ggaagcagtt gcagaacagg   160500
gagttgtagg ctttcctggg aagagagcag caggggtgct ggagaagcag gccacacttg   160560
ctgcatgggg ttgctctcgg ccccactctt ggtgcacagc gagtcactgt gggttcatta   160620
gcatctggtt atgagacagt aactgctcct ttggaggggc tcgtggagac catgcaggag   160680
ggcacggtct tgaggtcatg ccgtccagag cacacctgag gataggccag gacgggctgc   160740
acgctgtagg taaaattcct ccagcaagct cttcactggc attgaggagt ccctgagtg   160800 cggtcatctg gaaggcagct gtaacaggca ctgcagtctc tccctgggtg ggtaccagag   160860
aggagcatag gggagcataa ccgatttaaa gagagggctt tcctgtggtg aggtaagaga   160920
ttagctggtc attatcatag agcccctct gcctttgtgc agatgggctg tgggaatcct   160980
ggggttccgt tgggtccttt gtcacctcac tgaaggcatg taagctgagc tggccagacc   161040
gtgagctgat cctgccactt gaacagcatc aagcctgcct ctggattctt ctgtgcatgg   161100
cacttgtctg agcacctcac gcacagagaa ctggacttca gagtttacag aaataagctg   161160
tatggttcat tttcatgcct gcttgccaat aaacatatct gagctgaacc tcattgaacg   161220 cctgcctta ttctagcaca gcacctgctg tttgtgggcg aggggtgctg tctctaactc   161280
ctgcctgctt ctcccagcac tccctgagtg gggtgtgcca gcagcctcag gatgaggaca   161340
ggaagtggga gggcagagca gatttgggag ggccacttga tggggaagga agtcccagga   161400
agcagttgga gctgttttct gggggagaag gtgccagctc tgggacagtg ttggggtagt   161460
gaggagggag cccagtggag agaagtcggg cttcctgctt cctcacagta tgtctgtcct   161520
gactcaactc ggatgatgtc acttcctttt catcttctca ggtgtggaag cttggatggt   161580
cacccaaacc gggaggggat tttggcacag cattccctga gatccccgtg gagttcctcc   161640
aggaaaagga agtctttaag gagttcatct accgcatcaa cacactaggt actcttgggg   161700
cctctccttc aggtcaccat tgtcggacat ctaccgggag gaaatccaga gcccccagta   161760
ctgggatctt ctcatttgac tccagaaaag atttaagcat gataataata caaacctatg   161820
tgaatacatt ttgcagtgtt ggcaaaactc cttttatact gagaaaatag atcccagttc   161880
ctgtgttttg tggcttgaat cccagctttg tgtattccgg gcttgtttga agtcaggaaa   161940
ggttcatgtg tagtggacaa cgtgagacca aattctgcct tagattttgc atttaggcta   162000
aacagtggca gcacttgtct cagaatgttt tcttgtgttc accagtctga tcctgttgtg   162060
tctcagtggt ccattttctc atatgggaac aagcagacgg gagcagatgg agtcaggttt   162120
cttggcactc gccttcccca gagcctgag gcagcatggg gagaaagcag gcttgggct    162180 cagacagtcc tggtctgctt ccagcccctcc tacctgagca gcgcagggca agtccgtcta   162240
```

```
acctctagag accctcagtt tgtcatatg taaaatgggg gtcgtgtcta tttcatagaa   162300
ttgttgcaga tttagaaatt acatttctaa acaaatgtta ccccttattt ctaaataagt   162360
gtctaaatga ataagtcacc acttttgccc ctatttgatg gcaagaggtg tgatcttgtg   162420
gtgggactgt aatcagtcag ttctcagtga ctgtgccctg ctgtggtgtt tcctggaatg   162480
ttcctgtctt gtcctagaaa gtctggcagg ggcaccctga ctccactgtc cagtcctctc   162540
cccagtccct cgggcttctg cagatttgag gcttgtttgg atcccagaag gttgtggcag   162600
gagacacctt gcctctactt tcccctttat aattcaatgt ccaaagagag ccctgagcag   162660
gtacctcacg ccagctgcct cacggagctc ctcctcttcc tggctgtgag gatcggtatc   162720
agtggcctcc tgctctctcc cccttgccta acacgagcac ctttgcttac ttgggtgccc   162780
ttgctcttga actgcccatc ggacgtgcgt gacccaagac tgtgccgcag tccttgcctt   162840
gtctgtgctc attttctttg ttcattttt tccctgtaac gtaaattgtt atatttgtct   162900
gtatctgtgt ctgaatcagt cctgcacgct ctccttctct ctgtctcttg ttctttcttt   162960
accccgttta tcacggggac cccgatgtcc attgctctag ttctcctgtc ctaagcaccc   163020
catcccgtct ctctggcctt accacaagtg gcgtggctgc ctcagacatc atgatgggga   163080
catgaagcac agctgtcaga acaactgtt cgttagatac actcgaatgc agctcatcaa   163140
tagggatgga gggtctgtcg gatgtatttt cactgaatcc ccgttcctac cttgatacac   163200
tcttttaat ctattcttct agacaggtca gaggaaccat tactttgact tttaaatttt   163260
tagcagcttt attgaggtag aattcacata ctacagattt cacccactct aagcggacag   163320
cttggtggcc attagtttta tccacagagt tgtgcagcca gctgcacagt ctcagggctg   163380
gactccaggg aagattttag cccatttagt gagtggggca gaagtggccc tggccctgca   163440
cgaggttgcc tgcatgggcg tccctgccct gtccctgtgt ctgctccact gggggttgac   163500
caggctgcca gggccgactt gggcctgtgc cacctgcctc tcatgtgtct cggacagtgc   163560
agccgatgtc tatacttcgg tttcctcaat gatgaaatgg aggggatagt gttccccgca   163620
tcatagaact gtgtgaggtt taagggactc actgcccttg gcgtggagcc ttctccaggg   163680
gccgtgctgt gtcggcgtag ctgtcagctc tccgttacag gcttgagaag ggttgacact   163740
ctctcatgta acatttatat ttctaggctg gaccagtcgt actcagtttg aagaaacttg   163800
ggccaccctc cttggtgtcc tggtgacgca gcccctcgtg atggagcagg aggagagccc   163860
accagaagta aggccacacc ctgtgctggt tggcacatgg gcagttatgg ccgcttgcag   163920
gcctttggtg gggaataaaa taaggcagca agctggtgtt cttttttct cttacccttat   163980
ttttgaaaga gtagctgaat ggtgtcttga ctgatattcc agagcaggga caaagcctgc   164040
tgaggtctgg gggctgcgat taccaatggc tggaatgcat tttattacgg tgcattccat   164100
gttaaggatc aatacgattg tgcccttcct ggaaaatatc ttttagttta tcaatattca   164160
gaggagtgta ggttgaatta aaatgaaaag gcactttata aaggccatga gtagtacctg   164220
gtttcatttt tctaatgtct tgcagagatt ttatcaggct tcttgaagtg ttcacgtaca   164280
ttacgctaac acgatattaa taataactgt gctctggtac agcggagcca gcagaatggg   164340
aagttgtgga atgcaggccc ttgattctga tagaaggtgt ggtttgaact cacagaaatg   164400
acagtttgga gggtagacat atgtcacaag tcatcaagat tgtctttaaa ttcatgcata   164460
gaagctaaca gggtgtcata agcaaggcct gtaaaatgta tgagggaatt caaagataat   164520
ttattaaaaa gtaattcatg tttggagttt tgtgcccaaa ggagtccttg atttgaaaaa   164580
tgggcttttg cccatcagat tgtttcaggg cccgtgtgtg cggaggccct gccttgtgcc   164640
```

```
ccgtgagctc agcctgacag aaatcctttg gtagcactta aggctcctct tcctcccatt   164700
gaggcaggga agactctggg ttctgcaggc agaggtggtt gtgggtgtct tgctgctctt   164760
gttgacatgt gggctctcct tccaggaaga cacagagagg acccagatca acgtcctggc   164820
cgtgcaggcc atcacctcac tggtgctcag tgcaatgact gtgcctgtgg ccggcaaccc   164880
agctgtaagc tgcttggagc agcagccccg gaacaagcct ctgaaagctc tcgacaccag   164940
gtttgcttga gttcccacgt gtctctggga catagcaggt gctggggaca gtgggttccc   165000
cgctgaagcg tccagcagct tcaaccaggc cgttttcctt cattgctaga attgaaaaca   165060
ccgtccgtgt ggcctgtgca ggagatgcag acccaaaggt ggcctcctgg tcagtgagaa   165120
gctggaaacg tgacaggaac tgacgtgggg ttattgagca tttaggggaa gacgttagca   165180
gagcaggaat gagcaggcaa ctagtagaac acccacttaa gggctcacgg acaggtgctc   165240
acttaggaag tgagtttcat ttggtattac accaggttcc tttaggcaaa gcggagggaa   165300
agttctggtg tttttcactt gtaagatttt gaaggaaaca aaacactctt taccttttt    165360 ctaaaatgta ggtttgggag gaagctgagc attatcagag ggattgtgga gcaagagatt   165420
caagcaatgg tttcaaagag agagaatatt gccacccatc atttatatca ggcatgggat   165480
cctgtccctt ctctgtctcc ggctactaca ggtacctgag ggaaagggtg cggggagcg    165540 gttgtacttg ggctagaatg agagaagact ggcatgctca ccacaccagt gatgcggaa    165600 gacctgagtg tggtctgagt tggaggctgt ggtgctaaat acgctgcccc tttcataagc   165660
aggagtctta gtcaggccca gggaggaagt aaaatctgga aatgaatgag aagcattctc   165720
tcctgccagt caagaaatga gaagcgaaag aattctcacg ggctgtaaga ccagcaggat   165780
ttaaaagttg aattagttgc ttatgttaag aactcaacca agttcatcta cacaagctga   165840
atctccagct tttcctaaga aaccatgtgt ggcagtggct gcagggcagg gcacagctgg   165900
gcctgagcac cccgctccct gcacctctcc cctccctggg ccctgcctgt cactgcccac   165960
tctcccacca agccttccgg ttgtgtgcct gccctatcac aggcatcgga gcttgtcacc   166020
tggtttaaaa gaagagagtt gtgtggggat ttgggatgca cgttttttcac tcaaaagtat   166080 tttagcgtag agctctgtga ttccgtagct atttaggagt ttaagcacct tgaaggcttt   166140
aattgcagaa agttctatgt ggacgtgcaa tgtgttatac gcagtgtcta tgagactcaa   166200
atgtttatta gggcgttgaa gtaaactgag cacttggagg gccatggatc cagccttcaa   166260
ggagctcata agtcaggagg acccaggagc aatgacctgt catagaaggc agaaaagagg   166320
ggcacagagg tgggtgggag gcatacacag gcagctcctg gagctccaag gggagcaagt   166380
gcttccaggg aaggggcgt ggaggccct ttggaggagg caagttgatc tggggtctgg    166440
cagagggtta gctggggaca tttagcggga ggctggtgcc cggaattgg ggggatgccc    166500 agcagaaaga catgaggagg ctggcctggg gcgtgggggg gtgtgaaagg ttaagtgggg   166560
gcattatcct gctcccgctc ctgccggctg tatctggtca gcctgggcac cgaggtgggg   166620
ttctggaagg cactgttcac caaaatgctt atctgggtcc cccagagagc ttgcctgcct   166680
ggactgtcgg ctcgcctgca actgctgact cctaagcttt tgcagctcag cccacaacca   166740
gttcctattc acagaggtgg gagctgaggg gtgacaagtg actgctgcag tcttatttgt   166800
catagagaaa aagtgacaga gtccagcttg cccactggcc ctgccagctt aactggttat   166860
aaagtgacaa atccccaaga cccacagggc tctgcacaac ctgggccctc ctgccagtgg   166920
cggcgagggc aggtggctca cggctgggtg cctgtctggg caggagctgg gctggtatgg   166980
```

```
ggtgggcctg cggccctgcc ccctgtgca gatcaagact cagggtgctg gtgttcacag   167040
gtgccctcat cagccacgag aagctgctgc tacagatcaa ccccgagcgg gagctgggga   167100
gcatgagcta caaactcggc caggtcagtc tcgcgccccc gccgcctggc ctctgtccgt   167160
ttctgtcctc agactttggc gcttgacaca cccaggagaa aagctcagtg cacttttaa    167220 atgaaaggaa gttttccttt tttttaaaaa aaaatttaat gttcattgtt tttatctgtt   167280
ttattcctag gtcccgcaag cagaggaagc attagttttg tttttattta tgttctgtat   167340
tccagaaagt agttaagaga cctcacatgt agcgatagag atgtgtgtaa gagacagtga   167400
gagggcgtga cttggactta agcaaggacc gtgagacaca aaaggggggg tgaggacaga   167460
gtggagtcag ctgaaatgct caggaggaag tagacgccat gaagggccat ggtatggggg   167520
gccgcaggcg tggccgtgag tgtccctggg gccagctctt ggggggctcc ctgagtgtcc   167580
ctgtccctgt ggccagttct gggtgggagc ccgtgtgca ggcagacagc tcggccactt    167640
cctagcaggt cacattggtc tgtgcttctg tttcctcctc agataagtga agggattcaa   167700
gggtctgggt gtggtggcta acacctgtaa tctataacat tttaggaggc tgaggcagga   167760
ggcttacctg agctcaggag gttgaggctg cagtgagcca tgattgcacc actgcactcc   167820
agcctgggca acagaccagt actctgtccc ttaaaaaaaa atgtaaacag aaacgtaggg   167880
ccatttgcat atgatggcac atggcgtgga ccctacagg tgtatgctgg gcggggcccg    167940
gctgtgctgg ccgacttgca cctttccctc caccccggtg ctgtgtcttt cgctcaccgg   168000
gttcctgatt tagtgaaagc agttgtgcag gacagttctc tttgtagctt ttgtttctgt   168060
ggaaatgggt cagaatatgg tgtttagaaa cacttatgag ctctgagagt ttcctcttct   168120
gagttcctgg cctgcagcct tcacagcaga aaccctgtga tgtcacaagc ctgtttctgt   168180
tccctgctct ctgcctgtac tgtcctgttt tgtgcctgcc ggtttcagtg acaggaagca   168240
gggagctact ggaccagcct gtatttttct agacatagtt ggaaaagaa gtcccactct   168300 tctgtccttt caccttgac agatgtttcc accccaagat aagtgaaaat gaccaatagg    168360
atgcactgta ttttcatga aagtgtttct gaagggcagg ctgagagtga gaggcctggg    168420
gctcactggg tgcctctggc cttgtcctgg gcccagggac actggtctgt gcccgaggta   168480
ttccctatcc ccccaacccc gctgcatttg gccacatcct tcaatgtttg cgttgtgtcc   168540
agcgtccgca aaccaactgt catgggatca tactggggct gaagtacggt cccacccctg   168600
ccctgtctgg ggctgaagta cagtgccacc cctgccctgt ctgggctga aggacagtgc    168660 caccctgcc ctgtctgggg ctgaagtaca gtgccacccc tgccctgtct ggggctgaag    168720
gacagtgcca ccccttccct gtctggggct gaaggacagt gccacccctg ccctgtctgg   168780
ggctgaagga cagtgccacc cctgccctgt ctgggctga aggacagtgc cacccctgcc    168840
ctgtctgggg ctgaaggaca gtgccacccc tgccctgtct ggggctgaag gacagtgcca   168900 ccctgccct gtctggggct gaaggacagt gccacccctg ccctgtctgg ggctgaagga    168960
cagtgccacc cctgccctgt ctgggctga aggacagtgc cacccctgcc ctgtctgggg    169020
ctgaaggaca gtgccacccc tgccctgtct ggggctgaag gacagtgcca ccctgccct    169080 gtctgggct gaaggacagt gccacccctg ccctgtctgg ggctgaagga cagtgccacc    169140
cctgccctgt ctgggctga aggacagtgc caccctgcc ctgtctgggg ctgaaggaca     169200
gtgccacccc tgccctgtct gggatgttta gccctagat gccactggac tgagccgcta    169260
cttgcttttg ggaagaggg gtggggtta ggggtctggg cgaggggagt gcaggggctc     169320
ctccttggcc tgagagctgt tcatacagac tcctcgccca ctccctgcag ggtgctgggt   169380
```

```
cccagggggg aaatggccct tggtgccaag aacgtgagtt ggggctagtg ccagtgatga    169440
tggagaacag cttttatgg gcacacagcc cacagcactg tgccaagtgc tcgaggcttc     169500
ccgagaacca ggcagaaagg aggacagtcg aggtgtgctg actgcgtggt ggctgcgtga    169560
tctagagcgc gggtcacaaa ggcgcgaggg agctctggcc ttgggtttac cgcaatgact    169620
gccagtgcgg gagactggaa aaggaatctc acgtattggt tccgtgtttt ggggactcca    169680
ttcagatgtc acttaggagt gaaagcatcc cttcgtagag cctctttctg tgtcaccctc    169740
ctcagctgct cctggggttg actggcccct gattcatgcc tttagcatgt gctggagctt    169800
cccagcagct gtccagcccc tgccccaccc tctctgtggg ctcccttgcc cgtaacctgg    169860
ggtgtctgaa cgacccttgc taaggggcag actgttagac ggtaggcatg tgctgagtcc    169920
cagtggccac acccacccac caggagcctg gcactgtggc cgcagcactg agcagtgccc    169980
cgtttctgtg gcaggtgtcc atacactccg tgtggctggg aacagcatc acacccctga    170040
gggaggagga atgggacgag gaagaggagg aggaggccga cgcccctgca ccttcgtcac    170100
cacccacgtc tccagtcaac tccaggtttt ccaatggcct ttttcttttt aacagaaatt    170160
tgaaatttct tatcagtcat ttgatttgtt tgaggtgctt cttgaaatga gcctctcatc    170220
tcatgtactt ggaaaatacc catctcgcat attccacagg aaacaccggg ctggagttga    170280
catccactcc tgttcgcagt ttttgcttga gttgtacagc cgctggatcc tgccgtccag    170340
ctcagccagg aggaccccgg ccatcctgat cagtgaggtg gtcagatccg taagtgagcc    170400
ttcccattcc cctcacacct gcacgtgcca cacgcaccac acgccaca caccccacac     170460
acacacaccg cccacacaca tgccacttgc acacacaccc ctcatgcatg caacacacac    170520
acaggccaca cgcaccatag acaccacaca cacatgccac atgcacacac atacacggca    170580
tgcaccatac acacaacaca cacagcacac atgccacaca cacgccacac accacatgca    170640
ccacacacat gccacatgca cacacactcc acatgcatgc accacacaca cacacacaca    170700
ccacacacac cacatgcacc acaccacaca ggttacatgc acacaacaca cacatgccac    170760
gtgcacacac cccacacacc acatgtatgt gccacacaca gcacacaacc acacacatgc    170820
accacacaca tgccacatgt gcatgcacca gacacatggc acacactaca cacacgccac    170880
gtgcacacac cccacacaca tgtacgcacc acacacatgc cacacacaca tgcaccacac    170940
acatgccaca tgtacacaca tgtatataca caccccacac cacacacaca ccacttgcac    171000
accacgcaca cacaccacat gcgcacacac acaccacata cgccacatgt acacaccata    171060
cacacaccat acatgcacca cgtgtaccac gcacccacac agacacagca cacgcataca    171120
ccacacacac acgcacacat gcgtcccgca cagtaatgtc tcttgggtgt aagaacacga    171180
cttgccagta gtagcgttct ggatgcgttg cctggattct aacagcgcga ttctccccett   171240
gccctcctgg tttttccacat ctccagcttc tagtggtctc agacttgttc accgagcgca    171300
accagtttga gctgatgtat gtgacgctga cagaactgcg aagggtgcac ccttcagaag    171360
acgagatcct cgctcagtac ctggtgcctg ccacctgcaa ggcagctgcc gtccttggga    171420
tggtaagtga caggtggcac agaggttttct gtgctgaagc cacggggggcc catctgcctt   171480
gggacctggt gttggccaga ggtgccgggt gcggctgcct ccttccaaga gttgacccga    171540
accggactcc acggcccacg tgagctgcag tgcttctcag atggagggggg ttcagcgacg   171600
gtcagtgcca ttcacaggtc actgtgatgt gggttgtggc ggccaagcca tggtttgggg    171660
tcccgtatcc ctgggcttat gacatcattg tagtagccca tccccacaga accacggtgt    171720
```

-continued

```
gtggtggcgc tgaggcatcg tagatggtgg aaatgctact ggcttcccca tgctctgccc   171780
tgaggcctga ctgcctcact ccccttctca gttatgttcc aggcccccg agcttcctgg    171840
ctggacagct tctctcctgg gggccgtttt gtcacagtga ccctgtgttt ctagtcccaa   171900
atctgggtgc tatagtctct ttttagcgtg gtggttgtct tagtctttt tggctgctac    171960
cacaagttac cttagactgg gtaatttata aacagtggaa atttacttct caccgttctg   172020
ggggctggaa gttttcatgg tcaaggtgcc agcagatttg gtgtgtgatg agggctgctc   172080
tctgcttcat agatggcatc ttctggctgg gtcctcacgg tggaaggagt gaacaagctc   172140
cctcaggcct tttagaaggg ccccaatcca caagggctct cccatcatga cctcatcacc   172200
tcccaaggcc ccaccttctt gtactgtggc actgcaaatt aggtgtcagt gtaggagttt   172260
caggagggat agaaacattc agaccatccc agcggtcaag tgttcatcct cttgagttcc   172320
tccttattct gcttctggtt tatcaggatt cagccagtgc agcatggtac ctgtattctg   172380
tggcacatca ccacatggta tttgccaagt atccatcacc tgcacacgtg aaatcattgc   172440
ccgtgggtcc cgacatctgg cgaagcatat tcaaggatgg cagaactgtc agagctggca   172500
cctctggttc cttgtcatgt ggcattacct agtaatccat tttatgatag caatggaaac   172560
tcatttcttc aacaaacacc tgagtggctg ccgtgtgcca gccgtctggg gcccttggtg   172620
agaatggcat ggtggtgccc atcagggcct gcctagcccg tgctctggac gggctcctgt   172680
gtgtcaggaa cgacaatgct gtcatgacgg tgaatgattt ttttttttgc catcactcca   172740
gccgctaaca tttgcggagc tcttcctccc gcaccccac ctgacaaggc caagggtgac    172800
cttggcccca ccctaggcgg ccaaggtcag aggttagctg gcttgtctgg gtcacacaaa   172860
atgcagcaga ggttgaggtg agcacatgtc cgtgacctgg agcctgactc cctctctgcg   172920
agtcttgact gctcttgcct agactctgtc ctccccgagc ccaaacgcca gtcatcttcc   172980
cttgtgggtg tccttcagcc tggtgccatg ctggtgactc agcagccgtc cagggagtgg   173040
aaacaattga gtgtgtgggt tccctgtgtg ggcatctctc ttcacggcga acaccctctg   173100
ggtgttgccc acacgatgtc aaagcggctc ttggaagggg tccttctcct tgtgggaag    173160
tttcagctgc tgggctaact tgaattgtaa ctgtggtttt gtgctcaggc ccagatcccc   173220
ctaggcaagt gttgtgccat cagtaatcaa atgagaaata atcattttga aaagcagatc   173280
ctaaggcagg atggtcatgg acactcactc ccagctcttt gtgcactcat gctttctgga   173340
agatggccat cctctgtgaa ggttttcagc gcgtcatgct tggtacccac gtatccagag   173400
catgtcgttt tgaggtattt gcccaccgtt gtgaaatccg tgccaccga gagcaggtcc     173460
tgatgtgggg ctttcagaag tgggacctgg ggccgtacgc agtccttagg gaggggccgt    173520
gtggcgttgt gcgtgtgagg ggatagcaca gggtgaggtg ggggcccaag aaggaagtga   173580
cccacaaaga acagcctcct cttttggtcc ttgttcctgg gatggctggg agtggcttct   173640
gtgtcgtccg gccatttccc ctgcggagag gctcctacca ctgccgagaa cctcatcatt   173700
ccacaaaaac aagaggccgc ctggccatcc agcgctccat gggaattctg tgtccccata   173760
gtcttgggct gaaggagggt gacattcctt gctgacttct gcagggtct cctcactgtt     173820
aaagagcaga ttgaaagtga agaacgtggg ctaagtgttt aggtcgatat ttaaccctgc   173880
taggttttgg atactaagtg aaattgaggc catttggtt gaagttgaca gaaaccacta     173940
tcagggatcc ccaagactac cccaggcttt tctagaaaga ctctcagcta agatgtgtta   174000
tggtaaaagc acacaaaaca aaatcagcaa agaaaattag caagggcaga ggcccatggg   174060
gcgatgtccc gaggacacca ggcttgagct tccagaatcc tctcccagcg gggtcgtgca   174120
```

```
ggacgcactt aactccccgc acagtgagcc gtgacagcgc gtgtgcagtg tcgtcgccag   174180
gaaagcacac tagagactcg gtgccagggt ttttactggg ggctgggcac atgggcaccc   174240
tctgcctgcc tcgtgcccag actctggact cccggaggga aggcaagttc tcagcaccaa   174300
ccctggtgcc cacacaagca gctgagcaca gggagcccct cctcagtgag gatggtgggc   174360
accgtcccaa caccagccag gggccagcct tgcacacagg cctctcagga tggtctccgg   174420
cctgctgtgt agtctcttct gcacacaagc gtgagggcag cgccccgcc tcggctgtgt   174480 ggaggagcca ctgggacgtg agctctggtg gcatgcagca gcttttgtct gtgtgtgcct   174540
aggacaaggc cgtggcggag cctgtcagcc gcctgctgga gagcacgctc aggagcagcc   174600
acctgcccag cagggttgga gccctgcacg gcgtcctcta tgtgctggag tgcgacctgc   174660
tggacgacac tgccaagcag ctcatcccgg tcatcagcga ctatctcctc tccaacctga   174720
aagggatcgc ccagtgagtg ggagcctggc tggggctggg gcggggtct cagaatgagc   174780 tgtgaaggaa gcagcatcac cctctccaag tgcccaggct cctggccaga tggcaggcca   174840
ggtatcagtg ggaacccagg tgggtgccat ggctgaggtc agtgagacgc aagagcacag   174900
gtgcgtccta gaggcttcct cgggcacctc cagcgagctg gagctctcgc ctctgctgct   174960
gtctcatgtg gcgcttagca cactctccca cgtgcccatt cctgactctg ctctcgaggc   175020
catcggctct cattctctgc tcccagaacc ctgttattac ccaggctagc ctcctctctg   175080
caccttcccc gccctggccc agtacctccc tcttgtttcc actgtgattc cgacctcacc   175140
ttatcttaaa gctgctggac ggcaggttct gtacacacgt gtccttgaca aagcacggct   175200
ggtgccgcaa ccctcagcg agcaagtcaa gctcttcaca gcgatgtctt acaagcgcag   175260
agggctctgt gacaccctgg tctcaccgcc actcttccaa agtcgcagag gctttagcag   175320
agatgggccc agcctctctg agtcatagcc ttctgcacac gggagctgtc tttagaggga   175380
gggtggaatt tcatcagcca cccacatggg ggagttgagg gcaagaatta ggagcaaaga   175440
tgggaagggg tctgggagga atggccagtg atcccctttg acaagtgggc aggaaacggg   175500
ggctaggtca aagttgagtg gaagacctgg agggagacgg gaaggtctct gtaggcacag   175560
ttcagacagg agggaggtgt gagccagggc acatgccggt ggccgtctgg caggatttgg   175620
gacatgctgg agcagggaca gcggctcatc aggggccatt gccctcatcc aggccagagt   175680
gtcacaagcc cgtggggagg cccttctcgc ctgtcatcct tgctgggcag tgggtgctgt   175740
gctagcagga caggcggacg gctggcaact gtctctgcat ccctggagcc tggcataggg   175800
ccaagtcaca cggggcacag gcctgcaaat caggcacata tgttggtgca gtgacgtgat   175860 tttgggggc agccccagaa caggcccag acacaggcca aagccctgcc tgtgctggtg   175920 tgtttgggctg ttctatggct cttgctgtgg gcatggagga ctcagggaag gagagttgag   175980
gtggtccagg agttgcgttt gggatgcaga gagcttgtgg catccaggta gaaatggtgc   176040
gtggggctga cctcagcacc atgggcagag gggccgtgtc acgtgcctcc gaggtggagg   176100
tgggaccacg tggtgacaga tatacgcatc actgggcacg tttttgtggg tgttgggggg   176160
catcgtattg gctcctctgt tcacagtggc cactcattca gtccctggct accaggtcct   176220
cactgtgcca tggggaaggc cggcgctgtc ggggatcac agaaggcagc acgtcatgat   176280
ggcatgtgcc atgaaggaaa agcacagggc actcaggaag tagaggggac tggcctgggg   176340
tgtgggaatc tagggcctcg ttgagggaca gagagaggaa gtgtgtggtg ccagcatgg   176400 aggtggccac aggggaggct gagttaggcc gagagggcag ggcgttgggg aggtagacgg   176460
```

```
gctcagccac tcagggagtg gtcaagcaga ggctgaaggg tcaggccagg ttgcaggggc   176520 ctggggagc  cactcagggt aggcgctccc gggagcccgc ctggcccata gctctacact   176580
cccgcgtggg gccggacatg ctgtgaagcc ctctccacgt tggatggggg tggctgagcc   176640
tggatgctgt ctcccgtttt cagctgcgtg aacattcaca gccagcagca cgtactggtc   176700
atgtgtgcca ctgcgtttta cctcattgag aactatcctc tggacgtagg gccggaattt   176760
tcagcatcaa taatacaggt gagtgggccc tggctgtctt cctctgcaca cggggagtgg   176820
gcttcccttc tcttttcctt gcaggatcat accagtgggc cagttttgac ttggtcggga   176880
ggaggcatga acacctgaga ctgtgcagcg attctttgac acagaggcct ttctccctgt   176940
gcagatgtgt ggggtgatgc tgtctggaag tgaggagtcc accccctcca tcatttacca   177000
ctgtgccctc agaggcctgg agcgcctcct gctctctgag cagctctccc gcctggatgc   177060
agaatcgctg gtcaagctga gtgtggacag agtgaacgtg cacagcccgc accgggccat   177120
ggcggctctg ggcctgatgc tcacctgcat gtacacaggt gagcatgtac acggtgccca   177180
taaggccagc ccaagtcctg ttcaagggag gcaggagcat gctcactcaa gggacctcga   177240
ctaggtgccc tctgatttca cacttctggt gttgccccaa gccggcccca tcaccttgca   177300
agaaaggctc tggagccccc agggctggag tacctggtca gggttgaccg tccctgtggt   177360
cactcatccc atgtggctga gctgggctgg gtcctgggca agcaaggggc tgatatcacc   177420
tgctttcaga tctccaggga ctcactggac ccctgtgtac aaagcactgt ctacagagcc   177480
tattgggttg tatagaggta accttcgtac tgaacacttt tgttacagga aaggagaaag   177540
tcagtccggg tagaacttca daccctaatc ctgcagcccc cgacagcgag tcagtgattg   177600
ttgctatgga gcgggtatct gttcttttg ataggtaaga agcgaagccc catccctcag   177660
ccgttagctt ccctagaact ttggcctgaa gctgtgcttt tgtgtgtgtc tgctgatccc   177720
ctggcgctgt tgctggagtc ctgccagtga ttccccacca cagcctgacc atgggctgcc   177780
ttggctcagg gttccactgg cgagctggtg gtccttggac cccagcactc aggtgtagcg   177840
ttgaccagtt ccaaggttgt cccagtgcct gcccatctct cctgagggct cagggacagt   177900
acctggcagt tgggggtgtg gcaggggggca ggaatgacca gcctctggga gggtggggca   177960
gaagcctgta cagtgaggag gagctggctc agcctggctg cctatcgtga gagggagcc    178020 cacgggggctg tgggagggggg gccgtggtgc ctgtgagcag ggtgaggagc agcggcagga   178080
ggatgaaggt ggaacccaca catgcatctt tgagaccccgt gtggtcagtg gcttctgccc   178140
cccaccaccc cccactgctg tgcgtgcata gaattggctt ccctcacctg ctctggaagt   178200
gggttaggag cttggtaggg ctttttctca aggacaaggg cccctgatt  gctctcaggc   178260 ctcagtcctg gcgacatggt ggatctggag ccttgttgca ctgccttgcc tgtgctctcc   178320
aatcagggtg gccagtgggg agccatttgg cttttctcaa gagcatactc aggtggacct   178380
tgctccactg tttgaccaga tgaggcattc tgaacagcca agcctgtgct ggtctgtttt   178440
catgttgatt tttttttttc ttttctttt  gagatggagt ttttcccttg tcacccaggc   178500
tggagtgcaa tggtgtgatc tcggctcact gcaacctccg cctcccgggt tcaagtgatt   178560
ctcctgcctc agcctcccta gtagctggga ttacaggcac acaccaccat gcccagctaa   178620
tttttgtgtt tttagtagag acggggtttc accgtgttgg ctgggctggt ctcgaactcc   178680
tgaactcaag tgatccaccc tccttggcct cccaaagtgc tgggattgca ggcgtgagcc   178740
actgcgcccg gcccccatgt cgattttaa  atgcacctct gcatcgttct tcagtcccca   178800
tatgctcact gagcaccact gcgactggca gacgggcaca gggaggcgcc acgaccagtc   178860
```

```
ctggccttca agggcttgt ggtctagtgg gcccaatgct aggtggcgag tgctccaaag 178920
agtgtggtgc acgccttccg cttgaccgct ctccagacgc cacagggagg cacctcgcag 178980
ctgaccacag atttctctct gtggagcagt gtcttcagag cggctgccat gccactgctg 179040
ggcgagggtc tgcgggcggg tagagccagg agcacctgtg aggaagtgca ctgccatttt 179100
cgtagctgct tcccgtgtgt ctcagttaca cacggctggc atgtgtgcac tgatgagacg 179160
ggaacgtgat ggttgctttt cagcactgaa agggatactg ctcaggggc gtgtttcagg 179220 atctggttag ggaagaagca gcgagagcac agatggggcc ctgtgtggta acaagaaaaa 179280
agtcctggtt gacaacagtg ccacgaagcg ttagaacaca tagggatgtt tgtggagcat 179340
ttgcatgtgg aaagcagcaa aaacataatg gaacgggtt cttttgttat gattttaaa 179400 aatctctttt gtaacatcct tcccgctgcg ccgtttctgc atattccttt atgtagcttt 179460
caaactcctc ttaggagttc tggtccctac agggcgtggg agcccaggct ttacgtagct 179520
ttcaaactcc tcttaggagt tctggtccct acagggtgtg ggagcccagg cctgtgccg 179580 agcagcctgc ctccacgagc tagacagagg aagggctggg gttttgcctt tttagtctca 179640
aaattcgtac tccagttgct taggctctga ctttccccac ttggaaagtc cctcacggcc 179700
gagggtccct cccagccctg atttcacatc ggcattttcc ccagtattag agccaaggcc 179760
ctccgcgggc aggtggggca gctgtgggag ctggtgccag tctctgacct gcgtccctcc 179820
tcccaggatc aggaaaggct ttccttgtga agccagagtg gtggccagga tcctgcccca 179880
gtttctagac gacttcttcc caccccagga catcatgaac aaagtcatcg gagagtttct 179940
gtccaaccag cagccatacc cccagttcat ggccaccgtg gtgtataagg tgaggttgca 180000
tgtgggatgg ggatggagtg ggaaagcctg gaggtggagt tgcctccgac ttcccagcag 180060
attcgccagc agagcccagc tcctccgctt taaagcagca atgcctctgg cccccacccc 180120 accccgcca cccaggcgca gcaggtgctt cccgtccccc cagccctgac actcaggcac 180180
ctgcttgctc cttgcaggtg tttcagactc tgcacagcac cgggcagtcg tccatggtcc 180240
gggactgggt catgctgtcc ctctccaact tcacgcagag ggccccggtc gccatggcca 180300
cgtggagcct ctcctgcttc tttgtcagcg cgtccaccag cccgtgggtc gcggcgatgt 180360
atcctctctg ggtccctggt gctggccccg tttcccttgt caacaccgag gctcatgttt 180420
catgataagg ttttgaaacc taaccttgc aaaaacccca cagatgccag ggtgacaggc 180480
cctcagcccc agggaagtaa aatgctgaca ggggtacaga aggagcacg tccagacatt 180540 tgctgaccag ggcctctcag aggggccggt gtatggcagg agggtcgcag ctgagggc 180600 tttctgtgga gggcctgggt gaggggagcg agggtgggcg gtggtctctg cagacgtccc 180660
gcccactcgc gggctctgtg tggctgggct tctcctgaca ctgcttctca ttagctttgg 180720
tcattgtgcc tcgatcgccc tctcggggaa aggcttaagt aaagatccag ttcccacccc 180780
cagatgctgg ctgccaggag tttccctttc cacagccctt ccccaagaca gaccacaaga 180840
gcctccaagc agcacagttg tcctggtgct gacagcacag ccttgcccgg cgtgcctggc 180900
acggctctgc cctcactgca ttggagcagg gctagtggag gccagcggaa gcaccggcca 180960
ccagcgctgc acaggagcca ggccaggtga gtgctgccga gtgggtgccc tgcctgcagg 181020
gcatccagcc agccaagggt tgcaggaatg gaggtggagg cgctgatgca gctggaggca 181080
tccaggtggc ccttccgggg ctctgctcgc tctccaggct ccctggaccc ctttgtgagc 181140
tgtttcagga gaggaactcc caggtgagga cagggaggca gcattcccct catttgccgg 181200
```

```
ccttttctcct taactcctgc accagcctcc cacatgtcat cagcaggatg ggcaagctgg  181260
agcaggtgga cgtgaacctt ttctgcctgg tcgccacaga cttctacaga caccagatag  181320
aggaggagct cgaccgcagg gccttccagt ctgtgcttga ggtggttgca gccccaggaa  181380
gcccatatca ccggctgctg acttgtttac gaaatgtcca caaggtcacc acctgctgag  181440
cgccatggtg ggagagactg tgaggcggca gctggggccg gagcctttgg aagtctgcgc  181500
ccttgtgccc tgcctccacc gagccagctt ggtccctatg gcttccgca catgccgcgg  181560
gcggccaggc aacgtgcgtg tctctgccat gtggcagaag tgctctttgt ggcagtggcc  181620
aggcagggag tgtctgcagt cctggtgggg ctgagcctga ggccttccag aaagcaggag  181680
cagctgtgct gcaccccatg tgggtgacca ggtcctttct cctgatagtc acctgctggt  181740
tgttgccagg ttgcagctgc tcttgcatct gggccagaag tcctccctcc tgcaggctgg  181800
ctgttggccc ctctgctgtc ctgcagtaga aggtgccgtg agcaggcttt gggaacactg  181860
gcctgggtct ccctggtggg gtgtgcatgc cacgccccgt gtctggatgc acagatgcca  181920
tggcctgtgc tgggccagtg gctggggtg ctagacaccc ggcaccattc tcccttctct  181980
cttttcttct caggatttaa aatttaatta tatcagtaaa gagattaatt ttaacgtaac  182040
tctttctatg cccgtgtaaa gtatgtgaat cgcaaggcct gtgctgcatg cgacagcgtc  182100
cggggtggtg gacagggccc ccggccacgc tccctctcct gtagccactg gcatagccct  182160
cctgagcacc cgctgacatt tccgttgtac atgttcctgt ttatgcattc acaaggtgac  182220
tgggatgtag agaggcgtta gtgggcaggt ggccacagca ggactgagga caggcccca  182280
ttatcctagg ggtgcgctca cctgcagccc ctcctcctcg ggcacagacg actgtcgttc  182340
tccacccacc agtcagggac agcagcctcc ctgtcactca gctgagaagg ccagccctcc  182400
ctggctgtga gcagcctcca ctgtgtccag agacatgggc ctcccactcc tgttccttgc  182460
tagccctggg gtggcgtctg cctaggagct ggctggcagg tgttgggacc tgctgctcca  182520
tggatgcatg ccctaagagt gtcactgagc tgtgttttgt ctgagcctct ctcggtcaac  182580
agcaaagctt ggtgtcttgg cactgttagt gacagagccc agcatccctt ctgccccgt  182640
tccagctgac atcttgcacg gtgacccctt ttagtcagga gagtgcagat ctgtgctcat  182700
cggagactgc cccacggccc tgtcagagcc gccactccta tccccaggcc aggtccctgg  182760
accagcctcc tgtttgcagg cccagaggag ccaagtcatt aaaatggaag tggattctgg  182820
atggccgggc tgctgctgat gtaggagctg gatttgggag ctctgcttgc cgactggctg  182880
tgagacgagg caggggctct gcttcctcag ccctagaggc gagccaggca aggttggcga  182940
ctgtcatgtg gcttggtttg gtcatgcccg tcgatgtttt gggtattgaa tgtggtaagt  183000
ggaggaaatg ttggaactct gtgcaggtgc tgccttgaga cccccaagct tccacctgtc  183060
cctctcctat gtggcagctg gggagcagct gagatgtgga cttgtatgct gcccacatac  183120
gtgaggggga gctgaaaggg agccctcct ctgagcagcc tctgccaggc ctgtatgagg  183180
cttttcccac cagctcccaa cagaggcctc ccccagccag gaccacctcg tcctcgtggc  183240
ggggcagcag gagcggtaga aaggggtccg atgtttgagg aggcccttaa gggaagctac  183300
tgaattataa cacgtaagaa aatcaccatt ccgtattggt tgggggctcc tgtttctcat  183360
cctagctttt tcctggaaag cccgctagaa ggtttgggaa cgaggggaaa gttctcagaa  183420
ctgttggctg ctccccaccc gcctcccgcc tcccccgcag gttatgtcag cagctctgag  183480
acagcagtat cacaggccag atgttgttcc tggctagatg tttacatttg taagaaataa  183540
cactgtgaat gtaaaacaga gccattccct tggaatgcat atcgctgggc tcaacataga  183600
```

```
gtttgtcttc ctcttgttta cgacgtgatc taaaccagtc cttagcaagg ggctcagaac   183660 acccgctct  ggcagtaggt gtcccccacc cccaaagacc tgcctgtgtg ctccggagat   183720
gaatatgagc tcattagtaa aaatgacttc acccacgcat atacataaag tatccatgca   183780
tgtgcatata gacacatcta taattttaca cacacacctc tcaagacgga gatgcatggc   183840
ctctaagagt gcccgtgtcg gttcttcctg gaagttgact ttccttagac ccgccaggtc   183900
aagttagccg cgtgacggac atccaggcgt gggacgtggt cagggcaggg ctcattcatt   183960
gcccactagg atcccactgg cgaagatggt ctccatatca gctctctgca gaagggagga   184020
agactttatc atgttcctaa aaatctgtgg caagcaccca tcgtattatc caaattttgt   184080
tgcaaatgtg attaatttgg ttgtcaagtt ttgggggtgg gctgtgggga gattgctttt   184140
gttttcctgc tggtaatatc gggaaagatt ttaatgaaac cagggtagaa ttgtttggca   184200
atgcactgaa gcgtgtttct ttcccaaaat gtgcctccct tccgctgcgg gcccagctga   184260
gtctatgtag gtgatgtttc cagctgccaa gtgctctttg ttactgtcca ccctcatttc   184320
tgccagcgca tgtgtccttt caaggggaaa atgtgaagct gaacccactc cagacaccca   184380
gaatgtagca tctgagaagg ccctgtgccc taaaggacac ccctcgcccc catcttcatg   184440 gaggggggtca tttcagagcc ctcggagcca atgaacagct cctcctcttg gagctgagat   184500 gagcccacg  tggagctcgg gacggatagt agacagcaat aactcggtgt gtggccgcct   184560
ggcaggtgga acttcctccc gttgcgggt ggagtgaggt tagttctgtg tgtctggtgg   184620
gtggagtcag gcttctcttg ctacctgtga gcatccttcc cagcagacat cctcatcggg   184680 cttttgtccct ccccgcttc ctccctctgc ggggaggacc cgggaccaca gctgctggcc   184740
agggtagact tggagctgtc ctccagaggg gtcacgtgta ggagtgagaa aaggaagat   184800 cttgagagct gctgagggac cttggagagc tcaggatggc tcagacgagg acactcgctt   184860
gccgggcctg ggcctcctgg gaaggaggga gctgctcaga atgccgcatg acaactgaag   184920
gcaacctgga aggttcaggg gccgctcttc ccccatgtgc ctgtcacgct ctggtgcagt   184980
caaaggaacg ccttccctc  agttgttct aagagcagag tctcccgctg caatctgggt   185040
ggtaactgcc agccttggag gatcgtggcc aacgtggacc tgcctacgga gggtgggctc   185100
tgacccaagt ggggcctcct tgtccaggtc tcactgcttt gcaccgtggt cagagggact   185160
gtcagctgag cttgagctcc cctggagcca gcagggctgt gatgggcgag tcccggagcc   185220
ccacccagac ctgaatgctt ctgagagcaa agggaaggac tgacgagaga tgtatattta   185280 atttttaac tgctgcaaac attgtacatc caaattaaag gaaaaaaatg gaaccatca   185340 gttgttgctg tgtgaggctt gctttgcttc atgagaacct agaccttgct gagctggagt   185400
cttaggaagc agtctcctaa gtgcttctcc agcaggggca gaaactgtcc caccagctaa   185460
catctggcat tatggagggt ccccaggca  gctgccagca gggacaggcc ccgtgttttc   185520
tgtagccagg gatgaggaag tggcccagg  gcatggccct ggctgggtgc ttctgcaagg   185580
gccttcccaa accacagtac aggtggtctt cctgccctgc agatgggagc tgtgggagct   185640
gctggagctg ctggagcctt catggtcaag tgacatcata agcttatatg acatacacaa   185700
gcctcaggac ttggcccatg gcactgaagc aggtcatcag gccagcacca gagactgagg   185760
ctgtgttctc acagggccca ccaccctccc acctccttgg ccattgacac ctgcgtccct   185820
ggcccagctg ctcccaggta accccaaag  cagctggcac atcccacctc tggtgtggcc   185880
ggggctgctg tgtgtccgca gggcctgccc cgtctattct agcttgtttg tcctgtctga   185940
```

```
accagcgcct actccaagaa gcctctgctc agcccagcgg ggatgcttct aagctccgga 186000
cgagcctctc ggaagccttg gtgattggtg gtgtagtcat cttgggatgc agatgtctta 186060
ccaacctgca agaacaaaaa ccctgtggct tcctctggtg cagggtattt agtcaatgtt 186120
tgctgaggtc ccgtctggtt ctggctaatt ggcaggggtc gtccacccat tctttccctg 186180
ctctgctgtc tgtgccagga gagacggggg ccagtcggcc aaggggccag ctcctgctgc 186240
ctgctcctct tgggcacgtg cggggccccc ctttctctga gcaggatag ggatcagtct 186300 gccggaggga tgtggtggac aggcctaaag catttggggc ggggcatgcc acttgagctc 186360
cctaaatctg tctcctcata ggtgacaccg ctccagggcc ccccagtggc ctctcctttc 186420
agagctacct aaattctggt cacttcagag aaatggagca ccccttctc cctggtccag 186480 gtgtggacag cctggcacac tgagcacacc tggcatggct ggtaatttca gaaagaagag 186540
gggccggggt ccagtgggaa gcagcggtga accctcgtg agtgggcttt gcagtccctc 186600
cccatgccac ggcagagctg ccctcaacac agccttcctc ttcctcatcg gagagcacac 186660
cctgtcccct tgccgagctg tgccctgtgc cttcggtggg atttgatttt ggctgctact 186720
ggctttgttg ggatctggaa gtcgcttccc ctgcgtggtg cgtggagcac tgtaagtcag 186780
atgagggaag tagccagggt gaggtgagta ccgggtggag ccgccactga agggactggg 186840 tagggggggcc ttgcctctac atgatgtgac acagccaacc gaggacagag gaagcccgt 186900 tcctgggggt gtgggggtgca ccccttcaggg aagcctgcag tggggcctga ggaaaggcat 186960
cctccgcgag cccacgagtc tggtccatga gcaccgtgac agtgtctgtg ggtagaggtg 187020
gacccggcct tgtgtcatca ccaggacctc ttttgggaaa ccatgtggac atcgcttgcg 187080
ggtcccccag gctctgcagc cccagcagcc tggctgcctt ttgggcaagt ggcttgagcc 187140
acagaggacc cagtcctgtt gcagccacat cctctggggg ggcccgccag tgtggccggc 187200
tttctccacc ctacaccagg cctccaggtg tcctggtcgg gggtgtctgg gccctgggtg 187260
ggccctgtgg acctgtgagg tcagggtcag ggcatcactg gaggcagagg gctgaagttg 187320
tgggtctggg ttcccttgt gtgcacaggc ccctgccctc catgcttggt caggcagcta 187380
cccccaaaac tgctaggaca ggctggtcct gaggtggatc ctggcccctg taccctctgg 187440
acagcccacc cgcccaacct tctaccctgc cccagcggcg gcagtgttgg ccacatcctt 187500
cccctcctgg ccccaattgc tctggggaag tccaggctcc ggagcctgcc caggggcccc 187560
ccgtgatttg ggcccaggac tccacgtggt tctctgcctt cacccaagcc ctgaactcct 187620
cagctgccaa atccccaccc atctgcacag gctgtgctca ccactgctgc tcctggaagg 187680
tgcccctcag tgggacgccc acctcctctc tgggcttctg tgtttgggag ccctgctgcc 187740
cccacccttg gtcagtcccc atgtcctgct ggcctgtcag gcagggcaga aaatccaccc 187800
agaaatgctg agcaggatga gagtctagtt gggcccagcc tcattattta gaagggatgg 187860
aggcctaggg agcatgcttc tagcctgagc ccagcagggc ccgcccatg tccaggtct 187920 gcaccaggga cagctcctgc cgaggcctga cctgcccctt ctccctcagg tgctgctggt 187980
tgaccagcct ctggccctag agacccccgt agcgactgag ggtcccagca ggccatgcag 188040
ctttgccaag gtacgagccc ctccccagca ggggacagat gtggggaccc tcccaggcag 188100
gagcagctgg gtgcctggtg ctgccatctg ctgcctgcct ggttcttgtc ctcacattgg 188160
aggtcagtgt gagggctctg cctcgggaaa ggccatggag cttgccctgt ccagggcctc 188220
ccatgtgcac tgagcctggg aagagagggt tggagttgag ccttttaccc tgggaatgct 188280
gcctggagga tggtgcgggt gtgggggtggc accctgccag gcagggccct gcctcccgtgc 188340
```

```
gcccactgga actcgggcag gcagggtgt aggtgcctcc tctagagccg tccggtgggg   188400
gcccccggca gtggtggtgg tgtccactgg ccagcagctg cccttcagc caggacagta   188460
ggcctgacgc tgtccccagc agctccaagg tggatttgtg aaggggta gagggcacgt    188520
agaggcccca tgacctcccc agggttctgg gagggctgtg cccccttagc cagcaccatg   188580
ctgggtgata tagtcagatc ctgttacccc tgttgtggag gtgaggaaac aggttagtgg   188640
ggaggacatg actaaggtcc atgctgagtc gctagagctg cacccagaac cactgctggg   188700
accccatgcc tttctgctta ccccttgtgc cgggagatgc caagagatgc tgggagccag   188760
ccccacctct gcccttggag tcatggctac ggaaagggca ttcggaccgg tccctgacct   188820
caccggggag ggccgaaccc tgttcctgag gagccagggc ttcctagagg aggtaggcct   188880
tctagtcact ccttcatctg caggcactcc acagagctct ctgtgccagc ccccagcacg   188940
gagggctgac cttagtcgag tggagatgcc ccagtgccag gcagtaggga tgatgtctcc   189000
tgaggcccag atggaaggga ctggactagt ctcatgggc tgatggtggg gccaggcctt    189060
gaccagggac ccagtgtagg gggtgcagag acccctctga gttcctcaca catccctggg   189120
gccctcccca tacacttcct atcctgactg cgggcaagag ggagccccag ttcgccttcc   189180
ctatgctggg cacccacagt ggggctgggc accccgcca tgcccctgcc ctgtccttcc    189240
cctgagagcc tcggtcccac ctccaaggtg cctcagagga cagcagggc agcgggcaga    189300
ggccgagatg cctcctcatt ccaggctcag ctgcccttct tggggcagcc cacacctgag   189360
agtctcctgc agttggtcag gcctgaggag ggcaggggg tgcctgctgt ccctctgctg    189420
accacagtgg catttagcct gggcaccgcg cccagcacag tccatgctgc acaggtgccg   189480
tgggctccac agagccctgc ctgacatgca tgtgttacgt ttcgggtgcc gatgcccttg   189540
ggcggcactt ctccgggcag aaccccagg ccaccgctcc ggttccggtt ccgctgcatc    189600
tggggctctc ggcaggctgt ggtcctccgg ccagcctggg ggcatctcag tccctcagcc   189660
ccacaggggc ctgccccgca gcctgggcct cgagccccgt ctccgcacgc tgtgccgaat   189720
ctggctgccc atcagctccc tgcgtaccca gactgtgccc tgccatgccc gtggctcttc   189780
ccaggagtgc cctgtggcct cccctggct tgctgggctg attccctcct gtgtctcaaa    189840
cagagctcac cttgccatc actgctgtcc tcaccggccg gtgccagagg cccgtgtctg    189900
tgtaccctgt gtctgcacct ctgggcaggg cctggctctg accaacccgg gcttccagtg   189960
tccacagacc taaggcccag ggcgcctggg ggctggagca agagaagcaa aaggagccaa   190020
gggtgggggt ttggggttct tgtgagggcc cagccccagg accccaggac caggacaccc   190080
aggagcccca gggcccagcc ccagttcaga aggcaggggc cttctgaggg agcttaaggg   190140
tcccacagcc caggaccccc accagggcca gtggccagcg ttgggggact cagcctcctc   190200
gtcgctcgtc ctctctgttt ctcccacctt ttgcccccctt tctccttgcc tgttcccacc   190260
cgaggccccc tcttggcctg cgtgagccgg ggcggcactg aactggggc cgatccgcct    190320
gggcggcggt gagaggcagg gccggagcc gggccgctgg gtttgggcct ggcccgctcg    190380
ccgcaatatt gatggcccgt cagtgcagcc ctgattcctg tgctttcagt taaaaggttt   190440
ctgttgttgt agcttatgca gttgctctgt tgctatggaa acgtgacatc aaaatgacgt   190500
ttcccgttta aaagctttta actaaattcc tgcctgtcag atgtaggccc catttttgagc   190560
gtggagctgc cttcgagcga gcgtgagcgg cgcctcccgc ccatggtgcg tggggccggg   190620
ccggggccct cgctgagcgc gctctctcac cccacaggcg cctccggcat ggcggcggcc   190680
```

-continued

```
gaggggcccg gctacctcgt gtctccccag gcggagaagc accggcgggc cgcaactgg  190740
acggacgccg agatgcgcgg cctcatgctg gtctgggagg agttcttcga cgagctcaag  190800
cagaccaagc gcaacgccaa ggtgtacgag aagatggcca gcaagctctt cgagatgacc  190860
ggcgagcgca ggctgggcga ggagatcaag atcaagatca ccaacatgac cttccagtac  190920
aggtgggcga gcgggcagtg tgggccccac caggacgggc gggcccgggc gtggcgggcc  190980
gctcctgact ttcttggagc tctgagtcgg gacgatgtgt gggtcgtggc ctgcctgtcg  191040
gtctcctctg gccgggtatg ggcagaaccc cacggggtga gacggggccc acggaaaccg  191100
tgtgtgcagc cttccattgg ggaagtgggg aaactgaggc ccagcaaggg caggaaacca  191160
gtctaagagc tgaggggtag caggggtggg gctggtgctg ggcagaggcc aggatggctc  191220
ccaggacgta tgggcggtct gggcactgtc cctcggaggc agcaacactc atggtggtgc  191280
ccactgacct cacaccctgc tcccccatag ggaggcggcg gctgccagtg ccctccccac  191340
caccaagctc ccaagctcag caggggtttc aggggcctac tgcgtcattg ggaaattga   191400
gactgcaagt gagaaggagg ctcagtgctc tgcgacttgg agcatccact gagcctctgc  191460
catgagccgg tgagccccac tgggctggcc ctagggtca cggtggggta tttccagaaa   191520
tcaccaggtg aggtgcagga ccagccgcg catggtggg gcttacggtg cgaagaagaa    191580
agaggtggag gcctgccctg gcccaggact cccagcgtgg gggctcccgg cctggcccca  191640
cctctgctcc tgctacatgg caggtgggcc cttcctgccc tggcaacctg cagggaaggc  191700
cggaggggac cacccagcca gggagatgtt ggcgtctagg aggggacagg tgtggtccca  191760
cacacccagc atcttaaagt gcgtgggtcc ccagcccatt aggacagggt cccgggtggg  191820
caggggtcat ggtggggtga aggtctcagg cacaggcaag gtcacaggtg cggtgagggt  191880
cttgcagggt gtgaaggtca taggtgtgcg gtgaaggtca caggtgtggg gtgatggttt  191940
tgggtgtggg gagggtcttg cacggagcga gggtggcagc aagagctgga agctgcaggg  192000
ggagaatggc agcagagagc acccggccct gtgggcggcc tggacagggc tgggcctggg  192060
gctgccggag agcctgtcag cttccaggat gggagtggcc tcactcagct gctccacctc  192120
cgggtcaggc aggtgagcct ggggcagaga ggctgagagc acctgagcca cttgtgagag  192180
aggccacccc cactgccccc ctcaggcgag gagccggcct ccagcacagc agaagggaac  192240
ccccagtccc cagccctagt gggagtgggg aagaggccca gcaaggcccc ggacagaccg  192300
ccagcctgtg aggtctccgc tttcagttgc gttgatttga ttttttctga gccttgaagg  192360
aggggtccgg ggcctggccc tgcccaaagg ccccctaggca ggccccaaag ccgggaccta  192420
gggtgctgag catgacggat gttgggtttg agcggctggc ttgcgacgtg agggctgagg  192480
tgtgagcctg ggtatcttca gaggttcggt ggacacaggc agctgcccgc ggccccactg  192540
ttcccgtggc ctcctagtcc tgctcaggca cctggtgagg aagggacgca gagggcagtg  192600
ggaggtggcc acgactgttc cagcaggctc ccctctgact caggaattca cgggcaccac  192660
ctccctggct ggctctggtt ggtgtctggc caggttattc attatttatg ctgaaagcct  192720
cttcagagtc caggggagg gtttctgtct ccattcctgg aggctgagag atgagggtgc   192780
agcagagtgg gggcctccac tccagaccct gcagtctggg ctggccaagg gctgcaccgg  192840
tgcactgcac gtcatggctg atgaagcact tccacaccgc agccctcag agctgccaca   192900
gtcagcctta gttcaccgag ggggaagctg aggcccagag catgagaggg acttgcccag  192960
ggccacatag tccttagcag aggaagctgt ggctgggtga ctcgatcttt gtcctttttc  193020
tttatacccg cagtctcccc atagcagagg cttttcttt tttttctt ttcttttttt    193080
```

```
tttttttaca agaactcttt atatattaag gctgttgggc tgaagaagcc tgagagggtg    193140
gctggttctg tggagcatgg tttgttgaag tacagtttgg gggcctccta cactgagaat    193200
aggccttttc tcgtttctcc aaagagtggg ctggctcaag tagggcagag agagaagcct    193260
ggggcagagg ttagggatgg gcacccagcg cctgccctca cacgctctgt gctggtgtct    193320
tcacagccac gtgccaccct gggcagcatc ccctgctcac catctggctg tgcctgtttg    193380
ctgggggcac ctcattcaga atccagctta ttgtttccaa cggccaatgg ccacaccctg    193440
gcaggtagca agagtaggag agaggagaca cccactccga gcacaggttg ggtttggagc    193500
ccggccttgg ggcactctgt cactcaaagg cagagtgggg agtgggcact gggccttagg    193560
aggtactggg tccagtgagg cagagatgcc cctgccccac ccccaccttg tggcttcttc    193620
cctggcctgg ccagagctgt ctggccgcca tggggccctg tgtctcctgc cttgacctcc    193680
cagagggcag ccgaggccca ggggaggcct gggacttag cctctcaggg caggacctgt    193740
ctgcaggagt aggtgggtgc tgggggtccc agtggtaatg aggcatcagg cagtgtggga    193800
aggggcccat ccggcccacc ccagggcctc tgggcaggtt gcaggttgta gcgctggatc    193860
taggctcctg cccagactgt aggttcaacc aagaatggca tgggagccca gcctgctgtt    193920
tgctttatta aatctgccct gtagctgggg gaggggctta ctttgatcat cactatgtca    193980
ttgatataaa aatagaggct cagagaggtg aatgaacctg cccaaagtca cacagcaaag    194040
tgtggagatg agatactgac tcagggctgt ggacactgaa gcctgtgctc taacgccagt    194100
ggctgtcgct ccctgaggca ttctctcccg aacaacacag ttattatatt acaaaatatt    194160
atcactatat ttatatatct tataataacct tattattaca ataaaacctt attactctac    194220
cttcaaaat gaattattta aaagcagta tttgctcatt gcagagagtc tagaaactat    194280
agaaaagcaa gggaaaagca ataggaccag ccccaaggtc ccagcatgca cagataacct    194340
tagtaatact gggacgtgtg cttcctttt aacatctgag cccgtgtagg tcctgaagcc    194400
cagcttcttt ctaagtccat tgtcatcttg accctggagc ctggccgatt ttgctgggga    194460
ggcccttgcc agccgagagc ggctcctgcc tgtgccggcg tggcgcgccc ctctgctgag    194520
gctgggcagg acagggctg ggccagctct gtttctcacc cttggctctt gtgtctctcg    194580
tttcaggaaa ttaaaatgca tgacagatag cgagtccgcc ccgcccgact ggccctatta    194640
cctagccatt gatgggattc tggccaaggt ccccgagtcc tgtgatggca aactgccgga    194700
cagccagccg ccggggccct ccacgtccca gaccgaggcg tccctgtcgc gcccgctaa    194760
gtccacccct ctgtacttcc cgtataacca gtgctcctac gaaggccgct tcgaggatga    194820
tcgctccgac agctcctcca gcttactgtc ccttaagttc aggtagtgtg tctgcttgtc    194880
cttcccctgc cctggggtat ctcagccccc accatttaga gaaagggact gggagtggca    194940
aggccggcgg cggcggccac agtggttgca gaggccgtgg ctgcgggcag cgcctccagg    195000
gacaggcggc ctcagaccag ggagggcttt agtgtccaca ggcagaccga gtttgtctcc    195060
cagctccatc acttttgagc tgcacggaaa gttccttgac ttctctggcc tcagtctccc    195120
tcctataaaa tgggggtaaa tcagtaccctt tctcagaggg tggctgggag catcacagga    195180
gagaagacgc agcatgggc ccggcacacg gagggagacc aagccccaga ccccagaatg    195240
cgccccctgg cctcccttag cccacacaga ccccacccctc acaggctagc tgccctctca    195300
gcactgggga gggtgtcggg ctgcacctca tcacgtgttg ccgtgggcat gacccgtccc    195360
ctctgccatc catcccacac ctcagacccg tcccgtgctg gccacgtgac tgtgcctgca    195420
```

```
agatgctcac agggcagccg ggagccaggc agcatgcagg acagacacct gcggggtggg   195480
cctggggagc ccagagaagg tgcttttgag gaggggacat ttggggtggg cttcaaggt    195540 aaaatagaag ttggccattt ggaggcaaga acaggaagat tgtggatttg agtcacagct   195600
tctcccctgc cctggtcttc aagtcttct gacaggaggt gtcagaaaag tatctttagt    195660
agagaaggcg tctccgagga gggtccctct catgccgggg gccgctgctt gactcaggat   195720
ttctcattga agacctgaga caaaaacgct tttgctggca gctagaagga accagcagga   195780
ggcctgagat ttgtggctgt tgttcccgtg gactgagccc agttctcaga ctcagctgcc   195840
tggggccttg cacaggactg gggcgtgggg gctgccctcc ctgatcaggc ccaaagcgcg   195900
gatctcacgc ccctgaggtt ggctgtaccc tctcagctca gagcagagtg tgggccaggg   195960
atgagcaggc actggagcag ggccctgggg tctgtgggtt ttggcagctc cctgcccttc   196020
agggaggtct gctgagacca cggggtgggcc ctacccagc agcagagctc tcaggaggcg   196080
cccacagggc tggactgcct ttactcacca cctctaccag agctctgagg tcctggggag   196140
agagcccagg cctcttgtgg gccccacacc ctctaggtgc ctgtccttct gcctctctac   196200
caaggtgtgc cggccccatt tctaggccgc cgggagataa gggggctcac atctcaggcc   196260
cttccttctg ggacctcagt ttccccatct gcctaaggcc gggtgggget ggtggtcttg   196320 gcttccctac aggggtcctg agtactctgc actacccagc accccccacc ctgccttca   196380 tctctccctg ggggtggtct ctccacccct ggccccaac tggggctgag ccccacctg    196440 cccagtttgg tgggtgaagg gtgctccctg gcaggatatg cccctctgca gcccagaaca   196500
tcccaccctt tccagaccga aggggtgtgg attgtcctgg gacccctggtc attggggtca   196560 tccgctagtc gcaaaggacg gcaatgcctg tggcctctct ttctttcttt tcttttttt    196620 tttttttga gacggagtct cgctcttgtg cagagcag tggcgcgatc ttggctcact     196680
gcaacctccg cctcgtgggt tcaagcgatt ctcctgcctc agcctcccga gtagctggga   196740
ttacaggcac ccgccacaac gcctggctaa tttttgtat tttagtagag atggggttc    196800 accatgttgg ccaggctggt cttgaactcc tgacctcagg tgatccacct gcctctgcct   196860
cccaaagtgc tgggattaca ggcataagcc tccacaccg gccacccctg ttactttctg    196920
tcaaaggcgg tgggttctgg cccctccttt gcacatggaa tatgagaccc tgagtaagtg   196980
acctgactcc ctgggggcctc agtttcccca tttgcccagt aggattgtcg ggagggtccg   197040
gtgaggcccc tggtgtgccc aggctctgtg ccagcacgt ccacagccgg cactgtcctt    197100
ccaggtcgga ggagcggccg gtgaagaagc gcaaggtgca gagctgccac ctgcagaaga   197160
agcagctgcg gctgctggag gccatggtgg aggagcagcg ccggctgagc cgcgccgtgg   197220
aggagacctg ccgcgaggtg cgccgcgtgc tggaccagca gcacatcctg caggtgcaga   197280
gcctgcagct gcaggagcgc atgatgagtc tgctggagag gatcatcacc aagtccagcg   197340
tctaggccag caggcggcgg cggcggcggg gccgggcggc tggtggtact gctcaggcca   197400
cccagggcag gccactcagg ccaggcgggc aaggggccg ccccgcgagc ggagaccgcc    197460
ttccacctgg cctctggcag gatgtcccctt ctgagggta ttttgaggaa ccccaggcc    197520 ctggggaccg tgaggctcca gtctccagca tgaatgccct tcctcggaca caggccaggg   197580 cctctgggt tcactccgag taagaacgtc ctagagccac tctccagtgt cgttactatc    197640
aatgatactt gacgtggctt tgatattaaa cgtatacttt ttcattcttg cctgaaacgg   197700
acagtttgct gttgctggct tggtgaggat gccctgattg atggatcccg aaaatgaaag   197760
cagatggaaa cggttggggg caggctggag ctggggagc tctctcctga agggaaccct   197820
```

-continued

```
gtgtcctccc tcaccaggac ctctgcgtct ctccttaaat ggcctctgac gcctgatgaa  197880
aaccccagcg accttccagg aggcttttat tcagctctgt ttggagcatc aggtgtttcc  197940
actgcctcct tagcaatgac actaataaaa gtcgtaacac ctgttcacat gcacagccct  198000
gttgagtgtt ctgggtgctg agatatcat ggtggatgac acaaaggccc tggcctcttg  198060
gagcttatgc tcccatgcgg ggaagacaca tgggtcagta gagaaatggt tgcaggttgt  198120
gataagtgct ggaagggagg ggttggcctg aggacacgga ggcagacata cgtggagctg  198180
ggaacagtgg ccacacaggg aacggccagt gcgaaggccc agaggcagag gacactggag  198240
caagcccagg agcagctagg aggctggtgg ccagcagcca ggccacggaa gcccgtgcag  198300
cccgtgggga ggagtgttca tgcttttcaa gcttagtggg agtcttttgg ccagtgcagc  198360
tctgggtctg acatcggtgg gggacagagg ggtggtggag cggccacagc tgcaagctca  198420
cctcactgcc ggcccttcca ccagtttcaa actctttcta gaagctccag ctttcccaaa  198480
gctgaattct ctatgagcct ccttggccgg gactcgggcg tctggttgcc ctggctgcaa  198540
aggaggctgg ggccaggtgt gtttgagtca cctcctggaa ttaggcaagt tgctgcccaa  198600
atagaaggtt gttggcaggt gggtcagcag gtgaacagca tggtttgact cagggttcag  198660
aaaaatctcc ctctggctgc caagcgagca ggccgtggag acaggtgcag aggcaggtgt  198720
ggcagcaggc atcctgccag gcagtgctgc agtcatcctg cgacaagcag cagcagctca  198780
tcctaccctc taggggtct tgaggtcagc caggcaagag agcagcttgg actccactgg  198840
gtgtgggacc agcctgtgga ccatggtggt gtggagggtg ccctcggcct gcctgtgtga  198900
aggagaggcc ggcgtgttct gtggagccca aaggggagct gggcaagcag gattcacttc  198960
actctgaggg tcctggagct cccaccctcc tcagccatct ccccagagcc tgtgtgccga  199020
ggactcggcc catgttgctg tgggatgaga ggcagagtgt cgtgagggtg taaggagcgg  199080
cggcagtggt gggaggaggg agcagcagcc agcgctacgg tgccagtttc cagctgccag  199140
atgacgccgc tgaccctgtg gttgagaaga gatgcacaga gccagctctt gcaagccagt  199200
gtggctgcca tagcacctgc cgagaagcag aaggaagggt ggcccagga ggacagagga  199260 tgcgggcaca tctgatgcgg gcctgagttt tgggagcttt tgctctagcc agtttccagc  199320
tccgggaccc acccgcctcg taggcaagac accacccaag aaatcatttg cttaacaaac  199380
acactgggct ccaactggac acctgtgcca ccctagatgc tgggaaccca gccatgcacac  199440 aggcacctgc ccccagctgc tgaccactga ggctggctag cagctcccat ggggccagtg  199500 tggggttcc cagcctccta acagggagcc agtcacaagc cctcgagagg gaagggtgcc  199560
cgcggccctg gcaggaaggt taggctggac gctcccacaa gacataacag atggaggttc  199620
taaatgatgt agcaacttct tcaccctgaa actgctgtag agtcagccat gacgcaccgg  199680
tacttcagta actgccaggc atccgggaca gcacaccgcg agtcgctgct gtgcttgggt  199740
tagaagtggt ttggtctgtt ttcttctcgc cctctctaat cagagtcagt gattcatgcc  199800
cttccatcac cttagagaag gggcaggcgc tgcccgacct tctccaggct ggagcagcat  199860
cgcctcatgt cagcagaact cagctgtaga atatcgtggg gttggtgcct ttcatcagca  199920
gcatgtcctt aacaactttc tgatttcttc cttagttgtt ggtccattaa ggagaaaaaa  199980
aatgatctca gccattgcta aaatatttga taagattcag caaagcagca tgttaacatt  200040
gaaaactaga atcaggagcc aggcagatgt gcttgctttt cacctgtagt atttcatgtt  200100
gttttgacgt ttttagctaa tgcattaaga taaataaaca aaagccgggc acggtggttc  200160
```

```
acgcctgtaa tcccagcact ttgggaggct gaggcgggag gatcctctga ggtcaggagt    200220
tcaagaccag cctgaccaac atggagaaac ctcgtcatta ctaaaaatac aaaattagct    200280
gggcgtggtg gtgcatgcct gtaatcccag ctacttggga ggctgaggca ggagaatcgc    200340
ttgaacccgg gaggcggagg ttgcagtgag ctgagattgc accactgcac tccagcctgg    200400
gtgacagtga aactcggtct caaaaaaaaa aaaaattaa aaaagataa ataaaataag      200460
caggataaga aatgaagaaa gtagagttac ctttgttttc agatttcatt tttgtatacc    200520
cagaaagcca aatgtacaaa agactgggag ctctttaaac cagcttaaac ttgttgaaaa    200580
tgaggatgaa gaaatatccc attcagagtt ggaatgaatt taacccagaa ggaacaggac    200640
ctctactgaa gagaactatg cagtcttact gaaaaatcta aataatacct gagcgctgga    200700
gaaacttcgc acactcctga agctccaaa gtcaatgtca tcattttat aatgtcattc      200760
caaacatagt ctcaataata tcacttcttg gttttgacat ggacgcgatg atgtttaaat    200820
tcatatgaaa aaagaacggg gccaaaagtc caaggccagt cagcgtgaga agaccgctcg    200880
gcctccctcg gagtcgggga gttggaaccg cagactgaga tcatgtggct gctggaggcc    200940
aggacgaacg tcgggaaatg gagactcctg cgttgctggt gggatgtggt gcagccgctt    201000
ccaggagcaa tttggtgtcc cgtcctaaag ctgaagaaac gcatttcctc tggtcagtgc    201060
cactcctaga caggccaccc tgcggcagcc gtcctcaaac tggtctgagg accctcaac    201120
gctcttaaaa atcattaaaa gtgggccagg tgcggtggct cacacctgta atcccagcac    201180
tttgggaggc caagacaggc ggatcacgag gtcaggacat tgagatcatc ctggctaaca    201240
cggtgaaacc ccgtctctac taaaaataca aaaattagc cgggcgtggt ggcgggcgc     201300
tgtagtccca gctacttggg aggctgagcc aggagaatgg cgtgaaccca ggaggtggag    201360
cttgcagtga gctgagatca ctccactgca ctccagcctg gcagcagag cgagactctg    201420
tctcaaaaaa aataataaa taaataaata aaataaaat aaaataaat tcattaaaag       201480
tgccaaagaa cttttgctta tgtgagttct aatgaccaat attaatacac attagaatat    201540
cttattagaa attaaacctg agacctttag aaaacatgta ttcatttcaa aatagcaata    201600
aacccatgac atattaacat aaataacaat tgtatgaaaa atatattttc caaaacaaaa    201660
agttttcggg agaagtgtgg catagtttta catggtcgta aatctctggc ttaagagaag    201720
cccactggcc tctcagcagg ctctgggtcc gtccactttg ggggtgtttt ggttgtgaag    201780
tataggagtg aatggagaag ctcattctta cccagatgtg tatttgaaaa gaaaggaac    201840
atttataataa cctttgcaaa taatcggtat attcttccgt gatcctattc caacactgga    201900
caggtggtgg tttgttttt ttttttggag acggagtccc gctctgtcac tcaggctgga    201960
gtgcagtggc gcgatttcag ctcactgcaa gctccgcctc c                       202001
```

<210> SEQ ID NO 2
<211> LENGTH: 13481
<212> TYPE: DNA
<213> ORGANISM: Homo sapiens
<220> FEATURE:
<221> NAME/KEY: CDS
<222> LOCATION: (146)..(9580)

<400> SEQUENCE: 2

```
gctgccggga cgggtccaag atggacggcc gctcaggttc tgcttttacc tgcggcccag         60
agccccattc attgccccgg tgctgagcgg cgccgcgagt cggcccgagg cctccgggga         120
ctgccgtgcc gggcgggaga ccgcc atg gcg acc ctg gaa aag ctg atg aag          172
                            Met Ala Thr Leu Glu Lys Leu Met Lys
```

-continued

```
                1               5
gcc ttc gag tcc ctc aag tcc ttc cag cag cag cag cag cag cag      220
Ala Phe Glu Ser Leu Lys Ser Phe Gln Gln Gln Gln Gln Gln Gln
 10              15                  20                  25 cag cag cag cag cag cag cag cag cag cag cag cag caa cag ccg      268
Gln Gln Gln Gln Gln Gln Gln Gln Gln Gln Gln Gln Gln Gln Pro
                 30                  35                  40 cca ccg ccg ccg ccg ccg ccg ccg cct cct cag ctt cct cag ccg      316
Pro Pro Pro Pro Pro Pro Pro Pro Pro Pro Gln Leu Pro Gln Pro
             45                  50                  55 ccg cag gca cag ccg ctg ctg cct cag ccg cag ccg ccc ccg ccg      364
Pro Gln Ala Gln Pro Leu Leu Pro Gln Pro Gln Pro Pro Pro Pro
         60                  65                  70 ccc ccg ccg cca ccc ggc ccg gct gtg gct gag gag ccg ctg cac cga  412
Pro Pro Pro Pro Pro Gly Pro Ala Val Ala Glu Glu Pro Leu His Arg
     75                  80                  85 cca aag aaa gaa ctt tca gct acc aag aaa gac cgt gtg aat cat tgt  460
Pro Lys Lys Glu Leu Ser Ala Thr Lys Lys Asp Arg Val Asn His Cys
 90                  95                 100                 105 ctg aca ata tgt gaa aac ata gtg gca cag tct gtc aga aat tct cca  508
Leu Thr Ile Cys Glu Asn Ile Val Ala Gln Ser Val Arg Asn Ser Pro
                    110                 115                 120 gaa ttt cag aaa ctt ctg ggc atc gct atg gaa ctt ttt ctg ctg tgc  556
Glu Phe Gln Lys Leu Leu Gly Ile Ala Met Glu Leu Phe Leu Leu Cys
                125                 130                 135 agt gat gac gca gag tca gat gtc agg atg gtg gct gac gaa tgc ctc  604
Ser Asp Asp Ala Glu Ser Asp Val Arg Met Val Ala Asp Glu Cys Leu
            140                 145                 150 aac aaa gtt atc aaa gct ttg atg gat tct aat ctt cca agg tta cag  652
Asn Lys Val Ile Lys Ala Leu Met Asp Ser Asn Leu Pro Arg Leu Gln
        155                 160                 165 ctc gag ctc tat aag gaa att aaa aag aat ggt gcc cct cgg agt ttg  700
Leu Glu Leu Tyr Lys Glu Ile Lys Lys Asn Gly Ala Pro Arg Ser Leu
170                 175                 180                 185 cgt gct gcc ctg tgg agg ttt gct gag ctg gct cac ctg gtt cgg cct  748
Arg Ala Ala Leu Trp Arg Phe Ala Glu Leu Ala His Leu Val Arg Pro
                    190                 195                 200 cag aaa tgc agg cct tac ctg gtg aac ctt ctg ccg tgc ctg act cga  796
Gln Lys Cys Arg Pro Tyr Leu Val Asn Leu Leu Pro Cys Leu Thr Arg
                205                 210                 215 aca agc aag aga ccc gaa gaa tca gtc cag gag acc ttg gct gca gct  844
Thr Ser Lys Arg Pro Glu Glu Ser Val Gln Glu Thr Leu Ala Ala Ala
            220                 225                 230 gtt ccc aaa att atg gct tct ttt ggc aat ttt gca aat gac aat gaa  892
Val Pro Lys Ile Met Ala Ser Phe Gly Asn Phe Ala Asn Asp Asn Glu
        235                 240                 245 att aag gtt ttg tta aag gcc ttc ata gcg aac ctg aag tca agc tcc  940
Ile Lys Val Leu Leu Lys Ala Phe Ile Ala Asn Leu Lys Ser Ser Ser
250                 255                 260                 265 ccc acc att cgg cgg aca gcg gct gga tca gca gtg agc atc tgc cag  988
Pro Thr Ile Arg Arg Thr Ala Ala Gly Ser Ala Val Ser Ile Cys Gln
                    270                 275                 280 cac tca aga agg aca caa tat ttc tat agt tgg cta cta aat gtg ctc  1036
His Ser Arg Arg Thr Gln Tyr Phe Tyr Ser Trp Leu Leu Asn Val Leu
                285                 290                 295 tta ggc tta ctc gtt cct gtc gag gat gaa cac tcc act ctg ctg att  1084
Leu Gly Leu Leu Val Pro Val Glu Asp Glu His Ser Thr Leu Leu Ile
            300                 305                 310 ctt ggc gtg ctg ctc acc ctg agg tat ttg gtg ccc ttg ctg cag cag  1132
```

-continued

| | | | | | | | | | | | | | | |
|---|---|---|---|---|---|---|---|---|---|---|---|---|---|---|
|Leu|Gly|Val|Leu|Leu|Thr|Leu|Arg|Tyr|Leu|Val|Pro|Leu|Leu|Gln|Gln|
| |315| | | |320| | | |325| | | | | |

```
cag gtc aag gac aca agc ctg aaa ggc agc ttc gga gtg aca agg aaa     1180
Gln Val Lys Asp Thr Ser Leu Lys Gly Ser Phe Gly Val Thr Arg Lys
330                 335                 340                 345 gaa atg gaa gtc tct cct tct gca gag cag ctt gtc cag gtt tat gaa     1228
Glu Met Glu Val Ser Pro Ser Ala Glu Gln Leu Val Gln Val Tyr Glu
                350                 355                 360 ctg acg tta cat cat aca cag cac caa gac cac aat gtt gtg acc gga     1276
Leu Thr Leu His His Thr Gln His Gln Asp His Asn Val Val Thr Gly
            365                 370                 375 gcc ctg gag ctg ttg cag cag ctc ttc aga acg cct cca ccc gag ctt     1324
Ala Leu Glu Leu Leu Gln Gln Leu Phe Arg Thr Pro Pro Pro Glu Leu
        380                 385                 390 ctg caa acc ctg acc gca gtc ggg ggc att ggg cag ctc acc gct gct     1372
Leu Gln Thr Leu Thr Ala Val Gly Gly Ile Gly Gln Leu Thr Ala Ala
    395                 400                 405 aag gag gag tct ggt ggc cga agc cgt agt ggg agt att gtg gaa ctt     1420
Lys Glu Glu Ser Gly Gly Arg Ser Arg Ser Gly Ser Ile Val Glu Leu
410                 415                 420                 425 ata gct gga ggg ggt tcc tca tgc agc cct gtc ctt tca aga aaa caa     1468
Ile Ala Gly Gly Gly Ser Ser Cys Ser Pro Val Leu Ser Arg Lys Gln
                430                 435                 440 aaa ggc aaa gtg ctc tta gga gaa gaa gaa gcc ttg gag gat gac tct     1516
Lys Gly Lys Val Leu Leu Gly Glu Glu Glu Ala Leu Glu Asp Asp Ser
            445                 450                 455 gaa tcg aga tcg gat gtc agc agc tct gcc tta aca gcc tca gtg aag     1564
Glu Ser Arg Ser Asp Val Ser Ser Ser Ala Leu Thr Ala Ser Val Lys
        460                 465                 470 gat gag atc agt gga gag ctg gct gct tct tca ggg gtt tcc act cca     1612
Asp Glu Ile Ser Gly Glu Leu Ala Ala Ser Ser Gly Val Ser Thr Pro
    475                 480                 485 ggg tca gca ggt cat gac atc atc aca gaa cag cca cgg tca cag cac     1660
Gly Ser Ala Gly His Asp Ile Ile Thr Glu Gln Pro Arg Ser Gln His
490                 495                 500                 505 aca ctg cag gcg gac tca gtg gat ctg gcc agc tgt gac ttg aca agc     1708
Thr Leu Gln Ala Asp Ser Val Asp Leu Ala Ser Cys Asp Leu Thr Ser
                510                 515                 520 tct gcc act gat ggg gat gag gag gat atc ttg agc cac agc tcc agc     1756
Ser Ala Thr Asp Gly Asp Glu Glu Asp Ile Leu Ser His Ser Ser Ser
            525                 530                 535 cag gtc agc gcc gtc cca tct gac cct gcc atg gac ctg aat gat ggg     1804
Gln Val Ser Ala Val Pro Ser Asp Pro Ala Met Asp Leu Asn Asp Gly
        540                 545                 550 acc cag gcc tcg tcg ccc atc agc gac agc tcc cag acc acc acc gaa     1852
Thr Gln Ala Ser Ser Pro Ile Ser Asp Ser Ser Gln Thr Thr Thr Glu
    555                 560                 565 ggg cct gat tca gct gtt acc cct tca gac agt tct gaa att gtg tta     1900
Gly Pro Asp Ser Ala Val Thr Pro Ser Asp Ser Ser Glu Ile Val Leu
570                 575                 580                 585 gac ggt acc gac aac cag tat ttg ggc ctg cag att gga cag ccc cag     1948
Asp Gly Thr Asp Asn Gln Tyr Leu Gly Leu Gln Ile Gly Gln Pro Gln
                590                 595                 600 gat gaa gat gag gaa gcc aca ggt att ctt cct gat gaa gcc tcg gag     1996
Asp Glu Asp Glu Glu Ala Thr Gly Ile Leu Pro Asp Glu Ala Ser Glu
            605                 610                 615 gcc ttc agg aac tct tcc atg gcc ctt caa cag gca cat tta ttg aaa     2044
Ala Phe Arg Asn Ser Ser Met Ala Leu Gln Gln Ala His Leu Leu Lys
        620                 625                 630
```

| | | |
|---|---|---|
| aac atg agt cac tgc agg cag cct tct gac agc agt gtt gat aaa ttt<br>Asn Met Ser His Cys Arg Gln Pro Ser Asp Ser Ser Val Asp Lys Phe<br>635 640 645 | | 2092 |
| gtg ttg aga gat gaa gct act gaa ccg ggt gat caa gaa aac aag cct<br>Val Leu Arg Asp Glu Ala Thr Glu Pro Gly Asp Gln Glu Asn Lys Pro<br>650 655 660 665 | | 2140 |
| tgc cgc atc aaa ggt gac att gga cag tcc act gat gat gac tct gca<br>Cys Arg Ile Lys Gly Asp Ile Gly Gln Ser Thr Asp Asp Asp Ser Ala<br>670 675 680 | | 2188 |
| cct ctt gtc cat tgt gtc cgc ctt tta tct gct tcg ttt ttg cta aca<br>Pro Leu Val His Cys Val Arg Leu Leu Ser Ala Ser Phe Leu Leu Thr<br>685 690 695 | | 2236 |
| ggg gga aaa aat gtg ctg gtt ccg gac agg gat gtg agg gtc agc gtg<br>Gly Gly Lys Asn Val Leu Val Pro Asp Arg Asp Val Arg Val Ser Val<br>700 705 710 | | 2284 |
| aag gcc ctg gcc ctc agc tgt gtg gga gca gct gtg gcc ctc cac ccg<br>Lys Ala Leu Ala Leu Ser Cys Val Gly Ala Ala Val Ala Leu His Pro<br>715 720 725 | | 2332 |
| gaa tct ttc ttc agc aaa ctc tat aaa gtt cct ctt gac acc acg gaa<br>Glu Ser Phe Phe Ser Lys Leu Tyr Lys Val Pro Leu Asp Thr Thr Glu<br>730 735 740 745 | | 2380 |
| tac cct gag gaa cag tat gtc tca gac atc ttg aac tac atc gat cat<br>Tyr Pro Glu Glu Gln Tyr Val Ser Asp Ile Leu Asn Tyr Ile Asp His<br>750 755 760 | | 2428 |
| gga gac cca cag gtt cga gga gcc act gcc att ctc tgt ggg acc ctc<br>Gly Asp Pro Gln Val Arg Gly Ala Thr Ala Ile Leu Cys Gly Thr Leu<br>765 770 775 | | 2476 |
| atc tgc tcc atc ctc agc agg tcc cgc ttc cac gtg gga gat tgg atg<br>Ile Cys Ser Ile Leu Ser Arg Ser Arg Phe His Val Gly Asp Trp Met<br>780 785 790 | | 2524 |
| ggc acc att aga acc ctc aca gga aat aca ttt tct ttg gcg gat tgc<br>Gly Thr Ile Arg Thr Leu Thr Gly Asn Thr Phe Ser Leu Ala Asp Cys<br>795 800 805 | | 2572 |
| att cct ttg ctg cgg aaa aca ctg aag gat gag tct tct gtt act tgc<br>Ile Pro Leu Leu Arg Lys Thr Leu Lys Asp Glu Ser Ser Val Thr Cys<br>810 815 820 825 | | 2620 |
| aag tta gct tgt aca gct gtg agg aac tgt gtc atg agt ctc tgc agc<br>Lys Leu Ala Cys Thr Ala Val Arg Asn Cys Val Met Ser Leu Cys Ser<br>830 835 840 | | 2668 |
| agc agc tac agt gag tta gga ctg cag ctg atc atc gat gtg ctg act<br>Ser Ser Tyr Ser Glu Leu Gly Leu Gln Leu Ile Ile Asp Val Leu Thr<br>845 850 855 | | 2716 |
| ctg agg aac agt tcc tat tgg ctg gtg agg aca gag ctt ctg gaa acc<br>Leu Arg Asn Ser Ser Tyr Trp Leu Val Arg Thr Glu Leu Leu Glu Thr<br>860 865 870 | | 2764 |
| ctt gca gag att gac ttc agg ctg gtg agc ttt ttg gag gca aaa gca<br>Leu Ala Glu Ile Asp Phe Arg Leu Val Ser Phe Leu Glu Ala Lys Ala<br>875 880 885 | | 2812 |
| gaa aac tta cac aga ggg gct cat cat tat aca ggg ctt tta aaa ctg<br>Glu Asn Leu His Arg Gly Ala His His Tyr Thr Gly Leu Leu Lys Leu<br>890 895 900 905 | | 2860 |
| caa gaa cga gtg ctc aat aat gtt gtc atc cat ttg ctt gga gat gaa<br>Gln Glu Arg Val Leu Asn Asn Val Val Ile His Leu Leu Gly Asp Glu<br>910 915 920 | | 2908 |
| gac ccc agg gtg cga cat gtt gcc gca gca tca cta att agg ctt gtc<br>Asp Pro Arg Val Arg His Val Ala Ala Ala Ser Leu Ile Arg Leu Val<br>925 930 935 | | 2956 |
| cca aag ctg ttt tat aaa tgt gac caa gga caa gct gat cca gta gtg<br>Pro Lys Leu Phe Tyr Lys Cys Asp Gln Gly Gln Ala Asp Pro Val Val<br>940 945 950 | | 3004 |

| | | |
|---|---|---|
| gcc gtg gca aga gat caa agc agt gtt tac ctg aaa ctt ctc atg cat<br>Ala Val Ala Arg Asp Gln Ser Ser Val Tyr Leu Lys Leu Leu Met His<br>955                    960                    965 | | 3052 |
| gag acg cag cct cca tct cat ttc tcc gtc agc aca ata acc aga ata<br>Glu Thr Gln Pro Pro Ser His Phe Ser Val Ser Thr Ile Thr Arg Ile<br>970                    975                    980                    985 | | 3100 |
| tat aga ggc tat aac cta cta cca agc ata aca gac gtc act atg   gaa<br>Tyr Arg Gly Tyr Asn Leu Leu Pro Ser Ile Thr Asp Val Thr Met   Glu<br>                             990                    995                    1000 | | 3148 |
| aat aac ctt tca   aga gtt att gca   gca   gtt tct cat gaa   cta   atc<br>Asn Asn Leu Ser   Arg Val Ile Ala   Ala   Val Ser His Glu   Leu   Ile<br>                  1005                          1010                          1015 | | 3193 |
| aca tca acc acc   aga gca ctc aca   ttt   gga tgc tgt gaa   gct   ttg<br>Thr Ser Thr Thr   Arg Ala Leu Thr   Phe   Gly Cys Cys Glu   Ala   Leu<br>                  1020                          1025                          1030 | | 3238 |
| tgt ctt ctt tcc   act gcc ttc cca   gtt   tgc att tgg agt   tta   ggt<br>Cys Leu Leu Ser   Thr Ala Phe Pro   Val   Cys Ile Trp Ser   Leu   Gly<br>                  1035                          1040                          1045 | | 3283 |
| tgg cac tgt gga   gtg cct cca ctg   agt   gcc tca gat gag   tct   agg<br>Trp His Cys Gly   Val Pro Pro Leu   Ser   Ala Ser Asp Glu   Ser   Arg<br>                  1050                          1055                          1060 | | 3328 |
| aag agc tgt acc   gtt ggg atg gcc   aca   atg att ctg acc   ctg   ctc<br>Lys Ser Cys Thr   Val Gly Met Ala   Thr   Met Ile Leu Thr   Leu   Leu<br>                  1065                          1070                          1075 | | 3373 |
| tcg tca gct tgg   ttc cca ttg gat   ctc   tca gcc cat caa   gat   gct<br>Ser Ser Ala Trp   Phe Pro Leu Asp   Leu   Ser Ala His Gln   Asp   Ala<br>                  1080                          1085                          1090 | | 3418 |
| ttg att ttg gcc   gga aac ttg ctt   gca   gcc agt gct ccc   aaa   tct<br>Leu Ile Leu Ala   Gly Asn Leu Leu   Ala   Ala Ser Ala Pro   Lys   Ser<br>                  1095                          1100                          1105 | | 3463 |
| ctg aga agt tca   tgg gcc tct gaa   gaa   gaa gcc aac cca   gca   gcc<br>Leu Arg Ser Ser   Trp Ala Ser Glu   Glu   Glu Ala Asn Pro   Ala   Ala<br>                  1110                          1115                          1120 | | 3508 |
| acc aag caa gag   gag gtc tgg cca   gcc   ctg ggg gac cgg   gcc   ctg<br>Thr Lys Gln Glu   Glu Val Trp Pro   Ala   Leu Gly Asp Arg   Ala   Leu<br>                  1125                          1130                          1135 | | 3553 |
| gtg ccc atg gtg   gag cag ctc ttc   tct   cac ctg ctg aag   gtg   att<br>Val Pro Met Val   Glu Gln Leu Phe   Ser   His Leu Leu Lys   Val   Ile<br>                  1140                          1145                          1150 | | 3598 |
| aac att tgt gcc   cac gtc ctg gat   gac   gtg gct cct gga   ccc   gca<br>Asn Ile Cys Ala   His Val Leu Asp   Asp   Val Ala Pro Gly   Pro   Ala<br>                  1155                          1160                          1165 | | 3643 |
| ata aag gca gcc   ttg cct tct cta   aca   aac ccc cct tct   cta   agt<br>Ile Lys Ala Ala   Leu Pro Ser Leu   Thr   Asn Pro Pro Ser   Leu   Ser<br>                  1170                          1175                          1180 | | 3688 |
| ccc atc cga cga   aag ggg aag gag   aaa   gaa cca gga gaa   caa   gca<br>Pro Ile Arg Arg   Lys Gly Lys Glu   Lys   Glu Pro Gly Glu   Gln   Ala<br>                  1185                          1190                          1195 | | 3733 |
| tct gta ccg ttg   agt ccc aag aaa   ggc   agt gag gcc agt   gca   gct<br>Ser Val Pro Leu   Ser Pro Lys Lys   Gly   Ser Glu Ala Ser   Ala   Ala<br>                  1200                          1205                          1210 | | 3778 |
| tct aga caa tct   gat acc tca ggt   cct   gtt aca aca agt   aaa   tcc<br>Ser Arg Gln Ser   Asp Thr Ser Gly   Pro   Val Thr Thr Ser   Lys   Ser<br>                  1215                          1220                          1225 | | 3823 |
| tca tca ctg ggg   agt ttc tat cat   ctt   cct tca tac ctc   aaa   ctg<br>Ser Ser Leu Gly   Ser Phe Tyr His   Leu   Pro Ser Tyr Leu   Lys   Leu<br>                  1230                          1235                          1240 | | 3868 |
| cat gat gtc ctg   aaa gct aca cac   gct   aac tac aag gtc   acg   ctg<br>His Asp Val Leu   Lys Ala Thr His   Ala   Asn Tyr Lys Val   Thr   Leu | | 3913 |

-continued

```
                  1245                1250                1255
gat ctt cag aac agc acg gaa aag ttt gga ggg ttt ctc cgc tca        3958
Asp Leu Gln Asn Ser Thr Glu Lys Phe Gly Gly Phe Leu Arg Ser
            1260                1265                1270 gcc ttg gat gtt ctt tct cag ata cta gag ctg gcc aca ctg cag        4003
Ala Leu Asp Val Leu Ser Gln Ile Leu Glu Leu Ala Thr Leu Gln
            1275                1280                1285 gac att ggg aag tgt gtt gaa gag atc cta gga tac ctg aaa tcc        4048
Asp Ile Gly Lys Cys Val Glu Glu Ile Leu Gly Tyr Leu Lys Ser
            1290                1295                1300 tgc ttt agt cga gaa cca atg atg gca act gtt tgt gtt caa caa        4093
Cys Phe Ser Arg Glu Pro Met Met Ala Thr Val Cys Val Gln Gln
            1305                1310                1315 ttg ttg aag act ctc ttt ggc aca aac ttg gcc tcc cag ttt gat        4138
Leu Leu Lys Thr Leu Phe Gly Thr Asn Leu Ala Ser Gln Phe Asp
            1320                1325                1330 ggc tta tct tcc aac ccc agc aag tca caa ggc cga gca cag cgc        4183
Gly Leu Ser Ser Asn Pro Ser Lys Ser Gln Gly Arg Ala Gln Arg
            1335                1340                1345 ctt ggc tcc tcc agt gtg agg cca ggc ttg tac cac tac tgc ttc        4228
Leu Gly Ser Ser Ser Val Arg Pro Gly Leu Tyr His Tyr Cys Phe
            1350                1355                1360 atg gcc ccg tac acc cac ttc acc cag gcc ctc gct gac gcc agc        4273
Met Ala Pro Tyr Thr His Phe Thr Gln Ala Leu Ala Asp Ala Ser
            1365                1370                1375 ctg agg aac atg gtg cag gcg gag cag gag aac gac acc tcg gga        4318
Leu Arg Asn Met Val Gln Ala Glu Gln Glu Asn Asp Thr Ser Gly
            1380                1385                1390 tgg ttt gat gtc ctc cag aaa gtg tct acc cag ttg aag aca aac        4363
Trp Phe Asp Val Leu Gln Lys Val Ser Thr Gln Leu Lys Thr Asn
            1395                1400                1405 ctc acg agt gtc aca aag aac cgt gca gat aag aat gct att cat        4408
Leu Thr Ser Val Thr Lys Asn Arg Ala Asp Lys Asn Ala Ile His
            1410                1415                1420 aat cac att cgt ttg ttt gaa cct ctt gtt ata aaa gct tta aaa        4453
Asn His Ile Arg Leu Phe Glu Pro Leu Val Ile Lys Ala Leu Lys
            1425                1430                1435 cag tac acg act aca aca tgt gtg cag tta cag aag cag gtt tta        4498
Gln Tyr Thr Thr Thr Thr Cys Val Gln Leu Gln Lys Gln Val Leu
            1440                1445                1450 gat ttg ctg gcg cag ctg gtt cag tta cgg gtt aat tac tgt ctt        4543
Asp Leu Leu Ala Gln Leu Val Gln Leu Arg Val Asn Tyr Cys Leu
            1455                1460                1465 ctg gat tca gat cag gtg ttt att ggc ttt gta ttg aaa cag ttt        4588
Leu Asp Ser Asp Gln Val Phe Ile Gly Phe Val Leu Lys Gln Phe
            1470                1475                1480 gaa tac att gaa gtg ggc cag ttc agg gaa tca gag gca atc att        4633
Glu Tyr Ile Glu Val Gly Gln Phe Arg Glu Ser Glu Ala Ile Ile
            1485                1490                1495 cca aac atc ttt ttc ttc ttg gta tta cta tct tat gaa cgc tat        4678
Pro Asn Ile Phe Phe Phe Leu Val Leu Leu Ser Tyr Glu Arg Tyr
            1500                1505                1510 cat tca aaa cag atc att gga att cct aaa atc att cag ctc tgt        4723
His Ser Lys Gln Ile Ile Gly Ile Pro Lys Ile Ile Gln Leu Cys
            1515                1520                1525 gat ggc atc atg gcc agt gga agg aag gct gtg aca cat gcc ata        4768
Asp Gly Ile Met Ala Ser Gly Arg Lys Ala Val Thr His Ala Ile
            1530                1535                1540 ccg gct ctg cag ccc ata gtc cac gac ctc ttt gta tta aga gga        4813
```

-continued

| | | | | | | | | | | | | |
|---|---|---|---|---|---|---|---|---|---|---|---|---|
| Pro | Ala | Leu | Gln | Pro | Ile | Val | His | Asp | Leu | Phe | Val | Leu | Arg | Gly |
| | | | 1545 | | | | 1550 | | | | | 1555 | |

```
aca aat aaa gct gat gca gga aaa gag ctt gaa acc caa aaa gag      4858
Thr Asn Lys Ala Asp Ala Gly Lys Glu Leu Glu Thr Gln Lys Glu
        1560            1565                1570 gtg gtg gtg tca atg tta ctg aga ctc atc cag tac cat cag gtg      4903
Val Val Val Ser Met Leu Leu Arg Leu Ile Gln Tyr His Gln Val
    1575            1580                1585 ttg gag atg ttc att ctt gtc ctg cag cag tgc cac aag gag aat      4948
Leu Glu Met Phe Ile Leu Val Leu Gln Gln Cys His Lys Glu Asn
1590                1595                1600 gaa gac aag tgg aag cga ctg tct cga cag ata gct gac atc atc      4993
Glu Asp Lys Trp Lys Arg Leu Ser Arg Gln Ile Ala Asp Ile Ile
        1605            1610                1615 ctc cca atg tta gcc aaa cag cag atg cac att gac tct cat gaa      5038
Leu Pro Met Leu Ala Lys Gln Gln Met His Ile Asp Ser His Glu
    1620            1625                1630 gcc ctt gga gtg tta aat aca tta ttt gag att ttg gcc cct tcc      5083
Ala Leu Gly Val Leu Asn Thr Leu Phe Glu Ile Leu Ala Pro Ser
1635                1640                1645 tcc ctc cgt ccg gta gac atg ctt tta cgg agt atg ttc gtc act      5128
Ser Leu Arg Pro Val Asp Met Leu Leu Arg Ser Met Phe Val Thr
        1650            1655                1660 cca aac aca atg gcg tcc gtg agc act gtt caa ctg tgg ata tcg      5173
Pro Asn Thr Met Ala Ser Val Ser Thr Val Gln Leu Trp Ile Ser
    1665            1670                1675 gga att ctg gcc att ttg agg gtt ctg att tcc cag tca act gaa      5218
Gly Ile Leu Ala Ile Leu Arg Val Leu Ile Ser Gln Ser Thr Glu
1680                1685                1690 gat att gtt ctt tct cgt att cag gag ctc tcc ttc tct ccg tat      5263
Asp Ile Val Leu Ser Arg Ile Gln Glu Leu Ser Phe Ser Pro Tyr
        1695            1700                1705 tta atc tcc tgt aca gta att aat agg tta aga gat ggg gac agt      5308
Leu Ile Ser Cys Thr Val Ile Asn Arg Leu Arg Asp Gly Asp Ser
    1710            1715                1720 act tca acg cta gaa gaa cac agt gaa ggg aaa caa ata aag aat      5353
Thr Ser Thr Leu Glu Glu His Ser Glu Gly Lys Gln Ile Lys Asn
1725                1730                1735 ttg cca gaa gaa aca ttt tca agg ttt cta tta caa ctg gtt ggt      5398
Leu Pro Glu Glu Thr Phe Ser Arg Phe Leu Leu Gln Leu Val Gly
        1740            1745                1750 att ctt tta gaa gac att gtt aca aaa cag ctg aag gtg gaa atg      5443
Ile Leu Leu Glu Asp Ile Val Thr Lys Gln Leu Lys Val Glu Met
    1755            1760                1765 agt gag cag caa cat act ttc tat tgc cag gaa cta ggc aca ctg      5488
Ser Glu Gln Gln His Thr Phe Tyr Cys Gln Glu Leu Gly Thr Leu
1770                1775                1780 cta atg tgt ctg atc cac atc ttc aag tct gga atg ttc cgg aga      5533
Leu Met Cys Leu Ile His Ile Phe Lys Ser Gly Met Phe Arg Arg
        1785            1790                1795 atc aca gca gct gcc act agg ctg ttc cgc agt gat ggc tgt ggc      5578
Ile Thr Ala Ala Ala Thr Arg Leu Phe Arg Ser Asp Gly Cys Gly
    1800            1805                1810 ggc agt ttc tac acc ctg gac agc ttg aac ttg cgg gct cgt tcc      5623
Gly Ser Phe Tyr Thr Leu Asp Ser Leu Asn Leu Arg Ala Arg Ser
1815                1820                1825 atg atc acc acc cac ccg gcc ctg gtg ctc ctc tgg tgt cag ata      5668
Met Ile Thr Thr His Pro Ala Leu Val Leu Leu Trp Cys Gln Ile
        1830            1835                1840
```

| | | | | | | | | | | | | |
|---|---|---|---|---|---|---|---|---|---|---|---|---|
| ctg | ctg | ctt | gtc | aac | cac | acc | gac | tac | cgc | tgg | tgg | gca | gaa | gtg | 5713 |
| Leu | Leu | Leu | Val | Asn | His | Thr | Asp | Tyr | Arg | Trp | Trp | Ala | Glu | Val | |
| | | | 1845 | | | | 1850 | | | | | 1855 | | | |

| cag | cag | acc | ccg | aaa | aga | cac | agt | ctg | tcc | agc | aca | aag | tta | ctt | 5758 |
| Gln | Gln | Thr | Pro | Lys | Arg | His | Ser | Leu | Ser | Ser | Thr | Lys | Leu | Leu | |
| | | 1860 | | | | 1865 | | | | | 1870 | | | | |

| agt | ccc | cag | atg | tct | gga | gaa | gag | gag | gat | tct | gac | ttg | gca | gcc | 5803 |
| Ser | Pro | Gln | Met | Ser | Gly | Glu | Glu | Glu | Asp | Ser | Asp | Leu | Ala | Ala | |
| | | 1875 | | | | 1880 | | | | | 1885 | | | | |

| aaa | ctt | gga | atg | tgc | aat | aga | gaa | ata | gta | cga | aga | ggg | gct | ctc | 5848 |
| Lys | Leu | Gly | Met | Cys | Asn | Arg | Glu | Ile | Val | Arg | Arg | Gly | Ala | Leu | |
| | | 1890 | | | | 1895 | | | | | 1900 | | | | |

| att | ctc | ttc | tgt | gat | tat | gtc | tgt | cag | aac | ctc | cat | gac | tcc | gag | 5893 |
| Ile | Leu | Phe | Cys | Asp | Tyr | Val | Cys | Gln | Asn | Leu | His | Asp | Ser | Glu | |
| | | 1905 | | | | 1910 | | | | | 1915 | | | | |

| cac | tta | acg | tgg | ctc | att | gta | aat | cac | att | caa | gat | ctg | atc | agc | 5938 |
| His | Leu | Thr | Trp | Leu | Ile | Val | Asn | His | Ile | Gln | Asp | Leu | Ile | Ser | |
| | | 1920 | | | | 1925 | | | | | 1930 | | | | |

| ctt | tcc | cac | gag | cct | cca | gta | cag | gac | ttc | atc | agt | gcc | gtt | cat | 5983 |
| Leu | Ser | His | Glu | Pro | Pro | Val | Gln | Asp | Phe | Ile | Ser | Ala | Val | His | |
| | | 1935 | | | | 1940 | | | | | 1945 | | | | |

| cgg | aac | tct | gct | gcc | agc | ggc | ctg | ttc | atc | cag | gca | att | cag | tct | 6028 |
| Arg | Asn | Ser | Ala | Ala | Ser | Gly | Leu | Phe | Ile | Gln | Ala | Ile | Gln | Ser | |
| | | 1950 | | | | 1955 | | | | | 1960 | | | | |

| cgt | tgt | gaa | aac | ctt | tca | act | cca | acc | atg | ctg | aag | aaa | act | ctt | 6073 |
| Arg | Cys | Glu | Asn | Leu | Ser | Thr | Pro | Thr | Met | Leu | Lys | Lys | Thr | Leu | |
| | | 1965 | | | | 1970 | | | | | 1975 | | | | |

| cag | tgc | ttg | gag | ggg | atc | cat | ctc | agc | cag | tcg | gga | gct | gtg | ctc | 6118 |
| Gln | Cys | Leu | Glu | Gly | Ile | His | Leu | Ser | Gln | Ser | Gly | Ala | Val | Leu | |
| | | 1980 | | | | 1985 | | | | | 1990 | | | | |

| acg | ctg | tat | gtg | gac | agg | ctt | ctg | tgc | acc | cct | ttc | cgt | gtg | ctg | 6163 |
| Thr | Leu | Tyr | Val | Asp | Arg | Leu | Leu | Cys | Thr | Pro | Phe | Arg | Val | Leu | |
| | | 1995 | | | | 2000 | | | | | 2005 | | | | |

| gct | cgc | atg | gtc | gac | atc | ctt | gct | tgt | cgc | cgg | gta | gaa | atg | ctt | 6208 |
| Ala | Arg | Met | Val | Asp | Ile | Leu | Ala | Cys | Arg | Arg | Val | Glu | Met | Leu | |
| | | 2010 | | | | 2015 | | | | | 2020 | | | | |

| ctg | gct | gca | aat | tta | cag | agc | agc | atg | gcc | cag | ttg | cca | atg | gaa | 6253 |
| Leu | Ala | Ala | Asn | Leu | Gln | Ser | Ser | Met | Ala | Gln | Leu | Pro | Met | Glu | |
| | | 2025 | | | | 2030 | | | | | 2035 | | | | |

| gaa | ctc | aac | aga | atc | cag | gaa | tac | ctt | cag | agc | agc | ggg | ctc | gct | 6298 |
| Glu | Leu | Asn | Arg | Ile | Gln | Glu | Tyr | Leu | Gln | Ser | Ser | Gly | Leu | Ala | |
| | | 2040 | | | | 2045 | | | | | 2050 | | | | |

| cag | aga | cac | caa | agg | ctc | tat | tcc | ctg | ctg | gac | agg | ttt | cgt | ctc | 6343 |
| Gln | Arg | His | Gln | Arg | Leu | Tyr | Ser | Leu | Leu | Asp | Arg | Phe | Arg | Leu | |
| | | 2055 | | | | 2060 | | | | | 2065 | | | | |

| tcc | acc | atg | caa | gac | tca | ctt | agt | ccc | tct | cct | cca | gtc | tct | tcc | 6388 |
| Ser | Thr | Met | Gln | Asp | Ser | Leu | Ser | Pro | Ser | Pro | Pro | Val | Ser | Ser | |
| | | 2070 | | | | 2075 | | | | | 2080 | | | | |

| cac | ccg | ctg | gac | ggg | gat | ggg | cac | gtg | tca | ctg | gaa | aca | gtg | agt | 6433 |
| His | Pro | Leu | Asp | Gly | Asp | Gly | His | Val | Ser | Leu | Glu | Thr | Val | Ser | |
| | | 2085 | | | | 2090 | | | | | 2095 | | | | |

| ccg | gac | aaa | gac | tgg | tac | gtt | cat | ctt | gtc | aaa | tcc | cag | tgt | tgg | 6478 |
| Pro | Asp | Lys | Asp | Trp | Tyr | Val | His | Leu | Val | Lys | Ser | Gln | Cys | Trp | |
| | | 2100 | | | | 2105 | | | | | 2110 | | | | |

| acc | agg | tca | gat | tct | gca | ctg | ctg | gaa | ggt | gca | gag | ctg | gtg | aat | 6523 |
| Thr | Arg | Ser | Asp | Ser | Ala | Leu | Leu | Glu | Gly | Ala | Glu | Leu | Val | Asn | |
| | | 2115 | | | | 2120 | | | | | 2125 | | | | |

| cgg | att | cct | gct | gaa | gat | atg | aat | gcc | ttc | atg | atg | aac | tcg | gag | 6568 |
| Arg | Ile | Pro | Ala | Glu | Asp | Met | Asn | Ala | Phe | Met | Met | Asn | Ser | Glu | |
| | | 2130 | | | | 2135 | | | | | 2140 | | | | |

|  |  |  |  |  |  |  |  |  |  |  |
|---|---|---|---|---|---|---|---|---|---|---|
| ttc | aac | cta | agc | ctg | cta | gct | cca | tgc | tta | agc | cta | ggg | atg | agt | 6613 |
| Phe | Asn | Leu | Ser | Leu | Leu | Ala | Pro | Cys | Leu | Ser | Leu | Gly | Met | Ser |  |
|  |  | 2145 |  |  |  | 2150 |  |  |  | 2155 |  |  |  |  |  |

| gaa | att | tct | ggt | ggc | cag | aag | agt | gcc | ctt | ttt | gaa | gca | gcc | cgt | 6658 |
| Glu | Ile | Ser | Gly | Gly | Gln | Lys | Ser | Ala | Leu | Phe | Glu | Ala | Ala | Arg |
|  |  | 2160 |  |  |  | 2165 |  |  |  | 2170 |

| gag | gtg | act | ctg | gcc | cgt | gtg | agc | ggc | acc | gtg | cag | cag | ctc | cct | 6703 |
| Glu | Val | Thr | Leu | Ala | Arg | Val | Ser | Gly | Thr | Val | Gln | Gln | Leu | Pro |
|  |  | 2175 |  |  |  | 2180 |  |  |  | 2185 |

| gct | gtc | cat | cat | gtc | ttc | cag | ccc | gag | ctg | cct | gca | gag | ccg | gcg | 6748 |
| Ala | Val | His | His | Val | Phe | Gln | Pro | Glu | Leu | Pro | Ala | Glu | Pro | Ala |
|  |  | 2190 |  |  |  | 2195 |  |  |  | 2200 |

| gcc | tac | tgg | agc | aag | ttg | aat | gat | ctg | ttt | ggg | gat | gct | gca | ctg | 6793 |
| Ala | Tyr | Trp | Ser | Lys | Leu | Asn | Asp | Leu | Phe | Gly | Asp | Ala | Ala | Leu |
|  |  | 2205 |  |  |  | 2210 |  |  |  | 2215 |

| tat | cag | tcc | ctg | ccc | act | ctg | gcc | cgg | gcc | ctg | gca | cag | tac | ctg | 6838 |
| Tyr | Gln | Ser | Leu | Pro | Thr | Leu | Ala | Arg | Ala | Leu | Ala | Gln | Tyr | Leu |
|  |  | 2220 |  |  |  | 2225 |  |  |  | 2230 |

| gtg | gtg | gtc | tcc | aaa | ctg | ccc | agt | cat | ttg | cac | ctt | cct | cct | gag | 6883 |
| Val | Val | Val | Ser | Lys | Leu | Pro | Ser | His | Leu | His | Leu | Pro | Pro | Glu |
|  |  | 2235 |  |  |  | 2240 |  |  |  | 2245 |

| aaa | gag | aag | gac | att | gtg | aaa | ttc | gtg | gtg | gca | acc | ctt | gag | gcc | 6928 |
| Lys | Glu | Lys | Asp | Ile | Val | Lys | Phe | Val | Val | Ala | Thr | Leu | Glu | Ala |
|  |  | 2250 |  |  |  | 2255 |  |  |  | 2260 |

| ctg | tcc | tgg | cat | ttg | atc | cat | gag | cag | atc | ccg | ctg | agt | ctg | gat | 6973 |
| Leu | Ser | Trp | His | Leu | Ile | His | Glu | Gln | Ile | Pro | Leu | Ser | Leu | Asp |
|  |  | 2265 |  |  |  | 2270 |  |  |  | 2275 |

| ctc | cag | gca | ggg | ctg | gac | tgc | tgc | tgc | ctg | gcc | ctg | cag | ctg | cct | 7018 |
| Leu | Gln | Ala | Gly | Leu | Asp | Cys | Cys | Cys | Leu | Ala | Leu | Gln | Leu | Pro |
|  |  | 2280 |  |  |  | 2285 |  |  |  | 2290 |

| ggc | ctc | tgg | agc | gtg | gtc | tcc | tcc | aca | gag | ttt | gtg | acc | cac | gcc | 7063 |
| Gly | Leu | Trp | Ser | Val | Val | Ser | Ser | Thr | Glu | Phe | Val | Thr | His | Ala |
|  |  | 2295 |  |  |  | 2300 |  |  |  | 2305 |

| tgc | tcc | ctc | atc | tac | tgt | gtg | cac | ttc | atc | ctg | gag | gcc | gtt | gca | 7108 |
| Cys | Ser | Leu | Ile | Tyr | Cys | Val | His | Phe | Ile | Leu | Glu | Ala | Val | Ala |
|  |  | 2310 |  |  |  | 2315 |  |  |  | 2320 |

| gtg | cag | cct | gga | gag | cag | ctt | ctt | agt | cca | gaa | aga | agg | aca | aat | 7153 |
| Val | Gln | Pro | Gly | Glu | Gln | Leu | Leu | Ser | Pro | Glu | Arg | Arg | Thr | Asn |
|  |  | 2325 |  |  |  | 2330 |  |  |  | 2335 |

| acc | cca | aaa | gcc | atc | agc | gag | gag | gag | gag | gaa | gta | gat | cca | aac | 7198 |
| Thr | Pro | Lys | Ala | Ile | Ser | Glu | Glu | Glu | Glu | Glu | Val | Asp | Pro | Asn |
|  |  | 2340 |  |  |  | 2345 |  |  |  | 2350 |

| aca | cag | aat | cct | aag | tat | atc | act | gca | gcc | tgt | gag | atg | gtg | gca | 7243 |
| Thr | Gln | Asn | Pro | Lys | Tyr | Ile | Thr | Ala | Ala | Cys | Glu | Met | Val | Ala |
|  |  | 2355 |  |  |  | 2360 |  |  |  | 2365 |

| gaa | atg | gtg | gag | tct | ctg | cag | tcg | gtg | ttg | gcc | ttg | ggt | cat | aaa | 7288 |
| Glu | Met | Val | Glu | Ser | Leu | Gln | Ser | Val | Leu | Ala | Leu | Gly | His | Lys |
|  |  | 2370 |  |  |  | 2375 |  |  |  | 2380 |

| agg | aat | agc | ggc | gtg | ccg | gcg | ttt | ctc | acg | cca | ttg | cta | agg | aac | 7333 |
| Arg | Asn | Ser | Gly | Val | Pro | Ala | Phe | Leu | Thr | Pro | Leu | Leu | Arg | Asn |
|  |  | 2385 |  |  |  | 2390 |  |  |  | 2395 |

| atc | atc | atc | agc | ctg | gcc | cgc | ctg | ccc | ctt | gtc | aac | agc | tac | aca | 7378 |
| Ile | Ile | Ile | Ser | Leu | Ala | Arg | Leu | Pro | Leu | Val | Asn | Ser | Tyr | Thr |
|  |  | 2400 |  |  |  | 2405 |  |  |  | 2410 |

| cgt | gtg | ccc | cca | ctg | gtg | tgg | aag | ctt | gga | tgg | tca | ccc | aaa | ccg | 7423 |
| Arg | Val | Pro | Pro | Leu | Val | Trp | Lys | Leu | Gly | Trp | Ser | Pro | Lys | Pro |
|  |  | 2415 |  |  |  | 2420 |  |  |  | 2425 |

| gga | ggg | gat | ttt | ggc | aca | gca | ttc | cct | gag | atc | ccc | gtg | gag | ttc | 7468 |
| Gly | Gly | Asp | Phe | Gly | Thr | Ala | Phe | Pro | Glu | Ile | Pro | Val | Glu | Phe |

-continued

|  |  |  |  |
|---|---|---|---|
| | 2430 | 2435 | 2440 |
| ctc cag gaa aag gaa gtc ttt aag gag ttc atc tac cgc atc aac<br>Leu Gln Glu Lys Glu Val Phe Lys Glu Phe Ile Tyr Arg Ile Asn<br>2445              2450              2455 | | | 7513 |
| aca cta ggc tgg acc agt cgt act cag ttt gaa gaa act tgg gcc<br>Thr Leu Gly Trp Thr Ser Arg Thr Gln Phe Glu Glu Thr Trp Ala<br>2460              2465              2470 | | | 7558 |
| acc ctc ctt ggt gtc ctg gtg acg cag ccc ctc gtg atg gag cag<br>Thr Leu Leu Gly Val Leu Val Thr Gln Pro Leu Val Met Glu Gln<br>2475              2480              2485 | | | 7603 |
| gag gag agc cca cca gaa gaa gac aca gag agg acc cag atc aac<br>Glu Glu Ser Pro Pro Glu Glu Asp Thr Glu Arg Thr Gln Ile Asn<br>2490              2495              2500 | | | 7648 |
| gtc ctg gcc gtg cag gcc atc acc tca ctg gtg ctc agt gca atg<br>Val Leu Ala Val Gln Ala Ile Thr Ser Leu Val Leu Ser Ala Met<br>2505              2510              2515 | | | 7693 |
| act gtg cct gtg gcc ggc aac cca gct gta agc tgc ttg gag cag<br>Thr Val Pro Val Ala Gly Asn Pro Ala Val Ser Cys Leu Glu Gln<br>2520              2525              2530 | | | 7738 |
| cag ccc cgg aac aag cct ctg aaa gct ctc gac acc agg ttt ggg<br>Gln Pro Arg Asn Lys Pro Leu Lys Ala Leu Asp Thr Arg Phe Gly<br>2535              2540              2545 | | | 7783 |
| agg aag ctg agc att atc aga ggg att gtg gag caa gag att caa<br>Arg Lys Leu Ser Ile Ile Arg Gly Ile Val Glu Gln Glu Ile Gln<br>2550              2555              2560 | | | 7828 |
| gca atg gtt tca aag aga gag aat att gcc acc cat cat tta tat<br>Ala Met Val Ser Lys Arg Glu Asn Ile Ala Thr His His Leu Tyr<br>2565              2570              2575 | | | 7873 |
| cag gca tgg gat cct gtc cct tct ctg tct ccg gct act aca ggt<br>Gln Ala Trp Asp Pro Val Pro Ser Leu Ser Pro Ala Thr Thr Gly<br>2580              2585              2590 | | | 7918 |
| gcc ctc atc agc cac gag aag ctg ctg cta cag atc aac ccc gag<br>Ala Leu Ile Ser His Glu Lys Leu Leu Leu Gln Ile Asn Pro Glu<br>2595              2600              2605 | | | 7963 |
| cgg gag ctg ggg agc atg agc tac aaa ctc ggc cag gtg tcc ata<br>Arg Glu Leu Gly Ser Met Ser Tyr Lys Leu Gly Gln Val Ser Ile<br>2610              2615              2620 | | | 8008 |
| cac tcc gtg tgg ctg ggg aac agc atc aca ccc ctg agg gag gag<br>His Ser Val Trp Leu Gly Asn Ser Ile Thr Pro Leu Arg Glu Glu<br>2625              2630              2635 | | | 8053 |
| gaa tgg gac gag gaa gag gag gag gag gcc gac gcc cct gca cct<br>Glu Trp Asp Glu Glu Glu Glu Glu Ala Asp Ala Pro Ala Pro<br>2640              2645              2650 | | | 8098 |
| tcg tca cca ccc acg tct cca gtc aac tcc agg aaa cac cgg gct<br>Ser Ser Pro Pro Thr Ser Pro Val Asn Ser Arg Lys His Arg Ala<br>2655              2660              2665 | | | 8143 |
| gga gtt gac atc cac tcc tgt tcg cag ttt ttg ctt gag ttg tac<br>Gly Val Asp Ile His Ser Cys Ser Gln Phe Leu Leu Glu Leu Tyr<br>2670              2675              2680 | | | 8188 |
| agc cgc tgg atc ctg ccg tcc agc tca gcc agg agg acc ccg gcc<br>Ser Arg Trp Ile Leu Pro Ser Ser Ser Ala Arg Arg Thr Pro Ala<br>2685              2690              2695 | | | 8233 |
| atc ctg atc agt gag gtg gtc aga tcc ctt cta gtg gtc tca gac<br>Ile Leu Ile Ser Glu Val Val Arg Ser Leu Leu Val Val Ser Asp<br>2700              2705              2710 | | | 8278 |
| ttg ttc acc gag cgc aac cag ttt gag ctg atg tat gtg acg ctg<br>Leu Phe Thr Glu Arg Asn Gln Phe Glu Leu Met Tyr Val Thr Leu<br>2715              2720              2725 | | | 8323 |
| aca gaa ctg cga agg gtg cac cct tca gaa gac gag atc ctc gct | | | 8368 |

```
                Thr Glu Leu Arg Arg Val His Pro Ser Glu Asp Glu Ile Leu Ala
                            2730            2735            2740 cag tac ctg gtg cct gcc acc tgc aag gca gct gcc gtc ctt ggg         8413
Gln Tyr Leu Val Pro Ala Thr Cys Lys Ala Ala Ala Val Leu Gly
            2745            2750            2755 atg gac aag gcc gtg gcg gag cct gtc agc cgc ctg ctg gag agc         8458
Met Asp Lys Ala Val Ala Glu Pro Val Ser Arg Leu Leu Glu Ser
            2760            2765            2770 acg ctc agg agc agc cac ctg ccc agc agg gtt gga gcc ctg cac         8503
Thr Leu Arg Ser Ser His Leu Pro Ser Arg Val Gly Ala Leu His
            2775            2780            2785 ggc gtc ctc tat gtg ctg gag tgc gac ctg ctg gac gac act gcc         8548
Gly Val Leu Tyr Val Leu Glu Cys Asp Leu Leu Asp Asp Thr Ala
            2790            2795            2800 aag cag ctc atc ccg gtc atc agc gac tat ctc ctc tcc aac ctg         8593
Lys Gln Leu Ile Pro Val Ile Ser Asp Tyr Leu Leu Ser Asn Leu
            2805            2810            2815 aaa ggg atc gcc cac tgc gtg aac att cac agc cag cag cac gta         8638
Lys Gly Ile Ala His Cys Val Asn Ile His Ser Gln Gln His Val
            2820            2825            2830 ctg gtc atg tgt gcc act gcg ttt tac ctc att gag aac tat cct         8683
Leu Val Met Cys Ala Thr Ala Phe Tyr Leu Ile Glu Asn Tyr Pro
            2835            2840            2845 ctg gac gta ggg ccg gaa ttt tca gca tca ata ata cag atg tgt         8728
Leu Asp Val Gly Pro Glu Phe Ser Ala Ser Ile Ile Gln Met Cys
            2850            2855            2860 ggg gtg atg ctg tct gga agt gag gag tcc acc ccc tcc atc att         8773
Gly Val Met Leu Ser Gly Ser Glu Glu Ser Thr Pro Ser Ile Ile
            2865            2870            2875 tac cac tgt gcc ctc aga ggc ctg gag cgc ctc ctg ctc tct gag         8818
Tyr His Cys Ala Leu Arg Gly Leu Glu Arg Leu Leu Leu Ser Glu
            2880            2885            2890 cag ctc tcc cgc ctg gat gca gaa tcg ctg gtc aag ctg agt gtg         8863
Gln Leu Ser Arg Leu Asp Ala Glu Ser Leu Val Lys Leu Ser Val
            2895            2900            2905 gac aga gtg aac gtg cac agc ccg cac cgg gcc atg gcg gct ctg         8908
Asp Arg Val Asn Val His Ser Pro His Arg Ala Met Ala Ala Leu
            2910            2915            2920 ggc ctg atg ctc acc tgc atg tac aca gga aag gag aaa gtc agt         8953
Gly Leu Met Leu Thr Cys Met Tyr Thr Gly Lys Glu Lys Val Ser
            2925            2930            2935 ccg ggt aga act tca gac cct aat cct gca gcc ccc gac agc gag         8998
Pro Gly Arg Thr Ser Asp Pro Asn Pro Ala Ala Pro Asp Ser Glu
            2940            2945            2950 tca gtg att gtt gct atg gag cgg gta tct gtt ctt ttt gat agg         9043
Ser Val Ile Val Ala Met Glu Arg Val Ser Val Leu Phe Asp Arg
            2955            2960            2965 atc agg aaa ggc ttt cct tgt gaa gcc aga gtg gtg gcc agg atc         9088
Ile Arg Lys Gly Phe Pro Cys Glu Ala Arg Val Val Ala Arg Ile
            2970            2975            2980 ctg ccc cag ttt cta gac gac ttc ttc cca ccc cag gac atc atg         9133
Leu Pro Gln Phe Leu Asp Asp Phe Phe Pro Pro Gln Asp Ile Met
            2985            2990            2995 aac aaa gtc atc gga gag ttt ctg tcc aac cag cag cca tac ccc         9178
Asn Lys Val Ile Gly Glu Phe Leu Ser Asn Gln Gln Pro Tyr Pro
            3000            3005            3010 cag ttc atg gcc acc gtg gtg tat aag gtg ttt cag act ctg cac         9223
Gln Phe Met Ala Thr Val Val Tyr Lys Val Phe Gln Thr Leu His
            3015            3020            3025
```

| | | | | | | | | | | | | |
|---|---|---|---|---|---|---|---|---|---|---|---|---|
| agc | acc | ggg | cag | tcg | tcc | atg | gtc | cgg | gac | tgg | gtc | atg | ctg | tcc | 9268 |
| Ser | Thr | Gly | Gln | Ser | Ser | Met | Val | Arg | Asp | Trp | Val | Met | Leu | Ser | |
| | | | 3030 | | | | 3035 | | | | 3040 | | | | |
| ctc | tcc | aac | ttc | acg | cag | agg | gcc | ccg | gtc | gcc | atg | gcc | acg | tgg | 9313 |
| Leu | Ser | Asn | Phe | Thr | Gln | Arg | Ala | Pro | Val | Ala | Met | Ala | Thr | Trp | |
| | | | 3045 | | | | 3050 | | | | 3055 | | | | |
| agc | ctc | tcc | tgc | ttc | ttt | gtc | agc | gcg | tcc | acc | agc | ccg | tgg | gtc | 9358 |
| Ser | Leu | Ser | Cys | Phe | Phe | Val | Ser | Ala | Ser | Thr | Ser | Pro | Trp | Val | |
| | | | 3060 | | | | 3065 | | | | 3070 | | | | |
| gcg | gcg | atc | ctc | cca | cat | gtc | atc | agc | agg | atg | ggc | aag | ctg | gag | 9403 |
| Ala | Ala | Ile | Leu | Pro | His | Val | Ile | Ser | Arg | Met | Gly | Lys | Leu | Glu | |
| | | | 3075 | | | | 3080 | | | | 3085 | | | | |
| cag | gtg | gac | gtg | aac | ctt | ttc | tgc | ctg | gtc | gcc | aca | gac | ttc | tac | 9448 |
| Gln | Val | Asp | Val | Asn | Leu | Phe | Cys | Leu | Val | Ala | Thr | Asp | Phe | Tyr | |
| | | | 3090 | | | | 3095 | | | | 3100 | | | | |
| aga | cac | cag | ata | gag | gag | gag | ctc | gac | cgc | agg | gcc | ttc | cag | tct | 9493 |
| Arg | His | Gln | Ile | Glu | Glu | Glu | Leu | Asp | Arg | Arg | Ala | Phe | Gln | Ser | |
| | | | 3105 | | | | 3110 | | | | 3115 | | | | |
| gtg | ctt | gag | gtg | gtt | gca | gcc | cca | gga | agc | cca | tat | cac | cgg | ctg | 9538 |
| Val | Leu | Glu | Val | Val | Ala | Ala | Pro | Gly | Ser | Pro | Tyr | His | Arg | Leu | |
| | | | 3120 | | | | 3125 | | | | 3130 | | | | |
| ctg | act | tgt | tta | cga | aat | gtc | cac | aag | gtc | acc | acc | tgc | tga | | 9580 |
| Leu | Thr | Cys | Leu | Arg | Asn | Val | His | Lys | Val | Thr | Thr | Cys | | | |
| | | | 3135 | | | | 3140 | | | | | | | | | gcgccatggt gggagagact gtgaggcggc agctggggcc ggagcctttg gaagtctgcg 9640 cccttgtgcc ctgcctccac cgagccagct tggtccctat gggcttccgc acatgccgcg 9700 ggcggccagg caacgtgcgt gtctctgcca tgtggcagaa gtgctctttg tggcagtggc 9760 caggcaggga gtgtctgcag tcctggtggg gctgagcctg aggccttcca gaaagcagga 9820 gcagctgtgc tgcaccccat gtgggtgacc aggtcctttc tcctgatagt cacctgctgg 9880 ttgttgccag gttgcagctg ctcttgcatc tgggccagaa gtcctccctc ctgcaggctg 9940 gctgttggcc cctctgctgt cctgcagtag aaggtgccgt gagcaggctt gggaacact 10000 ggcctgggtc tccctggtgg ggtgtgcatg ccacgccccg tgtctggatg cacagatgcc 10060 atggcctgtg ctgggccagt ggctgggggt gctagacacc cggcaccatt ctcccttctc 10120 tcttttcttc tcaggattta aaatttaatt atatcagtaa agagattaat tttaacgtaa 10180 ctctttctat gcccgtgtaa agtatgtgaa tcgcaaggcc tgtgctgcat gcgacagcgt 10240 ccggggtggt ggacagggcc cccggccacg ctccctctcc tgtagccact ggcatagccc 10300 tcctgagcac ccgctgacat ttccgttgta catgttcctg tttatgcatt cacaaggtga 10360 ctgggatgta gagaggcgtt agtgggcagg tggccacagc aggactgagg acaggccccc 10420 attatcctag gggtgcgctc acctgcagcc cctcctcctc gggcacagac gactgtcgtt 10480 ctccacccac cagtcaggga cagcagcctc cctgtcactc agctgagaag gccagccctc 10540 cctggctgtg agcagcctcc actgtgtcca gagacatggg cctcccactc ctgttccttg 10600 ctagccctgg ggtggcgtct gcctaggagc tggctggcag gtgttgggac ctgctgctcc 10660 atggatgcat gccctaagag tgtcactgag ctgtgttttg tctgagcctc tctcggtcaa 10720 cagcaaagct tggtgtcttg gcactgttag tgacagagcc cagcatccct tctgcccccg 10780 ttccagctga catcttgcac ggtgacccct tttagtcagg agagtgcaga tctgtgctca 10840 tcggagactg ccccacggcc ctgtcagagc cgccactcct atcccaggc caggtccctg 10900 gaccagcctc ctgtttgcag gcccagagga gccaagtcat taaaatggaa gtggattctg 10960 gatggccggg ctgctgctga tgtaggagct ggatttggga gctctgcttg ccgactggct 11020

```
gtgagacgag gcagggcctc tgcttcctca gccctagagg cgagccaggc aaggttggcg    11080
actgtcatgt ggcttggttt ggtcatgccc gtcgatgttt tgggtattga atgtggtaag    11140
tggaggaaat gttggaactc tgtgcaggtg ctgccttgag accccaagc ttccacctgt     11200
ccctctccta tgtggcagct ggggagcagc tgagatgtgg acttgtatgc tgcccacata    11260
cgtgaggggg agctgaaagg gagcccctcc tctgagcagc ctctgccagg cctgtatgag    11320
gcttttccca ccagctccca acagaggcct cccccagcca ggaccacctc gtcctcgtgg    11380
cggggcagca ggagcggtag aaaggggtcc gatgtttgag gaggccctta agggaagcta    11440
ctgaattata acacgtaaga aaatcaccat tccgtattgg ttgggggctc ctgtttctca    11500
tcctagcttt ttcctggaaa gcccgctaga aggtttggga acgaggggaa agttctcaga    11560
actgttggct gctccccacc cgcctcccgc ctcccccgca ggttatgtca gcagctctga    11620
gacagcagta tcacaggcca gatgttgttc ctggctagat gtttacattt gtaagaaata    11680
acactgtgaa tgtaaaacag agccattccc ttggaatgca tatcgctggg ctcaacatag    11740
agtttgtctt cctcttgttt acgacgtgat ctaaaccagt ccttagcaag gggctcagaa    11800
cacccccgctc tggcagtagg tgtcccccac ccccaaagac ctgcctgtgt gctccggaga    11860
tgaatatgag ctcattagta aaatgactt cacccacgca tatacataaa gtatccatgc     11920
atgtgcatat agacacatct ataattttac acacacacct ctcaagacgg agatgcatgg    11980
cctctaagag tgcccgtgtc ggttcttcct ggaagttgac tttccttaga cccgccaggt    12040
caagttagcc gcgtgacgga catccaggcg tgggacgtgg tcaggcagg gctcattcat     12100
tgcccactag gatcccactg gcgaagatgg tctccatatc agctctctgc agaagggagg    12160
aagactttat catgttccta aaaatctgtg gcaagcaccc atcgtattat ccaaattttg    12220
ttgcaaatgt gattaatttg gttgtcaagt tttgggggtg ggctgtgggg agattgcttt    12280
tgttttcctg ctggtaatat cgggaaagat tttaatgaaa ccagggtaga attgtttggc    12340
aatgcactga agcgtgtttc tttcccaaaa tgtgcctccc ttccgctgcg ggcccagctg    12400
agtctatgta ggtgatgttt ccagctgcca agtgctcttt gttactgtcc accctcattt    12460
ctgccagcgc atgtgtcctt tcaaggggaa aatgtgaagc tgaaccccct ccagacaccc    12520
agaatgtagc atctgagaag gccctgtgcc ctaaaggaca cccctcgccc ccatcttcat    12580
ggaggggtc atttcagagc cctcggagcc aatgaacagc tcctcctctt ggagctgaga    12640
tgagccccac gtggagctcg ggacggatag tagacagcaa taactcggtg tgtggccgcc    12700
tggcaggtgg aacttcctcc cgttgcgggg tggagtgagg ttagttctgt gtgtctggtg    12760
ggtggagtca ggcttctctt gctacctgtg agcatccttc ccagcagaca tcctcatcgg    12820
gctttgtccc tccccgcctt cctccctctg cggggaggac ccgggaccac agctgctggc    12880
cagggtagac ttggagctgt cctccagagg ggtcacgtgt aggagtgaga agaaggaaga    12940
tcttgagagc tgctgaggga ccttggagag ctcaggatgg ctcagacgag gacactcgct    13000
tgccgggcct gggcctcctg gaaggaggg agctgctcag aatgccgcat gacaactgaa      13060
ggcaacctgg aaggttcagg ggccgctctt cccccatgtg cctgtcacgc tctggtgcag    13120
tcaaaggaac gccttcccct cagttgtttc taagagcaga gtctcccgct gcaatctggg    13180
tggtaactgc cagccttgga ggatcgtggc caacgtggac ctgcctacgg agggtgggct    13240
ctgacccaag tggggcctcc ttgtccaggt ctcactgctt tgcaccgtgg tcagagggac    13300
tgtcagctga gcttgagctc ccctggagcc agcagggctg tgatgggcga gtcccggagc    13360
```

-continued

```
cccacccaga cctgaatgct tctgagagca aagggaagga ctgacgagag atgtatattt    13420
aattttttaa ctgctgcaaa cattgtacat ccaaattaaa ggaaaaaaat ggaaaccatc    13480
a                                                                    13481
```

<210> SEQ ID NO 3
<211> LENGTH: 20
<212> TYPE: DNA
<213> ORGANISM: Artificial sequence
<220> FEATURE:
<223> OTHER INFORMATION: Primer

<400> SEQUENCE: 3

```
gggaccctga tcaacaccat                                                    20
```

<210> SEQ ID NO 4
<211> LENGTH: 24
<212> TYPE: DNA
<213> ORGANISM: Artificial sequence
<220> FEATURE:
<223> OTHER INFORMATION: Primer

<400> SEQUENCE: 4

```
ccagttcttg attttgtcga aaca                                               24
```

<210> SEQ ID NO 5
<211> LENGTH: 18
<212> TYPE: DNA
<213> ORGANISM: Artificial sequence
<220> FEATURE:
<223> OTHER INFORMATION: Probe

<400> SEQUENCE: 5

```
tgggtggtct ccgcggcc                                                      18
```

<210> SEQ ID NO 6
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: n is a, c, g, or t

<400> SEQUENCE: 6

```
nnnnnnnnnn nnnnnn                                                        16
```

<210> SEQ ID NO 7
<211> LENGTH: 14
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(14)
<223> OTHER INFORMATION: n is a, c, g, or t

<400> SEQUENCE: 7

```
nnnnnnnnnn nnnn                                                          14
```

<210> SEQ ID NO 8
<211> LENGTH: 20
<212> TYPE: DNA
<213> ORGANISM: Artificial sequence

```
<220> FEATURE:
<223> OTHER INFORMATION: Synthetic oligonucleotide
<220> FEATURE:
<221> NAME/KEY: misc_feature
<222> LOCATION: (1)..(20)
<223> OTHER INFORMATION: n is a, c, g, or t

<400> SEQUENCE: 8
nnnnnnnnnn nnnnnnnnnn                                               20

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
ccttccctga aggttcctcc                                               20

<210> SEQ ID NO 10
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 10
taaattgtca tcacc                                                    15

<210> SEQ ID NO 11
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: bases at this postion are RNA

<400> SEQUENCE: 11
taaattguca tcacc                                                    15

<210> SEQ ID NO 12
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or t

<400> SEQUENCE: 12
taaattgnca tcacc                                                    15

<210> SEQ ID NO 13
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: bases at this position are RNA
```

```
<400> SEQUENCE: 13
taaautgtca tcacc                                                        15

<210> SEQ ID NO 14
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 14
taaattgtca tcacca                                                       16

<210> SEQ ID NO 15
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 15
taaattgtca tcacctta                                                     18

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
taaattgtca tcaccattta                                                   20

<210> SEQ ID NO 17
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 17
taaattgtca tcaccta                                                      17

<210> SEQ ID NO 18
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 18
taaattgtca tcaccttta                                                    19

<210> SEQ ID NO 19
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 19
gtaaattgtc atcacc                                                       16

<210> SEQ ID NO 20
<211> LENGTH: 17
```

```
<212> TYPE: DNA
<213> ORGANISM: Artificial sequence
<220> FEATURE:
<223> OTHER INFORMATION: Synthetic oligonucleotide

<400> SEQUENCE: 20
ggtaaattgt catcacc                                                    17

<210> SEQ ID NO 21
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 21
ggttaaattg tcatcacc                                                   18

<210> SEQ ID NO 22
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 22
ggtgtaaatt gtcatcacc                                                  19

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
ggtgataaat tgtcatcacc                                                 20

<210> SEQ ID NO 24
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 24
ggctaaattg tcatcaccgc c                                               21

<210> SEQ ID NO 25
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 25
gctaaattgt catcaccgc                                                  19

<210> SEQ ID NO 26
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 26
```
taataaattg tcatcacctt a          21

<210> SEQ ID NO 27
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 27
aataaattgt catcacctt              19

<210> SEQ ID NO 28
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 28
tcttaaattg tcatcaccag a          21

<210> SEQ ID NO 29
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 29
cttaaattgt catcaccag              19

<210> SEQ ID NO 30
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 30
taataaattg tcatcacc               18

<210> SEQ ID NO 31
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 31
aataaattgt catcacc                17

<210> SEQ ID NO 32
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 32
ataaattgtc atcacca                17

<210> SEQ ID NO 33
<211> LENGTH: 17
<212> TYPE: DNA
<213> ORGANISM: Artificial sequence

```
<220> FEATURE:
<223> OTHER INFORMATION: Synthetic oligonucleotide

<400> SEQUENCE: 33
ataaattctc atcacca                                                        17

<210> SEQ ID NO 34
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 34
ataaatagtc atcacca                                                        17

<210> SEQ ID NO 35
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 35
ataaattgtg atcacca                                                        17

<210> SEQ ID NO 36
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 36
ataaattgtc ttcacca                                                        17

<210> SEQ ID NO 37
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 37
ataaattgtc aacacca                                                        17

<210> SEQ ID NO 38
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 38
taaattctca tcacc                                                          15

<210> SEQ ID NO 39
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 39
taaaatgtca tcacc                                                          15
```

```
<210> SEQ ID NO 40
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 40
taaattgtga tcacc                                                       15

<210> SEQ ID NO 41
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 41
taaattgtct tcacc                                                       15

<210> SEQ ID NO 42
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 42
taaattgtca acacc                                                       15

<210> SEQ ID NO 43
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 43
ttaaattgtc atcacca                                                     17

<210> SEQ ID NO 44
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 44
aaaaattgtc atcacca                                                     17

<210> SEQ ID NO 45
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 45
attaattgtc atcacca                                                     17

<210> SEQ ID NO 46
<211> LENGTH: 17
<212> TYPE: DNA
<213> ORGANISM: Artificial sequence
<220> FEATURE:
<223> OTHER INFORMATION: Synthetic oligonucleotide
```

```
<400> SEQUENCE: 46
atatattgtc atcacca                                                17

<210> SEQ ID NO 47
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 47
ataatttgtc atcacca                                                17

<210> SEQ ID NO 48
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 48
ataaattgtc atgacca                                                17

<210> SEQ ID NO 49
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 49
ataaattgtc atctcca                                                17

<210> SEQ ID NO 50
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 50
ataaattgtc atcagca                                                17

<210> SEQ ID NO 51
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 51
ataaattgtc atcacga                                                17

<210> SEQ ID NO 52
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 52
ataaattgtc atcacct                                                17

<210> SEQ ID NO 53
```

```
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 53
taagttgtca tcacc                                                         15

<210> SEQ ID NO 54
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 54
taaagtgtca tcacc                                                         15

<210> SEQ ID NO 55
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 55
taaatggtca tcacc                                                         15

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
tctctattgc acattccaag                                                    20

<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 57
ccttccctga aggttcctcc                                                    20

<210> SEQ ID NO 58
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 58
aattgtcatc accagaa                                                       17

<210> SEQ ID NO 59
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 59
```
aattgtcatc accagaa                                              17

<210> SEQ ID NO 60
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 60
aaattgtcat caccaga                                              17

<210> SEQ ID NO 61
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 61
taaattgtca tcaccag                                              17

<210> SEQ ID NO 62
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 62
aataaattgt catcacc                                              17

<210> SEQ ID NO 63
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 63
taataaattg tcatcac                                              17

<210> SEQ ID NO 64
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 64
ttaataaatt gtcatca                                              17

<210> SEQ ID NO 65
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 65
attgtcatca ccaga                                                15

<210> SEQ ID NO 66
<211> LENGTH: 15
<212> TYPE: DNA

```
<213> ORGANISM: Artificial sequence
<220> FEATURE:
<223> OTHER INFORMATION: Synthetic oligonucleotide

<400> SEQUENCE: 66
ttaataaatt gtcat                                                      15

<210> SEQ ID NO 67
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 67
ttgtcatcac cagaa                                                      15

<210> SEQ ID NO 68
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 68
aattgtcatc accag                                                      15

<210> SEQ ID NO 69
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 69
aaattgtcat cacca                                                      15

<210> SEQ ID NO 70
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 70
aataaattgt catca                                                      15

<210> SEQ ID NO 71
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 71
attaataaat tgtca                                                      15

<210> SEQ ID NO 72
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 72
tattaataaa ttgtc                                                      15
```

<210> SEQ ID NO 73
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 73
gtcatcacca gaaaa                                                      15

<210> SEQ ID NO 74
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 74
tgtcatcacc agaaa                                                      15

<210> SEQ ID NO 75
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 75
ataaattgtc atcac                                                      15

<210> SEQ ID NO 76
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 76
taataaattg tcatc                                                      15

<210> SEQ ID NO 77
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 77
ataaaatgtc atcacca                                                    17

<210> SEQ ID NO 78
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 78
taaatagtca tcacc                                                      15

<210> SEQ ID NO 79
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 79
ctcgactaaa gcaggatttc          20

<210> SEQ ID NO 80
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 80
aataaattgt catcaccag          19

<210> SEQ ID NO 81
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 81
cacagtgcta cccaacctt          19

<210> SEQ ID NO 82
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 82
tcacagctat cttctcatc          19

<210> SEQ ID NO 83
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 83
tcccatttca ggagacctgg          20

<210> SEQ ID NO 84
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 84
gctgattaga gagaggtccc          20

<210> SEQ ID NO 85
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 85
atcatggctg cagctt          16

```
<210> SEQ ID NO 86
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 86
ttcagtcatg acttcc                                                       16

<210> SEQ ID NO 87
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 87
tggctgcagc ttccga                                                       16

<210> SEQ ID NO 88
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 88
atggctgcag cttccg                                                       16

<210> SEQ ID NO 89
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 89
catggctgca gcttcc                                                       16

<210> SEQ ID NO 90
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 90
tcatggctgc agcttc                                                       16

<210> SEQ ID NO 91
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 91
catcatggct gcagct                                                       16

<210> SEQ ID NO 92
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 92
ccatcatggc tgcagc                                               16

<210> SEQ ID NO 93
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 93
tccatcatgg ctgcag                                               16

<210> SEQ ID NO 94
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 94
ttccatcatg gctgca                                               16
```

UNITED STATES PATENT AND TRADEMARK OFFICE
CERTIFICATE OF CORRECTION

PATENT NO. : 11,732,261 B2
APPLICATION NO. : 17/011395
DATED : August 22, 2023
INVENTOR(S) : Seth et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 190 days.

Signed and Sealed this
Twelfth Day of November, 2024

Katherine Kelly Vidal
*Director of the United States Patent and Trademark Office*